United States Patent
van Dijk et al.

(10) Patent No.: US 11,613,764 B2
(45) Date of Patent: Mar. 28, 2023

(54) T CELL RECEPTORS THAT BIND TO NY-ESO-1 AND METHODS OF USE THEREOF

(71) Applicant: MINK Therapeutics, Inc., New York, NY (US)

(72) Inventors: Marc van Dijk, Bosch en Duin (NL); Volker Seibert, Lörrach (DE); Cornelia Anne Mundt, Lörrach (DE); Arthur Andrew Hurwitz, Bedford, MA (US); Mark Adrian Exley, Brookline, MA (US); Benjamin Jacob Wolf, Boston, MA (US); Daniel Leventhal, Medford, MA (US); Sébastien Lalevée, Saint Louis (FR); Reed Masakayan, Lincoln, MA (US)

(73) Assignee: MiNK Therapeutics, Inc., New York, NY (US)

( * ) Notice: Subject to any disclaimer, the term of this patent is extended or adjusted under 35 U.S.C. 154(b) by 448 days.

(21) Appl. No.: 16/512,031

(22) Filed: Jul. 15, 2019

(65) Prior Publication Data

US 2020/0040358 A1 Feb. 6, 2020

Related U.S. Application Data

(63) Continuation of application No. PCT/US2018/013624, filed on Jan. 12, 2018.

(60) Provisional application No. 62/446,084, filed on Jan. 13, 2017.

(51) Int. Cl.
| | |
|---|---|
| *C12N 15/85* | (2006.01) |
| *A61K 47/64* | (2017.01) |
| *C07K 14/725* | (2006.01) |
| *C07K 16/18* | (2006.01) |
| *A61K 47/65* | (2017.01) |
| *C07K 14/085* | (2006.01) |
| *C07K 14/74* | (2006.01) |

(52) U.S. Cl.
CPC .......... *C12N 15/85* (2013.01); *A61K 47/6425* (2017.08); *A61K 47/65* (2017.08); *C07K 14/085* (2013.01); *C07K 14/7051* (2013.01); *C07K 14/70539* (2013.01); *C07K 16/18* (2013.01); *C07K 2317/32* (2013.01); *C07K 2317/34* (2013.01); *C07K 2317/565* (2013.01); *C07K 2319/02* (2013.01)

(58) Field of Classification Search
CPC .... C12N 15/85; A61K 47/6425; A61K 47/65; C07K 14/7051; C07K 14/70539; C07K 16/18; C07K 2317/32; C07K 2317/34; C07K 2317/565; C07K 2319/02
See application file for complete search history.

(56) References Cited

FOREIGN PATENT DOCUMENTS

| | | | |
|---|---|---|---|
| JP | 2015-525208 A | 9/2015 | |
| WO | WO 2005/113595 A2 | 12/2005 | |
| WO | WO 2012/038055 A1 | 3/2012 | |
| WO | WO 2013/177247 A1 | 11/2013 | |
| WO | WO 2014/160030 A2 | 10/2014 | |
| WO | WO 2017/109496 A1 | 6/2017 | |
| WO | WO-2017109496 A1 * | 6/2017 | ............. A61K 35/17 |

OTHER PUBLICATIONS

Rossjohn et al.T Cell Antigen Receptor Recognition of Antigen-Presenting Molecules(Annual Review Immunology 2015. 33:169-200) (Year: 2015).*
Song et al.Broad TCR repertoire and diverse structural solutions for recognition of an immunodominant CD8+ T cell epitope. Nature Structural and Molecular Biology, vol. 24, No. 4, Apr. 2017 (Year: 2017).*
Alignment WO2017109496A1 SEQ ID No. 43 (Year: 2022).*
Invitation to Pay Additional Fees for Application No. PCT/US2018/013624, dated Jun. 7, 2018.
International Search Report and Written Opinion for Application No. PCT/US2018/013624, dated Aug. 20, 2018.
International Preliminary Report on Patentability for Application No. PCT/US2018/013624, dated Jul. 25, 2019.
Robbins et al., Single and dual amino acid substitutions in TCR CDRs can enhance antigen-specific T cell functions. J Immunol. May 1, 2008;180(9):6116-31. doi: 10.4049/jimmunol.180.9.6116.
Singh et al., T cells targeting NY-ESO-1 demonstrate efficacy against disseminated neuroblastoma. Oncoimmunology. Aug. 12, 2015;5(1):e1040216. doi: 10.1080/2162402X.2015.1040216. eCollection 2016.
Zhao et al., Abstract# 2752 Primary Human Lymphocytes Retrovirally Transduced With Ny-Es0-1 Antigen Specific Tcr Genes Recognize and Kill Ny-Es0-1 Positive Melanoma as Well as Other Tumors. Blood, Journal of American Society of Hematology. Nov. 16, 2003; 11: 746a.

* cited by examiner

*Primary Examiner* — Amy E Juedes
*Assistant Examiner* — Brian Hartnett
(74) *Attorney, Agent, or Firm* — Wolf, Greenfield & Sacks, P.C.

(57) ABSTRACT

Provided are TCRs (e.g., TCRs that bind to NY-ESO-1), cells and pharmaceutical compositions comprising these TCRs, nucleic acids encoding these TCRs, expression vectors and host cells for making these TCRs, and methods of treating a subject using these TCRs.

8 Claims, 54 Drawing Sheets

Figure 1:
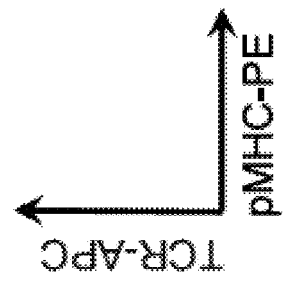
Figure 1:
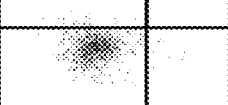
Figure 1:
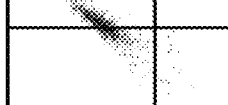
Figure 1:

Specification includes a Sequence Listing.

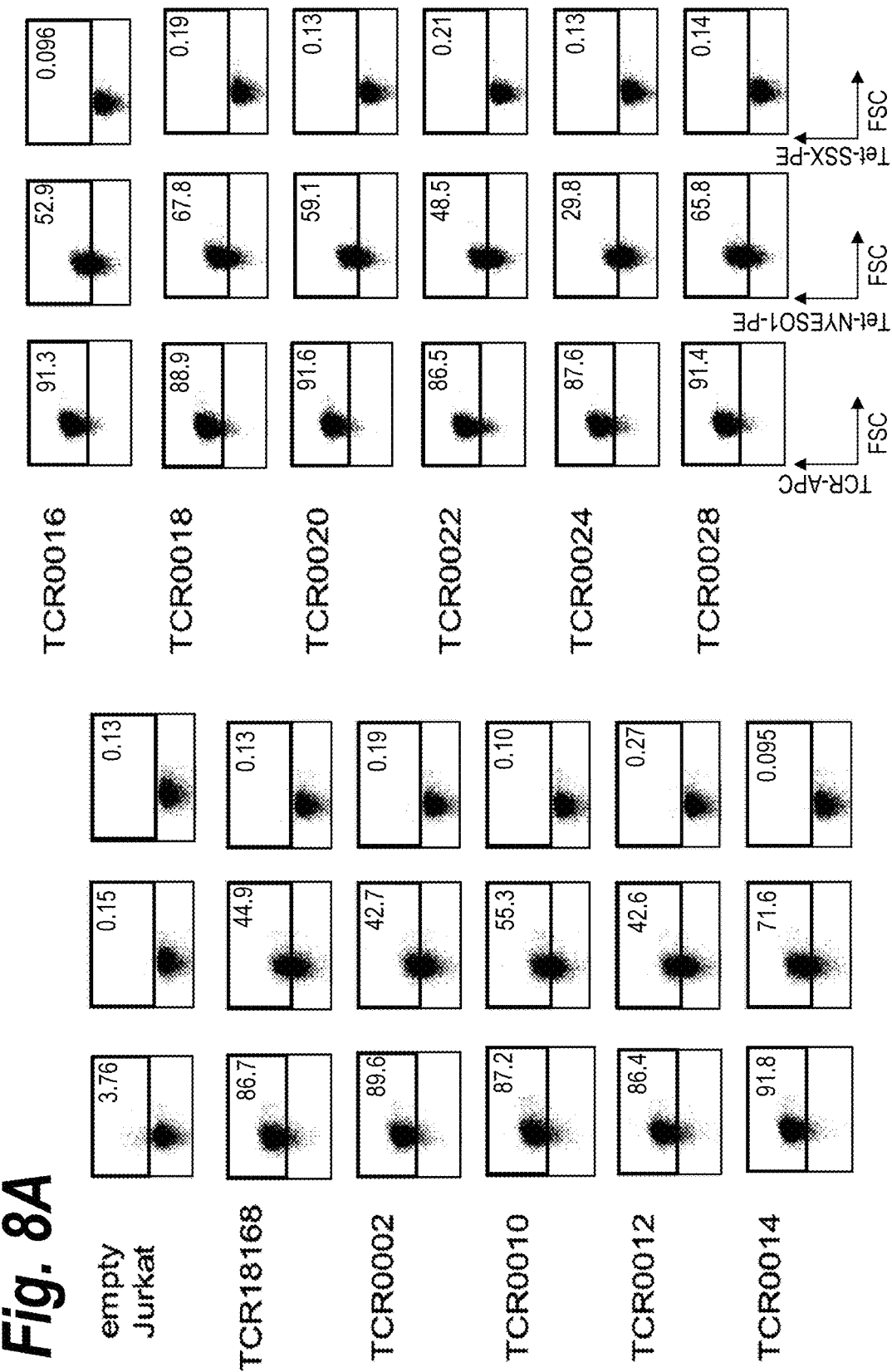

Fig. 20A

Fig. 20E

T CELL RECEPTORS THAT BIND TO NY-ESO-1 AND METHODS OF USE THEREOF

1. RELATED APPLICATIONS

This application is a continuation of International Patent Application No. PCT/US2018/013624, filed Jan. 12, 2018, which claims the benefit of U.S. Provisional Application No: 62/446,084, filed Jan. 13, 2017, which are incorporated by reference herein in their entirety.

1. FIELD

The instant disclosure relates to T cell receptors (TCRs) that bind to an NY-ESO-1 peptide and methods of using the same.

2. BACKGROUND

NY-ESO-1 is a tumor-associated antigen encoded by the Cancer/Testis Antigen 1A or 1B (CTAG1A or CTAG1B) gene. It is a cytoplasmic protein having a glycine-rich N-terminal region and a hydrophobic C-terminal region. NY-ESO-1 is expressed in germ cells but not normal somatic tissues. Aberrant expression of NY-ESO-1 has been identified in many types of tumors, such as melanoma, prostate cancer, multiple myeloma, breast cancer, and lung cancer. In view of its tumor-specific expression profile, NY-ESO-1 holds great promise as a target for cancer therapies.

Accordingly, there is a need in the art for novel compositions that can recognize cancer cells expressing NY-ESO-1 and direct an immune response against these cells.

3. SUMMARY

The instant disclosure provides TCRs (e.g., TCRs that bind to NY-ESO-1), cells and pharmaceutical compositions comprising these TCRs, nucleic acids encoding these TCRs, expression vectors and host cells for making these TCRs, and methods of treating a subject using these TCRs. The TCRs disclosed herein are particularly useful for directing an immune response against cancer cells expressing NY-ESO-1, and hence for treating an NY-ESO-1-expressing cancer in a subject.

Accordingly, in one aspect, the instant disclosure provides an isolated T cell receptor (TCR) that binds to a peptide consisting of the amino acid sequence set forth in SEQ ID NO: 1 or 2, the TCR comprising an α chain variable region (Vα) comprising complementarily determining region CDR3, wherein the CDR3α comprises the amino acid sequence set forth in SEQ ID NO: 61, 62, 63, 64, or 65. In certain embodiments, the CDR3α comprises the amino acid sequence set forth in SEQ ID NO: 64 or 65. In certain embodiments, the CDR3α comprises an amino acid sequence selected from the group consisting of SEQ ID NOs: 7 and 39-60. In certain embodiments, the CDR3α comprises an amino acid sequence selected from the group consisting of SEQ ID NOs: 7, 39, 40, 43, 45, 47, 49, and 54.

In certain embodiments, the Vα comprises CDR1α and CDR2α, comprising the amino acid sequences set forth in SEQ ID NOs: 5 and 6, respectively. In certain embodiments, the Vα comprises CDR1α, CDR2α, and CDR3α, comprising the amino acid sequences set forth in SEQ ID NOs: 5, 6, and 7; 5, 6, and 39; 5, 6, and 40; 5, 6, and 41; 5, 6, and 42; 5, 6, and 43; 5, 6, and 44; 5, 6, and 45; 5, 6, and 46; 5, 6, and 47; 5, 6, and 48; 5, 6, and 49; 5, 6, and 50; 5, 6, and 51; 5, 6, and 52; 5, 6, and 53; 5, 6, and 54; 5, 6, and 55; 5, 6, and 56; 5, 6, and 57; 5, 6, and 58; 5, 6, and 59; or 5, 6, and 60, respectively. In certain embodiments, the Vα comprises an amino acid sequence selected from the group consisting of SEQ ID NOs: 87-91. In certain embodiments, the Vα comprises an amino acid sequence selected from the group consisting of SEQ ID NOs: 3 and 66-86. In certain embodiments, the Vα comprises an amino acid sequence selected from the group consisting of SEQ ID NOs: 3, 66, 69, 71, 73, 75, and 80. In certain embodiments, the isolated TCR comprises an α chain comprising an amino acid sequence selected from the group consisting of SEQ ID NOs: 13, 93-96, 105-118, 120-123, 125-128, and 408-415. In certain embodiments, the isolated TCR comprises an α chain comprising an amino acid sequence selected from the group consisting of SEQ ID NOs: 13, 105, 110, 115, 120, 125, 408, and 412.

In certain embodiments, the TCR comprises a β chain variable region (Vβ) comprising CDR3β, wherein the CDR3β comprises the amino acid sequence set forth in SEQ ID NO: 10. In certain embodiments, the Vβ comprises CDR1β and CDR2β comprising the amino acid sequences set forth in SEQ ID NOs: 8 and 9, respectively. In certain embodiments, the Vβ comprises the amino acid sequence set forth in SEQ ID NO: 4. In certain embodiments, the isolated TCR comprises a β chain comprising an amino acid sequence selected from the group consisting of SEQ ID NOs: 14, 25, and 97-104.

In another aspect, the instant disclosure provides an isolated T cell receptor (TCR) that binds to a peptide consisting of the amino acid sequence set forth in SEQ ID NO: 1 or 2, the TCR comprising a β chain variable region (Vβ) comprising complementarity determining region CDR3β, wherein the CDR3β comprises the amino acid sequence set forth in SEQ ID NO: 10. In certain embodiments, the Vβ comprises CDR1β and CDR2β comprising the amino acid sequences set forth in SEQ ID NOs: 8 and 9, respectively. In certain embodiments, the Vβ comprises the amino acid sequence set forth in SEQ ID NO: 4. In certain embodiments, the isolated TCR comprises a β chain comprising an amino acid sequence selected from the group consisting of SEQ ID NOs: 14, 25, and 97-104.

In another aspect, the instant disclosure provides an isolated T cell receptor (TCR) that binds to a peptide consisting of the amino acid sequence set forth in SEQ ID NO: 1 or 2, the TCR comprising an α chain variable region (Vα) comprising an amino acid sequence at least 75%, 80%, 85%, 90%, 95%, 99%, or 100% identical to the amino acid sequence set forth in SEQ ID NO: 18. In certain embodiments, the Vα comprises the amino acid sequence set forth in SEQ ID NO: 18. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 19. In certain embodiments, the Vβ comprises the amino acid sequence set forth in SEQ ID NO: 19.

In another aspect, the instant disclosure provides an isolated T cell receptor (TCR) that binds to a peptide consisting of the amino acid sequence set forth in SEQ ID NO: 1 or 2, the TCR comprising a β chain variable region (Vβ) comprising an amino acid sequence at least 75%, 80%, 85%, 90%, 95%, 99%, or 100% identical to the amino acid sequence set forth in SEQ ID NO: 19. In certain embodiments, the Vβ comprises the amino acid sequence set forth in SEQ ID NO: 19.

In certain embodiments of any aspect of TCR disclosed herein, the TCR comprises an α chain variable region (Vα)

comprising CDR1α, CDR2α, and CDR3α, and a chain variable region (Vβ) comprising CDR1β, CDR2β, and CDR3β, wherein the CDR1α, CDR2α, CDR3α, CDR1β, CDR2β, and CDR3β, comprise the amino acid sequences set forth in SEQ ID NOs: 5, 6, 7, 8, 9, and 10; 5, 6, 39, 8, 9, and 10; 5, 6, 40, 8, 9, and 10; 5, 6, 41, 8, 9, and 10; 5, 6, 42, 8, 9, and 10; 5, 6, 43, 8, 9, and 10; 5, 6, 44, 8, 9, and 10; 5, 6, 45, 8, 9, and 10; 5, 6, 42, 8, 9 and 10; 5, 6, 47, 8, 9 and 10; 5, 6, 48, 8, 9, and 10; 5, 6, 49, 8, 9 and 10; 5, 6, 50, 8, 9, and 10; 5, 6, 51, 8, 9, and 10; 5, 6, 52, 8, 9, and 10; 5, 6, 53, 8, 9, and 10; 5, 6, 54, 8, 9, and 10; 5, 6, 55, 8, 9, and 10; 5, 6, 56, 8, 9, and 10; 5, 6, 57, 8, 9, and 10; 5, 58, 8, 9, and 10; 5, 6, 59, 8, 9, and 10; or 5, 6, 60, 8, 9, and 10, respectively.

In another aspect, the instant disclosure provides an isolated TCR comprising an α chain variable region (Vα) comprising complementarity determining regions CDR1α, CDR2α, and CDR3α, and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 5, 6, 7, 8, 9, and 10; 5, 6, 39, 8, 9, and 10; 5, 6, 40, 8, 9, and 10; 5, 6, 41, 8, 9, and 10; 5, 6, 42, 8, 9, and 10; 5, 6, 43, 8, 9, and 10; 5, 6, 44, 8, 9, and 10; 5, 6, 45, 8, 9, and 10; 5, 6, 46, 8, 9, and 10; 5, 6, 47, 8, 9, and 10; 5, 6, 48, 8, 9, and 10; 5, 6, 49, 8, 9, and 10; 5, 6, 50, 8, 9, and 10; 5, 6, 51, 8, 9, and 10; 5, 6, 52, 8, 9, and 10; 5, 6; 53, 8, 9, and 10; 5, 6, 54, 8; 9, and 10; 5, 6; 55, 8, 9, and 10; 5, 6, 56, 8, 9, and 10; 5, 6, 57, 8, 9, and 10; 5, 6, 58, 8, 9, and 10; 5, 6, 59, 8, 9, and 10; or 5, 6, 60, 8, 9, and 10, respectively. In certain embodiments, the Vα and Vβ comprise the amino acid sequences set forth in SEQ ID NOs: 3 and 4, 66 and 4, 67 and 4; 68 and 4, 69 and 4, 70 and 4, 71 and 4, 72 and 4, 73 and 4, 74 and 4, 75 and 4, 76 and 4, 77 and 4, 78 and 4, 79 and 4, 80 and 4, 81 and 4, 82 and 4, 83 and 4, 84 and 4, 85 and 4, or 86 and 4, respectively.

In certain embodiments, the TCR comprises an α chain comprising an α chain constant region comprising the amino acid sequence set forth in SEQ ID NO: 15, 26, or 92. In certain embodiments, the α chain constant region comprises the amino acid sequence set forth in SEQ ID NO: 26. In certain embodiments, the TCR comprises a β chain comprising a β chain constant region comprising the amino acid sequence set forth in SEQ ID NO: 16 or 17. In certain embodiments, the β chain constant region comprises the amino acid sequence set forth in SEQ ID NO: 16.

In another aspect, the instant disclosure provides an isolated TCR comprising an α chain and a β chain, wherein the α chain comprises an amino acid sequence selected from the group consisting of SEQ NOs: 13, 93-96, 105-118, 120-123, 125-128, and 408-415, and the β chain comprises an amino acid sequence selected from the group consisting of SEQ ID NOs: 14, 25, and 97-104. In certain embodiments, the α chain comprises an amino acid sequence selected from the group consisting of SEQ ID NOs: 13, 105, 110, 115, 120, 125, 408, and 412, and the β chain comprises an amino acid sequence selected from the group consisting of SEQ ID NOs: 14, 25, and 97-104.

In certain embodiments of any aspect of TCR disclosed herein, the α chain and the β chain comprise the amino acid sequences set forth in SEQ ID NOs: 13 and 14; 13 and 25; 13 and 97; 13 and 98; 13 and 99; 13 and 100; 13 and 101; 13 and 102; 13 and 103; 13 and 104; 93 and 14; 93 and 25; 93 and 97; 93 and 98; 93 and 99; 93 and 100; 93 and 101; 93 and 102; 93 and 103; 93 and 104; 94 and 14; 94 and 25; 94 and 97; 94 and 98; 94 and 99; 94 and 100; 94 and 101; 94 and 102; 94 and 103; 94 and 104; 95 and 14; 95 and 25; 95 and 97; 95 and 98; 95 and 99; 95 and 100; 95 and 101; 95 and 102; 95 and 103; 95 and 104; 96 and 14; 96 and 25; 96 and 97; 96 and 98; 96 and 99; 96 and 100; 96 and 101; 96 and 102; 96 and 103; 96 and 104; 105 and 14; 105 and 25; 105 and 97; 105 and 98; 105 and 99; 105 and 100; 105 and 101; 105 and 102; 105 and 103; 105 and 104; 106 and 14; 106 and 25; 106 and 97; 106 and 98; 106 and 99; 106 and 100; 106 and 101; 106 and 102; 106 and 103; 106 and 104; 107 and 14; 107 and 25; 107 and 97; 107 and 98; 107 and 99; 107 and 100; 107 and 101; 107 and 102; 107 and 103; 107 and 104; 108 and 14; 108 and 25; 108 and 97; 108 and 98; 108 and 99; 108 and 100; 108 and 101; 108 and 102; 108 and 103; 108 and 104; 109 and 14; 109 and 25; 109 and 97; 109 and 98; 109 and 99; 109 and 100; 109 and 101; 109 and 102; 109 and 103; 109 and 104; 110 and 14; 110 and 25; 110 and 97; 110 and 98; 110 and 99; 110 and 100; 110 and 101; 110 and 102; 110 and 103; 110 and 104; 111 and 14; 111 and 25; 111 and 97; 111 and 98; 111 and 99; 111 and 100; 111 and 101; 111 and 102; 111 and 103; 111 and 104; 112 and 14; 112 and 25; 112 and 97; 112 and 98; 112 and 99; 112 and 100; 112 and 101; 112 and 102; 112 and 103; 112 and 104; 113 and 14; 113 and 25; 113 and 97; 113 and 98; 113 and 99; 113 and 100; 113 and 101; 113 and 102; 113 and 103; 113 and 104; 114 and 14; 114 and 25; 114 and 97; 114 and 98; 114 and 99; 114 and 100; 114 and 101; 114 and 102; 114 and 103; 114 and 104; 115 and 14; 115 and 25; 115 and 97; 115 and 98; 115 and 99; 115 and 100; 115 and 101; 115 and 102; 115 and 103; 115 and 104; 116 and 14; 116 and 25; 116 and 97; 116 and 98; 116 and 99; 116 and 100; 116 and 101; 116 and 102; 116 and 103; 116 and 104; 117 and 14; 117 and 25; 117 and 97; 117 and 98; 117 and 99; 117 and 100; 117 and 101; 117 and 102; 117 and 103; 117 and 104; 118 and 14; 11.8 and 25; 118 and 97; 118 and 98; 118 and 99; 118 and 100; 118 and 101; 118 and 102; 118 and 103; 118 and 104; 120 and 14; 120 and 25; 120 and 97; 120 and 98; 120 and 99; 120 and 100; 120 and 101; 120 and 102; 120 and 103; 120 and 104; 121 and 14; 121 and 25; 121 and 97; 121 and 98; 121 and 99; 121 and 100; 121 and 101; 121 and 102; 121 and 103; 121 and 104; 122 and 14; 122 and 25; 122 and 97; 122 and 98; 122 and 99; 122 and 100; 122 and 101; 122 and 102, 122 and 103; 122 and 104; 123 and 14; 123 and 25; 123 and 97; 123 and 98; 123 and 99; 123 and 100; 123 and 101; 123 and 102; 123 and 103; 123 and 104; 125 and 14; 125 and 25; 125 and 97; 125 and 98; 125 and 99; 125 and 100; 125 and 101; 125 and 102; 125 and 103; 125 and 104; 126 and 14; 126 and 25; 126 and 97; 126 and 98; 126 and 99; 126 and 100; 126 and 101; 126 and 102; 126 and 103; 126 and 104; 127 and 14; 127 and 25; 127 and 97; 127 and 98; 127 and 99; 127 and 100; 127 and 101; 127 and 102; 127 and 103; 127 and 104; 128 and 14; 128 and 25; 128 and 97; 128 and 98; 128 and 99; 128 and 100; 128 and 101; 128 and 102; 128 and 103; 128 and 104; 408 and 14; 408 and 25; 408 and 97; 408 and 98; 408 and 99; 408 and 100; 408 and 101; 408 and 102; 408 and 103; 408 and 104; 409 and 14; 409 and 25; 409 and 97; 409 and 98; 409 and 99; 409 and 100; 409 and 101; 409 and 102; 409 and 103; 409 and 104; 410 and 14; 410 and 25; 410 and 97; 410 and 98; 410 and 99; 410 and 100; 410 and 101; 410 and 102; 410 and 103; 410 and 104; 411 and 14; 411 and 25; 411 and 97; 411 and 98; 411 and 99; 411 and 100; 411 and 101; 411 and 102; 411 and 103; 411 and 104; 412 and 14; 412 and 25; 412 and 97; 412 and 98; 412 and 99; 412 and 100; 412 and 101; 412 and 102; 412 and 103; 412 and 104; 413 and 14; 413 and 25; 413 and 97; 413 and 98; 413 and 99; 413 and 100; 413 and 101; 413 and 102; 413 and 103; 413 and 104; 414 and 14; 414 and 25; 414 and 97; 414 and 98; 414 and 99; 414 and 100; 414 and 101; 414 and 102; 414 and 103; 414 and 104; 415 and 14; 415 and 25; 415 and 97; 415 and 98; 415 and 99; 415 and 100; 415 and 101;

415 and 102; 415 and 103; or 415 and 104, respectively. In certain embodiments, the α chain and the β chain comprise the amino acid sequences set forth in SEQ ID NOs: 13 and 14; 13 and 25; 105 and 14; 105 and 25; 110 and 14; 110 and 25; 115 and 14; 115 and 25; 120 and 14; 120 and 25; 125 and 14; 125 and 25; 408 and 14; 408 and 25; 412 and 14; or 412 and 25, respectively. In certain embodiments, the α chain and the β chain comprise the amino acid sequences set forth in SEQ ID NOs: 13 and 14; 105 and 14; 110 and 14; 115 and 14; 120 and 14; 125 and 14; 408 and 14; or 412 and 14, respectively. In certain embodiments, the TCR binds to a peptide consisting of the amino acid sequence set forth in SEQ ID NO: 1 or 2.

In another aspect, the instant disclosure provides a polypeptide comprising an α chain variable region (Vα) and a β chain variable region (Vβ) of a T cell receptor (TCR) that binds to a peptide consisting of the amino acid sequence set forth in SEQ ID NO: 1 or 2, wherein the Vα comprises complementarity determining region CDR3α, wherein the CDR3α comprises the amino acid sequence set forth in SEQ ID NO: 61, 62, 63, 64, or 65. In certain embodiments, the CDR3α comprises the amino acid sequence set forth in SEQ ID NO: 64 or 65. In certain embodiments, the CDR3α comprises an amino acid sequence selected from the group consisting of SEQ ID NOs: 7 and 39-60. In certain embodiments, the CDR3α comprises an amino acid sequence selected from the group consisting of SEQ ID NOs: 7, 39, 40, 43, 45, 47, 49, and 54.

In certain embodiments, the Vα comprises CDR1α and CDR2α, comprising the amino acid sequences set forth in SEQ ID NOs: 5 and 6, respectively. In certain embodiments, the Vα comprises CDR1α, CDR2α, and CDR3α, comprising the amino acid sequences set forth in SEQ ID NOs: 5, 6, and 7; 5, 6, and 39; 5, 6, and 40; 5, 6, and 41; 5, 6, and 42; 5, 6, and 43; 5, 6, and 44; 5, 6, and 45; 5, 6, and 46; 5, 6, and 47; 5, 6, and 48; 5, 6, and 49; 5, 6, and 50; 5, 6, and 51; 5, 6, and 52; 5, 6, and 53; 5, 6, and 54; 5, 6, and 55; 5, 6, and 56; 5, 6, and 57; 5, 6, and 58; 5, 6, and 59; or 5, 6, and 60, respectively. In certain embodiments, the Vα comprises an amino acid sequence selected from the group consisting of SEQ ID NOs: 87-91. In certain embodiments, the Vα comprises an amino acid sequence selected from the group consisting of SEQ ID NOs: 3 and 66-86. In certain embodiments, the Vα comprises an amino acid sequence selected from the group consisting of SEQ ID NOs: 3, 66, 69, 71, 73, 75, and 80. In certain embodiments, the polypeptide comprises an α chain comprising an amino acid sequence selected from the group consisting of SEQ ID NOs: 13, 93-96, 105-118, 120-123, 125-128, and 408-415. In certain embodiments, the polypeptide comprises an α chain comprising an amino acid sequence selected from the group consisting of SEQ ID NOs: 13, 105, 110, 115, 120, 125, 408, and 412.

In certain embodiments, the Vβ comprises CDR3β, wherein the CDR3β comprises the amino acid sequence set forth in SEQ ID NO: 10. In certain embodiments, the Vβ comprises CDR1β and CDR2β comprising the amino acid sequences set forth in SEQ NOs: 8 and 9, respectively. In certain embodiments, the Vβ comprises the amino acid sequence set forth in SEQ ID NO: 4. In certain embodiments, the polypeptide comprises a 1 chain comprising an amino acid sequence selected from the group consisting of SEQ ID NOs: 14, 25, and 97-104.

In another aspect, the instant disclosure provides a polypeptide comprising a Vα and a Vβ of a TCR that binds to a peptide consisting of the amino acid sequence set forth in SEQ ID NO: 1 or 2, wherein the Vβ comprises complementarity determining region CDR3β, and wherein the CDR3β comprises the amino acid sequence set forth in SEQ ID NO: 10. In certain embodiments, the Vβ comprises CDR1β and CDR2β, comprising the amino acid sequences set forth in SEQ ID NOs: 8 and 9, respectively. In certain embodiments, the Vβ comprises the amino acid sequence set forth in SEQ ID NO: 4. In certain embodiments, the polypeptide comprises a β chain comprising an amino acid sequence selected from the group consisting of SEQ ID NOs: 14, 25, and 97-104.

In another aspect, the instant disclosure provides a polypeptide comprising a Vα and a Vβ of a TCR that binds to a peptide consisting of the amino acid sequence set forth in SEQ ID NO: 1 or 2, wherein the Vα comprises an amino acid sequence at least 75%, 80%, 85%, 90%, 95%, 99%, or 100% identical to the amino acid sequence set forth in SEQ ID NO: 18. In certain embodiments, the Vα comprises the amino acid sequence set forth in SEQ ID NO: 18. In certain embodiments, the Vβ comprises an amino acid sequence at least 75%, 80%, 85%, 90%, 95%, 99%, or 100% identical to the amino acid sequence set forth in SEQ ID NO: 19. In certain embodiments, the Vβ comprises the amino acid sequence set forth in SEQ ID NO: 19.

In another aspect, the instant disclosure provides a polypeptide comprising a Vα and a Vβ of a TCR that binds to a peptide consisting of the amino acid sequence set forth in SEQ ID NO: 1 or 2, wherein the Vβ comprises an amino acid sequence at least 75%, 80%, 85%, 90%, 95%, 99%, or 100% identical to the amino acid sequence set forth in SEQ ID NO: 19. In certain embodiments, the Vβ comprises the amino acid sequence set forth in SEQ ID NO: 19.

In certain embodiments of any aspect of polypeptide disclosed herein, the Vα comprises CDR1α, CDR2α, and CDR3α, and the Vβ comprises CDR1β, CDR2β, and CDR3β, wherein the CDR1α, CDR2α, CDR3α, CDR1β, CDR2β, and CDR3β comprise the amino acid sequences set thrum in SEQ ID NOs: 5, 6, 7, 8, 9, and 10; 5, 6, 39, 8, 9, and 10; 5, 6; 40, 8, 9, and 10; 5, 6, 41, 8, 9, and 10; 5, 6; 42, 8, 9, and 10; 5, 6, 43, 8, 9, and 10; 5, 6; 44, 8, 9 and 10; 5, 6, 45, 8, 9, and 10; 5, 6, 46, 8, 9, and 10; 5, 6, 47, 8, 9, and 10; 5, 6, 48, 8, 9, and 10; 5, 6, 49, 8, 9, and 10; 5, 6, 50, 8, 9, and 10; 5, 6, 51, 8, 9, and 10; 5, 6, 52, 8, 9, and 10; 5, 6, 53, 8, 9, and 10; 5, 6, 54, 8; 9, and 10; 5, 6; 55, 8, 9, and 10; 5, 6, 56, 8, 9, and 10; 5, 6, 57, 8, 9, and 10; 5, 6, 58, 8, 9, and 10; 5, 6, 59, 8, 9, and 10; or 5, 6, 60, 8, 9, and 10, respectively.

In another aspect, the instant disclosure provides a polypeptide comprising a Vα and a Vβ of a TCR, wherein the Vα comprises complementarity determining regions CDR1α, CDR2α, and CDR3α, and the Vβ comprises CDR1β, CDR2β, and CDR3β, wherein the CDR1α, CDR2α, CDR3α, CDR1β, CDR2β, and CDR3β comprise the amino acid sequences set forth in SEQ ID NOs: 5, 6, 7, 8, 9, and 10; 5, 6, 39, 8, 9, and 10; 5, 6, 40, 8, 9, and 10; 5, 6, 41, 8, 9, and 10; 5, 6, 42, 8, 9, and 10; 5, 6, 43, 8, 9, and 10; 5, 6, 44, 8, 9, and 10; 5, 6, 45, 8, 9, and 10; 5, 6, 46, 8, 9, and 10; 5, 6, 47, 8, 9, and 10; 5, 6, 48, 8, 9, and 10; 5, 6, 49, 8, 9, and 10; 5, 6, 50, 8, 9, and 10; 5, 6, 51, 8, 9 and 10; 5, 6, 52, 8, 9; and 10; 5, 6, 53, 8, 9, and 10; 5, 6, 54, 8, 9, and 10; 5, 6, 55, 8, 9, and 10; 5, 6, 56, 8, 9, and 10; 5, 6, 57, 8, 9, and 10; 5, 6, 58, 8, 9, and 10; 5, 6, 59, 8, 9, and 10; or 5, 6, 60, 8, 9, and 10, respectively. In certain embodiments, the Vα and Vβ comprise the amino acid sequences set forth in SEQ ID NOs: 3 and 4, 66 and 4, 67 and 4, 68 and 4, 69 and 4, 70 and 4, 71 and 4, 72 and 4, 73 and 4, 74 and 4, 75 and 4, 76 and 4, 77 and 4, 78 and 4, 79 and 4, 80 and 4, 81 and 4, 82 and 4, 83 and 4, 84 and 4, 85 and 4, or 86 and 4, respectively.

In certain embodiments, an α chain comprising an α chain constant region comprising the amino acid sequence set forth in SEQ ID NO: 15, 26, or 92. In certain embodiments, the α chain constant region comprises the amino acid sequence set forth in SEQ ID NO: 26. In certain embodiments, the polypeptide comprises a β chain comprising a β chain constant region comprising the amino acid sequence set forth in SEQ ID NO: 16 or 17. In certain embodiments, the β chain constant region comprises the amino acid sequence set forth in SEQ ID NO: 16.

In certain embodiments of the foregoing aspects, the α chain comprises an amino acid sequence selected from the group consisting of SEQ ID NOs: 13, 93-96, 105-118, 120-123, 125-128, and 408-415, and the β chain comprises an amino acid sequence selected from the group consisting of SEQ ID NOs: 14, 25, and 97-104. In certain embodiments, the ac chain comprises an amino acid sequence selected from the group consisting of SEQ ID NOs: 13, 105, 110, 115, 120, 125, 408, and 412, and the β chain comprises an amino acid sequence selected from the group consisting of SEQ ID NOs: 14, 25, and 97-104. In certain embodiments, the α chain comprises an amino acid sequence selected from the group consisting of SEQ ID NOs: 13, 105, 110, 115, 120, 125, 408, and 412, and the β chain comprises an amino acid sequence selected from the group consisting of SEQ ID NOs: 14, 97, 99, 101, and 103.

In another aspect, the instant disclosure provides a polypeptide comprising an α chain and an β chain of a TCR, wherein the α chain comprises an amino acid sequence selected from the group consisting of SEQ ID NOs: 13, 93-96, 105-118, 120-123, 125-128, and 408-415, and the β chain comprises an amino acid sequence selected from the group consisting of SEQ ID NOs: 14, 25, and 97-104. In certain embodiments, the α chain comprises an amino acid sequence selected from the group consisting of SEQ ID NOs: 13, 105, 110, 115, 120, 125, 408, and 412, and the β chain comprises an amino acid sequence selected from the group consisting of SEQ ID NOs: 14, 25, and 97-104. In certain embodiments, the α chain comprises an amino acid sequence selected from the group consisting of SEQ ID NOs; 13, 105, 110, 115, 120, 125, 408, and 412, and the β chain comprises an amino acid sequence selected from the group consisting of SEQ ID NOs: 14, 97, 99, 101, and 103.

In certain embodiments of any aspect of polypeptide disclosed herein, wherein the α chain and the β chain comprise the amino acid sequences set forth in SEQ NOs: 13 and 14; 13 and 25; 13 and 97; 13 and 98; 13 and 99; 13 and 100; 13 and 101; 13 and 102; 13 and 103; 13 and 104; 93 and 14; 93 and 25; 93 and 97; 93 and 98; 93 and 99; 93 and 100; 93 and 101; 93 and 102; 93 and 103; 93 and 104; 94 and 14; 94 and 25; 94 and 97; 94 and 98; 94 and 99; 94 and 100; 94 and 101; 94 and 102; 94 and 103; 94 and 104; 95 and 14; 95 and 25; 95 and 97; 95 and 98; 95 and 99; 95 and 100; 95 and 101; 95 and 102; 95 and 103; 95 and 104; 96 and 14; 96 and 25; 96 and 97; 96 and 98; 96 and 99; 96 and 100; 96 and 101; 96 and 102; 96 and 103; 96 and 104; 105 and 14; 105 and 25; 105 and 97; 105 and 98; 105 and 99; 105 and 100; 105 and 101; 105 and 102; 105 and 103; 105 and 104; 106 and 14; 106 and 25; 106 and 97; 106 and 98; 106 and 99; 106 and 100; 106 and 101; 106 and 102; 106 and 103; 106 and 104; 107 and 14; 107 and 25; 107 and 97; 107 and 98; 107 and 99; 107 and 100; 107 and 101; 107 and 102; 107 and 103; 107 and 104; 108 and 14; 108 and 25; 108 and 97; 108 and 98; 108 and 99; 108 and 100; 108 and 101; 108 and 102; 108 and 103; 108 and 104; 109 and 14; 109 and 25; 109 and 97; 109 and 98; 109 and 99; 109 and 100; 109 and 101; 109 and 102; 109 and 103; 109 and 104; 110 and 14; 110 and 25; 110 and 97; 110 and 98; 110 and 99; 110 and 100; 110 and 101; 110 and 102; 110 and 103; 110 and 104; 111 and 14; 111 and 25; 111 and 97; 111 and 98; 111 and 99; 111 and 100; 111 and 101; 111 and 102; 111 and 103; 111 and 104; 112 and 14; 112 and 25; 112 and 97; 112 and 98; 112 and 99; 112 and 100; 112 and 101; 112 and 102; 112 and 103; 112 and 104; 113 and 14; 113 and 25; 113 and 97; 113 and 98; 113 and 99; 113 and 100; 113 and 101; 113 and 102; 113 and 103; 113 and 104; 114 and 14; 114 and 5; 114 and 97; 114 and 98; 114 and 99; 114 and 100; 114 and 101; 114 and 102; 114 and 103; 114 and 104; 115 and 14; 115 and 25; 115 and 97; 115 and 98; 115 and 99; 115 and 100; 115 and 101; 115 and 102; 115 and 103; 115 and 104; 116 and 14; 116 and 25; 116 and 97; 116 and 98; 116 and 99; 116 and 100; 116 and 101; 116 and 102; 116 and 103; 116 and 104; 117 and 14; 117 and 25; 117 and 97; 117 and 98; 117 and 99; 117 and 100; 117 and 101; 117 and 102; 117 and 103; 117 and 104; 118 and 14; 118 and 25; 118 and 97; 118 and 98; 118 and 99; 118 and 100; 118 and 101; 118 and 102; 118 and 103; 118 and 104; 120 and 14; 120 and 25; 120 and 97; 120 and 98; 120 and 99; 120 and 100; 120 and 101; 120 and 102; 120 and 103; 120 and 104; 121 and 14; 121 and 25; 121 and 97; 121 and 98; 121 and 99; 121 and 100; 121 and 101; 121 and 102; 121 and 103; 121 and 104; 122 and 14; 122 and 25; 122 and 97; 122 and 98; 122 and 99; 122 and 100; 122 and 101; 122 and 102; 122 and 103; 122 and 104; 123 and 14; 123 and 25; 123 and 97; 123 and 98; 123 and 99; 123 and 100; 123 and 101; 123 and 102; 123 and 103; 123 and 104; 125 and 14; 125 and 25; 125 and 97; 125 and 98; 125 and 99; 125 and 100; 125 and 101; 125 and 102; 125 and 103; 125 and 104; 126 and 14; 126 and 25; 126 and 97; 126 and 98; 126 and 99; 126 and 100; 126 and 101; 126 and 102; 126 and 103; 126 and 104; 127 and 14; 127 and 25; 127 and 97; 127 and 98; 127 and 99; 127 and 100; 127 and 101; 127 and 102; 127 and 103; 127 and 104; 128 and 14; 128 and 25; 128 and 97; 128 and 98; 128 and 99; 128 and 100; 128 and 101; 12.8 and 102; 128 and 103; 128 and 104; 408 and 14; 408 and 25; 408 and 97; 408 and 98; 408 and 99; 408 and 100; 408 and 101; 408 and 102; 408 and 103; 408 and 104; 409 and 14; 409 and 25; 409 and 97; 409 and 98; 409 and 99; 409 and 100; 409 and 101; 409 and 102; 409 and 103; 409 and 104; 410 and 14; 410 and 25; 410 and 97; 410 and 98; 410 and 99; 410 and 100; 410 and 101; 410 and 102; 410 and 103; 410 and 104; 411 and 14; 411 and 25; 411 and 97; 411 and 98; 411 and 99; 411 and 100; 411 and 101; 411 and 102; 411 and 103; 411 and 104; 412 and 14; 412 and 25; 412 and 97; 412 and 98; 412 and 99; 412 and 100; 412 and 101; 412 and 102; 412 and 103; 412 and 104; 413 and 14; 413 and 2.5; 413 and 97; 413 and 98; 413 and 99; 413 and 100; 413 and 101; 413 and 102; 413 and 103; 413 and 104; 414 and 14; 414 and 25; 414 and 97; 414 and 98; 414 and 99; 414 and 100; 414 and 101; 414 and 102; 414 and 103; 414 and 104; 415 and 14; 415 and 25; 415 and 97; 415 and 98; 415 and 99; 415 and 100; 415 and 101; 415 and 102; 415 and 103; or 415 and 104, respectively. In certain embodiments, the α chain and the β chain comprise the amino acid sequences set forth in SEQ NOs: 13 and 14; 13 and 25; 105 and 14; 105 and 25; 110 and 14; 110 and 25; 115 and 14; 115 and 25; 120 and 14; 120 and 25; 125 and 14; 125 and 25; 408 and 14; 408 and 25; 412 and 14; or 412 and 25, respectively. In certain embodiments, the α chain and the β chain comprise the amino acid sequence set forth in SEQ ID NOs: 13 and 14; 105 and 14; 110 and 14; 115 and 14; 120 and 14; 125 and 14; 408 and 14; or 412 and 14, respectively.

In certain embodiments of any polypeptide disclosed herein, the TCR binds to a peptide consisting of the amino acid sequence set forth in SEQ ID NO: 1 or 2.

In certain embodiments of any polypeptide disclosed herein, the polypeptide comprises only one α chain and one β chain. In certain embodiments, the α chain is N-terminal to the β chain. In certain embodiments, the α chain is C-terminal to the β chain. In certain embodiments, the polypeptide further comprises a peptide linker between the α chain and the β chain. In certain embodiments, the linker comprises a proteolytic cleavage site. In certain embodiments, the proteolytic cleavage site comprises a Furin cleavage site and/or a 2A cleavage site. In certain embodiments, the Furin cleavage site comprises an amino acid sequence selected from the group consisting of SEQ ID NOs: 29-31 and 131-133. In certain embodiments, the Furin cleavage site comprises the amino acid sequence set forth in SEQ ID NO: 132. In certain embodiments, the 2A cleavage site comprises an amino acid sequence selected from the group consisting of SEQ ID NOs: 32-38, 130, and 134-140. In certain embodiments, the 2A cleavage site comprises a porcine teschovirus-1 2A (P2A) cleavage site. In certain embodiments, the P2A cleavage site comprises the amino acid sequence set forth in SEQ ID NO: 33 or 134. In certain embodiments, the proteolytic cleavage site comprises a Furin cleavage site and a 2A cleavage site. In certain embodiments, the Furin cleavage site comprises the amino acid sequence set forth in SEQ ID NO: 132, and the 2A cleavage site comprises the amino acid sequence set forth in SEQ ID NO: 33 or 134.

In certain embodiments of the foregoing aspects, the polypeptide further comprises Gly-Ser at the C-terminus of the polypeptide. Without intention to limit the scope of the instant disclosure, such Gly-Ser extension to the isolated TCR or the polypeptide may result from a cloning scar from a previous cloning step.

In certain embodiments, the polypeptide comprises an amino acid sequence selected from the group consisting of SEQ ID NOs: 28, 141-143, 158-161, 176-179, 194, 196, 212, 214, 230, 232, 248, 250, 416, and 417. In certain embodiments, the polypeptide comprises an amino acid sequence selected from the group consisting of:
  (i) SEQ ID NOs: 28, 158, 176, 194, 212, 230, 248, and 416;
  (ii) SEQ ID NOs: 141, 159, and 177; or
  (iii) SEQ ID NOs: 142, 160, 178, 196, 214, 232, 250, and 417.

In certain embodiments, the polypeptide comprises an amino acid sequence selected from the group consisting of SEQ ID NOs: 146-149, 152-155, 164-167, 170-173, 182-185, 188-191, 200, 202, 206, 208, 218, 220, 224, 226, 236, 238, 242, 244, 254, 256, 260, 262, and 418-421. In certain embodiments, the polypeptide comprises an amino acid sequence selected from the group consisting of:
  (i) SEQ ID NOs: 146, 164, 182, 200, 218, 236, 254, and 418;
  (ii) SEQ ID NOs: 147, 165, and 183;
  (iii) SEQ ID NOs: 148, 166, 184, 202, 220, 238, 256, and 419;
  (iv) SEQ ID NOs: 149, 167, and 185;
  (v) SEQ ID NOs: 152, 170, 188, 206, 224, 242, 260, and 420;
  (vi) SEQ ID NOs: 153, 171, and 189;
  (vii) SEQ ID NOs: 154, 172, 190, 208, 226, 244, 262, and 421; or
  (viii) SEQ ID NOs: 155, 173, and 191.

In certain embodiments of any aspect of TCR or polypeptide disclosed herein, the TCR is a human TCR (e.g., a full-length human TCR). In certain embodiments, the TCR is a full-length TCR, a soluble TCR, or a single-chain TCR.

In certain embodiments, the peptide is presented in the context of HLA-A*0201. In certain embodiments, when the TCR is expressed on the surface of a T cell, the T cell is activated when co-cultured with a second cell displaying the peptide presented in the context of HLA-A*0201. In certain embodiments, the T cell exhibits (a) increased CD69 surface expression, (b) increased CD25 surface expression, (c) increased CD107a surface expression, (d) increased IFNγ secretion, or (e) increased nuclear factor of activated T-cells (NFAT) activation when co-cultured with the second cell displaying the peptide presented in the context of HLA-A*0201. In certain embodiments, the T cell induces apoptosis or death of the second cell displaying the peptide presented in the context of HLA-A*0201.

In certain embodiments, the TCR or the polypeptide is conjugated to an effector moiety. In certain embodiments, the effector moiety is a cytotoxic agent, cytostatic agent, toxin, radionuclide, detectable label, or binding moiety. In certain embodiments, the binding moiety is an antibody. In certain embodiments, the binding moiety is an antibody Fc region.

In another aspect, the instant disclosure provides an isolated polynucleotide comprising:
  (a) a first nucleic acid sequence encoding a Vα and/or a second nucleic acid sequence encoding a Vβ; or
  (b) a first nucleic acid sequence encoding an α chain and/or a second nucleic acid sequence encoding a β chain of a TCR disclosed herein. In certain embodiments, the first and second nucleic acid sequences are in frame.

In certain embodiments, the first nucleic acid sequence is 5' to the second nucleic acid sequence. In certain embodiments, the first nucleic acid sequence is 3' to the second nucleic acid sequence. In certain embodiments, the polynucleotide further comprises a third nucleic acid sequence encoding a peptide linker between the first and second nucleic acid sequences, wherein the first, second, and third nucleic acid sequences are in frame. In certain embodiments, the linker comprises a proteolytic cleavage site. In certain embodiments, the proteolytic cleavage site comprises a Furin cleavage site and/or a 2A cleavage site. In certain embodiments, the Furin cleavage site comprises an amino acid sequence selected from the group consisting of SEQ ID NOs: 29-31 and 131-133. In certain embodiments, the Furin cleavage site comprises the amino acid sequence set forth in SEQ ID NO: 132. In certain embodiments, the 2A cleavage site comprises an amino acid sequence selected from the group consisting of SEQ ID NOs: 32-38, 130, and 134-140. In certain embodiments, the 2A cleavage site comprises a porcine teschovirus-1 2A (P2A) cleavage site. In certain embodiments, the P2A cleavage site comprises the amino acid sequence set forth in SEQ ID NO: 33 or 134. In certain embodiments, the proteolytic cleavage site comprises a Furin cleavage site and a 2A cleavage site. In certain embodiments, the Furin cleavage site comprises the amino acid sequence set forth in SEQ ID NO: 132, and the 2A cleavage site comprises the amino acid sequence set forth in SEQ ID NO: 33 or 134. In certain embodiments, the polynucleotide further comprises a nucleic acid sequence encoding Gly-Ser 3' to the first and second nucleic acid sequence.

In certain embodiments, the polynucleotide encodes an amino acid sequence selected from the group consisting of SEQ ID NOs: 28, 141-143, 158-161, 176-179, 194, 196, 212, 214, 230, 232, 248, 250, 416, and 417. In certain embodiments, the polynucleotide encodes an amino acid sequence selected from the group consisting of:

(i) SEQ ID NOs: 28, 158, 176, 194, 212, 230, 248, and 416;
(ii) SEQ ID NOs: 141, 159, and 177; or
(iii) SEQ ID NOs: 142, 160, 178, 196, 214, 232, 250, and 417.

In certain embodiments, the polynucleotide encodes an amino acid sequence selected from the group consisting of SEQ ID NOs: 146-149, 152-155, 164-167, 170-173, 182-185, 188-191, 200, 202, 206, 208, 218, 220, 224, 226, 236, 238, 242, 244, 254, 256, 260, 262, and 418-421. In certain embodiments, the polynucleotide encodes an amino acid sequence selected from the group consisting of:
(i) SEQ ID NOs: 146, 164, 182, 200, 218, 236, 254, and 418;
(ii) SEQ ID NOs: 147, 165, and 183;
(iii) SEQ ID NOs: 148, 166, 184, 202, 220, 238, 256, and 419;
(iv) SEQ ID NOs: 149, 167, and 185;
(v) SEQ ID NOs: 152, 170, 188, 206, 224, 242, 260, and 420;
(vi) SEQ ID NOs: 153, 171, and 189;
(vii) SEQ ID NOs: 154, 172, 190, 208, 226, 244, 262, and 421; or
(viii) SEQ ID NOs: 155, 173, and 191.

In another aspect, the instant disclosure provides an isolated polynucleotide encoding the polypeptide of a polypeptide disclosed herein.

In another aspect, the instant disclosure provides an isolated vector comprising a polynucleotide disclosed herein. In certain embodiments, the vector is a viral vector selected from the group consisting of a lentiviral vector, a retroviral vector, an adenoviral vector, an adeno-associated viral vector, and a baculoviral vector.

In another aspect, the instant disclosure provides an engineered cell comprising the polynucleotide or the vector disclosed herein. In another aspect, the instant disclosure provides an engineered cell presenting a TCR disclosed herein on the cell surface. In certain embodiments, the cell expresses the TCR. In certain embodiments, the cell is a human lymphocyte. In certain embodiments, the cell is selected from the group consisting of a T cell, a CD8$^+$ T cell, a CD4$^+$ T cell, a natural killer T (NKT) cell, an invariant natural killer T (iNKT) cell, a mucosal-associated invariant T (MAiT) cell, and a natural killer (NK) cell.

In another aspect, the instant disclosure provides a pharmaceutical composition comprising an isolated TCR, polypeptide, polynucleotide, vector, or engineered cell disclosed herein, and a pharmaceutically acceptable carrier.

In another aspect, the instant disclosure provides a method of producing a TCR that binds to a peptide consisting of the amino acid sequence set forth in SEQ ID NO: 1 or 2, the method comprising culturing the engineered cell disclosed herein so that the polynucleotide is expressed and the TCR is produced. In another aspect, the instant disclosure provides an isolated TCR produced by such method.

In another aspect, the instant disclosure provides a method of producing an engineered cell expressing a TCR that binds to a peptide consisting of the amino acid sequence set forth in SEQ ID NO: 1 or 2, the method comprising contacting a cell with a polynucleotide disclosed herein (e.g., a polynucleotide encoding an α chain variable region and/or a β chain variable region disclosed herein, a polynucleotide encoding an α chain and/or a β chain of a TCR disclosed herein, or a vector comprising such polynucleotide(s)) under conditions that allow introduction of the vector into the cell. In certain embodiments, the cell is a human lymphocyte. In certain embodiments, the cell is selected from the group consisting of a T cell, a CD8$^+$ T cell, a CD4$^+$ T cell, a natural killer T (NKT) cell, an invariant natural killer T (iNKT) cell, a mucosal-associated invariant T (MAiT) cell, and a natural killer (NK) cell.

In another aspect, the instant disclosure provides a method of inducing an immune response to a cell displaying a peptide consisting of the amino acid sequence set forth in SEQ ID NO: 1 or 2 in a subject, the method comprising administering to the subject an effective amount of an isolated TCR, polypeptide, polynucleotide, vector, engineered cell, or pharmaceutical composition disclosed herein.

In another aspect, the instant disclosure provides a method of treating cancer in a subject, the method comprising administering to the subject an effective amount of an isolated TCR, polypeptide, polynucleotide, vector, engineered cell, or pharmaceutical composition disclosed herein.

In certain embodiments of the methods of inducing an immune response or the methods of treating cancer disclosed herein, the TCR, polynucleotide, vector, engineered cell, or pharmaceutical composition is administered intravenously. In certain embodiments, the method further comprises administering an additional therapeutic agent to the subject. In certain embodiments, the additional therapeutic agent is a chemotherapeutic, a radiotherapeutic, or a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an antagonist anti-TIGIT antibody, an agonist anti-CD137 antibody, an agonist anti-GITR antibody, and an agonist anti-OX40 antibody. In certain embodiments, the additional therapeutic agent is an anti-PD-1 antibody, optionally wherein the anti-PD-1 antibody is pembrolizumab or nivolumab. In certain embodiments, the additional therapeutic agent is an inhibitor of indoleamine-2,3-dioxygenase (IDO). In certain embodiments, the inhibitor is selected from the group consisting of epacadostat, F001287, indoximod, and NLG919. In certain embodiments, the inhibitor is epacadostat. In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 and is complexed with a tumor-associated antigenic peptide, wherein the HSPPC is derived from a tumor obtained from a subject.

In certain embodiments, the cancer is acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid leukemia, myeloma (e.g., chronic myeloid cancer), colon cancer, esophageal cancer, cervical cancer, gastrointestinal carcinoid tumor. Hodgkin's lymphoma, hypopharynx cancer, kidney cancer, larynx cancer, liver cancer, lung cancer (e.g., non-small cell lung cancer), malignant mesothelioma, melanoma, multiple myeloma, nasopharynx cancer, non-Hodgkin's lymphoma, ovarian cancer, pancreatic cancer, peritoneum, omentum, and mesentery cancer, pharynx cancer, prostate cancer, rectal cancer, renal cancer (e.g., renal cell carcinoma (RCC)), gastric cancer, small intestine cancer, soft tissue cancer, stomach cancer, carcinoma, sarcoma (e.g., synovial sarcoma, rhabdomyosarcoma), testicular cancer, thyroid cancer, head and neck cancer, ureter cancer, and urinary bladder cancer. In certain embodiments, the cancer is melanoma, breast cancer, lung cancer, prostate cancer, thyroid cancer, ovarian cancer, or synovial sarcoma. In one embodiment, the cancer is synovial sarcoma or liposarcoma (e.g., myxoid/round cell liposarcoma). In one embodiment, the cancer is multiple myeloma. In one embodiment, the cancer is renal cell carcinoma. In one embodiment, the cancer is cervical cancer, in one embodiment, the cancer is ovarian cancer.

4. BRIEF DESCRIPTION OF THE DRAWINGS

FIG. 1 is a set of flow cytometry plots showing the staining of AK-D10R3 cells or AK-D10R3 cells expressing TCR18168c using an APC-labeled anti-mouse TCR β chain antibody and PE-labeled HLA-A*0201 tetramers loaded with a wild type NY-ESO-1 peptide SLLMWITQC (SEQ ID NO: 1), an MHC anchor-optimized NY-ESO-1 peptide SLLMWITQV (SEQ ID NO: 2), or a negative control peptide. The percentage of tetramer+ TCR+ cells is indicated in each plot.

Figure 2:
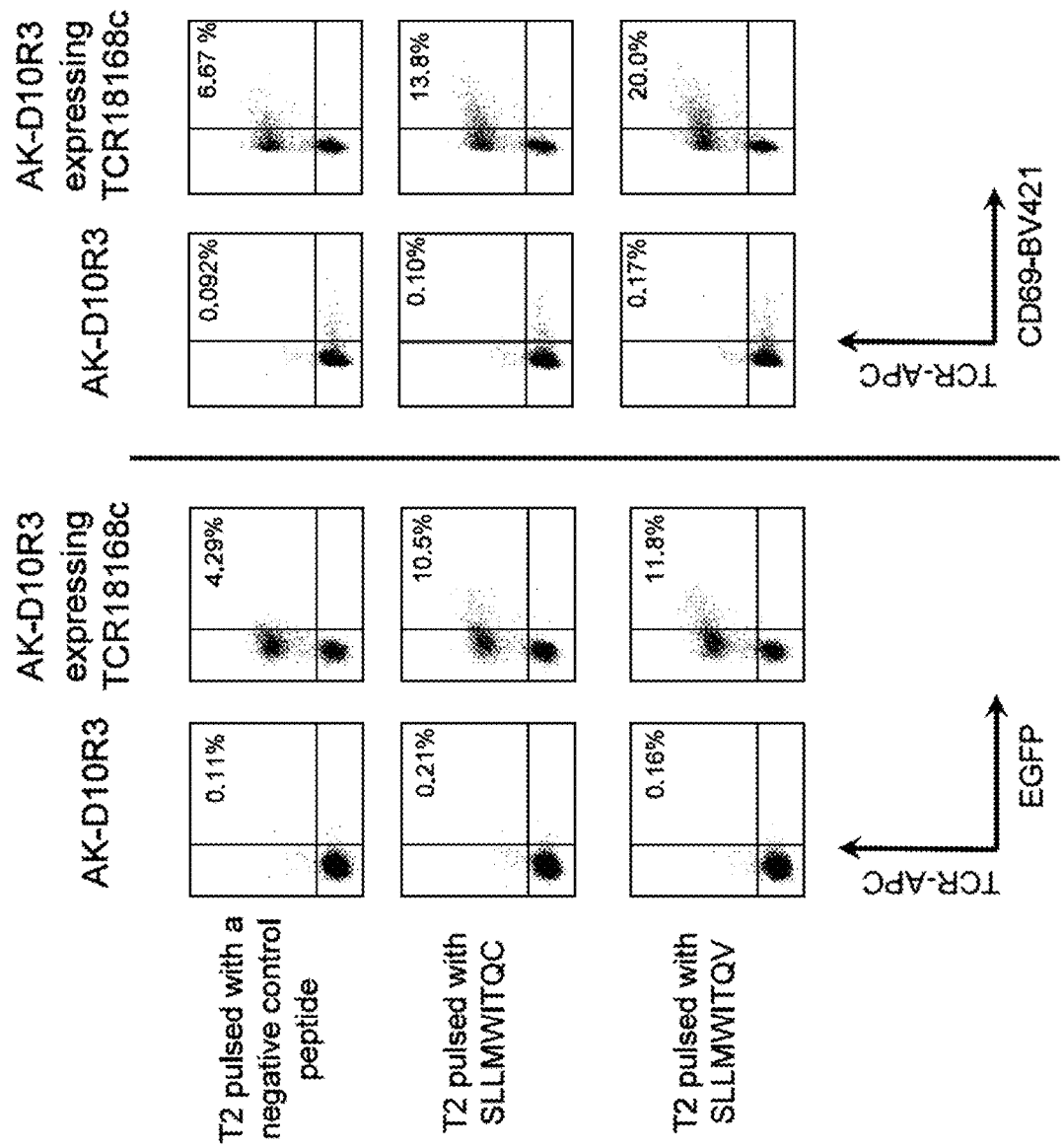

FIG. 2 is a set of flow cytometry plots showing results from an assay testing activation of AK-D10R3 cells expressing TCR18168c after co-culture with T2 cells pulsed with 50 μg/ml of a wild type NY-ESO-1 peptide SLLMWITQC (SEQ ID NO: 1), an anchor-optimized NY-ESO-1 peptide SLLMWITQV (SEQ ID NO: 2), or a negative control peptide. In the flow cytometry plots, y-axis shows surface TCR staining and x-axis shows Enhanced. Green Fluorescent. Protein (EGFP) expression resulting from the activation of an IL-2-(NFAT)$_3$-EGFP reporter construct or CD69 activation marker expression. AK-D10R3 cells without TCR expression were used as a negative control. The percentages of TCR$^+$EGFP+ cells and TCR$^+$CD69+ cells are indicated in the upper right panel of each plot.

Figure 3A:
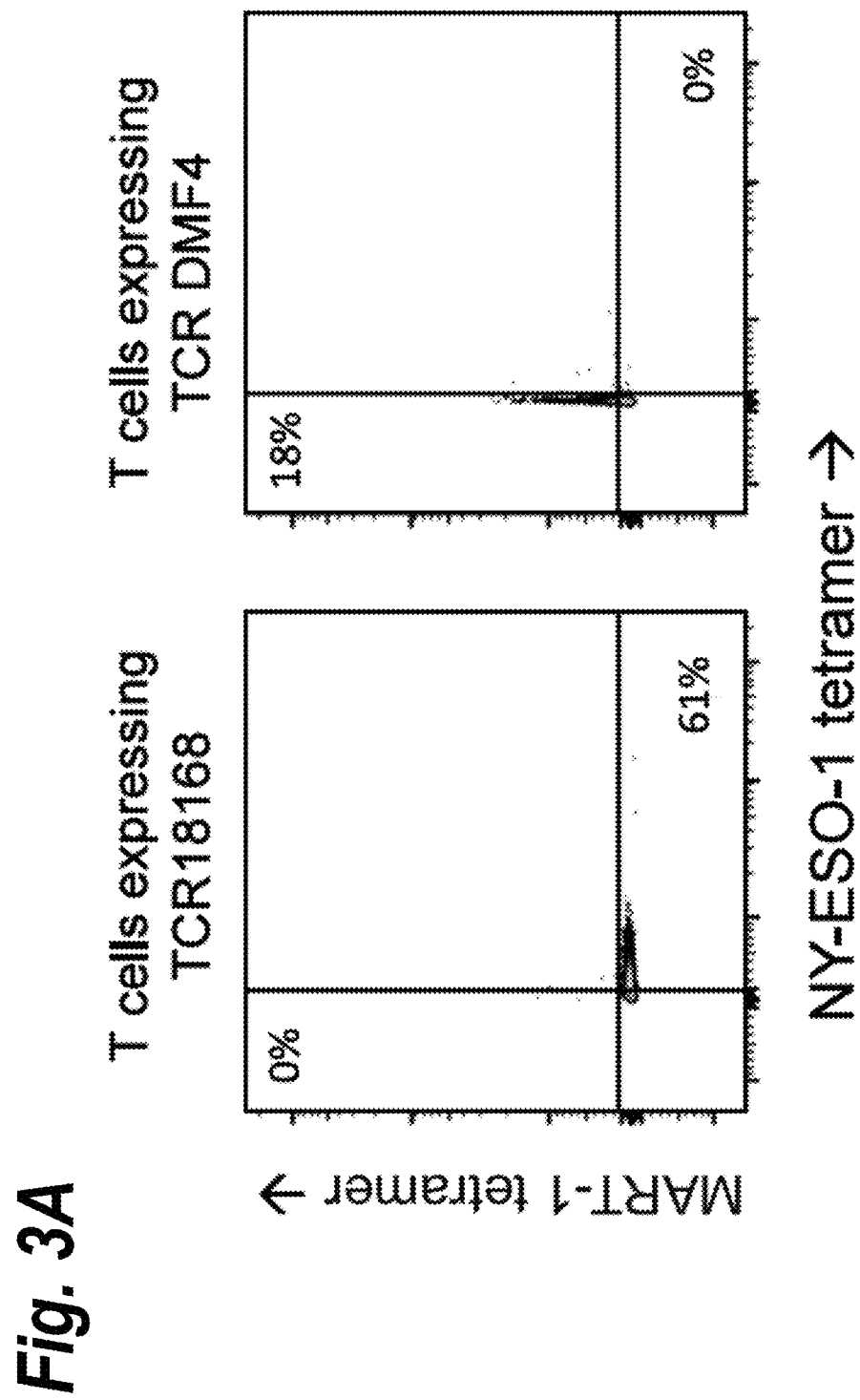
Figure 3C:
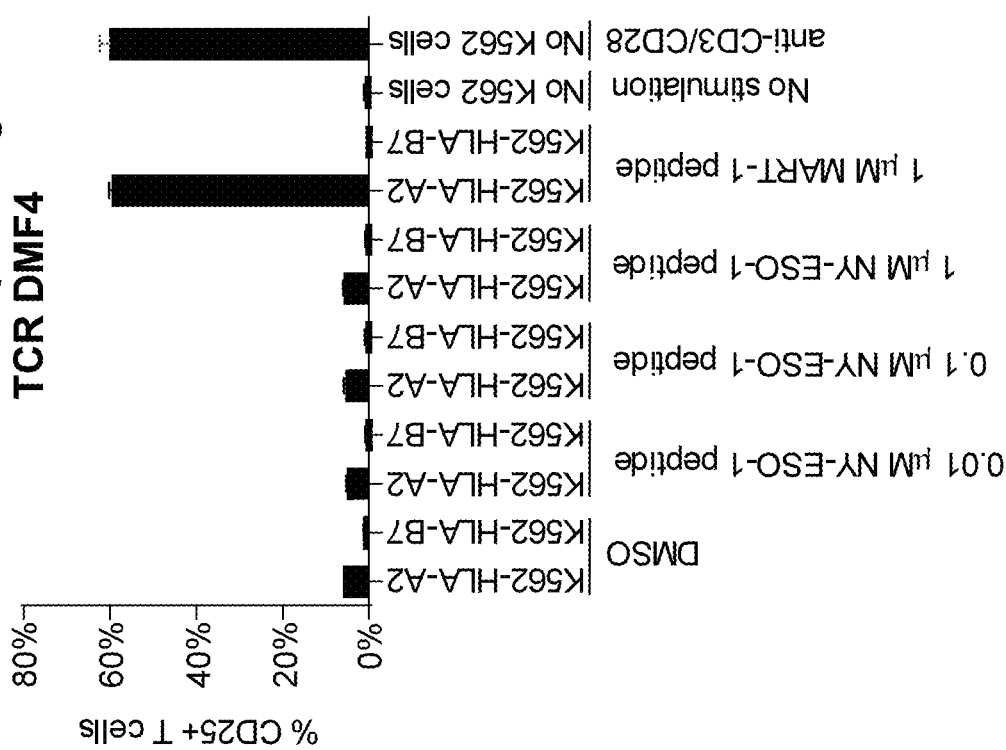
Figure 3B:
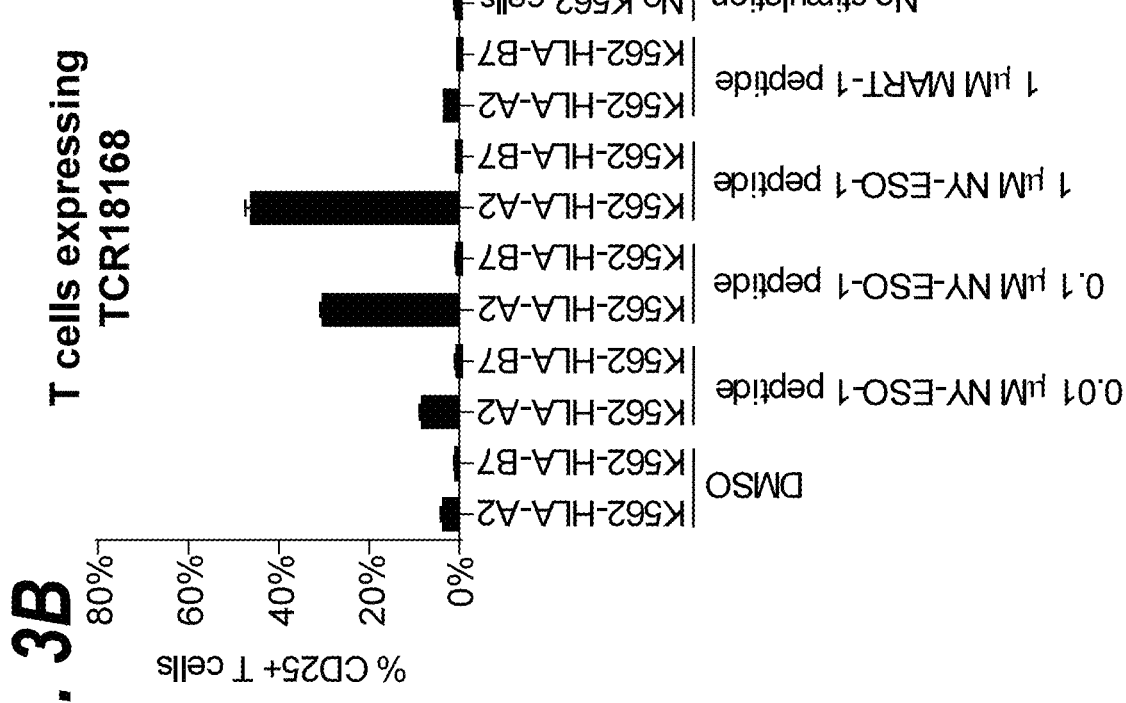
Figure 3E:
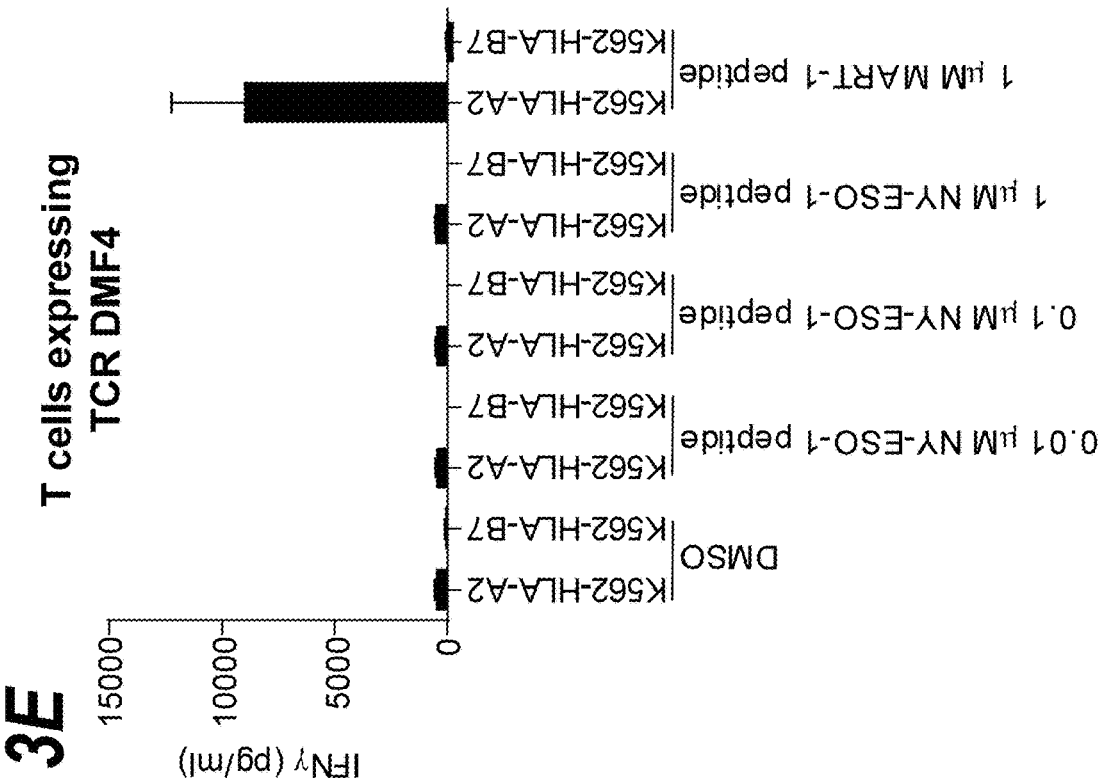
Figure 3D:
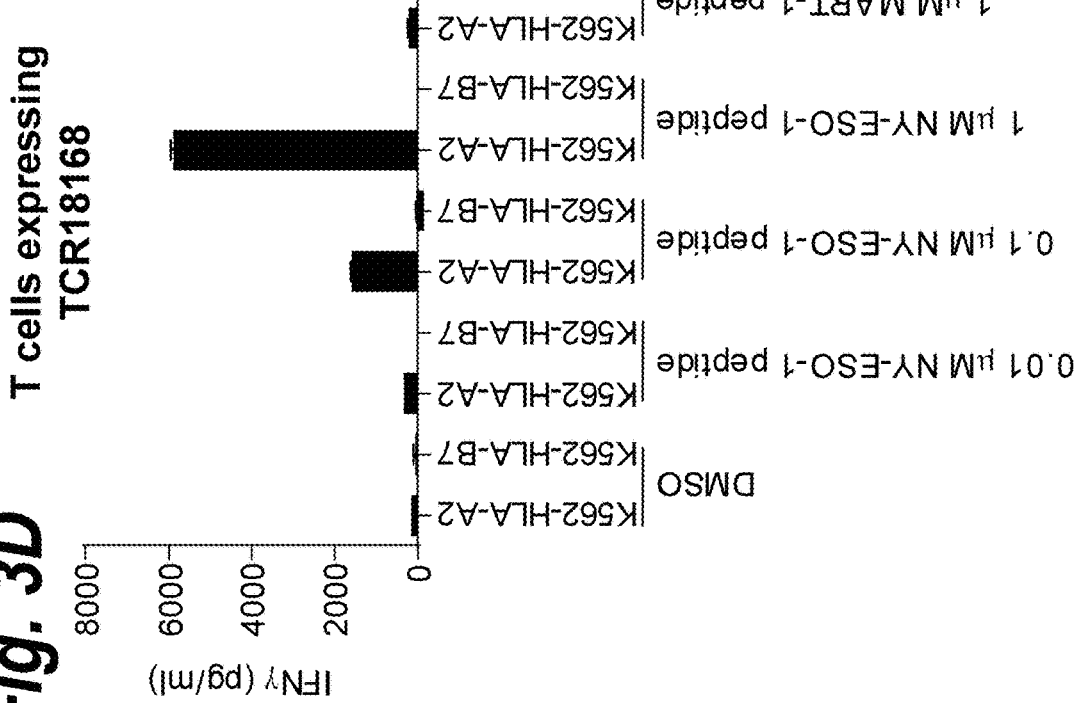

FIGS. 3A, 3B, 3C, 3D, and 3E are graphs showing the results from a study analyzing primary human T cells from a healthy donor that were transfected to express the fully human NY-ESO-1 TCR, TCR18168, or a MART-1 TCR DMF4. Transfected T cells were co-cultured with peptide-pulsed K562 cells expressing either HLA-A2 or HLA-B7 for 16 hours. Effector cell activation (CD25 expression and IFNγ secretion) and target cell killing (caspase-3/7 activity) were then measured. FIG. 3A is a pair of flow cytometry plots showing the staining of TCR18168-expressing or DMF4-expressing T cells using HLA-A*0201 tetramers loaded with an NY-ESO-1 peptide SLLMWITQC (SEQ ID NO: 1) or a MART-1 peptide ELAGIGILTV (SEQ ID NO: 22). The percentages of NY-ESO-1 tetramer positive/MART-1 tetramer negative cells are indicated in the lower right panel of each plot. The percentages of NY-ESO-1 tetramer negative/MART-1 tetramer positive cells are indicated in the upper left panel of each plot. FIGS. 3B and 3C are bar graphs showing the percentages of CD25+ T cells, measured by flow cytometry following co-culture with K562 target cells. As indicated in the figures, the HLA-A2-expressing ("K562-HLA-A2") or HLA-B7-expressing ("K562-HLA-B7") K562 target cells were pulsed with DMSO vehicle, 0.01, 0.1, or 1 μM of the NY-ESO-1 peptide, or 1 μM of the MART-1 peptide. Also shown are the percentages of CD25+ T cells without any stimulation (basal activation levels) or stimulated by anti-CD3/anti-CD28 antibodies (maximum activation levels) in the absence of K562 target cells. FIGS. 3D and 3E are bar graphs showing the concentration of IFNγ, as measured by ELISA, in the media taken from co-cultures at the completion of the assay.

Figure 4A:
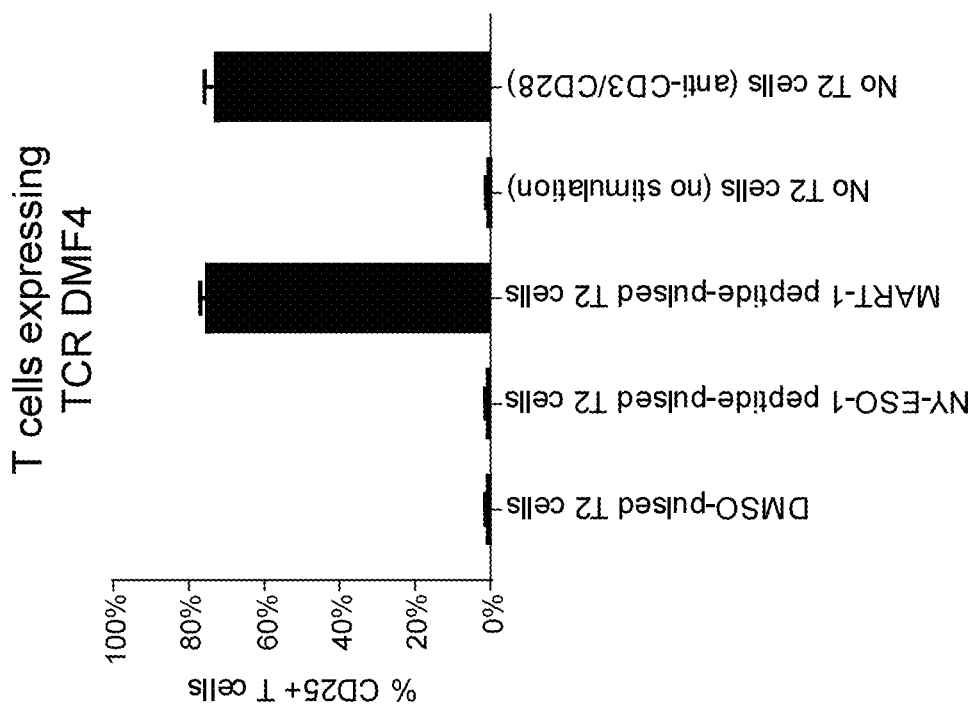
Figure 4B:
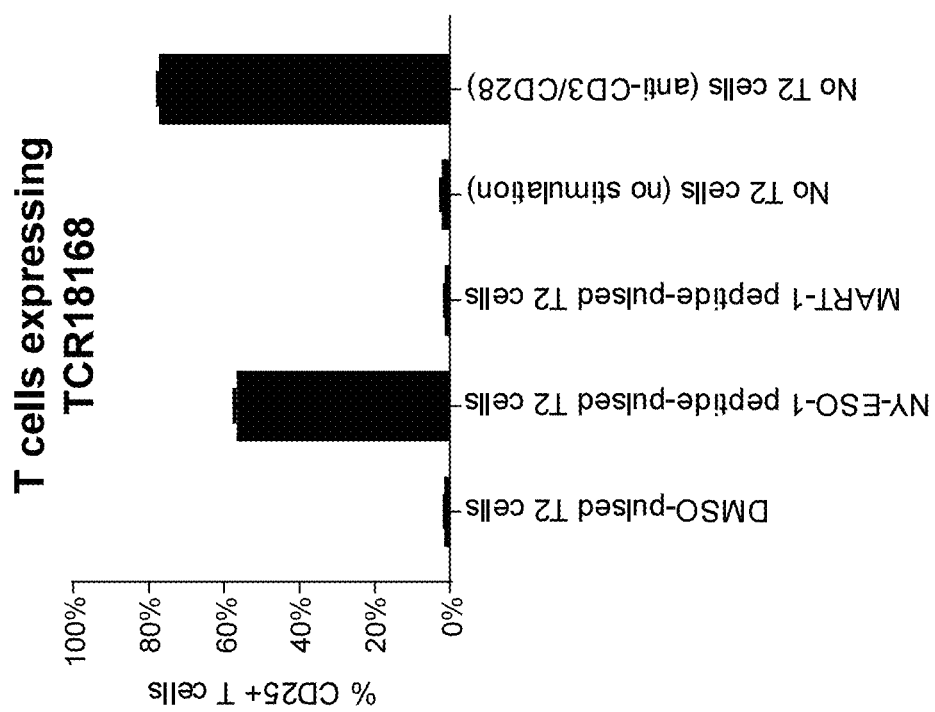
Figure 4C:
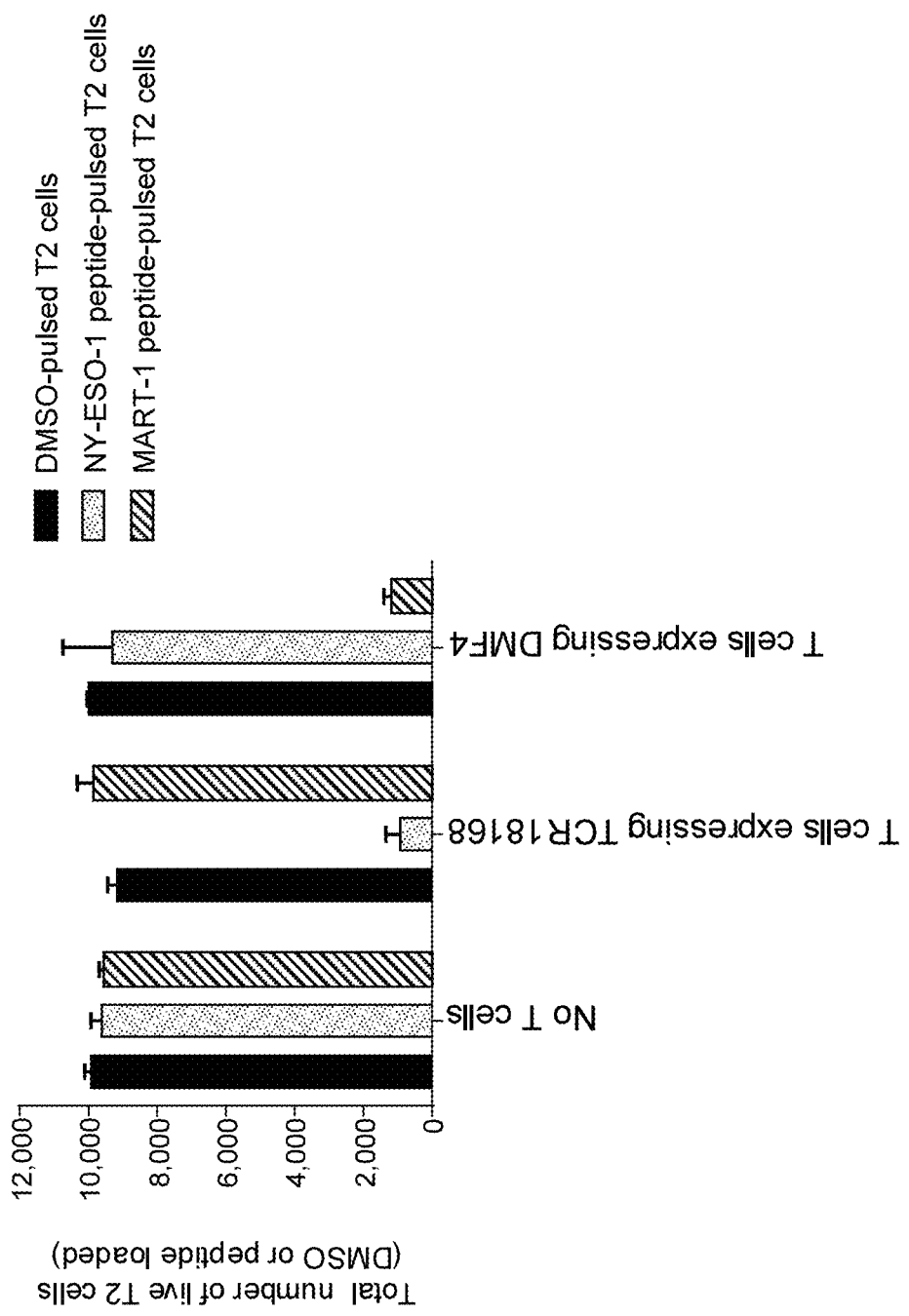

FIGS. 4A, 4B, and 4C are graphs showing the results from a co-culture study similar to the study shown in FIGS. 3A-3E. Primary T cells from a different healthy donor were transfected to express TCR18168 or the MART-1 TCR DMF4. Transfected T cells were co-cultured with Cell-Trace™ violet dye-labeled, peptide-pulsed T2 cells for 16 hours. T cell activation, as measured by surface CD25 expression, and target cell killing, as measured by loss of target cells, were examined. FIGS. 4A and 4B are bar graphs showing the percentages of CD25+ T cells, measured by flow cytometry following co-culture with T2 target cells pulsed with DMSO vehicle, 1 μM of an NY-ESO-1 peptide SLLMWITQC (SEQ ID NO: 1), or 1 μM of a MART-1 peptide ELAGIGILTV (SEQ ID NO: 22). Also shown are the percentages of CD25+ T cells without any stimulation (basal activation levels) or stimulated by anti-CD3/anti-CD28 antibodies (maximum activation levels) in the absence of the T2 target cells. FIG. 4C is a bar graph showing the total number of live T2 cells in the absence of T cells or in the presence of T cells expressing TCR18168 or DMF4. As indicated in the figure, the T2 cells were pulsed with DMSO, the NY-ESO-1 peptide, or the MART-1 peptide before the co-culture study.

Figure 5B:
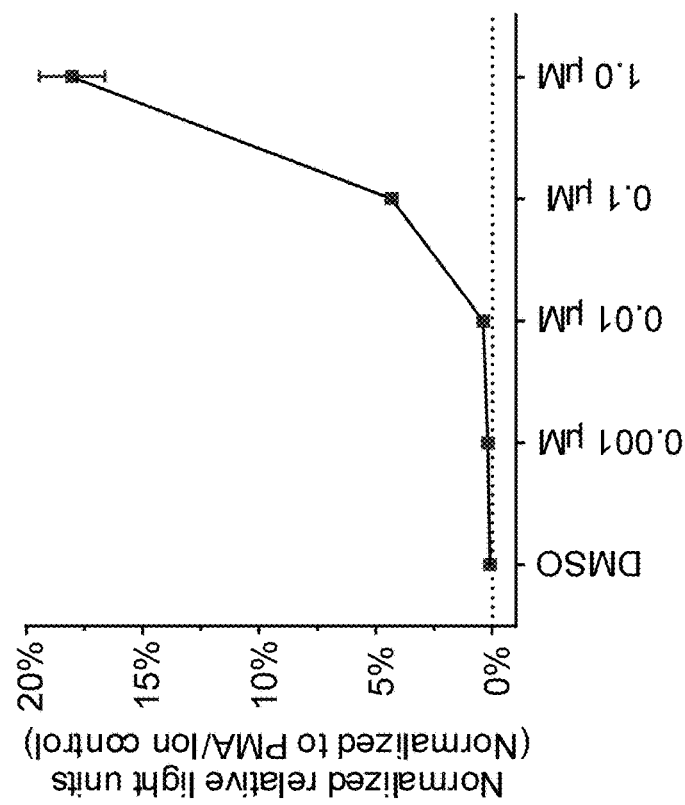
Figure 5A:
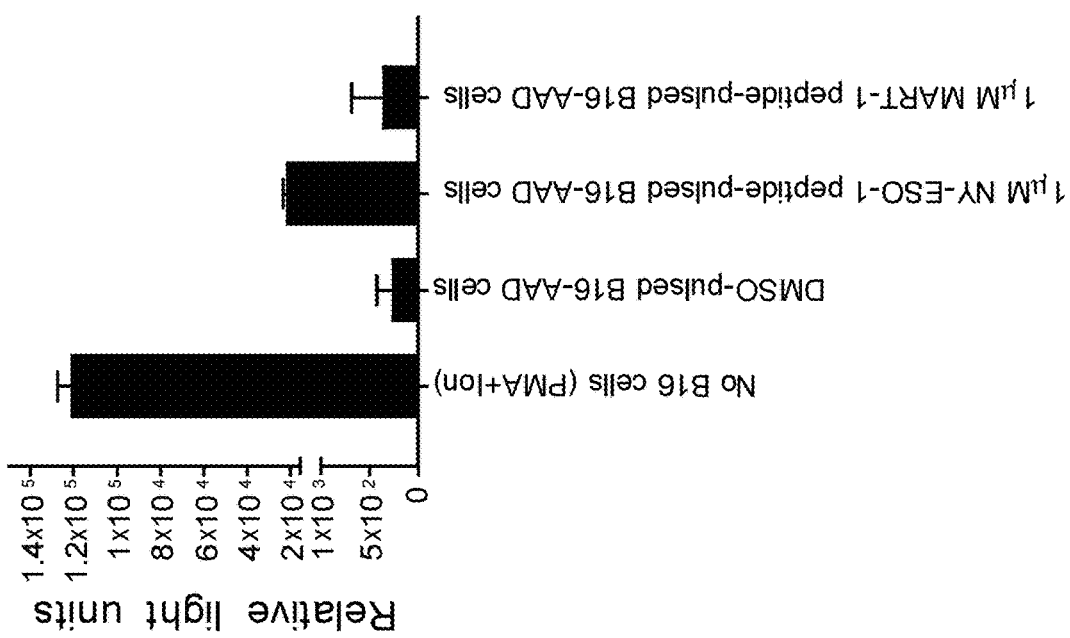

FIGS. 5A and 5β are graphs showing the results from a study in which a TCRβ-negative Jurkat-NEAT-luciferase reporter cell line lentivirally transduced to express TCR18168 was co-cultured with AAD-expressing, peptide-pulsed B16 cells for 16 hours before analysis. AAD is a chimeric molecule comprising the α1 and α2 domains of the HLA-A*0201 molecule, the α3 domain of the mouse H-2D$^b$ molecule, and human β$_2$ microglobulin. FIG. 5A is a bar graph showing relative light units produced by TCR18168-expressing Jurkat reporter cells stimulated with phorbol 12-myristate 13-acetate (PMA) and lonomycin (representing maximum NFAT-luciferase expression) or AAD-expressing B16 cells pulsed with DMSO, a negative control MART-1 peptide, or an NY-ESO-1 peptide (target peptide). FIG. 5B is a line graph showing relative light units produced by TCR18168-expressing Jurkat reporter cells co-cultured with AAD-expressing B16 cells pulsed with varying concentrations of the NY-ESO-1 target peptide, normalized to the mean relative light units produced by the PMA and lonomycin control group. The x-axis shows the concentration of peptide used to pulse AAD-expressing B16 cells.

Figure 6:
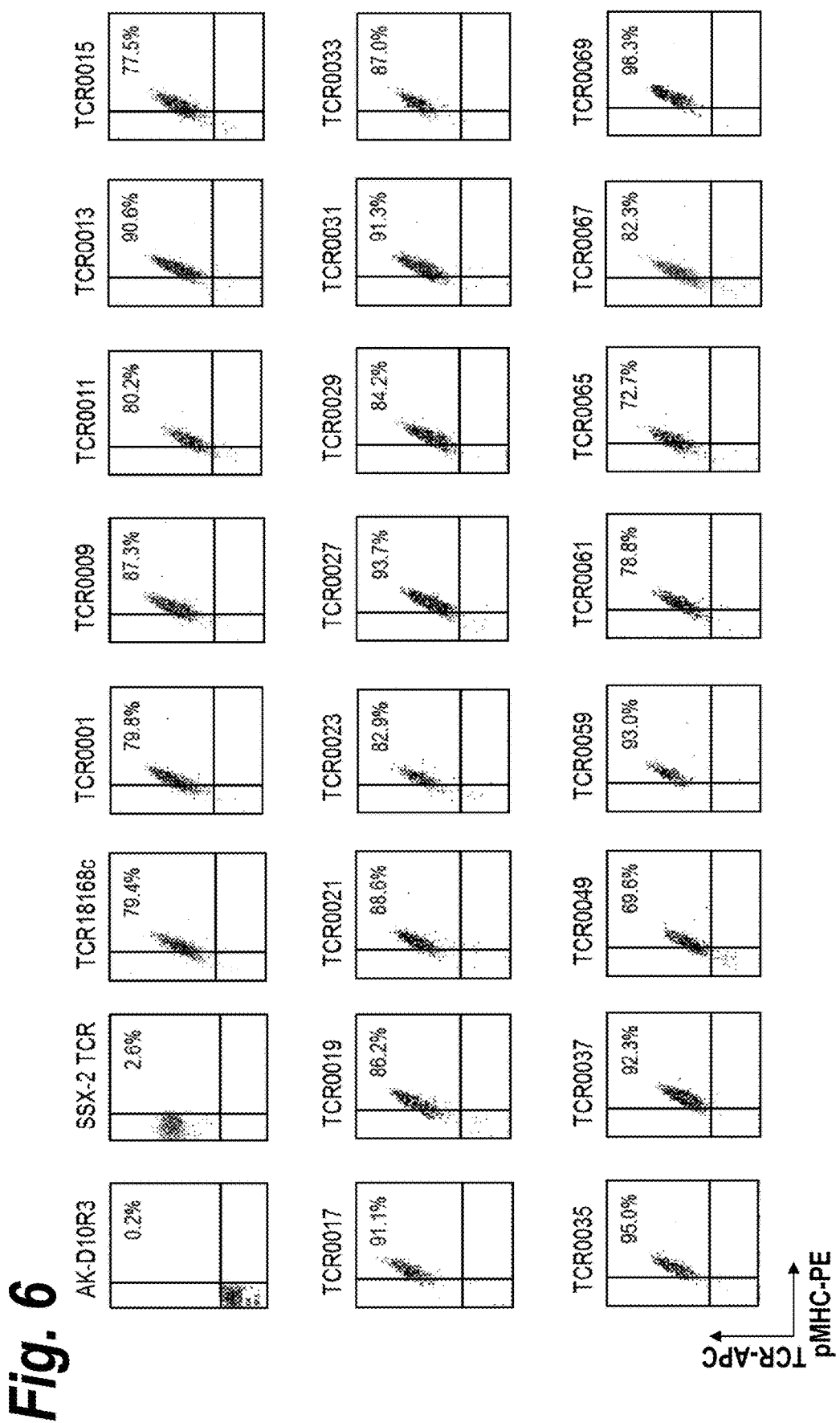
Figure 7:
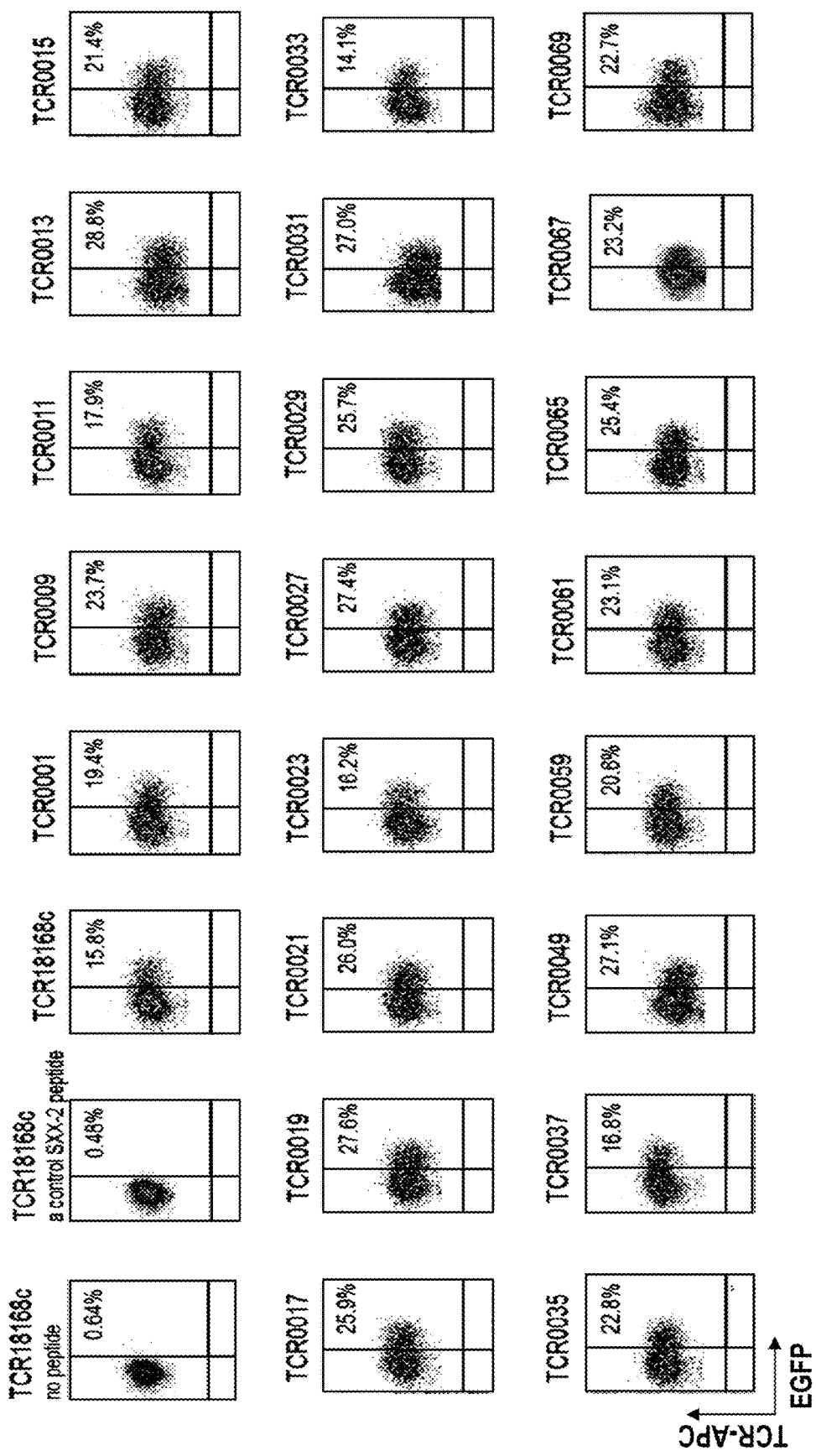

FIG. 6 is a set of flow cytometry plots showing, the staining of AK-D10R3 cells expressing the chimeric TCRs TCR18168c, TCR0001, TCR0009, TCR0011, TCR0013, TCR0015, TCR0017, TCR0019, TCR0021, TCR0023, TCR0027, TCR0029, TCR0031, TCR0033, TCR0035, TCR0037, TCR0049, TCR0059, TCR0061, TCR0065, TCR0067, TCR0069, a reference TCR that binds to SSX-2, or TCR-negative AK-D10R3 cells using an APC-labeled anti-mouse TCR β chain antibody and PE-labeled HLA-A*0201 tetramers loaded with a wild type NY-ESO-1 peptide SLLMWITQC (SEQ ID NO: 1). The percentage of tetramer+ TCR+ cells is indicated in each plot, FIG. 7 is a set of flow cytometry plots showing results from an assay testing activation of AK-D10R3 cells expressing the chimeric TCRs TCR18168c, TCR0001, TCR0009, TCR0011, TCR0013, TCR0015, TCR0017, TCR0019, TCR0021, TCR0023, TCR0027, TCR0029, TCR0031, TCR0033, TCR0035, TCR0037, TCR0049, TCR0059, TCR0061, TCR0065 TCR0067 or TCR0069 after co-culture with T2 cells pulsed with 50 μg/ml of a wild type NY-ESO-1 peptide SLLMWITQC (SEQ ID NO: 1). AK-D10R3 cells expressing TCR18168c co-cultured with T2 cells pulsed with a control SXX-2 peptide or no peptide were used as controls. In the flow cytometry plots, y-axis shows surface TCR staining and x-axis shows EGFP expression resulting from the activation of an IL-2-(NFAT)$_3$-EGFP reporter construct in AK-D10R3 cells. The percentages of TCR+EGFP+ cells are indicated in the upper right panel of each plot.

Figure 8B:
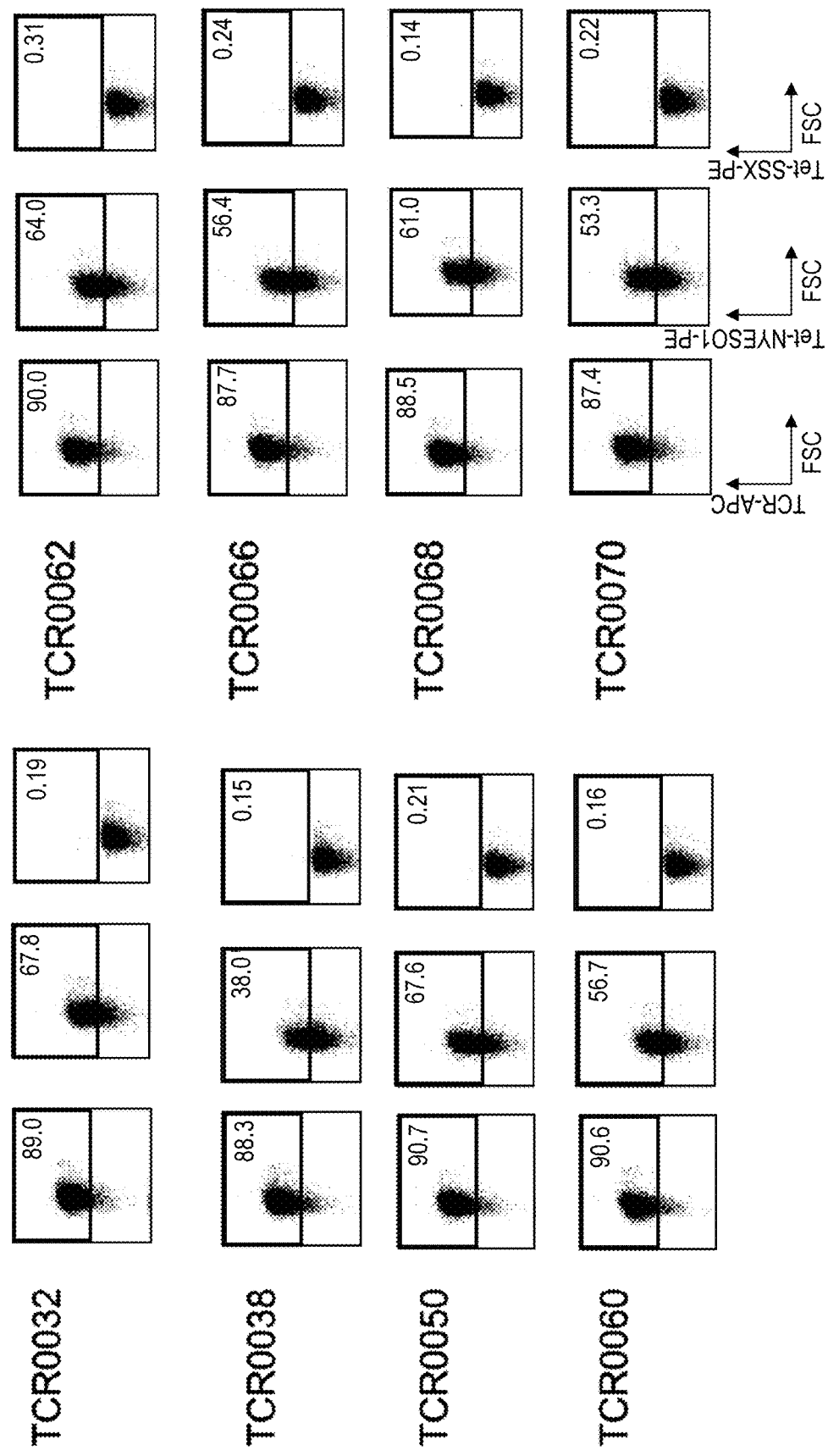

FIGS. 8A and 8B are a set of flow cytometry plots showing the staining of Jurkat cells expressing the fully human TCRs TCR18168, TCR0002, TCR0010, TCR0012, TCR0014, TCR0016, TCR0018, TCR0020, TCR0022, TCR0024, TCR0028, TCR0032, TCR0038, TCR0050, TCR0060, TCR0062, TCR0066, TCR0068, or TCR0070, or TCR-negative Jurkat cells using an APC-labeled anti-human TCR antibody, PE-labeled HLA-A*0201 tetramers loaded with a wild type NY-ESO-1 peptide SLLMWITQC (SEQ ID NO: 1), or PE-labeled HLA-A*0201 tetramers loaded with a control SSX-2 peptide KASEKIFYV (SEQ ID NO: 274). The percentage of TCR+ or tetramer+ cells is indicated in each plot.

Figure 9A:
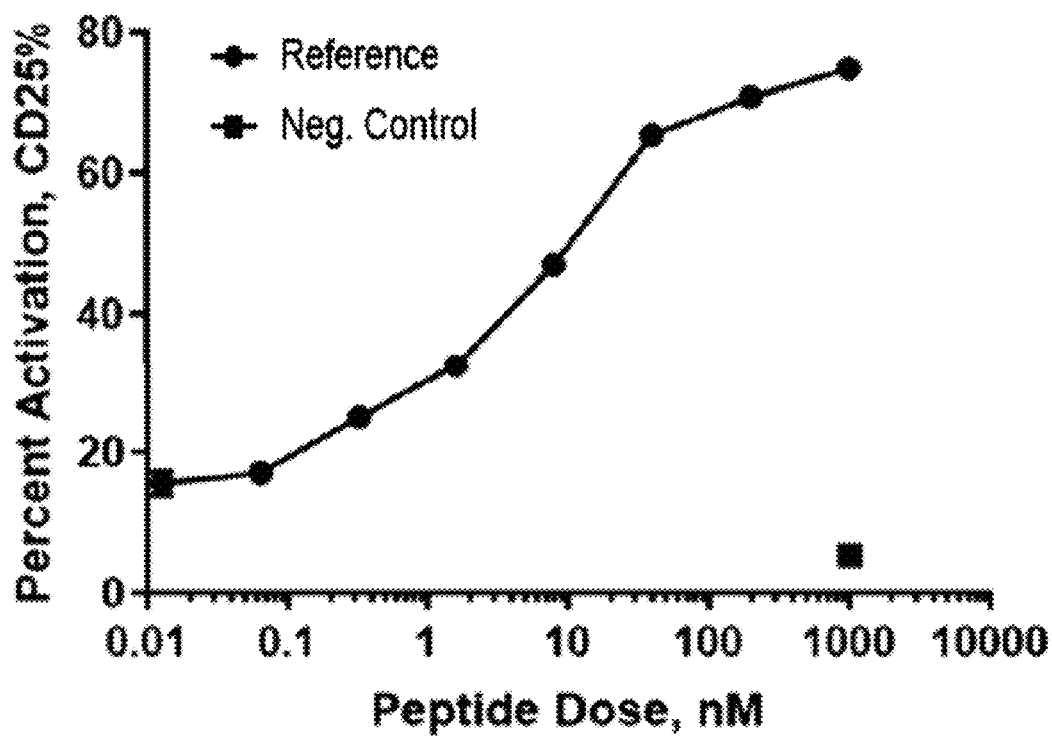
Figure 9B:
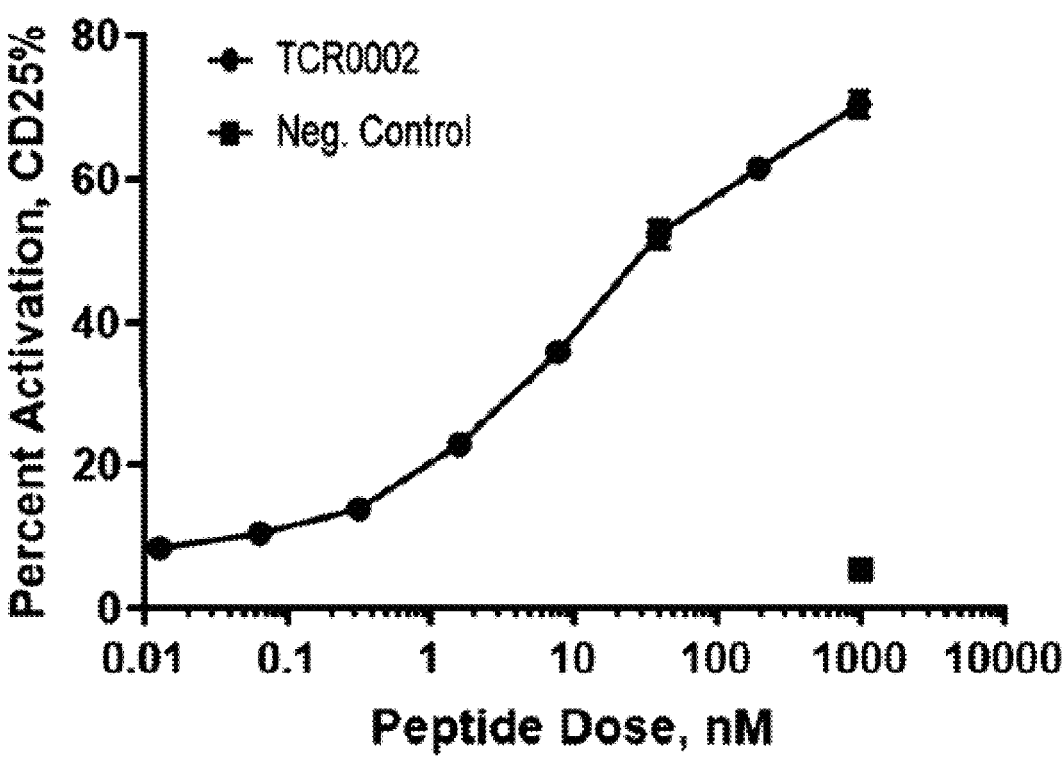
Figure 9C:
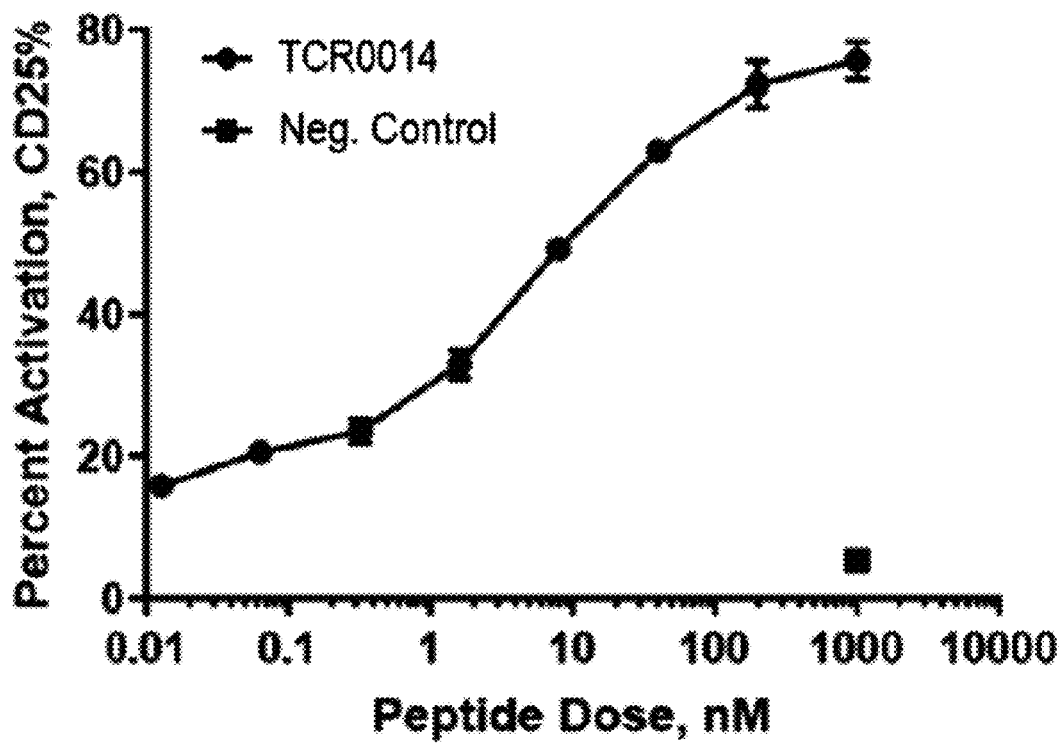
Figure 9D:
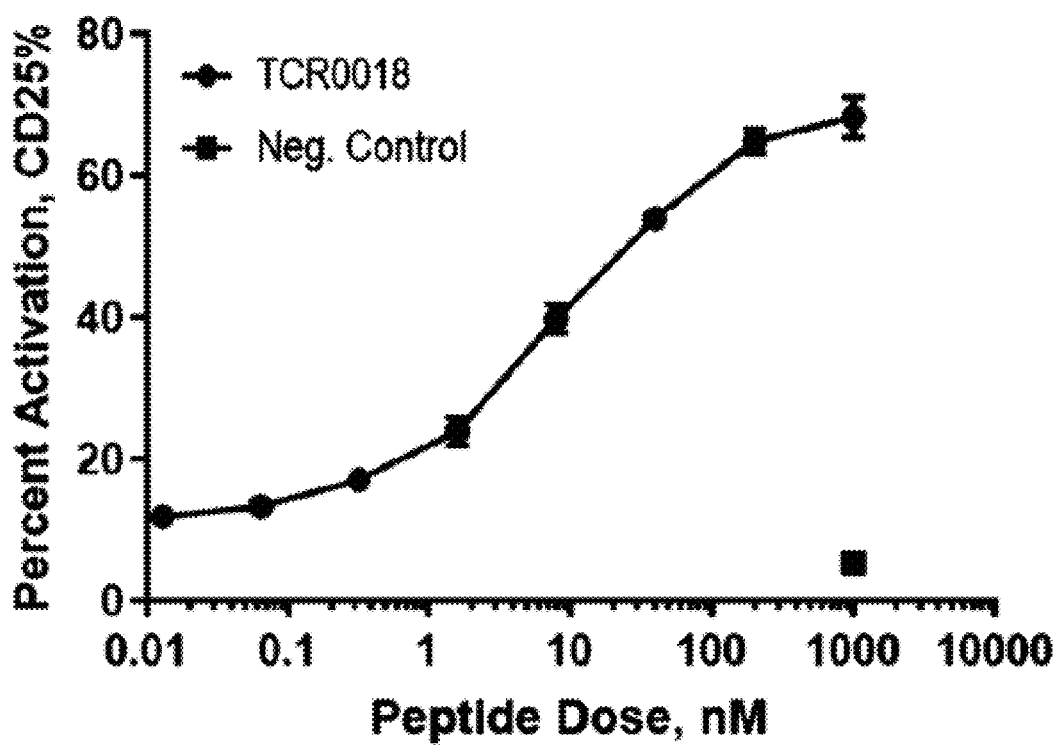
Figure 9E:
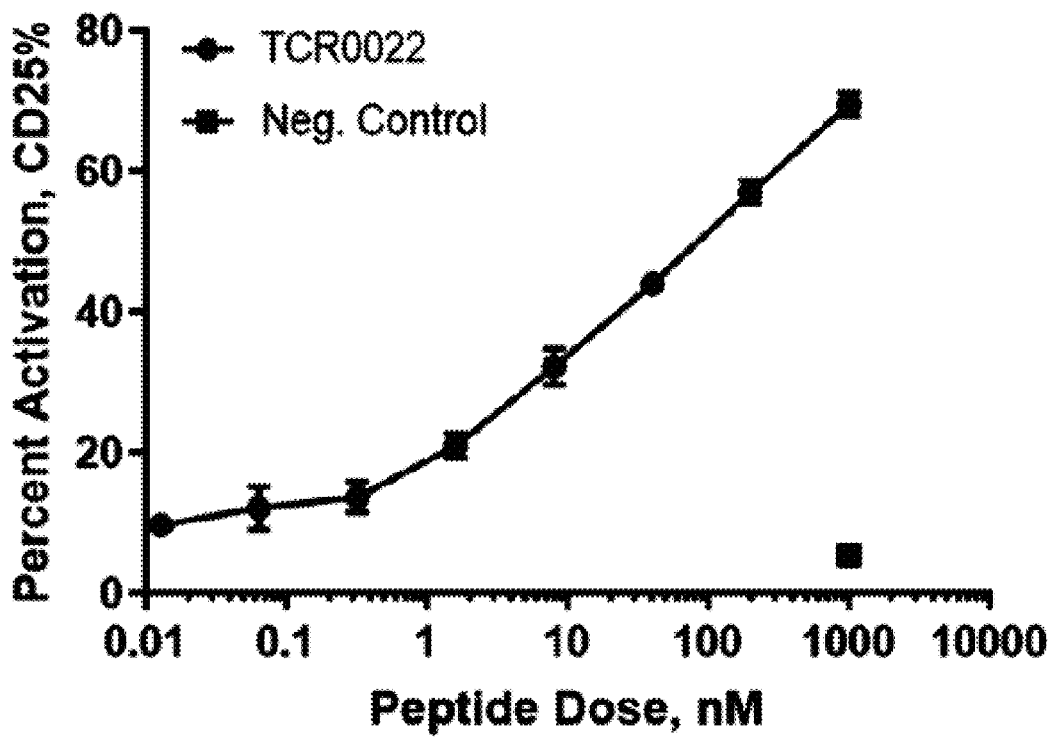
Figure 9F:
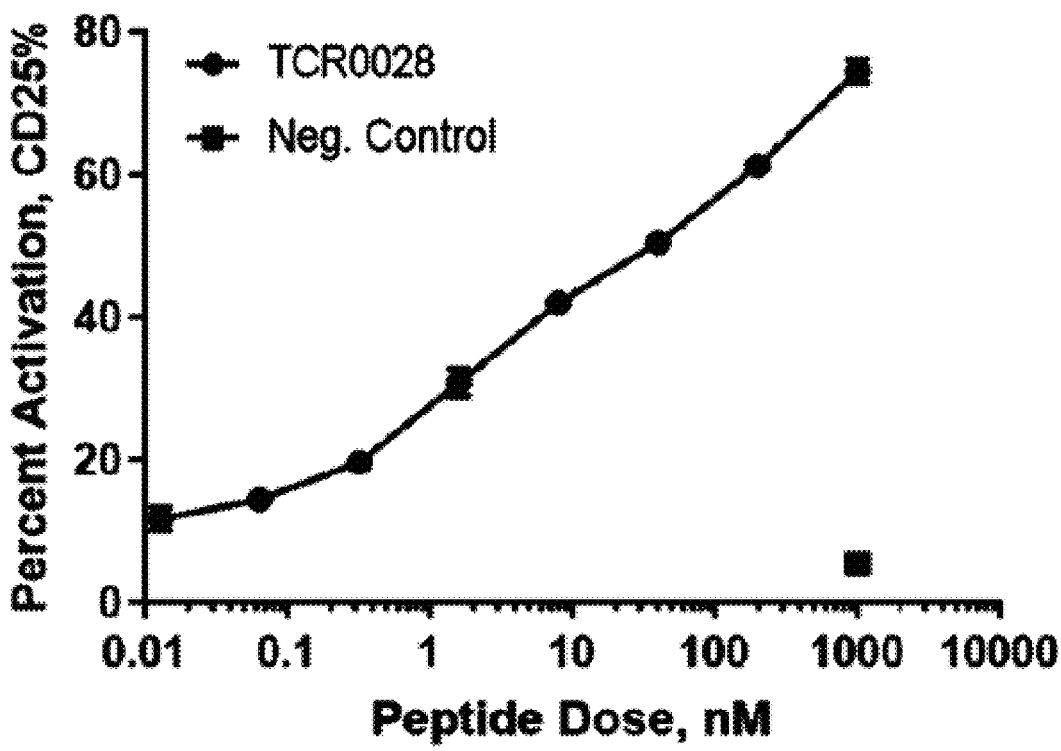
Figure 9G:
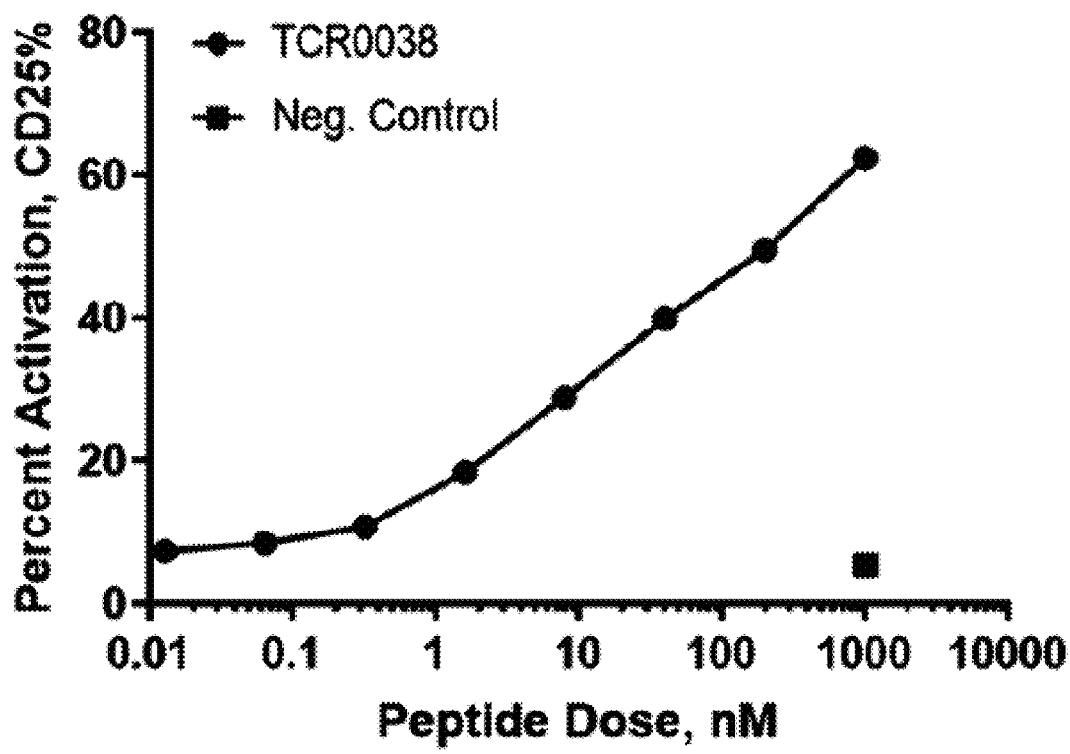
Figure 9H:
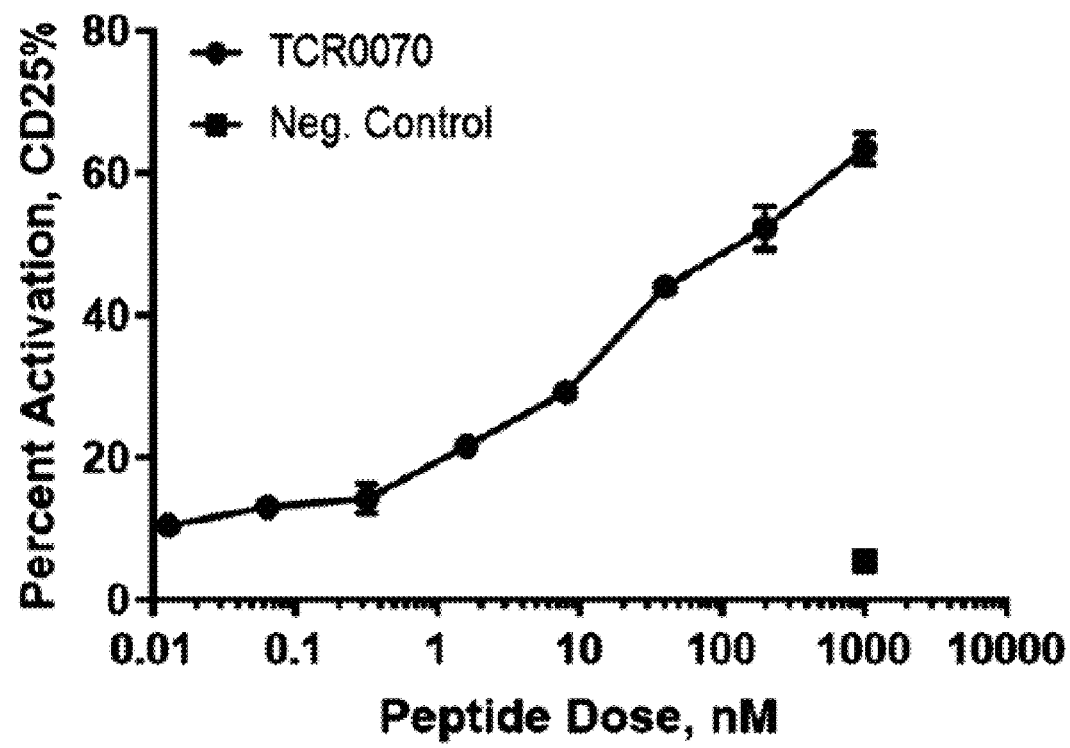

FIGS. 9A-9H are a set of graphs showing the percentage of CD25 expression, a marker of activation, following co-culture of TCR-transfected T cells with T2 cells pulsed with varying concentrations of the NY-ESO-1 target peptide. The experiment was set up at a 1:1 effector:target ratio with read-out at 16 hours after plating. Percent activation values for each of the indicated TCR candidates (FIG. 9A: reference TCR; FIG. 9B: TCR0002; FIG. 9C: TCR0014; FIG. 9D: TCR0018; FIG. 9E: TCR0022; FIG. 9F: TCR0028; FIG. 9G: TCR0038; and FIG. 9H: TCR0070) were plotted at varying peptide doses.

Figure 10A:
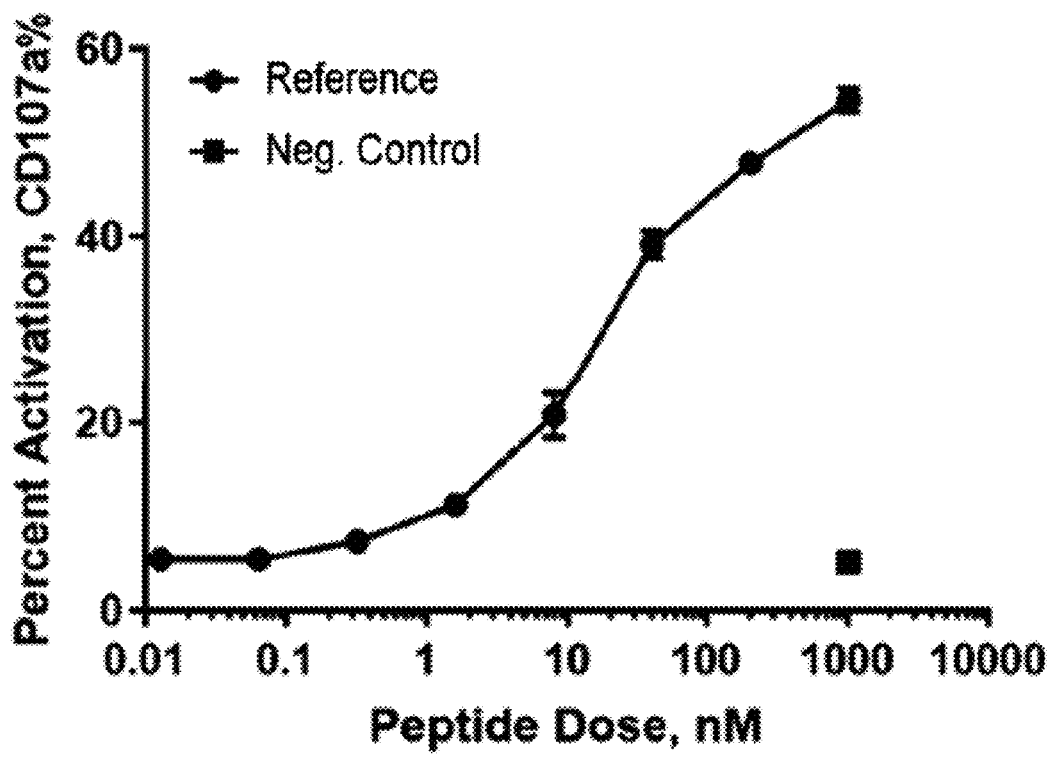
Figure 10B:
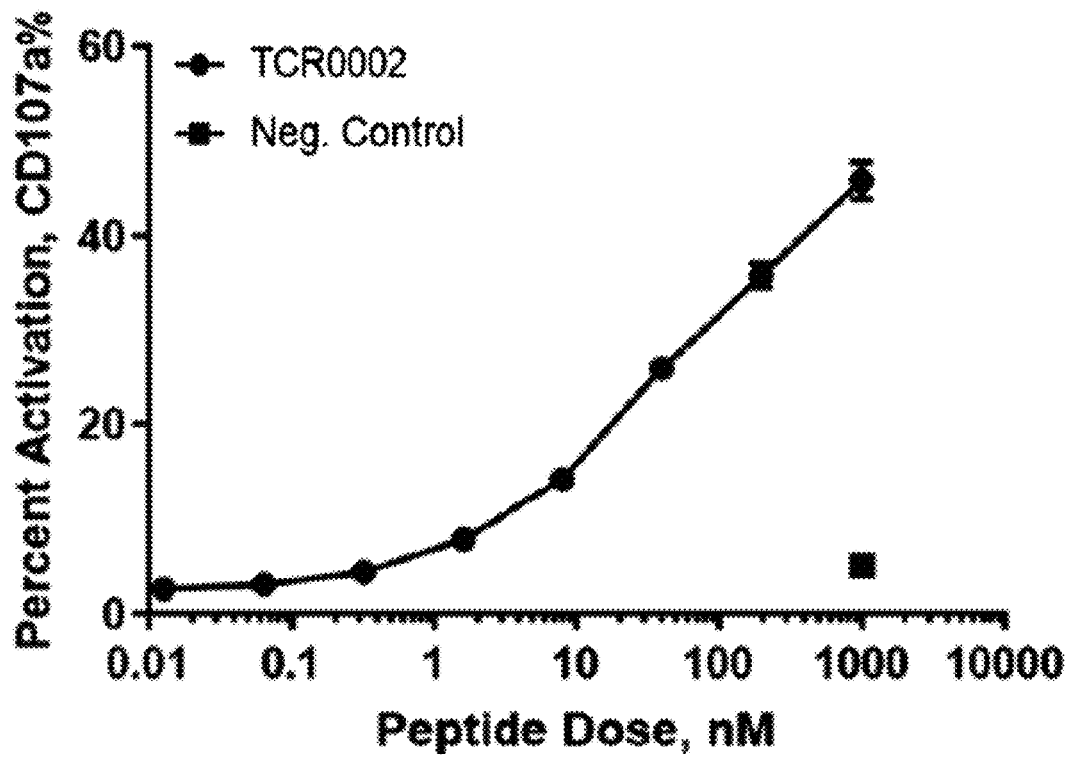
Figure 10C:
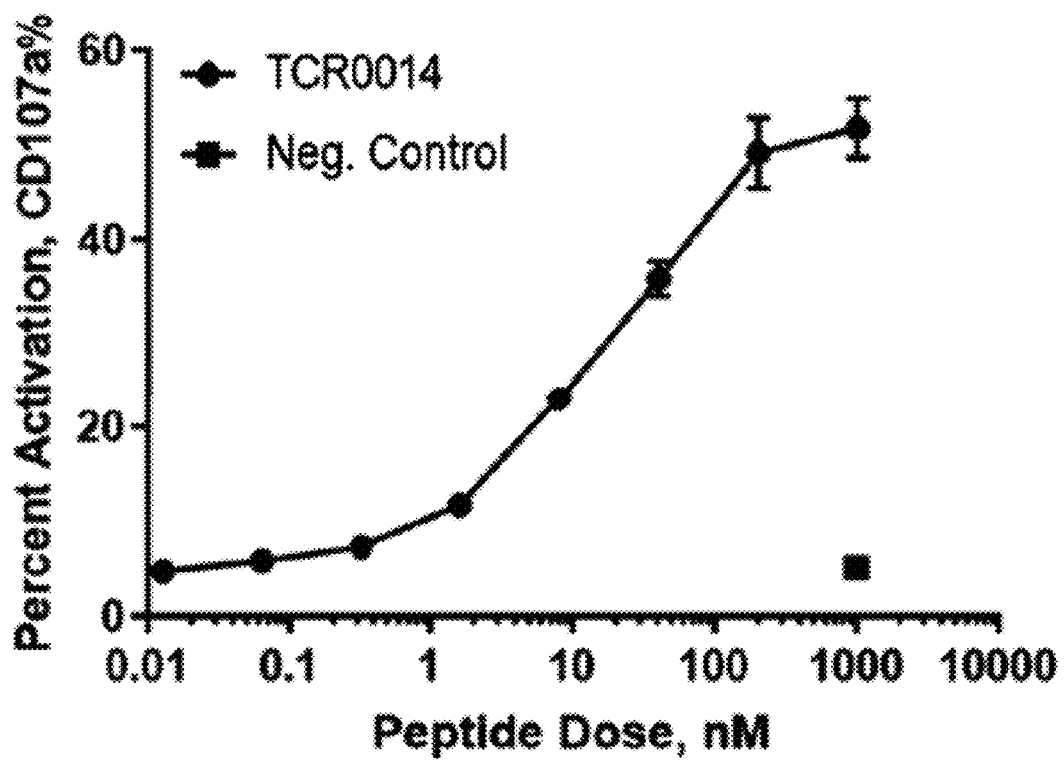
Figure 10D:
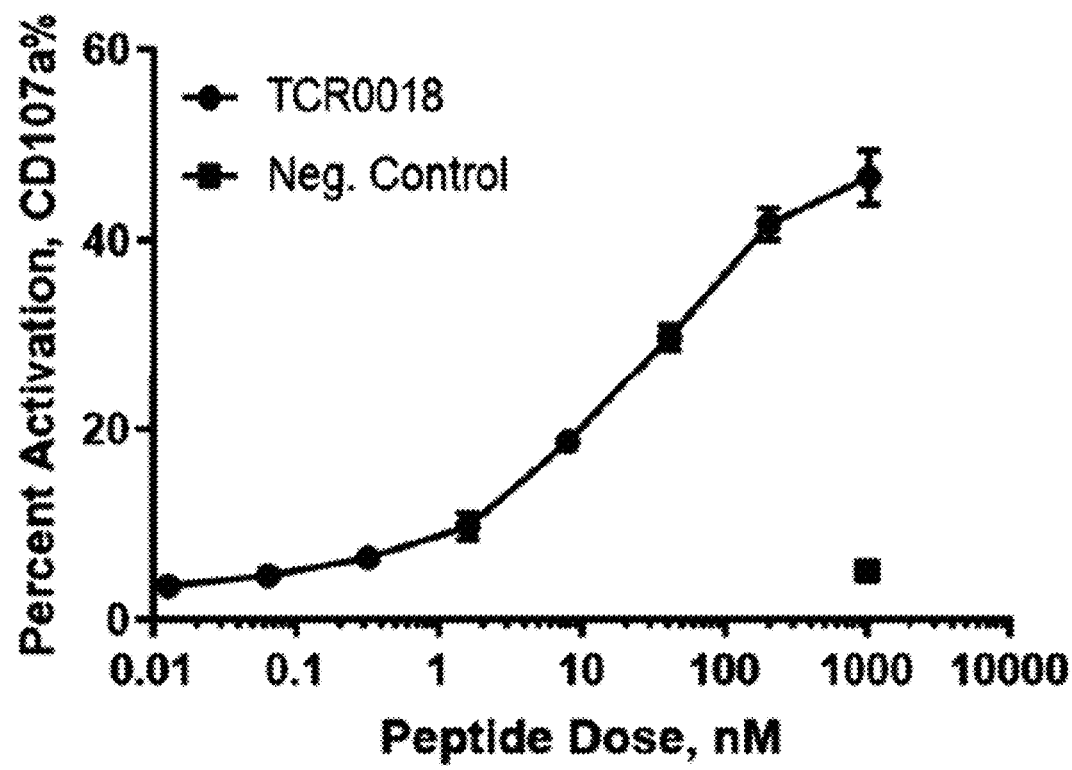
Figure 10E:
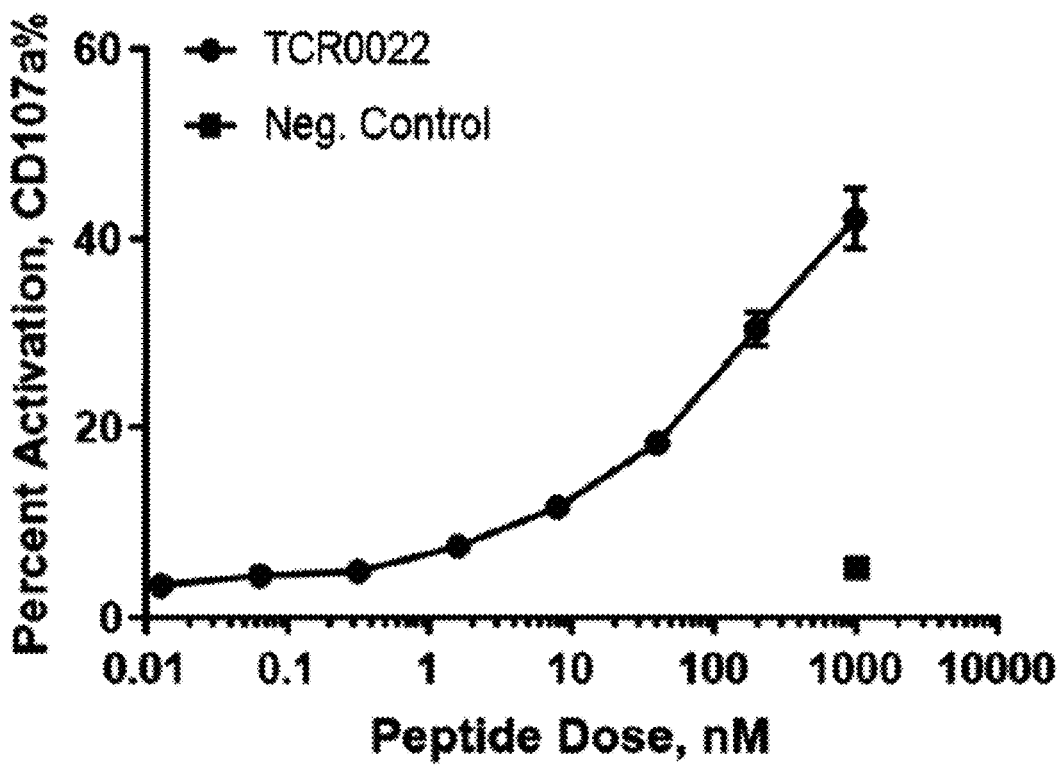
Figure 10F:
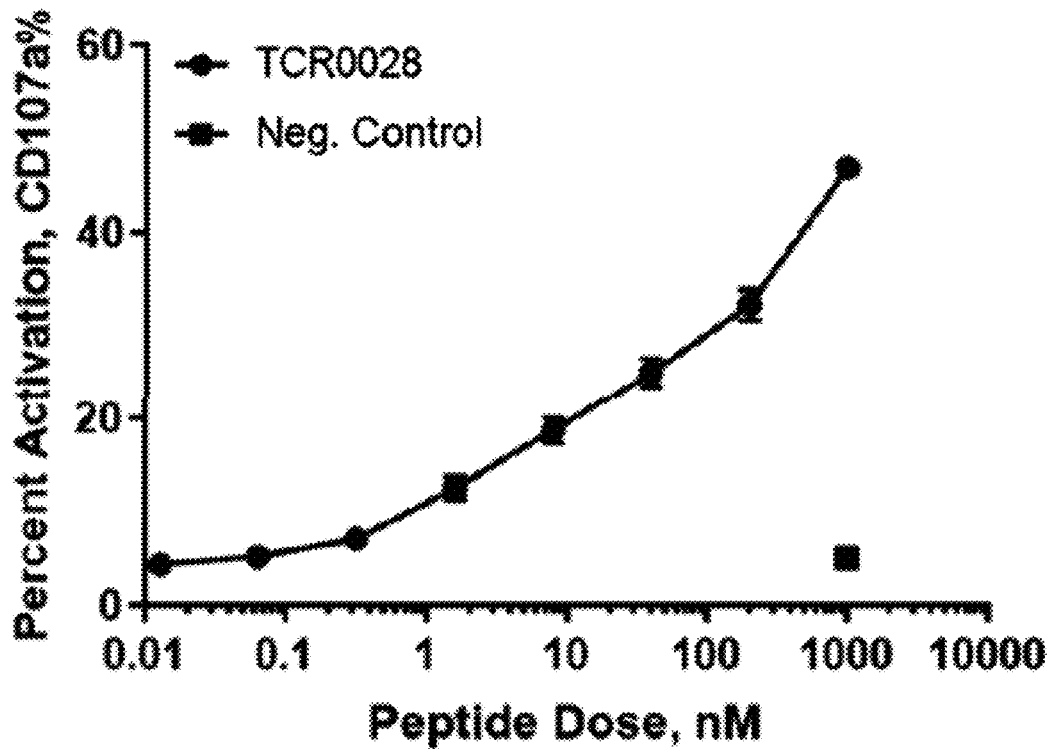
Figure 10G:
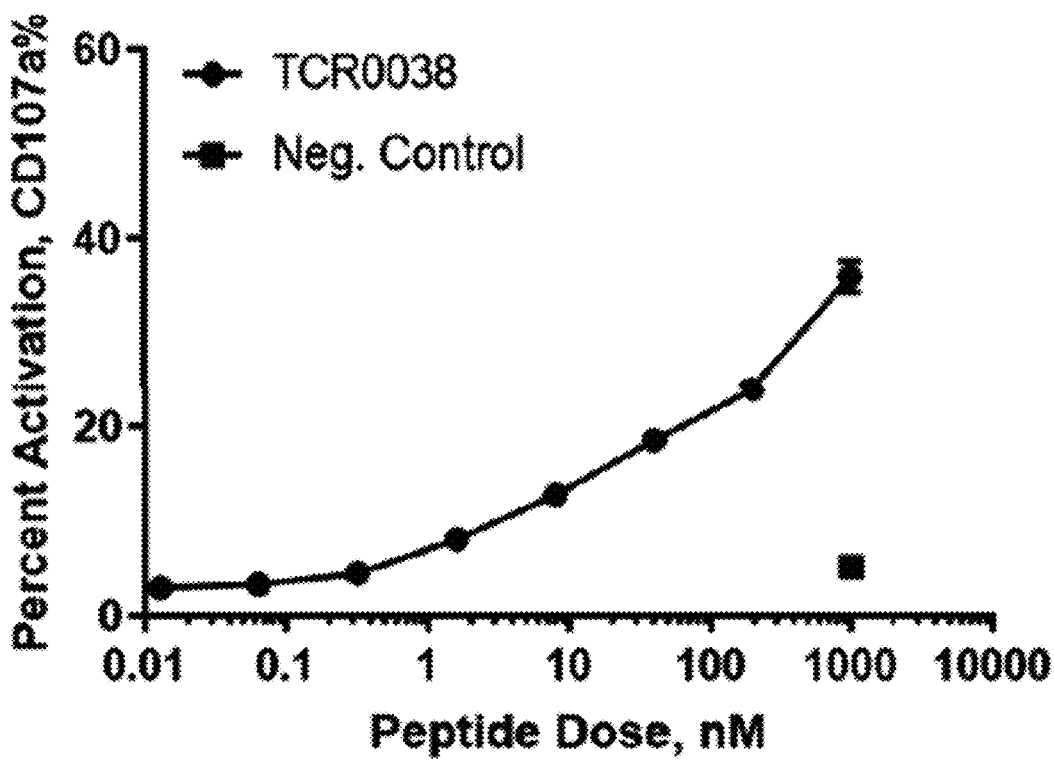
Figure 10H:
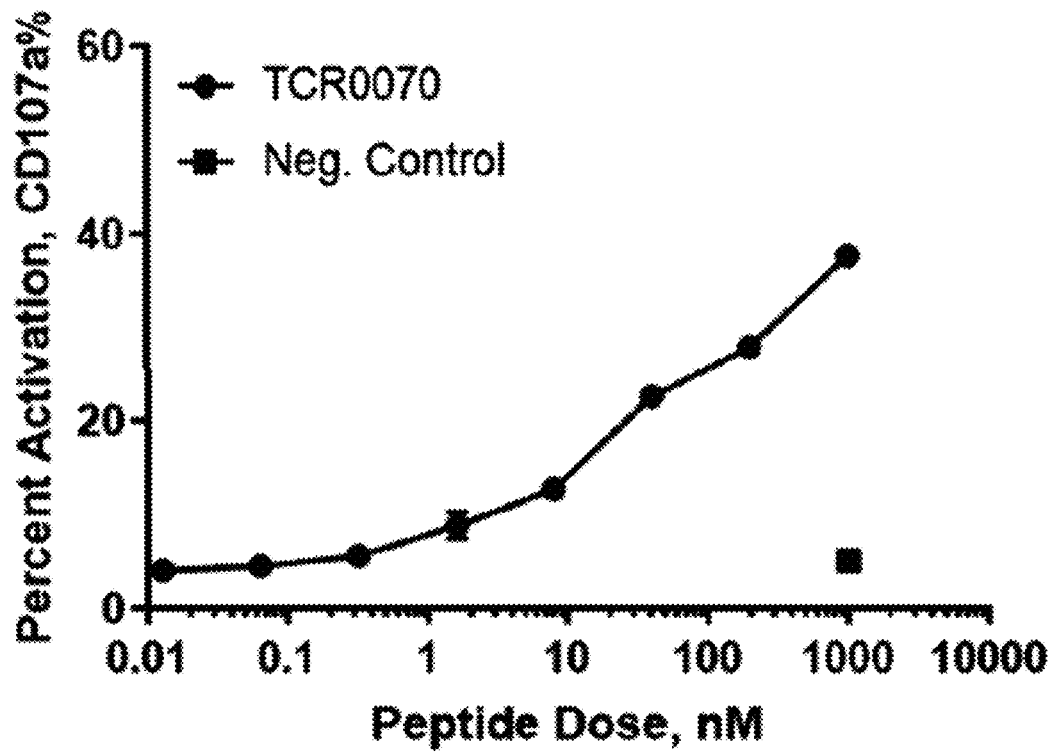

FIGS. 10A-10H are a set of graphs showing the percentage of CD107a expression, a marker of cytolytic potential and degranulation, following co-culture of TCR-transfected T cells with T2 cells pulsed with varying concentrations of the NY-ESO-1 target peptide. The experiment was set up at a 1:1 effector:target ratio, with read-out at 16 hours after plating. Percent activation values for each of the indicated TCR candidates (FIG. 10A: reference TCR; FIG. 10B: TCR0002; FIG. 10C: TCR0014, FIG. 10D: TCR0018; FIG. 10E: TCR0022; FIG. 10F: TCR0028; FIG. 10G: TCR0038; and FIG. 10H: TCR0070) were plotted at varying peptide doses.

Figure 11A:
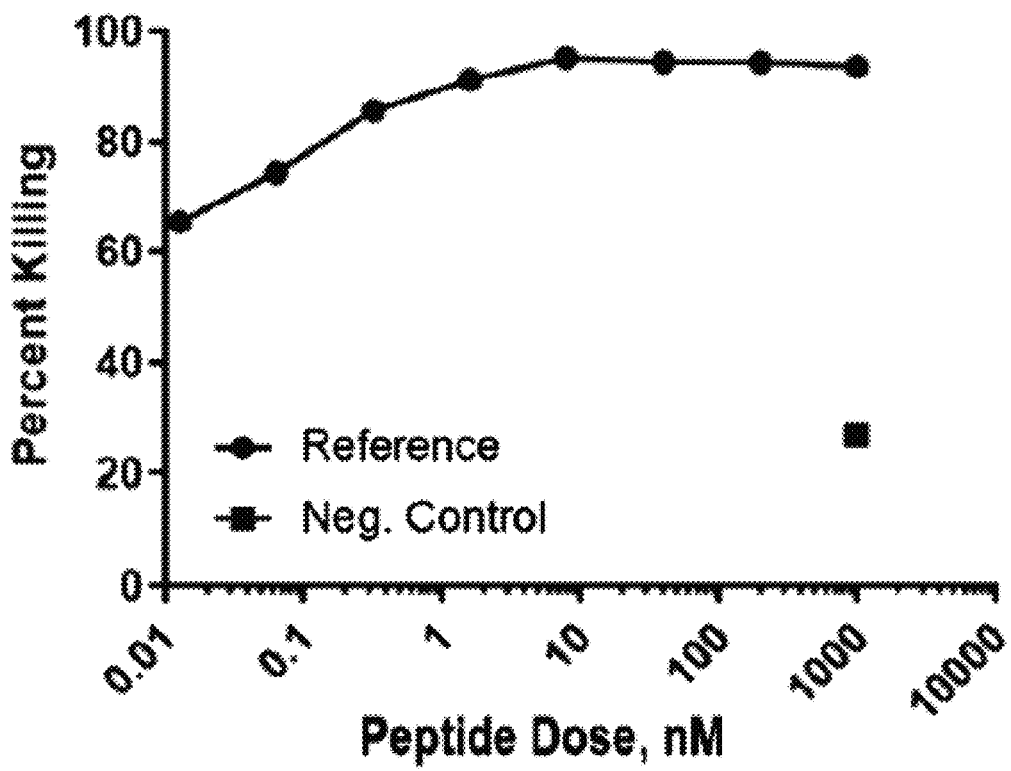
Figure 11B:
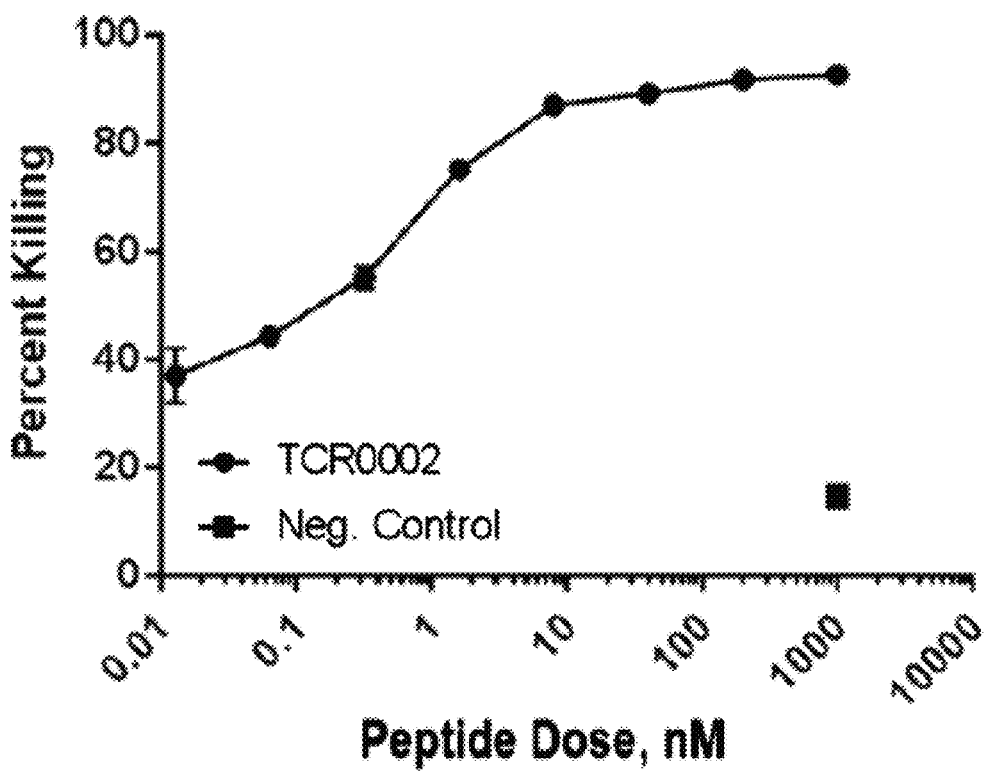
Figure 11C:
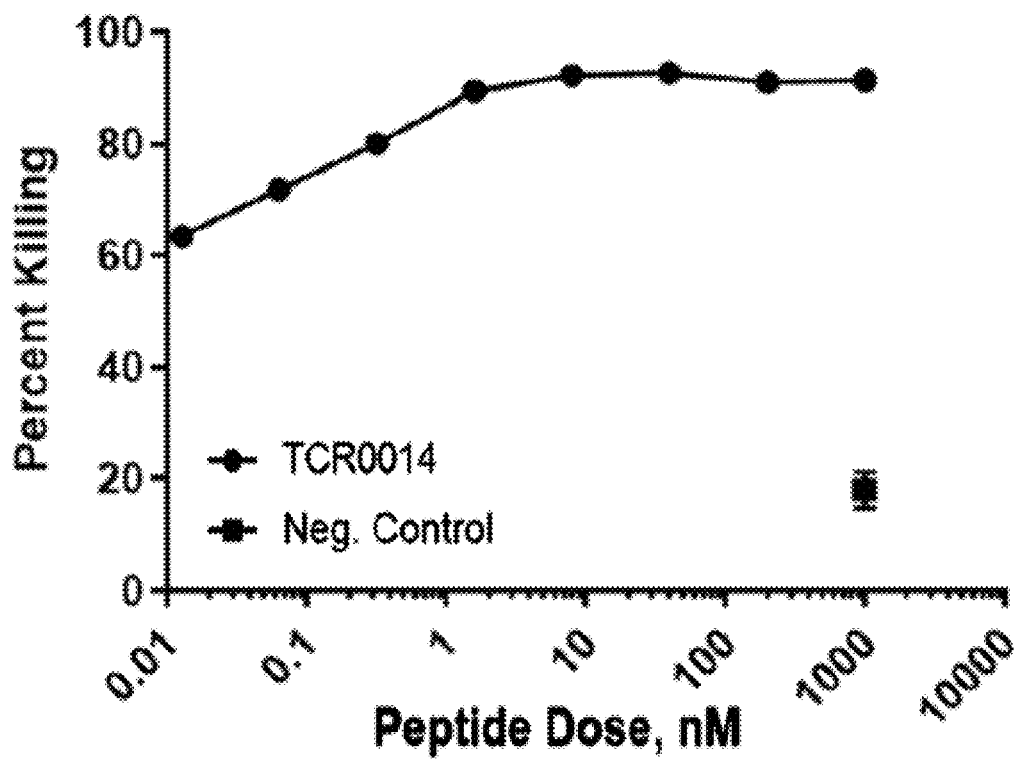
Figure 11D:
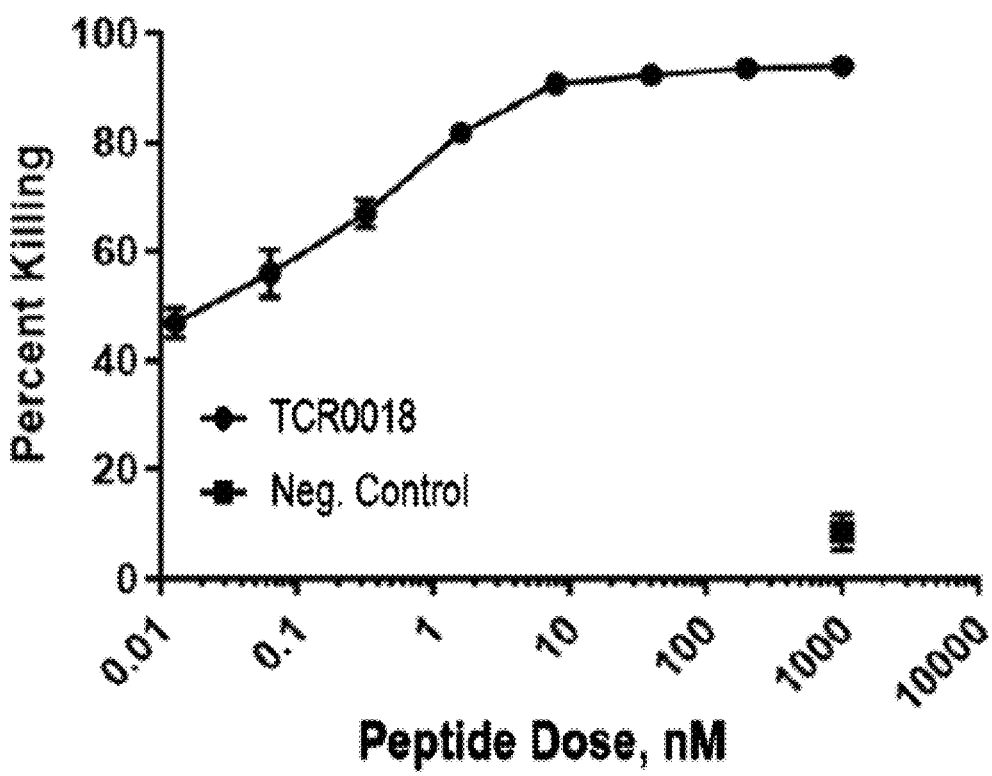
Figure 11E:
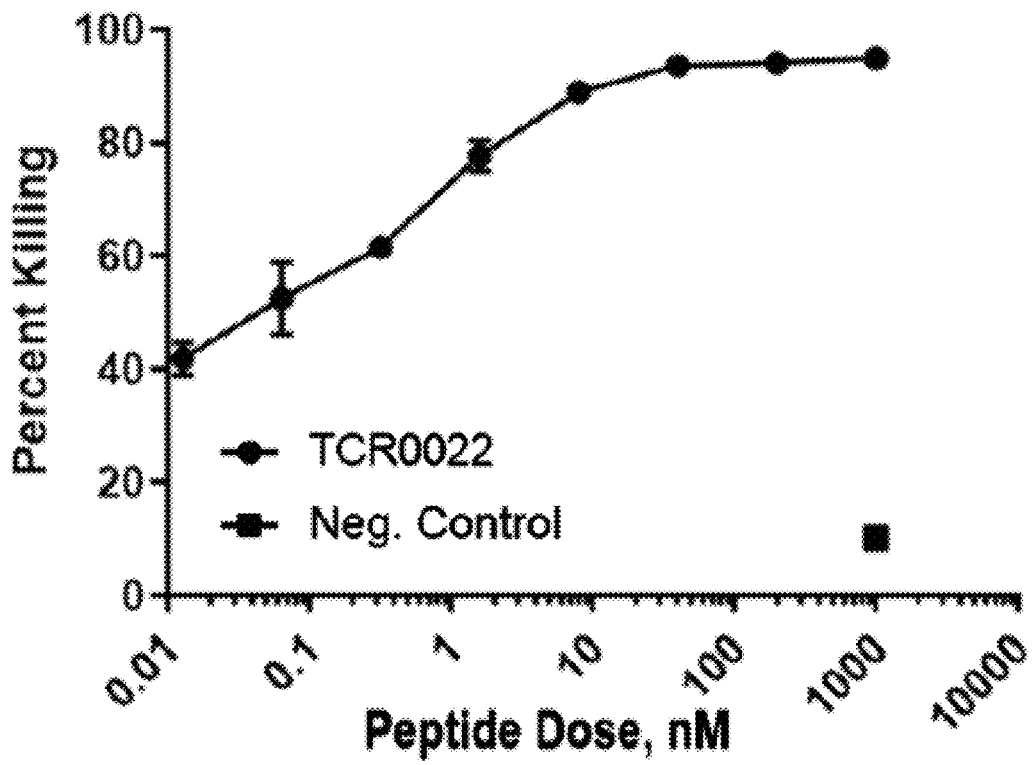
Figure 11F:
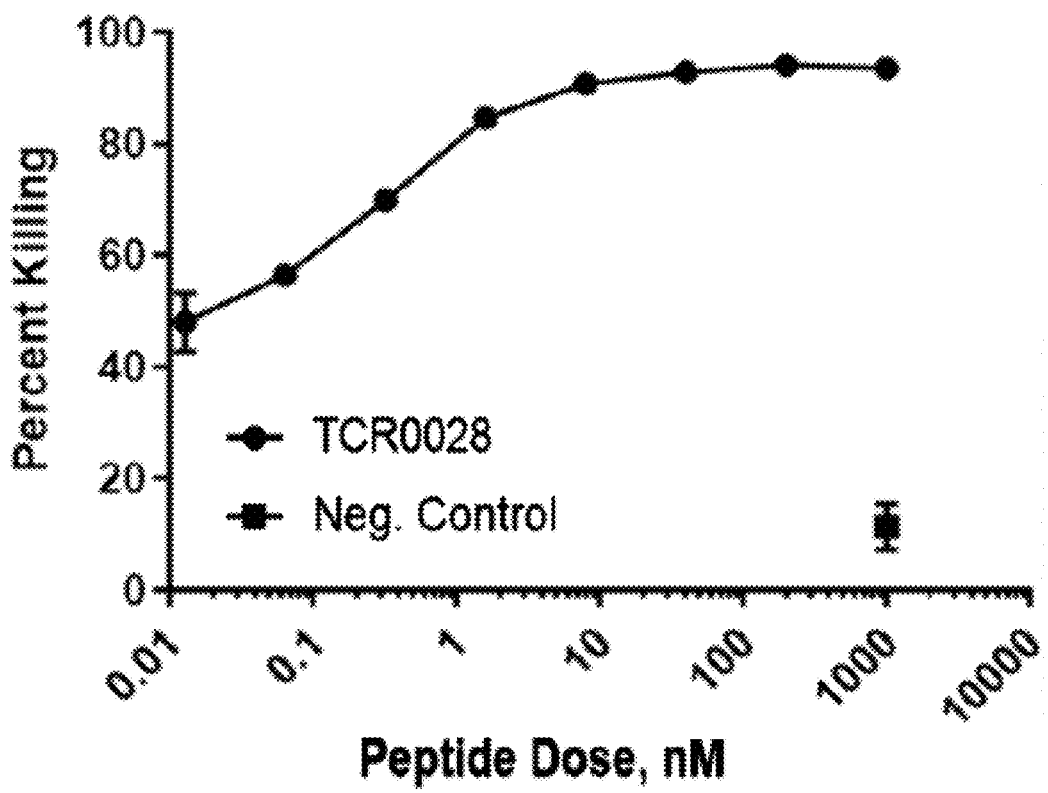
Figure 11G:
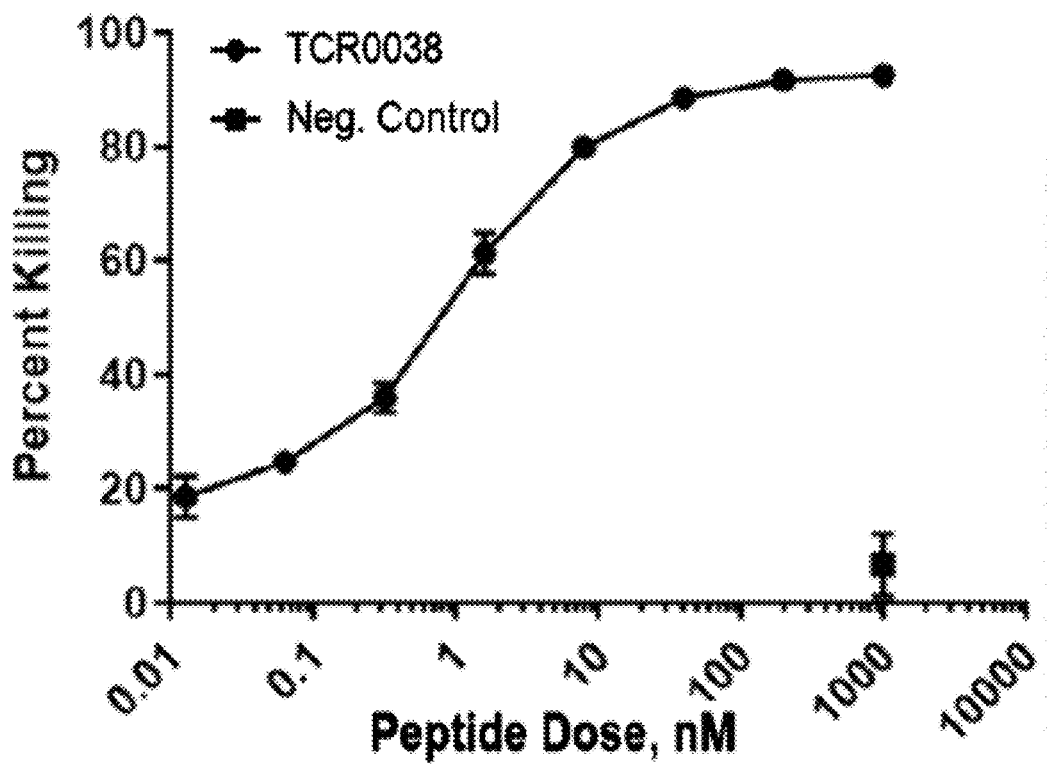
Figure 11H:
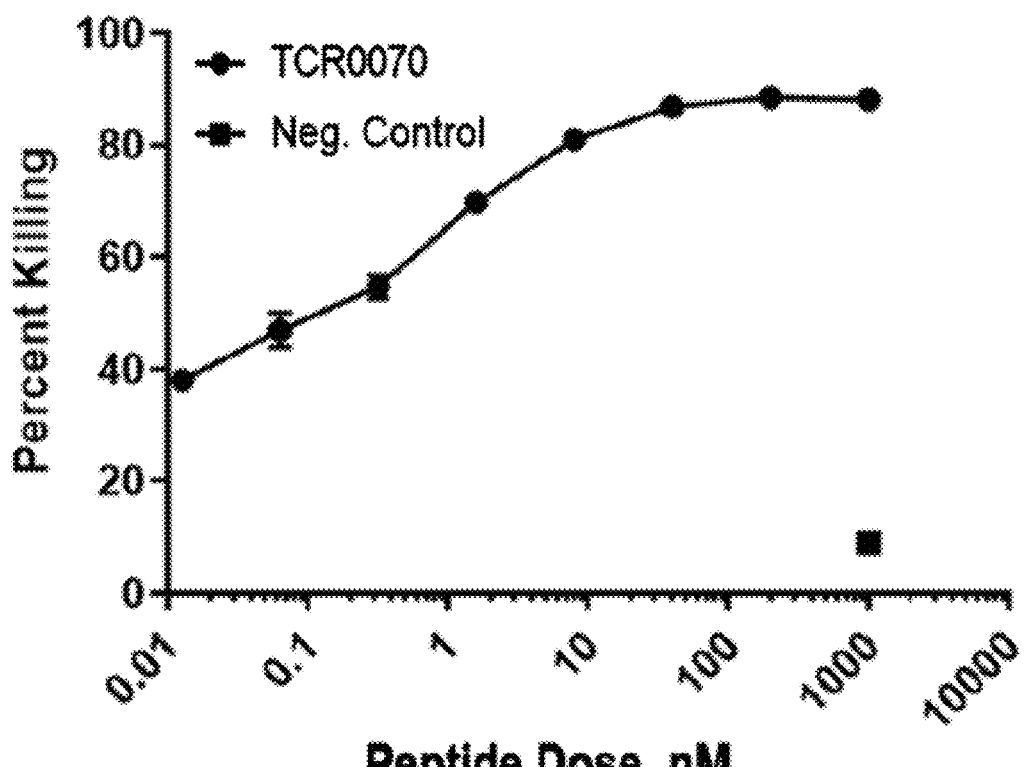

FIGS. 11A-11H are a set of graphs showing percentage killing of peptide-pulsed T2 cells by TCR-transfected T cells. The experiment was set up at a 1:1 effector:target ratio, with read-out at 16 hours after plating. Values were calculated as the difference between the number of control target cells and the number of specific target cells in the sample well, divided by the number of control target cells (multiplied by 100). Percent killing values for each of the indicated TCR candidates (FIG. 11A: reference TCR; FIG. 11B: TCR0002; FIG. 11C: TCR0014; FIG. 11D: TCR0018; FIG. 11E: TCR0022; FIG. 11F: TCR0028; FIG. 11G: TCR0038; and FIG. 11H: TCR0070) were plotted at varying peptide doses.

Figure 12A:
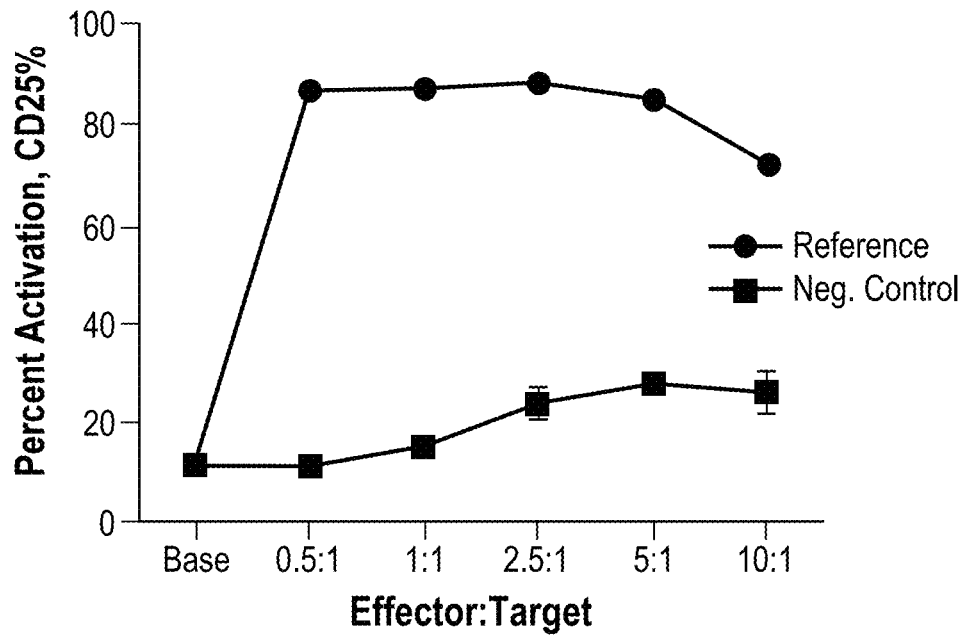
Figure 12B:
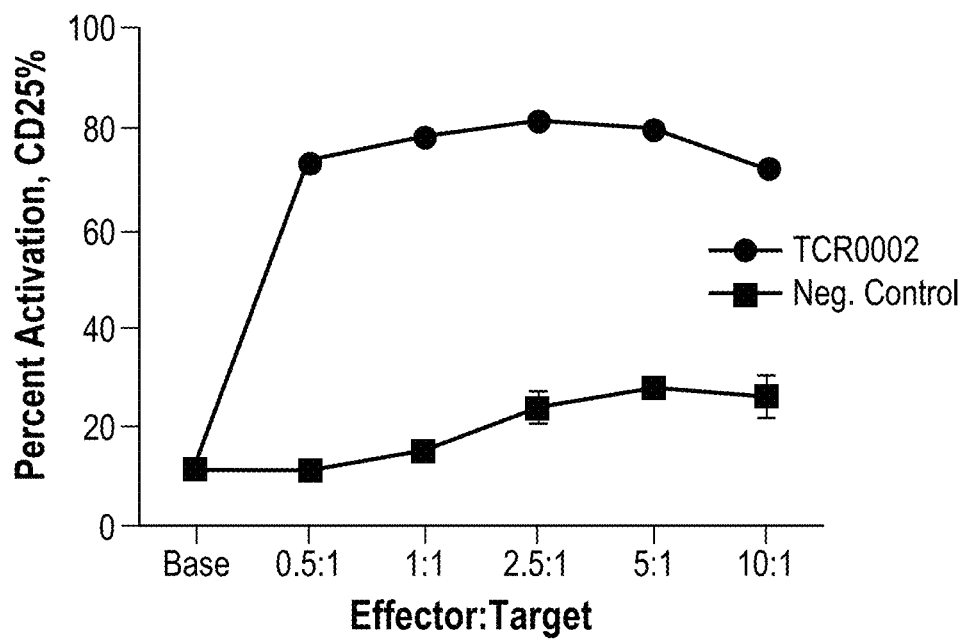
Figure 12C:
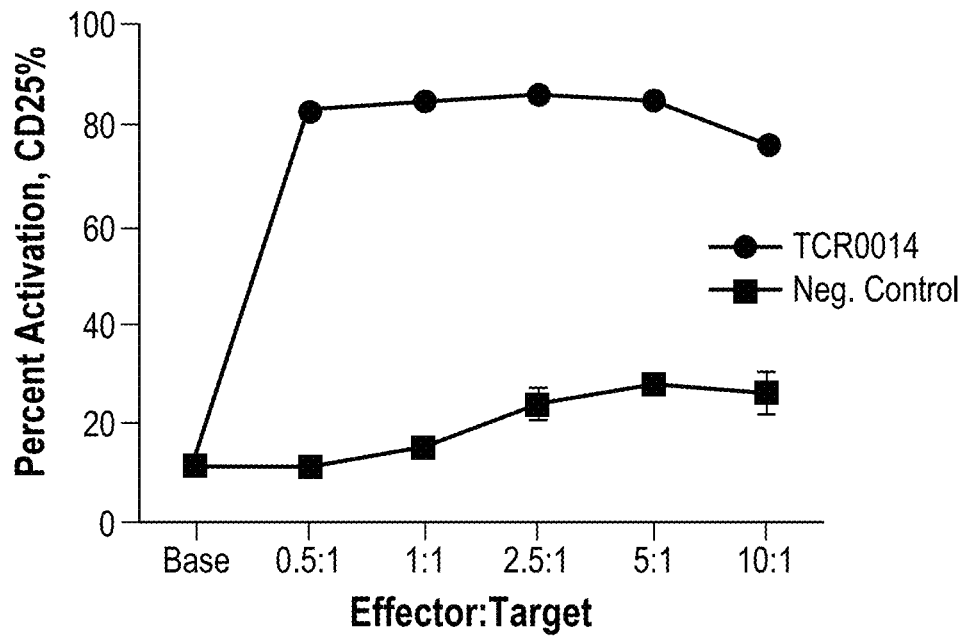
Figure 12D:
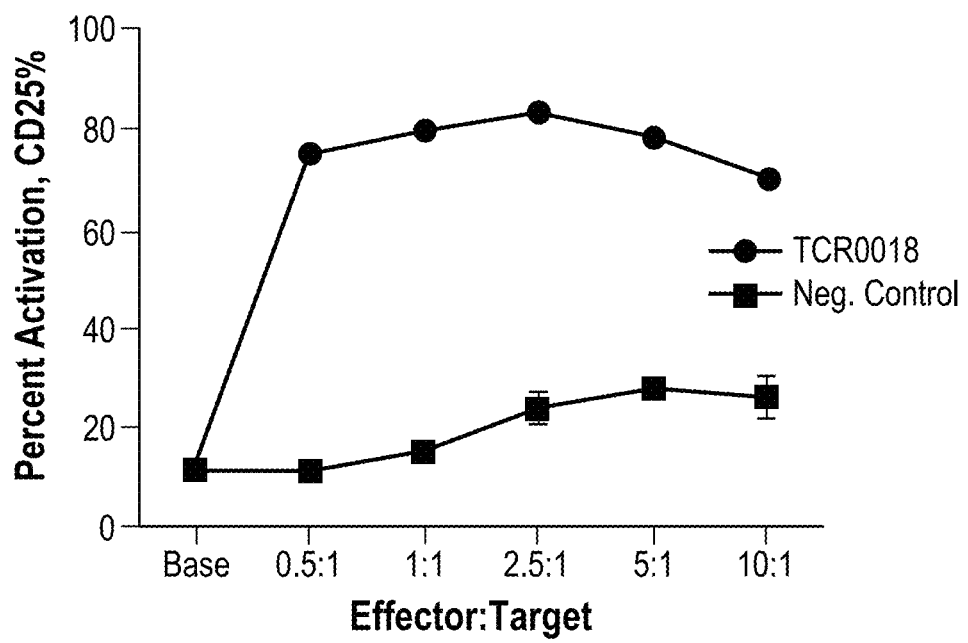
Figure 12E:
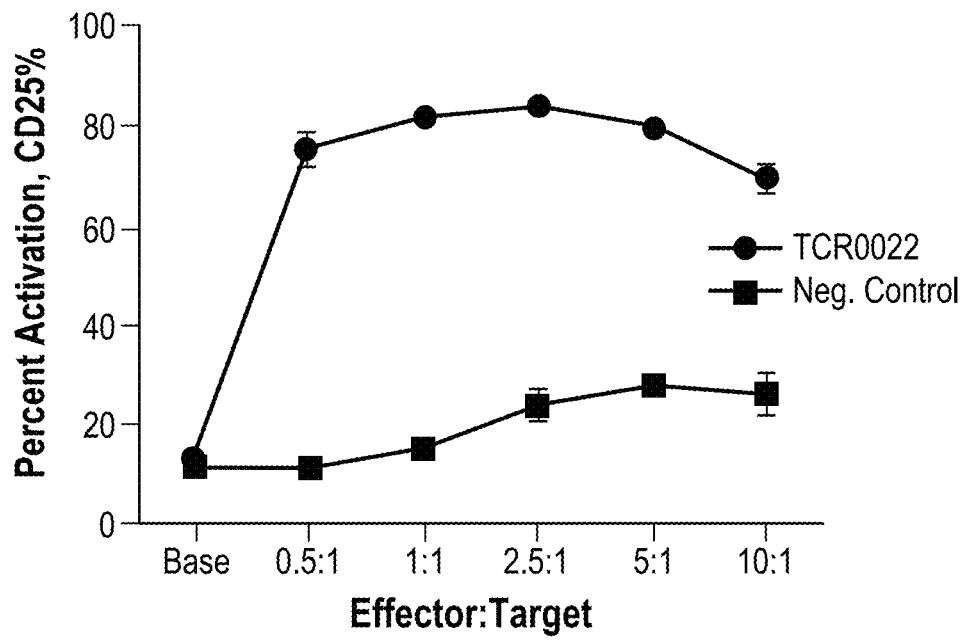
Figure 12F:
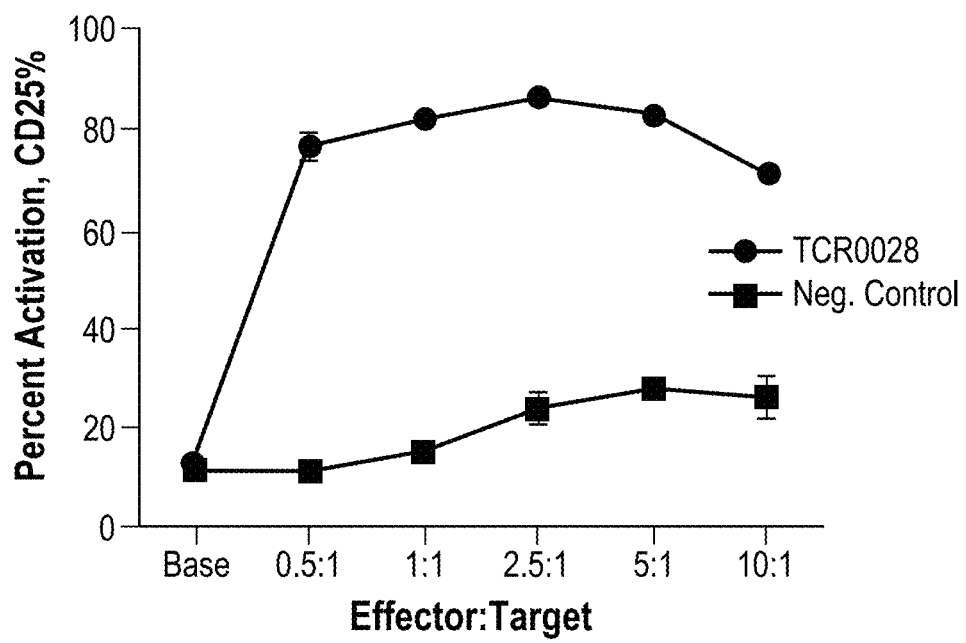
Figure 12G:
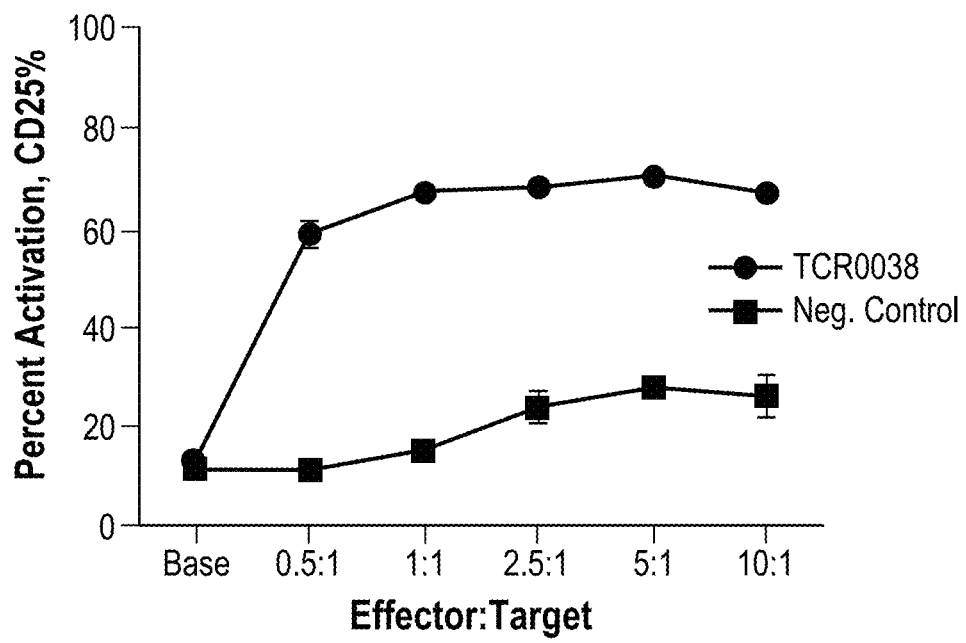
Figure 12H:
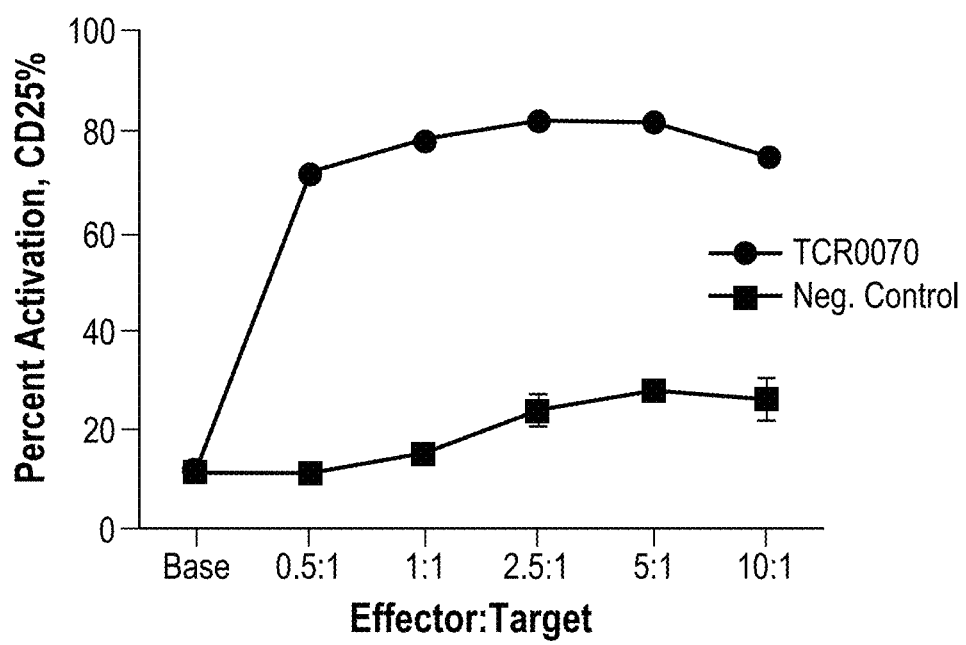

FIGS. 12A-12H are a set of graphs showing the percentage of CD25 expression, a marker of activation, by transfected T cells following 16 hours of stimulation by a fixed number of HLA-A*0201- and NY-ESO-1-transduced K562 target cells, cultured at the indicated ratios. Percent activation values for each of the indicated TCR candidates (FIG. 12A: reference TCR; FIG. 12B: TCR0002; FIG. 12C: TCR0014; FIG. 12D: TCR0018; FIG. 12E: TCR0022; FIG. 12F: TCR0028; FIG. 12G: TCR0038; and FIG. 12H: TCR0070) were plotted at varying effector-to-target ratios, varying the number of transfected T cells while maintaining a constant number of target cells.

Figure 13A:
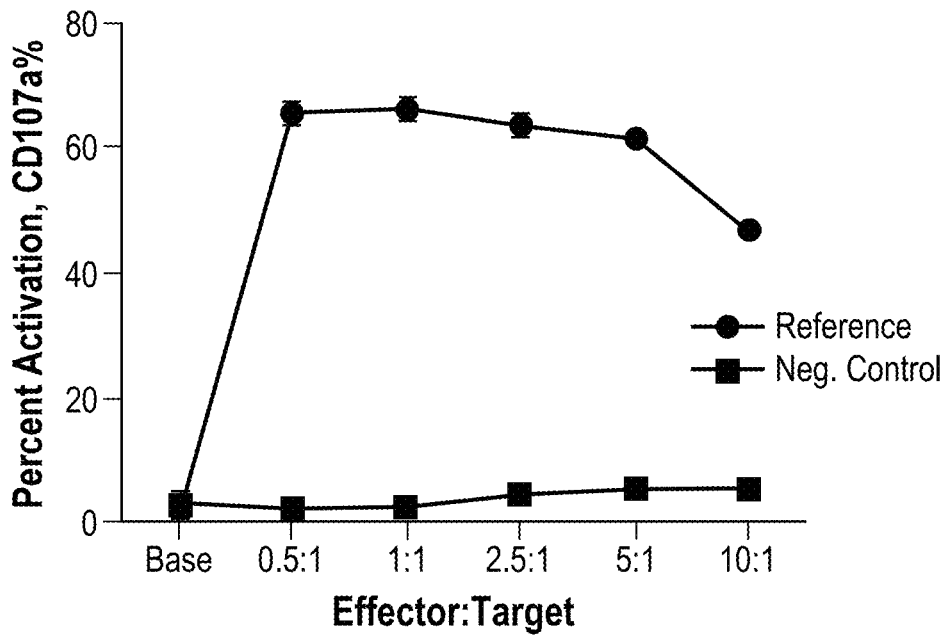
Figure 13B:
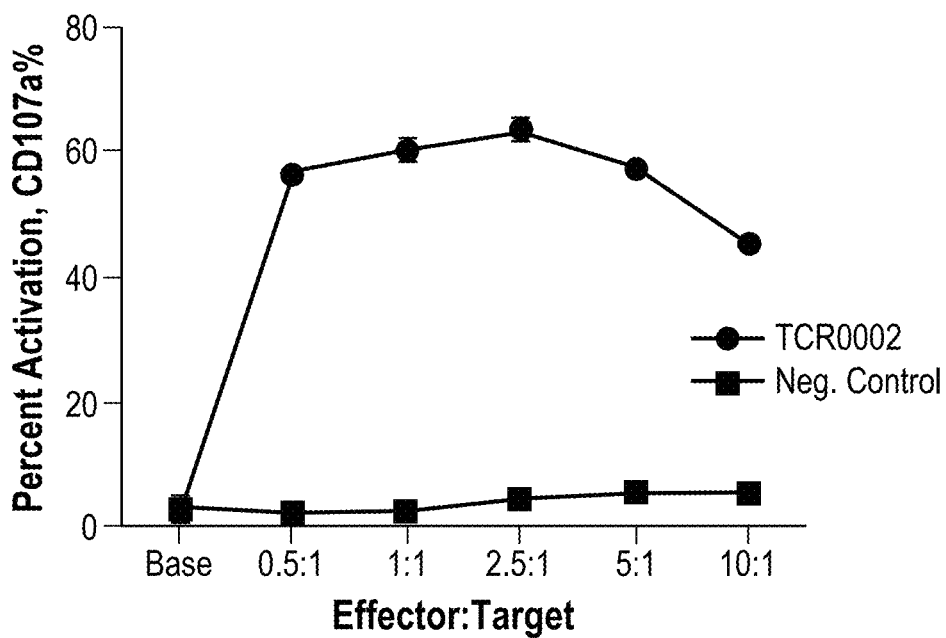
Figure 13C:
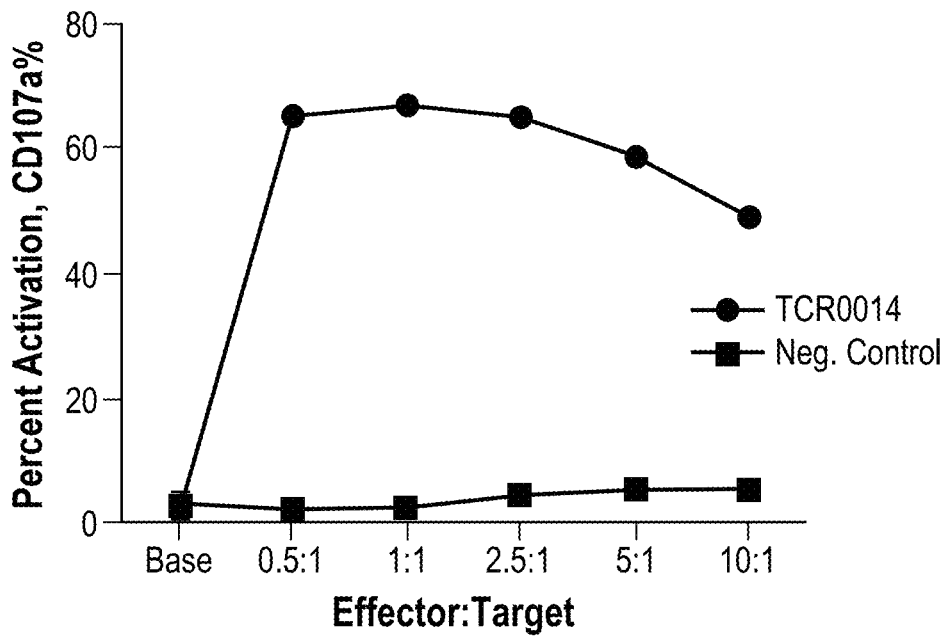
Figure 13D:
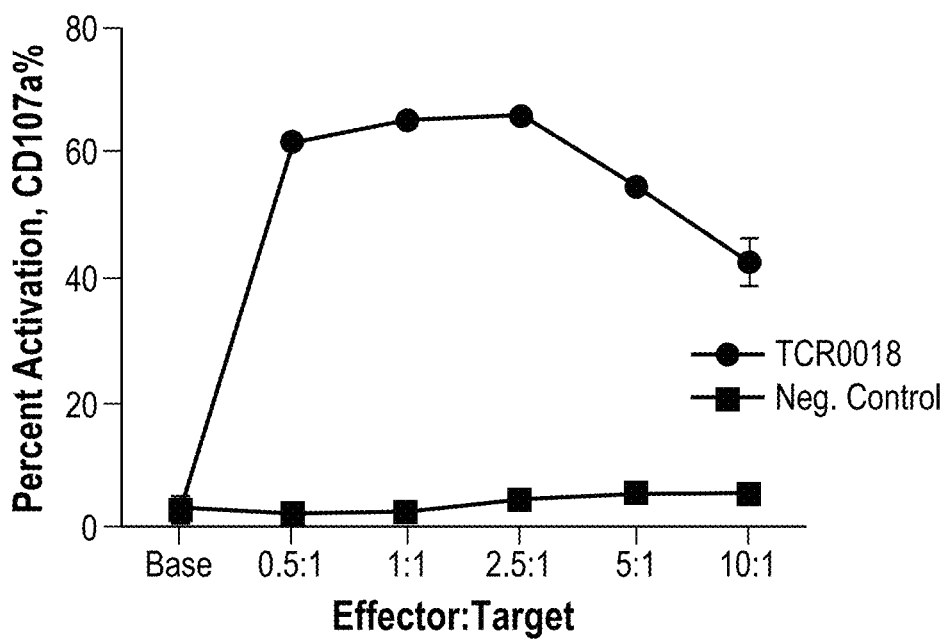
Figure 13E:
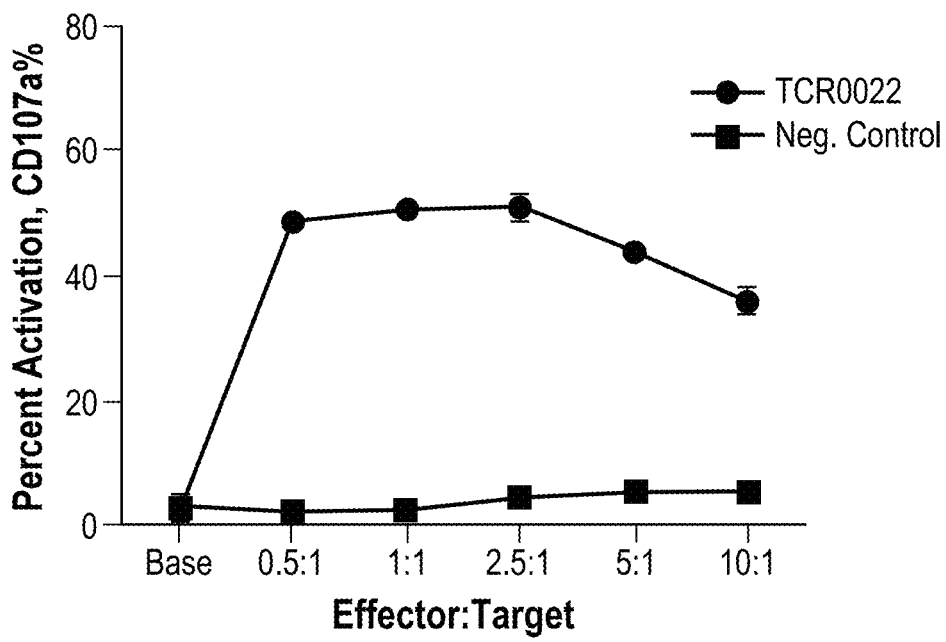
Figure 13F:
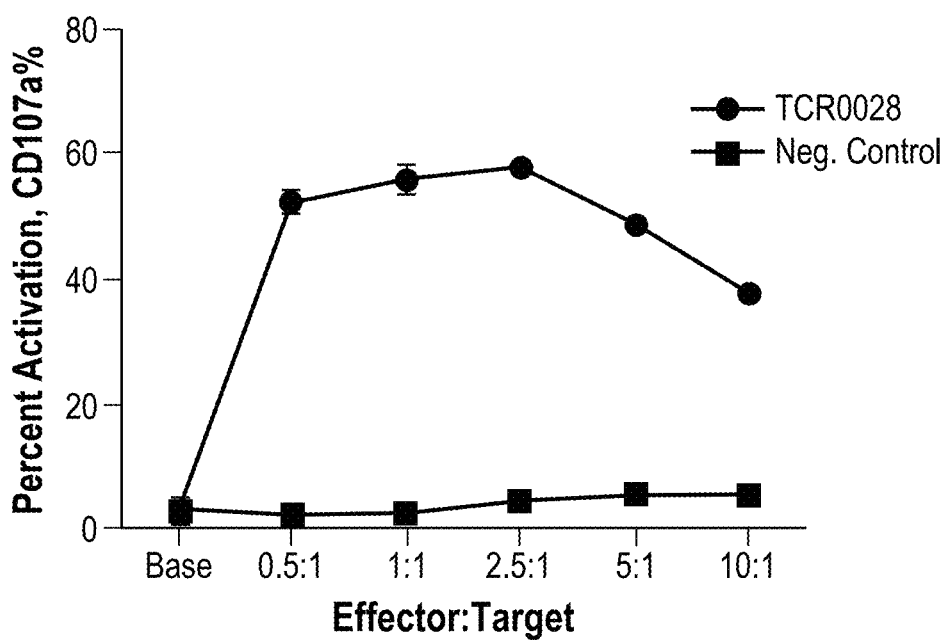
Figure 13G:
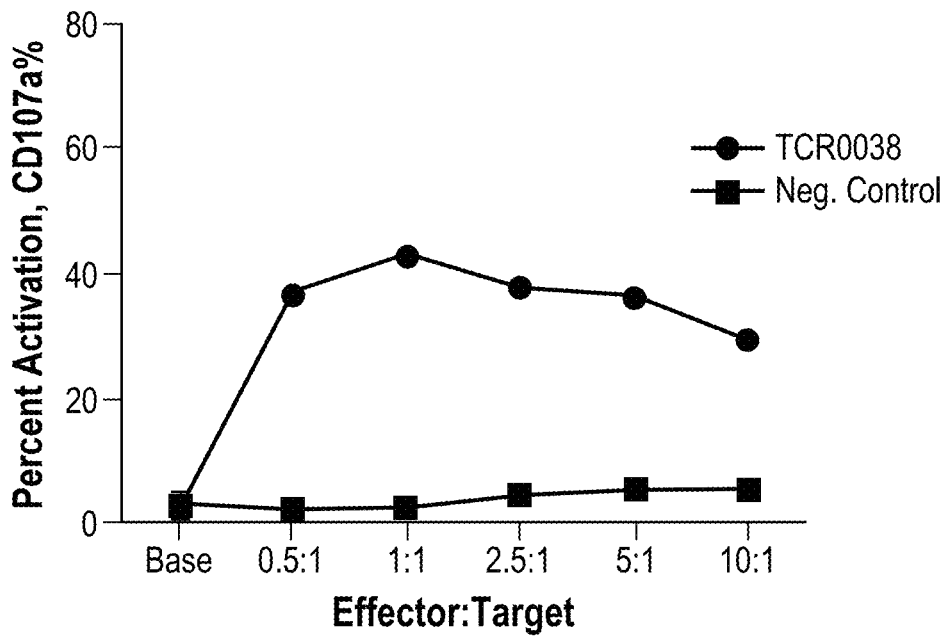
Figure 13H:
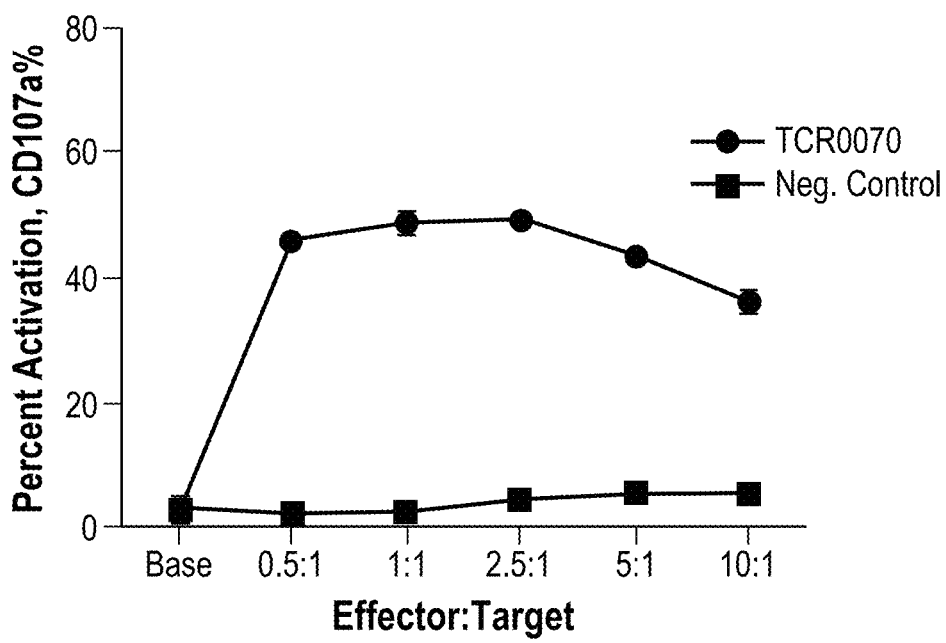

FIGS. 13A-13H are a set of graphs showing the percentage of CD107a expression, a marker of cytolytic potential and degranulation, following co-culture of TCR-transfected T cells with a fixed number of HLA-A*0201- and NY-ESO-1-transduced K562 target cells at the indicated ratios. Percent activation values for each of the indicated TCR candidates (FIG. 13A: reference TCR; FIG. 13B: TCR0002; FIG. 13C: TCR0014; FIG. 13D: TCR0018; FIG. 13E: TCR0022 FIG. 13F: TCR0028; FIG. 13G: TCR0038; and FIG. 13H: TCR0070) were plotted at varying effector-to-target ratios, varying the number of transfected T cells while maintaining a constant number of target cells.

Figure 14A:
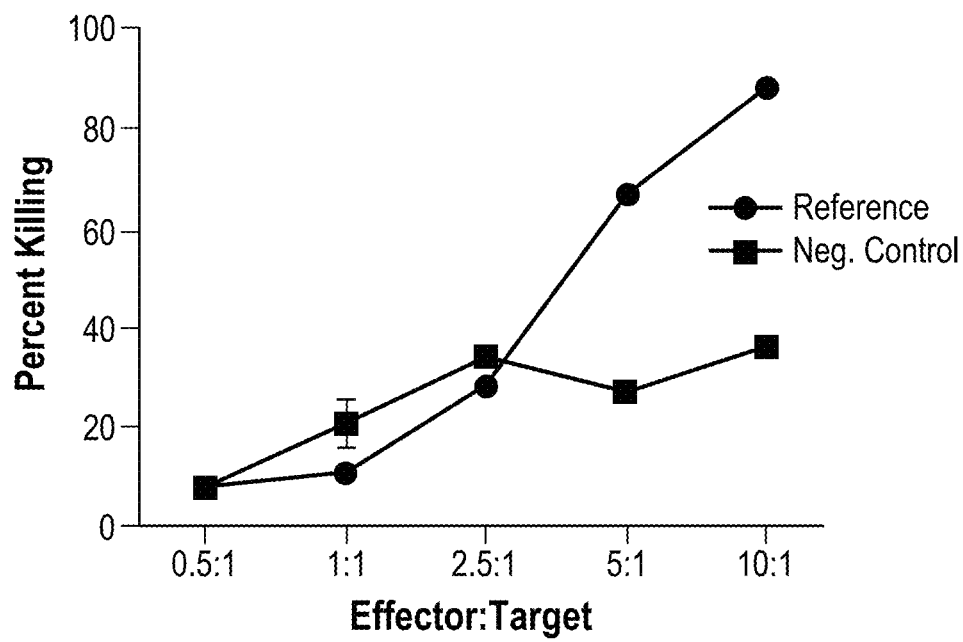
Figure 14B:
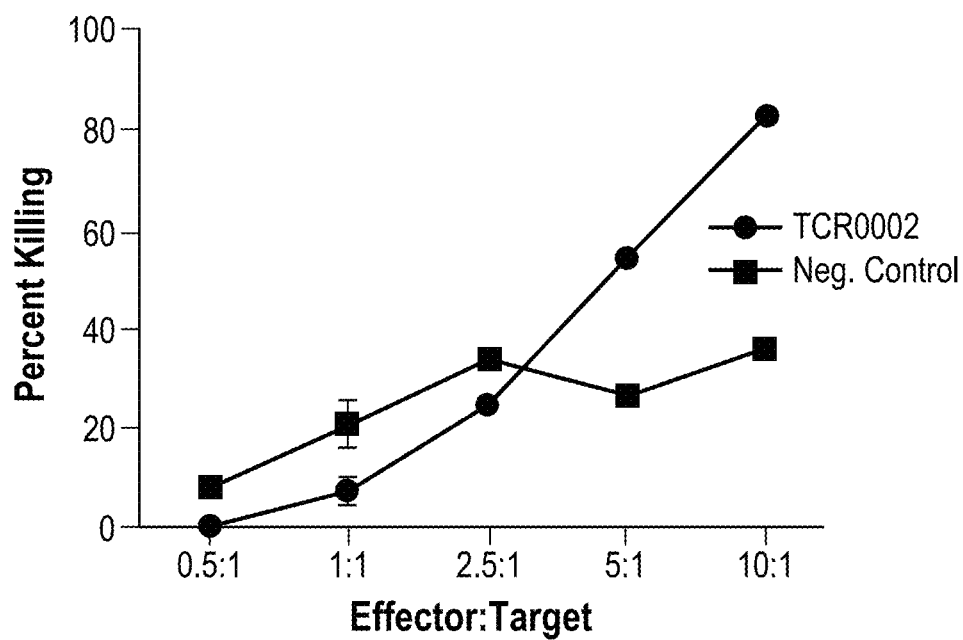
Figure 14C:
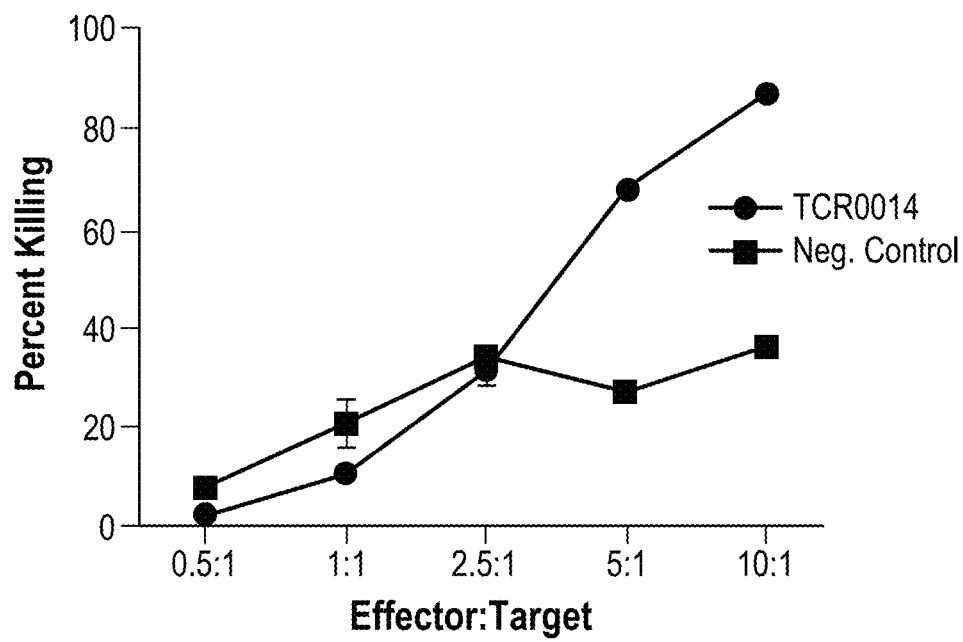
Figure 14D:
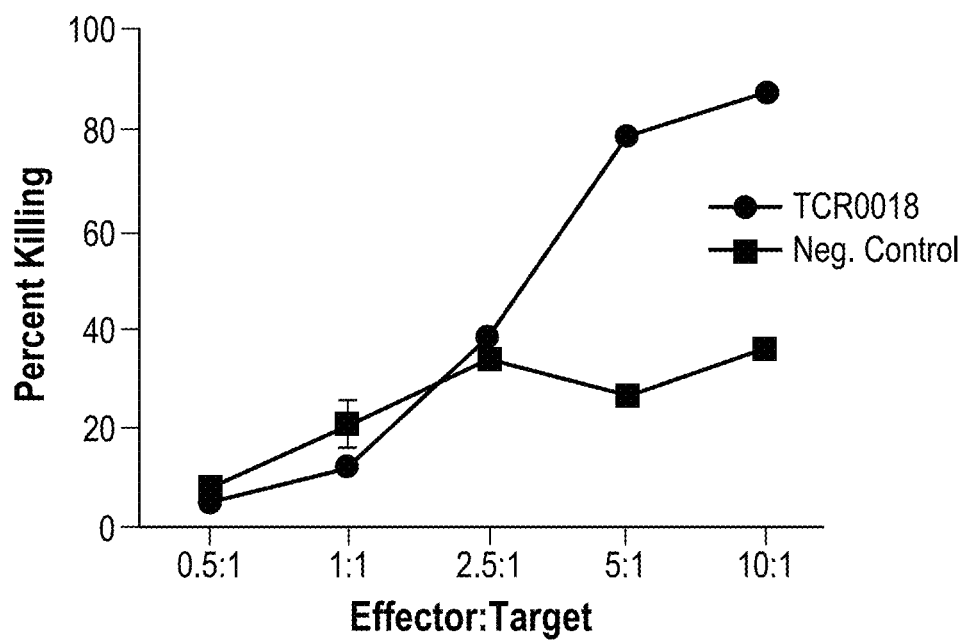
Figure 14E:
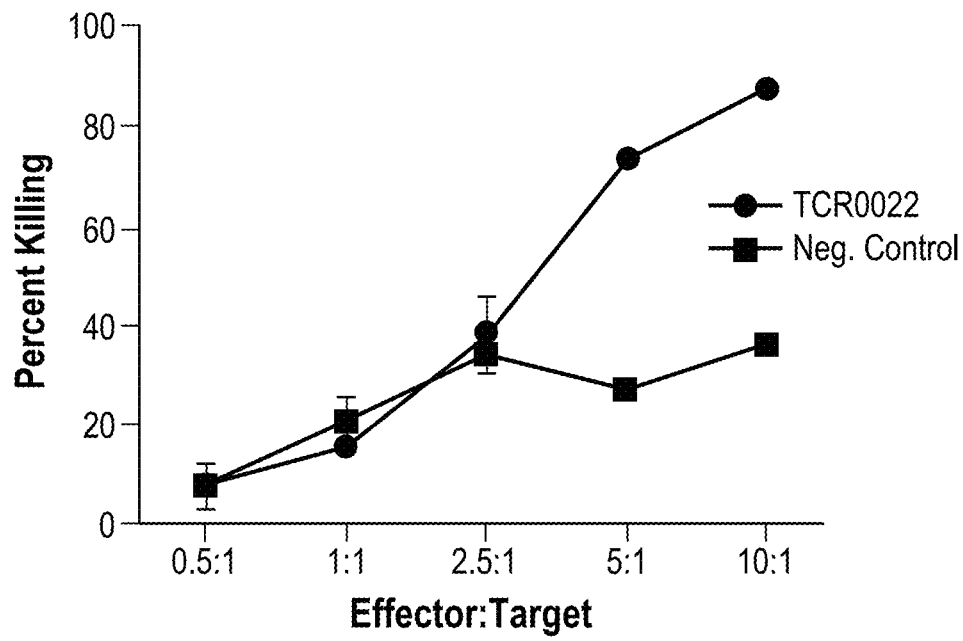
Figure 14F:
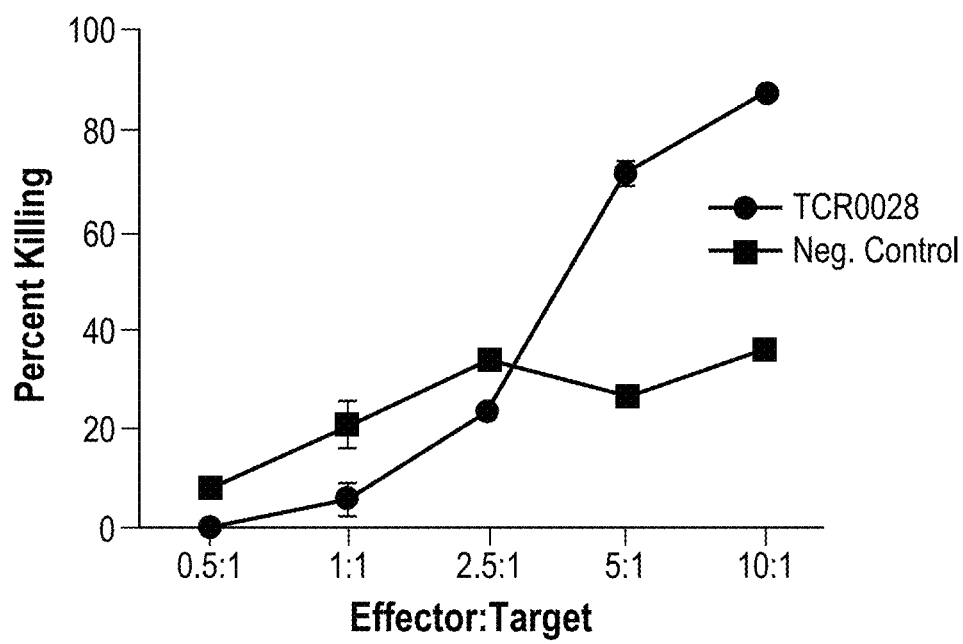
Figure 14G:
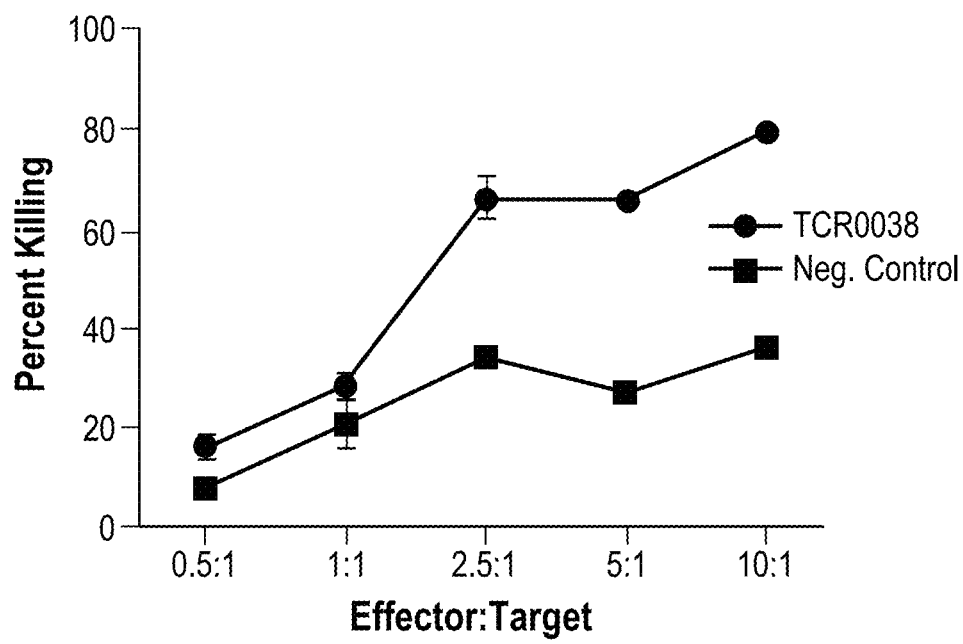
Figure 14H:
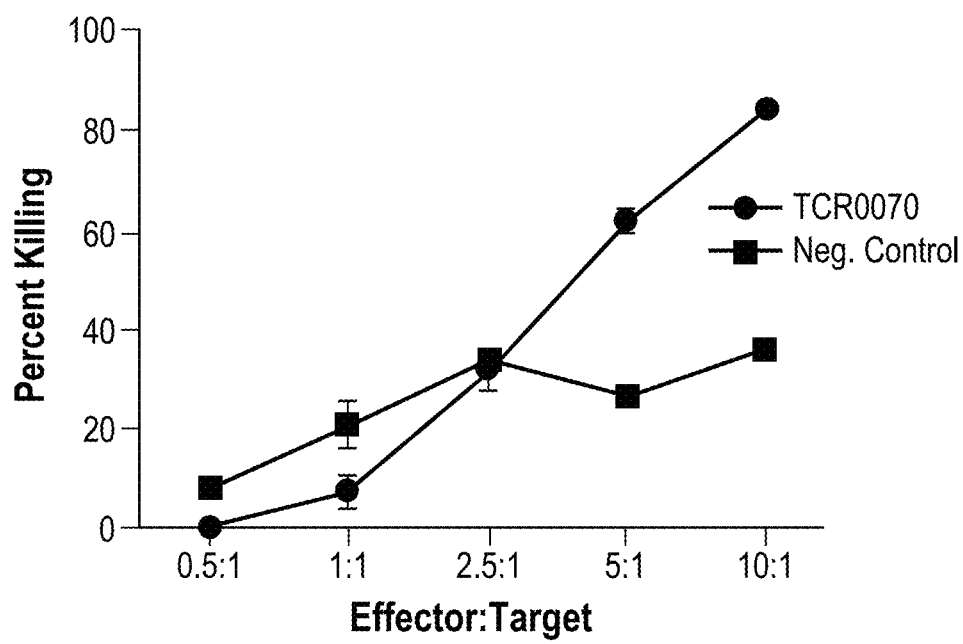

FIGS. 14A-14H are a set of graphs showing percentage killing of K562 cells transduced to express HLA-A*0201 and NY-ESO-1 at the indicated ratios. Percentage killing was calculated as the difference between the number of control target cells and the number of specific target cells in the sample well, divided by the number of control target cells (multiplied by 100). Percent killing values for each of the indicated TCR candidates (FIG. 14A: reference TCR; FIG. 14B: TCR0002; FIG. 14C: TCR0014; FIG. 14D: TCR0018; FIG. 14E: TCR0022; FIG. 14F: TCR0028; FIG. 14G: TCR0038; and FIG. 14H: TCR0070) were plotted at varying effector-to-target ratios, varying the number of transfected T cells while maintaining a constant number of target cells.

Figure 15:
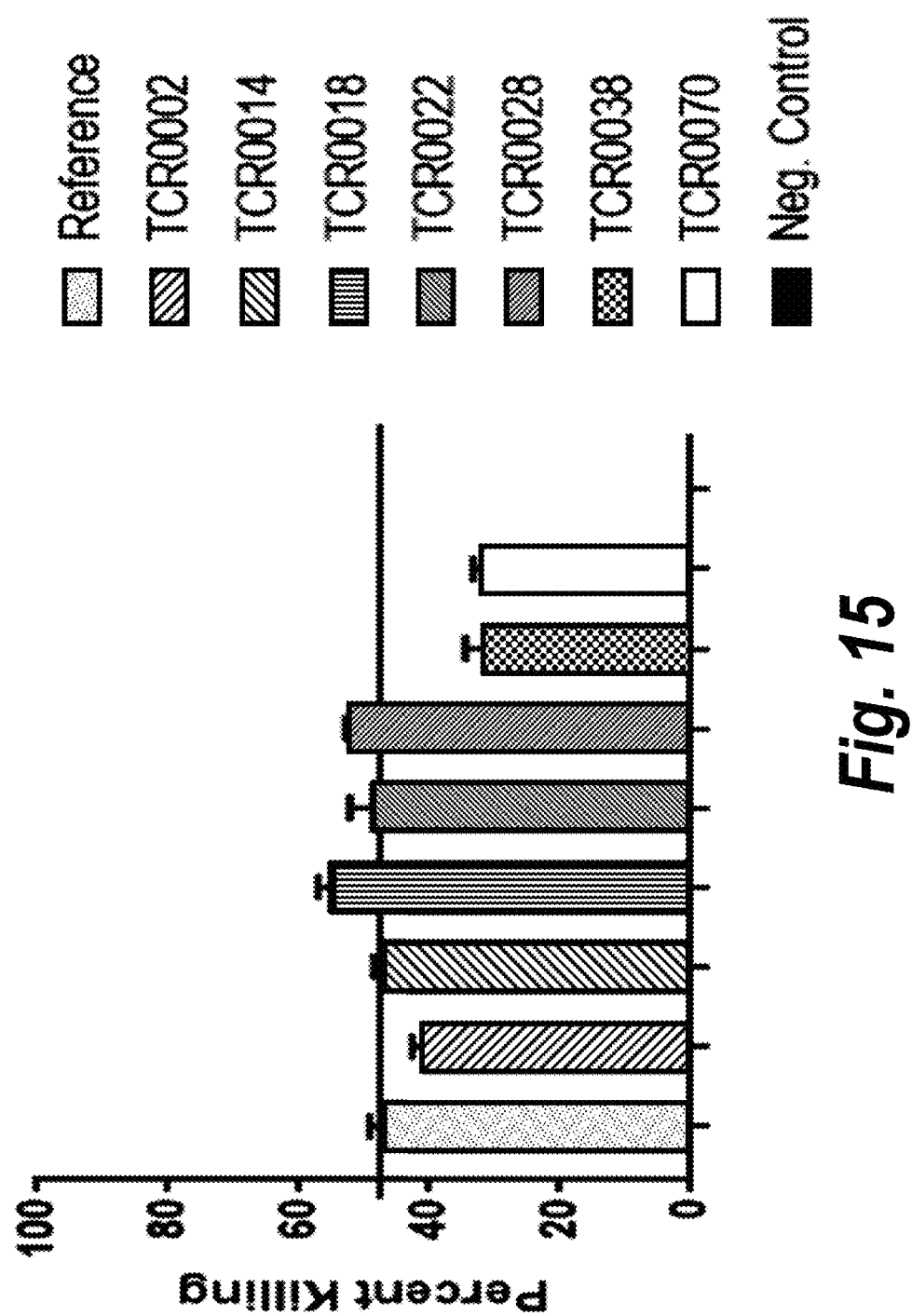

FIG. 15 is a graph showing percent preferential killing of HLA-A*0201- and NY-ESO-1-transduced K562 cells versus HLA-B*0702-transduced K562 cells following co-culture with TCR-transfected T cells at a 5:1 effector:target ratio.

Figure 16A:
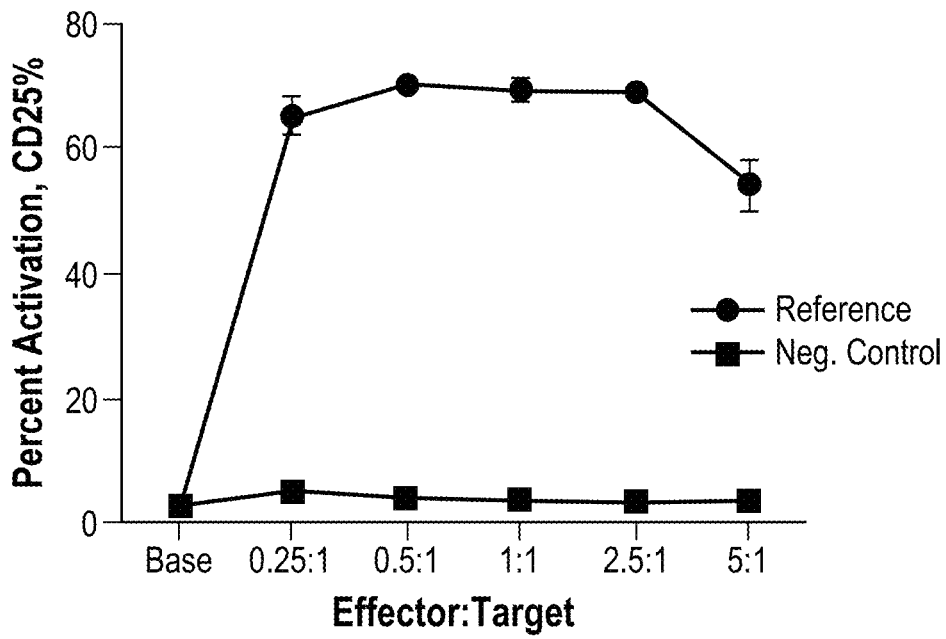
Figure 16B:
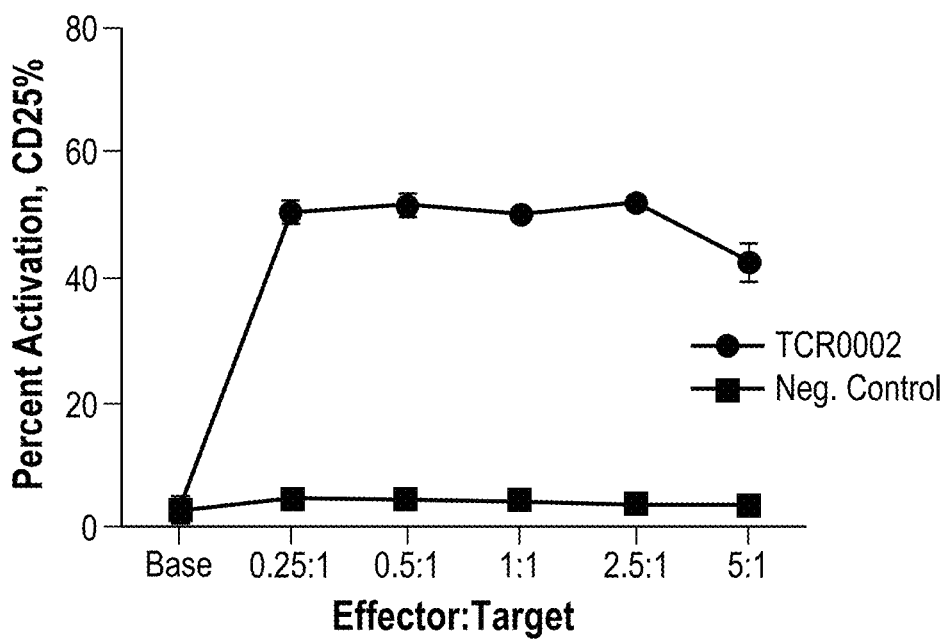
Figure 16C:
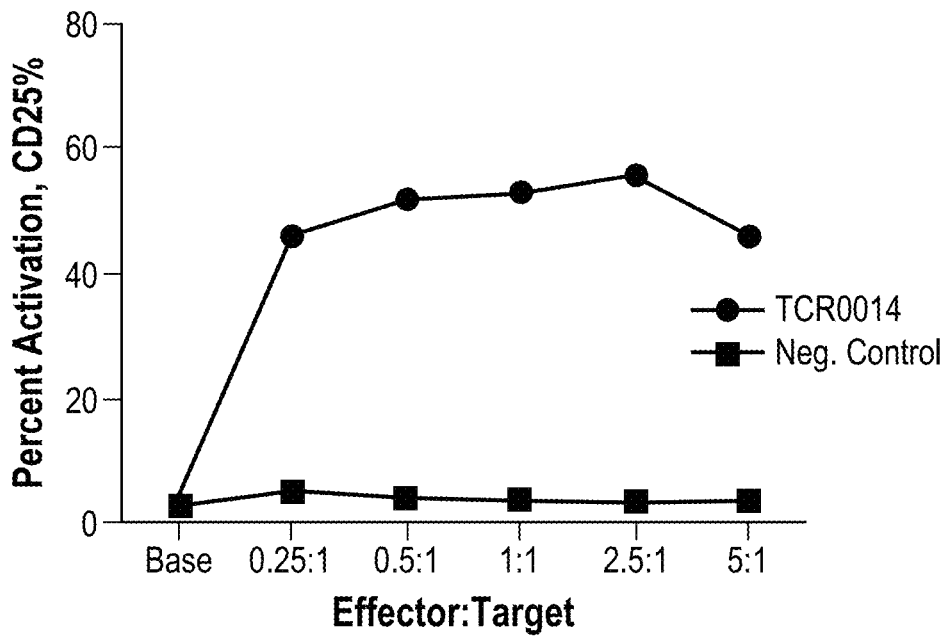
Figure 16D:
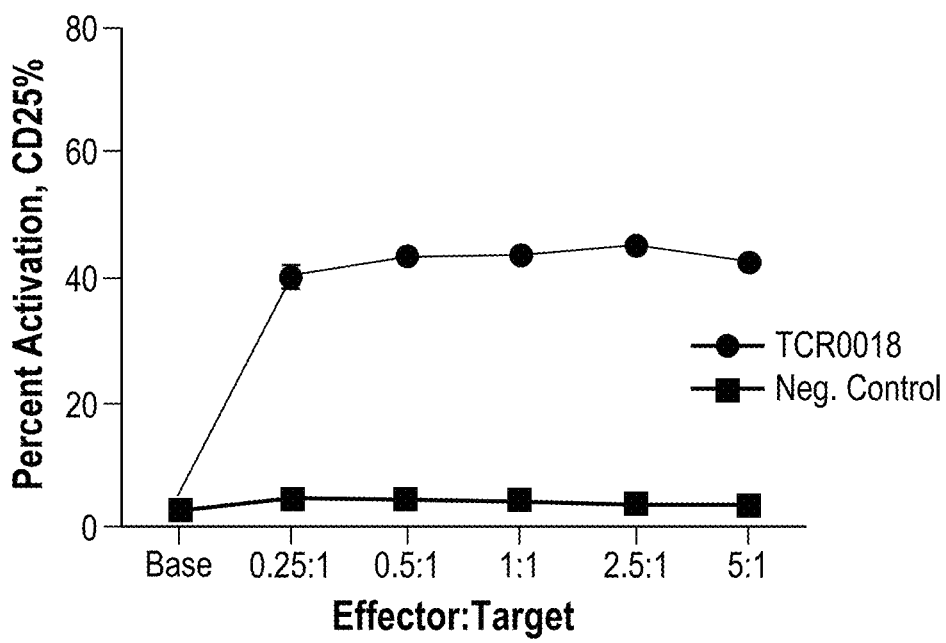
Figure 16E:
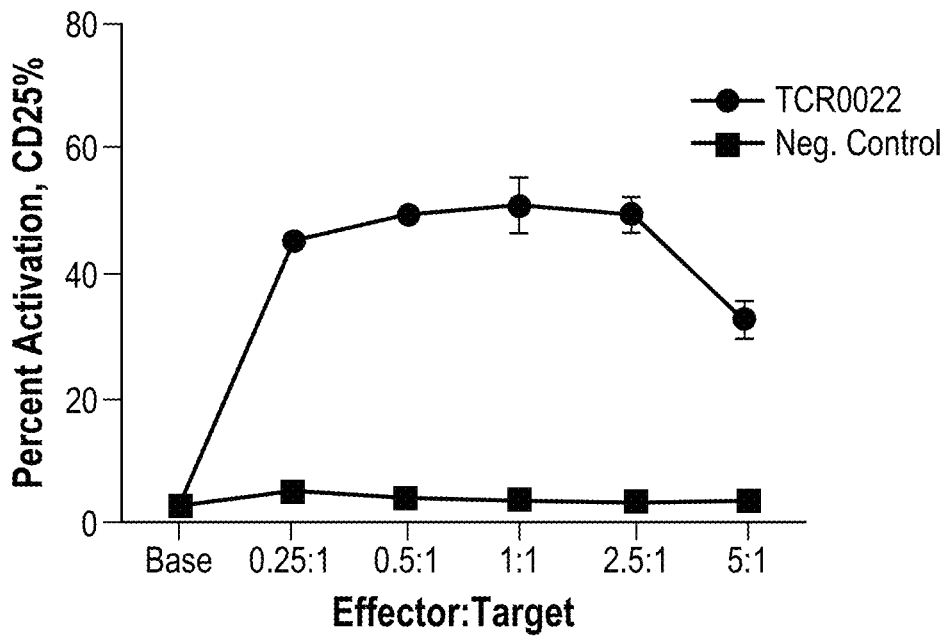
Figure 16F:
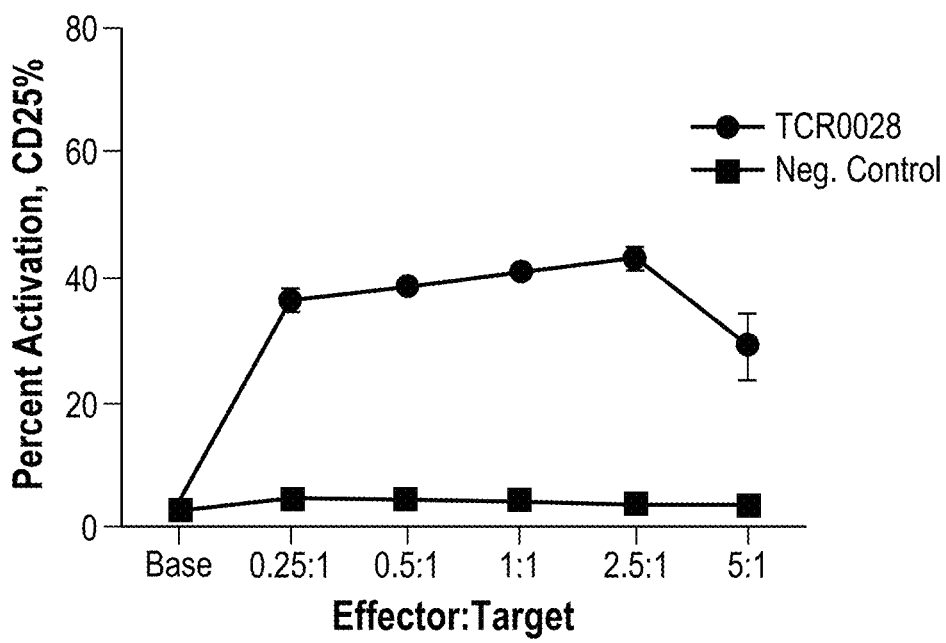

FIGS. 16A-16F are a set of graphs showing the percentage of CD25 expression, a marker of activation, following co-culture of TCR-transfected T cells with SLM2-mel melanoma cells, which express endogenous levels of HLA-A*0201 and NY-ESO-1, in varying ratios. Percent activation values for each of the indicated TCR candidates (FIG. 16A: reference TCR; FIG. 16B: TCR0002; FIG. 16C: TCR0014; FIG. 16D: TCR0018; FIG. 16E: TCR0022; and FIG. 16F: TCR0028) were plotted at varying effector-to-target ratios, varying the number of transfected T cells while maintaining a constant number of target cells.

Figure 17A:
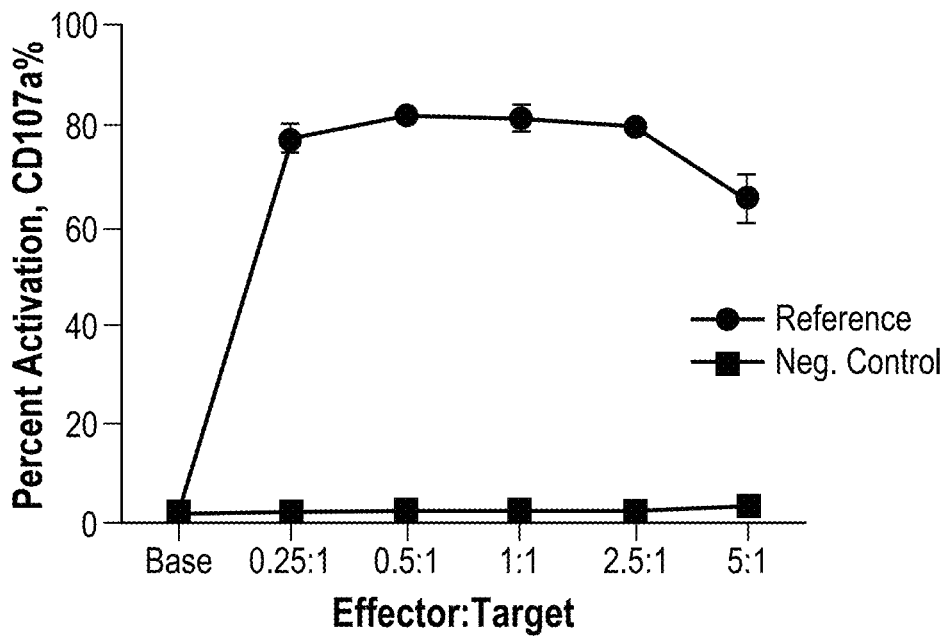
Figure 17B:
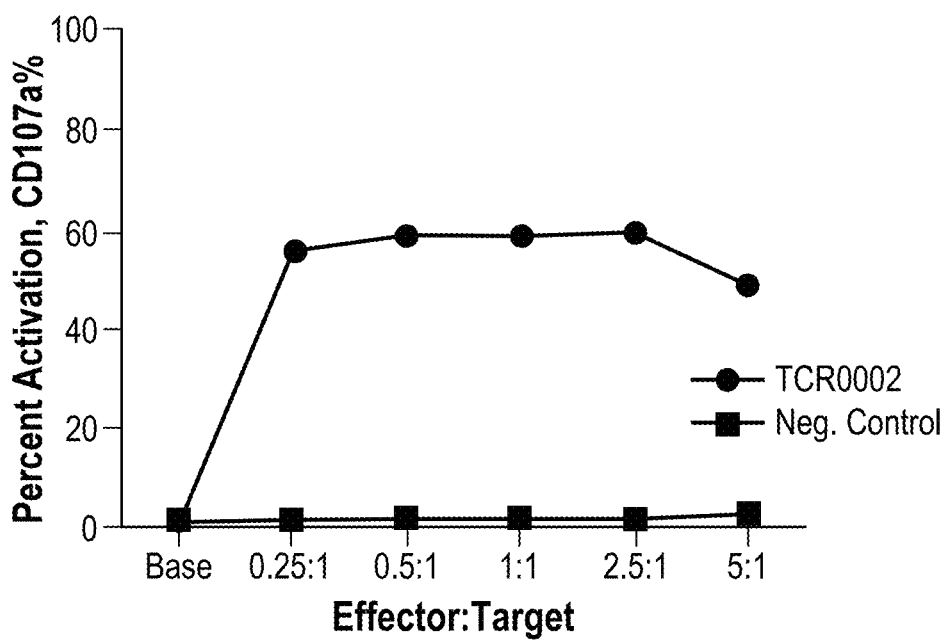
Figure 17C:
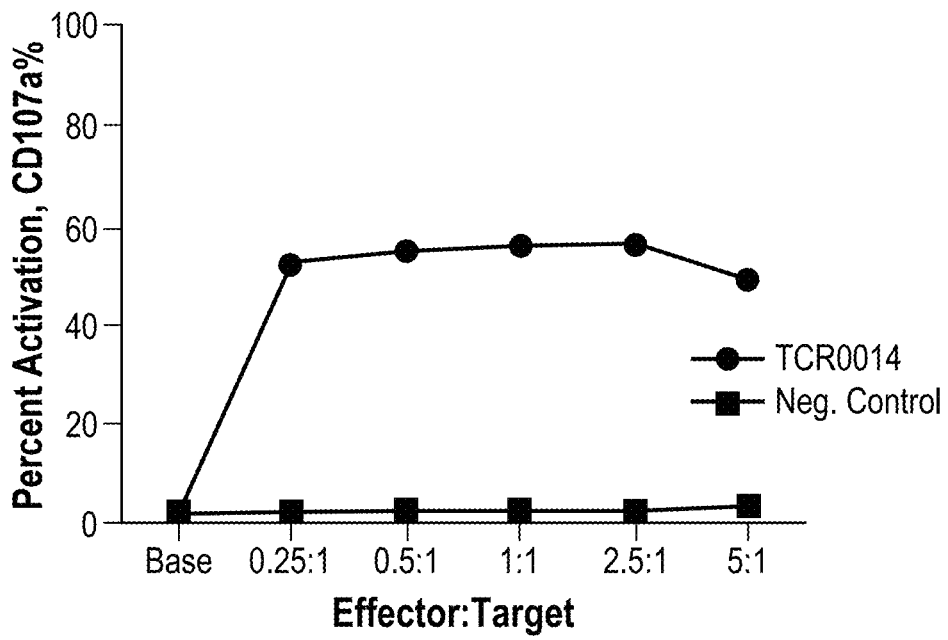
Figure 17D:
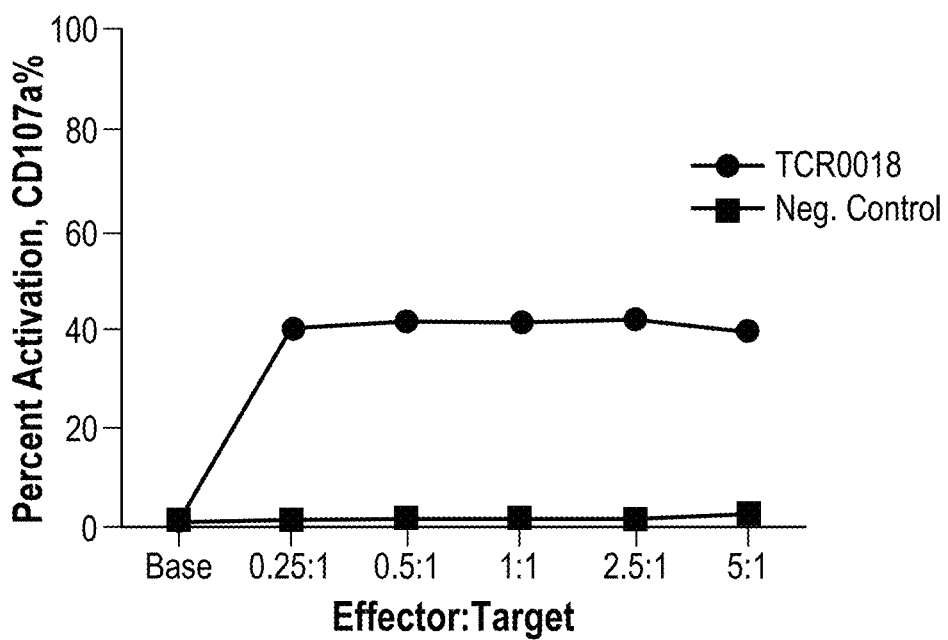
Figure 17E:
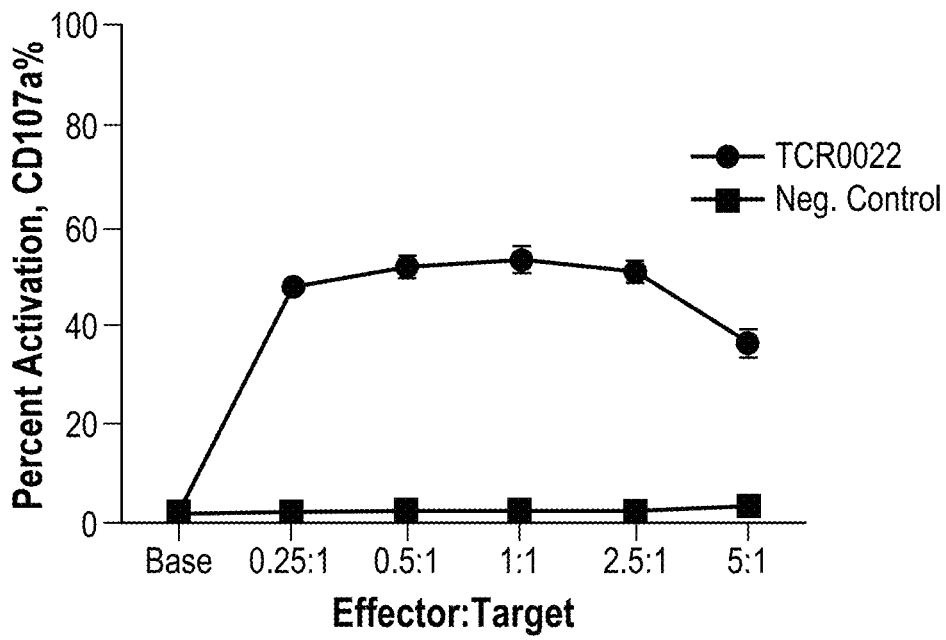
Figure 17F:
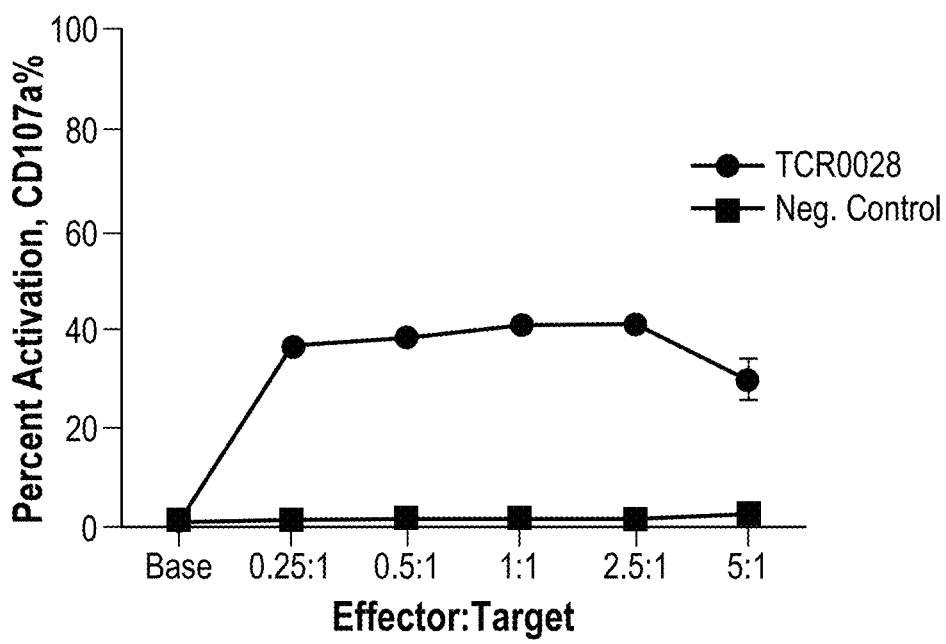

FIGS. 17A-17F are a set of graphs showing the percentage of CD107a expression, a marker of cytolytic potential and degranulation, when transfected T cells were co-cultured with SLM2-mel cells in varying ratios. Percent activation values for each of the indicated TCR candidates (FIG. 17A: reference TCR; FIG. 17B: TCR0002; FIG. 17C: TCR0014; FIG. 17D: TCR0018; FIG. 17E: TCR0022; and FIG. 17F: TCR0028) were plotted at varying effector-to-target ratios, varying the number of transfected T cells while maintaining a constant number of target cells.

Figure 18A:
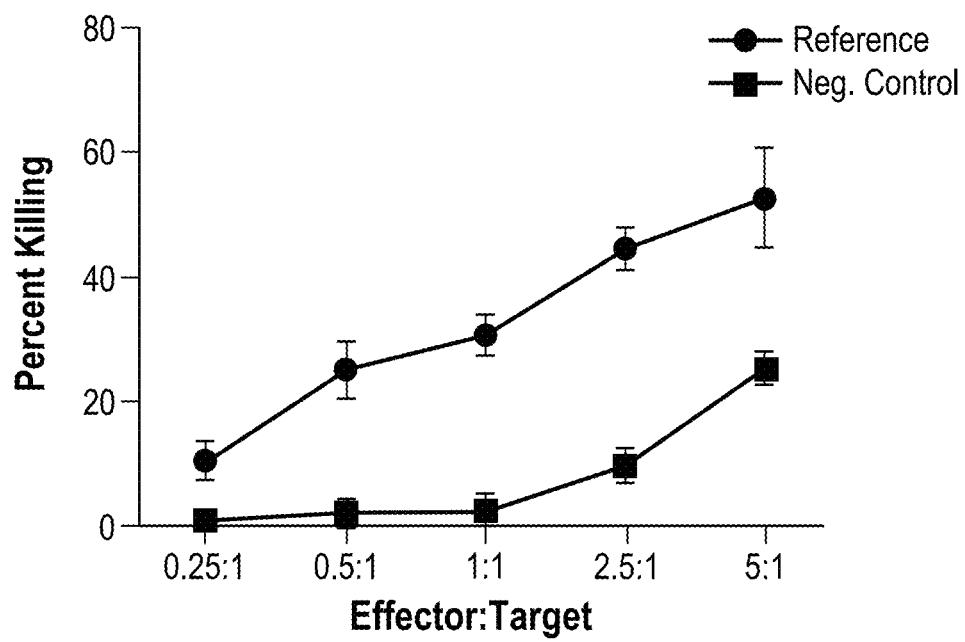
Figure 18B:
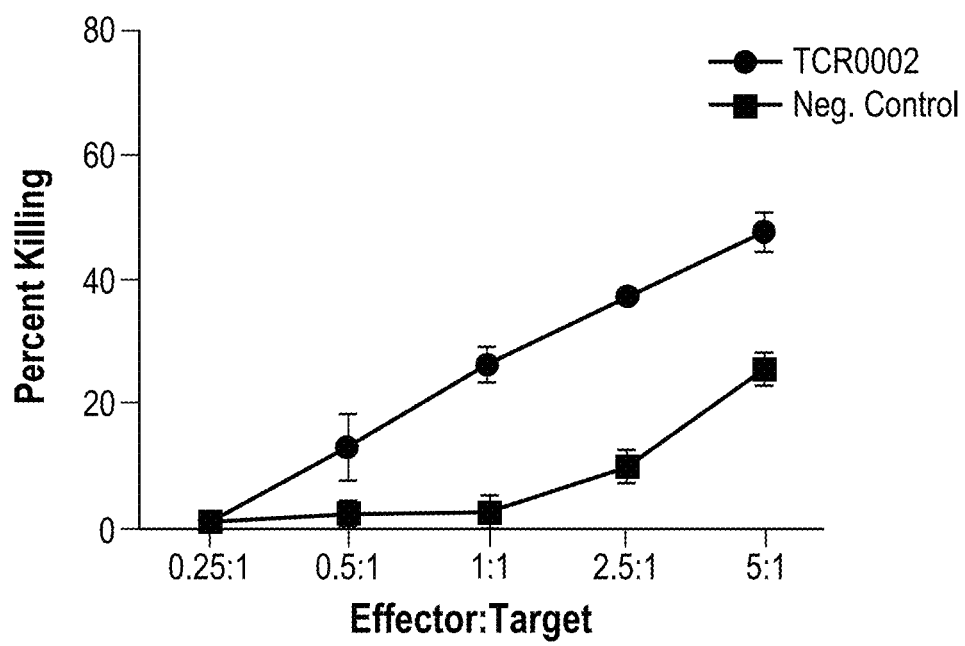
Figure 18C:
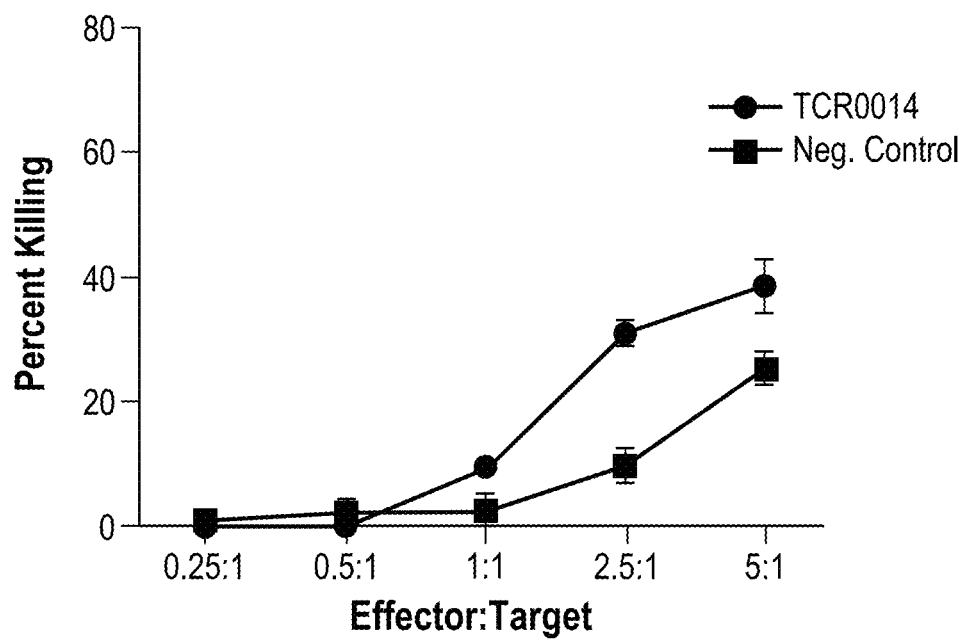
Figure 18D:
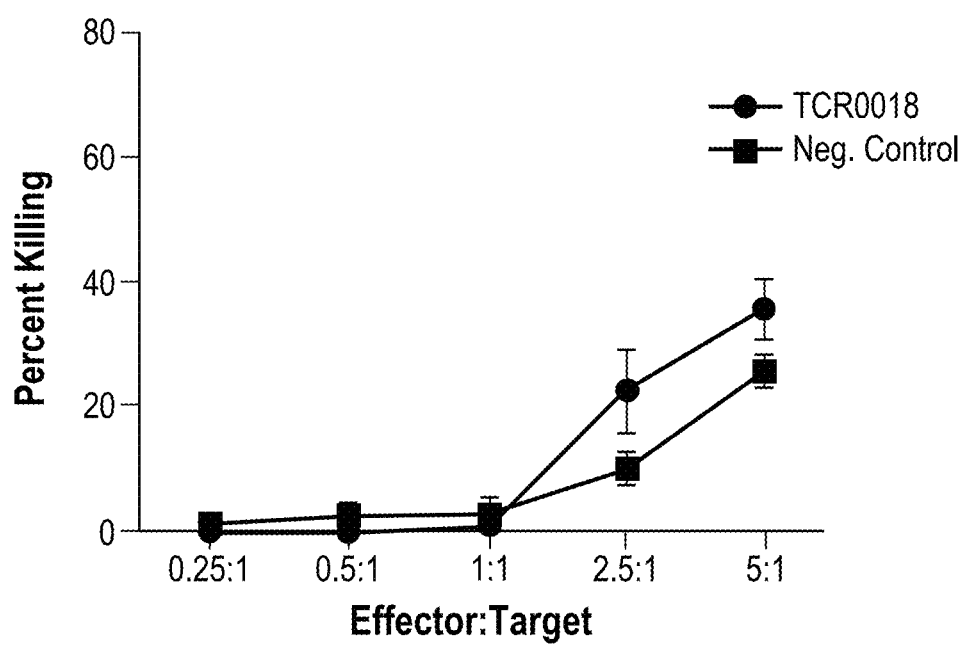
Figure 18E:
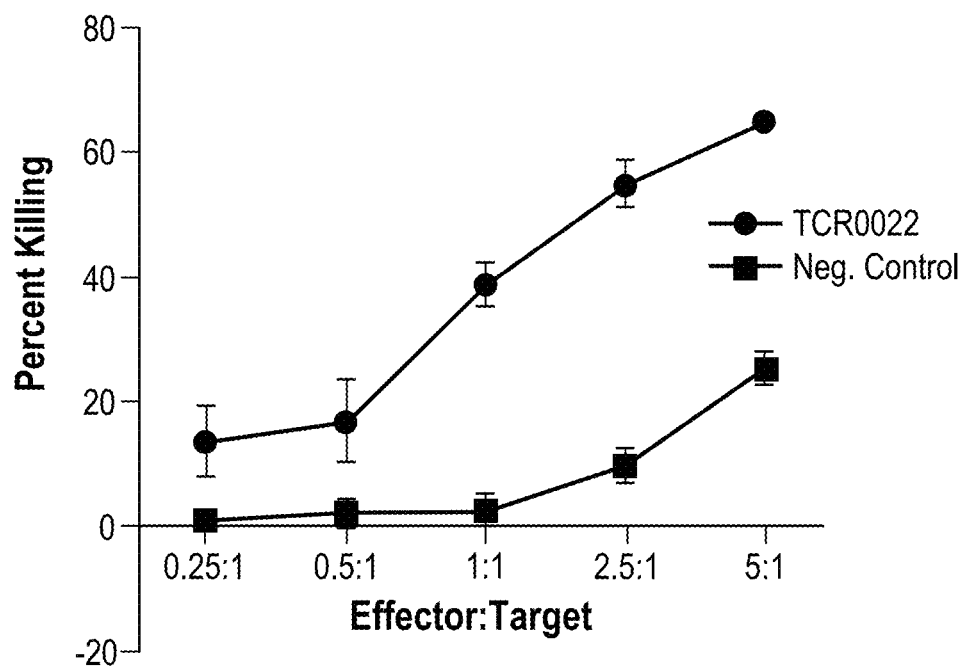
Figure 18F:
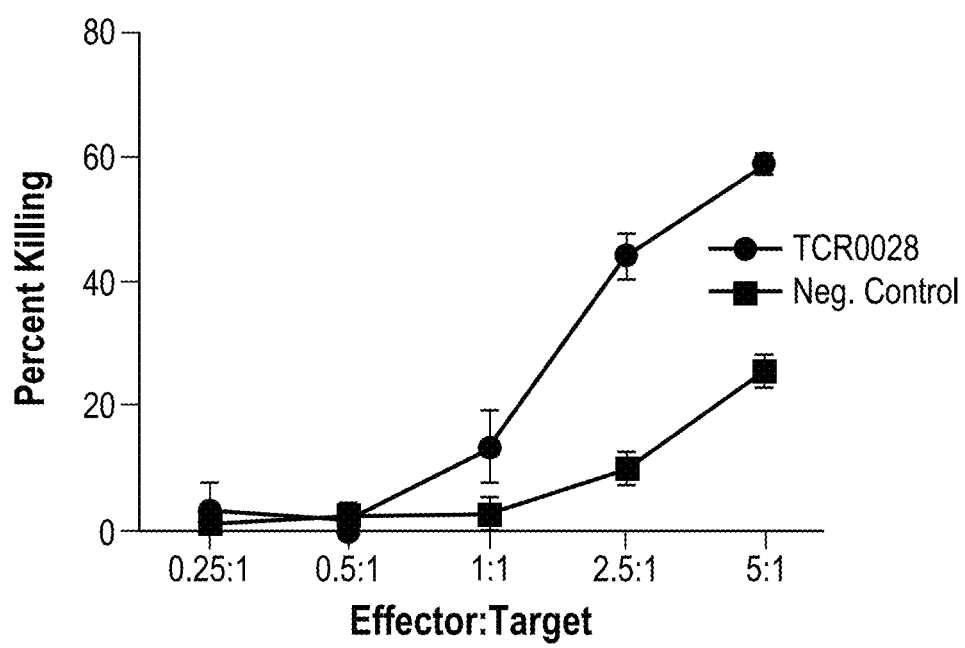

FIGS. 18A-18F are a set of graphs showing percentage killing of SLM2-mel melanoma cells expressing endogenous levels of HLA-A*0201 and NY-ESO-1 peptide. Cytotoxicity values for each of the indicated TCR candidates (FIG. 18A: reference TCR; FIG. 18B: TCR0002; FIG. 18C: TCR0014, FIG. 18D: TCR0018, FIG. 18E: TCR0022; and FIG. 18F: TCR0028) were plotted at varying effector-to-target ratios, varying the number of transfected T cells while maintaining a constant number of target cells.

Figures 19A, 19B:
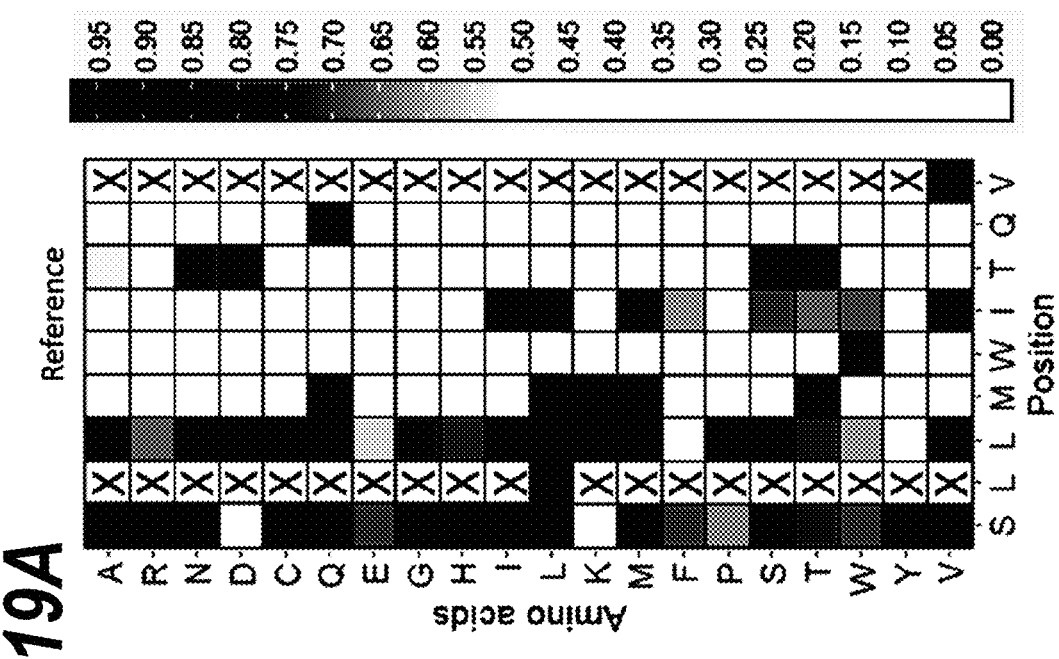
Figure 19C:
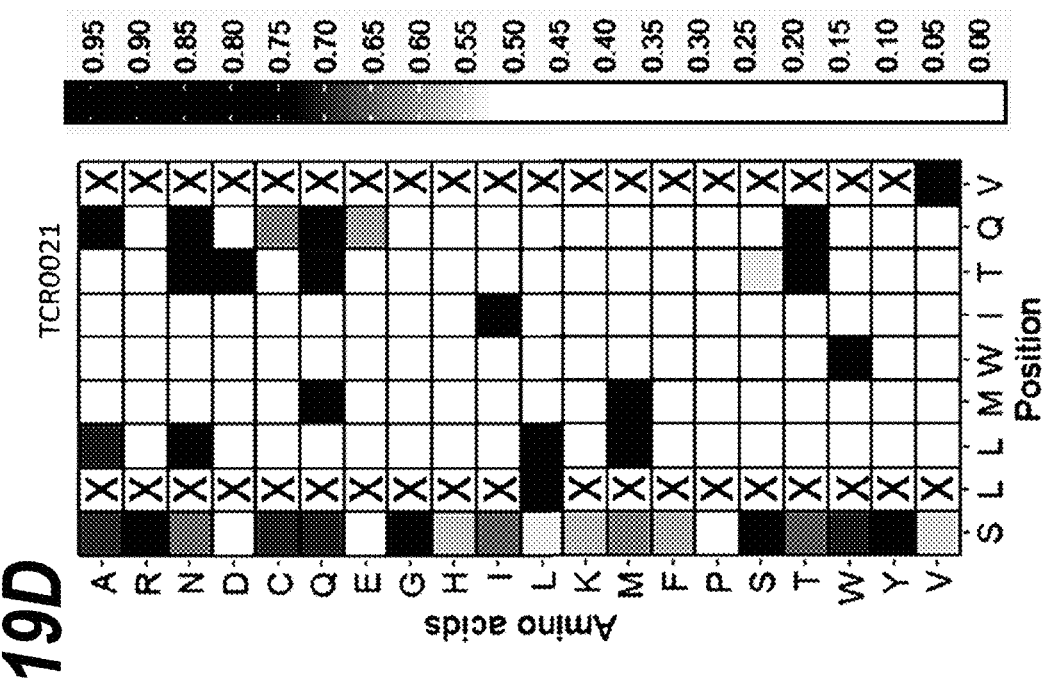
Figure 19D:
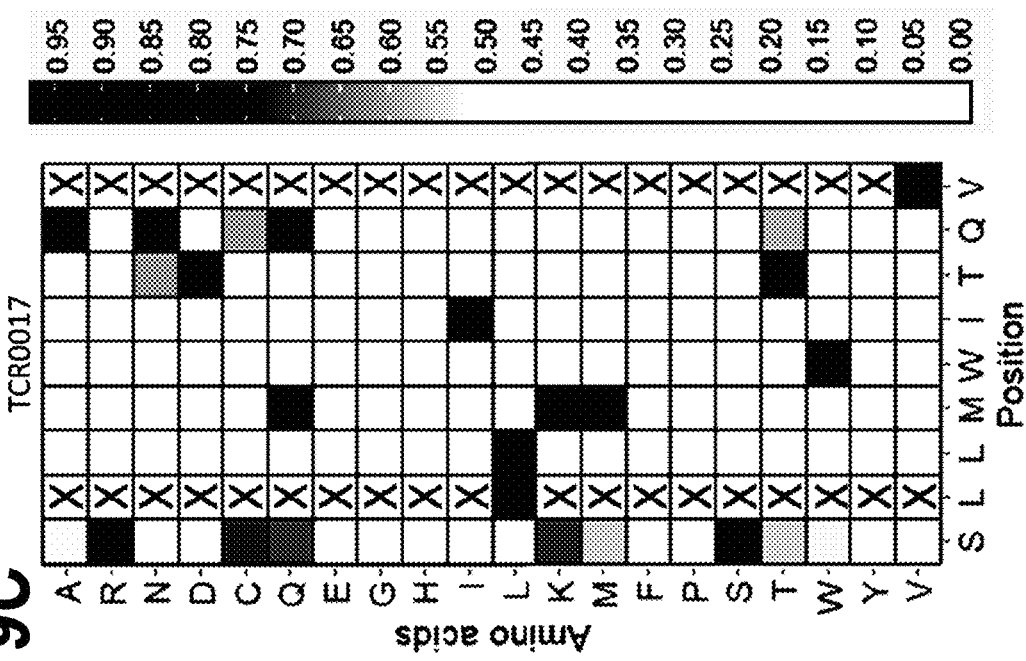
Figure 19E:
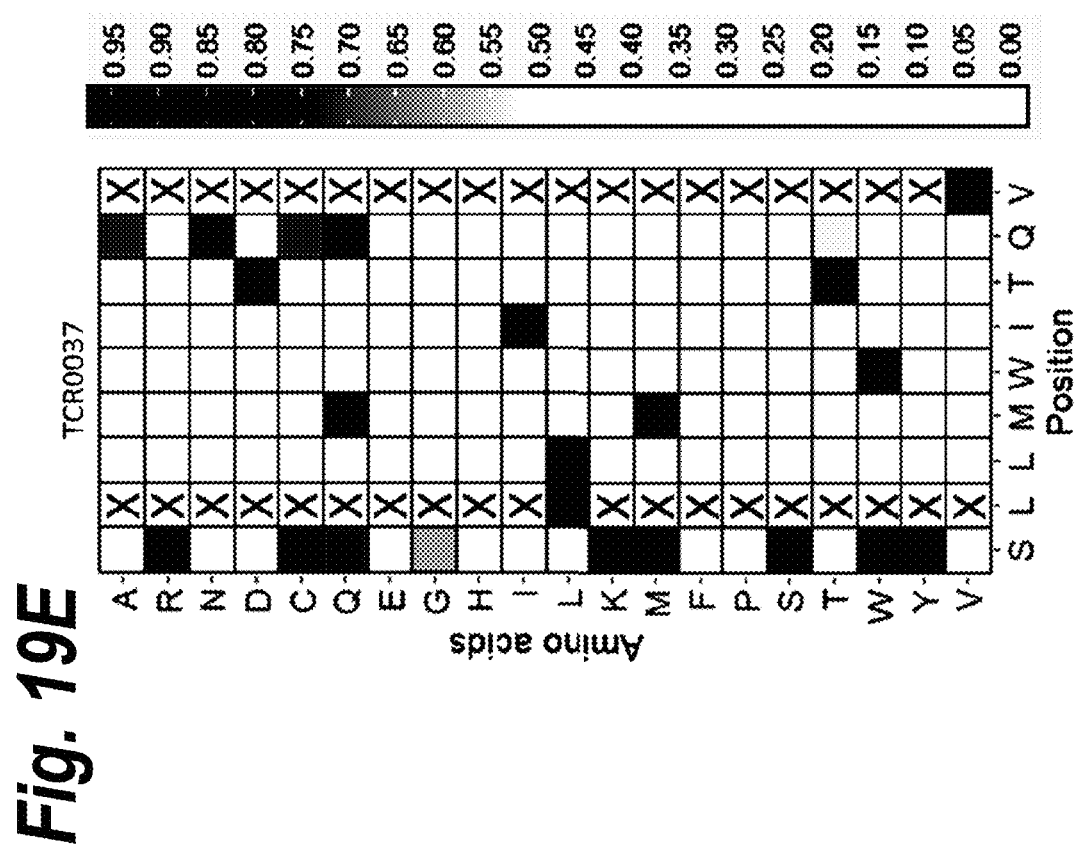

FIGS. 19A-19E are a set of heat maps comparing specificities of the indicated TCRs (FIG. 19A: reference TCR; FIG. 19B: TCR0001; FIG. 19C: TCR0017; FIG. 19D: TCR0021; FIG. 19E: TCR0037) to a group of 9-mer peptides which are single point mutations of the anchor-optimized NY-ESO-1 peptide SLLMWITQV (SEQ ID NO: 2). Each position (except for P2 and P9) of the 9-mer peptide was substituted with one of 19 different amino acid residues. Each resulting peptide was used to pulse T2 target cells, which were co-cultured with TCR-expressing effector cells (NY-ESO AK-D10R3 cells). Upon binding of the TCR to a resulting mutant peptide, the effector cells were activated to express an EGFP reporter, which was detected by FACS. The results are shown as heat maps in which each block, representing the amino acid residue substitution of the native residue in the anchor-optimized NY-ESO-1 peptide SLLMWITQV (SEQ ID NO: 2) on the horizontal axis in place of the residue indicated on the vertical axis, is shaded in scale to the normalized mean activation (with normalized values cropped to a minimum of 0.0 and to a maximum of 1.0). "X" denotes untested mutants. Background activation (no peptide loaded) was subtracted from all peptide-loaded samples (altered and native sequences).

Figure 20A:
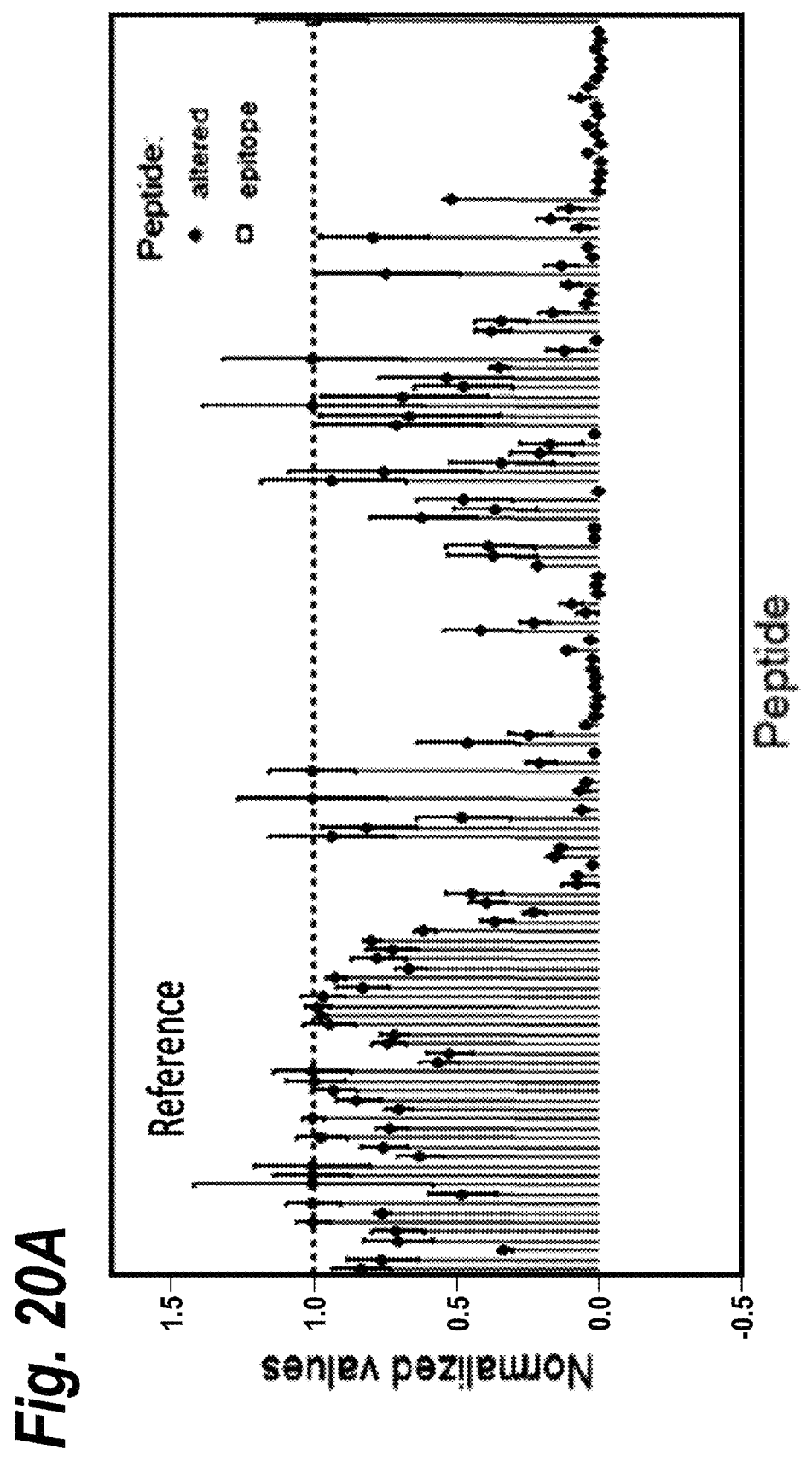
Figure 20B:
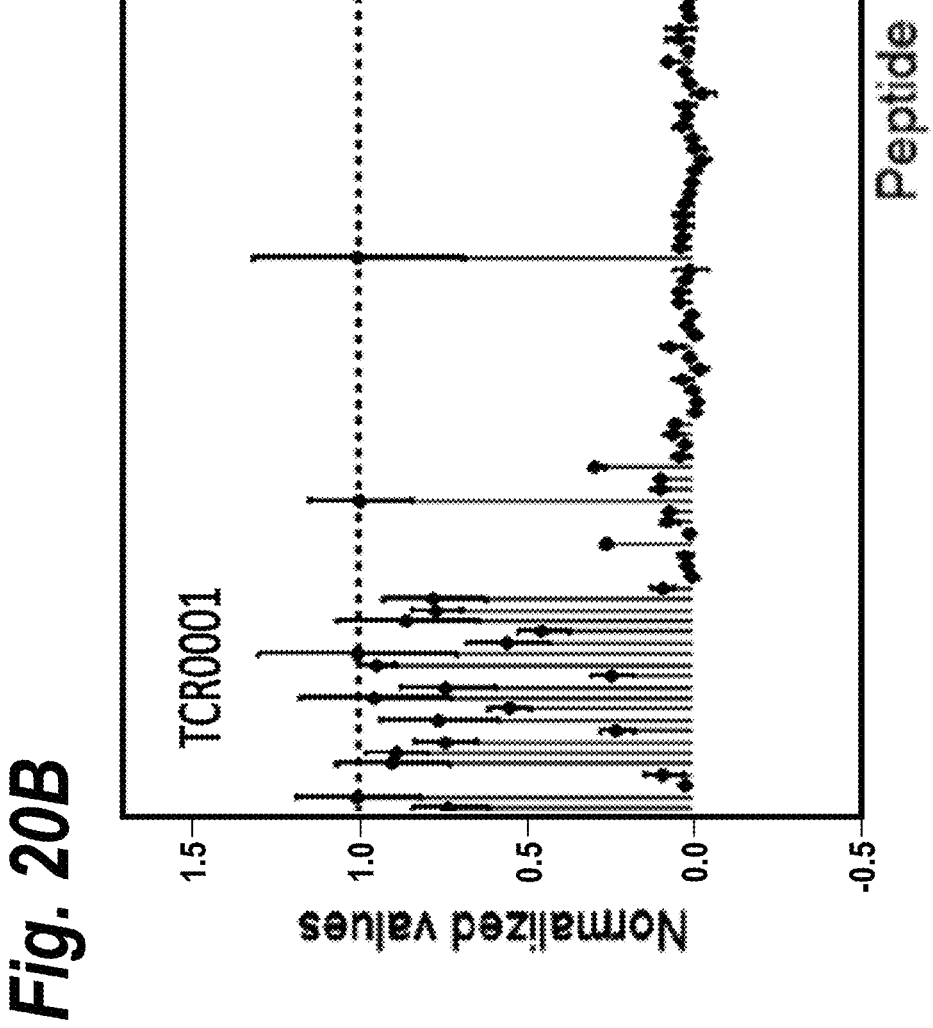
Figure 20C:
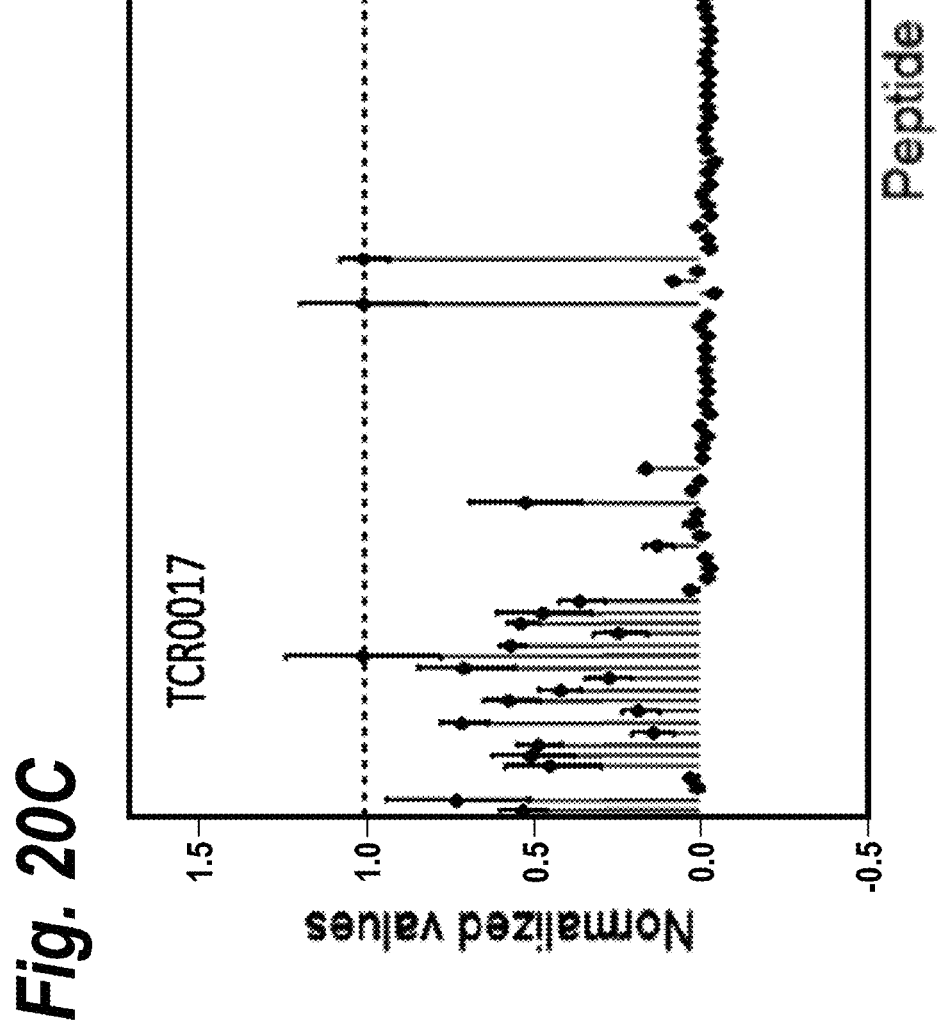
Figure 20D:
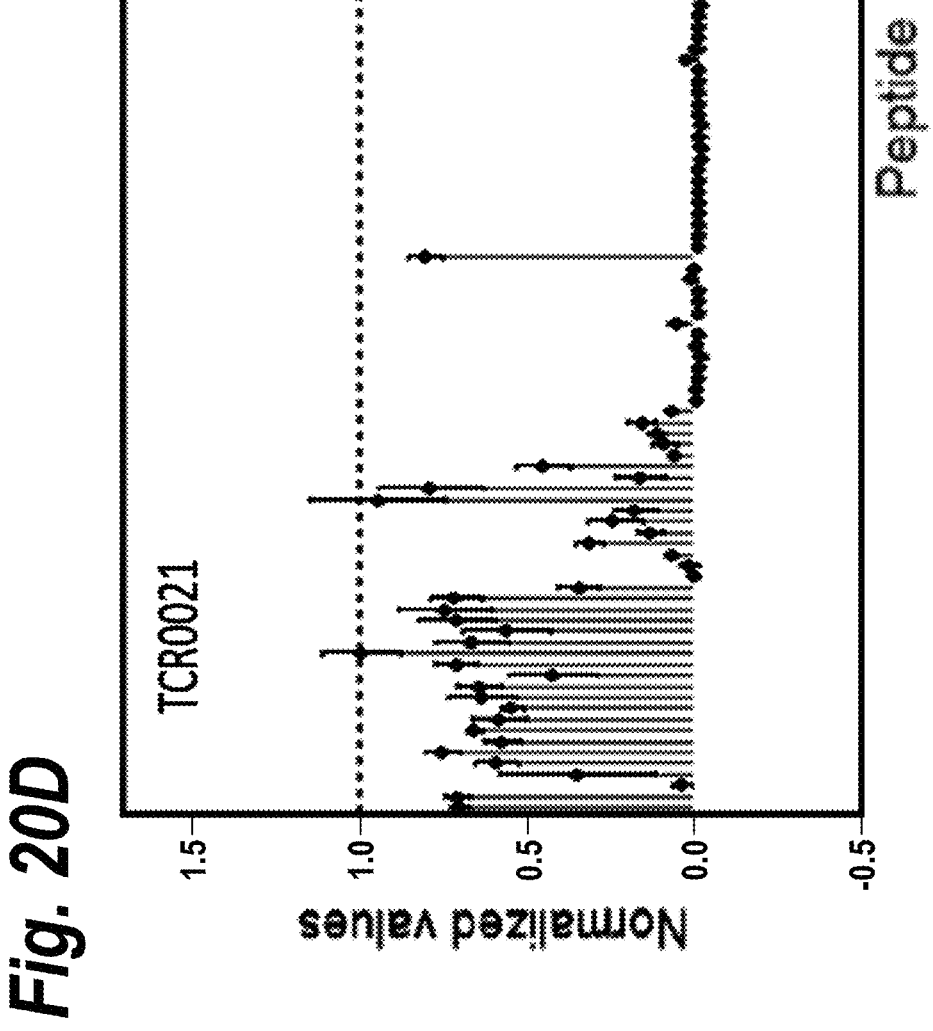
Figure 20E:
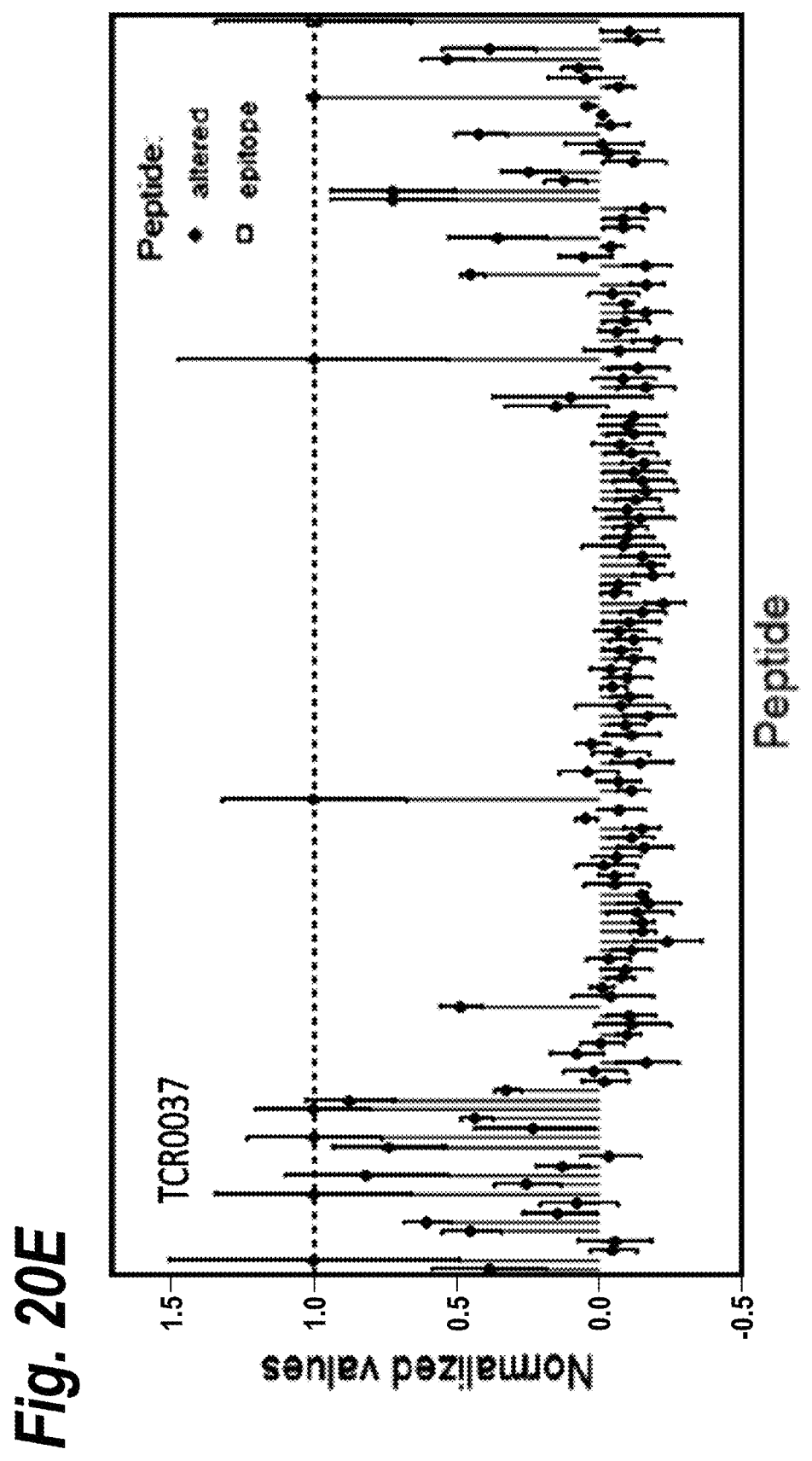

FIGS. 20A-20E are a set of bar graphs comparing the specificity profiles of the indicated TCRs (FIG. 20A: reference TCR; FIG. 20B: TCR0001; FIG. 20C: TCR0017; FIG. 20D: TCR0021; FIG. 20E: TCR0037) showing normalized mean activation values for each mutant NY-ESO-1 peptide (black diamond, "altered") as described for FIGS. 19A-19E, as well as the cognate anchor-optimized NY-ESO-1 peptide SLLMWITQV (SEQ ID NO: 2) (open square, "epitope"). Normalized mean activation values (cropped to a maximum of 1.0) corresponding to the peptides of SEQ ID NOs: 275-407 are displayed, left to right, in the sequential increasing order of the SEQ NOs., except for the "epitope" peptide value 1:5 corresponding to the anchor-optimized NY-ESO-1 peptide SLLMWITQV (SEQ ID NO: 2), which is shown at the far right of each figure. Error bars (black) represent the standard error of the mean (SEM).

5. DETAILED DESCRIPTION

Provided are TCRs (e.g., TCRs that bind to NY-ESO-1), cells and pharmaceutical compositions comprising these TCRs, nucleic acids encoding these TCRs, expression vectors and host cells for making these TCRs, and methods of treating a subject using these TCRs. The TCRs disclosed herein are particularly useful for directing an immune response against cancer cells expressing NY-ESO-1, and hence for treating an NY-ESO-1-expressing cancer in a subject.

5.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "NY-ESO-1" refers to a human cancer/testis antigen encoded by a CTAG1A or CTAG1B gene.

As used herein, the terms "T cell receptor" and "TCR" are used interchangeably and refer to molecules comprising CDRs or variable regions from αβ or γδ T cell receptors. Examples of TCRs include, but are not limited to, full-length TCRs, antigen-binding fragments of TCRs, soluble TCRs lacking transmembrane and cytoplasmic regions, single-chain TCRs containing variable regions of TCRs attached by a flexible linker, TCR chains linked by an engineered disulfide bond, single TCR variable domains, single peptide-MHC-specific TCRs, multi-specific TCRs (including bispecific TCRs), TCR fusions, TCRs comprising co-stimulatory regions, human TCRs, humanized TCRs, chimeric TCRs, recombinantly produced TCRs, and synthetic TCRs. In certain embodiments, the TCR is a full-length TCR comprising a full-length α chain and a full-length β chain. In certain embodiments, the TCR is a soluble TCR lacking transmembrane and/or cytoplasmic region(s). In certain embodiments, the TCR is a single-chain TCR (scTCR) comprising Vα and Vβ linked by a peptide linker, such as a scTCR having a structure as described in PCT Publication No.: WO 2003/020763, WO 2004/033685, or WO 2011/044186, each of which is incorporated by reference herein in its entirety. In certain embodiments, the TCR comprises a transmembrane region. In certain embodiment, the TCR comprises a co-stimulatory signaling region.

As used herein, the term "full-length TCR" refers to a TCR comprising a dimer of a first and a second polypeptide chain, each of which comprises a TCR variable region and a TCR constant region comprising a TCR transmembrane region and a TCR cytoplasmic region. In certain embodiments, the full-length TCR comprises one or two unmodified TCR chains, e.g., unmodified α, β, γ, or δ TCR chains. In certain embodiments, the full-length TCR comprises one or two altered TCR chains, such as chimeric TCR chains and/or TCR chains comprising one or more amino acid substitutions, insertions, or deletions relative to an unmodified TCR chain. In certain embodiments, the full-length TCR comprises a mature, full-length TCR α chain and a mature, full-length TCR β chain. In certain embodiments, the full-length TCR comprises a mature, full-length TCR γ chain and a mature, full-length TCR δ chain.

As used herein, the term "TCR variable region" refers to the portion of a mature TCR polypeptide chain (e.g., a TCR α chain or β chain) which is not encoded by the TRAC gene for TCR α chains, either the TRBC1 or TRBC2 genes for TCR β chains, the TRDC gene for TCR δ chains, or either the TRGC1 or TRGC2 gene for TCR γ chains. In some embodiments, the TCR variable region of a TCR α chain encompasses all amino acids of a mature TCR α chain polypeptide which are encoded by a TRAV and/or TRAJ gene, and the TCR variable region of a TCR β chain encompasses all amino acids of a mature TCR β chain polypeptide which are encoded by a TRBV, TRBD, and/or TRBJ gene (see, e.g., *T cell receptor Factsbook*, (2001) LeFranc and LeFranc, Academic Press, ISBN 0-12-441352-8, which is incorporated by reference herein in its entirety). TCR variable regions generally comprise framework regions (FR) 1, 2, 3 and 4 and complementarity determining regions (CDR) 1, 2 and 3.

As used herein, the terms "α chain variable region" and "Vα" are used interchangeably and refer to the variable region of a TCR α chain.

As used herein, the terms "β chain variable region" and "Vβ" are used interchangeably and refer to the variable region of a TCR β chain.

As used herein in the context of a TCR, the term "CDR" or "complementarity determining region" means the non-contiguous antigen combining sites found within the variable regions of a TCR chain (e.g., an α chain or β chain). These regions have been described in Lefranc, (1999) The Immunologist 7: 132-136, Lefranc et al., (1999) Nucleic Acids Res 27: 209-212, Lefranc (2001) *T cell receptor Factsbook*, Academic Press, ISBN 0-12-441352-8, Lefranc et al., (2003) Dev Comp Immunol. 27(1):55-77, and in Kabat et al., (1991) *Sequences of protein of immunological*

*interest*, each of which is herein incorporated by reference in its entirety. In certain embodiments, CDRs are determined according to the IMGT numbering system described in Lefranc (1999) supra. In certain embodiments, CDRs are defined according to the Kabat numbering system described in Kabat supra. In certain embodiments, CDRs are defined empirically, e.g., based upon a structural analysis of the interaction of a TCR with a cognate antigen (e.g., a peptide or a peptide-MHC complex). In certain embodiments, the α chain and β chain CDRs of a TCR are defined according to different conventions (e.g., according to the Kabat or IMGT numbering systems, or empirically based upon structural analysis).

As used herein, the term "framework amino acid residues" refers to those amino acids in the framework region of a TCR chain (e.g., an α chain or a β chain). The tetra "framework region" or "FR" as used herein includes the amino acid residues that are part of the TCR variable region, but are not part of the CDRs.

As used herein, the term "constant region" with respect to a TCR refers to the portion of a TCR that is encoded by the TRAC gene (for TCR α chains), either the TRBC1 or TRBC2 gene (for TCR β chains), the TRDC gene (for TCR δ chains), or either the TRGC1 or TRGC2 gene (for TCR γ chains), optionally lacking all or a portion of a transmembrane region and/or all or a portion of a cytoplasmic region. In certain embodiments, a TCR constant region lacks a transmembrane region and a cytoplasmic region. A TCR constant region does not include amino acids encoded by a TRAV, TRAJ, TRBV, TRBD, TRBJ, TRDV, TRDD, TRDJ, TRGV, or TRGJ gene (see, e.g., *T cell receptor Factsbook*, (2001) LeFranc and LeFranc, Academic Press, ISBN 0-12-441352-8, which is incorporated by reference herein in its entirety).

As used herein, the terms "major histocompatibility complex" and "MHC" are used interchangeably and refer to an MHC class I molecule and/or an MHC class II molecule.

As used herein, the term "MHC class I" refers to a dimer of an MHC class I α chain and a β2 microglobulin chain and the term "MHC class II" refers to a dimer of an MHC class II α chain and an MHC class II β chain.

As used herein, the term "peptide-MHC complex" refers to an MHC molecule (MHC class I or MHC class II) with a peptide bound in the art-recognized peptide binding pocket of the MHC. In some embodiments, the MHC molecule is a membrane-bound protein expressed on cell surface. In some embodiments, the MHC molecule is a soluble protein lacking transmembrane or cytoplasmic regions.

As used herein, the term "extracellular" with respect to TCR refers to the portion or portions of a recombinant transmembrane protein that are located outside of a cell.

As used herein, the term "transmembrane" with respect to a TCR chain refers to the portion or portions of a TCR chain that are embedded in the plasma membrane of a cell.

As used herein, the term "cytoplasmic" with respect to a TCR chain refers to the portion or portions of a TCR chain that are located in the cytoplasm of a cell.

As used herein, the term "co-stimulatory signaling region" refers to the intracellular portion of a co-stimulatory molecule that is responsible for mediating intracellular signaling events.

"Binding affinity" generally refers to the strength of the sum total of non-covalent interactions between a single binding site of a molecule (e.g., a TCR) and its binding partner (e.g., a peptide-MHC complex). Unless indicated otherwise, as used herein, "binding affinity" refers to intrinsic binding affinity which reflects a 1:1 interaction between members of a binding pair (e.g., a TCR and a peptide-MHC complex). The affinity of a molecule X for its partner Y can generally be represented by the dissociation constant ($K_D$). Affinity can be measured and/or expressed in a number of ways known in the art, including, but not limited to, equilibrium dissociation constant ($K_D$) and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., a TCR to a peptide-MHC complex, and $k_{off}$ refers to the dissociation rate constant of, e.g., a TCR to a peptide-MHC complex. The $k_{on}$ and $k_{off}$ can be determined by techniques known to one of ordinary skill in the art, such as use of BIAcore® or KinExA. As used herein, a "lower affinity" refers to a larger $K_D$.

As used herein, the term "specifically binds to" refers to the ability of a TCR to preferentially bind to a particular antigen (e.g., a specific peptide or a specific peptide-MHC complex combination) as such binding is understood by one skilled in the art. For example, a TCR that specifically binds to an antigen can bind to other antigens, generally with lower affinity as determined by, e.g., BIAcore®, or other immunoassays known in the art (see, e.g., Savage et al., Immunity. 1999, 10(4):485-92, which is incorporated by reference herein in its entirety). In a specific embodiment, a TCR that specifically binds to an antigen binds to the antigen with an association constant ($K_a$) that is at least 2-fold, 5-fold, 10-fold, 50-fold, 100-fold, 500-fold, 1,000-fold, 5,000-fold, or 10,000-fold greater than the $K_a$ when the TCR binds to another antigen. In certain embodiments, the TCRs disclosed herein specifically hind to a peptide consisting of the amino acid sequence set forth in SEQ ID NO: 1 or 2.

As used herein, an "epitope" is a term in the art and refers to a localized region of an antigen (e.g., a peptide or a peptide-MHC complex) to which a TCR can bind. In certain embodiments, the epitope to which a TCR binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), flow cytometry analysis, mutagenesis mapping (e.g., site-directed mutagenesis mapping), and/or structural modeling. For X-ray crystallography, crystallization may be accomplished using any of the known methods in the art (e.g., Giege R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). TCR:antigen crystals may be studied using well-known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), each of which is herein incorporated by reference in its entirety. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. In a specific embodiment, the epitope of an antigen is determined using alanine scanning mutagenesis studies. In a specific embodiment, the epitope of an antigen is determined using hydrogen/deuterium exchange coupled with mass spectrometry. In certain embodiments, the antigen is a peptide-MHC complex. In certain embodiments, the antigen is a peptide presented by an MHC molecule.

As used herein, the terms "treat," "treating," and "treatment" refer to therapeutic or preventative measures described herein. In some embodiments, the methods of "treatment" employ administration of a TCR or a cell expressing a TCR to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., at score=100, wordlength=12 to obtain nucleotide sequences homologous to a nucleic acid molecule described herein. BLAST protein searches can be performed with the XBLAST program parameters set, e.g., at score=50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules. Id. When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "effector moiety" refers to a component or functional group of a molecule that increases or decreases a natural activity of the molecule, or confers a novel activity upon the molecule. In certain embodiments, the effector moiety is a binding moiety. In an embodiment, the binding moiety binds to a cell surface protein. In certain embodiments, the binding moiety is an antibody.

As used herein, the terms "antibody" and "antibodies" include full-length antibodies, antigen-binding fragments of full-length antibodies, and molecules comprising antibody CDRs, VH regions or YL regions. Examples of antibodies include monoclonal antibodies, recombinantly produced antibodies, monospecific antibodies, multi-specific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')$_2$ fragments, disulfide-linked Fvs (sdfv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g. IgG, IgE, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

5.2 T-Cell Receptors

In one aspect, the instant disclosure provides TCRs that bind to a peptide consisting of the amino acid sequence of SLLMWITQC (SEQ ID NO: I) or its anchor-optimized variant SLLMWITQV (SEQ ID NO: 2). In certain embodiments, the TCR specifically binds to a peptide consisting of the amino acid sequence of SLLMWITQC (SEQ ID NO: 1) or its anchor-optimized variant SLLMWITQV (SEQ ID NO: 2). In certain embodiments, the TCR hinds to a peptide-MHC complex comprising a peptide consisting of the amino acid sequence of SLLMWITQC (SEQ ID NO: 1) or its anchor-optimized variant SLLMWITQV (SEQ ID NO: 2). In certain embodiments, the TCR specifically binds to the peptide-MHC complex comprising a peptide consisting of the amino acid sequence set forth in SEQ ID NO: 1 or 2. In one aspect, the instant, disclosure provides TCRs that, bind to SLLMWITQC (SEQ ID NO: 1) or SLLMWITQV (SEQ ID NO: 2) presented by a major histocompatibility complex (MHC) molecule. In one aspect, the instant disclosure provides TCRs that bind to a SLLMWITQC (SEQ ID NO: 1)-HLA-A*0201 complex or a SLLMWITQV (SEQ ID NO: 2)-HLA-A*0201 complex. The amino acid sequences of exemplary TCRs are set forth in Table 1, herein.

TABLE 1

Amino acid and nucleic acid sequences of exemplary TCRs*.

| SEQ ID NO: | Description (protein sequences unless otherwise indicated) | Sequence |
|---|---|---|
| 3 | TCR18168 α chain variable region | QSVAQPEDQVNVAEGNPLTVKCTYSVSGNPYLFWYVQYP NRGLQFLLKYITGDNLVKGSYGFEAFNKSQTSFHLKKPSA LVSDSALYFCAVRELYSGAGSYQLTFGKGTKLSVIP |
| 4 | TCR18168 β chain variable region | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVL |
| 5 | TCR18168 CDR1α | VSGNPY |
| 6 | TCR18168 CDR2α | YITGDNLV |
| 7 | TCR18168 CDR3α | RELYSGAGSYQLT |
| 8 | TCR18168 CDR1β | SQVTM |
| 9 | TCR18168 CDR2β | ANQGSEA |
| 10 | TCR18168 CDR3β | SVGGAGVTDTQY |
| 11 | TCR18168 α chain chimeric full-length sequence | QSVAQPEDQVNVAEGNPLTVKCTYSVSGNPYLFWYVQYP NRGLQFLLKYITGDNLNKGSYGFEAEFNKSQTSFHLKKPSA LVSDSALYFCAVRELYSGAGSYQLTFGKGTKLSVIPYIQNP EPAVYQLKDPRSQDSTLCLFTDFDSQINVPKTMESGTFTID KTVLDMKAMDSKSNGAIAWSNQTSFTCQDIFKETNATYPS SDVPCDATLTEKSFETDMNLNFQNLSVMGLRILLLKVAGF NLLMTLRLWSS |
| 12 | TCR18168 β chain chimeric full-length sequence | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVEDLRNVTPPKVSLF EPSKAEIANKQKATLVCLARGFFPDHVELSWWVNGKEVHS GVSTDPQAYKESNYSYCLSSRLRVSATFWHNPRNHFRCQV QFHGLSEEDKWPEGSPKPVTQNISAEAWGRADCGITSASY HQGVLSATILYEILLGKATLYAVLVSGLVLMAMVKKKNS |
| 13 | TCR18168 α chain human full-length sequence | QSVAQPEDQVNVAEGNPLTVKCTYSVSGNPYLFWYVQYP NRGLQFLLKYITGDNLVKGSYGFEAFNKSQTSFHLKKPSA LVSDSALYFCAVRELYSGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSS |
| 14 | TCR18168 β chain human full-length sequence | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVEDLNKVFPPEVAVF EPSEAEISHTQKATLVCLATGFFPDHVELSWWVNGKEVHS GVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDF |
| 25 | TCR181688 β chain human full-length sequence | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVEDLKNVFPPEVAVF EPSEAEISHNKATLVCLATGFYPDHVELSWWVNGKEVHS GVSTDPQPLKEQPALNDSRYCLSSRLRVSATFWQNPRNHF RCQVQFYGLSENDEWTQDRAKPVTQIVSAEAWGRADCGF TSESYQQGVLSATILYEILLGKATLYAVLVSALVLMAMVK RKDSRG |

TABLE 1-continued

Amino acid and nucleic acid sequences of exemplary TCRs*.

| SEQ ID NO: | Description (protein sequences unless otherwise indicated) | Sequence |
|---|---|---|
| 15 | TCR α chain constant region (TRAC*01) | XIQNPDPAVYQLRDSKSSDKSVCLFTDFDSQTNVSQSKDSD VYITDKTVLDMRSMDFKSNSAVAWSNKSDFACANAFNNSI IPEDTFFPSPESSCDVKLVEKSFETDTNLNFQNLSVIGFRILL LKVAGFNLLMTLRLWSS, wherein X is N, Y, H, or D |
| 26 | TCR α chain constant region | NIQNPDPAVYQLRDSKSSDKSVCLFTDFDSQTNVSQSKDSD VYITDKTVLDMRSMDFKSNSAVAWSNKSDFACANAFNNSI IPEDTFFPSPESSCDVKLVEKSFETDTNLNFQNLSVIGFRILL LKVAGFNLLMTLRLWSS |
| 16 | TCR β chain constant region (TRBC1*01) | EDLNKVFPPEVAVFEPSEAEISHTQKATLVCLATGFFPDHV ELSWWVNGKEVHSGVSTDPQPLKEQPALNDSRYCLSSRLR VSATFWQNPRNHFRCQVQFYGLSENDEWTQDRAKPVTQI VSAEAWGRADCGFTSVSYQQGVLSATILYEIILLGKATLYA VLVSALVLMAMVKRKDF |
| 17 | TCR β chain constant region (TRBC2*01) | EDLKNVFPPEVAVFEPSEAEISHTQKATLVCLATGFYPDHV ELSWWVNGKEVHSGVSTDPQPLKEQPALNDSRYCLSSRLR VSATFWQNPRNHFRCQVQFYGLSENDEWTQDRAKPVTQI VSAEAWGRADCGFTSESYQQGVLSATILYEILLGKATLYA VLVSALVLMAMVKRKDSRG |
| 18 | TCR α chain germline sequence TRAV3*01 | QSVAQPDEDQVNVAEGNPLTVKCTYSVSGNPYLFWYVQYP NRGLQFLLKYITGDNLVKGSYGFEAEFNKSQTSFHLKKPSA LVSDSALYFCAV |
| 19 | TCR β chain germline sequence TRBV29-1*01 | QKPSRDICQRGTSLTIQCQVDSQVTMMFWYRQQPGQSLTLI ATANQGSEATYESGFVIDKFPISRPNLTFSTLTVSNMSPEDS STYLC |
| 28 | TCR18168 α chain-furin cleavage site-P2A cleavage site-TCR18168 β chain sequence | MASAPISMLAMLFTLSGLRAQSVAQPDEDQVNVAEGNPLTV KCTYSVSGNPYLFWYVQYPNRGLQFLLKYITGDNLVKGSY GFEAEFNKSQTSFHLKKPSALVSDSALYFCAVRELYSGAGS YQLTFGKGTKLSVIPNIQNPDPAVYQLRDSKSSDKSVCLFT DFDSQTNVSQSKDSDVYITDKTVLDMRSMDFKSNSAVAW SNKSDFACANAFNNSIIPEDTFFPSPESSCDVKLVEKSFETDT NLNFQNLSVIGFRILLLKVAGFNLLMTLRLWSSRAKRSGSG ATNFSLLKQAGDVEENPGPMLSLLLLLLGLGSVFSAVISQK PSRDICQRGTSLTIQCQVDSQVTMMFWYRQQPGQSLTLIAT ANQGSEATYESGFVIDKFPISRPNLTFSTLTVSNMSPEDSSIY LCSVGGAGVTDTQYFGPGTRLTVLEDLNKVFPPEVAVFEPS EAEISHTQKATLYCLATGFFPDHVELSWWVNGKEVHSGVS TDPQPLKEQPALNDSRYCLSSRLRVSATFWQNPRNHFRCQ VQFYGLSENDEWTQDRAKPVTQIVSAEAWGRADCGFTSV SYQQGVLSATILYEILLGKATLYAVLVSALVLMAMVKRKD F |
| 20 | DMF4 α chain full-length sequence | GQQLNQSPQSMFIQEGEDVSMNCTSSSIFNTWLWYKQDPG EGPVLLIALYKAGELTSNGRLTAQFGITRKDSFLNISASIPSD VGIYFCAGGTGNQFYFGTGTSLTVIPNIQNPDPAVYQLRDS KSSDKSVCLFTDFDSQTNVSQSKDSDVYITDKTVLDMRSM DFKSNSAVAWSNKSDFACANAFNNSIIPEDTFFPSPESSCDV KLVEKSFETDTNLNFQNLSVIGFRILLLKVAGFNLLMTLRL WSS |
| 21 | DMF4 β chain full-length sequence | DAGITQSPRHKVTETGTPVTLRCHQTENHRYMYWYRQDP GHGLRLIHYSYGVKDTDKGEVSDGYSVSRSKTEDFLLTLES ATSSQTSVYFCAISEVGVGQPQHFGDGTRLSILEDLNKVFPP EVAVFEPSEAEISHTQKATLVCLATGFFPDHVELSWWVNG KEVHSGVSTDPQPLKEQPALNDSRYCLSSRLRVSATFWQN PRNHFRCQVQFYGLSENDEWTQDRAKPVTQIVSAEAWGR ADCGFTSVSYQQGVLSATILYEILLGKATLYAVLVSALVLM AMVKRKDF |
| 39 | TCR18168 CDR3α | AVRELYSGAGSYQLT |
| 40 | TCR0002 CDR3α | AVRDIKSGAGSYQLT |

TABLE 1-continued

Amino acid and nucleic acid sequences of exemplary TCRs*.

| SEQ ID NO: | Description (protein sequences unless otherwise indicated) | Sequence |
|---|---|---|
| 41 | TCR0010 CDR3α | AVRDSFEGAGSYQLT |
| 42 | TCR0012 CDR3α | AVRGLLNGAGSYQLT |
| 43 | TCR0014 CDR3α | AVRDLFTGAGSYQLT |
| 44 | TCR0016 CDR3α | AVRDGRTGAGSYQLT |
| 45 | TCR0018 CDR3α | AVRDLSDGAGSYQLT |
| 46 | TCR0020 CDR3α | AVRSSYEGAGRYQLT |
| 47 | TCR0022 CDR3α | AVRDDLVGAGSYQLT |
| 48 | TCR0024 CDR3α | AVRDQALGAGSYQLT |
| 49 | TCR0028 CDR3α | AVRDMANGAGSYQLT |
| 50 | TCR0030 CDR3α | AVRDSKAGAGSYQLT |
| 51 | TCR0032 CDR3α | AVRDLFCGAGSYQLT |
| 52 | TCR0034 CDR3α | AVRDLRGGAGSYQLT |
| 53 | TCR0036 CDR3α | AVRDLTTGAGSYQLT |
| 54 | TCR0038 CDR3α | AVRDVASGAGSYQLT |
| 55 | TCR0050 CDR3α | AVRELYSVAVRYQLT |
| 56 | TCR0060 CDR3α | AVRELYSRGVKWQLT |
| 57 | TCR0062 CDR3α | AVRELYSTTFGWQLT |
| 58 | TCR0066 CDR3α | AVRELYSALVTYQLI |
| 59 | TCR0068 CDR3α | AVRELYSPRLMWQLT |
| 60 | TCR0070 CDR3α | AVRELYSATVDYQLT |
| 61 | CDR3α consensus 1 | AVRX$_1$X$_2$X$_3$X$_4$X$_5$X$_6$X$_7$X$_8$X$_9$QLT, wherein: X$_1$ is E, D, G, or S, X$_2$ is L, I, S, G, D, Q, M, or V, X$_3$ is Y, K, F, L, R, S, A, or T, X$_4$ is S, E, N, T, D, V, L, A, C or G, X$_5$ is G, V, R, T, A, or P, X$_6$ is A, G, T, L, or R, X$_7$ is G, V, F, or L, X$_8$ is S, R, K, G, T, M, or D, and X$_9$ is Y or W. |
| 62 | CDR3α consensus 2 | AVRX$_1$X$_2$X$_3$X$_4$GAGSYQLT, wherein: X$_1$ is E, D, G, or S, X$_2$ is L, I, S, G, D, Q, M, or V, X$_3$ is V, K, F, L, R, S, A, or T, and X$_4$ is S, E, N, T, D, V, L, A, C or G. |
| 63 | CDR3α consensus 3 | AVRELYSX$_1$X$_2$X$_3$X$_4$X$_5$QLT, wherein: X$_1$ is G, V, R, T, A, or P, X$_2$ is A, G, T, L, or R, X$_3$ is G, V, F, or L, X$_4$ is S, R, K, G, T, M, or D, and X$_5$ is Y or W. |
| 64 | CDR3α consensus 4 | AVRX$_1$X$_2$X$_3$X$_4$GAGSYQLT, wherein: X$_1$ is D or E, X$_2$ is D, L, M, I, or V, X$_3$ is L, A, K, S, F, or Y, and X$_4$ is V, N, S, D, or T. |

TABLE 1-continued

Amino acid and nucleic acid sequences of exemplary TCRs*.

| SEQ ID NO: | Description (protein sequences unless otherwise indicated) | Sequence |
|---|---|---|
| 65 | CDR3α consensus 5 | AVRDX$_1$X$_2$X$_3$GAGSYQLT, wherein:<br>X$_1$ is D, L, M, I, or V,<br>X$_2$ is L, A, K, S, or F, and<br>X$_3$ is V, N, S, D, or T. |
| 66 | TCR0002 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LYSDSALYFCAVRDIKSGAGSYQLTFGKGTKLSVIP |
| 67 | TCR0010 α-chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRDSFEGAGSYQLTFGKGTKLSVIP |
| 68 | TCR0012 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRGLLNGAGSYQLTFGKGTKLSVIP |
| 69 | TCR0014 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRDLFTGAGSYQLTFGKGTKLSVIP |
| 70 | TCR0016 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRDGRTGAGSYQLTFGKGTKLSVIP |
| 71 | TCR0018 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRDLSDGAGSYQLTFGKGTKLSVIP |
| 72 | TCR0020 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRSSYEGAGRYQLTFGKGTKLSVIP |
| 73 | TCR0022 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRDDLVGAGSYQLTFGKGTKLSVIP |
| 74 | TCR0024 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRDQALGAGSYQLTFGKGTKLSVIP |
| 75 | TCR0028 α chain variable region | QSVAQPEDQVNVAEGNPLTVKCTYSVSGNPYLFWYVQYP<br>NRGLQFLLKYITGDNLVKGSYGFEAFFNKSQTSFHLKKPSA<br>LVSDSALYFCAVRDMANGAGSYQLTFGKGTKLSVIP |
| 76 | TCR0030 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRDSKAGAGSYQLTFGKGTKLSVIP |
| 77 | TCR0032 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRDLFCGAGSYQLTFGKGTKLSVIP |
| 78 | TCR0034 α chain variable region | QSVAQPEDQVNVAEGNPLTVKCTYSVSGNPYLFWYVQYP<br>NRGLQFLLKYITGDNLVKGSYGFEAFNKSQTSFHLKKPSA<br>LVSDSALYFCAVRDLRGGAGSYQLTFGKGTKLSVIP |
| 79 | TCR0036 α chain variable region | QSVAQPEDQVNVAEGNPLTVKCTYSVSGNPYLFWYVQYP<br>NRGLQFLLKYITGDNVLKGSYGFEAEFNKSQTSFHLKKPSA<br>LVSDSALYFCAVRDLTTGAGSYQLTFGKGTKLSVIP |
| 80 | TCR0038 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRDVASGAGSYQLTFGKGTKLSVIP |
| 81 | TCR0050 α chain variable region | QSVAQPEDQVNVAEGNPLTVKCTYSVSGNPYLFWYVQYP<br>NRGLQFLLKYITGDNLVKGSYGFEAEFNKSQTSFHLKKPSA<br>LVSDSALYFCAVRELYSVAVRYQLTFGKGTKLSVIP |

TABLE 1-continued

Amino acid and nucleic acid sequences of exemplary TCRs*.

| SEQ ID NO: | Description (protein sequences unless otherwise indicated) | Sequence |
|---|---|---|
| 82 | TCR0060 α chain variable region | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSRGVKWQLTFGKGTKLSVIP |
| 83 | TCR0062 α chain variable region | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSTTFGWQLTGKGTKLSVIP |
| 84 | TCR0066 α chain variable region | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSALVTYQLTFGKGTKLSVIP |
| 85 | TCR0068 α chain variable region | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSPRLMWQLTFGKGTKLSVIP |
| 86 | TCR0070 α chain variable region | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSATVDYQLTFGKGTKLSVIP |
| 87 | Vα consensus 1 | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRX$_1$X$_2$X$_3$X$_4$X$_5$X$_6$X$_7$X$_8$X$_9$QLTFGKGTKLSVIP, wherein: X$_1$ is E, D, G, or S, X$_2$ is L, I, S, G, D, Q, M, or V, X$_3$ is Y, K, F, L, R, S, A, or T, X$_4$ is S, E, N, T, D, V, L, A, C or G, X$_5$ is G, V, R, T, A, or P, X$_6$ is A, G, T, L, or R, X$_7$ is G, V, F, or L, X$_8$ is S, R, K, G, T, M, or D, and X$_9$ is Y or W. |
| 88 | Vα consensus 2 | QSVAQPEDQVNVAEGNPLTVKCTYSVSGNPYLFWYVQYP NRGLQFLLKYITGDNLVKGSYGFEAEINKSQTSFHLKKPSA LVSDSALYFCAVRX$_1$X$_2$X$_3$X$_4$GAGSYQLTFGKGTKLSVIP, wherein: X$_1$ is E, D, G, or S, X$_2$ is L, I, S, G, D, Q, M, or V, X$_3$ is Y, K, F, L, R, S, A, or T, and X$_4$ is S, E, N, T, D, V, L, A, C or G. |
| 89 | Vα consensus 3 | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSX$_1$X$_2$X$_3$X$_4$X$_5$QLTFGKGTKLSVIP, wherein: X$_1$ is G, V. R, T, A, or P, X$_2$ is A, G, T, L, or R, X$_3$ is G, V, F, or L, X$_4$ is S, R, K, G, T, M, or D. and X$_5$ is Y or W. |
| 90 | Vα consensus 4 | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRX$_1$X$_2$X$_3$X$_4$GAGSYQLTFGKGTKLSVIP, wherein: X$_1$ is D or E, X$_2$ is D, L, M, I, or V, X$_3$ is L, A, K, S, F, or Y, and X$_4$ is V, N, S, D, or T. |
| 91 | Vα consensus 5 | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDX$_1$X$_2$X$_3$GAGSYQLTFGKGTKLSVIP, wherein: X$_1$ is D, L, M, I, or V, X$_2$ is L, A, K, S, or F, and X$_3$ is V, N, S, D, or T. |

TABLE 1-continued

Amino acid and nucleic acid sequences of exemplary TCRs*.

| SEQ ID NO: | Description (protein sequences unless otherwise indicated) | Sequence |
|---|---|---|
| 92 | TCR α chain constant region (murine) | YIQNPEPAVYQLKDPRSQDSTLCLFTDFDSQINVPKTMESG TFITDKTVLDMKAMDSKSNGAIAWSNQTSFTCQDIFKETN ATYPSSDVPCDATLTEKSFETDMNLNFQNLSVMGLRILLLK VAGFNLLMTLRLWSS |
| 93 | TCR18168 α chain human full-length sequence with additional C-terminal GS | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSGS |
| 94 | TCR18168 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRAKR |
| 95 | TCR18168 α chain human full-length sequence with additional C-terminal Furin residues after cleavage | QSVAQPEDQVNVAEGNPLTVKCTYSVSGNPYLFWYVQYP NRGLQFLLKYITGDNLNKGSYGFEAEFNKSQTSFHLKKPSA LVSDSALYFCAVRELYSGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRA |
| 96 | TCR18168 α chain human full-length sequence with additional C-terminal P2A residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSGSGATNFSLLKQAGDVEENPG |
| 97 | TCR18168 β chain human full-length sequence with additional C-terminal GS | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVEDLNKVFPPEVAVF EPSEAEISHTQKATLVCLATGFFPDHVELSWWVNGKEVHS GVSTDPQPLKEQPALNDSRYCLSSRLRVSATFWQNPLNHF RCQVQFYGLSENDEWTQDRAKPVTQIVSAEAWGRADCGF TSVSYQQGVLSATILYEILLGKATLYAVLVSALVLMAMVK RKDFGS |
| 98 | TCR18168 β chain human full-length sequence with additional C-terminal GS | QKPSRDICQRGTSLTIQCQVDSQVTMMFWYRQQPGQSLTLI ATANQGSEATYESGFVIDKFPISRPNLTFSTLTVSNMSPEDS STYLCSVGGAGVTDTQYFGPGTRLTVEDLKNVFPPEVAVF EPSEAEISHTQKATLVCLATGFYPDHVELSWWVNGKEVHS GVSTDPQPLKEQPALNDSRYCLSSRLRVSATFWQNPRNHF RCQVQFYGLSENDEWTQDRAKPVTQIVSAEAWGRADCGF TSESYQQGVLSATILYEILLGKATLYAVLVSALVLMAMVK RKDSRGGS |
| 99 | TCR18168 β chain human full-length sequence with additional C-terminal Furin residues after cleavage | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVEDLNKVFPPEVAVF EPSEAEISHTQKATLVCLATGFFPDHVELSWWVNGKEVHS GVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDFRAKR |

TABLE 1-continued

Amino acid and nucleic acid sequences of exemplary TCRs*.

| SEQ ID NO: | Description (protein sequences unless otherwise indicated) | Sequence |
|---|---|---|
| 100 | TCR18168 β chain human full-length sequence with additional C-terminal Furin residues after cleavage | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVLEDLKNVFPPEVAVF EPSEAEISHTQKATLVCLATGFYPDHVELSWWVNGKEVHS GVSTDPQPLKEQPALNDSRYCLSSRLRVSATFWQNPRNHF RCQVQFYGLSENDEWTQDRAKPVTQIVSAEAWGRADCGF TSESYQQGVLSATILYEILLGKATLYAVLVSALVLMAMVK RKDSRGRAKR |
| 101 | TCR18168 β chain human full-length sequence with additional C-terminal Furin residues after cleavage | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVLEDLKNVFPPEVAVF EPSEAEISHTQKATLVCLATGFFPDHVELSWWVNGKEVHS GVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDFRA |
| 102 | TCR18168 β chain human full-length sequence with additional C-terminal Furin residues after cleavage | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVLEDLKNVFPPEVAVF EPSEAEISHTQKATLVCLATGFYPDHVELSWWVNGKEVHS GVSTDPQPLKEQPALNDSRYCLSSRLRYSATFWQNPRNHF RCQVQFYGLSENDEWTQDRAKPVTQIVSAEAWGRADCGF TSESYQQGVLSATILYEILLGKATLYAVLVSALVLMAMVK RKDSRGRA |
| 103 | TCR18168 β chain human full-length sequence with additional C-terminal P2A residues after cleavage | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVLEDLKNVFPPEVAVF EPSEAEISHTQKATLVCLATGFFPDHVELSWWVNGKEVHS GVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDFGSGATNFSLLKQAGDVEENPG |
| 104 | TCR18168 β chain human full-length sequence with additional C-terminal P2A residues after cleavage | QKPSRDICQRGTSLTIQCQVDSQVTMMFWYRQQPGQSLTLI ATANQGSEATYESGFVIDKFPISRPNLTFSTLTVSNMSPEDS SIYLCSVGGAGVTDTQYFGPGTRLTVLEDLKNVFPPEVAVF EPSEAEISHTQKATLVCLATGFYPDHVELSWWVNGKEVHS GVSTDPQPLKEQPALNDSRYCLSSRLRVSATFWQNPRNHF RCQVQFYGLSENDEWTQDRAKPVTQIVSAEAWGRADCGF TSESYQQGVLSATILYEILLGKATLYAVLVSALVLMAMVK RKDSRGGSATNFSLLKQAGDVEENPG |
| 105 | TCR0002 α chain human full-length sequence | QSVAQPEDQVNVAEGNPLTVKCTYSVSGNPYLFWYVQYP NRGLQFLLKYITGDNLNKGSYGFEAEFNKSQTSFHLKKPSA LVSDSALYFCAVRIDIKSGAGSYQLTFGKGTFKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSS |
| 106 | TCR0002 α chain human full-length sequence with additional C-terminal GS | QSVAQPEDQVNVAEGNPLTVKCTYSVSGNPYLFWYVQYP NRGLQFLLKYITGDNLVKGSYGFEAFNKSQTSFHLKKPSA LVSDSALYFCAVRDIKSGAGSVQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFFNLLMTLRLWSSGS |
| 107 | TCR0002 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAFFNKSQTSFHLKKPSA LVSDSALYFCAVRDIKSGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRAKR |

TABLE 1-continued

Amino acid and nucleic acid sequences of exemplary TCRs*.

| SEQ ID NO: | Description (protein sequences unless otherwise indicated) | Sequence |
|---|---|---|
| 108 | TCR0002 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDIKSGAGSYQLTFFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLIKVA GFNLLMTLRLWSSRA |
| 109 | TCR0002 α chain human full-length sequence with additional C-terminal P2A residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDIKSGAGSYQLTGGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSGSGATNFSLLKQAGDVEENPG |
| 110 | TCR0014 α chain human full-length sequence | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDLFTGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSS |
| 111 | TCR0014 α chain human full-length sequence with additional C-terminal GS | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDLFTGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSGS |
| 112 | TCR0014 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDLFTGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRAKR |
| 113 | TCR0014 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDLFTGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRA |
| 114 | TCR0014 α chain human full-length sequence with additional C-terminal P2A residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDLFTGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILILKVA GFNLLMTLRLWSSGSGATNFSLLKQAGDVEENPG |
| 115 | TCR0018 α chain human full-length sequence | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDLSDGAGSYQLTFGKGTKLSVIPNIQNP DPAVYQLRDSKSSDKSVCLFTDFDSQTNVSQSKDSLYVYITD KTVLDMRSMDFKSNSAVAWSNKSDFACANAFNNSIIIPEDT FFPSPESSCDVKLVEKSFETDTNLNFQNLSVIGFRILLLKVA GFNLLMTLRLWSS |
| 116 | TCR0018 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LNSDSALYFCAVRDLSDGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRAKR |

TABLE 1-continued

Amino acid and nucleic acid sequences of exemplary TCRs*.

| SEQ ID NO: | Description (protein sequences unless otherwise indicated) | Sequence |
|---|---|---|
| 117 | TCR0018 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDLSDGAGSYQLTGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRA |
| 118 | TCR0018 α chain human full-length sequence with additional C-terminal P2A residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDLSDGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSGSGATNFSLLKQAGDVEENPG |
| 120 | TCR0022 α chain human full-length sequence | QSVAQPEDQVNVAEGNPLTVKCTYSVSGNPYLFWYVQYP NRGLQFLLKYITGDNLVKGSYGFEAEFFNKSQTSTHLKKPSA LVSDSALYFCAVRDDLVGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSS |
| 121 | TCR0022 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDDLVGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRAKR |
| 122 | TCR0022 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDDLVGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRA |
| 123 | TCR0022 α chain human full-length sequence with additional C-terminal P2A residues after cleavage | QSVAQPEDQVNVAEGNPLTVKCTYSVSGNPYLFWYVQYP NRGLQFLLKYITGDNLNKGSYGFEAEFNKSQTSFHLKKPSA LVSDSALYFCAVRDDLVGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSGSGATNFSLLKQAGDVEENPG |
| 125 | TCR0028 α chain human full-length sequence | QSVAQPEDQVNVAEGNPLTVKCTYSVSGNPYLFWYVQYP NRGLQFLLKYITGDNLVKGSYGFEAFFNKSQTSFHLKKPSA LVSDSALYFCAVRDMANGAGSYQLTFGKGTKLSVIPNIQN PDPAVYQLRDSKSSDKSVCLFTDFDSQTNVSQSKDSDVYIT DKTVLDMRSMDFKSNSAVAWSNKSDFACANAFNNSIIPED TFFPSPESSCDVKLVEKSFETDTNLNFQNLSVIGFRILLLKV AGFNLLMTLRLWSS |
| 126 | TCR0028 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDMANGAGSYQLTFGKGTKLSVIPNIQN PDPAVYQLRDSKSSDKSVCLFTDFDSQTNVSQSKDSDVYIT DKTVLDMRSMDFKSNSAVAWSNKSDFACANAFNNSIIPED TFFPSPESSCDVKLVEKSFETDTNLNFQNLSVIGFRILLLKV AGFNLLMTLRLWSSRAKR |
| 127 | TCR0028 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDMANGAGSYQLTFGKGTKLSVIPNIQN PDPAVYQLRDSKSSDKSVCLFTDFDSQTNVSQSKDSDVYIT DKTVLDMRSMDFKSNSAVAWSNKSDFACANAFNNSIIPED TFFPSPESSCDVKLVEKSFETDTNLNFQNLSVIGFRILLLKV AGFNLLMTLRLWSSRA |

TABLE 1-continued

Amino acid and nucleic acid sequences of exemplary TCRs*.

| SEQ ID NO: | Description (protein sequences unless otherwise indicated) | Sequence |
|---|---|---|
| 128 | TCR0028 α chain human full-length sequence with additional C-terminal P2A residues after cleavage | QSVAQPEDQVNVAEGNPLTVKCTYSVSGNPYLFWYVQYP NRGLQFLLKYITGDNLNKGSYGFEAEFNKSQTSFHLKKPSA LVSDSALYFCAVRDMANGAGSYQLTFGKGTKLSVIPNIQN PDPAVYQLRDSKSSDKSVCLFTDFDSQTNVSQSKDSDVYIT DKTVLDMRSMDFKSNSAVAWSNKSDFACANAFNNSIIPED TFFPSPESSCDVKLVEKSFETDTNLNFQNLSVIGFRILLLKV AGFNLLMTLRLWSSGSGATNFSLLKQAGDVEENPG |
| 408 | TCR0038 α chain human full-length sequence | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDVASGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSS |
| 409 | TCR0038 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDVASGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRAKR |
| 410 | TCR0038 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDVASGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRA |
| 411 | TCR0038 α chain human full-length sequence with additional C-terminal P2A residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRDVASGAGSYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSGSGATNFSLLKQAGDVEENPG |
| 412 | TCR0070 α chain human full-length sequence | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSATVDYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSS |
| 413 | TCR0070 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSATVDYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRAKR |
| 414 | TCR0070 α chain human full-length sequence with additional C-terminal Furin residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSATVDYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSRA |
| 415 | TCR0070 α chain human full-length sequence with additional C-terminal P2A residues after cleavage | QSVAQPEDQVNVAEGNPLTVKCTYSVSGNPYLFWYVQYP NRGLQFLLKYITGDNLVKGSYGFEAEFNKSQTSFHLKKPSA LVSDSALYFCAVRELYSATVDYQLTFGKGTKLSVIPNIQNP DPAVYQLRDSKSSDKSVCLFTDFDSQTNVSQSKDSDVYITD KTVLDMRSMDFKSNSAVAWSNKSDFACANAFNNSIIPEDT FFPSPESSCDVKLVEKSFETDTNLNFQNLSVIGFRILLLKVA GFNLLMTLRLWSSGSGATNFSLLKQAGDVEENPG |

TABLE 1-continued

Amino acid and nucleic acid sequences of exemplary TCRs*.

| SEQ ID NO: | Description (protein sequences unless otherwise indicated) | Sequence |
|---|---|---|
| 130 | Dual P2A-T2A peptide | ATNFSLLKQAGDVEENPGPEGRGSLLTCGDVEENPGP |
| 131 | furin cleavage site | RX$_1$X$_2$RS wherein X$_1$ can be any amino acid and X$_2$ is K or R |
| 132 | furin cleavage site | RAKRS |
| 133 | Furin cleavage site | RX$_1$X$_2$RS wherein X$_1$ is K or R, and X$_2$ is K or R |
| 134 | porcine teschovirus-1 2A (P2A) | GSGATNFSLLKQAGDVEENPGP |
| 135 | Thosea asigna virus 2A peptide (T2A) | GSGEGRGSLLTCGDVEENPGP |
| 136 | equine rhinitis A virus 2A peptide (E2A) | GSGQCTNYALLKLAGDVESNPGP |
| 137 | foot-and-mouth disease virus 2A peptide (F2A) | GSGVKQTLNFDLLKLAGDVESNPGP |
| 138 | cytoplasmic polyhedrosis virus 2A peptide (BmCPV 2A) | GSGDVFRSNYDLLKLCGDIESNPGP |
| 139 | flacherie virus of B. mori 2A peptide (BmIFV 2A) | GSGTLTRAKIEDELIRAGIESNPGP |
| 140 | Dual P2A-T2A peptide | GSGATNFSLLKQAGDVEENPGPGSGEGRGSLLTCGDVEEN PGP |
| 141 | TCR18168 α chain-furin cleavage site-P2A cleavage site-TCR18168 β chain sequence with additional C-terminal GS (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRELYSGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFSPESSCDVKLVEKSFET DTNLNFQNLSVIGFRILLLKVAGFNLLMTLRWSSRAKRSG SGATNFSLLKQAGDVEENPGPMLSLLLLLLGLGSVFSAVI SQKPSRDICQRGTSLTIQCQVDSQVTMMFWYRQQPGQSLT LIATANQGSEATYESGFVIDKFPISRPNLTFSTLVSNMSPED SSIYLCSVGGAGVTDTQYFGPGTRLTVLEDLNKVFPPEVAV FEPSEAEISHTQKATLVCLATGFFPDHVELSWWVNGKEVH SGVSTDPQPLKEQPALNDSRYCLSSRLRVSKSATFWQNPRNHF RCQVQFYGLSENDEWTQDRAKPVTQIVSAEAWGRADCGF TSVSYQQGVLSATILYEILLGKATLYAVLVSALVLMAMVK RKDFGS |
| 142 | TCR18168 α chain-P2A cleavage site-TCR18168 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRELYSGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFSPESSCDVKLVEKSFET DTNLNFQNLSVIGFRILLLKVAGFNLLMTLRWSSGSGATN FSLLKQAGDVEENPGPMLSLLLLLLGLGSVFSAVISQKPS RDICQRGTSLTIQCQVDSQVTMMFWYRQQPGQSLTLIATA NQGSEATYESGFVIDKFPISRPNLTFSTLTVSNMSPEDSSIYL CSVGGAGVTDTQYFGPGTRLTVLEDLNKVFPPEVAVFEPSE AEISHTQKATLVCLATGFFPDHVELSWWVNGKEVHSGVST DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKDF |

TABLE 1-continued

Amino acid and nucleic acid sequences of exemplary TCRs*.

| SEQ ID NO: | Description (protein sequences unless otherwise indicated) | Sequence |
|---|---|---|
| 143 | TCR18168 α chain-P2A cleavage site-TCR18168 β chain sequence with additional C-terminal GS (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRELYSGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSGSGATN FSLLKQAGDVEENPGPMLSLLLLLLGLGSVFSAVISQKPS RDICQRGTSLTIQCQVDSQVTMMFWYRQQPGQSLTLIATA NQGSEATYESGFVIDKFPISRPNLTFSTLTVSNMSPEDSSIYL CSVGGAGVTDTQYFGPGTRLTVLEDLNKVFPPEVAVFEPSE AEISHTQKATLVCLATGFFPDHVELSWWVNGKEVHSGVST DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKDF GS |
| 146 | TCR18168 β chain-Furin cleavage site-P2A cleavage site-TCR18168 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFRAKRSGSGATNFSLL KQAGDVEENPGPMASAPISMLAMLFTLSGLRAQSVAQPE DQVNVAEGNPLTVKCTYSVSGNPYLFWYVQYPNRGLQFL LKYITGDNLVKGSYGFEAFTNKSQTSFHLKKPSALVSDSAL YFCAVRELYSGAGSYQLTFGKGTKLSVIPNIQNPDPAVYQL RDSKSSDKSVCLFTDFDSQTNVSQSKDSDVYITDKTVLDM RSMDFKSNSAVAWSNKSDFACANAFNNSIIPEDTFFPSPESS CDVKLVEKSFETDTNLNFQNLSVIGFRILLLKVAGFNLLMT LRLWSS |
| 147 | TCR18168 β chain-Furin cleavage site-P2A cleavage site-TCR18168 α chain sequence with additional C-terminal GS (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFRAKRSGSGATNFSLL KQAGDVEENPGPMASAPISMLAMLFTLSGLRAQSVAQPE DQVNVAEGNPLTVKCTYSVSGNPYLFWYVQYPNRGLQFL LKYITGDNLVKGSYGFEAFTNKSQTSFHLKKPSALVSDSAL YFCAVRELYSGAGSYQLTFGKGTKLSVIPNIQNPDPAVYQL RDSKSSDKSVCLFTDFDSQTNVSQSKDSDVYITDKTVLDM RSMDFKSNSAVAWSNKSDFACANAFNNSIIPEDTFFPSPESS CDVKLVEKSFETDTNLNFQNLSVIGFRILLLKVAGFNLLMT LRLWSS |
| 148 | TCR18168 β chain-P2A cleavage site-TCR18168 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFGSGATNFSLLKQAGD VEENPGPMASAPISMLAMLFTLSGLRAQSVAQPEDQVNV AEGNPLTVKCTYSVSGNPYLFWYVQYPNRGLQFLLKYITG DNLVKGSYGFEAFTNKSQTSFHLKKPSALVSDSALYFCAV RELYSGAGSYQLTFGKGTKLSVIPNIQNPDPAVYQLRDSKS SDKSVCLFTDFDSQTNVSQSKDSDVYITDKTVLDMRSMDF KSNSAVAWSNKSDFACANAFNNSIIPEDTFFPSPESSCDVKL VEKSFETDTNLNFQNLSVIGFRILLLKVAGFNLLMTLRLWS S |

TABLE 1-continued

Amino acid and nucleic acid sequences of exemplary TCRs*.

| SEQ ID NO: | Description (protein sequences unless otherwise indicated) | Sequence |
|---|---|---|
| 149 | TCR18168 β chain-P2A cleavage site-TCR18168 α chain sequence with additional C-terminal GS (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFGSGATNFSLLKQAGD VEENPGPMASAPISMLAMLFTLSGLRAQSVAQPEDQVNV AEGNPLTVKCTYSVSGNPYLFWYVQYPNRGLQFLLKYITG DNLVKGSYGFEAFTNKSQTSFHLKKPSALVSDSALYFCAV RELYSGAGSYQLTFGKGTKLSVIPNIQNPDPAVYQLRDSKS SDKSVCLFTDFDSQTNVSQSKDSDVYITDKTVLDMRSMDF KSNSAVAWSNKSDFACANAFNNSIIPEDTFFPSPESSCDVKL VEKSFETDTNLNFQNLSVIGFRILLLLKVAGFNLLMTLRLWS SGS |
| 152 | TCR18168 β chain-Furin cleavage site-P2A cleavage site-TCR18168 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAEFNKSQTSFHLKKPSALVSDSA LYFCAVRELYSGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL MTLRLWSS |
| 153 | TCR18168 β chain-Furin cleavage site-P2A cleavage site-TCR18168 α chain sequence, with optimized N-terminal leader sequence and additional C-terminal GS (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAEFNKSQTSFHLKKPSALVSDSA LYFCAVRELYSGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL MTLRLWSSGS |
| 154 | TCR18168 β chain-P2A cleavage site-TCR18168 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFGSGATNFSLLKQAG DVEENPGPMASAPISMLAMLFTLSGLRAQSVAQPEDQVN VAEGNPLTVKCTYSVSGNPYLFWYVQYPNRGLQFLLKYIT GDNLVKGSYGFEAEFNKSQTSFHLKKPSALVSDSALYFCA VRELYSGAGSYQLTFGKGTKLSVIPNIQNPDPAVYQLRDSK SSDKSVCLFTDFDSQTNVSQSKDSDVYITDKTVLDMRSMD FKSNSAVAWSNKSDFACANAFNNSIIPEDTFFPSPESSCDVK LVEKSFETDTNLNFQNLSVIGFRILLLLKVAGFNLLMTLRLW SS |

TABLE 1-continued

Amino acid and nucleic acid sequences of exemplary TCRs*.

| SEQ ID NO: | Description (protein sequences unless otherwise indicated) | Sequence |
|---|---|---|
| 155 | TCR18168 β chain-P2A cleavage site-TCR18168 α chain sequence, with optimized N-terminal leader sequence and additional C-terminal GS (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFGSGATNFSLLKQAG DVEENPGPMASAPISMLAMLFTLSGLRAQSVAQPEDQVN VAEGNPLTVKCTYSVSGNPYLFWYVQYPNRGLQFLLKYIT GDNLVKGSYGFEAEFNKSQTSFHLKKPSALVSDSALYFCA VRELYSGAGSYQLTFGKGTKLSVIPNIQNPDPAVYQLRDSK SSDKSVCLFTDFDSQTNVSQSKDSDVYITDKTVLDMRSMD FKSNSAVAWSNKSDFACANAFNNSIIPEDTFFPSPESSCDVK LVEKSFETDTNLNFQNLSVIGFRILLLKVAGFNLLMTLRLW SSGS |
| 158 | TCR0002 α chain-furin cleavage site-P2A cleavage site-TCR0002 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRDIKSGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSRAKRSG SGATNFSLLKQAGDVEENPGPMLSLLLLLLGLGSVFSAVI SQKPSRDICQRGTSLTIQCQVDSQVTMMFWYRQQPGQSLT LIATANQGSEATYESGFVIDKFPISRPNLTFSTLTVSNMSPED SSIYLCSVGGAGVTDTQYFGPGTRLTVLEDLNKVFPPEVAV FEPSEAEISHTQKATLVCLATGFFPDHVELSWWVNGKEVH SGVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDF |
| 159 | TCR0002 α chain-furin cleavage site-P2A cleavage site-TCR0002 β chain sequence with additional C-terminal GS (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRDIKSGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSRAKRSG SGATNFSLLKQAGDVEENPGPMLSLLLLLLGLGSVFSAVI SQKPSRDICQRGTSLTIQCQVDSQVTMMFWYRQQPGQSLT LIATANQGSEATYESGFVIDKFPISRPNLTFSTLTVSNMSPED SSIYLCSVGGAGVTDTQYFGPGTRLTVLEDLNKVFPPEVAV FEPSEAEISHTQKATLVCLATGFFPDHVELSWWVNGKEVH SGVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDFGS |
| 160 | TCR0002 α chain-P2A cleavage site-TCR0002 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRDIKSGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSGSGATN FSLLKQAGDVEENPGPMLSLLLLLLGLGSVFSAVISQKPS RDICQRGTSLTIQCQVDSQVTMMFWYRQQPGQSLTLIATA NQGSEATYESGFVIDKFPISRPNLTFSTLTVSNMSPEDSSIYL CSVGGAGVTDTQYFGPGTRLTVLEDLNKVFPPEVAVFEPSE AEISHTQKATLVCLATGFFPDHVELSWWVNGKEVHSGVST DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKDF |

TABLE 1-continued

Amino acid and nucleic acid sequences of exemplary TCRs*.

| SEQ ID NO: | Description (protein sequences unless otherwise indicated) | Sequence |
|---|---|---|
| 161 | TCR0002 α chain-P2A cleavage site-TCR0002 β chain sequence with additional C-terminal GS (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRDIKSGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSGSGATN FSLLKQAGDVEENPGPMLSLLLLLLGLGSVFSAVISQKPS RDICQRGTSLTIQCQVDSQVTMMFWYRQQPGQSLTLIATA NQGSEATYESGFVIDKFPISRPNLTFSTLTVSNMSPEDSSIYL CSVGGAGVTDTQYFGPGTRLTVLEDLNKVFPPEVAVFEPSE AEISHTQKATLVCLATGFFPDHVELSWWVNGKEVHSGVST DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKDF GS |
| 164 | TCR0002 β chain-Furin cleavage site-P2A cleavage site-TCR0002 α chain sequence (the leader sequences are bold) | MLSLLLLLLGLGSVFSAVISQKPSRDICQRGTSLTIQCQVD SQVTMMFWYRQQPGQSLTLIATANQGSEATYESGFIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLNSALVLMAMVKRKDFRAKRSGSGATNFSLL KQAGDVEENPGPMASAPISMLAMLFTLSGLRAQSVAQPE DQVNVAEGNPLTVKCTYSVSGNPYLFWYVQYPNRGLQFL LKYITGDNLVKGSYGFEAFNKSQTSFHLKKPSALVSDSAL YFCAVRDIKSGAGSYQLTFGKGTKLSVIPNIQNPDPAVYQL RDSKSSDKSVCLFTDFDSQTNVSQSKDSDVYITDKTVLDM RSMDFKSNSAVAWSNKSDFACANAFNNSIIPEDTFFPSPESS CDVKLVEKSFETDTNLNFQNLSVIGFRILLLKVAGFNLLMT LRLWSS |
| 165 | TCR0002 β chain-Furin cleavage site-P2A cleavage site-TCR0002 α chain sequence with additional C-terminal GS (the leader sequences are bold) | MLSLLLLLLGLGSVFSAVISQKPSRDICQRGTSLTIQCQVD SQVTMMFWYRQQPGQSLTLIATANQGSEATYESGFIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLNSALVLMAMVKRKDFRAKRSGSGATNFSLL KQAGDVEENPGPMASAPISMLAMLFTLSGLRAQSVAQPE DQVNVAEGNPLTVKCTYSVSGNPYLFWYVQYPNRGLQFL LKYITGDNLVKGSYGFEAFNKSQTSFHLKKPSALVSDSAL YFCAVRDIKSGAGSYQLTFGKGTKLSVIPNIQNPDPAVYQL RDSKSSDKSVCLFTDFDSQTNVSQSKDSDVYITDKTVLDM RSMDFKSNSAVAWSNKSDFACANAFNNSIIPEDTFFPSPESS CDVKLVEKSFETDTNLNFQNLSVIGFRILLLKVAGFNLLMT LRLWSSGS |
| 166 | TCR0002 β chain-P2A cleavage site-TCR0002 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFGSGATNFSLLKQAGD VEENPGPMASAPISMLAMLFTLSGLRAQSVAQPEDQVNV AEGNPLTVKCTYSVSGNPYLFWYVQYPNRGLQFLLKYITG DNLVKGSYGFEAEFNKSQTSFHLKKPSALVSDSALYFCAV RDIKSGAGSYQLTFGKGTKLSVIPNIQNPDPAVYQLRDSKS SDKSVCLFTDFDSQTNVSQSKDSDVYITDKTVLDMRSMDF KSNSAVAWSNKSDFACANAFNNSIIPEDTFFPSPESSCDVKL VEKSFETDTNLNFQNLSVIGFRILLLKVAGFNLLMTLRLWS S |

TABLE 1-continued

Amino acid and nucleic acid sequences of exemplary TCRs*.

| SEQ ID NO: | Description (protein sequences unless otherwise indicated) | Sequence |
|---|---|---|
| 167 | TCR0002 β chain-P2A cleavage site-TCR0002 α chain sequence with additional C-terminal GS (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFGSGATNFSLLKQAGD VEENPGPMASAPISMLAMLFTLSGLRAQSVAQPEDQVNV AEGNPLTVKCTYSVSGNPYLFWYVQYPNRGLQFLLKYITG DNLVKGSYGFEAEFNKSQTSFHLKKPSALVSDSALYFCAV RDIKSGAGSYQLTFGKGTKLSVIPNIQNPDPAVYQLRDSKS SDKSVCLFTDFDSQTNVSQSKDSDVYITDKTVLDMRSMDF KSNSAVAWSNKSDFACANAFNNSIIPEDTFFPSPESSCDVKL VEKSFETDTNLNFQNLSVIGFRILLLLKVAGFNLLMTLRLWS SGS |
| 170 | TCR0002 β chain-Furin cleavage site-P2A cleavage site-TCR0002 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAEFNKSQTSFHLKKPSALVSDSA LYFCAVRDIKSGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL MTLRLWSS |
| 171 | TCR0002 β chain-Furin cleavage site-P2A cleavage site-TCR0002 α chain sequence, with optimized N-terminal leader sequence and additional C-terminal GS (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAEFNKSQTSFHLKKPSALVSDSA LYFCAVRDIKSGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL MTLRLWSSGS |
| 172 | TCR0002 β chain-P2A cleavage site TCR0002 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFGSGATNFSLLKQAG DVEENPGPMASAPISMLAMLFTLSGLRAQSVAQPEDQVN VAEGNPLTVKCTYSVSGNPYLFWYVQYPNRGLQFLLKYIT GDNLVKGSYGFEAFNKSQTSFHLKKPSALVSDSALYFCA VRDIKSGAGSYQLTFGKGTKLSVIPNIQNPDPAVYQLRDSK SSDKSVCLFTDFDSQTNVSQSKDSDVYITDKTVLDMRSMD FKSNSAVAWSNKSDFACANAFNNSIIPEDTFFPSPESSCDVK LVEKSFETDTNLNFQNLSVIGFRILLIKVAGFNLLMTLRLW SS |

TABLE 1-continued

Amino acid and nucleic acid sequences of exemplary TCRs*.

| SEQ ID NO: | Description (protein sequences unless otherwise indicated) | Sequence |
|---|---|---|
| 173 | TCR0002 β chain-P2A cleavage site-TCR0002 α chain sequence, with optimized N-terminal leader sequence and additional C-terminal GS (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFGSGATNFSLLKQAG DVEENPGPMASAPISMLAMLFTLSGLRAQSVAQPEDQVN VAEGNPLTVKCTYSVSGNPYLFWYVQYPNRGLQFLLKYIT GDNLVKGSYGFEAFNKSQTSFHLKKPSALVSDSALYFCA VRDIKSGAGSYQLTFGKGTKLSVIPNIQNPDPAVYQLRDSK SSDKSVCLFTDFDSQTNVSQSKDSDVYITDKTVLDMRSMD FKSNSAVAWSNKSDFACANAFNNSIIPEDTFFPSPESSCDVK LVEKSFETDTNLNFQNLSVIGFRILLLIKVAGFNLLMTLRLW SSGS |
| 176 | TCR0014 α chain-furin cleavage site-P2A cleavage site-TCR0014 β chain sequence (the leader sequences are bold) | MASAPISMLAMLFTLSGLRAQSVAQPEDQVNVAEGNPLT VKCTYSVSGNPYLFWYVQPNRGLQFLLKYITGDNLVKGS YGFEAEFNKSQTSFHLKKPSALVSDSALYFCAVRDLFTGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSRAKRSG SGATNFSLLKQAGDVEENPGPMLSLLLLLLGLGSVFSAVI SQKPSRDICQRGTSLTIQCQVDSQVTMMFWYRQQPGQSLT LIATANQGSEATYESGFVIDKFPISRPNLTFSTLTVSNMSPED SSIYLCSVGGAGVTDTQYFGPGTRLTVLEDLNKVFPPEVAV FEPSEAEISHTQKATLVCLATGFFPDHVELSWWVNGKEVH SGVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDF |
| 177 | TCR0014 α chain-furin cleavage site-P2A cleavage site-TCR0014 β chain sequence with additional C-terminal GS (the leader sequences are bold) | MASAPISMLAMLFTLSGLRAQSVAQPEDQVNVAEGNPLT VKCTYSVSGNPYLFWYVQPNRGLQFLLKYITGDNLVKGS YGFEAEFNKSQTSFHLKKPSALVSDSALYFCAVRDLFTGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSRAKRSG SGATNFSLLKQAGDVEENPGPMLSLLLLLLGLGSVFSAVI SQKPSRDICQRGTSLTIQCQVDSQVTMMFWYRQQPGQSLT LIATANQGSEATYESGFVIDKFPISRPNLTFSTLTVSNMSPED SSIYLCSVGGAGVTDTQYFGPGTRLTVLEDLNKVFPPEVAV FEPSEAEISHTQKATLVCLATGFFPDHVELSWWVNGKEVH SGVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDFGS |
| 178 | TCR0014 α chain-P2A cleavage site-TCR0014 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRDLFTGAG SYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSGSGATN FSLLKQAGDVEENPGPMLSLLLLLLGLGSVFSAVISQKPS RDICQRGTSLTIQCQVDSQVTMMFWYRQQPGQSLTLIATA NQGSEATYESGFVIDKFPISRPNLTFSTLTVSNMSPEDSSIYL CSVGGAGVTDTQYFGPGTRLTVLEDLNKVFPPEVAVFEPSE AEISHTQKATLVCLATGFFPDHVELSWWVNGKEVHSGVST DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKDF |

TABLE 1-continued

Amino acid and nucleic acid sequences of exemplary TCRs*.

| SEQ ID NO: | Description (protein sequences unless otherwise indicated) | Sequence |
|---|---|---|
| 179 | TCR0014 α chain-P2A cleavage site-TCR0014 β chain sequence with additional C-terminal GS (the leader sequences are bold) | MASAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDLFTGAGSYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSSGSGATNFSLLKQAGDVEENPGPMLSLLLLLLGLGSVFSAVISQKPSRDICQRGTSLTIQCQVDSQVTMMFWYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDFGS |
| 182 | TCR0014 β chain-Furin cleavage site-P2A cleavage site-TCR0014 α chain sequence (the leader sequences are bold) | MLSLLLLLLGLGSVFSAVISQKPSRDICQRGTSLTIQCQVDSQVTMMFWLYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDFRAKRSGSGATNFSLLKQAGDVEENPGPMASAPISMLAMLFTLSGLRAQSVAQPEDQVNVAEGNPLTVKCTYSVSGNPYLFWYVQYPNRGLQFLLKYITGDNVKGSYGFEAEFNKSQTSFHLKKPSALVSDSALYFCAVRDLFTGAGSYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 183 | TCR0014 β chain-Furin cleavage site-P2A cleavage site-TCR0014 α chain sequence with additional C-terminal GS (the leader sequences are bold) | MLSLLLLLLGLGSVFSAVISQKPSRDICQRGTSLTIQCQVDSQVTMMFWLYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDFRAKRSGSGATNFSLLKQAGDVEENPGPMASAPISMLAMLFTLSGLRAQSVAQPEDQVNVAEGNPLTVKCTYSVSGNPYLFWYVQYPNRGLQFLLKYITGDNVKGSYGFEAEFNKSQTSFHLKKPSALVSDSALYFCAVRDLFTGAGSYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSSGS |
| 184 | TCR0014 β chain-P2A cleavage site-TCR0014 α chain sequence (the leader sequences are bold) | MLSLLLLLLGLGSVFSAVISQKPSRDICQRGTSLTIQCQVDSQVTMMFWYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDFGSGATNFSLLKQAGDVEENPGPMASAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDLFTGAGSYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |

TABLE 1-continued

Amino acid and nucleic acid sequences of exemplary TCRs*.

| SEQ ID NO: | Description (protein sequences unless otherwise indicated) | Sequence |
|---|---|---|
| 185 | TCR0014 β chain-P2A cleavage site-TCR0014 α chain sequence with additional C-terminal GS (the leader sequences are bold) | MLSLLLLLLGLGSVFSAVISQKPSRDICQRGTSLTIQCQVD SQVTMMFWYRQQPGQSLTLIATANQGSEATYESGPVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFGSGATNFSLLKQAGD VEENPGPMASAPISMLAMLFTLSGLRAQSVAQPEDQVNV AEGNPLTVKCTYSVSGNPYLFWYVQYPNRGLQFLLKYITG DNLVKGSYGFEAEFNKSQTSFHLKKPSALVSDSALYFCAV RDLFTGAGSYQLTFGKGTKLSVIPNIQNPDPAVYQLRDSKS SDKSVCLFTDFDSQTNVSQSKDSDVYITDKTVLDMRSMDF KSNSAVAWSNKSDFACANAFNNSIIPEDTFFPSPESSCDVKL VEKSFETDTNLNFQNLSVIGFRILLLLKVAGFNLLMTLRLWS SGS |
| 188 | TCR0014 β chain-Furin cleavage site-P2A cleavage site-TCR0014 α chain sequence, with optimized N-terminal leader sequence (the leader sequences are bold) | MKSVLLLLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYILCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAFFNKSQTSFHLKKPSALVSDSA LYFCAVRDLFTGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL MTLRLWSS |
| 189 | TCR0014 β chain-Furin cleavage site-P2A cleavage site-TCR0014 α chain sequence, with optimized N-terminal leader sequence and additional C-terminal GS (the leader sequences are bold) | MKSVLLLLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYILCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAFFNKSQTSFHLKKPSALVSDSA LYFCAVRDLFTGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL MTLRLWSSGS |
| 190 | TCR0014 β chain-P2A cleavage site-TCR0014 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFGSGATNFSLLKQAG DVEENPGPMASAPISMLAMLFTLSGLRAQSVAQPEDQVN VAEGNPLTVKCTYSVSGNPYLFWYVQYPNRGLQFLLKYIT GDNLVKGSYGFEAFNKSQTSFHLKKPSALVSDSALYFCA VRDLFTGAGSYQLTFGKGTKLSVIPNIQNPDPAVYQLRDSK SSDKSVCLFTDFDSQTNVSQSKDSDVYITDKTVLDMRSMD FKSNSAVAWSNKSDFACANAFNNSIIPEDTFFPSPESSCDVK LVEKSFETDTNLNFQNLSVIGFRILLLLKVAGFNLLMTLRLW SS |

TABLE 1-continued

Amino acid and nucleic acid sequences of exemplary TCRs*.

| SEQ ID NO: | Description (protein sequences unless otherwise indicated) | Sequence |
|---|---|---|
| 191 | TCR0014 β chain-P2A cleavage site-TCR0014 α chain sequence, with optimized N-terminal leader sequence and additional C-terminal GS (the leader sequences are bold) | MKSVLLLTTLLVPAHLVAAVISQKPSRDICQRGTSLTIQCQVDSQVTMMWFYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDFGSGATNFSLLKQAGDVEENPGPMASAPISMLAMLFTLSGLRAQSVAQPEDQVNVAEGNPLTVKCTYSVSGNPYLFWYVQYPNRGLQFLLKYITGDNLVKGSYGFEAFNKSQTSFHLKKPSALVSDSALYFCAVRDLFTGAGSYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSSGS |
| 194 | TCR0018 α chain-furin cleavage site-P2A cleavage site-TCR0018 β chain sequence (the leader sequences are bold) | MASAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDLSDGAGSYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSSRAKRSGSGATNFSLLKQAGDVEENPGPMLSLLLLLLGLGSVFSAVISQKPSRDICQRGTSLTIQCQVDSQVTMMWFYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 1961 | TCR0018 α chain-P2A cleavage site-TCR0018 β chain sequence (the leader sequences are bold) | MASAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDLSDGAGSYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSSGSGATNFSLLKQAGDVEENPGPMLSLLLLLLGLGSVFSAVISQKPSRDICQRGTSLTIQCQVDSQVTMMWFYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDF |
| 200 | TCR0018 β chain-Furin cleavage site-P2A cleavage site-TCR0018 α chain sequence (the leader sequences are bold) | MLSLLLLLLGLGSVFSAVISQKPSRDICQRGTSLTIQCQVDSQVTMMWFYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDFRAKRSGSGATNFSLLKQAGDVEENPGPMASAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDLSDGAGSYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |

TABLE 1-continued

Amino acid and nucleic acid sequences of exemplary TCRs*.

| SEQ ID NO: | Description (protein sequences unless otherwise indicated) | Sequence |
|---|---|---|
| 202 | TCR0018 β chain-P2A cleavage site-TCR0018 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFGSGATNFSLLKQAGD VEENPGPMASAPISMLAMLFTLSGLRAQSVAQPEDQVNV AEGNPLTVKCTYSVSGNPYLFWYVQYPNRGLQFLLKYITG DNLVKGSYGFEAEFNKSQTSFHLKKPSALVSDSALYFCAV RDLSDGAGSYQLTFGKGTKLSVIPNIQNPDPAVYQLRDSKS SDKSVCLFTDFDSQTNVSQSKDSDVYITDKTVLDMRSMDF KSNSAVAWSNKSDFACANAFNNSIIPEDTFFPSPESSCDVKL VEKSFETDTNLNFQNLSVIGFRILLLLKVAGFNLLMTLRLWS S |
| 206 | TCR0018 β chain-Furin cleavage site-P2A cleavage site-TCR0018 α chain sequence, with optimized N-terminal leader sequence (the leader sequences are bold) | MKSVLLLTTLLVPAHLVAAVISQKPSRDICQRGTSLTIQC QVDSQVTMMFWVRQQPGQSLTLIATANQGSEATYESGFVI DKFPISRPNLTFSTLTVSNMSPEDSSIYILCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAEFNKSQTSFHLKKPSALVSDSA LYFCAVRDLSDGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL MTLRLWSS |
| 208 | TCR0018 β chain-P2A cleavage site-TCR0018 α chain sequence, with optimized N-terminal leader sequence (the leader sequences are bold) | MKSVLLLTTLLVPAHLVAAVISQKPSRDICQRGTSLTIQC QVDSQVTMMFWVRQQPGQSLTLIATANQGSEATYESGFVI DKFPISRPNLTFSTLTVSNMSPEDSSIYILCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFGSGATNFSLLKQAG DVEENPGPMASAPISMLAMLFTLSGLRAQSVAQPEDQVN VAEGNPLTVKCTYSVSGNPYLFWYVQYPNRGLQFLLKYIT GDNLVKGSYGFEAEFNKSQTSFHLKKPSALVSDSALYFCA VRDLSDGAGSYQLTFGKGTKLSVIPNIQNPDPAVYQLRDSK SSDKSVCLFTDFDSQTNVSQSKDSDVYITDKTVLDMRSMD FKSNSAVAWSNKSDFACANAFNNSIIPEDTFFPSPESSCDVK LVEKSFETDTNLNFQNLSVIGFRILLLLKVAGFNLLMTLRLW SS |
| 212 | TCR0022 α chain-furin cleavage site-P2A cleavage site-TCR0022 β chain sequence (the leader sequences are bold) | MASAPISMLAMLFTLSGLRAQSVAQPEDQVNVAEGNPLT VKCTYSVSGNPYLFWYVPNRGLQFLLKYITGDNLVKGS YGFEAEFNKSQTSFHLKKPSALVSDSALYFCAVRDDLVGA GSYQLTFGKGTKLSVIPNIQNPDPAVYQLRDSKSSDKSVCL FTDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLLKVAGFNLLMTLRLWSSRAKRSG SGATNFSLLKQAGDVEENPGPMLSLLLLLLGLGSVFSAVI SQKPSRDICQRGTSLTIQCQVDSQVTMMFWYRQQPGQSLT LIATANQGSEATYESGFVIDKFPISRPNLTFSTLTVSNMSPED SSIYLCSVGGAGVTDTQYFGPGTRLTVLEDLNKVFPPEVAV FEPSEAEISHTQKATLVCLATGFFPDHVELSWWVNGKEVH SGVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDF |

TABLE 1-continued

Amino acid and nucleic acid sequences of exemplary TCRs*.

| SEQ ID NO: | Description (protein sequences unless otherwise indicated) | Sequence |
|---|---|---|
| 214 | TCR0022 α chain-P2A cleavage site-TCR0022 β chain sequence (the leader sequences are bold) | MASAPISMLAMLFTLSGLRAQSVAQPEDQVNVAEGNPLT VKCTYSVSGNPYLFWYWYPNRGLQFLLKYITGDNLVKGS YGFEAEFNKSQTSFHLKKPSALVSDSALYFCAVRDDLVGA GSYQLTFGKGTKLSVIPNIQNPDPAVYQLRDSKSSDKSVCL FTDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSGSGATN FSLLKQAGDVEENPGPMLSLLLLLLGLGSVFSAVISQKPS RDICQRGTSLTIQCQVDSQVTMMFWYRQQPGQSLTLIATA NQGSEATYESGFVIDKFPISRPNLTFSTLTVSNMSPEDSSIYL CSVGGAGVTDTQYFGPGTRLTVLEDLNKVFPPEVAVFEPSE AEISHTQKATLVCLATGFFPDHVELSWWVNGKEVHSGVST DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKDF |
| 218 | TCR0022 β chain-Furin cleavage site-P2A cleavage site-TCR0022 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFRAKRSGSGATNFSLL KQAGDVEENPGPMASAPISMLAMLFTLSGLRAQSVAQPE DQVNVAEGNPLTVKCTYSVSGNPYLFWYVQYPNRGLQFL LKYITGDNLVKGSYGFEAEFNKSQTSFHLKKPSALVSDSAL YFCAVRDDLVGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLKVAGFNLL MTLRLWSS |
| 220 | TCR0022 β chain-P2A cleavage site-TCR0022 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFGSGATNFSLLKQAGD VEENPGPMASAPISMLAMLFTLSGLRAQSVAQPEDQVNV AEGNPLTVKCTYSVSGNPYLFWYVQYPNRGLQFLLKYITG DNLVKGSYGFEAEFNKSQTSFHLKKPSALVSDSALYFCAV RDDLVGAGSYQLTFGKGTKLSVIPNIQNPDPAVYQLRDSKS SDKSVCLFTDFDSQTNVSQSKDSDVYITDKTVLDMRSMDF KSNSAVAWSNKSDFACANAFNNSIIPEDTFFPSPESSCDVKL VEKSFETDTNLNFQNLSVIGFRILLLKVAGFNLLMTLRLWS S |
| 224 | TCR0022 β chain-Furin cleavage site-P2A cleavage site-TCR0022 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAEFNKSQTSFHLKKPSALVSDSA LYFCAVRDDLVGAGSYQLTFGKGTKLSVIPNIQNPDPAVY QLRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLKVAGFNLL MTLRLWSS |

TABLE 1-continued

Amino acid and nucleic acid sequences of exemplary TCRs*.

| SEQ ID NO: | Description (protein sequences unless otherwise indicated) | Sequence |
|---|---|---|
| 226 | TCR0022 β chain-P2A cleavage site-TCR0022 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYLCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFGSGATNFSLLKQAG DVEENPGPMASAPISMLAMLFTLSGLRAQSVAQPEDQVN VAEGNPLTVKCTYSVSGNPYLFWYVQYPNRGLQFLLKYIT GDNLVKGSYGFEAFFNKSQTSFHLKKPSALVSDSALYFCA VRDDLVGAGSYQLTFGKGTKLSVIPNIQNPDPAVYQLRDS KSSDKSVCLFTDFDSQTNVSQSKDSDVYITDKTVLDMRSM DFKSNSAVAWSNKSDFACANAFNNSIIPEDTFFPSPESSCDV KLVEKSFETDTNLNFQNLSVIGFRILLLKVAGFNLLMTLRL WSS |
| 230 | TCR0028 α chain-furin cleavage site-P2A cleavage site-TCR0028 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRDMANGA GSYQLTFGKGTKLSVIPNIQNPDPAVYQLRDSKSSDKSVCL FTDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSRAKRSG SGATNFSLLKQAGDVEENPGPMLSLLLLLLGLGSVFSAVI SQKPSRDICQRGTSLTIQCQVDSQVTMMFWYRQQPGQSLT LIATANQGSEATYESGFVIDKFPISRPNLTFSTLTVSNMSPED SSIYLCSVGGAGVTDTQYFGPGTRLTVLEDLNKVFPPEVAV FEPSEAEISHTQKATLVCLATGFFPDHVELSWWVNGKEVH SGVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDF |
| 232 | TCR0028 α chain-P2A cleavage site-TCR0028 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRDMANGA GSYQLTFGKGTKLSVIPNIQNPDPAVYQLRDSKSSDKSVCL FTDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWSSGSGATN FSLLKQAGDVEENPGPMLSLLLLLLGLGSVFSAVISQKPS RDICQRGTSLTIQCQVDSQVTMMFWYRQQPGQSLTLIATA NQGSEATYESGFVIDKFPISRPNLTFSTLTVSNMSPEDSSIYL CSVGGAGVTDTQYFGPGTRLTVLEDLNKVFPPEVAVFEPSE AEISHTQKATLVCLATGFFPDHVELSWWVNGKEVHSGVST DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKDF |
| 236 | TCR0028 β chain-Furin cleavage site-P2A cleavage site-TCR0028 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFRAKRSGSGATNFSLL KQAGDVEENPGPMASAPISMLAMLFTLSGLRAQSVAQPE DQVNVAEGNPLTVKCTYSVSGNPYLFWYVQYPNRGLQFL LKYITGDNLVKGSYGFEAEFNKSQTSFHLKKPSALVSDSAL YFCAVRDMANGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLKVAGFNLL MTLRLWSS |

TABLE 1-continued

Amino acid and nucleic acid sequences of exemplary TCRs*.

| SEQ ID NO: | Description (protein sequences unless otherwise indicated) | Sequence |
|---|---|---|
| 238 | TCR0028 β chain-P2A cleavage site-TCR0028 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFGSGATNFSLLKQAGD VEENPGPMASAPISMLAMLFTLSGLRAQSVAQPEDQVNV AEGNPLTVKCTYSVSGNPYLFWYVQYPNRGLQFLLKYITG DNLVKGSYGFEAEFNKSQTSFHLKKPSALVSDSALYFCAV RDMANGAGSYQLTFGKGTKLSVIPNIQNPDPAVYQLRDSK SSDKSVCLFTDFDSQTNVSQSKDSDVYITDKTVLDMRSMD FKSNSAVAWSNKSDFACANAFNNSIIPEDTFFPSPESSCDVK LVEKSFETDTNLNFQNLSVIGFRILLLKVAGFNLLMTLRLW SS |
| 242 | TCR0028 β chain-Furin cleavage site-P2A cleavage site-TCR0028 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYILCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAFFNKSQTSFHLKKPSALVSDSA LYFCAVRDMANGAGSYQLTFGKGTKLSVIPNIQNPDPAVY QLRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL MTLRLWSS |
| 244 | TCR00280 β chain-P2A cleavage site-TCR0028 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYILCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFGSGATNFSLLKQAG DVEENPGPMASAPISMLAMLFTLSGLRAQSVAQPEDQVN VAEGNPLTVKCTYSVSGNPYLFWYVQYPNRGLQFLLKYIT GDNLVKGSYGFEAFFNKSQTSFHLKKPSALVSDSALYFCA VRDMANGAGSYQLTFGKGTKLSVIPNIQNPDPAVYQLRDS KSSDKSVCLFTDFDSQTNVSQSKDSDVYITDKTVLDMRSM DFKSNSAVAWSNKSDFACANAFNNSIIPEDTFFPSPESSCDV KLVEKSFETDTNLNFQNLSVIGFRILLLKVAGFNLLMTLRL WSS |
| 248 | TCR0038 α chain-furin cleavage site-P2A cleavage site-TCR0038 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRDVASGA GSYQLTFGKGTKLSVIPNIQNPDPAVYQLRDSKSSDKSVCL FTDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLKVAGFNLLMTLRLWVSSRAKRSG SGATNFSLLKQAGDVEENPGPMLSLLLLLLGLGSVFSAVI SQKPSRDICQRGTSLTIQCQVDSQVTMMFWYRQQPGQSLT LIATANQGSEATYESGFVIDKFPISRPNLTFSTLTVSNMSPED SSIYLCSVGGAGVTDTQYFGPGTRLTVLEDLNKVFPPEVAV FEPSEAEISHTQKATLVCLATGFFPDHVELSWWVNGKEVH SGVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDF |

TABLE 1-continued

Amino acid and nucleic acid sequences of exemplary TCRs*.

| SEQ ID NO: | Description (protein sequences unless otherwise indicated) | Sequence |
|---|---|---|
| 250 | TCR0038 α chain-P2A cleavage site-TCR0038 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRDVASGA GSYQLTFGKGTKLSVIPNIQNPDPAVYQLRDSKSSDKSVCL FTDFDSQTNVSQSKDSDVYITDKTVLDMRSMDFKSNSAVA WSNKSDFACANAFNNSIIPEDTFFPSPESSCDVKLVEKSFET DTNLNFQNLSVIGFRILLLLKVAGFNLLMTLRLWVSSGSGATN FSLLKQAGDVEENPGPMLSLLLLLLGLGSVFSAVISQKPS RDICQRGTSLTIQCQVDSQVTMMFWYRQQPGQSLTLIATA NQGSEATYESGFVIDKFPISRPNLTFSTLTVSNMSPEDSSIYL CSVGGAGVTDTQYFGPGTRLTVLEDLNKVFPPEVAVFEPSE AEISHTQKATLVCLATGFFPDHVELSWWVNGKEVHSGVST DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKDF |
| 254 | TCR0038 β chain-Furin cleavage site-P2A cleavage site-TCR0038 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLNSALVLMAMVKRKDFRAKRSGSGATNFSLL KQAGDVEENPGPMASAPISMLAMLFTLSGLRAQSVAQPE DQVNVAEGNPLTVKCTYSVSGNPYLFWYVQYPNRGLQFL LKYITGDNLVKGSYGFEAEFNKSQTSFHLKKPSALVSDSAL YFCAVRDVASGAGSYQLTFGKGTKLSVIPNIQNPDPAVYQ LRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL MTLRLWSS |
| 256 | TCR0038 β chain-P2A cleavage site-TCR0038 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLNSALVLMAMVKRKDFGSGATNFSLLKQAGD VEENPGPMASAPISMLAMLFTLSGLRAQSVAQPEDQVNV AEGNPLTVKCTYSVSGNPYLFWYVQYPNRGLQFLLKYITG DNLVKGSYGFEAEFNKSQTSFHLKKPSALVSDSALYFCAV RDVASGAGSYQLTFGKGTKLSVIPNIQNPDPAVYQLRDSKS SDKSVCLFTDFDSQTNVSQSKDSDVYITDKTVLDMRSMDF KSNSAVAWSNKSDFACANAFNNSIIPEDTFFPSPESSCDVKL VEKSFETDTNLNFQNLSVIGFRILLLLKVAGFNLLMTLRLWS S |
| 260 | TCR0038 β chain-Furin cleavage site-P2A cleavage site-TCR0038 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYILCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFRAKRSGSGATNFSL LKQAGDVEENPGPMASAPISMLAMLFTLSGLRAQSVAQP EDQVNVAEGNPLTVKCTYSVSGNPYLFWYVQYPNRGLQF LLKYITGDNLVKGSYGFEAEFFNKSQTSFHLKKPSALVSDSA LYFCAVRDVASGAGSYQLTFGKGTKLSVIPNIQNPDPAVY QLRDSKSSDKSVCLFTDFDSQTNVSQSKDSDVYITDKTVLD MRSMDFKSNSAVAWSNKSDFACANAFNNSIIPEDTFFPSPE SSCDVKLVEKSFETDTNLNFQNLSVIGFRILLLLKVAGFNLL, MTLRLWSS |

TABLE 1-continued

Amino acid and nucleic acid sequences of exemplary TCRs*.

| SEQ ID NO: | Description (protein sequences unless otherwise indicated) | Sequence |
|---|---|---|
| 262 | TCR00380 β chain-P2A cleavage site-TCR0038 α chain sequence, with optimized N-terminal leader sequence (the leader sequences are bold) | MKSVLLLTTLLVPAHLVAAVISQKPSRDICQRGTSLTIQC QVDSQVTMMFWYRQQPGQSLTLIATANQGSEATYESGFVI DKFPISRPNLTFSTLTVSNMSPEDSSIYILCSVGGAGVTDTQY FGPGTRLTVLEDLNKVFPPEVAVFEPSEAEISHTQKATLVCL ATGFFPDHVELSWWVNGKEVHSGVSTDPQPLKEQPALNDS RYCLSSRLRVSATFWQNPRNHFRCQVQFYGLSENDEWTQ DRAKPVTQIVSAEAWGRADCGFTSVSYQQGVLSATILYEIL LGKATLYAVLVSALVLMAMVKRKDFGSGATNFSLLKQAG DVEENPGPMASAPISMLAMLFTLSGLRAQSVAQPEDQVN VAEGNPLTVKCTYSVSGNPYLFWYVQYPNRGLQFLLKYIT GDNLVKGSYGFEAFFNKSQTSFHLKKPSALVSDSALYFCA VRDVASGAGSYQLTFGKGTKLSVIPNIQNPDPAVYQLRDS KSSDKSVCLFTDFDSQTNVSQSKDSDVYITDKTVLDMRSM DFKSNSAVAWSNKSDFACANAFNNSIIPEDTFFPSPESSCDV KLVEKSFETDTNLNFQNLSVIGFRILLLKVAGFNLLMTLRL WSS |
| 416 | TCR0070 α chain-Furin cleavage site-P2A cleavage site-TCR0070 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRELYSATV DYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDITFFPSPESSCDVKLVEKSFET DTNLNFQNLSVIGFRILLLKVAGFNLLMTLRLWSSRAKRSG SGATNFSLLKQAGDVEENPGPMLSLLLLLLGLGSVFSAVI SQKPSRDICQRGTSLTIQCQVDSQVTMMFWYRQQPGQSLT LIATANQGSEATYESGFVIDKFPISRPNLTFSTLTVSNMSPED SSIYLCSVGGAGVTDTQYFGPGTRLTVLEDLNKVFPPEVAV FEPSEAEISHTQKATLVCLATGFFPDHVELSWWVNGKEVH SGVSTDPQPLKEQPALNDSRYCLSSRLRVSATFWQNPRNHF RCQVQFYGLSENDEWTQDRAKPVTQIVSAEAWGRADCGF TSVSYQQGVLSATILYEILLGKATLYAVLVSALVLMAMVK RKDF |
| 417 | TCR0070 α chain-P2A cleavage site-TCR0070 β chain sequence (the leader sequences are bold) | MASAPISMLAMLFTLSGLRAQSVAQPEDQVNVAEGNPLT VKCTYSVSGNPYLFWYVQYPNRGLQFLLKYITGDNLVKGS YGFEAEFNKSQTSFHLKKPSALVSDSALYFCAVRELYSATV DYQLTFGKGTKLSVIPNIQNPDPAVYQLRDSKSSDKSVCLF TDFDSQTNVSQSKDSDVYITDKTVLDMRSMDFKSNSAVA WSNKSDFACANAFNNSIIPEDITFFPSPESSCDVKLVEKSFET DTNLNFQNLSVIGFRILLLKVAGFNLLMTLRLWSSGSGATN FSLLKQAGDVEENPGPMLSLLLLLLGLGSVFSAVISQKPS RDICQRGTSLTIQCQVDSQVTMMFWYRQQPGQSLTLIATA NQGSEATYESGFVIDKFPISRPNLTFSTLTVSNMSPEDSSIYL CSVGGAGVTDTQYFGPGTRLTVLEDLNKVFPPEVAVFEPSE AEISHTQKATLVCLATGFFPDHVELSWWVNGKEVHSGVST DPQPLKEQPALNDSRYCLSSRLRVSATFWQNPRNHFRCQV QFYGLSENDEWTQDRAKPVTQIVSAEAWGRADCGFTSVS YQQGVLSATILYEILLGKATLYAVLVSALVLMAMVKRKDF |
| 418 | TCR0070 β chain-Furin cleavage site-P2A cleavage site-TCR0070 α chain sequence (the leader sequences are bold) | MLSLLLLLLGLGSVFSAVISQKPSRDICQRGTSLTIQCQVD SQVTMMFWYRQQPGQSLTLIATANQGSEATYESGFVIDKF PISRPNLTFSTLTVSNMSPEDSSIYLCSVGGAGVTDTQYFGP GTRLTVLEDLNKVFPPEVAVFEPSEAEISHTQKATLVCLAT GFFPDHVELSWWVNGKEVHSGVSTDPQPLKEQPALNDSR YCLSSRLRVSATFWQNPRNHFRCQVQFYGLSENDEWTQD RAKPVTQIVSAEAWGRADCGFTSVSYQQGVLSATILYEILL GKATLYAVLVSALVLMAMVKRKDFRAKRSGSGATNFSLL KQAGDVEENPGPMASAPISMLAMLFTLSGLRAQSVAQPE DQVNVAEGNPLTVKCTYSVSGNPYLFWYVQYPNRGLQFL LKYITGDNLVKGSYGFEAEFNKSQTSFHLKKPSALVSDSAL YFCAVRELYSATVDYQLTFGKGTKLSVIPNIQNPDPAVYQL RDSKSSDKSVCLFTDFDSQTNVSQSKDSDVYITDKTVLDM RSMDFKSNSAVAWSNKSDFACANAFNNSIIPEDTFFPSPESS CDVKLVEKSFETDTNLNFQNLSVIGFRILLLKVAGFNLLMT LRLWSS |

TABLE 1-continued

Amino acid and nucleic acid sequences of exemplary TCRs*.

| SEQ ID NO: | Description (protein sequences unless otherwise indicated) | Sequence |
|---|---|---|
| 419 | TCR0070 β chain-P2A cleavage site-TCR0070 α chain sequence (the leader sequences are bold) | MLSLLLLLLGLGSVFSAVISQKPSRDICQRGTSLTIQCQVDSQVTMMFWYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDFGSGATNFSLLKQAGDVEENPGPMASAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRELYSATVDYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 420 | TCR0070 β chain-Furin cleavage site-P2A cleavage site-TCR0070 α chain sequence, with optimized N-terminal leader sequence (the leader sequences are bold) | MKSVLLLTTLLVPAHLVAAVISQKPSRDICQRGTSLTIQCQVDSQVTMMFWYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDFRAKRSGSGATNFSLLKQAGDVEENPGPMASAPISMLAMLFTLSGLRAQSVAQPEDQVNVAEGNPLTVKCTYSVSGNPYLFWYVQYPNRGLQFLLKYITGDNLVKGSYGFEAFFNKSQTSFHLKKPSALVSDSALYFCAVRELYSATVDYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 421 | TCR0070 β chain-P2A cleavage site-TCR0070 α chain sequence, with optimized N-terminal leader sequence (the leader sequences are bold) | MKSVLLLTTLLVPAHLVAAVISQKPSRDICQRGTSLTIQCQVDSQVTMMFWYRQQPGQSLTLIATANQGSEATYESGFVIDKFPISRPNLTFSTLTVSNMSPEDSSIYLCSVGGAGVTDTQYFGPGTRLTVLEDLNKVFPPEVAVFEPSEAEISHTQKATLVCLATGFFPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSVSYQQGVLSATILYEILLGKATLYAVLVSALVLMAMVKRKDFGSGATNFSLLKQAGDVEENPGPMASAPISMLAMLFTLSGLRAQSVAQPEDQVNVAEGNPLTVKCTYSVSGNPYLFWYVQYPNRGLQFLLKYITGDNLVKGSYGFEAFFNKSQTSFHLKKPSALVSDSALYFCAVRELYSATVDYQLTFGKGTKLSVIPNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |

* CDRs are defined according to the IMGT numbering system (Lefranc et al., Dev Comp Immunol. 2003; 27(1): 55-77.)

TABLE 2

Alpha chain CDR amino acid sequences of exemplary NY-ESO-1 TCRs. *

| Vα (SEQ ID NO:) | CDR1α (SEQ ID NO:) | CDR2α (SEQ ID NO:) | CDR3α (SEQ ID NO:) |
|---|---|---|---|
| TCR1816 Vα (3) | VSGNPY (5) | YITGDNLV (6) | AVRELYSGAGSYQLT (39) |
| TCR0002 Vα (66) | VSGNPY (5) | YITGDNLV (6) | AVRDIKSGAGSYQLT (40) |
| TCR0010 Vα (67) | VSGNPY (5) | YITGDNLV (6) | AVRDSFEGAGSYQLT (41) |
| TCR0012 Vα (68) | VSGNPY (5) | YITGDNLV (6) | AVRGLLNGAGSYQLT (42) |

TABLE 2-continued

Alpha chain CDR amino acid sequences of exemplary NY-ESO-1 TCRs. *

| Vα (SEQ ID NO:) | CDR1α (SEQ ID NO:) | CDR2α (SEQ ID NO:) | CDR3α (SEQ ID NO:) |
|---|---|---|---|
| TCR0014 Vα (69) | VSGNPY (5) | YITGDNLV (6) | AVRDLFTGAGSYQLT (43) |
| TCR0016 Vα (70) | VSGNPY (5) | YITGDNLV (6) | AVRDGRTGAGSYQLT (44) |
| TCR0018 Vα (71) | VSGNPY (5) | YITGDNLV (6) | AVRDLSDGAGSYQLT (45) |
| TCR0020 Vα (72) | VSGNPY (5) | YITGDNLV (6) | AVRSSYEGAGRYQLT (46) |
| TCR0022 Vα (73) | VSGNPY (5) | YITGDNLV 6) | AVRDDLVGAGSYQLT (47) |
| TCR0024 Vα (74) | VSGNPY (5) | YITGDNLV (6) | AVRDQALGAGSYQLT (48) |
| TCR0028 Vα (75) | VSGNPY (5) | YITGDNLV (6) | AVRDMANGAGSYQLT (49) |
| TCR0030 Vα (76) | VSGNPY (5) | YITGDNLV (6) | AVRDSKAGAGSYQLT (50) |
| TCR0032 Vα (77) | VSGNPY (5) | YITGDNLV (6) | AVRDLFCGAGSYQLT (51) |
| TCR0034 Vα (78) | VSGNPY (5) | YITGDNLV (6) | AVRDLRGGAGSYQLT (52) |
| TCR0036 Vα (79) | VSGNPY (5) | YITGDNLV (6) | AVRDLTTGAGSYQLT (53) |
| TCR0038 Vα (80) | VSGNPY (5) | YITGDNLV (6) | AVRDVASGAGSYQLT (54) |
| TCR0050 Vα (81) | VSGNPY (5) | YITGDNLV (6) | AVRELYSVAVRYQLT (55) |
| TCR0060 Vα (82) | VSGNPY (5) | YITGDNLV (6) | AVRELYSRGVKWQLT (56) |
| TCR0062 Vα (83) | VSGNPY (5) | YITGDNLV (6) | AVRELYSTTFGWQLT (57) |
| TCR0066 Vα (84) | VSGNPY (5) | YITGDNLV (6) | AVRELYSALVTYQLT (58) |
| TCR0068 Vα (85) | VSGNPY (5) | YITGDNLV (6) | AVRELYSPRLMWQLT (59) |
| TCR0070 Vα (86) | VSGNPY (5) | YITGDNLV (6) | AVRELYSATVDYQLT (60) |

* CDRs are defined according to Lefranc et al., Dev Comp Immunol. 2003; 27(1): 55-77.

TABLE 3

Beta chain CDR amino acid sequences of exemplary NY-ESO-1 TCRs. *

| Vβ (SEQ ID NO:) | CDR1β (SEQ ID NO:) | CDR2β (SEQ ID NO:) | CDR3β1 (SEQ ID NO:) |
|---|---|---|---|
| TCR18168 Vβ (4) | SQVTM (8) | ANQGSEA (9) | SVGGAGVTDTQY (10) |
| TCR0002 Vβ (4) | SQVTM (8) | ANQGSEA (9) | SVGGAGVTDTQY (10) |
| TCR0010 Vβ (4) | SQVTM (8) | ANQGSEA (9) | SVGGAGVTDTQY (10) |
| TCR0012 Vβ (4) | SQVTM (8) | ANQGSEA (9) | SVGGAGVTDTQY (10) |
| TCR0014 Vβ (4) | SQVTM (8) | ANQGSEA (9) | SVGGAGVTDTQY (10) |
| TCR0016 Vβ (4) | SQVTM (8) | ANQGSEA (9) | SVGGAGVTDTQY (10) |
| TCR0018 Vβ (4) | SQVTM (8) | ANQGSEA (9) | SVGGAGVTDTQY (10) |
| TCR0020 Vβ (4) | SQVTM (8) | ANQGSEA (9) | SVGGAGVTDTQY (10) |
| TCR0022 Vβ (4) | SQVTM (8) | ANQGSEA (9) | SVGGAGVTDTQY (10) |
| TCR0024 Vβ (4) | SQVTM (8) | ANQGSEA (9) | SVGGAGVTDTQY (10) |
| TCR0028 Vβ (4) | SQVTM (8) | ANQGSEA (9) | SVGGAGVTDTQY (10) |
| TCR0030 Vβ (4) | SQVTM (8) | ANQGSEA (9) | SVGGAGVTDTQY (10) |
| TCR0032 Vβ (4) | SQVTM (8) | ANQGSEA (9) | SVGGAGVTDTQY (10) |
| TCR0034 Vβ (4) | SQVTM (8) | ANQGSEA (9) | SVGGAGVTDTQY (10) |

TABLE 3-continued

Beta chain CDR amino acid sequences of exemplary NY-ESO-1 TCRs. *

| Vβ (SEQ ID NO:) | CDR1β (SEQ ID NO:) | CDR2β (SEQ ID NO:) | CDR3β1 (SEQ ID NO:) |
|---|---|---|---|
| TCR0036 Vβ (4) | SQVTM (8) | ANQGSEA (9) | SVGGAGVTDTQY (10) |
| TCR0038 Vβ (4) | SQVTM (8) | ANQGSEA (9) | SVGGAGVTDTQY (10) |
| TCR0050 Vβ (4) | SQVTM (8) | ANQGSEA (9) | SVGGAGVTDTQY (10) |
| TCR0060 Vβ (4) | SQVTM (8) | ANQGSEA (9) | SVGGAGVTDTQY (10) |
| TCR0062 Vβ (4) | SQVTM (8) | ANQGSEA (9) | SVGGAGVTDTQY (10) |
| TCR0066 Vβ (4) | SQVTM (8) | ANQGSEA (9) | SVGGAGVTDTQY (10) |
| TCR0068 Vβ (4) | SQVTM (8) | ANQGSEA (9) | SVGGAGVTDTQY (10) |
| TCR0070 Vβ (4) | SQVTM (8) | ANQGSEA (9) | SVGGAGVTDTQY (10) |

* CDRs are defined according to Lefranc et al., Dev Comp Immunol. 2003; 27(1): 55-77.

TABLE 4

Variable region amino acid sequences of exemplary NY-ESO-1 TCRs.

| Chimeric TCR name | Human TCR name | SEQ ID NO of CDR3α | SEQ ID NO of Vα | SEQ ID NO of Full-length human α chain | SEQ ID NO of Vβ | SEQ ID NO of Full-length human β chain |
|---|---|---|---|---|---|---|
| TCR18168c | TCR18168 | 39 | 3 | 13 | 4 | 14 |
| TCR0001 | TCR0002 | 40 | 66 | 105 | 4 | 14 |
| TCR0009 | TCR0010 | 41 | 67 | N/A | 4 | 14 |
| TCR0011 | TCR0012 | 42 | 68 | N/A | 4 | 14 |
| TCR0013 | TCR0014 | 43 | 69 | 110 | 4 | 14 |
| TCR0015 | TCR0016 | 44 | 70 | N/A | 4 | 14 |
| TCR0017 | TCR0018 | 45 | 71 | 115 | 4 | 14 |
| TCR0019 | TCR0020 | 46 | 72 | N/A | 4 | 14 |
| TCR0021 | TCR0022 | 47 | 73 | 120 | 4 | 14 |
| TCR0023 | TCR0024 | 48 | 74 | N/A | 4 | 14 |
| TCR0027 | TCR0028 | 49 | 75 | 125 | 4 | 14 |
| TCR0029 | TCR0030 | 50 | 76 | N/A | 4 | 14 |
| TCR0031 | TCR0032 | 51 | 77 | N/A | 4 | 14 |
| TCR0033 | TCR0034 | 52 | 78 | N/A | 4 | 14 |
| TCR0035 | TCR0036 | 53 | 79 | N/A | 4 | 14 |
| TCR0037 | TCR0038 | 54 | 80 | 408 | 4 | 14 |
| TCR0049 | TCR0050 | 55 | 81 | N/A | 4 | 14 |
| TCR0059 | TCR0060 | 56 | 82 | N/A | 4 | 14 |
| TCR0061 | TCR0062 | 57 | 83 | N/A | 4 | 14 |
| TCR0065 | TCR0066 | 58 | 84 | N/A | 4 | 14 |
| TCR0067 | TCR0068 | 59 | 85 | N/A | 4 | 14 |
| TCR0069 | TCR0070 | 60 | 86 | 412 | 4 | 14 |

TABLE 5

Exemplary peptide sequences.

| SEQ ID NO: | Description | Amino acid Sequence |
|---|---|---|
| 1 | NY-ESO-1$_{157-165}$ | SLLMWITQC |
| 2 | NY-ESO-1$_{157-165}$ anchor optimized peptide | SLLMWITQV |
| 22 | MART-1 anchor optimized peptide | ELAGIGILTV |

In one aspect, the instant disclosure provides TCRs that bind to a peptide consisting of the amino acid The CDRs of a TCR disclosed herein can be defined using any art recognized numbering convention. Additionally or alternatively, the CDRs can be defined empirically, e.g., based upon structural analysis of the interaction of the TCR with a cognate antigen (e.g., a peptide or a peptide-MHC complex).

In certain embodiments, the instant disclosure provides a TCR that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), wherein the TCR comprises one, two, or all three of the CDRs of a Vα or Vβ disclosed in Table 1 herein, wherein the CDRs are defined according to the IMGT numbering system, for example, as described in Lefranc M-P (1999) supra and Lefranc M-P et al., (1999) supra.

In certain embodiments, the instant disclosure provides a TCR that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), wherein the TCR comprises one, two, or all three of the CDRs of a Vα or Vβ disclosed in Table 1 herein, wherein the CDRs are defined according to the Kabat numbering system described in Kabat supra.

In certain embodiments, the instant disclosure provides a TCR that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), wherein the TCR comprises one, two, or all three of the CDRs of a Vα or Vβ disclosed in Table 1 herein, wherein the CDRs are determined empirically, e.g., based upon structural analysis of the interaction of the TCR with a cognate antigen (e.g., a peptide-MHC complex).

In certain embodiments, the instant disclosure provides a TCR that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), wherein the TCR comprises one, two, or all three of the CDRs of a Vα or Vβ disclosed in Table 1 herein, wherein each CDR is defined in accordance with the IMGT or the Kabat numbering system, or is determined empirically, e.g., based upon structural analysis of the interaction of the TCR with a cognate antigen (e.g., a peptide or a peptide-MHC complex).

In certain embodiments, the instant disclosure provides a TCR (e.g., an isolated TCR) that binds to a peptide consisting of the amino acid sequence set forth in SEQ ID NO: or 2 (e.g, a TCR that binds to a SLLMWITQC (SEQ ID NO: 1) or SLLMWITQV (SEQ ID NO: 2)-HLA-A*0201 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences set forth in SEQ ID NOs: 5, 6, and 61; 5, 6, and 62; 5, 6, and 63; 5, 6, and 64; or 5, 6, and 65, respectively, preferably 5, 6, and 7; 5, 6, and 39; 5, 6, and 40; 5, 6, and 41; 5, 6, and 42; 5, 6, and 43; 5, 6, and 44; 5, 6, and 45; 5, 6, and 46; 5, 6, and 47; 5, 6, and 48; 5, 6, and 49; 5, 6, and 50; 5, 6, and 51; 5, 6, and 52; 5, 6, and 53; 5, 6, and 54; 5, 6, and 55; 5, 6, and 56; 5, 6, and 57; 5, 6, and 58; 5, 6, and 59; or 5, 6, and 60, respectively, and the CDR1β, CDR2β, and CDR3β comprise the CDR1β, CDR2β, and CDR3β amino acid sequences set forth in SEQ ID NO: 8, 9, and 10, respectively. In one embodiment, each CDR is defined in accordance with the IMGT numbering system. In one embodiment, each CDR is defined in accordance with the Kabat numbering system. In one embodiment, each CDR is defined empirically, e.g., based upon structural analysis of the interaction of the TCR with a cognate antigen (e.g., a peptide or a peptide-MHC complex). In one embodiment, each CDR is independently defined in accordance with the IMGT or Kabat numbering system, or is determined empirically, e.g., based upon structural analysis of the interaction of the TCR with a cognate antigen (e.g., a peptide-MHC complex).

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising
(a) a CDR1α comprising the amino acid sequence of SEQ ED NO: 5, and/or
(b) a CDR2α comprising the amino acid sequence of SEQ ID NO: 6, and/or
(c) a CDR3α comprising the amino acid sequence of SEQ ID NO: 61, and/or
(d) a CDR1β comprising the amino acid sequence of SEQ ID NO: 8, and/or
(e) a CDR2β comprising the amino acid sequence of SEQ ID NO: 9, and/or
(f) a CDR3β comprising the amino acid sequence of SEQ ID NO: 10.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising
(a) a CDR1α comprising the amino acid sequence of SEQ ID NO: 5, and/or
(b) a CDR2α comprising the amino acid sequence of SEQ ID NO: 6, and/or
(c) a CDR3α comprising the amino acid sequence of SEQ ID NO: 62, and/or
(d) a CDR1β comprising the amino acid sequence of SEQ ID NO: 8, and/or
(e) a CDR2β comprising the amino acid sequence of SEQ ID NO: 9, and/or
(f) a CDR3β comprising the amino acid sequence of SEQ ID NO: 10.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising
(a) a CDR1α comprising the amino acid sequence of SEQ ID NO: 5, and/or
(b) a CDR2α comprising the amino acid sequence of SEQ H) NO: 6, and/or
(c) a CDR3α comprising the amino acid sequence of SEQ ID NO: 63, and/or
(d) a CDR1β comprising the amino acid sequence of SEQ ID NO: 8, and/or
(e) a CDR2β comprising the amino acid sequence of SEQ ID NO: 9, and/or
(f) a CDR3β comprising the amino acid sequence of SEQ ID NO: 10.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising
(a) a CDR1α comprising the amino acid sequence of SEQ ID NO: 5, and/or
(b) a CDR2α comprising the amino acid sequence of SEQ II) NO: 6, and/or
(c) a CDR3α comprising the amino acid sequence of SEQ ID NO: 64, and/or
(d) a CDR1β comprising the amino acid sequence of SEQ ID NO: 8, and/or
(e) a CDR2β comprising the amino acid sequence of SEQ II) NO: 9, and/or
(f) a CDR3β comprising the amino acid sequence of SEQ ID NO: 10.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising
(a) a CDR1α comprising the amino acid sequence of SEQ ID NO: 5, and/or
(b) a CDR2α comprising the amino acid sequence of SEQ ID NO: 6, and/or
(c) a CDR3α comprising the amino acid sequence of SEQ ID NO: 65, and/or
(d) a CDR1β comprising the amino acid sequence of SEQ ID NO: 8, and/or
(e) a CDR2β comprising the amino acid sequence of SEQ ID NO: 9, and/or
(f) a CDR3β comprising the amino acid sequence of SEQ ID NO: 10.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising a CDR3α comprising an amino acid sequence selected from the group consisting of SEQ ID NOs: 7, 39, 40, 41, 42, 43, 44, 45, 46, 47, 48, 49, 50, 51, 52, 53, 54, 55, 56, 57, 58, 59, and 60.

In certain embodiments; the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising a CDR3β comprising the amino acid sequence of SEQ ID NO: 10.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), wherein the TCR comprises a Vα having the CDR1α, CDR2α, and CDR3α amino acid sequences set forth in SEQ ID NOs: 5, 6, and 7; 5, 6, and 39; 5, 6, and 40; 5, 6, and 41; 5, 6, and 42; 5, 6, and 43; 5, 6, and 44; 5, 6, and 45; 5, 6, and 46; 5, 6, and 47; 5, 6, and 48; 5, 6, and 49; 5, 6, and 50; 5, 6, and 51; 5, 6, and 52; 5, 6, and 53; 5, 6, and 54; 5, 6, and 55; 5, 6, and 56; 5, 6, and 57; 5, 6, and 58; 5, 6, and 59; or 5, 6, and 60, respectively.

In certain embodiments; the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), wherein the TCR comprises a Vβ having the CDR1β, CDR2β, and CDR3β amino acid sequences set forth in SEQ ID NOs: 8, 9, and 10, respectively.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), wherein the TCR comprises a Vα having CDR1α, CDR2α, and CDR3α, and a Vβ having CDR1β, CDR2β and CDR3β, and wherein the CDR1α, CDR2α, CDR3α, CDR1β, CDR2β, and CDR3β comprise the amino acid sequences set forth in SEQ ID NOs: 5, 6, 7, 8, 9, and 10; 5, 6, 39, 8, 9, and 10; 5, 6, 40, 8, 9, and 10; 5, 6, 41, 8, 9, and 10; 5, 6, 42, 8, 9, and 10; 5, 6, 43, 8, 9, and 10; 5, 6, 44, 8, 9, and 10; 5, 6, 45, 8, 9, and 10; 5, 6, 46, 8, 9, and 10; 5, 6, 47, 8, 9, and 10; 5, 6, 48, 8, 9, and 10; 5, 6, 49, 8, 9, and 10; 5, 6, 50, 8, 9, and 10; 5, 6, 51, 8, 9, and 10; 5, 6, 52, 8, 9, and 10; 5, 6, 53, 8, 9, and 10; 5, 6, 54, 8, 9, and 10; 5, 6, 55, 8, 9, and 10; 5, 6, 56, 8, 9, and 10; 5, 6, 57, 8, 9, and 10; 5, 6, 58, 8, 9, and 10; 5, 6, 59, 8, 9, and 10; or 5, 6, 60, 8, 9, and 10, respectively.

In certain embodiments, the instant disclosure provides a TCR (e.g, an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQC (SEQ ID NO: 2)-HLA-A*0201 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 3, 66, 67, 68, 69, 70, 71, 72, 73, 74, 75, 76, 77, 78, 79, 80, 81, 82, 83, 84, 85, or 86. In certain embodiments, the TCR comprises a Vα having the amino acid sequence set forth in SEQ ID NO: 3, 66, 67, 68, 69, 70, 71, 72, 73, 74, 75, 76, 77, 78, 79, 80, 81, 82, 83, 84, 85, or 86.

In certain embodiments, the instant, TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 4. In certain embodiments, the TCR comprises a Vβ having the amino acid sequence set forth in SEQ ID NO: 4.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQC (SEQ ID NO: 2)-HLA-A*0201 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 3, 66, 67, 68, 69, 70, 71, 72, 73, 74, 75, 76, 77, 78, 79, 80, 81, 82, 83, 84, 85, or 86, and a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 4. In certain embodiments, the TCR comprises a Vα and a Vβ comprising the amino acid sequences set forth in SEQ NOs: 3 and 4, 66 and 4, 67 and 4, 68 and 4, 69 and 4, 70 and 4, 71 and 4, 72 and 4, 73 and 4, 74 and 4, 75 and 4, 76 and 4, 77 and 4, 78 and 4, 79 and 4, 80 and 4, 81 and 4, 82 and 4, 83 and 4, 84 and 4, 85 and 4, or 86 and 4, respectively.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQC (SEQ ID NO: 2)-HLA-A*0201 complex), the TCR comprising (a) a CDR1α comprising the amino acid sequence of SEQ ID NO: 5, and/or (b) a CDR2α comprising the amino acid sequence of SEQ ID NO: 6, and/or (c) a CDR3α comprising an amino acid sequence selected from the group consisting of SEQ ID NOs: 7 and 39-60, and/or (d) a CDR1β comprising the amino acid sequence of SEQ ID NO:8, and/or (e) a CDR2β comprising the amino acid sequence of SEQ ID NO: 9, and/or (f) a CDR3β comprising the amino acid sequence of SEQ ID NO:10.

In certain embodiments, the instant disclosure provides a TCR (e.g., an isolated TCR) that binds to a peptide consisting of the amino acid sequence set forth in SEQ ID NO: 1 or 2 (e.g., a TCR that hinds to a SLLMWITQC (SEQ ID NO: 1) or SLLMWITQV (SEQ ID NO: 2)-HLA-A*0201 complex), the TCR comprising a CDR3α comprising an amino acid sequence selected from the group consisting of SEQ ID NOs: 7 and 39-60.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising a CDR30 comprising the amino acid sequence of SEQ ID NO: 10.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising a CDR3α comprising the amino acid sequence of SEQ ID NO: 7, and a CDR3β comprising the amino acid sequence of SEQ ID NO: 10. In certain embodiments, the instant disclosure provides a TCR (e.g., an isolated. TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising a CDR3α and a CDR3β comprising the amino acid sequences set forth in SEQ ID NOs: 39 and 10; 40 and 10; 41 and 10; 42 and 10; 43 and 10; 44 and 10; 45 and 10; 46 and 10; 47 and 10; 48 and 10; 49 and 10; 50 and 10; 51 and 10; 52 and 10; 53 and 10; 54 and 10; 55 and 10; 56 and 10; 57 and 10; 48 and 10; 59 and 10; or 60 and 10, respectively.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ NO: 2)-HLA-A*0201 complex), wherein the TCR comprises a Vα having the CDR1α, CDR2α, and CDR3α amino acid sequences set forth in SEQ ID NOs: 5, 6, and 7; 5, 6, and 39; 5, 6, and 40; 5, 6, and 41; 5, 6, and 42; 5, 6, and 43; 5, 6, and 44; 5, 6, and 45; 5, 6, and 46; 5, 6, and 47; 5, 6, and 48; 5, 6, and 49; 5, 6, and 50; 5, 6, and 51; 5, 6, and 52; 5, 6, and 53; 5, 6, and 54; 5, 6, and 55; 5, 6, and 56; 5, 6, and 57; 5, 6, and 58; 5, 6, and 59; or 5, 6, and 60, respectively.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), wherein the TCR comprises a Vα having the CDR1β, CDR2β, and CDR3β amino acid sequences set forth in SEQ ID NOs: 8, 9, and 10, respectively.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), wherein the TCR comprises a Vα having CDR1α, CDR2α, and CDR3α, and a Vβ having CDR1β, CDR2β, and CDR3β, and wherein the CDR1α, CDR2α, CDR3α, CDR1β, CDR2β, and CDR3β comprise the amino acid sequences set forth in SEQ ID NOs: 5, 6, 7, 8, 9, and 10; 5, 6, 39, 8, 9, and 10; 5, 6, 40, 8, 9, and 10; 5, 6, 41, 8, 9 and 10; 5, 6, 42, 8, 9 and 10; 5, 6, 43, 8, 9, and 10; 5, 6, 44, 8, 9 and 10; 5, 6, 45, 8, 9 and 10; 5, 6, 46, 8, 9, and 10; 5, 6, 47, 8, 9, and 10; 5, 6, 48, 8, 9, and 10; 5, 6, 49, 8, 9, and 10; 5, 6, 50, 8, 9, and 10; 5, 6, 51, 8, 9, and 10; 5, 6, 52, 8, 9, and 10; 5, 6, 53, 8, 9, and 10; 5, 6, 54, 8, 9, and 10; 5, 6, 55, 8, 9, and 10; 5, 6, 56, 8, 9, and 10, 5, 6, 57, 8, 9, and 10; 5, 6, 58, 8, 9, and 10; 5, 6, 59, 8, 9, and 10; or 5, 6, 60, 8, 9, and 10, respectively.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HA-A*0201 complex), the TCR comprising a Vα having an amino acid sequence that is at least 75%, 80%, 85%, 90%, 95%, or 100% at least 86, 87, 88, 89, 90, 91, 92, 93, 94, 95, 96, 97, 98 or 99%) identical to the amino acid sequence selected from the group consisting of SEQ ID NOs: 3 and 66-86. In certain embodiments, the TCR comprises a Vα having the amino acid sequence set forth in SEQ ID NO: 3. In certain embodiments, the TCR comprises a Vα having the amino acid sequence set forth in SEQ ID NO: 66. In certain embodiments, the TCR comprises a Vat having the amino acid sequence set forth in SEQ ID NO: 67. In certain embodiments, the TCR comprises a Vat having the amino acid sequence set forth in SEQ ID NO: 68. In certain embodiments, the TCR comprises a Vα having the amino acid sequence set forth in SEQ ID NO: 69. In certain embodiments, the TCR comprises a Vα having the amino acid sequence set forth in SEQ ID NO: 70. In certain embodiments, the TCR comprises a Vα having the amino acid sequence set forth in SEQ ID NO: 71. In certain embodiments, the TCR comprises a Vα having the amino acid sequence set forth in SEQ ID NO: 72. In certain embodiments, the TCR comprises a Vα having the amino acid sequence set forth in SEQ ID NO: 73. In certain embodiments, the TCR comprises a Vα having the amino acid sequence set forth in SEQ ID NO: 74. In certain embodiments, the TCR comprises a Vu having the amino acid sequence set forth in SEQ ID NO: 75. In certain embodiments, the TCR comprises a Vα having the amino acid sequence set forth in SEQ ID NO: 76. In certain embodiments, the TCR comprises a Vα having the amino acid sequence set forth in SEQ ID NO: 77, in certain embodiments, the TCR comprises a Vα having the amino acid sequence set forth in SEQ ID NO: 78. In certain embodiments, the TCR comprises a Vα having the amino acid sequence set forth in SEQ ID NO: 79. In certain embodiments, the TCR comprises a Vα having the amino acid sequence set forth in SEQ ID NO: 80. In certain embodiments, the TCR comprises a Vα having the amino acid sequence set forth in SEQ ID NO: 81. In certain embodiments, the TCR comprises a Vα having the amino acid sequence set forth in SEQ ID NO: 82. In certain embodiments, the TCR comprises a Vα having the amino acid sequence set forth in SEQ NO: 83. In certain embodiments, the TCR comprises a Vα having the amino acid sequence set forth in SEQ ID NO: 84. In certain embodiments, the TCR comprises a Vα having the amino acid sequence set forth in SEQ ID NO: 85. In certain embodiments, the TCR comprises a Vα, having the amino acid sequence set forth in SEQ ID NO: 86.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 4. In certain embodiments, the TCR comprises a Vβ having the amino acid sequence set forth in SEQ ID NO: 4.

In certain embodiments, the instant disclosure provides a TCR (e.g, an isolated TCR) that binds to a peptide consisting of the amino acid sequence set forth in SEQ ID NO: 1 (e.g., a TCR that binds to a SLLMWITQC (SEQ ID NO: I)-HLA-A*0201 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence selected from the group consisting of SEQ ID NOs: 3 and 66-86, and a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 4. In certain embodiments, the TCR comprises a Vα having the amino acid sequence set forth in SEQ ID NO: 3, 66, 67, 68, 69, 70, 71, 72, 73, 74, 75, 76, 77, 78, 79, 80, 81, 82, 83, 84, 85, or 86, and a Vβ having the amino acid sequence set forth in SEQ ID NO: 4.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) SLLMWITQV (SEQ NO: 2)-HLA-A*0201 complex), the TCR comprising a Vα having an amino acid sequence derived from a human TRAV3 germline sequence (e.g., TRAV3*01, e.g., comprising the amino acid sequence of SEQ ID NO: 18). In certain embodiments, the TRAV3*01 germline sequence further comprises an N-terminal alanine residue and/or the amino acid sequence RD at the C terminus. One or more regions selected from framework 1, framework 2, framework 3, CDR1α, and CDR2α(e.g., two, three, four, or five of these regions) can be derived from a human TRAV3 germline sequence (e.g., TRAV3*01, e.g., comprising the amino acid sequence of SEQ ID NO: 18). In certain embodiments, framework 1, framework 2, framework 3, CDR1α, and CDR2α are all derived from a human TRAV3 germline sequence (e.g., TRAV3*01, e.g., comprising the amino acid sequence of SEQ NO: 18). In certain embodiments, the TCR comprises a Vα having an amino acid sequence derived from a human TRAV3 germline sequence (e.g., TRAV3*01, e.g., comprising the amino acid sequence of SEQ ID NO: 18) and a CDR3α having the amino acid sequence set forth in SEQ ID NO: 7, 39, 40, 41, 42, 43, 44, 45, 46, 47, 48, 49, 50, 51, 52, 53, 54, 55, 56, 57, 58, 59, or 60.

In certain embodiments, the instant disclosure provides a TCR (e.g., an isolated. TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising a Vβ having an amino acid sequence derived from a human TRBV29-1 germline sequence (e.g., TRBV29-1*01, e.g., comprising the amino acid sequence of SEQ ID NO: 19). In certain embodiments, the TRBV29-1*01 germline sequence further comprises the amino acid sequence SAVIS (SEQ ID NO: 27) at the N terminus and/or the amino acid sequence SVE at the C terminus. One or more regions selected from framework 1, framework 2, framework 3, CDR1β, and CDR2β (e.g., two, three, four or five of these regions) can be derived from a human TRBV29-1 germline sequence (e.g., TRBV29-1*01, e.g., comprising the amino acid sequence of SEQ ID NO: 19). In certain embodiments, framework 1, framework 2, framework 3, CDR1β, and CDR2β are all derived from a human TRBV29-1 germline sequence (e.g., TRBV29-1*01, e.g., comprising the amino acid sequence of SEQ ID NO: 19). In certain embodiments, the TCR comprises a Vβ having an amino acid sequence derived from a human TRBV29-1 germline sequence (e.g., TRBV29-1*01, e.g., comprising the amino acid sequence of SEQ ID NO: 19) and a CDR3β having the amino acid sequence set forth in SEQ ID NO: 10.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising an α chain comprising an amino acid sequence selected from the group consisting of SEQ ID NOs: 11, 13, 93-96, 105-118, 120-123, 125-128, and 408-415. Any one of the α chains disclosed herein (e.g., an α chain having a sequence disclosed in Table 1) can comprise at its C-terminus: the amino acid sequence of GS (e.g., as a cloning scar): the portion of a Furin recognition sequence N-terminal to the cleavage site; and/or the portion of a 2A recognition sequence N-terminal to the cleavage site. In certain embodiments, the α chain further comprises the portion of a Furin recognition sequence N-terminal to the cleavage site, wherein the portion of the Ruin recognition sequence is at the C-terminus of the α chain. In certain embodiments, the portion of the Furin recognition sequence comprises the amino acid sequence of RAKR (SEQ ID NO: 30) or RAKRS (SEQ ID NO: 132). In certain embodiments, the portion of the Furin recognition sequence comprises the amino acid sequence of RA. In certain embodiments, the α chain further comprises the amino acid sequence of GS (e.g., as the scar residues from cloning at the C-terminus). In certain embodiments, the α chain further comprises the portion of a 2A recognition sequence N-terminal to the cleavage site, wherein the portion of the 2A recognition sequence is at the C-terminus of the α chain. In certain embodiments, the 2A recognition sequence is selected from the group consisting of the sequences in Table 7, optionally wherein the cleavage site is the peptide bond adjacently N-terminal to Pro at the C-terminus. In certain embodiments, the 2A recognition sequence is from P2A (GS-GATNFSLLKQAGDVEENPGP (SEQ ID NO: 134)), optionally wherein the cleavage site is the peptide bond adjacently N-terminal to Pro at the C-terminus.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising a β chain comprising the amino acid sequence set forth in SEQ 113 NO: 12, 14, 25, or 97-104. Any one of a chains disclosed herein (e.g., the β chain having the sequences disclosed in Table 1) can comprise the amino acid sequence of GS (e.g., as a cloning scar), the portion of a Furin recognition sequence N-terminal to the cleavage site, or the portion of a 2A recognition sequence N-terminal to the cleavage site, at the C-terminus of the β chain. In certain embodiments, the β chain further comprises the portion of a Furin recognition sequence N-terminal to the cleavage site, wherein the portion of the Furin recognition sequence is at the C-terminus of the β chain. In certain embodiments, the portion of the Furin recognition sequence comprises the amino acid sequence of RAKR (SEQ ID NO: 30) or RAKRS (SEQ ID NO: 132). In certain embodiments, the portion of the Furin recognition sequence comprises the amino acid sequence of RA. In certain embodiments, the β chain further comprises the amino acid sequence of GS (e.g., as the scar residues from cloning at the C-terminus). In certain embodiments, the β chain further comprises the portion of a 2A recognition sequence N-terminal to the cleavage site, wherein the portion of the 2A recognition sequence is at the C-terminus of the α chain. In certain embodiments, the 2A recognition sequence is selected from the group consisting of the sequences in Table 7, optionally wherein the cleavage site is the peptide bond adjacently N-terminal to Pro at the C-terminus. In certain embodiments, the 2A recognition sequence is P2A (GS-GATNFSLLKQAGDVEENPGP (SEQ ID NO: 134)), optionally wherein the cleavage site is the peptide bond adjacently N-terminal to Pro at the C-terminus.

In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising an α chain and a β chain comprising the amino acid sequences set, forth in SEQ ID NOs: 13 and 14, respectively. In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising an α chain and a chain comprising the amino acid sequences set forth in SEQ ID NOs: 13 and 25, respectively. In certain embodiments, the instant disclosure provides a TCR (e.g., an isolated TCR) that binds to a peptide consisting of the amino acid sequence set forth in SEQ ID NO: 1 or 2 (e.g., a TCR that binds to a SLLMWITQC (SEQ ID NO: 1) or SLLMWITQV (SEQ ID NO: 2)-HLA-A*0201 complex), the TCR comprising an α chain and a β chain comprising the amino acid sequences set forth in SEQ NOs: 11 and 12, respectively. In certain embodiments, the α chain further comprises the amino acid sequence of RA, RAKR (SEQ ID NO: 30), or RAKRS (SEQ ID NO: 132) at the C-terminus, or the β chain further comprises the amino acid sequence of RA, RAKR (SEQ ID NO: 30), or RAKRS (SEQ ID NO: 13:2) at the C-terminus.

In certain embodiments, the instant disclosure provides an isolated TCR comprising an α chain and a β chain, wherein the α chain comprises an amino acid sequence selected from the group consisting of SEQ ID NOs: 13, 93-96, 105-118, 120-123, 125-128, and 408-415, and the β chain comprises an amino acid sequence selected from the group consisting of SEQ ID NOs: 14, 25, and 97-104. In addition to the mature sequence of the α chain and/or the β chain, additional amino acid residues may be added to the C-terminus of at least one chain. For example, Gly-Ser may be added from a cloning scar. Residues from Furin cleavage or 2A cleavage (as shown in Table 7) may be added when the chain is cleaved from a fusion protein.

Any TCR constant region from any species can be used in the TCRs disclosed herein. In certain embodiments, the TCR comprises a human α, β, γ, or δ TCR constant region. In certain embodiments, the TCR comprises a wild-type constant region. In certain embodiments, the TCR comprises an altered constant region, such as a chimeric constant region or constant region comprising one or more amino acid substitutions, insertions, or deletions relative to a wild-type constant region. In some embodiments, the TCR comprises an α chain comprising an α chain constant region of SEQ ID NO: 15, in some embodiments, the TCR comprises an α chain comprising an α chain constant region of SEQ ID NO: 26. In some embodiments, the TCR comprises an α chain comprising an α chain constant region of SEQ ID NO: 92. In some embodiments, the TCR comprises a β chain comprising a β chain constant region of SEQ ID NO: 16 or 17.

In certain embodiments, the instant disclosure provides an isolated TCR comprising an α chain and a β chain, wherein the α chain comprises an amino acid sequence selected from the group consisting of SEQ ID NOs: 13, 93-96, 105-118, 120-123, 125-128, and 408-415, and/or the β chain comprises an amino acid sequence selected from the group consisting of SEQ ID NOs: 14, 25, 97, 98, 99, 100, 101, 102, 103, and 104. In certain embodiments, the instant disclosure provides an isolated TCR that binds to a peptide consisting of the amino acid sequence set forth in SEQ ID NO: 1 or 2, the TCR comprising an α chain and a β chain, wherein the α chain comprises an amino acid sequence selected from the group consisting of SEQ ID NOs: 13, 93-96, 105-118, 120-123, 125-128, and 408-415, and/or the β chain comprises an amino acid sequence selected from the group consisting of SEQ ID NOs: 14, 25, 97, 98, 99, 100, 101, 102, 103, and 104. In certain embodiments, the α chain comprises an amino acid sequence selected from the group consisting of SEQ ID NOs: 13, 105, 110, 115, 120, 125, 408, or 412, and the β chain comprises an amino acid sequence selected from the group consisting of SEQ ID NOs: 14, 25, 97, 98, 99, 100, 101, 102, 103, and 104. In certain embodiments, the α chain and the β chain comprise the amino acid sequences set forth in SEQ ID NOs: 13 and 14; 13 and 25; 13 and 97; 13 and 98; 13 and 99; 13 and 100; 13 and 101; 13 and 102; 13 and 103; 13 and 104; 93 and 14; 93 and 25; 93 and 97; 93 and 98; 93 and 99; 93 and 100; 93 and 101; 93 and 102; 93 and 103; 93 and 104; 94 and 14; 94 and 25; 94 and 97; 94 and 98; 94 and 99; 94 and 100; 94 and 101; 94 and 102; 94 and 103; 94 and 104; 95 and 14; 95 and 25; 95 and 97; 95 and 98; 95 and 99; 95 and 100; 95 and 101; 95 and 102; 95 and 103; 95 and 104; 96 and 14; 96 and 25; 96 and 97; 96 and 98; 96 and 99; 96 and 100; 96 and 101; 96 and 102; 96 and 103; 96 and 104; 105 and 14; 105 and 25; 105 and 97; 105 and 98; 105 and 99; 105 and 100; 105 and 101; 105 and 102; 105 and 103; 105 and 104; 106 and 14; 106 and 25; 106 and 97; 106 and 98; 106 and 99; 106 and 100; 106 and 101; 106 and 102; 106 and 103; 106 and 104; 107 and 14; 107 and 25; 107 and 97; 107 and 98; 107 and 99; 107 and 100; 107 and 101; 107 and 102; 107 and 103; 107 and 104; 108 and 14; 108 and 25; 108 and 97; 108 and 98; 108 and 99; 108 and 100; 108 and 101; 108 and 102; 108 and 103; 108 and 104; 109 and 14; 109 and 25; 109 and 97; 109 and 98; 109 and 99; 109 and 100; 109 and 101; 109 and 102; 109 and 103; 109 and 104; 110 and 14; 110 and 25; 110 and 97; 110 and 98; 110 and 99; 110 and 100; 110 and 101; 110 and 102; 110 and 103; 110 and 104; 111 and 14; 111 and 25; 111 and 97; ill and 98; 111 and 99; 111 and 100; 111 and 101; 111 and 102; 111 and 103; 111 and 104; 112 and 14; 112 and 25; 112 and 97; 112 and 98; 112 and 99; 112 and 100; 112 and 101; 112 and 102; 112 and 103; 112 and 104; 113 and 14; 113 and 25; 113 and 97; 113 and 98; 113 and 99; 113 and 100; 113 and 101; 113 and 102; 113 and 103; 113 and 104; 114 and 14; 114 and 25; 114 and 97; 114 and 98; 114 and 99; 114 and 100; 114 and 101; 114 and 102; 114 and 103; 114 and 104; 115 and 14; 115 and 25; 115 and 97; 115 and 98; 115 and 99; 115 and 100; 115 and 101; 115 and 102; 115 and 103; 115 and 104; 116 and 14; 116 and 25; 116 and 97; 116 and 98; 116 and 99; 116 and 100; 116 and 101; 116 and 102; 116 and 103; 116 and 104; 117 and 14; 117 and 25; 117 and 97; 117 and 98; 117 and 99; 117 and 100; 117 and 101; 117 and 102; 117 and 103; 117 and 104; 118 and 14; 118 and 25; 118 and 97; 118 and 98; 118 and 99; 118 and 100; 118 and 101; 118 and 102; 118 and 103; 118 and 104; 120 and 14; 120 and 25; 120 and 97; 120 and 98; 120 and 99; 120 and 100; 120 and 101; 120 and 102; 120 and 103; 120 and 104; 121 and 14; 121 and 25; 121 and 97; 121 and 98; 121 and 99; 121 and 100; 121 and 101; 121 and 102; 121 and 103; 121 and 104; 122 and 14; 122 and 25; 122 and 97; 122 and 98; 122 and 99; 122 and 100; 122 and 101; 122 and 102; 122 and 103; 122 and 104; 123 and 14; 123 and 25; 123 and 97; 123 and 98; 123 and 99; 123 and 100; 123 and 101; 123 and 102; 123 and 103; 123 and 104; 125 and 14; 125 and 25; 125 and 97; 125 and 98; 125 and 99; 125 and 100; 125 and 101; 125 and 102; 125 and 103; 125 and 104; 126 and 14; 126 and 25; 126 and 97; 126 and 98; 126 and 99; 126 and 100; 126 and 101; 126 and 102; 126 and 103; 126 and 104; 127 and 14; 127 and 25; 127 and 97; 127 and 98; 127 and 99; 127 and 100; 127 and 101; 127 and 102; 127 and 103; 127 and 104; 128 and 14; 128 and 25; 128 and 97; 128 and 98; 128 and 99; 128 and 100; 128 and 101; 128 and 102; 128 and 103; 128 and 104; 408 and 14; 408 and 25; 408 and 97; 408 and 98; 408 and 99; 408 and 100; 408 and 101; 408 and 102; 408 and 103; 408 and 104; 409 and 14; 409 and 25; 409 and 97; 409 and 98; 409 and 99; 409 and 100; 409 and 101; 409 and 102; 409 and 103; 409 and 104; 410 and 14; 410 and 25; 410 and 97; 410 and 98; 410 and 99; 410 and 100; 410 and 101; 410 and 102; 410 and 103; 410 and 104; 411 and 14; 411 and 25; 411 and 97; 411 and 98; 411 and 99; 411 and 100; 411 and 101; 411 and 102; 411 and 103; 411 and 104; 412 and 14; 412 and 25; 412 and 97; 412 and 98; 412 and 99; 412 and 100; 412 and 101; 412 and 102; 412 and 103; 412 and 104; 413 and 14; 413 and 25; 413 and 97; 413 and 98; 413 and 99; 413 and 100; 413 and 101; 413 and 102; 413 and 103; 413 and 104; 414 and 14; 414 and 25; 414 and 97; 414 and 98; 414 and 99; 414 and 100; 414 and 101; 414 and 102; 414 and 103; 414 and 104; 415 and 14; 415 and 25; 415 and 97; 415 and 98; 415 and 99; 415 and 100; 415 and 101; 415 and 102; 415 and 103; or 415 and 104, respectively. In certain embodiments, the α chain and the β chain comprise the amino acid sequences set forth in SEQ ID NOs: 13 and 14; 13 and 25; 105 and 14; 105 and 25; 110 and 14; 110 and 25; 115 and 14; 115 and 25; 120 and 14; 120 and 25; 125 and 14; 125 and 25; 408 and 14; 408 and 25; 412 and 14; or 412 and 25, respectively. In certain embodiments, the α chain and the β chain comprise the amino acid sequences set forth in SEQ ID NOs: 13 and 14; 105 and 14; 110 and 14; 115 and 14; 120 and 14; 125 and 14; 408 and 14; or 412 and 14, respectively. In certain embodiments, the α chain and the β chain comprise the amino acid sequences set forth in SEQ ID NOs: 13 and 14, respectively. In certain embodiments, the α chain and the β chain comprise the amino acid sequences set forth in SEQ ID NOs: 105 and 14, respectively. In certain embodiments, the α chain and the β chain comprise the amino acid sequences set forth in SEQ ID NOs: 110 and 14, respectively. In certain embodiments, the α chain and the β chain comprise the amino acid sequences set forth in SEQ ID NOs: 115 and 14, respectively. In certain embodiments, the α chain and the β chain comprise the amino acid sequences set forth in SEQ ID NOs: 120 and 14, respectively. In certain embodiments, the α chain and the β chain comprise the amino acid sequences set forth in SEQ NOs: 125 and 14, respectively. In certain embodiments, the α chain and the β chain comprise the amino acid sequences set forth in SEQ ID NOs: 408 and 14, respectively. In certain embodiments, the α chain and the β chain comprise the amino acid sequences set forth in SEQ NOs: 412 and 14, respectively.

The TCRs disclosed herein can be used in any TCR structural format. For example, in certain embodiments, the TCR is a full-length TCR comprising a full-length α chain and a full-length chain. The transmembrane regions (and optionally also the cytoplasmic regions) can be removed from a full-length TCR to produce a soluble TCR. Accordingly, in certain embodiments, the TCR is a soluble TCR lacking transmembrane and/or cytoplasmic region(s). The methods of producing soluble TCRs are well-known in the art. In some embodiments; the soluble TCR comprises an engineered disulfide bond that facilitates dimerization, see, e.g., U.S. Pat. No. 7,329,731, which is incorporated by reference herein in its entirety. In some embodiments, the soluble TCR is generated by fusing the extracellular domain of a TCR described herein to other protein domains; e.g., maltose binding protein; thioredoxin, human constant kappa domain, or leucine zippers; see, e.g., Loset et al., Front Oncol. 2014; 4: 378, which is incorporated by reference herein in its entirety. A single-chain TCR (scTCR) compris-ing Vα and Vβ linked by a peptide linker can also be generated. Such scTCRs can comprise Vα and Vβ, each linked to a TCR constant region. Alternatively, the scTCRs can comprise Vα and Vβ, where either the Vα, the Vβ, or both the Vα and Vβ are not linked to a TCR constant region. Exemplary scTCRs are described in PCT Publication Nos. WO 2003/020763; WO 2004/033685, and WO 2011/044186, each of which is incorporated by reference herein in its entirety. Furthermore, the TCRs disclosed herein can comprise two polypeptide chains (e.g., an α chain and a β chain) in which the chains have been engineered to each have a cysteine residue that can form an interchain disulfide bond. Accordingly, in certain embodiments, the TCRs disclosed herein comprise two polypeptide chains linked by an engineered disulfide bond. Exemplary TCRs having an engineered disulfide bond are described in U.S. Pat. Nos. 8,361,794 and 8,906,383, each of which is incorporated by reference herein in its entirety.

In certain embodiments, the TCRs disclosed herein comprise one or more chains (e.g., an α chain and/or a β chain) having a transmembrane region. In certain embodiments, the TCRs disclosed herein comprise two chains (e.g., an α chain and a β chain) having a transmembrane region. The transmembrane region can be the endogenous transmembrane region of that TCR chain, a variant of the endogenous transmembrane region, or a heterologous transmembrane region. In certain embodiments, the TCRs disclosed herein comprise an α chain and a β chain having endogenous transmembrane regions.

In certain embodiments, the TCRs disclosed herein comprise one or more chains (e.g., an α chain and/or a β chain) having a cytoplasmic region. In certain embodiments, the TCRs disclosed herein comprise two chains (e.g., an α chain and a β chain) each having a cytoplasmic region. The cytoplasmic region can be the endogenous cytoplasmic region of that TCR chain, variant of the endogenous cytoplasmic region, or a heterologous cytoplasmic region. In certain embodiments, the TCRs disclosed herein comprise two chains (e.g., an α chain and a β chain) where both chains have transmembrane regions but one chain is lacking a cytoplasmic region. In certain embodiments, the TCRs disclosed herein comprise two chains (e.g., an α chain and a β chain) where both chains have endogenous transmembrane regions but lack an endogenous cytoplasmic region. In certain embodiments, the TCRs disclosed herein comprise an α chain and a β chain where both chains have endogenous transmembrane regions but lack an endogenous cytoplasmic region. In certain embodiments, the TCRs disclosed herein comprise a co-stimulatory signaling region from a co-stimulatory molecule; see, e.g., PCT Publication Nos.: WO 1996/018105, WO 1999/057268, and WO 2000/031239, and U.S. Pat. No. 7,052,906, all of which incorporated herein by reference in their entireties.

In certain embodiments, the TCRs described herein bind to a peptide-MHC complex comprising a peptide having the amino acid sequence set forth in SEQ ID NO: 1 or wherein the MHC may be any MHC. In certain embodiments, the MHC is a human MHC. In certain embodiments, the MHC is an MHC class I molecule comprising an MHC class I heavy chain (e.g, an HLA-A, an HLA-B, or an HLA-C, including any subtypes in any polymorphic forms) and a β2-microglobulin light chain. In certain embodiments, the MHC is HLA-A*0201. In certain embodiments, the peptide-MHC complex is SLLMWITQC (SEQ ID NO: 1)-HLA-A*0201. In certain embodiments, the MHC is an MHC class II molecule comprising an MHC class II α chain (e.g., an α chain of an HLA-DR, an HLA-DQ, or an HLA-DP, including any subtypes in any polymorphic forms) and an MHC class II β chain (e.g., a β chain of an HLA-DR, an HLA-DQ, or an HLA-DP, including any subtypes in any polymorphic forms). In certain embodiments, the MHC class II α chain and the MHC class II β chain are derived from the same type (e.g., HLA-DR, HLA-DO, or HLA-DP).

In certain embodiments, the instant disclosure provides a polypeptide comprising an α chain variable region (Vα) and a β chain variable region (Vβ) of a TCR fused together. For example, such polypeptide may comprise the Vα N-terminal to or C-terminal to the Vβ, optionally with a linker (e.g., a peptide linker) between the two chains. For example, a Furin and/or a 2A cleavage site (selected from any one of the sequences in Table 7), or combinations thereof, may be used in the linker for the Vα/Vβ fusion polypeptide.

In certain embodiments, the instant disclosure provides a polypeptide comprising an α chain and a β chain of a TCR fused together. For example, such polypeptide may comprise the α chain N-terminal to or C-terminal to the β chain, optionally with a linker (e.g., a peptide linker) between the two chains. For example, a Furin and/or a 2A cleavage site (selected from any one of the sequences in Table 7), or combinations thereof, may be used in the linker for the α/β fusion polypeptide. For example, a fusion polypeptide may comprise, from the N-terminus to the C-terminus: the α chain of a TCR, a furin cleavage site, a 2A cleavage site, and the β chain of the TCR. In certain embodiments, the polypeptide comprises, from the N-terminus to the C-terminus: the β chain of a TCR, a furin cleavage site, a 2A element, and the α chain of the TCR. In certain embodiments, the polypeptide comprises, from the N-terminus to the C-terminus: the α chain of the TCR, a 2A cleavage site, and the β chain of the TCR. In certain embodiments, the polypeptide comprises from the N-terminus to the C-terminus: the β chain of the TCR, a 2A element, and the α chain of the TCR. In certain embodiments, the polypeptide comprises, from the N-terminus to the C terminus: the α chain of the TCR, a Furin cleavage site, and the β chain of the TCR. In certain embodiments, the polypeptide comprises from the N-terminus to the C-terminus: the β chain of the TCR, a Furin element, and the α chain of the TCR. Exemplary fusion TCR sequences are given in Table 8.

In another aspect, provided herein are TCRs which bind to the same epitope (e.g., the same amino acid residues) of a peptide comprising the amino acid sequence set forth in SEQ ID NO: 1 or 2 as the TCRs or polypeptides described supra. In certain embodiments, the peptide is in complex with an MHC as described supra (e.g., HLA-A*0201). In certain embodiments, the TCR comprises sequences that do not naturally exist within the TCR germline repertoire of an animal or mammal (e.g., human) in vivo.

5.3 Cells Presenting T-Cell Receptors

In another aspect, the instant disclosure provides a mammalian cell (e.g., an engineered mammalian cell) or a population thereof presenting a TCR disclosed herein on the cell surface. Any mammalian cell can be used to present a TCR disclosed herein. In certain embodiments, the mammalian cell expresses CD3 (e.g., a CD3γ chain, a CD3δ chain, and two CD3ε chains). In certain embodiments, the mammalian cell is a human cell. Effector cells of the cellular immune system are particularly useful for presenting a TCR disclosed herein because the cell surface TCR can target these effector cells to tumor cells expressing the NY-ESO-1 polypeptide, thereby facilitating killing of the tumor cells. Accordingly, in certain embodiments, the mammalian cell is a lymphocyte (e.g., a human lymphocyte), such as a T cell or a natural killer (NK) cell. In certain embodiments, the lymphocyte is a T cell. Any T cell at any developmental stage can be used to present a TCR disclosed herein. For example, in certain embodiments, the T cell is selected from the group consisting of a $CD8^+$ cytotoxic T cell, a $CD4^+$ cytotoxic T cell, a $CD4^+$ helper T cell (e.g., a Th1 or a Th2 cell), a CD4/CD8 double positive T cells, a tumor infiltrating T cell, a thymocyte, a memory T cell, a naïve cell, and a natural killer T cell, e.g., an invariant natural killer cell. Precursor cells of the cellular immune system (e.g., precursors of T lymphocytes) are also useful for presenting a TCR disclosed herein because these cells may differentiate, develop, or mature into effector cells. Accordingly, in certain embodiments, the mammalian cell is a pluripotent stem cell (e.g., an embryonic stem cell, an induced pluripotent stem cell), a hematopoietic stem cell, or a lymphocyte progenitor cell. In certain embodiments, the hematopoietic stem cell or lymphocyte progenitor cell is isolated and/or enriched from, e.g., bone marrow, umbilical cord blood, or peripheral blood.

Cells can be obtained from numerous sources, including but not limited to, tumor, blood, bone marrow, lymph node, thymus, or another tissue or bodily fluid, or an apheresis product. In certain embodiments, cells are obtained from a patient directly following a treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, in certain embodiments, cells are collected from blood, bone marrow, lymph node, thymus, or another tissue or bodily fluid, or an apheresis product, during this recovery phase.

In certain embodiments, the mammalian cell is a population of cells presenting a TCR disclosed herein on the cell surface. The population of cells can be heterogeneous or homogenous. In certain embodiments, at least 50% (e.g., at least 60%, 70%, 80%, 90%, 95%, 99%, 99.5%, or 99.9%) of the population is a cell as described herein. In certain embodiments, the population is substantially pure, wherein at least 50% (e.g., at least 60%, 70%, 80%, 90%, 95%, 99%, 99.5%, or 99.9%) of the population is homogeneous. In certain embodiments, the population is heterogeneous and comprises a mixed population of cells (e.g., the cells have different cell types, developmental stages, origins, are isolated, purified, or enriched by different methods, are stimulated with different agents, and/or are engineered by different methods). In certain embodiments, the cells are a population of peripheral blood mononuclear cells (PBMC) (e.g., human PBMCs).

Populations of cells can be enriched or purified, as needed. In certain embodiments, regulatory T cells (e.g., $CD25^+$ T cells) are depleted from the population, e.g., by using an anti-CD25 antibody conjugated to a surface such as a bead, particle, or cell. In certain embodiments, an anti-CD25 antibody is conjugated to a fluorescent dye (e.g., for use in fluorescence-activated cell sorting). In certain embodiments, cells expressing checkpoint receptors (e.g., CTLA-4, PD-1, TIM-3, LAG-3, TIGIT, VISTA, BTLA, TIGIT, CD137, or CEACAM1) are depleted from the population, e.g., by using an antibody that binds specifically to a checkpoint receptor conjugated to a surface such as a bead, particle, or cell. In certain embodiments, a T cell population can be selected so that it expresses one or more of IFNγ, TNFα, IL-17A, IL-2, IL-3, IL-4, GM-CSF, IL-13, granzyme (e.g., granzyme B), and perforin, or other appropriate molecules, e.g., other cytokines. Methods for determining such expression are described, for example, in PCT Publication No.: WO 2013/126712, which is incorporated by reference herein in its entirety.

Cells can be stimulated ex: vivo to increase viability, proliferation, and/or activity. In some embodiments, the induction does not include any defined antigen, thus providing a cell population which is polyclonal with respect to antigen reactivity. In certain embodiments, the cell is contacted with a first agent, which induces or activates a TCR/CD3 complex-associated signal (e.g., an anti-CD3 antibody). In certain embodiments, the cell is contacted with a second agent, which stimulates an accessory molecule on the T cell surface (e.g., a ligand of CD28 or an anti-CD28 antibody). In certain embodiments, the cell is contacted with a molecule or complex that interacts with both CD3 and CD28, wherein the molecule or complex may be presented on a surface (e.g., a bead, particle, or cell). In certain embodiments, the cell is contacted with a surface (e.g., a bead, particle, or cell) presenting an anti-CD3 antibody and an anti-CD28 antibody. In certain embodiments, the cell is contacted with one or more agents that bind to cell surface receptors to increase T cell viability, proliferation, and/or activity (e.g., IL2 or IL-7). In certain embodiments, the cell is contacted with phytohemagglutinin. In certain embodiments, the cell is contacted with an agent that stimulates one or more intracellular signals such as $Ca^{2+}$ release (e.g., phorbol 12-myristate 13-acetate and/or ionomycin). Alternatively, the induction may include an antigen comprising a peptide (e.g., an NY-ESO-1 peptide) which binds to the TCR presented on the cell surface, thus providing, a cell population which is enriched (e.g., monoclonal) with respect to antigen reactivity. The antigen may further comprise an MHC molecule (e.g., an HLA molecule) in complex with the peptide. The antigen may be presented as a soluble form, bound to a membrane, or presented on a surface. The agents as described above can be used in any combination, and may be contacted with the effector cell or precursor thereof either simultaneously or sequentially. The contact can be terminated while the cell may remain in a state of increased viability, proliferation, and/or activity. Sustained proliferation of T cells over an extended period of time can yield a multi-fold increase in the number of cells relative to the original T cell population. In some embodiments, activation may be performed to promote metabolic fitness through provision of bioenergetic fuel sources, which enables conditioning of T cells for optimal biological activity and survival.

In certain embodiments, the mammalian cell (e.g., lymphocyte) expresses a TCR disclosed herein from a transgene introduced into the cell and presents the TCR on the cell surface. The TCR may be displayed constitutively on the cell surface. Alternatively, the cell may be capable of conditional expression and/or display of the TCR. For example, the expression or display of the TCR may be induced by an exogenous stimulus or by cellular differentiation. In certain embodiments, the transgene encodes a TCR α chain and/or β chain, or a fragment thereof (e.g., Vα, Vβ, CDR3α and/or CDR3β). In certain embodiments, the transgene is operably linked to an exogenous transcriptional and/or translational control sequence (e.g., a promoter, an enhancer, and/or a Kozak sequence). In certain embodiments, the transgene is operably linked to an endogenous transcriptional and/or translational control sequence (e.g., a promoter, an enhancer, and/or a Kozak sequence) not at its native genomic locus (e.g., introduced by a vector). In certain embodiments, the transgene is operably linked to an endogenous transcriptional and/or translational control sequence (e.g., a promoter, an enhancer, and/or a Kozak sequence) at its native genomic locus (e.g., by inserting the transgene into the native genomic locus).

In certain embodiments, the transgene is a DNA integrated into the host cell genome, wherein the integration occurs through site-specific integration (e.g., homologous recombination) or random insertion of the DNA. In certain embodiments, the transgene is a DNA not integrated into the host cell genome (e.g., maintained as a non-integrating viral genome or as an episomal DNA). In certain embodiments, the transgene is a polynucleotide (including but not limited to DNA, RNA, modified DNA, and modified RNA) that can be transcribed and/or translated to express the TCR disclosed herein. In certain embodiments, the transgene is an RNA having a cap on the 5' end and/or a poly(N) tail on the 3' end, wherein the cap and the poly(A) tail may modulate ribosome binding, initiation of translation and stability of the RNA in the cell.

In certain embodiments, the transgene comprises a first and a second sequence, the first sequence encoding a polypeptide comprising a TCR α chain or a fragment thereof (e.g., Vα or CDR3α), and the second sequence encoding a polypeptide comprising a TCR β chain or a fragment thereof (e.g., Vβ or CDR3β). In certain embodiments, the first and the second sequences are each operably linked to a transcriptional and/or translational control sequence (e.g., a promoter, an enhancer, and/or a Kozak sequence). In certain embodiments, the first and second sequences are in different polynucleotides (e.g., DNA, RNA, modified DNA, or modified RNA) molecules. In certain embodiments, the first and second sequences of the transgene are in the same polynucleotide (e.g., DNA, RNA, modified DNA, or modified RNA) molecule, in certain embodiments, the first and second sequences are operably linked by a linker sequence that promotes the production of two separate polypeptides (e.g., an internal ribosome entry site (IRES), a self-cleavage peptide (e.g., a 2A peptide), or a peptide sequence recognized by an intracellular or an extracellular protease), in certain embodiments, the first and second sequences can be transcribed and/or translated independently. In certain embodiments, the first and second sequences are each integrated into the host cell genome. In certain embodiments, the first and second sequences are each integrated into different regions of the host cell genome.

Alternatively, in certain embodiments, the cell does not express the TCR, but instead the TCR is attached to the outside surface of the cell by chemical means or by binding of the TCR to a cell surface antigen. Accordingly, in certain embodiments, the TCR is linked to a binding moiety that binds to a cell surface antigen. Any type of binding moiety can be linked (covalently or non-covalently) to a TCR disclosed herein. In certain embodiments, the TCR is fused (chemically or genetically) to an antibody or antigen binding fragment thereof that specifically binds to a cell surface antigen of the cell (e.g., lymphocyte).

In certain embodiments, the cell further comprises a polynucleotide encoding a polypeptide capable of inducing cell death. In certain embodiments, the polypeptide is a chimeric polypeptide comprising a multimerization (e.g., dimerization or oligomerization) region and a cell death-inducing region, wherein the cell death-inducing region is activated by multimerization. In certain embodiments, the cell death-inducing region comprises a sequence of a caspase (e.g., caspase-9) that has protease activity. In certain embodiments, the cell death-inducing region comprises the full-length human caspase-9 polypeptide. In certain embodiments, the cell death-inducing region comprises a truncated human caspase-9 polypeptide (e.g., wherein the CARD domain of caspase-9 is deleted).

In certain embodiments, the cell further comprises a polynucleotide encoding a polypeptide capable of inducing T cell activation. In certain embodiments, the polypeptide is an inducible chimeric stimulating molecule, for example, as described in PCT Publication No. WO 2015/123527, incorporated herein by reference in its entirety. In certain embodiments, the polypeptide comprises a multimerization (e.g., dimerization or oligomerization) region, wherein the polypeptide induces T cell activation upon multimerization.

*Systems Biology and Drug Design* (Wiley, 2007), the contents of which are incorporated by reference herein in their entireties.

In certain embodiments, the polypeptide capable of inducing cell death is a chimeric polypeptide comprising an FKBP12 polypeptide and a full-length or truncated caspase-9 (e.g, human caspase-9) polypeptide. In certain embodiments, the FKBP12 polypeptide comprises a valine at position 36. In certain embodiments, the FKBP12 polypeptide comprises the amino acid sequence set forth in SEQ ID NO: 23. In certain embodiments, the ligand capable of inducing FKBP12 multimerization is AP1903 (CAS Registry Number: 195514-63-7; Molecular Formula: C78H98N4O20; Molecular Weight: 1411.65). In certain embodiments, the ligand is AP20187 or an AP20187 analog (e.g., AP1510). In certain embodiments, the caspase-9 polypeptide comprises the amino acid sequence set forth in SEQ ID NO: 24.

TABLE 6

FKBP12 and caspase-9 sequences.

| SEQ ID NO: | Description | Amino add Sequence |
|---|---|---|
| 23 | FKBP12 | GVQVETISPGDGRTFPKRGQTCVVHYTGMLEDGKKVDS SRDRNKPFKFMLGKQEVIRGWEEGVAQMSVGQRAKLTI SPDYAYGATGHPGIIPPHATLVFDVELLKLE |
| 24 | caspase-9 | GFGDVGALESLRGNADLAYILSMEPCGHCLIINNVNFCR ESGLRTRTGSNIDCEKLRRRFSSLHFMVEVKGDLTAKKM VLALLELAQQDHGALDCCVVVILSHGCQASHLQFPGAV YGTDGCPVSVEKIVNIFNGTSCPSLGGKPKLFFIQACGGE QKDHGFEVASTSPEDESPGSNPEPDATPFQEGLRTFDQL DAISSLPTPSDIFVSYSTFPGFVSWRDPKSGSWYVETLDDI FEQWAHSEDLQSLLLRVANAVSVKGIYKQMPGCFNFLR KKLFFKTS |

A multimerization region present, for example, in a polypeptide capable of inducing cell death or a polypeptide capable of inducing T cell activation, can comprise a ligand-binding domain that will multimerize upon binding to a ligand (e.g., a synthetic ligand). The ligand may have two or more binding sites, each binding site capable of binding to a ligand-binding domain of the chimeric polypeptide. In certain embodiments, the ligand has two binding sites and is capable of inducing dimerization of the chimeric polypeptide. A variety of synthetic ligands and corresponding ligand-binding domains can be employed. For example, a multimeric (e.g., dimeric) FK506 can be used to multimerize an FK506 binding protein (FKBP; e.g., FKBP12 or a variant thereof); a multimeric (e.g., dimeric) cyclosporin A can be used to multimerize a cyclophilin receptor; a multimeric dimeric) estrogen can be used to multimerize an estrogen receptor; a multimeric (e.g., dimeric) glucocorticoid can be used to multimerize a glucocorticoid receptor; a multimeric (e.g., dimeric) tetracycline can be used to multimerize a tetracycline receptor; a multimeric dimeric) vitamin D can be used to multimerize a vitamin 1) receptor. The ligand-binding domain can be internal or external to the cellular membrane, depending upon the nature of the construct and the choice of ligand. Non-limiting examples of ligands and corresponding ligand-binding domains are described in U.S. Pat. No. 9,089,520; Kopytek, S. J., et al., Chemistry & Biology 7:313-(2000); Gestwicki, J. E., et al., Combinatorial Chem. & High Throughput Screening 10:667-675 (2007); Clackson T Chem Biol Drug Des 67:440-2 (2006); and Schreiber; et al., *Chemical Biology From Small Molecules to*

In certain embodiments, the polynucleotide encoding the polypeptide capable of inducing cell death is operably linked to a transcriptional and/or translational control sequence (e.g., a promoter, an enhancer, and/or a Kozak sequence). The polynucleotide may be integrated into the host cell genome. Alternatively, the polynucleotide may be maintained as a non-integrating viral genome or as an episomal DNA. In certain embodiments, the polynucleotide is operably linked to the first and/or second sequences encoding a TCR by a linker sequence that promotes the production of two separate polypeptides (e.g., an internal ribosome entry site (IRES), a self-cleavage peptide (e.g., a 2A peptide), or a peptide sequence recognized by an intracellular or an extracellular protease). In certain embodiments, the polynucleotide is transcribed and/or translated independently from the first and/or second sequences.

In certain embodiments, the cell is provided in a solution. In certain embodiments, the cell is cryopreserved at about or lower than −80° C. (e.g., in a liquid nitrogen storage tank). Methods of cryopreservation are well-known in the art, e.g., as described in U.S. Pat. Nos. 5,580,714 and 6,740,484, which are incorporated by reference herein in their entireties. The cryopreserved cell may be recovered by thawing, and any of the isolation, purification, enrichment, stimulation, and display of the TCR as described above may be conducted prior to the cryopreservation or after the recovery.

5.4 Methods of Use

In another aspect, the instant disclosure provides a method of treating a subject using the TCRs, polynucleotides, vectors, engineered cells a cell comprising a heterologous and/or recombinant nucleic acid), or pharmaceutical compositions disclosed herein. Any disease or disorder in a subject that would benefit from the targeting of a TCR to an NY-ESO-1 peptide can be treated using the TCRs disclosed herein. The TCRs, polynucleotides, vectors, engineered cells, and pharmaceutical compositions disclosed herein are particularly useful for inducing immunity to tumors displaying an NY-ESO-1 peptide (e.g., a peptide-MI-IC complex comprising an NY-ESO-1 peptide), and accordingly can be used as an immunotherapy for subjects with NY-ESO-1-positive cancer. For example, in certain embodiments, the instant disclosure provides a method of inducing cell-mediated immunity in response to an NY-ESO-1 peptide in a subject, the method comprising administering to the subject an effective amount of a TCR, polynucleotide, vector, engineered cell, or pharmaceutical composition as described herein. In certain embodiments, the instant disclosure provides a method of treating cancer in a subject, the method comprising administering to the subject an effective amount of the TCR, polynucleotide, vector, engineered cell, or pharmaceutical composition, as disclosed herein.

In certain embodiments, the method comprises administering to the subject an effective amount of a cell or population thereof as disclosed herein. In certain embodiments, the cell is engineered to constitutively display a TCR as disclosed herein on the cell surface. In certain embodiments, the cell is engineered to conditionally display a TCR as disclosed herein on the cell surface in response to an induction event. This induction event can be either a stimulus by an exogenous agent administered prior to, simultaneously with, or after the administration of the cell. Additionally or alternatively, the induction event can be a stimulus by a cell, tissue, or lesion in the subject.

In certain embodiments, the cell further comprises a polynucleotide encoding a chimeric polypeptide comprising a ligand-binding multimerization dimerization or oligomerization) region and a cell death-inducing region, and the method further comprises a step of administering a ligand of the multimerization region. In certain embodiments, the chimeric polypeptide comprises an FKBP12 polypeptide and a caspase-9 (e.g., human caspase-9) polypeptide, and the method further comprises a step of administering an FKBP12 ligand (e.g., AP1903). In certain embodiments, the FKBP12 ligand is administered after observing an indication of an improvement of a disease (e.g, shrinkage of a cancer, reduction of a cancer marker, and/or improvement of a cancer symptom) or after identifying an intolerable side effect (e.g., a high level of an inflammatory cytokine, and/or a rejection of the administered cell by the host).

As disclosed supra, cells administered to the subject can be autologous or allogeneic. In certain embodiments, autologous cells are obtained from a patient directly following a cancer treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, in certain embodiments, cells are collected from blood, bone marrow, lymph node, thymus, or another tissue or bodily fluid, or in an apheresis product, during this recovery phase. Further, in certain aspects, mobilization and conditioning regimens can be used to create a condition in a subject wherein repopulation, recirculation, regeneration, and/or expansion of particular cell types is favored, especially during a defined window of time following therapy. The mobilization agent can be selected from the group consisting of CXCL12-interacting heparinoids, GM-CSF, G-CSF (e.g., unmodified, glycosylated, or PEGylated), IL-2 (e.g., unmodified, glycosylated, or PEGylated), CXCR4 antagonists (e.g., plerixafor), integrin α4β1 antagonists (e.g., BIO5192), cyclophosphamide, 5-fluorouracil, cisplatin, etoposide, ifosfamide, cytarabine, and a combination thereof.

The number of cells that are employed will depend upon a number of circumstances including, the lifetime of the cells, the protocol to be used (e.g., the number of administrations), the ability of the cells to multiply, the stability of the recombinant construct, and the like. In certain embodiments, the cells are applied as a dispersion, generally being injected at or near the site of interest. The cells may be administered in any physiologically acceptable medium.

Cancers that can be treated with the TCRs, polynucleotide, vector, engineered cells, or pharmaceutical compositions disclosed herein can be any tumor expressing NY-ESO-1. Examples of tumors expressing NY-ESO-1 have been disclosed, e.g., in Jager, et al., supra. Also see Chen, et al., supra, Stockert, et al., J. Exp. Med. 187:1349 (1998); Wang, et al, J. Immunol 161:3598-3606 (1998); Jungbluth, et al. Int. J. Cancer 92:856-860(2001); Jungbluth, et al, hit. J. Cancer 94:252-256(2001); Gnjatic, S. et al (2004) Ado Cancer Res 95: 1-30; WO2004078776; 102013177247; WO2014160030; and WO2010106431, each of which is incorporated by reference herein in its entirety.

In certain embodiments, the cancer is acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid leukemia, myeloma (e.g., chronic myeloid cancer), colon cancer, esophageal cancer, cervical cancer, gastrointestinal carcinoid tumor. Hodgkin's lymphoma, hypopharynx cancer, kidney cancer, larynx cancer, liver cancer, lung cancer (e.g., non-small cell lung cancer), malignant mesothelioma, melanoma, multiple myeloma, nasopharynx cancer, non-Hodgkin's lymphoma, ovarian cancer, pancreatic cancer, peritoneum, omentum, and mesentery cancer, pharynx cancer, prostate cancer, rectal cancer, renal cancer (e.g., renal cell carcinoma (RCC)), gastric cancer, small intestine cancer, soft tissue cancer, stomach cancer, carcinoma, sarcoma (e.g., synovial sarcoma, rhabdomyosarcoma), testicular cancer, thyroid cancer, head and neck cancer, ureter cancer, and urinary bladder cancer. In certain embodiments, the cancer is melanoma, breast cancer, lung cancer, prostate cancer, thyroid cancer, ovarian cancer, or synovial sarcoma. In one embodiment, the cancer is synovial sarcoma or liposarcoma myxoid/round cell liposarcoma). In certain embodiments, the cancer is selected from the group consisting of multiple myeloma, synovial sarcoma, liposarcoma, renal cell carcinoma, cervical cancer, and ovarian cancer.

In certain embodiments, these methods further comprise administering an additional therapeutic agent to the subject. In certain embodiments, the additional therapeutic agent is a chemotherapeutic, radiotherapeutic, or a checkpoint targeting agent. In certain embodiments, the chemotherapeutic agent is a hypomethylating agent (e.g, azacitidine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist, anti-CEACAM1 antibody, an agonist anti-GITR antibody, and an agonist anti-OX40 antibody.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck &. Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, which are incorporated herein by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCI Publication No. WO 2016/015685 A1; and PCT Publication No. WO 2016/0208056 A1.

In certain embodiments; an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelutnab, also known as MSB0010718C; developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, which are incorporated herein by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, a TCR cell, or pharmaceutical composition disclosed herein is administered to a subject in combination with a compound that targets an immunomodulatory enzyme(s) such as IDO (indoleamine-(2,3)-dioxygenase) and/or TDO (tryptophan 2,3-dioxygenase). In certain embodiments, such compound is selected from the group consisting of epacadostat (Incyte Corp; see, e.g., PCT Publication No. WO 2010/005958 which is incorporated by reference herein in its entirety), F001287 (Flexus Biosciences/Bristol-Myers Squibb), indoximod (NewLink Genetics), and NLG919 (NewLink Genetics), hi one embodiment, the compound is epacadostat. In another embodiment, the compound is F001287. In another embodiment, the compound is indoximod. In another embodiment, the compound is NLG919. In a specific embodiment, the TCR, cell, or pharmaceutical composition disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the TCR, cell, or pharmaceutical composition as described herein and the IDO inhibitor as described herein can be administered separately, sequentially, or concurrently as separate dosage forms. In one embodiment, the cell, or pharmaceutical composition is administered parenterally, and the IDO inhibitor is administered orally. In particular embodiments, the inhibitor is selected from the group consisting of epacadostat (Incyte Corporation), F001287 (Plexus Biosciences/Bristol-Myers Squibb), indoximod (NewLink Genetics), and NLG919 (NewLink Genetics). Epacadostat has been described in PCT Publication No. WO 2010/005958, which is incorporated herein by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, a TCR, cell, or pharmaceutical composition disclosed herein is administered to a subject in combination with a vaccine. The vaccine can be, e.g., a peptide vaccine, a DNA vaccine, or an RNA vaccine. In certain embodiments, the vaccine is a heat shock protein based tumor vaccine or a heat shock protein based pathogen vaccine. In a specific embodiment, a TCR, cell, or pharmaceutical composition disclosed herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress, or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors, HSPPC internalization results in functional maturation of the APCs with chemokine and cytokine production leading to activation of natural killer cells (NK), monocytes, and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins hsp70 or hsc70) or a peptide-binding domain thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. P0DMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, a TCR, cell, or pharmaceutical composition disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, which are incorporated herein by reference herein in their entireties, U.S. Pat. Nos. 6,391,306, 6,383,492, 6,403,095, 6,410,026, 6,436,404, 6,447,780, 6,447,781 and 6,610,659.

In certain embodiments, a TCR, cell, or pharmaceutical composition disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immuno-stimulating complexes such as saponins, Quil A, QS-21, QS-7, ISCOMATRIX, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678; and 7,858,589, all of which are incorporated herein by reference in their entireties. In one embodiment, the adjuvant used herein is QS-21 STIMULON.

In certain embodiments, a TCR, polynucleotide, vector, engineered cell, or pharmaceutical composition disclosed herein is administered to a subject in combination with a tumor microenvironment (TME)-conditioning agent. In certain embodiments, the TME-conditioning agent is a cytokine (e.g., interleukin-2, interferon-α, interferon-β, interferon-γ, tumor necrosis factor superfamily member 14 (INFSF14)). In certain embodiments, the cytokine is a chemokine (e.g., (C—C motif) ligand 21 (CCL21) and C—X—C motif chemokine 10 (CXCL10)). In certain embodiments, the TME-conditioning agent is an agonist of a pattern recognition receptor (PRR). In certain embodiments, the agonist is a synthetic agonist of TLR9 (e.g., CpG). In certain embodiments, the agonist is a synthetic agonist of STING (e.g., cGAMP).

The TCR, polynucleotide, vector, engineered cell, or pharmaceutical composition and the additional therapeutic agent (e.g., chemotherapeutic, radiotherapeutic, checkpoint targeting agent, IDO inhibitor, vaccine, adjuvant, and/or TME-conditioning agent) can be administered separately, sequentially or concurrently as separate dosage forms. In one embodiment, the TCR, polynucleotide, vector, engineered cell, or pharmaceutical composition is administered parenterally, and an IDO inhibitor is administered orally.

A TCR, polynucleotide, vector, engineered cell, or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intrathecal, and subcutaneous routes. Pulmonary administration can also be employed, e.g., by use of an inhaler or nebulizer, and formulation with an aerosolizing agent for use as a spray. In certain embodiments, the TCR, polynucleotide, vector, engineered cell, or pharmaceutical composition described herein is delivered intravenously. In certain embodiments, the TCR, polynucleotide, vector, engineered cell, or pharmaceutical composition described herein is delivered subcutaneously. In certain embodiments, the TCR, polynucleotide, vector, engineered cell, or pharmaceutical composition described herein is delivered intratumorally. In certain embodiments, the TCR, polynucleotide, vector, engineered cell, or pharmaceutical composition described herein is delivered into a tumor draining lymph node.

The amount of the TCR, polynucleotide, vector, engineered cell, or pharmaceutical composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, and health), whether the patient is a human or an animal, other medications administered, or whether treatment is prophylactic or therapeutic. Usually, the patient is a human but non-human mammals including transgenic mammals can also be treated. Treatment dosages are optimally titrated to optimize safety and efficacy.

A TCR described herein can also be used to assay the levels of a peptide-MHC complex comprising an NY-ESO-1 peptide and/or the numbers of cells displaying a peptide-MHC complex comprising an NY-ESO-1 peptide in a biological sample using classical immunohistological methods known to those of skill in the art, including immunoassays, such as the enzyme linked immunosorbent assay (ELISA), immunoprecipitation, or Western blotting. Suitable TCR assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label a TCR described herein. Alternatively, a molecule that recognizes a TCR described herein can be labeled and used in combination with a TCR described herein to detect a peptide-MHC complex comprising an NY-ESO-1 peptide and/or the numbers of cells displaying a peptide-MHC complex comprising an NY-ESO-1 peptide in a biological sample.

Assaying for the levels of a peptide-MHC complex comprising an NY-ESO-1 peptide is intended to include qualitatively or quantitatively measuring or estimating the level of a peptide-MHC complex comprising an NY-ESO-1 peptide in a first biological sample either directly by determining or estimating absolute protein level) or relatively (e.g., by comparing to the disease associated protein level in a second biological sample). The level of a peptide-MHC complex comprising an NY-ESO-1 peptide in the first biological sample can be measured or estimated and compared to a standard level, the standard being taken from a second biological sample obtained from an individual not having the disease or being determined by averaging levels from a population of individuals not having the disease. As will be appreciated in the art, once the "standard" level is known, it can be used repeatedly as a standard for comparison.

As used herein, the term "biological sample" refers to any biological sample obtained from a subject, cell line, tissue, or other source of cells potentially displaying a peptide-MHC complex comprising an NY-ESO-1 peptide. Methods for obtaining tissue biopsies and body fluids from animals (e.g., humans) are well-known in the art. Biological samples include peripheral mononuclear blood cells.

A TCR described herein can be used for prognostic, diagnostic, monitoring and screening applications, including in vitro and in vivo applications well-known and standard to the skilled artisan and based on the present description. Prognostic, diagnostic, monitoring and screening assays and kits for in vitro assessment and evaluation of immune system status and/or immune response may be utilized to predict, diagnose, and monitor to evaluate patient samples including those known to have or suspected of having a disorder associated with cells displaying a peptide-MHC complex comprising an NY-ESO-1 peptide (e.g., an NY-ESO-1-positive cancer). In viva applications include directed cell therapy and immune system modulation and radio imaging of a cell, tissue, or organ displaying a peptide-MHC complex comprising an NY-ESO-1 peptide (e.g, an NY-ESO-1-positive cancer).

In one embodiment, a TCR described herein can be used for detecting a peptide-MHC complex comprising an NY-ESO-1 peptide and/or the numbers of cells displaying a peptide-MHC complex comprising an NY-ESO-1 peptide in immunohistochemistry of biopsy samples. A TCRs described herein may carry a detectable or functional label. When fluorescence labels are used, currently available microscopy and fluorescence-activated cell sorter analysis (FACS) or a combination of both methods known in the art may be utilized to identify and to quantitate the specific binding members. A TCR described herein may carry a fluorescence label. Exemplary fluorescence labels include, for example, reactive and conjugated probes, e.g., aminocoumarin, fluorescein and Texas red, Alexa Fluor dyes, Cy dyes, and DyLight dyes. A TCR described herein may carry a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of the TCR to a peptide-MHC complex comprising an NY-ESO-1 peptide. In the instance where the label is an enzyme, detection may be accomplished by any of the presently utilized colorimetric, spectrophotometric, fluorospectrophotometric, amperometric, or gasometric techniques as known in the art. This can be achieved by contacting a sample or a control sample with a TCR described herein under conditions that allow for the formation of a complex between the TCR and the peptide-MHC complex comprising an NY-ESO-1 peptide. Any complexes formed between the TCR and the peptide-MHC complex are detected and compared in the sample and the control. In light of the specific binding of the TCRs described herein for a peptide-MHC complex comprising an NY-ESO-1 peptide, the TCRs can be used to detect cells displaying a peptide-MHC complex comprising an NY-ESO-1 peptide. The TCR described herein can also be used to purify such a complex or cell via immunoaffinity purification. Also included herein is an assay system which may be prepared in the form of a test kit for semi-quantitative or quantitative analysis of the extent of the presence of, for instance, a peptide-MHC complex comprising an NY-ESO-1 peptide, or a complex comprising the peptide-WIC complex. The system or test kit may comprise a labeled component, e.g., a labeled TCR, and one or more additional immunochemical reagents.

5.5 Polynucleotides, Vectors and Methods of Producing TCRs

In another aspect, provided herein are polynucleotides comprising a nucleotide sequence encoding a TCR described herein (e.g., α chain, β chain, Vα domain, and/or Vβ domain) that binds to an NY-ESO-1 peptide, and vectors, e.g., vectors comprising such polynucleotides for recombinant expression in host cells (e.g., *E. coli* and mammalian cells). Provided herein are polynucleotides comprising nucleotide sequences encoding an α chain and/or β chain of any of the TCRs provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotides or nucleic acid molecules having less than about 15%, 10%, 5%, 2%, 1%, 0.5%, or 0.1% (in particular less than about 10%) of other material, e.g., cellular material, culture medium, other nucleic acid molecules, chemical precursors, and/or other chemicals. In a specific embodiment, a nucleic acid molecule(s) encoding a TCR described herein is isolated or purified.

In a particular aspect, provided herein are polynucleotides comprising nucleotide sequences encoding TCRs which bind to the same epitope of a peptide comprising the amino acid sequence set forth in SEQ ID NO:1 as the TCRs described supra. In certain embodiments, the peptide is in complex with an MHC as described supra (e.g., HLA-A*0201). In certain embodiments, the TCR comprises sequences that do not naturally exist within the TCR germline repertoire of an animal or mammal (e.g., human) in vivo. In certain embodiments, the polynucleotide comprises sequences that do not naturally exist within the TCR-encoding DNA germline repertoire of an animal or mammal (e.g., human) in vivo.

In certain aspects, provided herein are polynucleotides comprising a nucleotide sequence encoding the α chain and/or β chain of a TCR described herein. The polynucleotides can comprise nucleotide sequences encoding an α chain comprising the α chain FRs and CDRs of TCRs described herein (see, e.g., Table 1) or nucleotide sequences encoding a β chain comprising the 11 chain FRs and CDRs of TCRs described herein (see, e.g., Table 1).

In certain embodiments, the polynucleotide comprises a first nucleic acid sequence encoding an α chain and a second nucleic acid encoding a β chain of a TCR described herein. In certain embodiments, the polynucleotide comprises a first nucleic acid sequence encoding a Vα and a second nucleic acid encoding a Vβ of a TCR described herein. In certain embodiments, the first and second nucleic acid sequences are in frame. The first nucleic acid sequence can be either 5' or 3' to the second nucleic acid sequence. In certain embodiments, the polynucleotide further comprises a third nucleic acid sequence encoding a peptide linker between the first and second nucleic acid sequences, wherein the first, second, and third nucleic acid sequences are in frame. The linker can comprise any proteolytic cleavage site. Exemplary proteolytic cleavage sites include without limitation Furin cleavage sites, 2A cleavage sites (selected from any one of the sequences in Table 7), or combinations thereof. In certain embodiments, the linker comprises a Furin cleavage site (e.g., comprising the amino acid sequence set forth in SEQ ID NO: 132) and a 2A cleavage site (e.g., comprising the amino acid sequence set forth in SEQ ID NO: 33 or 134).

In certain embodiments, the polynucleotide comprises from 5' to 3': the first, third, and second nucleic acid sequences, wherein the third nucleic acid sequence encodes from N-terminus to C-terminus a furin cleavage site and a 2A cleavage site. In certain embodiments, the polynucleotide comprises from 5' to 3': the second, third, and first nucleic acid sequences, wherein the third nucleic acid sequence encodes from N-terminus to C-terminus a furin cleavage site and a 2A element. In certain embodiments, the polynucleotide comprises from 5' to 3': the first, third, and second nucleic acid sequences, wherein the third nucleic acid sequence encodes a 2A cleavage site. In certain embodiments, the polynucleotide comprises from 5' to 3': the second, third, and first nucleic acid sequences, wherein the third nucleic acid sequence encodes a 2A element. In certain embodiments, the polynucleotide comprises from 5' to 3': the first, third, and second nucleic acids, wherein the third nucleic acid sequence encodes a Furin cleavage site. In certain embodiments, the polynucleotide comprises from 5' to 3': the second, third, and first nucleic acid sequences, wherein the third nucleic acid sequence encodes a Furin cleavage site. In certain embodiments, the polynucleotide encodes any one of the amino acid sequences provided in Table 8. The furin cleavage site generally has a consensus sequence of $RX_1X_2R$, wherein $X_1$ can be any amino acid, and $X_2$, is K or R (SEQ ID NO: 29). In certain embodiments, $X_1$ is K or R. In certain embodiments, the furin cleavage site has a sequence of RAKR (SEQ ID NO: 30). In certain embodiments, the furin cleavage site has a consensus sequence of $RX_1X_2RS$ (SEQ ID NO: 131), wherein $X_1$ can be any amino acid, and $X_2$ is K or R. In certain embodiments, the furin cleavage site has a sequence of RAKRS (SEQ ID NO: 132). In certain embodiments, the furin cleavage site has a consensus sequence of $RX_1X_2RS$ (SEQ ID NO: 133), wherein $X_1$ is K or R, and $X$, is K or R. In certain embodiments, the furin cleavage site is cleaved after the second arginine residue. The 2A cleavage site generally comprises a consensus sequence of $X_1X_2EX_3NPGP$, wherein $X_1$ is D or G, $X_2$ is V or I, and $X_3$ is any amino acid (SEQ ID NO: 32). In certain embodiments, the 2A cleavage site is cleaved between the C-terminal proline residue and the preceding glycine residue. In certain embodiments, the 2A cleavage site comprises an amino acid sequence selected from SEQ ID NOs: 33-38, 130, and 134-140 (Table 7). In certain embodiments, the 2A cleavage site is a porcine teschovirus-1 2A (P2A) cleavage site having the amino acid sequence set forth in SEQ ID NO: 33. In certain embodiments, the 2A cleavage site is a porcine teschovirus-1 2A (P2A) cleavage site having the amino acid sequence set forth in SEQ ID NO: 134. In certain embodiments, the polynucleotide comprises a nucleic acid sequence encoding SEQ ID NO:

TABLE 7

Exemplary 2A cleavage sites.

| SEQ ID NO: | Description | Amino acid Sequence |
|---|---|---|
| 33 | porcine teschovirus-1 2A (P2A) | ATNFSLLKQAGDVEENPGP |
| 34 | thosea-asigna virus 2A peptide (T2A) | EGRGSLLTCGDVEENPGP |
| 35 | equine rhinitis A virus 2A peptide (E2A) | QCTNYALLKLAGDVESNPGP |
| 36 | foot-and-mouth disease virus 2A peptide (F2A) | VKQTLNFDLLKLAGDVESNPGP |
| 37 | cytoplasmic polyhedrosis virus 2A peptide (BmCPV 2A) | DVFRSNYDLLKLCGDIESNPGP |
| 38 | flacherie virus of B. mori 2A peptide (BmIFV 2A) | TLTRAKIEDELIRAGIESNPGP |
| 130 | Dual P2A-T2A peptide | ATNFSLLKQAGDVEENPGPEGRGSLLTCGDVEENPGP |
| 134 | porcine teschovirus-1 2A (P2A) | GSGATNFSLLKQAGDVEENPGP |
| 135 | Thosea asigna virus 2A peptide (T2A) | GSGEGRGSLLTCGDVEENPGP |
| 136 | equine rhinitis A virus 2A peptide (E2A) | GSGQCTNYALLKLAGDVESNPGP |
| 137 | foot-and-mouth disease virus 2A peptide (F2A) | GSGVKQTLNFDLLKLAGDVESNPGP |
| 138 | cytoplasmic polyhedrosis virus 2k peptide (BmCPV 2A) | GSGDVFRSNYDLLKLCGDIESNPGP |
| 139 | flacherie virus of B. mori 2A peptide (BmlFV 2A) | GSGTLTRAKIEDELIRAGIESNPGP |
| 140 | Dual P2A-T2A peptide | GSGATNFSLLKQAGDVEENPGPGSGEGRGSLLTCGDVEENPGP |

TABLE 8

Exemplary TCR fusion proteins

| Exemplary TCR Fusion Format | TCR 18168 | | TCR 0002 | | TCR 0014 | | TCR 0018 | | TCR 0022 | | TCR 0028 | | TCR 0038 | | TCR 0070 | |
|---|---|---|---|---|---|---|---|---|---|---|---|---|---|---|---|---|
| | − | + | − | + | − | + | − | + | − | + | − | + | − | + | − | + |
| alpha-Furin-2A-beta | 28 | N/A | 158 | N/A | 176 | N/A | 194 | N/A | 212 | N/A | 230 | N/A | 248 | N/A | 416 | N/A |
| alpha-Furin-2A-beta-GS | 141 | N/A | 159 | N/A | 177 | N/A | N/A | N/A | N/A | N/A | N/A | N/A | N/A | N/A | N/A | N/A |
| alpha-2A-beta | 142 | N/A | 160 | N/A | 178 | N/A | 196 | N/A | 214 | N/A | 232 | N/A | 250 | N/A | 417 | N/A |
| alpha-2A-beta-GS | 143 | N/A | 161 | N/A | 179 | N/A | N/A | N/A | N/A | N/A | N/A | N/A | N/A | N/A | N/A | N/A |

TABLE 8-continued

Exemplary TCR fusion proteins

Exemplary SEQ ID NO. for each Format, with (+) or without (−) N-terminal leader sequence optimization

| Exemplary TCR Fusion Format | TCR 18168 − | TCR 18168 + | TCR 0002 − | TCR 0002 + | TCR 0014 − | TCR 0014 + | TCR 0018 − | TCR 0018 + | TCR 0022 − | TCR 0022 + | TCR 0028 − | TCR 0028 + | TCR 0038 − | TCR 0038 + | TCR 0070 − | TCR 0070 + |
|---|---|---|---|---|---|---|---|---|---|---|---|---|---|---|---|---|
| beta-Furin-2A-alpha | 146 | 152 | 164 | 170 | 182 | 188 | 200 | 206 | 218 | 224 | 236 | 242 | 254 | 260 | 418 | 420 |
| beta-Furin-2A-alpha-GS | 147 | 153 | 165 | 171 | 183 | 189 | N/A | N/A | N/A | N/A | N/A | N/A | N/A | N/A | N/A | N/A |
| beta-2A-alpha | 148 | 154 | 166 | 172 | 184 | 190 | 202 | 208 | 220 | 226 | 238 | 244 | 256 | 262 | 419 | 421 |
| beta-2A-alpha-GS | 149 | 155 | 167 | 173 | 185 | 191 | N/A | N/A | N/A | N/A | N/A | N/A | N/A | N/A | N/A | N/A |

Also provided herein are polynucleotides encoding a TCR described herein that are optimized, e.g., by codon/RNA optimization, replacement with heterologous signal sequences, and elimination of mRNA instability elements. Methods to generate optimized nucleic acids encoding a TCR (e.g., α chain, β chain, Vα domain, and/or Vβ domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of a TCR by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of a TCR encoded by polynucleotides that have not been optimized.

In certain embodiments, an optimized polynucleotide sequence encoding a TCR described herein (e.g., α chain, β chain, Vα domain and/or Vβ domain) can hybridize to an antisense (e.g., complementary) polynucleotide of an unoptimized polynucleotide sequence encoding a TCR described herein (e.g., α chain, β chain, Vα domain, and/or Vβ domain). In specific embodiments, an optimized nucleotide sequence encoding a TCR described herein under high stringency conditions to antisense polynucleotide of an unoptimized polynucleotide sequence encoding a TCR described herein. In a specific embodiment, an optimized nucleotide sequence encoding a TCR described herein hybridizes under high stringency, intermediate or lower stringency hybridization conditions to an antisense polynucleotide of an unoptimized nucleotide sequence encoding a TCR described herein. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding TCRs described herein, e.g., TCRs described in Tables 1-4, and modified versions of these TCRs can be determined using methods well-known in the art, i.e., nucleotide codons known to encode particular amino acids are assembled in such a way to generate a nucleic acid that encodes the TCR. Such a polynucleotide encoding the TCR can be assembled from chemically synthesized oligonucleotides (e.g, as described in Kutmeier G et al., (1994), Biotechniques 17: 242-6), which, briefly, involves the synthesis of overlapping oligonucleotides containing portions of the sequence encoding the TCR, annealing and ligating of those oligonucleotides, and then amplification of the ligated oligonucleotides by PCR.

Alternatively, a polynucleotide encoding a TCR described herein can be generated from nucleic acid from a suitable source (e.g., a T lymphocyte) using methods well-known in the art (e.g., PCR and other molecular cloning methods). For example, PCR amplification using synthetic primers hybridizable to the 3' and 5' ends of a known sequence can be performed using genomic DNA obtained from T cells expressing the TCR of interest. Such PCR amplification methods can be used to obtain nucleic acids comprising the sequence encoding the α chain and/or β chain of a TCR. Such PCR amplification methods can be used to obtain nucleic acids comprising the sequence encoding the Vα domain and/or Vβ domain of a TCR. The amplified nucleic acids can be cloned into vectors for expression in host cells and for further cloning, for example, to venerate chimeric and humanized TCRs.

If a clone containing a nucleic acid encoding a particular TCR is not available, but the sequence of the TCR molecule is known, a nucleic acid encoding the TCR can be chemically synthesized or obtained from a suitable source (e.g., a TCR cDNA library or a cDNA library generated from, or nucleic acid, e.g., poly A$^+$ RNA, isolated from, any tissue or cells expressing the TCR, such as T lymphocytes selected to express a TCR described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes TCRs. Amplified nucleic acids generated by PCR can then be cloned into replicable cloning vectors using any method well-known in the art.

DNA encoding TCRs described herein can be readily isolated and sequenced using conventional procedures, e.g., by using oligonucleotide probes that are capable of binding specifically to genes encoding the α chain and/or β chain of the TCR. T lymphocytes can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce TCR protein, to obtain the synthesis of TCRs in the recombinant host cells.

To generate whole TCRs, PCR primers including Vα or Vβ nucleotide sequences, a restriction site, and a flanking sequence to protect the restriction site can be used to amplify the Vα or Vβ sequences into clones, e.g., clones of individual Vα or Vβ nucleotide sequences, or clones of single-chain TCRs containing variable regions of TCRs attached by a flexible linker. Utilizing cloning techniques known to those of skill in the art, the PCR amplified Vα domains can be cloned into vectors expressing an α chain constant region, and the PCR amplified Vβ domains can be cloned into vectors expressing a β chain constant region. In certain embodiments, the vectors for expressing the Vα or Vβ domains comprise an EF-1α promoter, a secretion signal, a cloning site for the variable region, constant domains, and a selection marker such as neomycin. The α chain and β chain vectors are then co-transfected into cell lines, either simultaneously or sequentially, to generate stable or transient cell lines that express whole TCRs using techniques known to those of skill in the art. The Vα or Vβ domains can also be cloned into one vector expressing the necessary constant regions. The vector is then transfected into cell lines to generate stable or transient cell lines that express whole TCRs using techniques known to those of skill in the art.

The DNA also can be modified, for example, by substituting the coding sequence for human α chain and β chain constant domains in place of the murine sequences, or by covalently joining to the TCR coding sequence all or part of the coding sequence for a non-TCR polypeptide.

Also provided are polynucleotides that hybridize under high, intermediate, or low stringency hybridization conditions to polynucleotides that encode a TCR described herein. In specific embodiments, polynucleotides described herein hybridize under high, intermediate, or low stringency hybridization conditions to polynucleotides encoding a Vα domain and/or Vβ domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausuhel F M et al., eds., (1989) *Current Protocols in Molecular Biology*, Vol. I, Green Publishing Associates, Inc. and John Wiley & Sons, Inc., New York at pages 6.3.1-6.3.6 and 2.10.3.

In certain aspects, provided herein are cells (e.g., host cells) expressing (e.g., recombinantly) TCRs described herein which bind to an NY-ESO-1 peptide, and related polynucleotides and expression vectors. Provided herein are vectors (e.g., expression vectors) comprising polynucleotides comprising nucleotide sequences encoding such TCRs for recombinant expression in host cells, e.g., in mammalian cells. Also provided herein are host cells comprising such vectors for recombinantly expressing TCRs described herein (e.g., human or humanized TCR). In a particular aspect, provided herein are methods for producing a TCR described herein, comprising expressing such TCR from a host cell.

In another aspect, provided herein are methods for producing an engineered cell (e.g., a cell comprising a heterologous and/or recombinant nucleic acid) as described herein. In certain embodiments, the method comprises contacting a cell with a vector as described herein under conditions that allow introduction of the vector into the cell. In certain embodiments, the condition allows transfection of the cell with the vector (e.g., by liposome or electroporation), in one embodiment, the condition allows transfection of the cell with an mRNA vector by electroporation. In certain embodiments, the vector is a viral vector, and the conditions allow transduction of the cell with the viral vector. In certain embodiments, the vector is introduced to the cell in vitro or ex vivo. In certain embodiments, the vector is introduced to the cell in vivo.

Recombinant expression of a TCR described herein (e.g., a full-length TCR, α chain and/or β chain of a TCR, or a single-chain TCR described herein) that binds to an NY-ESO-1 peptide involves construction of an expression vector containing a polynucleotide that encodes the TCR. Once a polynucleotide encoding a TCR described herein has been obtained, the vector for the production of the TCR molecule can be produced by recombinant DNA technology using techniques well-known in the art. Thus, methods for preparing a protein by expressing a polynucleotide containing a TCR encoding nucleotide sequence are described herein. Methods which are well-known to those skilled in the art can be used to construct expression vectors containing TCR encoding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding a TCR molecule described herein (e.g., a full-length TCR, α chain or β chain of a TCR, Vα or Vβ of a TCR, or an α or β chain CDR), operably linked to a promoter.

The vector can comprise any type of nucleotides (including but not limited to DNA and RNA) which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. In one embodiment, the non-naturally occurring or altered nucleotides or inter-nucleotide linkages do not hinder the transcription or replication of the vector. The expression vector can be a viral vector (e.g., a retroviral vector, an adenoviral vector, an adeno-associated viral vector, or a baculoviral vector). In certain embodiments, the retroviral vector is a lentiviral vector (e.g., a vector comprising genetic elements of the HIV-1 genome) or an equine infectious anemia viral vector. In certain embodiments, the vector is packaged with one or more viral capsid proteins to provide a viral particle.

An expression vector can be transferred to a cell (e.g., a host cell) by conventional techniques and the resulting cell can then be cultured by conventional techniques to produce a TCR described herein. Thus, provided herein are host cells containing a polynucleotide encoding a TCR molecule described herein (e.g., a full-length TCR, α chain or β chain of a TCR, Vα or Vβ of a TCR, or an α or β chain CDR) operably linked to a promoter for expression of such sequences in the host cell. In certain embodiments, for the expression of double-chained TCRs, vectors encoding both the α and β chains, individually, can be co-expressed in the host cell for expression of the entire TCR molecule, as detailed below. In certain embodiments, a host cell contains a vector comprising a polynucleotide encoding both the α chain and β chain of a TCR described herein. In specific embodiments, a host cell contains two different vectors, a first vector comprising a polynucleotide encoding an α chain or an α chain variable region of a TCR described herein, and a second vector comprising a polynucleotide encoding a β chain or a β chain variable region of a TCR described herein. In other embodiments, a first host cell comprises a first vector comprising a polynucleotide encoding an α chain or an α chain variable region of a TCR described herein, and a second host cell comprises a second vector comprising a polynucleotide encoding a β chain or a β chain variable region of a TCR described herein. In specific embodiments, an α chain or α chain variable region expressed by a first cell associated with a 3 chain or 3 chain variable region expressed by a second cell to form a TCR described herein. In certain embodiments, provided herein is a population of host cells comprising such first host cell and such second host cell.

In a particular embodiment, provided herein is a population of vectors comprising a first vector comprising a polynucleotide encoding an α chain or α chain variable region of a TCR described herein, and a second vector comprising a polynucleotide encoding a β chain or β chain variable region of a TCR described herein.

A variety of host-expression vector systems can be utilized to express TCR molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express a TCR molecule described herein in situ. These include but are not limited to microorganisms such as bacteria (e.g., *E. coli* and *B. subtilis*) transformed with recombinant bacteriophage DNA, plasmid DNA, or cosmid DNA expression vectors containing TCR coding sequences; yeast (e.g., *Saccharomyces Pichia*) transformed with recombinant yeast expression vectors containing TCR coding sequences; insect cell systems infected with recombinant virus expression vectors (e.g., baculovirus) containing TCR coding sequences; plant cell systems (e.g., green algae such as *Chlamydomonas reinhardtii*) infected with recombinant virus expression vectors (e.g., cauliflower mosaic virus, CAW; tobacco mosaic virus, TMV) or transformed with recombinant plasmid expression vectors (e.g., Ti plasmid) containing TCR coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-2931, HepG2, SP210; R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing TCRs described herein are CHO cells, for example CHO cells from the CHO GS System™ (Lonza). In a particular embodiment, cells for expressing TCRs described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant TCR molecule, are used for the expression of a recombinant TCR molecule. For example, mammalian cells such as Chinese hamster ovary (CHO) cells, in conjunction with a vector such as the major intermediate early gene promoter element from human cytomegalovirus, are an effective expression system for TCRs (Foecking M K & Hofstetter H (1986) Gene 45: 101-5; and Cockett M I et al., (1990) Biotechnology 8(7): 662-7). In certain embodiments, TCRs described herein are produced by CHO cells or NS0 cells. In a specific embodiment, the expression of nucleotide sequences encoding TCRs described herein is regulated by a constitutive promoter, inducible promoter, or tissue specific promoter.

In certain embodiments, the mammalian host cell is a lymphocyte (e.g., a human lymphocyte), such as a T cell or a natural killer (NK) cell. In certain embodiments, the lymphocyte is a T cell. Any T cell at any developmental stage can be used to express a TCR disclosed herein. For example, in certain embodiments, the T cell is selected from the group consisting of a $CD8^+$ cytotoxic T cell, a $CD4^+$ cytotoxic T cell, a $CD4^+$ helper T cell (e.g., a Th1 or a Th2 cell), a CD4/CD8 double positive T cells, a tumor infiltrating T cell, a thymocyte, a memory T cell, a naïve T cell, and a natural killer T cell (e.g., an invariant natural killer T cell). Precursor cells of the cellular immune system (e.g., precursors of T lymphocytes) are also useful for presenting a TCR disclosed herein because these cells may differentiate, develop, or mature into effector cells. Accordingly, in certain embodiments, the mammalian host cell is a pluripotent stem cell (e.g., an embryonic stein cell, an induced pluripotent stem cell), lymphocyte progenitor cell, or a hematopoietic stem cell (e.g., isolated and/or enriched from bone marrow, umbilical cord blood, or peripheral blood).

Cells can be obtained from numerous sources, including but not limited to, tumor, blood, bone marrow, lymph node, thymus, or another tissue or bodily fluid, or an apheresis product. In certain embodiments, cells are obtained from a patient directly following a treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex viva manipulation using the methods described herein, these cells may be in a preferred state for enhanced engraftment and in viva expansion. Thus, in certain embodiments, cells are collected from blood, bone marrow, lymph node, thymus, or another tissue or bodily fluid, or an apheresis product, during this recovery phase.

In certain embodiments, the mammalian host cell is a population of cells presenting a TCR disclosed herein on the cell surface. The population of cells can be heterogeneous or homogenous. In certain embodiments, at least 50% (e.g., at least 60%, 70%, 80%, 90%, 95%, 99%, 99.5%, or 99.9%) of the population is a cell as described herein. In certain embodiments, the population is substantially pure, wherein at least 50% (e.g., at least 60%, 70%, 80%, 90%, 95%, 99%, 99.5%, or 99.9%) of the population is homogeneous. In certain embodiments, the population is heterogeneous and comprises a mixed population of cells (e.g., the cells have different cell types, developmental stages, origins, are isolated, purified, or enriched by different methods, are stimulated with different agents, and/or are engineered by different methods). In certain embodiments, the cells are a population of peripheral blood mononuclear cells (PBMC) (e.g., human PBMCs).

In bacterial systems, a number of expression vectors can be advantageously selected depending upon the use intended for the TCR molecule being expressed. For example, when a large quantity of such a TCR is to be produced, for the generation of pharmaceutical compositions of a TCR molecule, vectors which direct the expression of high levels of fusion protein products that are readily purified can be desirable. Such vectors include, but are not limited to, the E coil expression vector pUR278 (Ruether U & Mueller-Hill B (1983) EMBO J 2: 1791-1794), in which the TCR coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol. Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The TCR coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the TCR encoding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the TCR molecule in infected hosts (e.g., see Logan 0.1 &. Shenk T (1984) PNAS 81(12): 3655-9). Specific initiation signals can also be required for efficient translation of inserted TCR coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BRK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2 SP210, R1.1, B-W, L-M, BSC1, BSC40, YB/20, BMT10 and HsS78Bst cells. In certain embodiments, TCR molecules described herein are produced in mammalian cells, such as CHO cells.

For long-term expression of the recombinant TCRs, stable expression cells can be generated. For example, cell lines which stably express a TCR described herein can be engineered. In specific embodiments, a cell provided herein stably expresses an α chain or α chain variable region and a β chain or β chain variable region which associate to form a TCR described herein.

In certain aspects, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express a TCR described herein. Such engineered cell lines can be particularly useful in screening and evaluation of compositions that interact directly or indirectly with the TCR molecule.

A number of selection systems can be used, including but not limited to, the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034), and adenine phosphoribosyltransferase (Lowy I et al., (1980) Cell 22(3): 817-23) genes in tk-, hgprt- or aprt-cells, respectively, each of which is incorporated by reference herein in its entirety. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Feigner P L (1993) Trends Biotechnol 11(5): 211-5); and hygro, which confers resistance to hygromycin (Santerre R F et al., (1984) Gene 30(1-3): 147-56), each of which is incorporated by reference herein in its entirety. Methods commonly known in the art of recombinant DNA technology can be routinely applied to select the desired recombinant clone and such methods are described, for example, in Ausuhel F M et al., (eds.), *Current Protocols in Molecular Biology*, John Wiley & Sons, N Y (1993); Kriegler M. *Gene Transfer and Expression*, A Laboratory Manual, Stockton Press, N Y (1990); and in Chapters 12 and 13, Dracopoli N C et al., (eds.), *Current Protocols in Human Genetics*, John Wiley & Sons, N Y (1994); Colbere-Garapin F et al., (1981) J Mol Biol 150: 1-14, which are incorporated by reference herein in their entireties.

The expression levels of a TCR molecule can be increased by vector amplification (for a review, see Bebbington C R & Hentschel C C G. The use of vectors based on gene amplification for the expression of cloned genes in mammalian cells in DNA cloning, Vol. 3 (Academic Press, New York, 1987), which is incorporated by reference herein in its entirety). When a marker in the vector system expressing TCR is amplifiable, increase in the level of inhibitor present in culture of host cells will result in selection of host cells with increased numbers of copies of the marker gene. Since the amplified region is associated with the TCR gene, production of the TCR will also increase (Crouse G F et al., (1983) Mol Cell Biol 3: 257-66, which is incorporated by reference herein in its entirety).

In other aspects, the host cell can be transduced with a viral vector (e.g., a retroviral vector, an adenoviral vector, an adeno-associated viral vector; or a baculoviral vector) comprising a sequence encoding a TCR as described herein. In certain embodiments, the retroviral vector is a lentiviral vector (e.g., a vector comprising genetic elements of the HIV-1 genome) or an equine infectious anemia viral vector. In certain embodiments, the vector is packaged with one or more viral capsid proteins to provide a viral particle.

In certain embodiments, the vector further comprises a transcriptional and/or translational control sequence (e.g., a promoter, an enhancer, and/or a Kozak sequence) operably linked to the sequence encoding a TCR as described herein. Alternatively, the sequence encoding the TCR may not be operably linked to a transcriptional and/or translational control sequence (e.g., a promoter, an enhancer, and/or a Kozak sequence), but is flanked by sequences homologous to the sequences flanking a locus of the host cell genome, wherein the integration of the TCR-coding sequence allows expression of the encoded TCR from the transcriptional and/or translational control sequence at or near the genomic locus.

The host cell can be co-transferred co-transfected or co-transduced) with two or more expression vectors described herein, the first vector encoding an α chain derived polypeptide and the second vector encoding a β chain derived polypeptide. The two vectors can contain identical selectable markers which enable equal expression of α chain and β chain polypeptides. The host cells can be co-transferred with different amounts of the two or more expression vectors. For example, host cells can be co-transferred with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50. In some embodiments, the coding sequences for the α and β chains are DNA. In some embodiments, the coding sequences for the α and β chains are RNA.

Alternatively, a single vector can be used which encodes, and is capable of expressing, both α and β chain polypeptides. The coding sequences for the α and β chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., β chain of a TCR described herein), and a second gene (e.g., a chain of a TCR described herein). In such an expression vector, the transcription of both genes can be driven by the promoter, whereas the translation of the mRNA from the first gene can be initiated by a cap-dependent scanning mechanism and the translation of the snRNA from the second gene can be by a cap-independent mechanism, e.g., by an IRES. Alternatively, the two genes can be operably linked by a self-cleavage peptide (e.g., a 2A peptide) or a peptide sequence recognized by an intracellular or an extracellular protease.

Once a TCR molecule described herein has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the TCR described herein can be fused to heterologous polypeptide sequences described herein or otherwise known in the art to facilitate purification.

In specific embodiments, a TCR described herein is isolated or purified. Generally, an isolated TCR is one that is substantially free of other TCRs with different antigenic specificities than the isolated TCRs. For example, in a particular embodiment, a preparation of a TCR described herein is substantially free of cellular material and/or chemical precursors. The language "substantially free of cellular material" includes preparations of a TCR in which the TCR is separated from cellular components of the cells from which it is isolated or recombinantly produced. Thus, a TCR that is substantially free of cellular material includes preparations of the TCR having less than about 30%, 20%, 10%, 5%, 2%, 1%, 0.5%, or 0.1% (by dry weight) of heterologous protein (also referred to herein as a "contaminating protein") and/or variants of the TCR, for example, different post-translational modified forms of the TCR or other different versions of the TCR (e.g., fragments thereof). When the TCR is recombinantly produced, it is also generally substantially free of culture medium, i.e., culture medium represents less than about 20%, 10%, 2%, 1%, 0.5%, or 0.1% of the volume of the protein preparation. When the TCR is produced by chemical synthesis, it is generally substantially free of chemical precursors or other chemicals, i.e., it is separated from chemical precursors or other chemicals which are involved in the synthesis of the TCR. Accordingly, such preparations of the TCR, have less than about 30%, 20%, 10%, or 5% (by dry weight) of chemical precursors or compounds other than the TCR of interest. In a specific embodiment, TCRs described herein are isolated or purified.

TCRs that bind to an NY-ESO-1 peptide can be produced by any method known in the art for the synthesis of TCRs, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) *Molecular Cloning: A Laboratory Manual*, Cold Spring Harbor Laboratory Press; Sambrook J et al., (1989), *Molecular Cloning: A Laboratory Manual*, Second Edition, Cold Spring Harbor Laboratory Press; Sambrook J et al., (2001) *Molecular Cloning: A Laboratory Manual*, Cold Spring Harbor Laboratory Press, Cold Spring Harbor, N.Y.; Ausubel F M et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren B et al., (eds.) (1999) *Genome Analysis: A Laboratory Manual*, Cold Spring Harbor Laboratory Press, each of which is incorporated by reference herein in its entirety.

In a specific embodiment, a TCR described herein is a TCR (e.g, recombinant TCR) prepared, expressed, created, or isolated by any means that involves creation, e.g., via synthesis, genetic engineering of DNA sequences. In certain embodiments, such TCR comprises sequences (e.g., DNA sequences, RNA sequences, or amino acid sequences) that do not naturally exist within the TCR germline repertoire of an animal or mammal (e.g., human) in vivo.

In one aspect, provided herein is a method of making a TCR that binds to an NY-ESO-1 peptide, the method comprising culturing a cell or host cell described herein. In a certain aspect, provided herein is a method of making a TCR which binds to an NY-ESO-1 peptide, the method comprising expressing (e.g., recombinantly expressing) the TCR using a cell or host cell described herein (e.g., a cell or a host cell comprising polynucleotides encoding a TCR described herein). In a particular embodiment, the cell is an isolated cell. In a particular embodiment, the exogenous polynucleotides have been introduced into the cell. In a particular embodiment, the method further comprises the step of purifying the TCR obtained from the cell or host cell.

The TCRs described herein can be generated using various phage display methods known in the art. In phage display methods, functional TCR domains are displayed on the surface of phage particles which carry the polynucleotide sequences encoding them. In particular, DNA sequences encoding Vα and Vβ domains are amplified from animal cDNA libraries (e.g., human or murine cDNA libraries of affected tissues). The DNA encoding the Vα and Vβ domains are connected with a peptide linker by PCR and cloned into a phagemid vector. The vector is electroporated in *E. coli* and the *E. coli* is infected with helper phage, Phage used in these methods are typically filamentous phage including fd and M13, and the Vα and Vβ domains are usually recombinantly fused to either the phage gene III or gene VIII. Phage expressing an antigen binding domain that binds to a particular antigen can be selected or identified with a peptide or a peptide-MHC complex, e.g., using such a complex displayed on the surface of a cell or captured to a solid surface or bead. Examples of phage display methods that can be used to make the TCRs described herein include those disclosed in Zhao Y et al., (2007) J Immunol 179: 5845-54, which is incorporated by reference herein in its entirety.

As described in the above references, after phage selection, the TCR coding regions from the phage can be isolated and used to generate whole TCRs, including human TCRs, and expressed in any desired host, including mammalian cells, insect cells, plant cells, yeast, and bacteria, e.g., as described below.

In certain embodiments, to generate whole TCRs, PCR primers including Vα or Vβ nucleotide sequences, a restriction site, and a flanking sequence to protect the restriction site can be used to amplify the Vα or Vβ sequences from a template, e.g., clones of single-chain TCRs containing variable regions of TCRs connected by a peptide linker. Utilizing cloning techniques known to those of skill in the art, the PCR amplified Vα domains can be cloned into vectors expressing a Vα constant region, and the PCR amplified Vβ domains can be cloned into vectors expressing a Vβ constant region. The α chain and β chain vectors are then co-transfected into cell lines, either simultaneously or sequentially, to generate stable or transient cell lines that express whole TCRs using techniques known to those of skill in the art. The Vα or Vβ domains can also be cloned into one vector expressing the necessary constant regions. The vector is then transfected into cell lines to generate stable or transient cell lines that express whole TCRs using techniques known to those of skill in the art.

In certain embodiments, to generate whole TCRs from a polynucleotide encoding the α chain and β chain of a TCR as described herein, or from a vector comprising thereof; a polypeptide comprising the α chain and β chain of the TCR is expressed from the polynucleotide or vector. The polypeptide is optionally isolated and/or purified. The polypeptide is contacted with a Furin enzyme. In certain embodiments, where the Furin cleavage site has the amino acid sequence of $RX_1X_2R$, wherein $X_1$ is K or R, and $X_2$ is K or R (SEQ ID NO: 31), the polypeptide is further contacted with a carboxypeptidases either simultaneously or subsequently, wherein the carboxypeptidase removes the basic amino acids, K or R, from the C-terminus of a polypeptide.

A chimeric TCR is a molecule in which different portions of the TCR are derived from different TCR molecules, e.g., TCRs from different species.

In particular embodiments, a TCR described herein, which binds to the same epitope of a peptide comprising the amino acid sequence set forth in SEQ ID NO: 1 or 2 as a TCR described herein, is a human TCR. Human TCRs can be produced using any method known in the art. For example, transgenic mice which are incapable of expressing functional endogenous TCRs, but which can express human TCR genes, can be used. In particular, the human α and β chain TCR genes can be introduced randomly or by homologous recombination into mouse embryonic stem cells. The mouse α and β chain TCR genes can be rendered non-functional separately or simultaneously with the introduction of human TCR loci by homologous recombination. In particular, homozygous deletion of the $J_H$ region prevents endogenous TCR production. The modified embryonic stem cells are expanded and microinjected into blastocysts to produce chimeric mice. The chimeric mice are then bred to produce homozygous offspring which express human TCRs. The transgenic mice are immunized in the normal fashion with a selected antigen, e.g., all or a portion of an antigen (e.g., an NY-ESO-1 peptide). T lymphocytes comprising TCRs directed against the antigen can be obtained from the immunized, transgenic mice. The human TCR transgenes harbored by the transgenic mice rearrange during T cell differentiation. Thus, using such a technique, it is possible to produce therapeutically useful TCRs arising from in vivo immunization.

Human TCRs which bind to an NY-ESO-1 peptide can be made by a variety of methods known in the art including phage display methods or mammalian display using TCR libraries derived from human TCR sequences.

5.6 Kits

Also provided are kits comprising one or more TCRs described herein, pharmaceutical compositions or conjugates thereof, polynucleotides (e.g., expression vectors) encoding one or more TCRs described herein, or cells expressing one or more TCRs described herein. In a specific embodiment, provided herein is a pharmaceutical pack or kit comprising one or more containers filled with one or more of the ingredients of the pharmaceutical compositions described herein, such as one or more TCRs, polynucleotides, or cells provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol 12-myristate 13-acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises a TCR described herein, e.g., a purified TCR, in one or more containers. In a specific embodiment, kits described herein contain a substantially isolated peptide-MHC complex comprising an NY-ESO-1 peptide as a control antigen. In another specific embodiment, the kits described herein further comprise a control TCR which does not react with a peptide-MHC complex comprising an NY-ESO-1 peptide. In another specific embodiment, kits described herein contain one or more elements for detecting the binding of a TCR to a peptide-MHC complex comprising an NY-ESO-1 peptide (e.g., the TCR can be conjugated to a detectable substrate such as a fluorescent compound, an enzymatic substrate, a radioactive compound or a luminescent compound, or a binding molecule which recognizes the TCR can be conjugated to a detectable substrate). In specific embodiments, a kit provided herein can include a recombinantly produced or chemically synthesized peptide-MHC complex comprising an NY-ESO-1 peptide. The peptide-MHC complex comprising an NY-ESO-1 peptide provided in the kit can be attached to a solid support (e.g. a solid surface or a bead) or be integrated into a lipid membrane (e.g., a liposome, or a fixed cell). In a more specific embodiment, the detecting means of the above described kit includes a solid support to which a peptide-MHC complex comprising an NY-ESO-1 peptide is attached. Such a kit can also include a non-attached reporter-labeled binding molecule which recognizes the TCR. In this embodiment, binding of the TCR to the peptide-MHC complex can be detected by binding of the said reporter-labeled binding molecule.

6. EXAMPLES

The examples in this Section (i.e., Section 6) are offered by way of illustration, and not by way of limitation.

6.1 Example 1: Characterization of a Novel NY-ESO-1 TCR, TCR18168c, in Murine Cells A novel TCR that binds to SLLMWITQC (SEQ ID NO: 1)-HLA-A*0201 was developed using a proprietary mammalian cell TCR display platform. The TCR, referred to herein as TCR18168c, comprises an α chain variable region (Vα) and a β chain variable region (Vβ) comprising the amino acid sequences set forth in SEQ ID NOs: 3 and 4, respectively. TCR18168c was expressed as a chimeric protein, with human variable regions fused to murine constant regions, on the surface of murine cell line AK-D10R3. The murine constant regions ensure proper anchoring and interaction with murine CD3 and proper triggering of murine signaling pathways. AK-D10R3 is a murine thymoma-derived mouse TCR-negative, mouse CD8-negative cell line that expresses chimeric CD8 (human CD8 α and β extracellular regions fused to the corresponding mouse CD8 α and β transmembrane and intracellular regions) and a T cell activation reporter construct comprising a minimal IL-2 promoter, which includes three NFAT binding sites, operably linked to EGFP. TCR18168c comprises an α chain and a β chain comprising the amino acid sequences set forth in SEQ ID NOs: 11 and 12, respectively.

6.1.1 Binding of Cells Expressing TCR18168c to Peptide-MHC Tetramers

First, AK-D10R3 cells expressing TCR18168c were tested for binding to cognate peptide-MHC tetramers or negative control peptide-MHC tetramers using flow cytometry. Briefly, AK-D10R3 cells expressing TCR18168c were plated in a 96-well assay plate and incubated with an APC-labeled anti-mouse TCR β chain antibody (BD Biosciences, Cat. No.: 553174, clone H57-597) and PE-labeled HLA-A*0201 tetramers loaded with a wild type NY-ESO-1 peptide SLLMWITQC (SEQ ID NO: 1) (MBL, Cat. No.: T01064), an anchor-optimized NY-ESO-1 peptide SLLMWITQV (SEQ ID NO: 2) (MBL, Cat. No.: TS-M105-1), or a negative control peptide. TCR-negative AK-D10R3 cells were also tested as a control. Following a 30-minute incubation at room temperature, the cells were washed twice and analyzed by flow cytometry using a BD FACSCanto II cytometer. The cells were analyzed for TCR expression (APC+) and peptide-MHC binding (PE+).

As shown in FIG. 1, TCR18168c, when expressed on the cell surface, bound to MLA-A*0201 tetramers loaded with the wild type NY-ESO-1 peptide SLLMWITQC (SEQ ID NO: 1) or the anchor-optimized peptide SLLMWITQV (SEQ ID NO: 2), but not to the negative control tetramers.

6.1.2 Activation of TCR-Expressing AK-D10R3 Cells Using Peptide-Pulsed T2 Cells Next, AK-D10R3 cells expressing TCR18168c were tested for their ability to be activated by 12 cells pulsed with a cognate NY-ESO-1 peptide or a negative control peptide. Briefly, T2 cells (human lymphoblast cells as described in Salter. EMBO J. 1986; 5(5):943-9, herein incorporated by reference in its entirety) were pulsed with 50 µg/ml of wild type NY-ESO-1 peptide SLLMWITQC (SEQ ID NO: 1) (P&E, custom order), anchor-optimized NY-ESO-1 peptide SLLMWITQV (SEQ ID NO: 2) (IBA, Cat. No.: 6-7013-901), or negative control peptide for 3 hours at 37° C. A total of $5.0 \times 10^4$ AK-D10R3 cells expressing TCR18168c were then incubated with $5.0 \times 10^4$ peptide-pulsed T2 cells in a 96-well assay plate for 18 hours at 37° C. and 10% $CO_2$. TCR-negative AK-D10R3 cells were used as a negative control. The cells were then stained with an APC-labeled anti-mouse TCR β chain antibody (BD Biosciences, Cat. No.: 553174, clone 1-157-597) and BV412-labeled anti-mouse CD69 antibody (Biolegend, Cat. No.: 104528, clone H1.2F) for 30 minutes at room temperature. Subsequently, the cells were washed twice and analyzed by flow cytometry using a BD FACSCanto II cytometer. The cells were analyzed for TCR expression (APC+) and T cell activation (EGFP+ or BV412+).

Upon interaction with T2 cells pulsed with the wild type or anchor-optimized NY-ESO-1 peptide, AK-D10R3 cells expressing TCR18168c showed activation of the IL-2-NEAT reporter construct and up-regulation of T cell activation marker CD69 (FIG. 2). The activation of AK-D10R3 cells was dependent on the interaction between the NY-ESO-1 Tea and its cognate peptide-MHC complex, since such activation was not observed, or was only observed to a minimal extent, when TCR-negative AK-DI ORS cells were tested or when AK-D10R3 cells expressing TCR18168c were incubated with T2 cells pulsed with the negative control peptide (FIG. 2).

6.2 Example 2: Characterization of a Novel NY-ESO-1 TCR, TCR18168, in Human T Cells In this example, a fully human version of TCR18168c named TCR18168 was expressed in primary human T cells or a human T cell reporter cell line and characterized in a number of functional assays as described below. TCR18168 includes the Vα and Vβ of TCR18168c fused to human constant regions. Specifically, TCR18168 comprises an α chain and a β chain comprising the amino acid sequences set forth in SEQ ID NOs: 13 and 14, respectively. The TCR DMF4, which is reactive with a MART-1 peptide in the context of HLA-A*0201, was used as a control. DMF4 is described in U.S. Pat. No. 7,915,036, which is herein incorporated by reference in its entirety. The full length TCR DMF4 comprises an α chain and a β chain comprising the amino acid sequences set forth in SEQ ID NOs: 20 and 21, respectively.

6.2.1 Characterization of Primary Human T Cells Expressing TCR18168 Co-Cultured with Peptide-Pulsed HLA-Expressing K562 Target Cells Messenger RNA (mRNA) for the full-length human TCRs TCR18168 and DMF4 was generated via in vitro transcription using the mMESSAGE mMACHINE T7 Ultra kit (Ambien, Cat. No.: AMB13455). TCR18168 mRNA was expressed from a vector encoding, in order, the TCR18168 α chain, a furin cleavage site, a P2A cleavage site, and the TCR18168 β chain. The resultant TCR18168 mRNA comprises a polynucleotide sequence encoding the amino acid sequence of SEQ ID NO: 28. DMF4 mRNA was expressed from a vector encoding the DMF4 β chain, a P2A cleavage site, and the DMF4 α chain. Primary human T cells isolated from a healthy donor and previously expanded with ImmunoCult™ Human CD3/28 T cell Activator (Stemcell Technologies) were mixed with 7.5 μg of TCR mRNA and electroporated using a MaxCyte GT (MaxCyte) electroporator. Approximately 20 hours post-electroporation, target TCR expression was evaluated by staining T cells with HLA-A*0201 tetramers containing either the NY-ESO-1 peptide SLLMWITQC (SEQ ID NO: 1) (MBL, Cat. No.: T01064B) or the MART-1 peptide ELAGIGILTV (SEQ ID NO: 22) (MBL, Cat. No.: T01022) and analyzed via flow cytometry using the BD LSR Fortessa. In parallel, K562 cells (ATCC, Cat. No.: CCL-243) lentivirally transduced to express HLA-A2 or HLA-B7 were pulsed with 0.01, 0.1, or 1 μM of the NY-ESO-1 peptide SLLMWITQC (SEQ ID NO: 1) (Genscript, custom order), 1 μM. of the MART-1 peptide ELAGIGILTV (SEQ ID NO: 22) (Genscript, custom order), or DMSO alone (vehicle control) (Fisher Scientific, Cat. No.: BP231-100). TCR18168-expressing or DMF4-expressing T cells were co-cultured with K562 target cells for 16 hours and then analyzed for the expression of the activation marker CD25 by flow cytometry using an anti-human CD25 antibody (eBioscience, Cat. No.: 17-0259-42) and secretion of IFNγ by ELBA using the Human IFN gamma ELISA Ready-Set-Go Kit (eBioscience, Cat. No.: 88-7316-88). As a positive control, TCR18168-expressing or DMF4-expressing T cells were also activated using ImmunoCult™ Human CD3/28 T cell Activator (Stemcell Technologies) for 16 hours in the absence of target cells and then examined for surface CD25 expression using flow cytometry.

Tetramer staining of human T cells expressing TCR18168 showed specific binding to the HLA-A*0201 tetramers containing the NY-ESO-1 peptide SLLMWITQC (SEQ ID NO: 1) and minimal binding to the HLA-A*0201 tetramers containing the negative control MART-1 peptide (FIG. 3A). In contrast, T cells expressing the TCR DMF4 only bound HLA-A*0201 tetramers containing the MART-1 peptide (FIG. 3A).

Following 16 hours of co-culture with HLA-A2-expressing K562 cells pulsed with the NY-ESO-1 peptide SLLMWITQC (SEQ ID NO: 1), T cells expressing TCR18168 exhibited a dose-dependent upregulation of CD25 surface expression (FIG. 3B) and IFNγ secretion (FIG. 3D). When co-cultured with HLA-B7-expressing K562 cells loaded with the NY-ESO-1 peptide or HLA-expressing K562 cells in the absence of the NY-ESO-1 peptide, TCR18168-expressing T cells did not show up-regulation of CD25 (FIG. 3B) or IFNγ (FIG. 3D). In comparison, as a specificity control, T cells expressing the TCR DMF4 showed increased CD25 expression (FIG. 3C) and IFNγ secretion (FIG. 3E) only after being co-cultured with HLA-A2-expressing K562 cells pulsed with the cognate MART-1 peptide.

6.2.2 Characterization of Primary Human Cells Expressing TCR18168 Co-cultured with Peptide-Pulsed T2 Target Cells Next, primary human T cells isolated from a healthy donor (different from the donor cells utilized in Section 6.2.1) and previously expanded with ImmunoCult™ Human CD3/28 T cell Activator (Stemcell Technologies) were transfected to express the human TCR18168 or DMF4 using electroporation as described above and analyzed in a similar co-culture study using T2 cells as target cells, which express HLA-A*0201 endogenously. Briefly, T2 cells (ATCC, Cat. No.: 174xCEM.T2) were labeled with CellTrace™ violet dye (Thermo Fisher, Cat. No.: C34557) and pulsed with 1 μM of the NY-ESO-1 peptide SLLMWITQC (SEQ ID NO: 1) (Genscript, custom order), 1 μM of the MART-1 peptide ELAGIGILTV (SEQ ID NO: 22) (Genscript, custom order), or DMSO alone (vehicle control) (Fisher Scientific, Cat. No.: BP231-100). TCR18168-expressing or DMF4-expressing T cells were co-cultured with T2 target cells for 16 hours and then analyzed for CD25 surface expression by flow cytometry using an anti-human CD25 antibody (eBioscience. Cat, No.: 17-0259-42). As a positive control, TCR8168-expressing or DMF4-expressing T cells were also activated using ImmunoCult™ Human CD3/28 T cell Activator (Stemcell Technologies) for 16 hours in the absence of target cells and then examined for surface CD25 expression using flow cytometry. T2 target cell killing was measured by analyzing loss of live T2 cells (i.e., loss of CellTrace™ violet dye positive cells) using Zombie NIR Live/Dead dye (Biolegend, Cat. No.: 423105).

Human T cells expressing TCR18168 only exhibited upregulation of CD25 surface expression after being co-cultured with T2 cells pulsed with the cognate NY-ESO-1 peptide or after stimulation by anti-CD3/CD28 antibodies (FIG. 4A). In addition, TCR18168-expressing T cells only killed T2 cells pulsed with the cognate NY-ESO-1 peptide but not T2 cells pulsed with DMSO vehicle or the MART-1 peptide, as measured by loss of CellTrace™ violet dye positive cells (FIG. 4C). In comparison, T cells expressing the TCR DMF4 were only activated by T2 cells loaded with the cognate MART-1 peptide (FIG. 4B) and only killed T2 cells loaded with the cognate MART-1 peptide (FIG. 4C).

6.2.3 Characterization of TCR18168 Using an NFAT-Luciferase Reporter T Cell Line TCRβ-negative Jurkat cells (ATCC, Cat, No.: TIB-153) were lentivirally transduced with (i) a luciferase reporter under the control of an NFAT response element and a short CMV minimal promoter, and (ii) TCR18168. B16-F10 cells (ATCC Cat. No.: CRL-6475) were lentivirally transduced to express AAD, which comprises the α1 and α2 domains of the HLA-A*0201 molecule, the α3 domain of the mouse H-2D$^b$ molecule, and human β$_2$ microglobulin, and pulsed with 1 nM to 1 of the NY-ESO-1 peptide SLLMWITQC (SEQ ID NO: 1) (Genscript, custom order), 1 of the MART-1 peptide ELAGIGILTV (SEQ NO: 22) (Genscript, custom order), or DMSO (vehicle control) (Fisher Scientific, Cat. No.: BP231-100). The TCR-expressing Jurkat reporter cells were co-cultured with peptide-pulsed AAD-expressing B16 cells for 16 hours. As a positive control for maximum NFAT reporter activity, the TCR-expressing Jurkat reporter cells were also stimulated with Cell Stimulation Cocktail containing PMA and Ionomycin (eBioscience, Cat. No.: 00-4970) for 16 hours. Luciferase reporter activity was measured using the Nano-Glo Luciferase Assay Kit (Promega, Cat. No.: N1120) and the EnVision Multimode Plate Reader (Perkin Elmer).

The Jurkat reporter cells expressing TCR18168 showed minimal luciferase reporter activity in the presence of AAD-expressing 131.6 cells pulsed with DMSO or with the MART-1 peptide (FIG. 5A). However, when co-cultured with AAD-expressing B16 cells pulsed with the cognate NY-ESO-1 peptide, the Jurkat reporter cells expressing TCR18168 exhibited a peptide-specific (FIG. 5A) and dose-dependent (FIG. 5B) activation response.

6.3 Example 3: Production and Characterization of TCR18168 Mutants

In this example, mutants of TCR18168 were generated and characterized for binding and T cell activation. These mutants were tested either as chimeric TCRs, which comprise human variable regions fused to murine constant regions, or as fully human TCRs.

6.3.1 TCR Screening Using TCR β Chain Guided Selection and/or NNK CDR3 Grafting Briefly, in a guided selection screening, the β chain of TCR18168c was used as a guide to screen against either a naïve cord blood-derived α chain library or two α chain libraries comprising the α chain of TCR18168c with randomized mutations in CDR3α (α-NNK1 and α-NNK2 libraries described below). Expression constructs for TCR18168c β chain and the α chain libraries were retrovirally transduced into AK-D10R3 cells to assess pMHC tetramer binding and AK-D10R3 T cell activation in the presence of T2/pMHC+ cells.

The CDR3 regions of TCR18168c α and β chains were randomized by NNK. CDR3 grafting. NNK triplet codons are composed of N: A/C/G/T and K: G/T nucleotides and allow covering all 20 canonical amino acids with 32 codons.

Two sets of single-strand NNK oligomers were used for α chain CDR3 and β chain CDR3 grafting. Oligomer libraries α-NNK1 and α-NNK2 (Microsynth, custom order) were used to randomize residues RELYS (SEQ ID NO: 266) and GAGSY (SEQ ID NO: 267), respectively, of TCR18168c α chain CDR3. Oligomer libraries β-NNK1 and β-NNK2 (Microsynth, custom order) were used to randomize residues GAGVT (SEQ ID NO: 268) and AGVTD (SEQ ID NO: 269) of TCR18168c β chain CDR3, respectively. Table 9 provides the sequences of the CDR3 NNK nucleotide oligomers used to randomize CDR3α and CDR3β sequences. The single strand NNK CDR3 library oligomers were subjected to a reverse priming PCR amplification to synthesize the reverse strand and generate double strand oligomers.

TABLE 9

CDR3 NNK library information.

| SEQ ID NO: | Library | Amino acid Sequence |
|---|---|---|
| 270 | α-NNK1 | 5'-TCG TCG GCA GCG TCA GAT GCT CTT CGT GTG CTG TGN NKN NKN NKN NKN NKG GGG CTG GGA GTT ACC AAC TCA CTT TCG GAT GAA GAG CCT CCG AGC CCA CGA GAC-3', wherein: N is A, C, G, or T; and K is G or T. |
| 271 | α-NNK2 | 5'-TCG TCG GCA GCG TCA GAT GCT CTT CGT GTG CTG TGA GAG AAT TAT ACT CTN NKN NKN NKN NKN NKC AAC TCA CTT TCG GAT GAA GAG CCT CCG AGC CCA CGA GAC-3', wherein: N is A, C, G, or T; and K is G or T. |
| 272 | β-NNK1 | 5'-TCG TCG GCA GCG TCA GAT GCT CTT CGT GTA GCG TTG GGN NKN NKN NKN NKN NKG ATA CGC AGT ATT TTG GGT GAA GAG CCT CCG AGC CCA CGA GAC-3', wherein: N is A, C, G, or T; and K is G or T. |

TABLE 9-continued

CDR3 NNK library information.

| SEQ ID NO: | Library | Amino acid Sequence |
|---|---|---|
| 273 | β-NNK2 | 5'-TCG TCG GCA GCG TCA GAT GCT CTT CGT GTA GCG TTG GGG GCN NKN NKN NKN NKN NKA CGC AGT ATT TTG GGT GAA GAG CCT CCG AGC CCA CGA GAC-3', wherein: N is A, C, G, or T; and K is G or T. |

Retroviral expression vectors containing the full length α and β chain sequences, with the exception of the α and β CDR3 regions being substituted by stuffier sequences, were digested to excise the stiffer sequences and subsequently gel purified. Double strand CDR3α and CDR3β library oligomers were then digested and ligated between framework 3 and framework 4 of the purified, linearized vectors to yield the full length TCR α and β chain sequences.

Reconstituted CDR3 randomized TCR18168c expression constructs were retroviral transduced into AK-D10R3 cells to assess pMHC tetramer binding and cell activation in the presence of T2/pMHC+ cells.

A total of 21 TCR18168c mutants were identified using guided selection and/or NNK mutagenesis: TCR0001, TCR0009, TCR0011, TCR0013, TCR0015, TCR0017, TCR0019, TCR0021, TCR0023, TCR0027, TCR0029, TCR0031, TCR0033, TCR0035, TCR0037, TCR0049, TCR0059, TCR0061, TCR0065, TCR0067, and TCR0069. Table 4 provides sequence information of the variable regions of these chimeric TCRs and their human counterparts.

6.32 Binding of NY-ESO-1 pMHC Tetramers to TCR-Expressing AK-D10R3 Cells

AK-D10R3 cells expressing NY-ESO-1-targeting chimeric TCRs TCR18168c, TCR0001, TCR0009, TCR0011, TCR0013, TCR0015, TCR0017, TCR0019, TCR0021, TCR0023, TCR0027, TCR0029, TCR0031 TCR0033, TCR0035, TCR0037, TCR0049, TCR0059, TCR0061, TCR0065, TCR0067, or TCR0069 were expanded for three days at 37° C. in a 10% $CO_2$ atmosphere using SF-IMDM media (BioConcept Cat. No.: 1-28S07-1). AK-D10R3 cells expressing a reference TCR that binds to SSX-2 or TCR-negative AK-D10R3 cells were used as controls. $1.0\times10^5$ cells were plated in each well of a 96-well assay plate, centrifuged at 300×g and 4° C. for 5 min, washed twice using 200 µL assay buffer (1x PBS supplemented with 2% KS), and resuspended in assay buffer at a concentration of $1.0\times10^5$ cells/100 µL. For staining, 20 µL of stock solutions of anti-mouse TCR β-chain-APC antibody (BD, Cat. No.: 553174, clone H57-597) (1:500) and PE-labeled HLA-A*0201 tetramers loaded with the wild type NY-ESO-1 peptide SLLMWITQC (SEQ ID NO: 1, produced in-house) (1:250) were added in each well. Following 30 min incubation at room temperature, cells were washed twice as described above and analyzed by flow cytometry using a BD FACSCanto II cytometer. Cells were gated for TCR expression (APC+) versus pMHC-binding (PE+). Using the FlowJo software dot plots were generated and the percentage C/O of TCR+pMHC+ cells was determined.

As shown in FIG. 6, TCR18168c and each of the TCR18168c mutants tested bound to HLA-A*0201 tetramers loaded with the wild type NY-ESO-1 peptide SLLMWITQC (SEQ ID NO: 1).

6.3.3 Activation of TCR-Expressing AK-D10R3 Cells by NY-ESO-1+ T2 Cells

AK-D10R3 cells expressing an IL-2-$(NFAT)_3$-EGFP reporter construct and NY-ESO-1-targeting chimeric TCRs TCR18168c, TCR0001, TCR0009, TCR0011, TCR0013, TCR0015, TCR0017, TCR0019, TCR0021, TCR0023, TCR0027, TCR0029, TCR0031, TCR0033, TCR0035, TCR0037, TCR0049, TCR0059, TCR0061, TCR0065, TCR0067, or TCR0069 were cultivated in SF-IMDM media as described above. In parallel, T2 target cells (human lymphoblast cells as described by Salter R D, EMBO J, 1986 May 5 (5):943-9 PMID 3522223) were pulsed with NY-ESO-1 antigen peptides. T2 cells were centrifuged at 300×g and 4° C. for 5 min, washed using ix PBS and resuspended in ix PBS supplemented with 50 µg/mL of NY-ESO-1 wild type antigen SLLMWITQC (SEQ ID NO: 1, produced in house) at a final concentration of $1.0\times10^6$ cells/250 µL. T2 cells pulsed with a SXX-2 peptide KASEKIFYV (SEQ ID NO: 274) (Peptides & Elephants, lot EP07005/3009P04) or no peptide served as controls. For peptide titrations, T2 cells were pulsed with a dose-range of the NY-ESO-1 antigen using 24, 2.4, 0.24, $2.4\times10^{-2}$, $2.4\times10^{-3}$, $2.4\times10^{-4}$, $2.4\times10^{-5}$, $2.4\times10^{-6}$, $2.4\times10^{-7}$, $2.4\times10^{-8}$, $2.4\times10^{-9}$, $2.4\times10^{-10}$, $2.4\times10^{-11}$, $2.4\times10^{-12}$, or $2.4\times10^{13}$ µg peptide per $1.0\times10^6$ cells. Cells were incubated for 3 hours at 37° C., washed twice using 1×PBS as described above, and resuspended at a final concentration of $5.0\times10^6$ cells/20 mL using SF-IMDM media.

200 µL ($5.0\times10^4$ cells) of the TCR-expressing AK-D10R3 cells were added in each well of a 96-well assay plate, centrifuged at 300×g for 5 min, and the supernatant discarded. Next, 200 µL ($5.0\times10^4$ cells) of the T2 target cell suspension were added in each well. AK-D10R3 cells were carefully resuspended and co-incubated with the 12 cells for 18 hours at 37° C. in a 10% $CO_2$ atmosphere. For co-staining, cell suspensions were sedimented at 300×g for 10 min, washed twice using assay buffer, resuspended using 20 µL/well of staining solution (1×PBS supplemented with 1:500 APC-labeled anti-mouse TCR β-chain antibody) and incubated for 30 min at room temperature. Subsequently, cells were washed twice using assay buffer as described above, resuspended in 80 µL assay buffer and analyzed by flow cytometry using a BD FACSCanto II cytometer. Cells were gated for TCR expression (APC+) versus T cell activation (EGFP+). Using the FlowJo software dot plots were generated and the percentage (%) of APC+ EGFP+ cells was determined. Each assay was performed in triplicate.

As shown in FIG. 7, TCR18168c and each of the TCR18168c mutants tested were able to mediate the activation of the IL-2-NFAT reporter construct in AK-D10R3 cells in the presence of T2 cells pulsed with the wild type NY-ESO-1 peptide SLLMWITQC (SEQ ID NO: 1) (FIG. 7).

6.3.4 Binding of NY-ESO-1 pMHC Tetramers to TCR-Expressing Jurkat Cells

The NY-ESO-1-targeting chimeric TCRs TCR18168c, TCR0001, TCR0009, TCR0011, TCR0013, TCR0015, TCR0017, TCR0019, TCR0021, TCR0023, TCR0027, TCR0031, TCR0037, TCR0049, TCR0059, TCR0061, TCR0065, TCR0067, or TCR0069 were converted into fully human TCRs and expressed in human Jurkat cells. The names of the fully-human TCRs corresponding to each chimeric TCR are listed in Table 4. In the expression constructs, the et and β chains of each TCR were linked via a P2A-furin site.

TCR-expressing Jurkat cells were expanded for three days at 37° C. in a 10% $CO_2$ atmosphere using RPMI media supplemented with L-Glutamine (BioConcept Cat. No.: 1-41F03-I, lot LA03485P). TCR-negative Jurkat cells were used as controls. $1.0 \times 10^5$ cells were plated in each well of a 96-well assay plate, centrifuged at 300×g and 4° C. for 5 min, washed twice using 200 μL assay buffer (1×PBS supplemented with 2% FCS), and resuspended in assay buffer at a concentration of $1.0 \times 10^5$ cells/1.00 pt. Cells were stained independently for TCR expression and pMHC binding. For staining, 20 μL of stock solutions of anti-human TCR-APC antibody (eBioscience, Cat. No.: 17-9985-42, clone IP26) (1:200) or PE-labeled. HLA-A*0201 tetramers loaded with the wild type NY-ESO-1 peptide SLLMWITQC (SEQ ID NO: 1) (MBL, Cat. No.: T01064, lot T1606011) (1:250) were added in each well. Following a 30-minute incubation at room temperature, cells were washed twice as described above and analyzed by flow cytometry using a BD FACSCanto II cytometer. In a control group, cells were stained with PE-labeled HLA-A*0201 tetramers loaded with a control SXX-2 antigen peptide KASEKIFYV (SEQ ID NO: 274) (MBL, Cat.No, TSM079-1, lot 001) (1:250). Cells were gated for TCR expression (APC+) versus FSC or pMFIC-binding (PE+) versus FSC. Using the FlowJo software dot plots were generated and the percentage (%) of TCR+ or pMHC+ cells was determined.

As shown in FIGS. 8A and 8B, TCR18168 and each of the TCR18168 mutants tested bound to HLA-A*0201 tetramers loaded with the wild type NY-ESO-1 peptide SLLMWITQC (SEQ ID NO: 1) when expressed on the surface of Jurkat cells as fully human TCRs.

6.3.5 Characterization of Primary Human T Cells Expressing TCR18168 Mutants Co-Cultured with Peptide-Pulsed T2 Target Cells mRNA molecules encoding fusion constructs of the α and β chains of TCR0002, TCR0014, TCR0018, TCR0022, TCR0028, TCR0038, TCR0070, or a reference TCR specific for HLA-A*0201 tetramer-hound NY-ESO-1 peptide SLLMWITQC (SEQ ID NO: 1), were generated via in vitro transcription using the mMESSAGE mMACHINE T7 Ultra kit (Ambion, Cat. No.: AMB13455). Each mRNA was expressed from a vector encoding, in 5' to 3' order, the TCR β chain, a Furin cleavage site, a P2A cleavage site, and the TCR α chain. Human Primary T Cells were then transfected with each of these mRNAs by electroporation using a MaxCyte GT electroporator. Transfection efficiency was evaluated 16 hours post-electroporation using an APC SLLMWITQC (SEQ ID NO: 1) Tetramer HLA-A*0201 (MBL Cat. No, T10605). Using the 96-well round bottom plate, transfected primary T cells labelled with Cell Trace Violet (CTV) were co-cultured, in a 1:1 effector-to-target ratio, with T2 target cells labelled with Carhoxyfluorescein succinimidyl ester (CFSE) that had been pulsed with varying concentrations of the SLIAIWITQC (SEQ ID NO: 1) peptide from a high dose of 1000 nM to a low concentration of 12.8 pM by 5× serial dilutions. After 16 hours of co-culturing under 37° C. and 5% $CO_2$, sample wells were analyzed with a BD LSRFortessa™ cell analyzer to assess biomarkers of cell activation (CD25, FIGS. 9A-9H), degranulation (CD107a, FIGS. 10A-10H) and viable cells (FIGS. 11A-11H). Analysis was carried out using FlowJo®, Microsoft® Excel®, and GraphPad Prism.

As shown in FIGS. 9A-9H, all of the NY-ESO-1-specific TCRs tested. (TCR0002, TCR0014, TCR0018, TCR0022, TCR0028, TCR0038, and TCR0070, and the reference TCR) induced cell activation, as shown by cell surface CD25 expression. The percentage of CD25 expression increased when higher levels of the NY-ESO-1 peptide were used for pulsing. Similarly, these TCRs all demonstrated increased cytolytic potential and cell degranulation (shown in FIGS. 10A-10H by CD107a expression on the cell surface) relative to the negative control. Negative controls for the experiments depicted in FIGS. 9A-9H and 10A-10H were human primary T cells transfected with a Mart-1 peptide-targeting TCR, DMF4, and co-cultured with T2 cells pulsed with 1 μM of NY-ESO-1. In addition, primary T cells expressing each one of the tested NY-ESO-1-specific TCRs exhibited increased cytotoxicity relative to the negative control (shown in FIGS. 11A-I III by the decreased numbers of viable target T2 cells). 1 μM of Mart-1 peptide was used as a negative control to pulse T2 cells.

6.36 Characterization of Primary Human T Cells Expressing TCR18168 Mutants Co-Cultured with Peptide-Expressing Tumor Cell Lines mRNA molecules as described in Section 6.3.5 were prepared and transfected into primary T cells by electroporation, using the same methods as in Section 6.3.5. The TCR-expressing T cells were then co-cultured, in various effector-to-target ratios, with chronic myeloid leukemia cell line K562, which expresses endogenous NY-ESO-1. Specifically, K562 cells were labelled with CFSE and transduced with human HLA-A*0201 and NY-ESO-1 (to overexpress the protein). Fixed numbers of target K562 cells were plated in a 96-well round-bottom tissue culture plate and co-cultured with varying quantities of transfected T cells in triplicate. The co-culture was incubated at 37° C. 5% CO2 for 16 hours and measured for bio-markers of activation (CD25), degranulation (CD107a) and target cell viability as described in section 6.3.5.

As shown in FIGS. 12A-12H, all the NY-ESO-1-specific TCRs tested (TCR0002 TCR0014, TCR0018, TCR0022, TCR0028, TCR0038, and TCR0070, and the reference TCR) induced cell activation, as shown by cell surface CD25 expression, under various effector-to-target ratios. Similarly, these TCRs all demonstrated increased cytolytic potential and cell degranulation (shown in FIGS. 13A-13H by CD107a expression on the cell surface). For detecting both CD25 and CD107a expression, human primary T cells transfected with DMF4 were used as negative controls. In addition, primary T cells expressing any one of the tested NY-ESO-1-specific TCRs exhibited increased cytotoxicity relative to the negative control at effector:target ratios of 5:1 and 10:1 (shown in in FIGS. 14A-14H by the decreased numbers of viable target K562 cells). For the cytotoxicity assays, T cells transfected with DMF4 were co-cultured with the target cells and tested as negative controls.

In another experiment, T cells transfected with mRNAs encoding the reference TCR described above, TCR0002, TCR001.4, TCR0018, TCR0022, TCR0028, TCR0038, TCR0070, or negative control TCR DMF4 were each co-cultured, in a 5:1 effector-target ratio, with a mixture of equal numbers of two groups of K562 target cells. The first group of K562 cells (Group 1) was transduced with human HLA-A*0201 and NY-ESO-1 protein, in order to display the cognate HLA-peptide complex recognized by the test TCRs, and was labeled with 4 µM CFSE. The second group of K562 cells (Group 2) was transduced with human HLA-B*0702 and labeled with 0.20 µM CFSE. In parallel, an identical mixture of K562 cells was prepared but not co-cultured with T cells. In each case, the numbers of each set of remaining viable K562 target cells were determined by flow cytometry, and a "percent killing" value was determined for each TCR tested by determining the ratio of remaining viable Group 1 cells to remaining viable Group 2 cells in the T cell co-culture mixture; determining the ratio of remaining viable Group 1 cells to remaining viable Group 2 cells in the non-T cell-co-cultured mixture; calculating the ratio of these two ratios; subtracting from 1; and multiplying by 100%. A positive value indicated preferential killing of Group 1 cells compared to Group 2 cells. As shown in FIG. 15, all TCRs tested, aside from the negative control, resulted in substantial preferential killing of K562 cells transduced with human HLA-A*0201 and NY-ESO-1 protein. The negative control sample exhibited no detectable preferential killing.

In another experiment, target tumor cells were co-cultured with TCR-expressing primary T cells without overexpression of either NY-ESO-1 or HLA-A*0201. Specifically, melanoma cells SLM2-mel expressing endogenous NY-ESO-1 and HLA-A*0201 were used as target cells and labeled with UV. Fixed number of target cells were co-cultured in a 96-round-bottom tissue culture plate with varying numbers of transfected primary T cells expressing the TCRs in triplicates. The co-culture plate was incubated at 37° C., 5% $CO_2$ for 16 hours and the number of viable cells was assessed using the same flow cytometry as described in this and previous sections. All of the NY-ESO-1-specific TCR2 tested increased surface CD25 (FIGS. 16A-16F) and CD107a (FIGS. 17A-17F) percentage expression relative to the negative control. As shown in FIGS. 18A-18F, all of the NY-ESO-1-specific TCRs tested exhibited increase cytotoxicity relative to the negative control. As negative controls for FIGS. 16A-16F, 17A-17F, and 18A-18F, T cells transfected with PBS were co-cultured with target cells at corresponding effector-to-target ratios.

6.3.7 Characterization of NY-ESO-1 TCR Specificity Profiles

This Example illustrates the use of a screening method to assess target specificity of several NY-ESO-1-specific TCRs described herein.

Briefly, a group of short polypeptides with high similarity to the NY-ESO-1 peptide sequence of SLLMWITQC (SEQ ID NO: 1) was prepared. An anchor-optimized variant with a valine at the C-terminus (SLLMWITQV, SEQ ID NO: 2) was used as the parent sequence for mutagenesis. Each position, except for the anchor positions P2 (L) and P9 (V), of SEQ ID NO: 2 was individually substituted with all 19 other possible naturally occurring amino acids, resulting in a total set of 133 altered peptides (SEQ ID NOs: 275-407 as shown in Table 10). The specificity profile of each TCR was evaluated by measuring activation of TCR-expressing effector cells after co-culturing with T2 target cells loaded with one of the 133 peptides or the parental SEQ ID NO: 2.

The effector cells (NY-ESO AK-D10R3 cells) were generated from mouse TCR negative thymoma cells, as described in Section 6.1, and stably transduced with chimeric TCRs TCR0001, TCR0017, TCR0021, TCR0037, or a reference TCR specific for NY-ESO-1 peptide SLLMWITQC (SEQ ID NO: 1); a chimeric mouse/human CD8; and an EGFP-reporter construct linked to a minimal IL-2 promoter comprising three NFAT-binding sites (3xNFAT). Cells were cultured in SF-IMDM (Amimed, UK) supplemented with 3% Fetal Calf Serum (FCS; Amimed), 1% Penicillin/Streptomycin (SIGMA-ALDRICH, St. Louis, Mo.), and 50 µM β-mercaptoethanol (Gibco, Fisher Scientific, UK) at 37° C. and 10% CO2. Antigen presenting Tap-deficient T2 (174 x CEM.T2) cells from ATCC were maintained in RPMI 1640 (SIGMA-ALDRICH) supplemented with 10% FCS and 1% penicillin/streptomycin at 37° C. and 5% CO2.

Peptides (purchased from Peptides and Elephants, Germany, or produced in-house) were suspended in DMSO and the concentration was adjusted to 4 mg/ml. Briefly, T2 cells were washed in PBS (Gibco) and incubated with 80 µg peptide per $1\times10^6$ cells for 2 hours at 37° C. and 5% CO2. After incubation, T2 cells were washed in PBS/2% FCS and then resuspended in SF-IMDM media. Effector cells expressing the TCR of interest were co-cultured with peptide-pulsed T2 cells in a 2:1 ratio (total 150,000 cells per well of a 96-well plate) for 16 hours in SF-IMDM media at 37° C. and 10% CO2. Cells were washed twice in 2% FBS/PBS and stained with anti-mouse TCR-β chain clone H57-597 (BD Pharmingen, San Jose; CA, 1:500) for 30 min at room temperature. Cells were washed twice, followed by FACS-analysis using a BD FACS Canto II.

Data analysis was performed using FlowJo V10 Software. Activation was calculated as the proportion of EGFP expressing cells in the NY-ESO AK-D10R3 population (AK-D10R3 cells were identified based on TCR expression). Background activation (no peptide loaded) was subtracted from all peptide-loaded samples (altered and native sequences). The mean and standard error of the mean (SEM) of background-subtracted values were calculated from all replicates (at least 3 replicates for each TCR) and values were normalized to those of the native sequence peptide, with normalized values cropped to a minimum of 0.0 (heat maps only) and to a maximum of 1.0 (both heat maps and bar charts) for display purposes. Normalized values are shown in heat map format in FIGS. 19A (reference TCR), 19B (TCR0001), 19C (TCR0017), 19D (TCR 0021), and 19E (TCR0037) and in bar chart format in FIGS. 20A (reference TCR), 20B (TCR0001), 20C (TCR0017), 20D (TCR 0021), and 20E (TCR0037).

The heat maps and bar charts reveal the distinct specificity profiles of each TCR tested. In general, a larger percentage of white (low normalized values) indicates lower tolerance for mutations in the NY-ESO-1 cognate peptide, indicating a higher degree of specificity for the NY-ESO-1 cognate peptide in the context of the above-described assay. As shown in FIGS. 19A-19E, TCR0001, TCR0017, TCR0021, and TCR0037 all exhibited a substantially higher degree of specificity for the NY-ESO-1 cognate peptide than did the reference TCR for the mutant peptides evaluated. Likewise, the bar charts in FIGS. 20A-20E reveal a larger percentage of low normalized activation values for the mutant peptides for each of TCR0001, TCR0017, TCR0021, and TCR0037 in comparison to the reference TCR.

TABLE 10

Altered peptides used to generate specificity profiles of chimeric TCRs.

| SEQ ID NO | Target Peptide Sequence |
|---|---|
| 275 | ALLMWITQV |
| 276 | CLLMWITQV |
| 277 | DLLMWITQV |
| 278 | ELLMWITQV |
| 279 | FLLMWITQV |
| 280 | GLLMWITQV |
| 281 | HLLMWITQV |
| 282 | ILLMWITQV |
| 283 | KLLMQITQV |
| 284 | LLLMWITQV |
| 285 | MLLMWITQV |
| 286 | NLLMWITQV |
| 287 | PLLMWITQV |
| 288 | QLLMWITQV |
| 289 | RLLMWITQV |
| 290 | TLLMWITQV |
| 291 | VLLMWITQV |
| 292 | WLLMQITQV |
| 293 | YLLMWITQV |
| 294 | SLAMWITQV |
| 295 | SLCMWITQV |
| 296 | SLDMWITQV |
| 297 | SLEMWITQV |
| 298 | SLFMWITQV |
| 299 | SLGMWITQV |
| 300 | SLHMWITQV |
| 301 | SLIMWITQV |
| 302 | SLKMWITQV |
| 303 | SLMMWITQV |
| 304 | SLNMWITQV |
| 305 | SLPMWITQV |
| 306 | SLQMWITQV |
| 307 | SLRMWITQV |
| 308 | SLSMWITQV |
| 309 | SLTMWITQV |
| 310 | SLVMWITQV |
| 311 | SLWMWITQV |
| 312 | SLYMWITQV |
| 313 | SLLAWITQV |
| 314 | SLLCWITQV |
| 315 | SLLDWITQV |
| 316 | SLLEWITQV |
| 317 | SLLFWITQV |
| 318 | SLLGWITQV |
| 319 | SLLHWITQV |
| 320 | SLLIWITQV |
| 321 | SLLKWITQV |
| 322 | SLLLWITQV |
| 323 | SLLNWITQV |
| 324 | SLLPWITQV |
| 325 | SLLQWITQV |
| 326 | SLLRWITQV |
| 327 | SLLSWITQV |
| 328 | SLLTWITQV |
| 329 | SLLVWITQV |
| 330 | SLLWWITQV |
| 331 | SLLYWITQV |
| 332 | SLLMAITQV |
| 333 | SLLMCITQV |
| 334 | SLLMDITQV |
| 335 | SLLMEITQV |
| 336 | SLLMFITQV |
| 337 | SLLMGITQV |
| 338 | SLLMHITQV |
| 339 | SLLMIITQV |
| 340 | SLLMKITQV |
| 341 | SLLMLITQV |
| 342 | SLLMMITQV |
| 343 | SLLMNITQV |
| 344 | SLLMPITQV |
| 345 | SLLMQITQV |
| 346 | SLLMRITQV |
| 347 | SLLMSITQV |

TABLE 10-continued

Altered peptides used to generate specificity profiles of chimeric TCRs.

| SEQ ID NO | Target Peptide Sequence |
|---|---|
| 348 | SLLMTITQV |
| 349 | SLLMVITQV |
| 350 | SLLMYITQV |
| 351 | SLLMWATQV |
| 352 | SLLMWCTQV |
| 353 | SLLMWDTQV |
| 354 | SLLMWETQV |
| 355 | SLLMWFTQV |
| 356 | SLLMWGTQV |
| 357 | SLLMWHTQV |
| 358 | SLLMWKTQV |
| 359 | SLLMWLTQV |
| 360 | SLLMWMTQV |
| 361 | SLLMWNTQV |
| 362 | SLLMWPTQV |
| 363 | SLLMWQTQV |
| 364 | SLLMWRTQV |
| 365 | SLLMWSTQV |
| 366 | SLLMWTTQV |
| 367 | SLLMWVTQV |
| 368 | SLLMWWTQV |
| 369 | SLLMWYTQV |
| 370 | SLLMWIAQV |
| 371 | SLLMWICQV |
| 372 | SLLMWIDQV |
| 373 | SLLMWIEQV |
| 374 | SLLMWIFQV |
| 375 | SLLMWIGQV |
| 376 | SLLMWIHQV |
| 377 | SLLMWIIQV |
| 378 | SLLMWIKQV |
| 379 | SLLMWILQV |
| 380 | SLLMWIMQV |
| 381 | SLLMWINQV |
| 382 | SLLMWIPQV |
| 383 | SLLMWIQQV |
| 384 | SLLMWIRQV |

TABLE 10-continued

Altered peptides used to generate specificity profiles of chimeric TCRs.

| SEQ ID NO | Target Peptide Sequence |
|---|---|
| 385 | SLLMWISQV |
| 386 | SLLMWIVQV |
| 387 | SLLMWIWQV |
| 388 | SLLMWIYQV |
| 389 | SLLMWITAV |
| 390 | SLLMWITCV |
| 391 | SLLMWITDV |
| 392 | SLLMWITEV |
| 393 | SLLMWITFV |
| 394 | SLLMWITGV |
| 395 | SLLMWITHV |
| 396 | SLLMWITIV |
| 397 | SLLMWITKV |
| 398 | SLLMWITLV |
| 399 | SLLMWITMV |
| 400 | SLLMWITNV |
| 401 | SLLMWITPV |
| 402 | SLLMWITRV |
| 403 | SLLMWITSV |
| 404 | SLLMWITTV |
| 405 | SLLMWITVV |
| 406 | SLLMWITWV |
| 407 | SLLMWITYV |
| 2 | SLLMWITQV (control) |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g, publication or patent or patent application) was specifically and individually indicated to be incorporated by reference in its entirety for all purposes.

Other embodiments are within the following claims.

What is claimed is:

1. An isolated TCR comprising an α chain variable region (Vα) comprising complementarity determining regions CDR1α, CDR2α, and CDR3α, and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 5, 6, 7, 8, 9, and 10; 5, 6, 39, 8, 9, and 10; 5, 6, 40, 8, 9, and 10; 5, 6, 41, 8, 9, and 10; 5, 6, 42, 8, 9, and 10; 5, 6, 43, 8, 9, and 10; 5, 6, 44, 8, 9, and 10; 5, 6, 45, 8, 9, and 10; 5, 6, 46, 8, 9, and 10; 5, 6, 47, 8, 9, and 10; 5, 6, 48, 8, 9, and 10; 5, 6, 49, 8, 9, and 10; 5, 6, 50, 8, 9, and 10; 5, 6, 51, 8, 9, and 10; 5, 6, 52, 8, 9, and 10; 5, 6, 53, 8, 9, and 10; 5, 6, 54, 8, 9, and 10; 5, 6, 55, 8, 9, and 10; 5, 6, 56, 8, 9, and 10; 5, 6, 57, 8, 9, and 10; 5, 6, 58, 8, 9, and 10; 5, 6, 59, 8, 9, and 10; or 5, 6, 60, 8, 9, and 10, respectively.

2. The isolated TCR of claim 1, wherein:
   (a) the TCR is a human TCR;
   (b) the TCR is a full-length TCR, a soluble TCR, or a single-chain TCR; and/or
   (c) the TCR is conjugated to an effector moiety, wherein the effector moiety is a cytotoxic agent, cytostatic agent, toxin, radionuclide, detectable label or binding moiety, an antibody or an antibody Fc region.

3. An engineered cell presenting the TCR of claim 1 on the cell surface, wherein the cell expresses the TCR and the cell is a human lymphocyte, selected from the group consisting of a T cell, a CD8+ T cell, a CD4+ T cell, a natural killer T (NKT) cell, an invariant natural killer T (iNKT) cell, a mucosal-associated invariant T (MAiT) cell, and a natural killer (NK) cell.

4. A pharmaceutical composition comprising the isolated TCR of claim 1, and a pharmaceutically acceptable carrier.

5. The isolated TCR of claim 1, wherein
   (a) the Vα and Vβ comprise the amino acid sequences set forth in SEQ ID NOs: 3 and 4, 66 and 4, 67 and 4, 68 and 4, 69 and 4, 70 and 4, 71 and 4, 72 and 4, 73 and 4, 74 and 4, 75 and 4, 76 and 4, 77 and 4, 78 and 4, 79 and 4, 80 and 4, 81 and 4, 82 and 4, 83 and 4, 84 and 4, 85 and 4, or 86 and 4, respectively;
   (b) the TCR comprises an α chain comprising an α chain constant region comprising the amino acid sequence set forth in SEQ ID NO: 15, 26, or 92; and/or
   (c) the TCR comprises a β chain comprising a β chain constant region comprising the amino acid sequence set forth in SEQ ID NO: 16 or 17.

6. An isolated TCR comprising an α chain and a β chain, wherein the α chain comprises an amino acid sequence selected from the group consisting of SEQ ID NOs: 13, 93-96, 105-118, 120-123, 125-128, and 408-415, and the β chain comprises an amino acid sequence selected from the group consisting of SEQ ID NOs: 14, 25, and 97-104.

7. The isolated TCR of claim 6, wherein:
   (a) the α chain comprises an amino acid sequence selected from the group consisting of SEQ ID NOs: 13, 105, 110, 115, 120, 125, 408, and 412, and the β chain comprises an amino acid sequence selected from the group consisting of SEQ ID NOs: 14, 25, and 97-104;
   (b) the α chain and the β chain comprise the amino acid sequences set forth in SEQ ID NOs: 13 and 14; 13 and 25; 13 and 97; 13 and 98; 13 and 99; 13 and 100; 13 and 101; 13 and 102; 13 and 103; 13 and 104; 93 and 14; 93 and 25; 93 and 97; 93 and 98; 93 and 99; 93 and 100; 93 and 101; 93 and 102; 93 and 103; 93 and 104; 94 and 14; 94 and 25; 94 and 97; 94 and 98; 94 and 99; 94 and 100; 94 and 101; 94 and 102; 94 and 103; 94 and 104; 95 and 14; 95 and 25; 95 and 97; 95 and 98; 95 and 99; 95 and 100; 95 and 101; 95 and 102; 95 and 103; 95 and 104; 96 and 14; 96 and 25; 96 and 97; 96 and 98; 96 and 99; 96 and 100; 96 and 101; 96 and 102; 96 and 103; 96 and 104; 105 and 14; 105 and 25; 105 and 97; 105 and 98; 105 and 99; 105 and 100; 105 and 101; 105 and 102; 105 and 103; 105 and 104; 106 and 14; 106 and 25; 106 and 97; 106 and 98; 106 and 99; 106 and 100; 106 and 101; 106 and 102; 106 and 103; 106 and 104; 107 and 14; 107 and 25; 107 and 97; 107 and 98; 107 and 99; 107 and 100; 107 and 101; 107 and 102; 107 and 103; 107 and 104; 108 and 14; 108 and 25; 108 and 97; 108 and 98; 108 and 99; 108 and 100; 108 and 101; 108 and 102; 108 and 103; 108 and 104; 109 and 14; 109 and 25; 109 and 97; 109 and 98; 109 and 99; 109 and 100; 109 and 101; 109 and 102; 109 and 103; 109 and 104; 110 and 14; 110 and 25; 110 and 97; 110 and 98; 110 and 99; 110 and 100; 110 and 101; 110 and 102; 110 and 103; 110 and 104; 111 and 14; 111 and 25; 111 and 97; 111 and 98; 111 and 99; 111 and 100; 111 and 101; 111 and 102; 111 and 103; 111 and 104; 112 and 14; 112 and 25; 112 and 97; 112 and 98; 112 and 99; 112 and 100; 112 and 101; 112 and 102; 112 and 103; 112 and 104; 113 and 14; 113 and 25; 113 and 97; 113 and 98; 113 and 99; 113 and 100; 113 and 101; 113 and 102; 113 and 103; 113 and 104; 114 and 14; 114 and 25; 114 and 97; 114 and 98; 114 and 99; 114 and 100; 114 and 101; 114 and 102; 114 and 103; 114 and 104; 115 and 14; 115 and 25; 115 and 97; 115 and 98; 115 and 99; 115 and 100; 115 and 101; 115 and 102; 115 and 103; 115 and 104; 116 and 14; 116 and 25; 116 and 97; 116 and 98; 116 and 99; 116 and 100; 116 and 101; 116 and 102; 116 and 103; 116 and 104; 117 and 14; 117 and 25; 117 and 97; 117 and 98; 117 and 99; 117 and 100; 117 and 101; 117 and 102; 117 and 103; 117 and 104; 118 and 14; 118 and 25; 118 and 97; 118 and 98; 118 and 99; 118 and 100; 118 and 101; 118 and 102; 118 and 103; 118 and 104; 120 and 14; 120 and 25; 120 and 97; 120 and 98; 120 and 99; 120 and 100; 120 and 101; 120 and 102; 120 and 103; 120 and 104; 121 and 14; 121 and 25; 121 and 97; 121 and 98; 121 and 99; 121 and 100; 121 and 101; 121 and 102; 121 and 103; 121 and 104; 122 and 14; 122 and 25; 122 and 97; 122 and 98; 122 and 99; 122 and 100; 122 and 101; 122 and 102; 122 and 103; 122 and 104; 123 and 14; 123 and 25; 123 and 97; 123 and 98; 123 and 99; 123 and 100; 123 and 101; 123 and 102; 123 and 103; 123 and 104; 125 and 14; 125 and 25; 125 and 97; 125 and 98; 125 and 99; 125 and 100; 125 and 101; 125 and 102; 125 and 103; 125 and 104; 126 and 14; 126 and 25; 126 and 97; 126 and 98; 126 and 99; 126 and 100; 126 and 101; 126 and 102; 126 and 103; 126 and 104; 127 and 14; 127 and 25; 127 and 97; 127 and 98; 127 and 99; 127 and 100; 127 and 101; 127 and 102; 127 and 103; 127 and 104; 128 and 14; 128 and 25; 128 and 97; 128 and 98; 128 and 99; 128 and 100; 128 and 101; 128 and 102; 128 and 103; 128 and 104; 408 and 14; 408 and 25; 408 and 97; 408 and 98; 408 and 99; 408 and 100; 408 and 101; 408 and 102; 408 and 103; 408 and 104; 409 and 14; 409 and 25; 409 and 97; 409 and 98; 409 and 99; 409 and 100; 409 and 101; 409 and 102; 409 and 103; 409 and 104; 410 and 14; 410 and 25; 410 and 97; 410 and 98; 410 and 99; 410 and 100; 410 and 101; 410 and 102; 410 and 103; 410 and 104; 411 and 14; 411 and 25; 411 and 97; 411 and 98; 411 and 99; 411 and 100; 411 and 101; 411 and 102; 411 and 103; 411 and 104; 412 and 14; 412 and 25; 412 and 97; 412 and 98; 412 and 99; 412 and 100; 412 and 101; 412 and 102; 412 and 103; 412 and 104; 413 and 14; 413 and 25; 413 and 97; 413 and 98; 413 and 99; 413 and 100; 413 and 101; 413 and 102; 413 and 103; 413 and 104; 414 and 14; 414 and 25; 414 and 97; 414 and 98; 414 and 99; 414 and 100; 414 and 101; 414 and 102; 414 and 103; 414 and 104; 415 and 14; 415 and 25; 415 and 97; 415 and 98; 415 and 99; 415 and 100; 415 and 101; 415 and 102; 415 and 103; or 415 and 104, respectively.

8. The isolated TCR of claim 7, wherein:

(i) the α chain and the β chain comprise the amino acid sequences set forth in SEQ ID NOs: 13 and 14; 13 and 25; 105 and 14; 105 and 25; 110 and 14; 110 and 25; 115 and 14; 115 and 25; 120 and 14; 120 and 25; 125 and 14; 125 and 25; 408 and 14; 408 and 25; 412 and 14; or 412 and 25, respectively, and/or (ii) the α chain and the β chain comprise the amino acid sequences set forth in SEQ ID NOs: 13 and 14; 105 and 14; 110 and 14; 115 and 14; 120 and 14; 125 and 14; 408 and 14; or 412 and 14, respectively.

* * * * *

UNITED STATES PATENT AND TRADEMARK OFFICE
CERTIFICATE OF CORRECTION

PATENT NO. : 11,613,764 B2
APPLICATION NO. : 16/512031
DATED : March 28, 2023
INVENTOR(S) : Marc van Dijk et al.

It is certified that error appears in the above-identified patent and that said Letters Patent is hereby corrected as shown below:

In the Claims

Claim 6, at Column 560, Line 18:
"and the f3"
Should read:
-- and the β --

Claim 7, at Column 560, Line 26:
"and 97-104;"
Should read:
-- and 97-104; and/or --

Signed and Sealed this
Sixth Day of June, 2023

Katherine Kelly Vidal
*Director of the United States Patent and Trademark Office*

SEQUENCE LISTING

<160> NUMBER OF SEQ ID NOS: 421

<210> SEQ ID NO 1
<211> LENGTH: 9
<212> TYPE: PRT
<213> ORGANISM: Homo sapiens

<400> SEQUENCE: 1

Ser Leu Leu Met Trp Ile Thr Gln Cys
1               5

<210> SEQ ID NO 2
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ser Leu Leu Met Trp Ile Thr Gln Val
1               5

<210> SEQ ID NO 3
<211> LENGTH: 116
<212> TYPE: PRT
<213> ORGANISM: Homo sapiens

<400> SEQUENCE: 3

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Gly Ala Gly Ser Tyr Gln Leu Thr Phe Gly Lys Gly Thr Lys Leu
            100                 105                 110

Ser Val Ile Pro
        115

<210> SEQ ID NO 4
<211> LENGTH: 110
<212> TYPE: PRT
<213> ORGANISM: Homo sapiens

<400> SEQUENCE: 4

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
        35                  40                  45

Glu Ala Thr Tyr Glu Ser Gly Phe Val Ile Asp Lys Phe Pro Ile Ser
    50                  55                  60

Arg Pro Asn Leu Thr Phe Ser Thr Leu Thr Val Ser Asn Met Ser Pro
 65                  70                  75                  80

Glu Asp Ser Ser Ile Tyr Leu Cys Ser Val Gly Gly Ala Gly Val Thr
                 85                  90                  95

Asp Thr Gln Tyr Phe Gly Pro Gly Thr Arg Leu Thr Val Leu
            100                 105                 110

<210> SEQ ID NO 5
<211> LENGTH: 6
<212> TYPE: PRT
<213> ORGANISM: Homo sapiens

<400> SEQUENCE: 5

Val Ser Gly Asn Pro Tyr
1               5

<210> SEQ ID NO 6
<211> LENGTH: 8
<212> TYPE: PRT
<213> ORGANISM: Homo sapiens

<400> SEQUENCE: 6

Tyr Ile Thr Gly Asp Asn Leu Val
1               5

<210> SEQ ID NO 7
<211> LENGTH: 13
<212> TYPE: PRT
<213> ORGANISM: Homo sapiens

<400> SEQUENCE: 7

Arg Glu Leu Tyr Ser Gly Ala Gly Ser Tyr Gln Leu Thr
1               5                   10

<210> SEQ ID NO 8
<211> LENGTH: 5
<212> TYPE: PRT
<213> ORGANISM: Homo sapiens

<400> SEQUENCE: 8

Ser Gln Val Thr Met
1               5

<210> SEQ ID NO 9
<211> LENGTH: 7
<212> TYPE: PRT
<213> ORGANISM: Homo sapiens

<400> SEQUENCE: 9

Ala Asn Gln Gly Ser Glu Ala
1               5

<210> SEQ ID NO 10
<211> LENGTH: 12
<212> TYPE: PRT
<213> ORGANISM: Homo sapiens

<400> SEQUENCE: 10

Ser Val Gly Gly Ala Gly Val Thr Asp Thr Gln Tyr
1               5                   10

<210> SEQ ID NO 11
<211> LENGTH: 253

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11
```

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Gly Ala Gly Ser Tyr Gln Leu Thr Phe Gly Lys Gly Thr Lys Leu
            100                 105                 110

Ser Val Ile Pro Tyr Ile Gln Asn Pro Glu Pro Ala Val Tyr Gln Leu
        115                 120                 125

Lys Asp Pro Arg Ser Gln Asp Ser Thr Leu Cys Leu Phe Thr Asp Phe
130                 135                 140

Asp Ser Gln Ile Asn Val Pro Lys Thr Met Glu Ser Gly Thr Phe Ile
145                 150                 155                 160

Thr Asp Lys Thr Val Leu Asp Met Lys Ala Met Asp Ser Lys Ser Asn
                165                 170                 175

Gly Ala Ile Ala Trp Ser Asn Gln Thr Ser Phe Thr Cys Gln Asp Ile
            180                 185                 190

Phe Lys Glu Thr Asn Ala Thr Tyr Pro Ser Ser Asp Val Pro Cys Asp
        195                 200                 205

Ala Thr Leu Thr Glu Lys Ser Phe Glu Thr Asp Met Asn Leu Asn Phe
210                 215                 220

Gln Asn Leu Ser Val Met Gly Leu Arg Ile Leu Leu Leu Lys Val Ala
225                 230                 235                 240

Gly Phe Asn Leu Leu Met Thr Leu Arg Leu Trp Ser Ser
                245                 250

```
<210> SEQ ID NO 12
<211> LENGTH: 283
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12
```

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
        35                  40                  45

Glu Ala Thr Tyr Glu Ser Gly Phe Val Ile Asp Lys Phe Pro Ile Ser

```
            50                  55                  60
Arg Pro Asn Leu Thr Phe Ser Thr Leu Thr Val Ser Asn Met Ser Pro
 65                  70                  75                  80

Glu Asp Ser Ser Ile Tyr Leu Cys Ser Val Gly Gly Ala Gly Val Thr
                 85                  90                  95

Asp Thr Gln Tyr Phe Gly Pro Gly Thr Arg Leu Thr Val Leu Glu Asp
            100                 105                 110

Leu Arg Asn Val Thr Pro Pro Lys Val Ser Leu Phe Glu Pro Ser Lys
        115                 120                 125

Ala Glu Ile Ala Asn Lys Gln Lys Ala Thr Leu Val Cys Leu Ala Arg
130                 135                 140

Gly Phe Phe Pro Asp His Val Glu Leu Ser Trp Trp Val Asn Gly Lys
145                 150                 155                 160

Glu Val His Ser Gly Val Ser Thr Asp Pro Gln Ala Tyr Lys Glu Ser
                165                 170                 175

Asn Tyr Ser Tyr Cys Leu Ser Ser Arg Leu Arg Val Ser Ala Thr Phe
            180                 185                 190

Trp His Asn Pro Arg Asn His Phe Arg Cys Gln Val Gln Phe His Gly
        195                 200                 205

Leu Ser Glu Glu Asp Lys Trp Pro Glu Gly Ser Pro Lys Pro Val Thr
210                 215                 220

Gln Asn Ile Ser Ala Glu Ala Trp Gly Arg Ala Asp Cys Gly Ile Thr
225                 230                 235                 240

Ser Ala Ser Tyr His Gln Gly Val Leu Ser Ala Thr Ile Leu Tyr Glu
                245                 250                 255

Ile Leu Leu Gly Lys Ala Thr Leu Tyr Ala Val Leu Val Ser Gly Leu
            260                 265                 270

Val Leu Met Ala Met Val Lys Lys Lys Asn Ser
        275                 280

<210> SEQ ID NO 13
<211> LENGTH: 257
<212> TYPE: PRT
<213> ORGANISM: Homo sapiens

<400> SEQUENCE: 13

Gln Ser Val Ala Gln Pro Glu Asp Gln Val Asn Val Ala Glu Gly Asn
 1               5                  10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Glu Leu Tyr
                 85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140
```

```
Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser

<210> SEQ ID NO 14
<211> LENGTH: 287
<212> TYPE: PRT
<213> ORGANISM: Homo sapiens

<400> SEQUENCE: 14

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
                20                  25                  30

Gln Pro Gly Gln Ser Leu Thr Leu Ile Ala Thr Ala Asn Gln Gly Ser
            35                  40                  45

Glu Ala Thr Tyr Glu Ser Gly Phe Val Ile Asp Lys Phe Pro Ile Ser
50                  55                  60

Arg Pro Asn Leu Thr Phe Ser Thr Leu Thr Val Ser Asn Met Ser Pro
65                  70                  75                  80

Glu Asp Ser Ser Ile Tyr Leu Cys Ser Val Gly Gly Ala Gly Val Thr
                85                  90                  95

Asp Thr Gln Tyr Phe Gly Pro Gly Thr Arg Leu Thr Val Leu Glu Asp
            100                 105                 110

Leu Asn Lys Val Phe Pro Pro Glu Val Ala Val Phe Glu Pro Ser Glu
        115                 120                 125

Ala Glu Ile Ser His Thr Gln Lys Ala Thr Leu Val Cys Leu Ala Thr
130                 135                 140

Gly Phe Phe Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
        195                 200                 205

Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

Cys Gly Phe Thr Ser Val Ser Tyr Gln Gln Gly Val Leu Ser Ala Thr
                245                 250                 255
```

```
Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe
        275                 280                 285

<210> SEQ ID NO 15
<211> LENGTH: 141
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Tyr" or "His" or "Asp"
<220> FEATURE:
<221> NAME/KEY: MISC_FEATURE
<222> LOCATION: (1)..(141)
<223> OTHER INFORMATION: /note="Variant residues given in the sequence
      have no preference with respect to those in the annotations
      for variant positions"

<400> SEQUENCE: 15

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 16
<211> LENGTH: 177
<212> TYPE: PRT
<213> ORGANISM: Homo sapiens

<400> SEQUENCE: 16

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110
```

```
Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 17
<211> LENGTH: 179
<212> TYPE: PRT
<213> ORGANISM: Homo sapiens

<400> SEQUENCE: 17

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 18
<211> LENGTH: 92
<212> TYPE: PRT
<213> ORGANISM: Homo sapiens

<400> SEQUENCE: 18

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
```

```
                65                  70                  75                  80
Leu Val Ser Asp Ser Ala Leu Tyr Phe Cys Ala Val
                85                  90

<210> SEQ ID NO 19
<211> LENGTH: 88
<212> TYPE: PRT
<213> ORGANISM: Homo sapiens

<400> SEQUENCE: 19

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
                20                  25                  30

Gln Pro Gly Gln Ser Leu Thr Leu Ile Ala Thr Ala Asn Gln Gly Ser
            35                  40                  45

Glu Ala Thr Tyr Glu Ser Gly Phe Val Ile Asp Lys Phe Pro Ile Ser
        50                  55                  60

Arg Pro Asn Leu Thr Phe Ser Thr Leu Thr Val Ser Asn Met Ser Pro
65                  70                  75                  80

Glu Asp Ser Ser Ile Tyr Leu Cys
                85

<210> SEQ ID NO 20
<211> LENGTH: 250
<212> TYPE: PRT
<213> ORGANISM: Homo sapiens

<400> SEQUENCE: 20

Gly Gln Gln Leu Asn Gln Ser Pro Gln Ser Met Phe Ile Gln Glu Gly
1               5                   10                  15

Glu Asp Val Ser Met Asn Cys Thr Ser Ser Ile Phe Asn Thr Trp
                20                  25                  30

Leu Trp Tyr Lys Gln Asp Pro Gly Glu Gly Pro Val Leu Leu Ile Ala
            35                  40                  45

Leu Tyr Lys Ala Gly Glu Leu Thr Ser Asn Gly Arg Leu Thr Ala Gln
        50                  55                  60

Phe Gly Ile Thr Arg Lys Asp Ser Phe Leu Asn Ile Ser Ala Ser Ile
65                  70                  75                  80

Pro Ser Asp Val Gly Ile Tyr Phe Cys Ala Gly Gly Thr Gly Asn Gln
                85                  90                  95

Phe Tyr Phe Gly Thr Gly Thr Ser Leu Thr Val Ile Pro Asn Ile Gln
            100                 105                 110

Asn Pro Asp Pro Ala Val Tyr Gln Leu Arg Asp Ser Lys Ser Ser Asp
        115                 120                 125

Lys Ser Val Cys Leu Phe Thr Asp Phe Asp Ser Gln Thr Asn Val Ser
130                 135                 140

Gln Ser Lys Asp Ser Asp Val Tyr Ile Thr Asp Lys Thr Val Leu Asp
145                 150                 155                 160

Met Arg Ser Met Asp Phe Lys Ser Asn Ser Ala Val Ala Trp Ser Asn
                165                 170                 175

Lys Ser Asp Phe Ala Cys Ala Asn Ala Phe Asn Asn Ser Ile Ile Pro
            180                 185                 190

Glu Asp Thr Phe Phe Pro Ser Pro Glu Ser Ser Cys Asp Val Lys Leu
        195                 200                 205

Val Glu Lys Ser Phe Glu Thr Asp Thr Asn Leu Asn Phe Gln Asn Leu
```

```
                 210                 215                 220
Ser Val Ile Gly Phe Arg Ile Leu Leu Lys Val Ala Gly Phe Asn
225                 230                 235                 240

Leu Leu Met Thr Leu Arg Leu Trp Ser Ser
                245                 250

<210> SEQ ID NO 21
<211> LENGTH: 290
<212> TYPE: PRT
<213> ORGANISM: Homo sapiens

<400> SEQUENCE: 21

Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
                20                  25                  30

Tyr Trp Tyr Arg Gln Asp Pro Gly His Gly Leu Arg Leu Ile His Tyr
            35                  40                  45

Ser Tyr Gly Val Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys Ala Ile Ser Glu Val
                85                  90                  95

Gly Val Gly Gln Pro Gln His Phe Gly Asp Gly Thr Arg Leu Ser Ile
            100                 105                 110

Leu Glu Asp Leu Asn Lys Val Phe Pro Pro Glu Val Ala Val Phe Glu
        115                 120                 125

Pro Ser Glu Ala Glu Ile Ser His Thr Gln Lys Ala Thr Leu Val Cys
130                 135                 140

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Val Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Phe
    290

<210> SEQ ID NO 22
<211> LENGTH: 10
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 22

Glu Leu Ala Gly Ile Gly Ile Leu Thr Val
1               5                   10

<210> SEQ ID NO 23
<211> LENGTH: 107
<212> TYPE: PRT
<213> ORGANISM: Unknown
<220> FEATURE:
<221> NAME/KEY: source
<223> OTHER INFORMATION: /note="Description of Unknown: FKBP12
      polypeptide"

<400> SEQUENCE: 23

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 24
<211> LENGTH: 282
<212> TYPE: PRT
<213> ORGANISM: Homo sapiens

<400> SEQUENCE: 24

Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160
```

Gly Phe Glu Val Ala Ser Thr Ser Pro Glu Asp Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280

<210> SEQ ID NO 25
<211> LENGTH: 289
<212> TYPE: PRT
<213> ORGANISM: Homo sapiens

<400> SEQUENCE: 25

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
        35                  40                  45

Glu Ala Thr Tyr Glu Ser Gly Phe Val Ile Asp Lys Phe Pro Ile Ser
    50                  55                  60

Arg Pro Asn Leu Thr Phe Ser Thr Leu Thr Val Ser Asn Met Ser Pro
65                  70                  75                  80

Glu Asp Ser Ser Ile Tyr Leu Cys Ser Val Gly Gly Ala Gly Val Thr
                85                  90                  95

Asp Thr Gln Tyr Phe Gly Pro Gly Thr Arg Leu Thr Val Leu Glu Asp
            100                 105                 110

Leu Lys Asn Val Phe Pro Pro Glu Val Ala Val Phe Glu Pro Ser Glu
        115                 120                 125

Ala Glu Ile Ser His Thr Gln Lys Ala Thr Leu Val Cys Leu Ala Thr
    130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
        195                 200                 205

Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

Cys Gly Phe Thr Ser Glu Ser Tyr Gln Gln Gly Val Leu Ser Ala Thr

```
                    245                 250                 255

Ile Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Ser Arg
        275                 280                 285

Gly

<210> SEQ ID NO 26
<211> LENGTH: 141
<212> TYPE: PRT
<213> ORGANISM: Homo sapiens

<400> SEQUENCE: 26

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ser Ala Val Ile Ser
1               5

<210> SEQ ID NO 28
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
```

```
                35                  40                  45
Asn Pro Tyr Leu Phe Trp Tyr Val Gln Tyr Pro Asn Arg Gly Leu Gln
 50                  55                  60

Phe Leu Leu Lys Tyr Ile Thr Gly Asp Asn Leu Val Lys Gly Ser Tyr
 65                  70                  75                  80

Gly Phe Glu Ala Glu Phe Asn Lys Ser Gln Thr Ser Phe His Leu Lys
                 85                  90                  95

Lys Pro Ser Ala Leu Val Ser Asp Ser Ala Leu Tyr Phe Cys Ala Val
                100                 105                 110

Arg Glu Leu Tyr Ser Gly Ala Gly Ser Tyr Gln Leu Thr Phe Gly Lys
                115                 120                 125

Gly Thr Lys Leu Ser Val Ile Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
                180                 185                 190

Phe Lys Ser Asn Ser Ala Val Ala Trp Ser Asn Lys Ser Asp Phe Ala
                195                 200                 205

Cys Ala Asn Ala Phe Asn Asn Ser Ile Ile Pro Glu Asp Thr Phe Phe
210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
                260                 265                 270

Arg Leu Trp Ser Ser Arg Ala Lys Arg Ser Gly Ser Gly Ala Thr Asn
                275                 280                 285

Phe Ser Leu Leu Lys Gln Ala Gly Asp Val Glu Glu Asn Pro Gly Pro
290                 295                 300

Met Leu Ser Leu Leu Leu Leu Leu Gly Leu Gly Ser Val Phe Ser
305                 310                 315                 320

Ala Val Ile Ser Gln Lys Pro Ser Arg Asp Ile Cys Gln Arg Gly Thr
                325                 330                 335

Ser Leu Thr Ile Gln Cys Gln Val Asp Ser Gln Val Thr Met Met Phe
                340                 345                 350

Trp Tyr Arg Gln Gln Pro Gly Gln Ser Leu Thr Leu Ile Ala Thr Ala
                355                 360                 365

Asn Gln Gly Ser Glu Ala Thr Tyr Glu Ser Gly Phe Val Ile Asp Lys
                370                 375                 380

Phe Pro Ile Ser Arg Pro Asn Leu Thr Phe Ser Thr Leu Thr Val Ser
385                 390                 395                 400

Asn Met Ser Pro Glu Asp Ser Ser Ile Tyr Leu Cys Ser Val Gly Gly
                405                 410                 415

Ala Gly Val Thr Asp Thr Gln Tyr Phe Gly Pro Gly Thr Arg Leu Thr
                420                 425                 430

Val Leu Glu Asp Leu Asn Lys Val Phe Pro Pro Glu Val Ala Val Phe
                435                 440                 445

Glu Pro Ser Glu Ala Glu Ile Ser His Thr Gln Lys Ala Thr Leu Val
450                 455                 460
```

```
Cys Leu Ala Thr Gly Phe Phe Pro Asp His Val Glu Leu Ser Trp Trp
465                 470                 475                 480

Val Asn Gly Lys Glu Val His Ser Gly Val Ser Thr Asp Pro Gln Pro
            485                 490                 495

Leu Lys Glu Gln Pro Ala Leu Asn Asp Ser Arg Tyr Cys Leu Ser Ser
        500                 505                 510

Arg Leu Arg Val Ser Ala Thr Phe Trp Gln Asn Pro Arg Asn His Phe
        515                 520                 525

Arg Cys Gln Val Gln Phe Tyr Gly Leu Ser Glu Asn Asp Glu Trp Thr
        530                 535                 540

Gln Asp Arg Ala Lys Pro Val Thr Gln Ile Val Ser Ala Glu Ala Trp
545                 550                 555                 560

Gly Arg Ala Asp Cys Gly Phe Thr Ser Val Ser Tyr Gln Gln Gly Val
                565                 570                 575

Leu Ser Ala Thr Ile Leu Tyr Glu Ile Leu Leu Gly Lys Ala Thr Leu
            580                 585                 590

Tyr Ala Val Leu Val Ser Ala Leu Val Leu Met Ala Met Val Lys Arg
        595                 600                 605

Lys Asp Phe
    610

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: VARIANT
<222> LOCATION: (3)..(3)
<223> OTHER INFORMATION: /replace="Arg"
<220> FEATURE:
<221> NAME/KEY: MISC_FEATURE
<222> LOCATION: (1)..(4)
<223> OTHER INFORMATION: /note="Variant residues given in the sequence
      have no preference with respect to those in the annotations
      for variant positions"

<400> SEQUENCE: 29

Arg Xaa Lys Arg
1

<210> SEQ ID NO 30
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Arg Ala Lys Arg
1

<210> SEQ ID NO 31
<211> LENGTH: 4
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Arg"
<220> FEATURE:
<221> NAME/KEY: VARIANT
<222> LOCATION: (3)..(3)
<223> OTHER INFORMATION: /replace="Arg"
<220> FEATURE:
<221> NAME/KEY: MISC_FEATURE
<222> LOCATION: (1)..(4)
<223> OTHER INFORMATION: /note="Variant residues given in the sequence
      have no preference with respect to those in the annotations
      for variant positions"

<400> SEQUENCE: 31

Arg Lys Lys Arg
1

<210> SEQ ID NO 32
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Gly"
<220> FEATURE:
<221> NAME/KEY: VARIANT
<222> LOCATION: (2)..(2)
<223> OTHER INFORMATION: /replace="Ile"
<220> FEATURE:
<221> NAME/KEY: MOD_RES
<222> LOCATION: (4)..(4)
<223> OTHER INFORMATION: Any amino acid
<220> FEATURE:
<221> NAME/KEY: MISC_FEATURE
<222> LOCATION: (1)..(8)
<223> OTHER INFORMATION: /note="Variant residues given in the sequence
      have no preference with respect to those in the annotations
      for variant positions"

<400> SEQUENCE: 32

Asp Val Glu Xaa Asn Pro Gly Pro
1               5

<210> SEQ ID NO 33
<211> LENGTH: 19
<212> TYPE: PRT
<213> ORGANISM: Porcine teschovirus

<400> SEQUENCE: 33

Ala Thr Asn Phe Ser Leu Leu Lys Gln Ala Gly Asp Val Glu Glu Asn
1               5                   10                  15

Pro Gly Pro

<210> SEQ ID NO 34
<211> LENGTH: 18
<212> TYPE: PRT
<213> ORGANISM: Thosea asigna virus

<400> SEQUENCE: 34
```

-continued

```
Glu Gly Arg Gly Ser Leu Leu Thr Cys Gly Asp Val Glu Glu Asn Pro
1               5                   10                  15

Gly Pro

<210> SEQ ID NO 35
<211> LENGTH: 20
<212> TYPE: PRT
<213> ORGANISM: Equine rhinitis A virus

<400> SEQUENCE: 35

Gln Cys Thr Asn Tyr Ala Leu Leu Lys Leu Ala Gly Asp Val Glu Ser
1               5                   10                  15

Asn Pro Gly Pro
            20

<210> SEQ ID NO 36
<211> LENGTH: 22
<212> TYPE: PRT
<213> ORGANISM: Foot and mouth disease virus

<400> SEQUENCE: 36

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 37
<211> LENGTH: 22
<212> TYPE: PRT
<213> ORGANISM: Cytoplasmic polyhedrosis virus

<400> SEQUENCE: 37

Asp Val Phe Arg Ser Asn Tyr Asp Leu Leu Lys Leu Cys Gly Asp Ile
1               5                   10                  15

Glu Ser Asn Pro Gly Pro
            20

<210> SEQ ID NO 38
<211> LENGTH: 22
<212> TYPE: PRT
<213> ORGANISM: Infectious flacherie virus

<400> SEQUENCE: 38

Thr Leu Thr Arg Ala Lys Ile Glu Asp Glu Leu Ile Arg Ala Gly Ile
1               5                   10                  15

Glu Ser Asn Pro Gly Pro
            20

<210> SEQ ID NO 39
<211> LENGTH: 15
<212> TYPE: PRT
<213> ORGANISM: Homo sapiens

<400> SEQUENCE: 39

Ala Val Arg Glu Leu Tyr Ser Gly Ala Gly Ser Tyr Gln Leu Thr
1               5                   10                  15

<210> SEQ ID NO 40
<211> LENGTH: 15
<212> TYPE: PRT
<213> ORGANISM: Homo sapiens

<400> SEQUENCE: 40
```

```
Ala Val Arg Asp Ile Lys Ser Gly Ala Gly Ser Tyr Gln Leu Thr
1               5                   10                  15

<210> SEQ ID NO 41
<211> LENGTH: 15
<212> TYPE: PRT
<213> ORGANISM: Homo sapiens

<400> SEQUENCE: 41

Ala Val Arg Asp Ser Phe Glu Gly Ala Gly Ser Tyr Gln Leu Thr
1               5                   10                  15

<210> SEQ ID NO 42
<211> LENGTH: 15
<212> TYPE: PRT
<213> ORGANISM: Homo sapiens

<400> SEQUENCE: 42

Ala Val Arg Gly Leu Leu Asn Gly Ala Gly Ser Tyr Gln Leu Thr
1               5                   10                  15

<210> SEQ ID NO 43
<211> LENGTH: 15
<212> TYPE: PRT
<213> ORGANISM: Homo sapiens

<400> SEQUENCE: 43

Ala Val Arg Asp Leu Phe Thr Gly Ala Gly Ser Tyr Gln Leu Thr
1               5                   10                  15

<210> SEQ ID NO 44
<211> LENGTH: 15
<212> TYPE: PRT
<213> ORGANISM: Homo sapiens

<400> SEQUENCE: 44

Ala Val Arg Asp Gly Arg Thr Gly Ala Gly Ser Tyr Gln Leu Thr
1               5                   10                  15

<210> SEQ ID NO 45
<211> LENGTH: 15
<212> TYPE: PRT
<213> ORGANISM: Homo sapiens

<400> SEQUENCE: 45

Ala Val Arg Asp Leu Ser Asp Gly Ala Gly Ser Tyr Gln Leu Thr
1               5                   10                  15

<210> SEQ ID NO 46
<211> LENGTH: 15
<212> TYPE: PRT
<213> ORGANISM: Homo sapiens

<400> SEQUENCE: 46

Ala Val Arg Ser Ser Tyr Glu Gly Ala Gly Arg Tyr Gln Leu Thr
1               5                   10                  15

<210> SEQ ID NO 47
<211> LENGTH: 15
<212> TYPE: PRT
<213> ORGANISM: Homo sapiens

<400> SEQUENCE: 47

Ala Val Arg Asp Asp Leu Val Gly Ala Gly Ser Tyr Gln Leu Thr
```

```
<210> SEQ ID NO 48
<211> LENGTH: 15
<212> TYPE: PRT
<213> ORGANISM: Homo sapiens

<400> SEQUENCE: 48

Ala Val Arg Asp Gln Ala Leu Gly Ala Gly Ser Tyr Gln Leu Thr
1               5                   10                  15

<210> SEQ ID NO 49
<211> LENGTH: 15
<212> TYPE: PRT
<213> ORGANISM: Homo sapiens

<400> SEQUENCE: 49

Ala Val Arg Asp Met Ala Asn Gly Ala Gly Ser Tyr Gln Leu Thr
1               5                   10                  15

<210> SEQ ID NO 50
<211> LENGTH: 15
<212> TYPE: PRT
<213> ORGANISM: Homo sapiens

<400> SEQUENCE: 50

Ala Val Arg Asp Ser Lys Ala Gly Ala Gly Ser Tyr Gln Leu Thr
1               5                   10                  15

<210> SEQ ID NO 51
<211> LENGTH: 15
<212> TYPE: PRT
<213> ORGANISM: Homo sapiens

<400> SEQUENCE: 51

Ala Val Arg Asp Leu Phe Cys Gly Ala Gly Ser Tyr Gln Leu Thr
1               5                   10                  15

<210> SEQ ID NO 52
<211> LENGTH: 15
<212> TYPE: PRT
<213> ORGANISM: Homo sapiens

<400> SEQUENCE: 52

Ala Val Arg Asp Leu Arg Gly Gly Ala Gly Ser Tyr Gln Leu Thr
1               5                   10                  15

<210> SEQ ID NO 53
<211> LENGTH: 15
<212> TYPE: PRT
<213> ORGANISM: Homo sapiens

<400> SEQUENCE: 53

Ala Val Arg Asp Leu Thr Thr Gly Ala Gly Ser Tyr Gln Leu Thr
1               5                   10                  15

<210> SEQ ID NO 54
<211> LENGTH: 15
<212> TYPE: PRT
<213> ORGANISM: Homo sapiens

<400> SEQUENCE: 54

Ala Val Arg Asp Val Ala Ser Gly Ala Gly Ser Tyr Gln Leu Thr
1               5                   10                  15
```

<210> SEQ ID NO 55
<211> LENGTH: 15
<212> TYPE: PRT
<213> ORGANISM: Homo sapiens

<400> SEQUENCE: 55

Ala Val Arg Glu Leu Tyr Ser Val Ala Val Arg Tyr Gln Leu Thr
1               5                   10                  15

<210> SEQ ID NO 56
<211> LENGTH: 15
<212> TYPE: PRT
<213> ORGANISM: Homo sapiens

<400> SEQUENCE: 56

Ala Val Arg Glu Leu Tyr Ser Arg Gly Val Lys Trp Gln Leu Thr
1               5                   10                  15

<210> SEQ ID NO 57
<211> LENGTH: 15
<212> TYPE: PRT
<213> ORGANISM: Homo sapiens

<400> SEQUENCE: 57

Ala Val Arg Glu Leu Tyr Ser Thr Thr Phe Gly Trp Gln Leu Thr
1               5                   10                  15

<210> SEQ ID NO 58
<211> LENGTH: 15
<212> TYPE: PRT
<213> ORGANISM: Homo sapiens

<400> SEQUENCE: 58

Ala Val Arg Glu Leu Tyr Ser Ala Leu Val Thr Tyr Gln Leu Thr
1               5                   10                  15

<210> SEQ ID NO 59
<211> LENGTH: 15
<212> TYPE: PRT
<213> ORGANISM: Homo sapiens

<400> SEQUENCE: 59

Ala Val Arg Glu Leu Tyr Ser Pro Arg Leu Met Trp Gln Leu Thr
1               5                   10                  15

<210> SEQ ID NO 60
<211> LENGTH: 15
<212> TYPE: PRT
<213> ORGANISM: Homo sapiens

<400> SEQUENCE: 60

Ala Val Arg Glu Leu Tyr Ser Ala Thr Val Asp Tyr Gln Leu Thr
1               5                   10                  15

<210> SEQ ID NO 61
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (4)..(4)
<223> OTHER INFORMATION: /replace="Asp" or "Gly" or "Ser"

-continued

```
<220> FEATURE:
<221> NAME/KEY: VARIANT
<222> LOCATION: (5)..(5)
<223> OTHER INFORMATION: /replace="Ile" or "Ser" or "Gly" or "Asp" or
      "Gln" or "Met" or "Val"
<220> FEATURE:
<221> NAME/KEY: VARIANT
<222> LOCATION: (6)..(6)
<223> OTHER INFORMATION: /replace="Lys" or "Phe" or "Leu" or "Arg" or
      "Ser" or "Ala" or "Thr"
<220> FEATURE:
<221> NAME/KEY: VARIANT
<222> LOCATION: (7)..(7)
<223> OTHER INFORMATION: /replace="Glu" or "Asn" or "Thr" or "Asp" or
      "Val" or "Leu" or "Ala" or "Cys" or "Gly"
<220> FEATURE:
<221> NAME/KEY: VARIANT
<222> LOCATION: (8)..(8)
<223> OTHER INFORMATION: /replace="Val" or "Arg" or "Thr" or "Ala" or
      "Pro"
<220> FEATURE:
<221> NAME/KEY: VARIANT
<222> LOCATION: (9)..(9)
<223> OTHER INFORMATION: /replace="Gly" or "Thr" or "Leu" or "Arg"
<220> FEATURE:
<221> NAME/KEY: VARIANT
<222> LOCATION: (10)..(10)
<223> OTHER INFORMATION: /replace="Val" or "Phe" or "Leu"
<220> FEATURE:
<221> NAME/KEY: VARIANT
<222> LOCATION: (11)..(11)
<223> OTHER INFORMATION: /replace="Arg" or "Lys" or "Gly" or "Thr" or
      "Met" or "Asp"
<220> FEATURE:
<221> NAME/KEY: VARIANT
<222> LOCATION: (12)..(12)
<223> OTHER INFORMATION: /replace="Trp"
<220> FEATURE:
<221> NAME/KEY: MISC_FEATURE
<222> LOCATION: (1)..(15)
<223> OTHER INFORMATION: /note="Variant residues given in the sequence
      have no preference with respect to those in the annotations
      for variant positions"

<400> SEQUENCE: 61

Ala Val Arg Glu Leu Tyr Ser Gly Ala Gly Ser Tyr Gln Leu Thr
1               5                   10                  15

<210> SEQ ID NO 62
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (4)..(4)
<223> OTHER INFORMATION: /replace="Asp" or "Gly" or "Ser"
<220> FEATURE:
<221> NAME/KEY: VARIANT
<222> LOCATION: (5)..(5)
<223> OTHER INFORMATION: /replace="Ile" or "Ser" or "Gly" or "Asp" or
      "Gln" or "Met" or "Val"
<220> FEATURE:
<221> NAME/KEY: VARIANT
<222> LOCATION: (6)..(6)
<223> OTHER INFORMATION: /replace="Lys" or "Phe" or "Leu" or "Arg" or
      "Ser" or "Ala" or "Thr"
<220> FEATURE:
<221> NAME/KEY: VARIANT
<222> LOCATION: (7)..(7)
<223> OTHER INFORMATION: /replace="Glu" or "Asn" or "Thr" or "Asp" or
      "Val" or "Leu" or "Ala" or "Cys" or "Gly"
<220> FEATURE:
<221> NAME/KEY: MISC_FEATURE
```

```
<222> LOCATION: (1)..(15)
<223> OTHER INFORMATION: /note="Variant residues given in the sequence
      have no preference with respect to those in the annotations
      for variant positions"

<400> SEQUENCE: 62

Ala Val Arg Glu Leu Tyr Ser Gly Ala Gly Ser Tyr Gln Leu Thr
1               5                   10                  15

<210> SEQ ID NO 63
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (8)..(8)
<223> OTHER INFORMATION: /replace="Val" or "Arg" or "Thr" or "Ala" or
      "Pro"
<220> FEATURE:
<221> NAME/KEY: VARIANT
<222> LOCATION: (9)..(9)
<223> OTHER INFORMATION: /replace="Gly" or "Thr" or "Leu" or "Arg"
<220> FEATURE:
<221> NAME/KEY: VARIANT
<222> LOCATION: (10)..(10)
<223> OTHER INFORMATION: /replace="Val" or "Phe" or "Leu"
<220> FEATURE:
<221> NAME/KEY: VARIANT
<222> LOCATION: (11)..(11)
<223> OTHER INFORMATION: /replace="Arg" or "Lys" or "Gly" or "Thr" or
      "Met" or "Asp"
<220> FEATURE:
<221> NAME/KEY: VARIANT
<222> LOCATION: (12)..(12)
<223> OTHER INFORMATION: /replace="Tyr"
<220> FEATURE:
<221> NAME/KEY: MISC_FEATURE
<222> LOCATION: (1)..(15)
<223> OTHER INFORMATION: /note="Variant residues given in the sequence
      have no preference with respect to those in the annotations
      for variant positions"

<400> SEQUENCE: 63

Ala Val Arg Glu Leu Tyr Ser Gly Ala Gly Ser Tyr Gln Leu Thr
1               5                   10                  15

<210> SEQ ID NO 64
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (4)..(4)
<223> OTHER INFORMATION: /replace="Glu"
<220> FEATURE:
<221> NAME/KEY: VARIANT
<222> LOCATION: (5)..(5)
<223> OTHER INFORMATION: /replace="Leu" or "Met" or "Ile" or "Val"
<220> FEATURE:
<221> NAME/KEY: VARIANT
<222> LOCATION: (6)..(6)
<223> OTHER INFORMATION: /replace="Ala" or "Lys" or "Ser" or "Phe" or
      "Tyr"
<220> FEATURE:
<221> NAME/KEY: VARIANT
<222> LOCATION: (7)..(7)
<223> OTHER INFORMATION: /replace="Asn" or "Ser" or "Asp" or "Thr"
```

```
<220> FEATURE:
<221> NAME/KEY: MISC_FEATURE
<222> LOCATION: (1)..(15)
<223> OTHER INFORMATION: /note="Variant residues given in the sequence
      have no preference with respect to those in the annotations
      for variant positions"

<400> SEQUENCE: 64

Ala Val Arg Asp Asp Leu Val Gly Ala Gly Ser Tyr Gln Leu Thr
1               5                   10                  15

<210> SEQ ID NO 65
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (5)..(5)
<223> OTHER INFORMATION: /replace="Leu" or "Met" or "Ile" or "Val"
<220> FEATURE:
<221> NAME/KEY: VARIANT
<222> LOCATION: (6)..(6)
<223> OTHER INFORMATION: /replace="Ala" or "Lys" or "Ser" or "Phe"
<220> FEATURE:
<221> NAME/KEY: VARIANT
<222> LOCATION: (7)..(7)
<223> OTHER INFORMATION: /replace="Asn" or "Ser" or "Asp" or "Thr"
<220> FEATURE:
<221> NAME/KEY: MISC_FEATURE
<222> LOCATION: (1)..(15)
<223> OTHER INFORMATION: /note="Variant residues given in the sequence
      have no preference with respect to those in the annotations
      for variant positions"

<400> SEQUENCE: 65

Ala Val Arg Asp Asp Leu Val Gly Ala Gly Ser Tyr Gln Leu Thr
1               5                   10                  15

<210> SEQ ID NO 66
<211> LENGTH: 116
<212> TYPE: PRT
<213> ORGANISM: Homo sapiens

<400> SEQUENCE: 66

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Ile Lys
                85                  90                  95

Ser Gly Ala Gly Ser Tyr Gln Leu Thr Phe Gly Lys Gly Thr Lys Leu
                100                 105                 110

Ser Val Ile Pro
        115

<210> SEQ ID NO 67
```

```
<211> LENGTH: 116
<212> TYPE: PRT
<213> ORGANISM: Homo sapiens

<400> SEQUENCE: 67

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Ser Phe
                85                  90                  95

Glu Gly Ala Gly Ser Tyr Gln Leu Thr Phe Gly Lys Gly Thr Lys Leu
            100                 105                 110

Ser Val Ile Pro
        115

<210> SEQ ID NO 68
<211> LENGTH: 116
<212> TYPE: PRT
<213> ORGANISM: Homo sapiens

<400> SEQUENCE: 68

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Gly Leu Leu
                85                  90                  95

Asn Gly Ala Gly Ser Tyr Gln Leu Thr Phe Gly Lys Gly Thr Lys Leu
            100                 105                 110

Ser Val Ile Pro
        115

<210> SEQ ID NO 69
<211> LENGTH: 116
<212> TYPE: PRT
<213> ORGANISM: Homo sapiens

<400> SEQUENCE: 69

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45
```

```
Tyr Ile Thr Gly Asp Asn Leu Val Lys Gly Ser Tyr Gly Phe Glu Ala
            50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Leu Phe
                85                  90                  95

Thr Gly Ala Gly Ser Tyr Gln Leu Thr Phe Gly Lys Gly Thr Lys Leu
               100                 105                 110

Ser Val Ile Pro
           115

<210> SEQ ID NO 70
<211> LENGTH: 116
<212> TYPE: PRT
<213> ORGANISM: Homo sapiens

<400> SEQUENCE: 70

Gln Ser Val Ala Gln Pro Glu Asp Gln Val Asn Val Ala Glu Gly Asn
 1               5                  10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
                35                  40                  45

Tyr Ile Thr Gly Asp Asn Leu Val Lys Gly Ser Tyr Gly Phe Glu Ala
            50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Gly Arg
                85                  90                  95

Thr Gly Ala Gly Ser Tyr Gln Leu Thr Phe Gly Lys Gly Thr Lys Leu
               100                 105                 110

Ser Val Ile Pro
           115

<210> SEQ ID NO 71
<211> LENGTH: 116
<212> TYPE: PRT
<213> ORGANISM: Homo sapiens

<400> SEQUENCE: 71

Gln Ser Val Ala Gln Pro Glu Asp Gln Val Asn Val Ala Glu Gly Asn
 1               5                  10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
                35                  40                  45

Tyr Ile Thr Gly Asp Asn Leu Val Lys Gly Ser Tyr Gly Phe Glu Ala
            50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Leu Ser
                85                  90                  95

Asp Gly Ala Gly Ser Tyr Gln Leu Thr Phe Gly Lys Gly Thr Lys Leu
               100                 105                 110

Ser Val Ile Pro
           115
```

-continued

<210> SEQ ID NO 72
<211> LENGTH: 116
<212> TYPE: PRT
<213> ORGANISM: Homo sapiens

<400> SEQUENCE: 72

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Ser Ser Tyr
                85                  90                  95

Glu Gly Ala Gly Arg Tyr Gln Leu Thr Phe Gly Lys Gly Thr Lys Leu
            100                 105                 110

Ser Val Ile Pro
            115

<210> SEQ ID NO 73
<211> LENGTH: 116
<212> TYPE: PRT
<213> ORGANISM: Homo sapiens

<400> SEQUENCE: 73

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Asp Leu
                85                  90                  95

Val Gly Ala Gly Ser Tyr Gln Leu Thr Phe Gly Lys Gly Thr Lys Leu
            100                 105                 110

Ser Val Ile Pro
            115

<210> SEQ ID NO 74
<211> LENGTH: 116
<212> TYPE: PRT
<213> ORGANISM: Homo sapiens

<400> SEQUENCE: 74

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys

```
        35                  40                  45
Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Gln Ala
                85                  90                  95

Leu Gly Ala Gly Ser Tyr Gln Leu Thr Phe Gly Lys Gly Thr Lys Leu
                100                 105                 110

Ser Val Ile Pro
        115

<210> SEQ ID NO 75
<211> LENGTH: 116
<212> TYPE: PRT
<213> ORGANISM: Homo sapiens

<400> SEQUENCE: 75

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Met Ala
                85                  90                  95

Asn Gly Ala Gly Ser Tyr Gln Leu Thr Phe Gly Lys Gly Thr Lys Leu
                100                 105                 110

Ser Val Ile Pro
        115

<210> SEQ ID NO 76
<211> LENGTH: 116
<212> TYPE: PRT
<213> ORGANISM: Homo sapiens

<400> SEQUENCE: 76

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Ser Lys
                85                  90                  95

Ala Gly Ala Gly Ser Tyr Gln Leu Thr Phe Gly Lys Gly Thr Lys Leu
                100                 105                 110

Ser Val Ile Pro
```

<210> SEQ ID NO 77
<211> LENGTH: 116
<212> TYPE: PRT
<213> ORGANISM: Homo sapiens

<400> SEQUENCE: 77

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Phe
                85                  90                  95

Cys Gly Ala Gly Ser Tyr Gln Leu Thr Phe Gly Lys Gly Thr Lys Leu
            100                 105                 110

Ser Val Ile Pro
        115

<210> SEQ ID NO 78
<211> LENGTH: 116
<212> TYPE: PRT
<213> ORGANISM: Homo sapiens

<400> SEQUENCE: 78

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Arg
                85                  90                  95

Gly Gly Ala Gly Ser Tyr Gln Leu Thr Phe Gly Lys Gly Thr Lys Leu
            100                 105                 110

Ser Val Ile Pro
        115

<210> SEQ ID NO 79
<211> LENGTH: 116
<212> TYPE: PRT
<213> ORGANISM: Homo sapiens

<400> SEQUENCE: 79

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

```
Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Thr
                85                  90                  95

Thr Gly Ala Gly Ser Tyr Gln Leu Thr Phe Gly Lys Gly Thr Lys Leu
            100                 105                 110

Ser Val Ile Pro
            115

<210> SEQ ID NO 80
<211> LENGTH: 116
<212> TYPE: PRT
<213> ORGANISM: Homo sapiens

<400> SEQUENCE: 80

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Val Ala
                85                  90                  95

Ser Gly Ala Gly Ser Tyr Gln Leu Thr Phe Gly Lys Gly Thr Lys Leu
            100                 105                 110

Ser Val Ile Pro
            115

<210> SEQ ID NO 81
<211> LENGTH: 116
<212> TYPE: PRT
<213> ORGANISM: Homo sapiens

<400> SEQUENCE: 81

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Val Ala Val Arg Tyr Gln Leu Thr Phe Gly Lys Gly Thr Lys Leu
            100                 105                 110
```

Ser Val Ile Pro
        115

<210> SEQ ID NO 82
<211> LENGTH: 116
<212> TYPE: PRT
<213> ORGANISM: Homo sapiens

<400> SEQUENCE: 82

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Arg Gly Val Lys Trp Gln Leu Thr Phe Gly Lys Gly Thr Lys Leu
            100                 105                 110

Ser Val Ile Pro
        115

<210> SEQ ID NO 83
<211> LENGTH: 116
<212> TYPE: PRT
<213> ORGANISM: Homo sapiens

<400> SEQUENCE: 83

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Thr Thr Phe Gly Trp Gln Leu Thr Phe Gly Lys Gly Thr Lys Leu
            100                 105                 110

Ser Val Ile Pro
        115

<210> SEQ ID NO 84
<211> LENGTH: 116
<212> TYPE: PRT
<213> ORGANISM: Homo sapiens

<400> SEQUENCE: 84

Gln Ser Val Ala Gln Pro Glu Asp Gln Val Asn Val Ala Glu Gly Asn
1               5                   10                  15

```
Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Ala Leu Val Thr Tyr Gln Leu Thr Phe Gly Lys Gly Thr Lys Leu
            100                 105                 110

Ser Val Ile Pro
            115

<210> SEQ ID NO 85
<211> LENGTH: 116
<212> TYPE: PRT
<213> ORGANISM: Homo sapiens

<400> SEQUENCE: 85

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Pro Arg Leu Met Trp Gln Leu Thr Phe Gly Lys Gly Thr Lys Leu
            100                 105                 110

Ser Val Ile Pro
            115

<210> SEQ ID NO 86
<211> LENGTH: 116
<212> TYPE: PRT
<213> ORGANISM: Homo sapiens

<400> SEQUENCE: 86

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95
```

```
Ser Ala Thr Val Asp Tyr Gln Leu Thr Phe Gly Lys Gly Thr Lys Leu
                100                 105                 110

Ser Val Ile Pro
        115

<210> SEQ ID NO 87
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (94)..(94)
<223> OTHER INFORMATION: /replace="Asp" or "Gly" or "Ser"
<220> FEATURE:
<221> NAME/KEY: VARIANT
<222> LOCATION: (95)..(95)
<223> OTHER INFORMATION: /replace="Ile" or "Ser" or "Gly" or "Asp" or
      "Gln" or "Met" or "Val"
<220> FEATURE:
<221> NAME/KEY: VARIANT
<222> LOCATION: (96)..(96)
<223> OTHER INFORMATION: /replace="Lys" or "Phe" or "Leu" or "Arg" or
      "Ser" or "Ala" or "Thr"
<220> FEATURE:
<221> NAME/KEY: VARIANT
<222> LOCATION: (97)..(97)
<223> OTHER INFORMATION: /replace="Glu" or "Asn" or "Thr" or "Asp" or
      "Val" or "Leu" or "Ala" or "Cys" or "Gly"
<220> FEATURE:
<221> NAME/KEY: VARIANT
<222> LOCATION: (98)..(98)
<223> OTHER INFORMATION: /replace="Val" or "Arg" or "Thr" or "Ala" or
      "Pro"
<220> FEATURE:
<221> NAME/KEY: VARIANT
<222> LOCATION: (99)..(99)
<223> OTHER INFORMATION: /replace="Gly" or "Thr" or "Leu" or "Arg"
<220> FEATURE:
<221> NAME/KEY: VARIANT
<222> LOCATION: (100)..(100)
<223> OTHER INFORMATION: /replace="Val" or "Phe" or "Leu"
<220> FEATURE:
<221> NAME/KEY: VARIANT
<222> LOCATION: (101)..(101)
<223> OTHER INFORMATION: /replace="Arg" or "Lys" or "Gly" or "Thr" or
      "Met" or "Asp"
<220> FEATURE:
<221> NAME/KEY: VARIANT
<222> LOCATION: (102)..(102)
<223> OTHER INFORMATION: /replace="Trp"
<220> FEATURE:
<221> NAME/KEY: MISC_FEATURE
<222> LOCATION: (1)..(116)
<223> OTHER INFORMATION: /note="Variant residues given in the sequence
      have no preference with respect to those in the annotations
      for variant positions"

<400> SEQUENCE: 87

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80
```

```
Leu Val Ser Asp Ser Ala Leu Tyr Phe Cys Ala Val Arg Glu Leu Tyr
                85                  90                  95

Ser Gly Ala Gly Ser Tyr Gln Leu Thr Phe Gly Lys Gly Thr Lys Leu
            100                 105                 110

Ser Val Ile Pro
        115

<210> SEQ ID NO 88
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: MOD_RES
<222> LOCATION: (94)..(94)
<223> OTHER INFORMATION: /replace="Asp" or "Gly" or "Ser"
<220> FEATURE:
<221> NAME/KEY: MOD_RES
<222> LOCATION: (95)..(95)
<223> OTHER INFORMATION: /replace="Ile" or "Ser" or "Gly" or "Asp" or
      "Gln" or "Met" or "Val"
<220> FEATURE:
<221> NAME/KEY: MOD_RES
<222> LOCATION: (96)..(96)
<223> OTHER INFORMATION: /replace="Lys" or "Phe" or "Leu" or "Arg" or
      "Ser" or "Ala" or "Thr"
<220> FEATURE:
<221> NAME/KEY: MOD_RES
<222> LOCATION: (97)..(97)
<223> OTHER INFORMATION: /replace="Glu" or "Asn" or "Thr" or "Asp" or
      "Val" or "Leu" or "Ala" or "Cys" or "Gly"
<220> FEATURE:
<221> NAME/KEY: MISC_FEATURE
<222> LOCATION: (1)..(116)
<223> OTHER INFORMATION: /note="Variant residues given in the sequence
      have no preference with respect to those in the annotations
      for variant positions"

<400> SEQUENCE: 88

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Gly Ala Gly Ser Tyr Gln Leu Thr Phe Gly Lys Gly Thr Lys Leu
            100                 105                 110

Ser Val Ile Pro
        115

<210> SEQ ID NO 89
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
```

```
         Synthetic consensus sequence"
<220> FEATURE:
<221> NAME/KEY: VARIANT
<222> LOCATION: (98)..(98)
<223> OTHER INFORMATION: /replace="Val" or "Arg" or "Thr" or "Ala" or
      "Pro"
<220> FEATURE:
<221> NAME/KEY: VARIANT
<222> LOCATION: (99)..(99)
<223> OTHER INFORMATION: /replace="Gly" or "Thr" or "Leu" or "Arg"
<220> FEATURE:
<221> NAME/KEY: VARIANT
<222> LOCATION: (100)..(100)
<223> OTHER INFORMATION: /replace="Val" or "Phe" or "Leu"
<220> FEATURE:
<221> NAME/KEY: VARIANT
<222> LOCATION: (101)..(101)
<223> OTHER INFORMATION: /replace="Arg" or "Lys" or "Gly" or "Thr" or
      "Met" or "Asp"
<220> FEATURE:
<221> NAME/KEY: VARIANT
<222> LOCATION: (102)..(102)
<223> OTHER INFORMATION: /replace="Trp"
<220> FEATURE:
<221> NAME/KEY: MISC_FEATURE
<222> LOCATION: (1)..(116)
<223> OTHER INFORMATION: /note="Variant residues given in the sequence
      have no preference with respect to those in the annotations
      for variant positions"

<400> SEQUENCE: 89

Gln Ser Val Ala Gln Pro Glu Asp Gln Val Asn Val Ala Glu Gly Asn
1               5                  10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Gly Ala Gly Ser Tyr Gln Leu Thr Phe Gly Lys Gly Thr Lys Leu
            100                 105                 110

Ser Val Ile Pro
        115

<210> SEQ ID NO 90
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (94)..(94)
<223> OTHER INFORMATION: /replace="Glu"
<220> FEATURE:
<221> NAME/KEY: VARIANT
<222> LOCATION: (95)..(95)
<223> OTHER INFORMATION: /replace="Leu" or "Met" or "Ile" or "Val"
<220> FEATURE:
<221> NAME/KEY: VARIANT
<222> LOCATION: (96)..(96)
<223> OTHER INFORMATION: /replace="Ala" or "Lys" or "Ser" or "Phe" or
      "Tyr"
<220> FEATURE:
```

```
<221> NAME/KEY: VARIANT
<222> LOCATION: (97)..(97)
<223> OTHER INFORMATION: /replace="Asn" or "Ser" or "Asp" or "Thr"
<220> FEATURE:
<221> NAME/KEY: MISC_FEATURE
<222> LOCATION: (1)..(116)
<223> OTHER INFORMATION: /note="Variant residues given in the sequence
      have no preference with respect to those in the annotations
      for variant positions"

<400> SEQUENCE: 90

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Asp Leu
                85                  90                  95

Val Gly Ala Gly Ser Tyr Gln Leu Thr Phe Gly Lys Gly Thr Lys Leu
            100                 105                 110

Ser Val Ile Pro
            115

<210> SEQ ID NO 91
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: VARIANT
<222> LOCATION: (95)..(95)
<223> OTHER INFORMATION: /replace="Leu" or "Met" or "Ile" or "Val"
<220> FEATURE:
<221> NAME/KEY: VARIANT
<222> LOCATION: (96)..(96)
<223> OTHER INFORMATION: /replace="Ala" or "Lys" or "Ser" or "Phe"
<220> FEATURE:
<221> NAME/KEY: VARIANT
<222> LOCATION: (97)..(97)
<223> OTHER INFORMATION: /replace="Asn" or "Ser" or "Asp" or "Thr"
<220> FEATURE:
<221> NAME/KEY: MISC_FEATURE
<222> LOCATION: (1)..(116)
<223> OTHER INFORMATION: /note="Variant residues given in the sequence
      have no preference with respect to those in the annotations
      for variant positions"

<400> SEQUENCE: 91

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
```

```
65                  70                  75                  80

Leu Val Ser Asp Ser Ala Leu Tyr Phe Cys Ala Val Arg Asp Leu
                85                  90                  95

Val Gly Ala Gly Ser Tyr Gln Leu Thr Phe Gly Lys Gly Thr Lys Leu
            100                 105                 110

Ser Val Ile Pro
        115

<210> SEQ ID NO 92
<211> LENGTH: 137
<212> TYPE: PRT
<213> ORGANISM: Mus sp.

<400> SEQUENCE: 92

Tyr Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Thr
            35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 93
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Gly Ala Gly Ser Tyr Gln Leu Thr Phe Gly Lys Gly Thr Lys Leu
            100                 105                 110
```

```
Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
            165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
            195                 200                 205

Ser Ser Cys Asp Val Lys Leu Val Glu Lys Ser Phe Glu Thr Asp Thr
            210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
            245                 250                 255

Ser Gly Ser

<210> SEQ ID NO 94
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
            165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
            195                 200                 205
```

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala Lys Arg
            260

<210> SEQ ID NO 95
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala

<210> SEQ ID NO 96
<211> LENGTH: 278
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 96

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Gly Ser Gly Ala Thr Asn Phe Ser Leu Leu Lys Gln Ala Gly Asp
            260                 265                 270

Val Glu Glu Asn Pro Gly
        275

<210> SEQ ID NO 97
<211> LENGTH: 289
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 97

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

```
Gln Pro Gly Gln Ser Leu Thr Leu Ile Ala Thr Ala Asn Gln Gly Ser
            35                  40                  45

Glu Ala Thr Tyr Glu Ser Gly Phe Val Ile Asp Lys Phe Pro Ile Ser
 50                  55                  60

Arg Pro Asn Leu Thr Phe Ser Thr Leu Thr Val Ser Asn Met Ser Pro
 65                  70                  75                  80

Glu Asp Ser Ser Ile Tyr Leu Cys Ser Val Gly Gly Ala Gly Val Thr
                 85                  90                  95

Asp Thr Gln Tyr Phe Gly Pro Gly Thr Arg Leu Thr Val Leu Glu Asp
            100                 105                 110

Leu Asn Lys Val Phe Pro Pro Glu Val Ala Val Phe Glu Pro Ser Glu
            115                 120                 125

Ala Glu Ile Ser His Thr Gln Lys Ala Thr Leu Val Cys Leu Ala Thr
130                 135                 140

Gly Phe Phe Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
        195                 200                 205

Gln Phe Tyr Gly Leu Ser Glu Asn Asp Glu Trp Thr Gln Asp Arg Ala
210                 215                 220

Lys Pro Val Thr Gln Ile Val Ser Ala Glu Ala Trp Gly Arg Ala Asp
225                 230                 235                 240

Cys Gly Phe Thr Ser Val Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe Gly
        275                 280                 285

Ser

<210> SEQ ID NO 98
<211> LENGTH: 291
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Lys Pro Ser Arg Asp Ile Cys Gln Arg Gly Thr Ser Leu Thr Ile
 1               5                  10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
            35                  40                  45

Glu Ala Thr Tyr Glu Ser Gly Phe Val Ile Asp Lys Phe Pro Ile Ser
 50                  55                  60

Arg Pro Asn Leu Thr Phe Ser Thr Leu Thr Val Ser Asn Met Ser Pro
 65                  70                  75                  80

Glu Asp Ser Ser Ile Tyr Leu Cys Ser Val Gly Gly Ala Gly Val Thr
```

-continued

```
                    85                  90                  95
Asp Thr Gln Tyr Phe Gly Pro Gly Thr Arg Leu Thr Val Leu Glu Asp
                100                 105                 110

Leu Lys Asn Val Phe Pro Pro Glu Val Ala Val Phe Glu Pro Ser Glu
            115                 120                 125

Ala Glu Ile Ser His Thr Gln Lys Ala Thr Leu Val Cys Leu Ala Thr
130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
        195                 200                 205

Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

Cys Gly Phe Thr Ser Glu Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Ser Arg
        275                 280                 285

Gly Gly Ser
    290

<210> SEQ ID NO 99
<211> LENGTH: 291
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
        35                  40                  45

Glu Ala Thr Tyr Glu Ser Gly Phe Val Ile Asp Lys Phe Pro Ile Ser
    50                  55                  60

Arg Pro Asn Leu Thr Phe Ser Thr Leu Thr Val Ser Asn Met Ser Pro
65                  70                  75                  80

Glu Asp Ser Ser Ile Tyr Leu Cys Ser Val Gly Gly Ala Gly Val Thr
                85                  90                  95

Asp Thr Gln Tyr Phe Gly Pro Gly Thr Arg Leu Thr Val Leu Glu Asp
                100                 105                 110

Leu Asn Lys Val Phe Pro Pro Glu Val Ala Val Phe Glu Pro Ser Glu
            115                 120                 125

Ala Glu Ile Ser His Thr Gln Lys Ala Thr Leu Val Cys Leu Ala Thr
130                 135                 140
```

```
Gly Phe Phe Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
            165                 170                 175

Pro Ala Leu Asn Asp Ser Arg Tyr Cys Leu Ser Ser Arg Leu Arg Val
        180                 185                 190

Ser Ala Thr Phe Trp Gln Asn Pro Arg Asn His Phe Arg Cys Gln Val
    195                 200                 205

Gln Phe Tyr Gly Leu Ser Glu Asn Asp Glu Trp Thr Gln Asp Arg Ala
210                 215                 220

Lys Pro Val Thr Gln Ile Val Ser Ala Glu Ala Trp Gly Arg Ala Asp
225                 230                 235                 240

Cys Gly Phe Thr Ser Val Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe Arg
        275                 280                 285

Ala Lys Arg
    290

<210> SEQ ID NO 100
<211> LENGTH: 293
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
        35                  40                  45

Glu Ala Thr Tyr Glu Ser Gly Phe Val Ile Asp Lys Phe Pro Ile Ser
50                  55                  60

Arg Pro Asn Leu Thr Phe Ser Thr Leu Thr Val Ser Asn Met Ser Pro
65                  70                  75                  80

Glu Asp Ser Ser Ile Tyr Leu Cys Ser Val Gly Gly Ala Gly Val Thr
                85                  90                  95

Asp Thr Gln Tyr Phe Gly Pro Gly Thr Arg Leu Thr Val Leu Glu Asp
            100                 105                 110

Leu Lys Asn Val Phe Pro Pro Glu Val Ala Val Phe Glu Pro Ser Glu
        115                 120                 125

Ala Glu Ile Ser His Thr Gln Lys Ala Thr Leu Val Cys Leu Ala Thr
130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
            165                 170                 175

Pro Ala Leu Asn Asp Ser Arg Tyr Cys Leu Ser Ser Arg Leu Arg Val
        180                 185                 190
```

```
Ser Ala Thr Phe Trp Gln Asn Pro Arg Asn His Phe Arg Cys Gln Val
            195                 200                 205

Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

Cys Gly Phe Thr Ser Glu Ser Tyr Gln Gln Gly Val Leu Ser Ala Thr
            245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Ser Arg
            275                 280                 285

Gly Arg Ala Lys Arg
            290

<210> SEQ ID NO 101
<211> LENGTH: 289
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
            35                  40                  45

Glu Ala Thr Tyr Glu Ser Gly Phe Val Ile Asp Lys Phe Pro Ile Ser
    50                  55                  60

Arg Pro Asn Leu Thr Phe Ser Thr Leu Thr Val Ser Asn Met Ser Pro
65                  70                  75                  80

Glu Asp Ser Ser Ile Tyr Leu Cys Ser Val Gly Gly Ala Gly Val Thr
                85                  90                  95

Asp Thr Gln Tyr Phe Gly Pro Gly Thr Arg Leu Thr Val Leu Glu Asp
            100                 105                 110

Leu Asn Lys Val Phe Pro Pro Glu Val Ala Val Phe Glu Pro Ser Glu
            115                 120                 125

Ala Glu Ile Ser His Thr Gln Lys Ala Thr Leu Val Cys Leu Ala Thr
    130                 135                 140

Gly Phe Phe Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
            165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
            195                 200                 205

Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

Cys Gly Phe Thr Ser Val Ser Tyr Gln Gln Gly Val Leu Ser Ala Thr
```

245                 250                 255
Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe Arg
            275                 280                 285

Ala

<210> SEQ ID NO 102
<211> LENGTH: 291
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
        35                  40                  45

Glu Ala Thr Tyr Glu Ser Gly Phe Val Ile Asp Lys Phe Pro Ile Ser
    50                  55                  60

Arg Pro Asn Leu Thr Phe Ser Thr Leu Thr Val Ser Asn Met Ser Pro
65                  70                  75                  80

Glu Asp Ser Ser Ile Tyr Leu Cys Ser Val Gly Ala Gly Val
                85                  90                  95

Asp Thr Gln Tyr Phe Gly Pro Gly Thr Arg Leu Thr Val Leu Glu Asp
            100                 105                 110

Leu Lys Asn Val Phe Pro Pro Glu Val Ala Val Phe Glu Pro Ser Glu
        115                 120                 125

Ala Glu Ile Ser His Thr Gln Lys Ala Thr Leu Val Cys Leu Ala Thr
    130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
        195                 200                 205

Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

Cys Gly Phe Thr Ser Glu Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Ser Arg
        275                 280                 285

Gly Arg Ala
    290

```
<210> SEQ ID NO 103
<211> LENGTH: 308
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
        35                  40                  45

Glu Ala Thr Tyr Glu Ser Gly Phe Val Ile Asp Lys Phe Pro Ile Ser
    50                  55                  60

Arg Pro Asn Leu Thr Phe Ser Thr Leu Thr Val Ser Asn Met Ser Pro
65                  70                  75                  80

Glu Asp Ser Ser Ile Tyr Leu Cys Ser Val Gly Gly Ala Gly Val Thr
                85                  90                  95

Asp Thr Gln Tyr Phe Gly Pro Gly Thr Arg Leu Thr Val Leu Glu Asp
            100                 105                 110

Leu Asn Lys Val Phe Pro Pro Glu Val Ala Val Phe Glu Pro Ser Glu
        115                 120                 125

Ala Glu Ile Ser His Thr Gln Lys Ala Thr Leu Val Cys Leu Ala Thr
    130                 135                 140

Gly Phe Phe Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
        195                 200                 205

Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

Cys Gly Phe Thr Ser Val Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Phe Gly
        275                 280                 285

Ser Gly Ala Thr Asn Phe Ser Leu Leu Lys Gln Ala Gly Asp Val Glu
    290                 295                 300

Glu Asn Pro Gly
305

<210> SEQ ID NO 104
<211> LENGTH: 310
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic polypeptide"

<400> SEQUENCE: 104

Gln Lys Pro Ser Arg Asp Ile Cys Gln Arg Gly Thr Ser Leu Thr Ile
1               5                   10                  15

Gln Cys Gln Val Asp Ser Gln Val Thr Met Met Phe Trp Tyr Arg Gln
            20                  25                  30

Gln Pro Gly Gln Ser Leu Thr Leu Ile Ala Thr Ala Asn Gln Gly Ser
        35                  40                  45

Glu Ala Thr Tyr Glu Ser Gly Phe Val Ile Asp Lys Phe Pro Ile Ser
    50                  55                  60

Arg Pro Asn Leu Thr Phe Ser Thr Leu Thr Val Ser Asn Met Ser Pro
65                  70                  75                  80

Glu Asp Ser Ser Ile Tyr Leu Cys Ser Val Gly Gly Ala Gly Val Thr
                85                  90                  95

Asp Thr Gln Tyr Phe Gly Pro Gly Thr Arg Leu Thr Val Leu Glu Asp
            100                 105                 110

Leu Lys Asn Val Phe Pro Pro Glu Val Ala Val Phe Glu Pro Ser Glu
        115                 120                 125

Ala Glu Ile Ser His Thr Gln Lys Ala Thr Leu Val Cys Leu Ala Thr
    130                 135                 140

Gly Phe Tyr Pro Asp His Val Glu Leu Ser Trp Trp Val Asn Gly Lys
145                 150                 155                 160

Glu Val His Ser Gly Val Ser Thr Asp Pro Gln Pro Leu Lys Glu Gln
                165                 170                 175

Pro Ala Leu Asn Asp Ser Arg Tyr Cys Leu Ser Ser Arg Leu Arg Val
            180                 185                 190

Ser Ala Thr Phe Trp Gln Asn Pro Arg Asn His Phe Arg Cys Gln Val
        195                 200                 205

Gln Phe Tyr Gly Leu Ser Glu Asn Asp Glu Trp Thr Gln Asp Arg Ala
    210                 215                 220

Lys Pro Val Thr Gln Ile Val Ser Ala Glu Ala Trp Gly Arg Ala Asp
225                 230                 235                 240

Cys Gly Phe Thr Ser Glu Ser Tyr Gln Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Ala Leu Val Leu Met Ala Met Val Lys Arg Lys Asp Ser Arg
        275                 280                 285

Gly Gly Ser Gly Ala Thr Asn Phe Ser Leu Leu Lys Gln Ala Gly Asp
    290                 295                 300

Val Glu Glu Asn Pro Gly
305                 310

<210> SEQ ID NO 105
<211> LENGTH: 257
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 105

Gln Ser Val Ala Gln Pro Glu Asp Gln Val Asn Val Ala Glu Gly Asn
1               5                   10                  15

```
Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Ile Lys
                85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
            165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
            195                 200                 205

Ser Ser Cys Asp Val Lys Leu Val Glu Lys Ser Phe Glu Thr Asp Thr
            210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser
```

<210> SEQ ID NO 106
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 106

```
Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Ile Lys
                85                  90                  95

Ser Gly Ala Gly Ser Tyr Gln Leu Thr Phe Gly Lys Gly Thr Lys Leu
```

```
                    100                 105                 110
Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
            165                 170                 175

Ser Ala Val Ala Trp Ser Asn Lys Ser Asp Phe Ala Cys Ala Asn Ala
        180                 185                 190

Phe Asn Asn Ser Ile Ile Pro Glu Asp Thr Phe Phe Pro Ser Pro Glu
    195                 200                 205

Ser Ser Cys Asp Val Lys Leu Val Glu Lys Ser Phe Glu Thr Asp Thr
        210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
            245                 250                 255

Ser Gly Ser

<210> SEQ ID NO 107
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Ile Lys
                85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190
```

```
Phe Asn Asn Ser Ile Ile Pro Glu Asp Thr Phe Phe Pro Ser Pro Glu
            195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
            245                 250                 255

Ser Arg Ala Lys Arg
            260

<210> SEQ ID NO 108
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Ile Lys
                85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala

<210> SEQ ID NO 109
```

```
<211> LENGTH: 278
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109
```

| | | | | | | | | | | | | | | |
|---|---|---|---|---|---|---|---|---|---|---|---|---|---|---|
| Gln | Ser | Val | Ala | Gln | Pro | Glu | Asp | Gln | Val | Asn | Val | Ala | Glu | Gly | Asn |
| 1 | | | | 5 | | | | | 10 | | | | | 15 | |

| | | | | | | | | | | | | | |
|---|---|---|---|---|---|---|---|---|---|---|---|---|---|
| Pro | Leu | Thr | Val | Lys | Cys | Thr | Tyr | Ser | Val | Ser | Gly | Asn | Pro | Tyr | Leu |
| | | | 20 | | | | | 25 | | | | | 30 | | |

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Ile Lys
                85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Gly Ser Gly Ala Thr Asn Phe Ser Leu Leu Lys Gln Ala Gly Asp
            260                 265                 270

Val Glu Glu Asn Pro Gly
            275

```
<210> SEQ ID NO 110
<211> LENGTH: 257
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110
```

Gln Ser Val Ala Gln Pro Glu Asp Gln Val Asn Val Ala Glu Gly Asn
1               5                   10                  15

-continued

```
Pro Leu Thr Val Lys Cys Thr Tyr Ser Val Ser Gly Asn Pro Tyr Leu
             20                  25                  30

Phe Trp Tyr Val Gln Tyr Pro Asn Arg Gly Leu Gln Phe Leu Leu Lys
         35                  40                  45

Tyr Ile Thr Gly Asp Asn Leu Val Lys Gly Ser Tyr Gly Phe Glu Ala
     50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Phe
                 85                  90                  95

Thr Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser
```

<210> SEQ ID NO 111
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 111

```
Gln Ser Val Ala Gln Pro Glu Asp Gln Val Asn Val Ala Glu Gly Asn
1               5                  10                  15

Pro Leu Thr Val Lys Cys Thr Tyr Ser Val Ser Gly Asn Pro Tyr Leu
             20                  25                  30

Phe Trp Tyr Val Gln Tyr Pro Asn Arg Gly Leu Gln Phe Leu Leu Lys
         35                  40                  45

Tyr Ile Thr Gly Asp Asn Leu Val Lys Gly Ser Tyr Gly Phe Glu Ala
     50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Phe
                 85                  90                  95

Thr Gly Ala Gly Ser Tyr Gln Leu Thr Phe Gly Lys Gly Thr Lys Leu
            100                 105                 110
```

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
            165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
            195                 200                 205

Ser Ser Cys Asp Val Lys Leu Val Glu Lys Ser Phe Glu Thr Asp Thr
            210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
            245                 250                 255

Ser Gly Ser

<210> SEQ ID NO 112
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Phe
                85                  90                  95

Thr Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
            165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu

```
              195                 200                 205
Ser Ser Cys Asp Val Lys Leu Val Glu Lys Ser Phe Glu Thr Asp Thr
210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala Lys Arg
            260

<210> SEQ ID NO 113
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Phe
                85                  90                  95

Thr Gly Ala Gly Ser Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
            195                 200                 205

Ser Ser Cys Asp Val Lys Leu Val Glu Lys Ser Phe Glu Thr Asp Thr
210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala

<210> SEQ ID NO 114
<211> LENGTH: 278
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 114

```
Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Phe
                85                  90                  95

Thr Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Gly Ser Gly Ala Thr Asn Phe Ser Leu Leu Lys Gln Ala Gly Asp
            260                 265                 270

Val Glu Glu Asn Pro Gly
        275
```

<210> SEQ ID NO 115
<211> LENGTH: 257
<212> TYPE: PRT
<213> ORGANISM: Homo sapiens

<400> SEQUENCE: 115

```
Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45
```

```
Tyr Ile Thr Gly Asp Asn Leu Val Lys Gly Ser Tyr Gly Phe Glu Ala
         50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Leu Ser
                     85                  90                  95

Asp Gly Ala Gly Ser Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
            130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
                180                 185                 190

Phe Asn Asn Ser Ile Ile Pro Glu Asp Thr Phe Phe Pro Ser Pro Glu
                195                 200                 205

Ser Ser Cys Asp Val Lys Leu Val Glu Lys Ser Phe Glu Thr Asp Thr
210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser

<210> SEQ ID NO 116
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gln Ser Val Ala Gln Pro Glu Asp Gln Val Asn Val Ala Glu Gly Asn
 1                   5                  10                  15

Pro Leu Thr Val Lys Cys Thr Tyr Ser Val Ser Gly Asn Pro Tyr Leu
                 20                  25                  30

Phe Trp Tyr Val Gln Tyr Pro Asn Arg Gly Leu Gln Phe Leu Leu Lys
             35                  40                  45

Tyr Ile Thr Gly Asp Asn Leu Val Lys Gly Ser Tyr Gly Phe Glu Ala
         50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Leu Ser
                     85                  90                  95

Asp Gly Ala Gly Ser Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
```

```
                130               135               140
Asp Ser Gln Thr Asn Val Ser Gln Ser Lys Asp Ser Asp Val Tyr Ile
145                 150               155                 160

Thr Asp Lys Thr Val Leu Asp Met Arg Ser Met Asp Phe Lys Ser Asn
                165               170               175

Ser Ala Val Ala Trp Ser Asn Lys Ser Asp Phe Ala Cys Ala Asn Ala
            180               185               190

Phe Asn Asn Ser Ile Ile Pro Glu Asp Thr Phe Phe Pro Ser Pro Glu
            195               200               205

Ser Ser Cys Asp Val Lys Leu Val Glu Lys Ser Phe Glu Thr Asp Thr
        210               215               220

Asn Leu Asn Phe Gln Asn Leu Ser Val Ile Gly Phe Arg Ile Leu Leu
225                 230               235                 240

Leu Lys Val Ala Gly Phe Asn Leu Leu Met Thr Leu Arg Leu Trp Ser
                245               250               255

Ser Arg Ala Lys Arg
                260

<210> SEQ ID NO 117
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Ser
                85                  90                  95

Asp Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220
```

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala

<210> SEQ ID NO 118
<211> LENGTH: 278
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Leu Ser
                85                  90                  95

Asp Gly Ala Gly Ser Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
        130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
                180                 185                 190

Phe Asn Asn Ser Ile Ile Pro Glu Asp Thr Phe Phe Pro Ser Pro Glu
            195                 200                 205

Ser Ser Cys Asp Val Lys Leu Val Glu Lys Ser Phe Glu Thr Asp Thr
        210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Gly Ser Gly Ala Thr Asn Phe Ser Leu Leu Lys Gln Ala Gly Asp
                260                 265                 270

Val Glu Glu Asn Pro Gly
            275

<210> SEQ ID NO 119

<400> SEQUENCE: 119

<210> SEQ ID NO 120
<211> LENGTH: 257
<212> TYPE: PRT
<213> ORGANISM: Homo sapiens

<400> SEQUENCE: 120

```
Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Asp Leu
                85                  90                  95

Val Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser
```

<210> SEQ ID NO 121
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 121

```
Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30
```

Phe Trp Tyr Val Gln Tyr Pro Asn Arg Gly Leu Gln Phe Leu Leu Lys
                35                  40                  45

Tyr Ile Thr Gly Asp Asn Leu Val Lys Gly Ser Tyr Gly Phe Glu Ala
 50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Asp Leu
                 85                  90                  95

Val Gly Ala Gly Ser Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu
                115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
                180                 185                 190

Phe Asn Asn Ser Ile Ile Pro Glu Asp Thr Phe Phe Pro Ser Pro Glu
                195                 200                 205

Ser Ser Cys Asp Val Lys Leu Val Glu Lys Ser Phe Glu Thr Asp Thr
                210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala Lys Arg
                260

<210> SEQ ID NO 122
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Gln Ser Val Ala Gln Pro Glu Asp Gln Val Asn Val Ala Glu Gly Asn
 1               5                  10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
                35                  40                  45

Tyr Ile Thr Gly Asp Asn Leu Val Lys Gly Ser Tyr Gly Phe Glu Ala
 50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Asp Leu
                 85                  90                  95

Val Gly Ala Gly Ser Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu

```
            115                 120                 125
Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
                195                 200                 205

Ser Ser Cys Asp Val Lys Leu Val Glu Lys Ser Phe Glu Thr Asp Thr
        210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala

<210> SEQ ID NO 123
<211> LENGTH: 278
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Asp Leu
                85                  90                  95

Val Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
                195                 200                 205
```

```
Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
            245                 250                 255

Ser Gly Ser Gly Ala Thr Asn Phe Ser Leu Leu Lys Gln Ala Gly Asp
        260                 265                 270

Val Glu Glu Asn Pro Gly
        275

<210> SEQ ID NO 124

<400> SEQUENCE: 124

000

<210> SEQ ID NO 125
<211> LENGTH: 257
<212> TYPE: PRT
<213> ORGANISM: Homo sapiens

<400> SEQUENCE: 125

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Met Ala
                85                  90                  95

Asn Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser
```

<210> SEQ ID NO 126
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 126

```
Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Met Ala
                85                  90                  95

Asn Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala Lys Arg
            260
```

<210> SEQ ID NO 127
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

```
Gln Ser Val Ala Gln Pro Glu Asp Gln Val Asn Val Ala Glu Gly Asn
1               5                   10                  15
```

```
Pro Leu Thr Val Lys Cys Thr Tyr Ser Val Ser Gly Asn Pro Tyr Leu
                 20                  25                  30

Phe Trp Tyr Val Gln Tyr Pro Asn Arg Gly Leu Gln Phe Leu Leu Lys
         35                  40                  45

Tyr Ile Thr Gly Asp Asn Leu Val Lys Gly Ser Tyr Gly Phe Glu Ala
     50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Met Ala
                 85                  90                  95

Asn Gly Ala Gly Ser Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu
                115                 120                 125

Arg Asp Ser Lys Ser Ser Asp Lys Ser Val Cys Leu Phe Thr Asp Phe
        130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
                180                 185                 190

Phe Asn Asn Ser Ile Ile Pro Glu Asp Thr Phe Phe Pro Ser Pro Glu
            195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala

<210> SEQ ID NO 128
<211> LENGTH: 278
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Gln Ser Val Ala Gln Pro Glu Asp Gln Val Asn Val Ala Glu Gly Asn
1                5                  10                  15

Pro Leu Thr Val Lys Cys Thr Tyr Ser Val Ser Gly Asn Pro Tyr Leu
                 20                  25                  30

Phe Trp Tyr Val Gln Tyr Pro Asn Arg Gly Leu Gln Phe Leu Leu Lys
         35                  40                  45

Tyr Ile Thr Gly Asp Asn Leu Val Lys Gly Ser Tyr Gly Phe Glu Ala
     50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Met Ala
                 85                  90                  95

Asn Gly Ala Gly Ser Tyr Gln Leu Thr Phe Gly Lys Gly Thr Lys Leu
                100                 105                 110
```

```
Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
        165                 170                 175

Ser Ala Val Ala Trp Ser Asn Lys Ser Asp Phe Ala Cys Ala Asn Ala
        180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
        210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Gly Ser Gly Ala Thr Asn Phe Ser Leu Leu Lys Gln Ala Gly Asp
        260                 265                 270

Val Glu Glu Asn Pro Gly
        275

<210> SEQ ID NO 129

<400> SEQUENCE: 129

000

<210> SEQ ID NO 130
<211> LENGTH: 37
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Ala Thr Asn Phe Ser Leu Leu Lys Gln Ala Gly Asp Val Glu Glu Asn
1               5                   10                  15

Pro Gly Pro Glu Gly Arg Gly Ser Leu Leu Thr Cys Gly Asp Val Glu
                20                  25                  30

Glu Asn Pro Gly Pro
        35

<210> SEQ ID NO 131
<211> LENGTH: 5
<212> TYPE: PRT
<213> ORGANISM: Unknown
<220> FEATURE:
<221> NAME/KEY: source
<223> OTHER INFORMATION: /note="Description of Unknown: Furin cleavage
      site sequence"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: /replace="Arg"
```

```
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations
      for variant positions"

<400> SEQUENCE: 131

Arg Xaa Lys Arg Ser
1               5

<210> SEQ ID NO 132
<211> LENGTH: 5
<212> TYPE: PRT
<213> ORGANISM: Unknown
<220> FEATURE:
<221> NAME/KEY: source
<223> OTHER INFORMATION: /note="Description of Unknown: Furin cleavage
      site sequence"

<400> SEQUENCE: 132

Arg Ala Lys Arg Ser
1               5

<210> SEQ ID NO 133
<211> LENGTH: 5
<212> TYPE: PRT
<213> ORGANISM: Unknown
<220> FEATURE:
<221> NAME/KEY: source
<223> OTHER INFORMATION: /note="Description of Unknown: Furin cleavage
      site sequence"
<220> FEATURE:
<221> NAME/KEY: VARIANT
<222> LOCATION: (2)..(2)
<223> OTHER INFORMATION: /replace="Arg"
<220> FEATURE:
<221> NAME/KEY: VARIANT
<222> LOCATION: (3)..(3)
<223> OTHER INFORMATION: /replace="Arg"
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations
      for variant positions"

<400> SEQUENCE: 133

Arg Lys Lys Arg Ser
1               5

<210> SEQ ID NO 134
<211> LENGTH: 22
<212> TYPE: PRT
<213> ORGANISM: Porcine teschovirus

<400> SEQUENCE: 134

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 135
<211> LENGTH: 21
<212> TYPE: PRT
<213> ORGANISM: Thosea asigna virus

<400> SEQUENCE: 135

Gly Ser Gly Glu Gly Arg Gly Ser Leu Leu Thr Cys Gly Asp Val Glu
```

```
                1               5                  10                  15

Glu Asn Pro Gly Pro
                20

<210> SEQ ID NO 136
<211> LENGTH: 23
<212> TYPE: PRT
<213> ORGANISM: Equine rhinitis A virus

<400> SEQUENCE: 136

Gly Ser Gly Gln Cys Thr Asn Tyr Ala Leu Leu Lys Leu Ala Gly Asp
1               5                   10                  15

Val Glu Ser Asn Pro Gly Pro
                20

<210> SEQ ID NO 137
<211> LENGTH: 25
<212> TYPE: PRT
<213> ORGANISM: Foot and mouth disease virus

<400> SEQUENCE: 137

Gly Ser Gly Val Lys Gln Thr Leu Asn Phe Asp Leu Leu Lys Leu Ala
1               5                   10                  15

Gly Asp Val Glu Ser Asn Pro Gly Pro
                20                  25

<210> SEQ ID NO 138
<211> LENGTH: 25
<212> TYPE: PRT
<213> ORGANISM: Cytoplasmic polyhedrosis virus

<400> SEQUENCE: 138

Gly Ser Gly Asp Val Phe Arg Ser Asn Tyr Asp Leu Leu Lys Leu Cys
1               5                   10                  15

Gly Asp Ile Glu Ser Asn Pro Gly Pro
                20                  25

<210> SEQ ID NO 139
<211> LENGTH: 25
<212> TYPE: PRT
<213> ORGANISM: Infectious flacherie virus

<400> SEQUENCE: 139

Gly Ser Gly Thr Leu Thr Arg Ala Lys Ile Glu Asp Glu Leu Ile Arg
1               5                   10                  15

Ala Gly Ile Glu Ser Asn Pro Gly Pro
                20                  25

<210> SEQ ID NO 140
<211> LENGTH: 43
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Gly Ser Gly Ala Thr Asn Phe Ser Leu Leu Lys Gln Ala Gly Asp Val
1               5                   10                  15

Glu Glu Asn Pro Gly Pro Gly Ser Gly Glu Gly Arg Gly Ser Leu Leu
                20                  25                  30
```

Thr Cys Gly Asp Val Glu Glu Asn Pro Gly Pro
        35                  40

<210> SEQ ID NO 141
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Glu Leu Tyr Ser Gly Ala Gly Ser Tyr Gln Leu Thr Phe Gly Lys
        115                 120                 125

Gly Thr Lys Leu Ser Val Ile Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Arg Ala Lys Arg Ser Gly Ser Gly Ala Thr Asn
        275                 280                 285

Phe Ser Leu Leu Lys Gln Ala Gly Asp Val Glu Glu Asn Pro Gly Pro
    290                 295                 300

Met Leu Ser Leu Leu Leu Leu Leu Gly Leu Gly Ser Val Phe Ser
305                 310                 315                 320

Ala Val Ile Ser Gln Lys Pro Ser Arg Asp Ile Cys Gln Arg Gly Thr
                325                 330                 335

Ser Leu Thr Ile Gln Cys Gln Val Asp Ser Gln Val Thr Met Met Phe 340                 345                 350

Trp Tyr Arg Gln Gln Pro Gly Gln Ser Leu Thr Leu Ile Ala Thr Ala
            355                 360                 365

Asn Gln Gly Ser Glu Ala Thr Tyr Glu Ser Gly Phe Val Ile Asp Lys
        370                 375                 380

Phe Pro Ile Ser Arg Pro Asn Leu Thr Phe Ser Thr Leu Thr Val Ser
385                 390                 395                 400

Asn Met Ser Pro Glu Asp Ser Ser Ile Tyr Leu Cys Ser Val Gly Gly
                405                 410                 415

Ala Gly Val Thr Asp Thr Gln Tyr Phe Gly Pro Gly Thr Arg Leu Thr
            420                 425                 430

Val Leu Glu Asp Leu Asn Lys Val Phe Pro Pro Glu Val Ala Val Phe
        435                 440                 445

Glu Pro Ser Glu Ala Glu Ile Ser His Thr Gln Lys Ala Thr Leu Val
    450                 455                 460

Cys Leu Ala Thr Gly Phe Phe Pro Asp His Val Glu Leu Ser Trp Trp
465                 470                 475                 480

Val Asn Gly Lys Glu Val His Ser Gly Val Ser Thr Asp Pro Gln Pro
                485                 490                 495

Leu Lys Glu Gln Pro Ala Leu Asn Asp Ser Arg Tyr Cys Leu Ser Ser
            500                 505                 510

Arg Leu Arg Val Ser Ala Thr Phe Trp Gln Asn Pro Arg Asn His Phe
        515                 520                 525

Arg Cys Gln Val Gln Phe Tyr Gly Leu Ser Glu Asn Asp Glu Trp Thr
    530                 535                 540

Gln Asp Arg Ala Lys Pro Val Thr Gln Ile Val Ser Ala Glu Ala Trp
545                 550                 555                 560

Gly Arg Ala Asp Cys Gly Phe Thr Ser Val Ser Tyr Gln Gln Gly Val
                565                 570                 575

Leu Ser Ala Thr Ile Leu Tyr Glu Ile Leu Leu Gly Lys Ala Thr Leu
            580                 585                 590

Tyr Ala Val Leu Val Ser Ala Leu Val Leu Met Ala Met Val Lys Arg
        595                 600                 605

Lys Asp Phe Gly Ser
    610

<210> SEQ ID NO 142
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

```
Gly Phe Glu Ala Glu Phe Asn Lys Ser Gln Thr Ser Phe His Leu Lys
                85                  90                  95
Lys Pro Ser Ala Leu Val Ser Asp Ser Ala Leu Tyr Phe Cys Ala Val
            100                 105                 110
Arg Glu Leu Tyr Ser Gly Ala Gly Ser Tyr Gln Leu Thr Phe Gly Lys
        115                 120                 125
Gly Thr Lys Leu Ser Val Ile Pro Asn Ile Gln Asn Pro Asp Pro Ala
    130                 135                 140
Val Tyr Gln Leu Arg Asp Ser Lys Ser Ser Asp Lys Ser Val Cys Leu
145                 150                 155                 160
Phe Thr Asp Phe Asp Ser Gln Thr Asn Val Ser Gln Ser Lys Asp Ser
            165                 170                 175
Asp Val Tyr Ile Thr Asp Lys Thr Val Leu Asp Met Arg Ser Met Asp
        180                 185                 190
Phe Lys Ser Asn Ser Ala Val Ala Trp Ser Asn Lys Ser Asp Phe Ala
    195                 200                 205
Cys Ala Asn Ala Phe Asn Asn Ser Ile Ile Pro Glu Asp Thr Phe Phe
210                 215                 220
Pro Ser Pro Glu Ser Ser Cys Asp Val Lys Leu Val Glu Lys Ser Phe
225                 230                 235                 240
Glu Thr Asp Thr Asn Leu Asn Phe Gln Asn Leu Ser Val Ile Gly Phe
            245                 250                 255
Arg Ile Leu Leu Leu Lys Val Ala Gly Phe Asn Leu Leu Met Thr Leu
        260                 265                 270
Arg Leu Trp Ser Ser Gly Ser Gly Ala Thr Asn Phe Ser Leu Leu Lys
        275                 280                 285
Gln Ala Gly Asp Val Glu Glu Asn Pro Gly Pro Met Leu Ser Leu Leu
    290                 295                 300
Leu Leu Leu Leu Gly Leu Gly Ser Val Phe Ser Ala Val Ile Ser Gln
305                 310                 315                 320
Lys Pro Ser Arg Asp Ile Cys Gln Arg Gly Thr Ser Leu Thr Ile Gln
            325                 330                 335
Cys Gln Val Asp Ser Gln Val Thr Met Met Phe Trp Tyr Arg Gln Gln
        340                 345                 350
Pro Gly Gln Ser Leu Thr Leu Ile Ala Thr Ala Asn Gln Gly Ser Glu
    355                 360                 365
Ala Thr Tyr Glu Ser Gly Phe Val Ile Asp Lys Phe Pro Ile Ser Arg
    370                 375                 380
Pro Asn Leu Thr Phe Ser Thr Leu Thr Val Ser Asn Met Ser Pro Glu
385                 390                 395                 400
Asp Ser Ser Ile Tyr Leu Cys Ser Val Gly Gly Ala Gly Val Thr Asp
            405                 410                 415
Thr Gln Tyr Phe Gly Pro Gly Thr Arg Leu Thr Val Leu Glu Asp Leu
        420                 425                 430
Asn Lys Val Phe Pro Pro Glu Val Ala Val Phe Glu Pro Ser Glu Ala
    435                 440                 445
Glu Ile Ser His Thr Gln Lys Ala Thr Leu Val Cys Leu Ala Thr Gly
    450                 455                 460
Phe Phe Pro Asp His Val Glu Leu Ser Trp Trp Val Asn Gly Lys Glu
465                 470                 475                 480
Val His Ser Gly Val Ser Thr Asp Pro Gln Pro Leu Lys Glu Gln Pro
            485                 490                 495
```

```
Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
            515                 520                 525

Phe Tyr Gly Leu Ser Glu Asn Asp Glu Trp Thr Gln Asp Arg Ala Lys
            530                 535                 540

Pro Val Thr Gln Ile Val Ser Ala Glu Ala Trp Gly Arg Ala Asp Cys
545                 550                 555                 560

Gly Phe Thr Ser Val Ser Tyr Gln Gln Gly Val Leu Ser Ala Thr Ile
            565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Phe
            595                 600                 605

<210> SEQ ID NO 143
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
            35                  40                  45

Asn Pro Tyr Leu Phe Trp Tyr Val Gln Tyr Pro Asn Arg Gly Leu Gln
        50                  55                  60

Phe Leu Leu Lys Tyr Ile Thr Gly Asp Asn Leu Val Lys Gly Ser Tyr
65              70                  75                  80

Gly Phe Glu Ala Glu Phe Asn Lys Ser Gln Thr Ser Phe His Leu Lys
            85                  90                  95

Lys Pro Ser Ala Leu Val Ser Asp Ser Ala Leu Tyr Phe Cys Ala Val
            100                 105                 110

Arg Glu Leu Tyr Ser Gly Ala Gly Ser Tyr Gln Leu Thr Phe Gly Lys
            115                 120                 125

Gly Thr Lys Leu Ser Val Ile Pro Asn Ile Gln Asn Pro Asp Pro Ala
            130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
            165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
            210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
```

```
                    245                 250                 255
Arg Ile Leu Leu Leu Lys Val Ala Gly Phe Asn Leu Leu Met Thr Leu
                260                 265                 270
Arg Leu Trp Ser Ser Gly Ser Gly Ala Thr Asn Phe Ser Leu Leu Lys
            275                 280                 285
Gln Ala Gly Asp Val Glu Glu Asn Pro Gly Pro Met Leu Ser Leu Leu
        290                 295                 300
Leu Leu Leu Leu Gly Leu Gly Ser Val Phe Ser Ala Val Ile Ser Gln
305                 310                 315                 320
Lys Pro Ser Arg Asp Ile Cys Gln Arg Gly Thr Ser Leu Thr Ile Gln
                325                 330                 335
Cys Gln Val Asp Ser Gln Val Thr Met Met Phe Trp Tyr Arg Gln Gln
            340                 345                 350
Pro Gly Gln Ser Leu Thr Leu Ile Ala Thr Ala Asn Gln Gly Ser Glu
        355                 360                 365
Ala Thr Tyr Glu Ser Gly Phe Val Ile Asp Lys Phe Pro Ile Ser Arg
370                 375                 380
Pro Asn Leu Thr Phe Ser Thr Leu Thr Val Ser Asn Met Ser Pro Glu
385                 390                 395                 400
Asp Ser Ser Ile Tyr Leu Cys Ser Val Gly Ala Gly Val Thr Asp
                405                 410                 415
Thr Gln Tyr Phe Gly Pro Gly Thr Arg Leu Thr Val Leu Glu Asp Leu
            420                 425                 430
Asn Lys Val Phe Pro Pro Glu Val Ala Val Phe Glu Pro Ser Glu Ala
        435                 440                 445
Glu Ile Ser His Thr Gln Lys Ala Thr Leu Val Cys Leu Ala Thr Gly
        450                 455                 460
Phe Phe Pro Asp His Val Glu Leu Ser Trp Trp Val Asn Gly Lys Glu
465                 470                 475                 480
Val His Ser Gly Val Ser Thr Asp Pro Gln Pro Leu Lys Glu Gln Pro
                485                 490                 495
Ala Leu Asn Asp Ser Arg Tyr Cys Leu Ser Ser Arg Leu Arg Val Ser
            500                 505                 510
Ala Thr Phe Trp Gln Asn Pro Arg Asn His Phe Arg Cys Gln Val Gln
        515                 520                 525
Phe Tyr Gly Leu Ser Glu Asn Asp Glu Trp Thr Gln Asp Arg Ala Lys
        530                 535                 540
Pro Val Thr Gln Ile Val Ser Ala Glu Ala Trp Gly Arg Ala Asp Cys
545                 550                 555                 560
Gly Phe Thr Ser Val Ser Tyr Gln Gln Gly Val Leu Ser Ala Thr Ile
                565                 570                 575
Leu Tyr Glu Ile Leu Leu Gly Lys Ala Thr Leu Tyr Ala Val Leu Val
            580                 585                 590
Ser Ala Leu Val Leu Met Ala Met Val Lys Arg Lys Asp Phe Gly Ser
        595                 600                 605
```

<210> SEQ ID NO 144

<400> SEQUENCE: 144

000

<210> SEQ ID NO 145

<400> SEQUENCE: 145

<210> SEQ ID NO 146
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 146

```
Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
                100                 105                 110

Ala Gly Val Thr Asp Thr Gln Tyr Phe Gly Pro Gly Thr Arg Leu Thr
            115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Ala
                325                 330                 335

Ser Ala Pro Ile Ser Met Leu Ala Met Leu Phe Thr Leu Ser Gly Leu
```

```
              340                 345                 350

Arg Ala Gln Ser Val Ala Gln Pro Glu Asp Gln Val Asn Val Ala Glu
            355                 360                 365

Gly Asn Pro Leu Thr Val Lys Cys Thr Tyr Ser Val Ser Gly Asn Pro
        370                 375                 380

Tyr Leu Phe Trp Tyr Val Gln Tyr Pro Asn Arg Gly Leu Gln Phe Leu
385                 390                 395                 400

Leu Lys Tyr Ile Thr Gly Asp Asn Leu Val Lys Gly Ser Tyr Gly Phe
                405                 410                 415

Glu Ala Glu Phe Asn Lys Ser Gln Thr Ser Phe His Leu Lys Lys Pro
            420                 425                 430

Ser Ala Leu Val Ser Asp Ser Ala Leu Tyr Phe Cys Ala Val Arg Glu
        435                 440                 445

Leu Tyr Ser Gly Ala Gly Ser Tyr Gln Leu Thr Phe Gly Lys Gly Thr
    450                 455                 460

Lys Leu Ser Val Ile Pro Asn Ile Gln Asn Pro Asp Pro Ala Val Tyr
465                 470                 475                 480

Gln Leu Arg Asp Ser Lys Ser Ser Asp Lys Ser Val Cys Leu Phe Thr
                485                 490                 495

Asp Phe Asp Ser Gln Thr Asn Val Ser Gln Ser Lys Asp Ser Asp Val
            500                 505                 510

Tyr Ile Thr Asp Lys Thr Val Leu Asp Met Arg Ser Met Asp Phe Lys
        515                 520                 525

Ser Asn Ser Ala Val Ala Trp Ser Asn Lys Ser Asp Phe Ala Cys Ala
    530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
        595                 600                 605

Trp Ser Ser
    610

<210> SEQ ID NO 147
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80
```

```
Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
               100                 105                 110

Ala Gly Val Thr Asp Thr Gln Tyr Phe Gly Pro Gly Thr Arg Leu Thr
           115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
               165                 170                 175

Val Asn Gly Lys Glu Val His Ser Gly Val Ser Thr Asp Pro Gln Pro
           180                 185                 190

Leu Lys Glu Gln Pro Ala Leu Asn Asp Ser Arg Tyr Cys Leu Ser Ser
       195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
               245                 250                 255

Gly Arg Ala Asp Cys Gly Phe Thr Ser Val Ser Tyr Gln Gln Gly Val
           260                 265                 270

Leu Ser Ala Thr Ile Leu Tyr Glu Ile Leu Leu Gly Lys Ala Thr Leu
       275                 280                 285

Tyr Ala Val Leu Val Ser Ala Leu Val Leu Met Ala Met Val Lys Arg
290                 295                 300

Lys Asp Phe Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Ala
               325                 330                 335

Ser Ala Pro Ile Ser Met Leu Ala Met Leu Phe Thr Leu Ser Gly Leu
           340                 345                 350

Arg Ala Gln Ser Val Ala Gln Pro Glu Asp Gln Val Asn Val Ala Glu
       355                 360                 365

Gly Asn Pro Leu Thr Val Lys Cys Thr Tyr Ser Val Ser Gly Asn Pro
       370                 375                 380

Tyr Leu Phe Trp Tyr Val Gln Tyr Pro Asn Arg Gly Leu Gln Phe Leu
385                 390                 395                 400

Leu Lys Tyr Ile Thr Gly Asp Asn Leu Val Lys Gly Ser Tyr Gly Phe
               405                 410                 415

Glu Ala Glu Phe Asn Lys Ser Gln Thr Ser Phe His Leu Lys Lys Pro
           420                 425                 430

Ser Ala Leu Val Ser Asp Ser Ala Leu Tyr Phe Cys Ala Val Arg Glu
       435                 440                 445

Leu Tyr Ser Gly Ala Gly Ser Tyr Gln Leu Thr Phe Gly Lys Gly Thr
450                 455                 460

Lys Leu Ser Val Ile Pro Asn Ile Gln Asn Pro Asp Pro Ala Val Tyr
465                 470                 475                 480

Gln Leu Arg Asp Ser Lys Ser Ser Asp Lys Ser Val Cys Leu Phe Thr
               485                 490                 495
```

```
Asp Phe Asp Ser Gln Thr Asn Val Ser Gln Ser Lys Asp Ser Asp Val
            500                 505                 510

Tyr Ile Thr Asp Lys Thr Val Leu Asp Met Arg Ser Met Asp Phe Lys
        515                 520                 525

Ser Asn Ser Ala Val Ala Trp Ser Asn Lys Ser Asp Phe Ala Cys Ala
530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
            595                 600                 605

Trp Ser Ser Gly Ser
    610

<210> SEQ ID NO 148
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 148

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
                100                 105                 110

Ala Gly Val Thr Asp Thr Gln Tyr Phe Gly Pro Gly Thr Arg Leu Thr
            115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
```

```
        225                 230                 235                 240
Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
                260                 265                 270

Leu Ser Ala Thr Ile Leu Tyr Glu Ile Leu Leu Gly Lys Ala Thr Leu
                275                 280                 285

Tyr Ala Val Leu Val Ser Ala Leu Val Leu Met Ala Met Val Lys Arg
                290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
                340                 345                 350

Ala Gln Pro Glu Asp Gln Val Asn Val Ala Glu Gly Asn Pro Leu Thr
                355                 360                 365

Val Lys Cys Thr Tyr Ser Val Ser Gly Asn Pro Tyr Leu Phe Trp Tyr
370                 375                 380

Val Gln Tyr Pro Asn Arg Gly Leu Gln Phe Leu Leu Lys Tyr Ile Thr
385                 390                 395                 400

Gly Asp Asn Leu Val Lys Gly Ser Tyr Gly Phe Glu Ala Glu Phe Asn
                405                 410                 415

Lys Ser Gln Thr Ser Phe His Leu Lys Lys Pro Ser Ala Leu Val Ser
                420                 425                 430

Asp Ser Ala Leu Tyr Phe Cys Ala Val Arg Glu Leu Tyr Ser Gly Ala
                435                 440                 445

Gly Ser Tyr Gln Leu Thr Phe Gly Lys Gly Thr Lys Leu Ser Val Ile
                450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
                500                 505                 510

Thr Val Leu Asp Met Arg Ser Met Asp Phe Lys Ser Asn Ser Ala Val
                515                 520                 525

Ala Trp Ser Asn Lys Ser Asp Phe Ala Cys Ala Asn Ala Phe Asn Asn
530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
                580                 585                 590

Ala Gly Phe Asn Leu Leu Met Thr Leu Arg Leu Trp Ser Ser
                595                 600                 605

<210> SEQ ID NO 149
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 149

```
Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
        50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
                100                 105                 110

Ala Gly Val Thr Asp Thr Gln Tyr Phe Gly Pro Gly Thr Arg Leu Thr
                115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
                195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
                260                 265                 270

Leu Ser Ala Thr Ile Leu Tyr Glu Ile Leu Leu Gly Lys Ala Thr Leu
                275                 280                 285

Tyr Ala Val Leu Val Ser Ala Leu Val Leu Met Ala Met Val Lys Arg
                290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
                340                 345                 350

Ala Gln Pro Glu Asp Gln Val Asn Val Ala Glu Gly Asn Pro Leu Thr
                355                 360                 365

Val Lys Cys Thr Tyr Ser Val Ser Gly Asn Pro Tyr Leu Phe Trp Tyr
                370                 375                 380

Val Gln Tyr Pro Asn Arg Gly Leu Gln Phe Leu Leu Lys Tyr Ile Thr
385                 390                 395                 400
```

```
Gly Asp Asn Leu Val Lys Gly Ser Tyr Gly Phe Glu Ala Glu Phe Asn
            405                 410                 415

Lys Ser Gln Thr Ser Phe His Leu Lys Lys Pro Ser Ala Leu Val Ser
        420                 425                 430

Asp Ser Ala Leu Tyr Phe Cys Ala Val Arg Glu Leu Tyr Ser Gly Ala
        435                 440                 445

Gly Ser Tyr Gln Leu Thr Phe Gly Lys Gly Thr Lys Leu Ser Val Ile
    450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
            485                 490                 495

Thr Asn Val Ser Gln Ser Lys Asp Ser Asp Val Tyr Ile Thr Asp Lys
        500                 505                 510

Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
    530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
            565                 570                 575

Phe Gln Asn Leu Ser Val Ile Gly Phe Arg Ile Leu Leu Leu Lys Val
        580                 585                 590

Ala Gly Phe Asn Leu Leu Met Thr Leu Arg Leu Trp Ser Ser Gly Ser
    595                 600                 605

<210> SEQ ID NO 150

<400> SEQUENCE: 150

000

<210> SEQ ID NO 151

<400> SEQUENCE: 151

000

<210> SEQ ID NO 152
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 152

Met Lys Ser Val Leu Leu Leu Thr Thr Leu Leu Val Pro Ala His Leu
1               5                   10                  15

Val Ala Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
        35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80
```

```
Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
            340                 345                 350

Gly Leu Arg Ala Gln Ser Val Ala Gln Pro Glu Asp Gln Val Asn Val
        355                 360                 365

Ala Glu Gly Asn Pro Leu Thr Val Lys Cys Thr Tyr Ser Val Ser Gly
    370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
            420                 425                 430

Lys Pro Ser Ala Leu Val Ser Asp Ser Ala Leu Tyr Phe Cys Ala Val
        435                 440                 445

Arg Glu Leu Tyr Ser Gly Ala Gly Ser Tyr Gln Leu Thr Phe Gly Lys
    450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495
```

```
Phe Thr Asp Phe Asp Ser Gln Thr Asn Val Ser Gln Ser Lys Asp Ser
                500                 505                 510

Asp Val Tyr Ile Thr Asp Lys Thr Val Leu Asp Met Arg Ser Met Asp
        515                 520                 525

Phe Lys Ser Asn Ser Ala Val Ala Trp Ser Asn Lys Ser Asp Phe Ala
        530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
        580                 585                 590

Arg Ile Leu Leu Leu Lys Val Ala Gly Phe Asn Leu Leu Met Thr Leu
        595                 600                 605

Arg Leu Trp Ser Ser
    610

<210> SEQ ID NO 153
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

Met Lys Ser Val Leu Leu Thr Thr Leu Leu Val Pro Ala His Leu
1               5                   10                  15

Val Ala Ala Val Ile Ser Gln Lys Pro Ser Arg Asp Ile Cys Gln Arg
                20                  25                  30

Gly Thr Ser Leu Thr Ile Gln Cys Gln Val Asp Ser Gln Val Thr Met
        35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
                100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
```

```
           225                 230                 235                 240
Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
            290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
                340                 345                 350

Gly Leu Arg Ala Gln Ser Val Ala Gln Pro Glu Asp Gln Val Asn Val
                355                 360                 365

Ala Glu Gly Asn Pro Leu Thr Val Lys Cys Thr Tyr Ser Val Ser Gly
            370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
                420                 425                 430

Lys Pro Ser Ala Leu Val Ser Asp Ser Ala Leu Tyr Phe Cys Ala Val
                435                 440                 445

Arg Glu Leu Tyr Ser Gly Ala Gly Ser Tyr Gln Leu Thr Phe Gly Lys
                450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
                500                 505                 510

Asp Val Tyr Ile Thr Asp Lys Thr Val Leu Asp Met Arg Ser Met Asp
                515                 520                 525

Phe Lys Ser Asn Ser Ala Val Ala Trp Ser Asn Lys Ser Asp Phe Ala
            530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
                580                 585                 590

Arg Ile Leu Leu Leu Lys Val Ala Gly Phe Asn Leu Leu Met Thr Leu
                595                 600                 605

Arg Leu Trp Ser Ser Gly Ser
        610                 615

<210> SEQ ID NO 154
<211> LENGTH: 608
<212> TYPE: PRT
<213> ORGANISM: Artificial Sequence
```

<220> FEATURE:
<221> NAME/KEY: source
<223> OTHER INFORMATION: /note="Description of Artificial Sequence: Synthetic polypeptide"

<400> SEQUENCE: 154

```
Met Lys Ser Val Leu Leu Thr Thr Leu Leu Val Pro Ala His Leu
1               5                   10                  15

Val Ala Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
                35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ala Ser Ala Pro
                325                 330                 335

Ile Ser Met Leu Ala Met Leu Phe Thr Leu Ser Gly Leu Arg Ala Gln
            340                 345                 350

Ser Val Ala Gln Pro Glu Asp Gln Val Asn Val Ala Glu Gly Asn Pro
        355                 360                 365

Leu Thr Val Lys Cys Thr Tyr Ser Val Ser Gly Asn Pro Tyr Leu Phe
370                 375                 380
```

```
Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
            405                 410                 415

Phe Asn Lys Ser Gln Thr Ser Phe His Leu Lys Lys Pro Ser Ala Leu
        420                 425                 430

Val Ser Asp Ser Ala Leu Tyr Phe Cys Ala Val Arg Glu Leu Tyr Ser
    435                 440                 445

Gly Ala Gly Ser Tyr Gln Leu Thr Phe Gly Lys Gly Thr Lys Leu Ser
    450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
        515                 520                 525

Ala Val Ala Trp Ser Asn Lys Ser Asp Phe Ala Cys Ala Asn Ala Phe
    530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
        595                 600                 605

<210> SEQ ID NO 155
<211> LENGTH: 610
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

Met Lys Ser Val Leu Leu Thr Thr Leu Leu Val Pro Ala His Leu
1               5                   10                  15

Val Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
            35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
```

```
            130                 135                 140
Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
            210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ala Ser Ala Pro
            325                 330                 335

Ile Ser Met Leu Ala Met Leu Phe Thr Leu Ser Gly Leu Arg Ala Gln
            340                 345                 350

Ser Val Ala Gln Pro Glu Asp Gln Val Asn Val Ala Glu Gly Asn Pro
            355                 360                 365

Leu Thr Val Lys Cys Thr Tyr Ser Val Ser Gly Asn Pro Tyr Leu Phe
            370                 375                 380

Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
            405                 410                 415

Phe Asn Lys Ser Gln Thr Ser Phe His Leu Lys Lys Pro Ser Ala Leu
            420                 425                 430

Val Ser Asp Ser Ala Leu Tyr Phe Cys Ala Val Arg Glu Leu Tyr Ser
            435                 440                 445

Gly Ala Gly Ser Tyr Gln Leu Thr Phe Gly Lys Gly Thr Lys Leu Ser
            450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
            485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
            515                 520                 525

Ala Val Ala Trp Ser Asn Lys Ser Asp Phe Ala Cys Ala Asn Ala Phe
            530                 535                 540

Asn Asn Ser Ile Ile Pro Glu Asp Thr Phe Phe Pro Ser Pro Glu Ser
545                 550                 555                 560
```

```
Ser Cys Asp Val Lys Leu Val Glu Lys Ser Phe Glu Thr Asp Thr Asn
            565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
            595                 600                 605

Gly Ser
    610
```

<210> SEQ ID NO 156

<400> SEQUENCE: 156

000

<210> SEQ ID NO 157

<400> SEQUENCE: 157

000

<210> SEQ ID NO 158
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 158

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
            35                  40                  45

Asn Pro Tyr Leu Phe Trp Tyr Val Gln Tyr Pro Asn Arg Gly Leu Gln
50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
            85                  90                  95

Lys Pro Ser Ala Leu Val Ser Asp Ser Ala Leu Tyr Phe Cys Ala Val
            100                 105                 110

Arg Asp Ile Lys Ser Gly Ala Gly Ser Tyr Gln Leu Thr Phe Gly Lys
            115                 120                 125

Gly Thr Lys Leu Ser Val Ile Pro Asn Ile Gln Asn Pro Asp Pro Ala
            130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
            165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
```

```
            210                 215                 220
Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
                260                 265                 270

Arg Leu Trp Ser Ser Arg Ala Lys Arg Ser Gly Ser Gly Ala Thr Asn
            275                 280                 285

Phe Ser Leu Leu Lys Gln Ala Gly Asp Val Glu Glu Asn Pro Gly Pro
        290                 295                 300

Met Leu Ser Leu Leu Leu Leu Leu Gly Leu Gly Ser Val Phe Ser
305                 310                 315                 320

Ala Val Ile Ser Gln Lys Pro Ser Arg Asp Ile Cys Gln Arg Gly Thr
                325                 330                 335

Ser Leu Thr Ile Gln Cys Gln Val Asp Ser Gln Val Thr Met Met Phe
                340                 345                 350

Trp Tyr Arg Gln Gln Pro Gly Gln Ser Leu Thr Leu Ile Ala Thr Ala
            355                 360                 365

Asn Gln Gly Ser Glu Ala Thr Tyr Glu Ser Gly Phe Val Ile Asp Lys
        370                 375                 380

Phe Pro Ile Ser Arg Pro Asn Leu Thr Phe Ser Thr Leu Thr Val Ser
385                 390                 395                 400

Asn Met Ser Pro Glu Asp Ser Ser Ile Tyr Leu Cys Ser Val Gly Gly
                405                 410                 415

Ala Gly Val Thr Asp Thr Gln Tyr Phe Gly Pro Gly Thr Arg Leu Thr
                420                 425                 430

Val Leu Glu Asp Leu Asn Lys Val Phe Pro Pro Glu Val Ala Val Phe
            435                 440                 445

Glu Pro Ser Glu Ala Glu Ile Ser His Thr Gln Lys Ala Thr Leu Val
        450                 455                 460

Cys Leu Ala Thr Gly Phe Phe Pro Asp His Val Glu Leu Ser Trp Trp
465                 470                 475                 480

Val Asn Gly Lys Glu Val His Ser Gly Val Ser Thr Asp Pro Gln Pro
                485                 490                 495

Leu Lys Glu Gln Pro Ala Leu Asn Asp Ser Arg Tyr Cys Leu Ser Ser
                500                 505                 510

Arg Leu Arg Val Ser Ala Thr Phe Trp Gln Asn Pro Arg Asn His Phe
            515                 520                 525

Arg Cys Gln Val Gln Phe Tyr Gly Leu Ser Glu Asn Asp Glu Trp Thr
        530                 535                 540

Gln Asp Arg Ala Lys Pro Val Thr Gln Ile Val Ser Ala Glu Ala Trp
545                 550                 555                 560

Gly Arg Ala Asp Cys Gly Phe Thr Ser Val Ser Tyr Gln Gln Gly Val
                565                 570                 575

Leu Ser Ala Thr Ile Leu Tyr Glu Ile Leu Leu Gly Lys Ala Thr Leu
                580                 585                 590

Tyr Ala Val Leu Val Ser Ala Leu Val Leu Met Ala Met Val Lys Arg
            595                 600                 605

Lys Asp Phe
    610

<210> SEQ ID NO 159
```

<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 159

```
Met Ala Ser Ala Pro Ile Ser Met Leu Ala Met Leu Phe Thr Leu Ser
1               5                   10                  15
Gly Leu Arg Ala Gln Ser Val Ala Gln Pro Glu Asp Gln Val Asn Val
            20                  25                  30
Ala Glu Gly Asn Pro Leu Thr Val Lys Cys Thr Tyr Ser Val Ser Gly
        35                  40                  45
Asn Pro Tyr Leu Phe Trp Tyr Val Gln Tyr Pro Asn Arg Gly Leu Gln
    50                  55                  60
Phe Leu Leu Lys Tyr Ile Thr Gly Asp Asn Leu Val Lys Gly Ser Tyr
65                  70                  75                  80
Gly Phe Glu Ala Glu Phe Asn Lys Ser Gln Thr Ser Phe His Leu Lys
                85                  90                  95
Lys Pro Ser Ala Leu Val Ser Asp Ser Ala Leu Tyr Phe Cys Ala Val
            100                 105                 110
Arg Asp Ile Lys Ser Gly Ala Gly Ser Tyr Gln Leu Thr Phe Gly Lys
        115                 120                 125
Gly Thr Lys Leu Ser Val Ile Pro Asn Ile Gln Asn Pro Asp Pro Ala
130                 135                 140
Val Tyr Gln Leu Arg Asp Ser Lys Ser Ser Asp Lys Ser Val Cys Leu
145                 150                 155                 160
Phe Thr Asp Phe Asp Ser Gln Thr Asn Val Ser Gln Ser Lys Asp Ser
                165                 170                 175
Asp Val Tyr Ile Thr Asp Lys Thr Val Leu Asp Met Arg Ser Met Asp
            180                 185                 190
Phe Lys Ser Asn Ser Ala Val Ala Trp Ser Asn Lys Ser Asp Phe Ala
        195                 200                 205
Cys Ala Asn Ala Phe Asn Asn Ser Ile Ile Pro Glu Asp Thr Phe Phe
    210                 215                 220
Pro Ser Pro Glu Ser Ser Cys Asp Val Lys Leu Val Glu Lys Ser Phe
225                 230                 235                 240
Glu Thr Asp Thr Asn Leu Asn Phe Gln Asn Leu Ser Val Ile Gly Phe
                245                 250                 255
Arg Ile Leu Leu Leu Lys Val Ala Gly Phe Asn Leu Leu Met Thr Leu
            260                 265                 270
Arg Leu Trp Ser Ser Arg Ala Lys Arg Ser Gly Ser Gly Ala Thr Asn
        275                 280                 285
Phe Ser Leu Leu Lys Gln Ala Gly Asp Val Glu Glu Asn Pro Gly Pro
    290                 295                 300
Met Leu Ser Leu Leu Leu Leu Leu Gly Leu Gly Ser Val Phe Ser
305                 310                 315                 320
Ala Val Ile Ser Gln Lys Pro Ser Arg Asp Ile Cys Gln Arg Gly Thr
                325                 330                 335
Ser Leu Thr Ile Gln Cys Gln Val Asp Ser Gln Val Thr Met Met Phe
            340                 345                 350
Trp Tyr Arg Gln Gln Pro Gly Gln Ser Leu Thr Leu Ile Ala Thr Ala
        355                 360                 365
```

```
Asn Gln Gly Ser Glu Ala Thr Tyr Glu Ser Gly Phe Val Ile Asp Lys
    370                 375                 380

Phe Pro Ile Ser Arg Pro Asn Leu Thr Phe Ser Thr Leu Thr Val Ser
385                 390                 395                 400

Asn Met Ser Pro Glu Asp Ser Ser Ile Tyr Leu Cys Ser Val Gly Gly
                405                 410                 415

Ala Gly Val Thr Asp Thr Gln Tyr Phe Gly Pro Gly Thr Arg Leu Thr
            420                 425                 430

Val Leu Glu Asp Leu Asn Lys Val Phe Pro Pro Glu Val Ala Val Phe
        435                 440                 445

Glu Pro Ser Glu Ala Glu Ile Ser His Thr Gln Lys Ala Thr Leu Val
    450                 455                 460

Cys Leu Ala Thr Gly Phe Phe Pro Asp His Val Glu Leu Ser Trp Trp
465                 470                 475                 480

Val Asn Gly Lys Glu Val His Ser Gly Val Ser Thr Asp Pro Gln Pro
                485                 490                 495

Leu Lys Glu Gln Pro Ala Leu Asn Asp Ser Arg Tyr Cys Leu Ser Ser
            500                 505                 510

Arg Leu Arg Val Ser Ala Thr Phe Trp Gln Asn Pro Arg Asn His Phe
        515                 520                 525

Arg Cys Gln Val Gln Phe Tyr Gly Leu Ser Glu Asn Asp Glu Trp Thr
    530                 535                 540

Gln Asp Arg Ala Lys Pro Val Thr Gln Ile Val Ser Ala Glu Ala Trp
545                 550                 555                 560

Gly Arg Ala Asp Cys Gly Phe Thr Ser Val Ser Tyr Gln Gln Gly Val
                565                 570                 575

Leu Ser Ala Thr Ile Leu Tyr Glu Ile Leu Leu Gly Lys Ala Thr Leu
            580                 585                 590

Tyr Ala Val Leu Val Ser Ala Leu Val Leu Met Ala Met Val Lys Arg
        595                 600                 605

Lys Asp Phe Gly Ser
    610

<210> SEQ ID NO 160
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
```

-continued

```
                100                 105                 110
Arg Asp Ile Lys Ser Gly Ala Gly Ser Tyr Gln Leu Thr Phe Gly Lys
            115                 120                 125
Gly Thr Lys Leu Ser Val Ile Pro Asn Ile Gln Asn Pro Asp Pro Ala
        130                 135                 140
Val Tyr Gln Leu Arg Asp Ser Lys Ser Ser Asp Lys Ser Val Cys Leu
145                 150                 155                 160
Phe Thr Asp Phe Asp Ser Gln Thr Asn Val Ser Gln Ser Lys Asp Ser
                165                 170                 175
Asp Val Tyr Ile Thr Asp Lys Thr Val Leu Asp Met Arg Ser Met Asp
            180                 185                 190
Phe Lys Ser Asn Ser Ala Val Ala Trp Ser Asn Lys Ser Asp Phe Ala
        195                 200                 205
Cys Ala Asn Ala Phe Asn Asn Ser Ile Ile Pro Glu Asp Thr Phe Phe
210                 215                 220
Pro Ser Pro Glu Ser Ser Cys Asp Val Lys Leu Val Glu Lys Ser Phe
225                 230                 235                 240
Glu Thr Asp Thr Asn Leu Asn Phe Gln Asn Leu Ser Val Ile Gly Phe
                245                 250                 255
Arg Ile Leu Leu Leu Lys Val Ala Gly Phe Asn Leu Leu Met Thr Leu
            260                 265                 270
Arg Leu Trp Ser Ser Gly Ser Gly Ala Thr Asn Phe Ser Leu Leu Lys
        275                 280                 285
Gln Ala Gly Asp Val Glu Glu Asn Pro Gly Pro Met Leu Ser Leu Leu
        290                 295                 300
Leu Leu Leu Leu Gly Leu Gly Ser Val Phe Ser Ala Val Ile Ser Gln
305                 310                 315                 320
Lys Pro Ser Arg Asp Ile Cys Gln Arg Gly Thr Ser Leu Thr Ile Gln
                325                 330                 335
Cys Gln Val Asp Ser Gln Val Thr Met Met Phe Trp Tyr Arg Gln Gln
            340                 345                 350
Pro Gly Gln Ser Leu Thr Leu Ile Ala Thr Ala Asn Gln Gly Ser Glu
        355                 360                 365
Ala Thr Tyr Glu Ser Gly Phe Val Ile Asp Lys Phe Pro Ile Ser Arg
        370                 375                 380
Pro Asn Leu Thr Phe Ser Thr Leu Thr Val Ser Asn Met Ser Pro Glu
385                 390                 395                 400
Asp Ser Ser Ile Tyr Leu Cys Ser Val Gly Gly Ala Gly Val Thr Asp
                405                 410                 415
Thr Gln Tyr Phe Gly Pro Gly Thr Arg Leu Thr Val Leu Glu Asp Leu
            420                 425                 430
Asn Lys Val Phe Pro Pro Glu Val Ala Val Phe Glu Pro Ser Glu Ala
        435                 440                 445
Glu Ile Ser His Thr Gln Lys Ala Thr Leu Val Cys Leu Ala Thr Gly
        450                 455                 460
Phe Phe Pro Asp His Val Glu Leu Ser Trp Trp Val Asn Gly Lys Glu
465                 470                 475                 480
Val His Ser Gly Val Ser Thr Asp Pro Gln Pro Leu Lys Glu Gln Pro
                485                 490                 495
Ala Leu Asn Asp Ser Arg Tyr Cys Leu Ser Ser Arg Leu Arg Val Ser
            500                 505                 510
Ala Thr Phe Trp Gln Asn Pro Arg Asn His Phe Arg Cys Gln Val Gln
        515                 520                 525
```

```
Phe Tyr Gly Leu Ser Glu Asn Asp Glu Trp Thr Gln Asp Arg Ala Lys
            530                 535                 540

Pro Val Thr Gln Ile Val Ser Ala Glu Ala Trp Gly Arg Ala Asp Cys
545                 550                 555                 560

Gly Phe Thr Ser Val Ser Tyr Gln Gln Gly Val Leu Ser Ala Thr Ile
                565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Phe
            595                 600                 605
```

<210> SEQ ID NO 161
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Ile Lys Ser Gly Ala Gly Ser Tyr Gln Leu Thr Phe Gly Lys
            115                 120                 125

Gly Thr Lys Leu Ser Val Ile Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270
```

Arg Leu Trp Ser Ser Gly Ser Gly Ala Thr Asn Phe Ser Leu Leu Lys
            275                 280                 285

Gln Ala Gly Asp Val Glu Glu Asn Pro Gly Pro Met Leu Ser Leu Leu
290                 295                 300

Leu Leu Leu Leu Gly Leu Gly Ser Val Phe Ser Ala Val Ile Ser Gln
305                 310                 315                 320

Lys Pro Ser Arg Asp Ile Cys Gln Arg Gly Thr Ser Leu Thr Ile Gln
                325                 330                 335

Cys Gln Val Asp Ser Gln Val Thr Met Met Phe Trp Tyr Arg Gln Gln
                340                 345                 350

Pro Gly Gln Ser Leu Thr Leu Ile Ala Thr Ala Asn Gln Gly Ser Glu
            355                 360                 365

Ala Thr Tyr Glu Ser Gly Phe Val Ile Asp Lys Phe Pro Ile Ser Arg
370                 375                 380

Pro Asn Leu Thr Phe Ser Thr Leu Thr Val Ser Asn Met Ser Pro Glu
385                 390                 395                 400

Asp Ser Ser Ile Tyr Leu Cys Ser Val Gly Gly Ala Gly Val Thr Asp
                405                 410                 415

Thr Gln Tyr Phe Gly Pro Gly Thr Arg Leu Thr Val Leu Glu Asp Leu
            420                 425                 430

Asn Lys Val Phe Pro Pro Glu Val Ala Val Phe Glu Pro Ser Glu Ala
        435                 440                 445

Glu Ile Ser His Thr Gln Lys Ala Thr Leu Val Cys Leu Ala Thr Gly
        450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
                485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
        515                 520                 525

Phe Tyr Gly Leu Ser Glu Asn Asp Glu Trp Thr Gln Asp Arg Ala Lys
530                 535                 540

Pro Val Thr Gln Ile Val Ser Ala Glu Ala Trp Gly Arg Ala Asp Cys
545                 550                 555                 560

Gly Phe Thr Ser Val Ser Tyr Gln Gln Gly Val Leu Ser Ala Thr Ile
                565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Phe Gly Ser
        595                 600                 605

<210> SEQ ID NO 162

<400> SEQUENCE: 162

000

<210> SEQ ID NO 163

<400> SEQUENCE: 163

000

<210> SEQ ID NO 164

```
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 164
```

| | | | | | | | | | | | | | | |
|---|---|---|---|---|---|---|---|---|---|---|---|---|---|---|
| Met | Leu | Ser | Leu | Leu | Leu | Leu | Gly | Leu | Gly | Ser | Val | Phe | Ser |
| 1 | | | 5 | | | | | 10 | | | | | 15 | |
| Ala | Val | Ile | Ser | Gln | Lys | Pro | Ser | Arg | Asp | Ile | Cys | Gln | Arg | Gly | Thr |
| | | | 20 | | | | | 25 | | | | | 30 | | |
| Ser | Leu | Thr | Ile | Gln | Cys | Gln | Val | Asp | Ser | Gln | Val | Thr | Met | Met | Phe |
| | | 35 | | | | | 40 | | | | | 45 | | | |
| Trp | Tyr | Arg | Gln | Gln | Pro | Gly | Gln | Ser | Leu | Thr | Leu | Ile | Ala | Thr | Ala |
| 50 | | | | | 55 | | | | | 60 | | | | | |
| Asn | Gln | Gly | Ser | Glu | Ala | Thr | Tyr | Glu | Ser | Gly | Phe | Val | Ile | Asp | Lys |
| 65 | | | | 70 | | | | | 75 | | | | | 80 | |
| Phe | Pro | Ile | Ser | Arg | Pro | Asn | Leu | Thr | Phe | Ser | Thr | Leu | Thr | Val | Ser |
| | | | | 85 | | | | | 90 | | | | | 95 | |
| Asn | Met | Ser | Pro | Glu | Asp | Ser | Ser | Ile | Tyr | Leu | Cys | Ser | Val | Gly | Gly |
| | | | 100 | | | | | 105 | | | | | 110 | | |
| Ala | Gly | Val | Thr | Asp | Thr | Gln | Tyr | Phe | Gly | Pro | Gly | Thr | Arg | Leu | Thr |
| | | | 115 | | | | | 120 | | | | | 125 | | |
| Val | Leu | Glu | Asp | Leu | Asn | Lys | Val | Phe | Pro | Pro | Glu | Val | Ala | Val | Phe |
| 130 | | | | | 135 | | | | | 140 | | | | | |
| Glu | Pro | Ser | Glu | Ala | Glu | Ile | Ser | His | Thr | Gln | Lys | Ala | Thr | Leu | Val |
| 145 | | | | | 150 | | | | | 155 | | | | | 160 |
| Cys | Leu | Ala | Thr | Gly | Phe | Phe | Pro | Asp | His | Val | Glu | Leu | Ser | Trp | Trp |
| | | | | 165 | | | | | 170 | | | | | 175 | |
| Val | Asn | Gly | Lys | Glu | Val | His | Ser | Gly | Val | Ser | Thr | Asp | Pro | Gln | Pro |
| | | | 180 | | | | | 185 | | | | | 190 | | |
| Leu | Lys | Glu | Gln | Pro | Ala | Leu | Asn | Asp | Ser | Arg | Tyr | Cys | Leu | Ser | Ser |
| | | 195 | | | | | 200 | | | | | 205 | | | |
| Arg | Leu | Arg | Val | Ser | Ala | Thr | Phe | Trp | Gln | Asn | Pro | Arg | Asn | His | Phe |
| 210 | | | | | 215 | | | | | 220 | | | | | |
| Arg | Cys | Gln | Val | Gln | Phe | Tyr | Gly | Leu | Ser | Glu | Asn | Asp | Glu | Trp | Thr |
| 225 | | | | | 230 | | | | | 235 | | | | | 240 |
| Gln | Asp | Arg | Ala | Lys | Pro | Val | Thr | Gln | Ile | Val | Ser | Ala | Glu | Ala | Trp |
| | | | | 245 | | | | | 250 | | | | | 255 | |
| Gly | Arg | Ala | Asp | Cys | Gly | Phe | Thr | Ser | Val | Ser | Tyr | Gln | Gln | Gly | Val |
| | | | 260 | | | | | 265 | | | | | 270 | | |
| Leu | Ser | Ala | Thr | Ile | Leu | Tyr | Glu | Ile | Leu | Leu | Gly | Lys | Ala | Thr | Leu |
| | | 275 | | | | | 280 | | | | | 285 | | | |
| Tyr | Ala | Val | Leu | Val | Ser | Ala | Leu | Val | Leu | Met | Ala | Met | Val | Lys | Arg |
| 290 | | | | | 295 | | | | | 300 | | | | | |
| Lys | Asp | Phe | Arg | Ala | Lys | Arg | Ser | Gly | Ser | Gly | Ala | Thr | Asn | Phe | Ser |
| 305 | | | | | 310 | | | | | 315 | | | | | 320 |
| Leu | Leu | Lys | Gln | Ala | Gly | Asp | Val | Glu | Glu | Asn | Pro | Gly | Pro | Met | Ala |
| | | | | 325 | | | | | 330 | | | | | 335 | |
| Ser | Ala | Pro | Ile | Ser | Met | Leu | Ala | Met | Leu | Phe | Thr | Leu | Ser | Gly | Leu |
| | | | 340 | | | | | 345 | | | | | 350 | | |
| Arg | Ala | Gln | Ser | Val | Ala | Gln | Pro | Glu | Asp | Gln | Val | Asn | Val | Ala | Glu |
| | | 355 | | | | | 360 | | | | | 365 | | | |

```
Gly Asn Pro Leu Thr Val Lys Cys Thr Tyr Ser Val Ser Gly Asn Pro
    370                 375                 380

Tyr Leu Phe Trp Tyr Val Gln Tyr Pro Asn Arg Gly Leu Gln Phe Leu
385                 390                 395                 400

Leu Lys Tyr Ile Thr Gly Asp Asn Leu Val Lys Gly Ser Tyr Gly Phe
                405                 410                 415

Glu Ala Glu Phe Asn Lys Ser Gln Thr Ser Phe His Leu Lys Lys Pro
            420                 425                 430

Ser Ala Leu Val Ser Asp Ser Ala Leu Tyr Phe Cys Ala Val Arg Asp
        435                 440                 445

Ile Lys Ser Gly Ala Gly Ser Tyr Gln Leu Thr Phe Gly Lys Gly Thr
    450                 455                 460

Lys Leu Ser Val Ile Pro Asn Ile Gln Asn Pro Asp Pro Ala Val Tyr
465                 470                 475                 480

Gln Leu Arg Asp Ser Lys Ser Ser Asp Lys Ser Val Cys Leu Phe Thr
                485                 490                 495

Asp Phe Asp Ser Gln Thr Asn Val Ser Gln Ser Lys Asp Ser Asp Val
            500                 505                 510

Tyr Ile Thr Asp Lys Thr Val Leu Asp Met Arg Ser Met Asp Phe Lys
        515                 520                 525

Ser Asn Ser Ala Val Ala Trp Ser Asn Lys Ser Asp Phe Ala Cys Ala
    530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
        595                 600                 605

Trp Ser Ser
    610

<210> SEQ ID NO 165
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 165

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
        50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
```

```
                100              105              110
Ala Gly Val Thr Asp Thr Gln Tyr Phe Gly Pro Gly Thr Arg Leu Thr
            115              120              125
Val Leu Glu Asp Leu Asn Lys Val Phe Pro Pro Glu Val Ala Val Phe
        130              135              140
Glu Pro Ser Glu Ala Glu Ile Ser His Thr Gln Lys Ala Thr Leu Val
145              150              155              160
Cys Leu Ala Thr Gly Phe Phe Pro Asp His Val Glu Leu Ser Trp Trp
                165              170              175
Val Asn Gly Lys Glu Val His Ser Gly Val Ser Thr Asp Pro Gln Pro
            180              185              190
Leu Lys Glu Gln Pro Ala Leu Asn Asp Ser Arg Tyr Cys Leu Ser Ser
        195              200              205
Arg Leu Arg Val Ser Ala Thr Phe Trp Gln Pro Arg Asn His Phe
210              215              220
Arg Cys Gln Val Gln Phe Tyr Gly Leu Ser Glu Asn Asp Glu Trp Thr
225              230              235              240
Gln Asp Arg Ala Lys Pro Val Thr Gln Ile Val Ser Ala Glu Ala Trp
                245              250              255
Gly Arg Ala Asp Cys Gly Phe Thr Ser Val Ser Tyr Gln Gln Gly Val
            260              265              270
Leu Ser Ala Thr Ile Leu Tyr Glu Ile Leu Leu Gly Lys Ala Thr Leu
        275              280              285
Tyr Ala Val Leu Val Ser Ala Leu Val Leu Met Ala Met Val Lys Arg
    290              295              300
Lys Asp Phe Arg Ala Lys Arg Ser Gly Ser Gly Ala Thr Asn Phe Ser
305              310              315              320
Leu Leu Lys Gln Ala Gly Asp Val Glu Glu Asn Pro Gly Pro Met Ala
                325              330              335
Ser Ala Pro Ile Ser Met Leu Ala Met Leu Phe Thr Leu Ser Gly Leu
                340              345              350
Arg Ala Gln Ser Val Ala Gln Pro Glu Asp Gln Val Asn Val Ala Glu
            355              360              365
Gly Asn Pro Leu Thr Val Lys Cys Thr Tyr Ser Val Ser Gly Asn Pro
        370              375              380
Tyr Leu Phe Trp Tyr Val Gln Tyr Pro Asn Arg Gly Leu Gln Phe Leu
385              390              395              400
Leu Lys Tyr Ile Thr Gly Asp Asn Leu Val Lys Gly Ser Tyr Gly Phe
            405              410              415
Glu Ala Glu Phe Asn Lys Ser Gln Thr Ser Phe His Leu Lys Lys Pro
        420              425              430
Ser Ala Leu Val Ser Asp Ser Ala Leu Tyr Phe Cys Ala Val Arg Asp
        435              440              445
Ile Lys Ser Gly Ala Gly Ser Tyr Gln Leu Thr Phe Gly Lys Gly Thr
        450              455              460
Lys Leu Ser Val Ile Pro Asn Ile Gln Asn Pro Asp Pro Ala Val Tyr
465              470              475              480
Gln Leu Arg Asp Ser Lys Ser Ser Asp Lys Ser Val Cys Leu Phe Thr
            485              490              495
Asp Phe Asp Ser Gln Thr Asn Val Ser Gln Ser Lys Asp Ser Asp Val
            500              505              510
Tyr Ile Thr Asp Lys Thr Val Leu Asp Met Arg Ser Met Asp Phe Lys
        515              520              525
```

```
Ser Asn Ser Ala Val Ala Trp Ser Asn Lys Ser Asp Phe Ala Cys Ala
    530                 535                 540

Asn Ala Phe Asn Asn Ser Ile Ile Pro Glu Asp Thr Phe Pro Ser
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
                580                 585                 590

Leu Leu Leu Lys Val Ala Gly Phe Asn Leu Leu Met Thr Leu Arg Leu
            595                 600                 605

Trp Ser Ser Gly Ser
    610
```

<210> SEQ ID NO 166
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 166

```
Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
                100                 105                 110

Ala Gly Val Thr Asp Thr Gln Tyr Phe Gly Pro Gly Thr Arg Leu Thr
            115                 120                 125

Val Leu Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
            195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255
```

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
            340                 345                 350

Ala Gln Pro Glu Asp Gln Val Asn Val Ala Glu Gly Asn Pro Leu Thr
        355                 360                 365

Val Lys Cys Thr Tyr Ser Val Ser Gly Asn Pro Tyr Leu Phe Trp Tyr
    370                 375                 380

Val Gln Tyr Pro Asn Arg Gly Leu Gln Phe Leu Leu Lys Tyr Ile Thr
385                 390                 395                 400

Gly Asp Asn Leu Val Lys Gly Ser Tyr Gly Phe Glu Ala Glu Phe Asn
                405                 410                 415

Lys Ser Gln Thr Ser Phe His Leu Lys Lys Pro Ser Ala Leu Val Ser
            420                 425                 430

Asp Ser Ala Leu Tyr Phe Cys Ala Val Arg Asp Ile Lys Ser Gly Ala
        435                 440                 445

Gly Ser Tyr Gln Leu Thr Phe Gly Lys Gly Thr Lys Leu Ser Val Ile
    450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
    530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser
        595                 600                 605

<210> SEQ ID NO 167
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167

Met Leu Ser Leu Leu Leu Leu Leu Leu Gly Leu Gly Ser Val Phe Ser

-continued

```
1               5                   10                  15
Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
        50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
        115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
            340                 345                 350

Ala Gln Pro Glu Asp Gln Val Asn Val Ala Glu Gly Asn Pro Leu Thr
        355                 360                 365

Val Lys Cys Thr Tyr Ser Val Ser Gly Asn Pro Tyr Leu Phe Trp Tyr
370                 375                 380

Val Gln Tyr Pro Asn Arg Gly Leu Gln Phe Leu Leu Lys Tyr Ile Thr
385                 390                 395                 400

Gly Asp Asn Leu Val Lys Gly Ser Tyr Gly Phe Glu Ala Glu Phe Asn
                405                 410                 415

Lys Ser Gln Thr Ser Phe His Leu Lys Lys Pro Ser Ala Leu Val Ser
            420                 425                 430
```

Asp Ser Ala Leu Tyr Phe Cys Ala Val Arg Asp Ile Lys Ser Gly Ala
            435                 440                 445

Gly Ser Tyr Gln Leu Thr Phe Gly Lys Gly Thr Lys Leu Ser Val Ile
        450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
            515                 520                 525

Ala Trp Ser Asn Lys Ser Asp Phe Ala Cys Ala Asn Ala Phe Asn Asn
        530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser Gly Ser
        595                 600                 605

<210> SEQ ID NO 168

<400> SEQUENCE: 168

000

<210> SEQ ID NO 169

<400> SEQUENCE: 169

000

<210> SEQ ID NO 170
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

Met Lys Ser Val Leu Leu Leu Thr Thr Leu Leu Val Pro Ala His Leu
1               5                   10                  15

Val Ala Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
        35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val

```
                100             105             110
Gly Gly Ala Gly Val Thr Asp Thr Gln Tyr Phe Gly Pro Gly Thr Arg
            115                 120                 125

Leu Thr Val Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
                340                 345                 350

Gly Leu Arg Ala Gln Ser Val Ala Gln Pro Glu Asp Gln Val Asn Val
            355                 360                 365

Ala Glu Gly Asn Pro Leu Thr Val Lys Cys Thr Tyr Ser Val Ser Gly
370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
            420                 425                 430

Lys Pro Ser Ala Leu Val Ser Asp Ser Ala Leu Tyr Phe Cys Ala Val
        435                 440                 445

Arg Asp Ile Lys Ser Gly Ala Gly Ser Tyr Gln Leu Thr Phe Gly Lys
        450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
                500                 505                 510

Asp Val Tyr Ile Thr Asp Lys Thr Val Leu Asp Met Arg Ser Met Asp
            515                 520                 525
```

Phe Lys Ser Asn Ser Ala Val Ala Trp Ser Asn Lys Ser Asp Phe Ala
    530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
            580                 585                 590

Arg Ile Leu Leu Leu Lys Val Ala Gly Phe Asn Leu Leu Met Thr Leu
    595                 600                 605

Arg Leu Trp Ser Ser
    610

<210> SEQ ID NO 171
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Met Lys Ser Val Leu Leu Leu Thr Thr Leu Leu Val Pro Ala His Leu
1               5                   10                  15

Val Ala Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
        35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

```
Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
            340                 345                 350

Gly Leu Arg Ala Gln Ser Val Ala Gln Pro Glu Asp Gln Val Asn Val
        355                 360                 365

Ala Glu Gly Asn Pro Leu Thr Val Lys Cys Thr Tyr Ser Val Ser Gly
    370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
            420                 425                 430

Lys Pro Ser Ala Leu Val Ser Asp Ser Ala Leu Tyr Phe Cys Ala Val
        435                 440                 445

Arg Asp Ile Lys Ser Gly Ala Gly Ser Tyr Gln Leu Thr Phe Gly Lys
    450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
            500                 505                 510

Asp Val Tyr Ile Thr Asp Lys Thr Val Leu Asp Met Arg Ser Met Asp
        515                 520                 525

Phe Lys Ser Asn Ser Ala Val Ala Trp Ser Asn Lys Ser Asp Phe Ala
    530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
            580                 585                 590

Arg Ile Leu Leu Leu Lys Val Ala Gly Phe Asn Leu Leu Met Thr Leu
        595                 600                 605

Arg Leu Trp Ser Ser Gly Ser
    610                 615

<210> SEQ ID NO 172
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 172

| | | | | | | | | | | | | | | |
|---|---|---|---|---|---|---|---|---|---|---|---|---|---|---|
|Met|Lys|Ser|Val|Leu|Leu|Thr|Thr|Leu|Leu|Val|Pro|Ala|His|Leu|
|1| | |5| | | | |10| | | | |15| |
|Val|Ala|Ala|Val|Ile|Ser|Gln|Lys|Pro|Ser|Arg|Asp|Ile|Cys|Gln|Arg|
| | | |20| | | |25| | | | |30| | |
|Gly|Thr|Ser|Leu|Thr|Ile|Gln|Cys|Gln|Val|Asp|Ser|Gln|Val|Thr|Met|
| | |35| | | | |40| | | | |45| | |
|Met|Phe|Trp|Tyr|Arg|Gln|Gln|Pro|Gly|Gln|Ser|Leu|Thr|Leu|Ile|Ala|
| |50| | | | |55| | | | |60| | | |
|Thr|Ala|Asn|Gln|Gly|Ser|Glu|Ala|Thr|Tyr|Glu|Ser|Gly|Phe|Val|Ile|
|65| | | | |70| | | | |75| | | | |80|
|Asp|Lys|Phe|Pro|Ile|Ser|Arg|Pro|Asn|Leu|Thr|Phe|Ser|Thr|Leu|Thr|
| | | | |85| | | | |90| | | | |95| |
|Val|Ser|Asn|Met|Ser|Pro|Glu|Asp|Ser|Ser|Ile|Tyr|Leu|Cys|Ser|Val|
| | | |100| | | | |105| | | | |110| | |
|Gly|Gly|Ala|Gly|Val|Thr|Asp|Thr|Gln|Tyr|Phe|Gly|Pro|Gly|Thr|Arg|
| | |115| | | | |120| | | | |125| | | |
|Leu|Thr|Val|Leu|Glu|Asp|Leu|Asn|Lys|Val|Phe|Pro|Pro|Glu|Val|Ala|
| |130| | | | |135| | | | |140| | | | |
|Val|Phe|Glu|Pro|Ser|Glu|Ala|Glu|Ile|Ser|His|Thr|Gln|Lys|Ala|Thr|
|145| | | | |150| | | | |155| | | | |160|
|Leu|Val|Cys|Leu|Ala|Thr|Gly|Phe|Phe|Pro|Asp|His|Val|Glu|Leu|Ser|
| | | | |165| | | | |170| | | | |175| |
|Trp|Trp|Val|Asn|Gly|Lys|Glu|Val|His|Ser|Gly|Val|Ser|Thr|Asp|Pro|
| | | |180| | | | |185| | | | |190| | |
|Gln|Pro|Leu|Lys|Glu|Gln|Pro|Ala|Leu|Asn|Asp|Ser|Arg|Tyr|Cys|Leu|
| | |195| | | | |200| | | | |205| | | |
|Ser|Ser|Arg|Leu|Arg|Val|Ser|Ala|Thr|Phe|Trp|Gln|Asn|Pro|Arg|Asn|
| |210| | | | |215| | | | |220| | | | |
|His|Phe|Arg|Cys|Gln|Val|Gln|Phe|Tyr|Gly|Leu|Ser|Glu|Asn|Asp|Glu|
|225| | | | |230| | | | |235| | | | |240| |
|Trp|Thr|Gln|Asp|Arg|Ala|Lys|Pro|Val|Thr|Gln|Ile|Val|Ser|Ala|Glu|
| | | | |245| | | | |250| | | | |255| |
|Ala|Trp|Gly|Arg|Ala|Asp|Cys|Gly|Phe|Thr|Ser|Val|Ser|Tyr|Gln|Gln|
| | | |260| | | | |265| | | | |270| | |
|Gly|Val|Leu|Ser|Ala|Thr|Ile|Leu|Tyr|Glu|Ile|Leu|Leu|Gly|Lys|Ala|
| | |275| | | | |280| | | | |285| | | |
|Thr|Leu|Tyr|Ala|Val|Leu|Val|Ser|Ala|Leu|Val|Leu|Met|Ala|Met|Val|
| |290| | | | |295| | | | |300| | | | |
|Lys|Arg|Lys|Asp|Phe|Gly|Ser|Gly|Ala|Thr|Asn|Phe|Ser|Leu|Leu|Lys|
|305| | | | |310| | | | |315| | | | |320| |
|Gln|Ala|Gly|Asp|Val|Glu|Glu|Asn|Pro|Gly|Pro|Met|Ala|Ser|Ala|Pro|
| | | | |325| | | | |330| | | | |335| |
|Ile|Ser|Met|Leu|Ala|Met|Leu|Phe|Thr|Leu|Ser|Gly|Leu|Arg|Ala|Gln|
| | | |340| | | | |345| | | | |350| | |
|Ser|Val|Ala|Gln|Pro|Glu|Asp|Gln|Val|Asn|Val|Ala|Glu|Gly|Asn|Pro|
| | |355| | | | |360| | | | |365| | | |
|Leu|Thr|Val|Lys|Cys|Thr|Tyr|Ser|Val|Ser|Gly|Asn|Pro|Tyr|Leu|Phe|
| |370| | | | |375| | | | |380| | | | |
|Trp|Tyr|Val|Gln|Tyr|Pro|Asn|Arg|Gly|Leu|Gln|Phe|Leu|Leu|Lys|Tyr|
|385| | | | |390| | | | |395| | | | |400| |
|Ile|Thr|Gly|Asp|Asn|Leu|Val|Lys|Gly|Ser|Tyr|Gly|Phe|Glu|Ala|Glu|
| | | | |405| | | | |410| | | | |415| |

```
Phe Asn Lys Ser Gln Thr Ser Phe His Leu Lys Lys Pro Ser Ala Leu
            420                 425                 430

Val Ser Asp Ser Ala Leu Tyr Phe Cys Ala Val Arg Asp Ile Lys Ser
            435                 440                 445

Gly Ala Gly Ser Tyr Gln Leu Thr Phe Gly Lys Gly Thr Lys Leu Ser
            450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
            485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
            515                 520                 525

Ala Val Ala Trp Ser Asn Lys Ser Asp Phe Ala Cys Ala Asn Ala Phe
            530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
            565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
            595                 600                 605

<210> SEQ ID NO 173
<211> LENGTH: 610
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Met Lys Ser Val Leu Leu Leu Thr Thr Leu Val Pro Ala His Leu
1               5                   10                  15

Val Ala Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
            35                  40                  45

Met Phe Trp Tyr Arg Gln Gln Pro Gly Gln Ser Leu Thr Leu Ile Ala
        50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
            115                 120                 125

Leu Thr Val Leu Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160
```

-continued

```
Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ala Ser Ala Pro
                325                 330                 335

Ile Ser Met Leu Ala Met Leu Phe Thr Leu Ser Gly Leu Arg Ala Gln
            340                 345                 350

Ser Val Ala Gln Pro Glu Asp Gln Val Asn Val Ala Glu Gly Asn Pro
        355                 360                 365

Leu Thr Val Lys Cys Thr Tyr Ser Val Ser Gly Asn Pro Tyr Leu Phe
    370                 375                 380

Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
                405                 410                 415

Phe Asn Lys Ser Gln Thr Ser Phe His Leu Lys Lys Pro Ser Ala Leu
            420                 425                 430

Val Ser Asp Ser Ala Leu Tyr Phe Cys Ala Val Arg Asp Ile Lys Ser
        435                 440                 445

Gly Ala Gly Ser Tyr Gln Leu Thr Phe Gly Lys Gly Thr Lys Leu Ser
    450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
        515                 520                 525

Ala Val Ala Trp Ser Asn Lys Ser Asp Phe Ala Cys Ala Asn Ala Phe
    530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
```

-continued

```
                580             585             590
Lys Val Ala Gly Phe Asn Leu Leu Met Thr Leu Arg Leu Trp Ser Ser
            595                 600                 605
Gly Ser
    610

<210> SEQ ID NO 174

<400> SEQUENCE: 174

000

<210> SEQ ID NO 175

<400> SEQUENCE: 175

000

<210> SEQ ID NO 176
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Leu Phe Thr Gly Ala Gly Ser Tyr Gln Leu Thr Phe Gly Lys
        115                 120                 125

Gly Thr Lys Leu Ser Val Ile Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240
```

```
Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Arg Ala Lys Arg Ser Gly Ser Gly Ala Thr Asn
        275                 280                 285

Phe Ser Leu Leu Lys Gln Ala Gly Asp Val Glu Glu Asn Pro Gly Pro
    290                 295                 300

Met Leu Ser Leu Leu Leu Leu Leu Gly Leu Gly Ser Val Phe Ser
305                 310                 315                 320

Ala Val Ile Ser Gln Lys Pro Ser Arg Asp Ile Cys Gln Arg Gly Thr
                325                 330                 335

Ser Leu Thr Ile Gln Cys Gln Val Asp Ser Gln Val Thr Met Met Phe
            340                 345                 350

Trp Tyr Arg Gln Gln Pro Gly Gln Ser Leu Thr Leu Ile Ala Thr Ala
        355                 360                 365

Asn Gln Gly Ser Glu Ala Thr Tyr Glu Ser Gly Phe Val Ile Asp Lys
    370                 375                 380

Phe Pro Ile Ser Arg Pro Asn Leu Thr Phe Ser Thr Leu Thr Val Ser
385                 390                 395                 400

Asn Met Ser Pro Glu Asp Ser Ser Ile Tyr Leu Cys Ser Val Gly Gly
                405                 410                 415

Ala Gly Val Thr Asp Thr Gln Tyr Phe Gly Pro Gly Thr Arg Leu Thr
            420                 425                 430

Val Leu Glu Asp Leu Asn Lys Val Phe Pro Pro Glu Val Ala Val Phe
        435                 440                 445

Glu Pro Ser Glu Ala Glu Ile Ser His Thr Gln Lys Ala Thr Leu Val
    450                 455                 460

Cys Leu Ala Thr Gly Phe Phe Pro Asp His Val Glu Leu Ser Trp Trp
465                 470                 475                 480

Val Asn Gly Lys Glu Val His Ser Gly Val Ser Thr Asp Pro Gln Pro
                485                 490                 495

Leu Lys Glu Gln Pro Ala Leu Asn Asp Ser Arg Tyr Cys Leu Ser Ser
            500                 505                 510

Arg Leu Arg Val Ser Ala Thr Phe Trp Gln Asn Pro Arg Asn His Phe
        515                 520                 525

Arg Cys Gln Val Gln Phe Tyr Gly Leu Ser Glu Asn Asp Glu Trp Thr
    530                 535                 540

Gln Asp Arg Ala Lys Pro Val Thr Gln Ile Val Ser Ala Glu Ala Trp
545                 550                 555                 560

Gly Arg Ala Asp Cys Gly Phe Thr Ser Val Ser Tyr Gln Gln Gly Val
                565                 570                 575

Leu Ser Ala Thr Ile Leu Tyr Glu Ile Leu Leu Gly Lys Ala Thr Leu
            580                 585                 590

Tyr Ala Val Leu Val Ser Ala Leu Val Leu Met Ala Met Val Lys Arg
        595                 600                 605

Lys Asp Phe
    610

<210> SEQ ID NO 177
<211> LENGTH: 613
<212> TYPE: PRT
<213> ORGANISM: Artificial Sequence
<220> FEATURE:
<221> NAME/KEY: source
```

<223> OTHER INFORMATION: /note="Description of Artificial Sequence: Synthetic polypeptide"

<400> SEQUENCE: 177

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Leu Phe Thr Gly Ala Gly Ser Tyr Gln Leu Thr Phe Gly Lys
        115                 120                 125

Gly Thr Lys Leu Ser Val Ile Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Arg Ala Lys Arg Ser Gly Ser Gly Ala Thr Asn
        275                 280                 285

Phe Ser Leu Leu Lys Gln Ala Gly Asp Val Glu Glu Asn Pro Gly Pro
    290                 295                 300

Met Leu Ser Leu Leu Leu Leu Leu Gly Leu Gly Ser Val Phe Ser
305                 310                 315                 320

Ala Val Ile Ser Gln Lys Pro Ser Arg Asp Ile Cys Gln Arg Gly Thr
                325                 330                 335

Ser Leu Thr Ile Gln Cys Gln Val Asp Ser Gln Val Thr Met Met Phe
            340                 345                 350

Trp Tyr Arg Gln Gln Pro Gly Gln Ser Leu Thr Leu Ile Ala Thr Ala
        355                 360                 365

Asn Gln Gly Ser Glu Ala Thr Tyr Glu Ser Gly Phe Val Ile Asp Lys
    370                 375                 380

Phe Pro Ile Ser Arg Pro Asn Leu Thr Phe Ser Thr Leu Thr Val Ser
385                 390                 395                 400
```

```
Asn Met Ser Pro Glu Asp Ser Ser Ile Tyr Leu Cys Ser Val Gly Gly
            405                 410                 415

Ala Gly Val Thr Asp Thr Gln Tyr Phe Gly Pro Gly Thr Arg Leu Thr
        420                 425                 430

Val Leu Glu Asp Leu Asn Lys Val Phe Pro Pro Glu Val Ala Val Phe
    435                 440                 445

Glu Pro Ser Glu Ala Glu Ile Ser His Thr Gln Lys Ala Thr Leu Val
450                 455                 460

Cys Leu Ala Thr Gly Phe Phe Pro Asp His Val Glu Leu Ser Trp Trp
465                 470                 475                 480

Val Asn Gly Lys Glu Val His Ser Gly Val Ser Thr Asp Pro Gln Pro
            485                 490                 495

Leu Lys Glu Gln Pro Ala Leu Asn Asp Ser Arg Tyr Cys Leu Ser Ser
        500                 505                 510

Arg Leu Arg Val Ser Ala Thr Phe Trp Gln Asn Pro Arg Asn His Phe
    515                 520                 525

Arg Cys Gln Val Gln Phe Tyr Gly Leu Ser Glu Asn Asp Glu Trp Thr
530                 535                 540

Gln Asp Arg Ala Lys Pro Val Thr Gln Ile Val Ser Ala Glu Ala Trp
545                 550                 555                 560

Gly Arg Ala Asp Cys Gly Phe Thr Ser Val Ser Tyr Gln Gln Gly Val
            565                 570                 575

Leu Ser Ala Thr Ile Leu Tyr Glu Ile Leu Leu Gly Lys Ala Thr Leu
        580                 585                 590

Tyr Ala Val Leu Val Ser Ala Leu Val Leu Met Ala Met Val Lys Arg
    595                 600                 605

Lys Asp Phe Gly Ser
    610

<210> SEQ ID NO 178
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
            85                  90                  95

Lys Pro Ser Ala Leu Val Ser Asp Ser Ala Leu Tyr Phe Cys Ala Val
        100                 105                 110

Arg Asp Leu Phe Thr Gly Ala Gly Ser Tyr Gln Leu Thr Phe Gly Lys
    115                 120                 125
```

```
Gly Thr Lys Leu Ser Val Ile Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Gly Ser Gly Ala Thr Asn Phe Ser Leu Leu Lys
        275                 280                 285

Gln Ala Gly Asp Val Glu Glu Asn Pro Gly Pro Met Leu Ser Leu Leu
290                 295                 300

Leu Leu Leu Leu Gly Leu Gly Ser Val Phe Ser Ala Val Ile Ser Gln
305                 310                 315                 320

Lys Pro Ser Arg Asp Ile Cys Gln Arg Gly Thr Ser Leu Thr Ile Gln
                325                 330                 335

Cys Gln Val Asp Ser Gln Val Thr Met Met Phe Trp Tyr Arg Gln Gln
            340                 345                 350

Pro Gly Gln Ser Leu Thr Leu Ile Ala Thr Ala Asn Gln Gly Ser Glu
        355                 360                 365

Ala Thr Tyr Glu Ser Gly Phe Val Ile Asp Lys Phe Pro Ile Ser Arg
370                 375                 380

Pro Asn Leu Thr Phe Ser Thr Leu Thr Val Ser Asn Met Ser Pro Glu
385                 390                 395                 400

Asp Ser Ser Ile Tyr Leu Cys Ser Val Gly Gly Ala Gly Val Thr Asp
                405                 410                 415

Thr Gln Tyr Phe Gly Pro Gly Thr Arg Leu Thr Val Leu Glu Asp Leu
            420                 425                 430

Asn Lys Val Phe Pro Pro Glu Val Ala Val Phe Glu Pro Ser Glu Ala
        435                 440                 445

Glu Ile Ser His Thr Gln Lys Ala Thr Leu Val Cys Leu Ala Thr Gly
450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
                485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
        515                 520                 525

Phe Tyr Gly Leu Ser Glu Asn Asp Glu Trp Thr Gln Asp Arg Ala Lys
530                 535                 540

Pro Val Thr Gln Ile Val Ser Ala Glu Ala Trp Gly Arg Ala Asp Cys
```

```
                545                 550                 555                 560
Gly Phe Thr Ser Val Ser Tyr Gln Gln Gly Val Leu Ser Ala Thr Ile
                    565                 570                 575

Leu Tyr Glu Ile Leu Leu Gly Lys Ala Thr Leu Tyr Ala Val Leu Val
                580                 585                 590

Ser Ala Leu Val Leu Met Ala Met Val Lys Arg Lys Asp Phe
                595                 600                 605

<210> SEQ ID NO 179
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
                20                  25                  30

Ala Glu Gly Asn Pro Leu Thr Val Lys Cys Thr Tyr Ser Val Ser Gly
            35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
                100                 105                 110

Arg Asp Leu Phe Thr Gly Ala Gly Ser Tyr Gln Leu Thr Phe Gly Lys
            115                 120                 125

Gly Thr Lys Leu Ser Val Ile Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Gly Ser Gly Ala Thr Asn Phe Ser Leu Leu Lys
        275                 280                 285

Gln Ala Gly Asp Val Glu Glu Asn Pro Gly Pro Met Leu Ser Leu Leu
    290                 295                 300
```

Leu Leu Leu Leu Gly Leu Gly Ser Val Phe Ser Ala Val Ile Ser Gln
305                 310                 315                 320

Lys Pro Ser Arg Asp Ile Cys Gln Arg Gly Thr Ser Leu Thr Ile Gln
            325                 330                 335

Cys Gln Val Asp Ser Gln Val Thr Met Met Phe Trp Tyr Arg Gln Gln
        340                 345                 350

Pro Gly Gln Ser Leu Thr Leu Ile Ala Thr Ala Asn Gln Gly Ser Glu
    355                 360                 365

Ala Thr Tyr Glu Ser Gly Phe Val Ile Asp Lys Phe Pro Ile Ser Arg
370                 375                 380

Pro Asn Leu Thr Phe Ser Thr Leu Thr Val Ser Asn Met Ser Pro Glu
385                 390                 395                 400

Asp Ser Ser Ile Tyr Leu Cys Ser Val Gly Gly Ala Gly Val Thr Asp
                405                 410                 415

Thr Gln Tyr Phe Gly Pro Gly Thr Arg Leu Thr Val Leu Glu Asp Leu
            420                 425                 430

Asn Lys Val Phe Pro Pro Glu Val Ala Val Phe Glu Pro Ser Glu Ala
        435                 440                 445

Glu Ile Ser His Thr Gln Lys Ala Thr Leu Val Cys Leu Ala Thr Gly
    450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
                485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
        515                 520                 525

Phe Tyr Gly Leu Ser Glu Asn Asp Glu Trp Thr Gln Asp Arg Ala Lys
    530                 535                 540

Pro Val Thr Gln Ile Val Ser Ala Glu Ala Trp Gly Arg Ala Asp Cys
545                 550                 555                 560

Gly Phe Thr Ser Val Ser Tyr Gln Gln Gly Val Leu Ser Ala Thr Ile
                565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Phe Gly Ser
        595                 600                 605

<210> SEQ ID NO 180

<400> SEQUENCE: 180

000

<210> SEQ ID NO 181

<400> SEQUENCE: 181

000

<210> SEQ ID NO 182
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 182

```
Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
        115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Ala
                325                 330                 335

Ser Ala Pro Ile Ser Met Leu Ala Met Leu Phe Thr Leu Ser Gly Leu
            340                 345                 350

Arg Ala Gln Ser Val Ala Gln Pro Glu Asp Gln Val Asn Val Ala Glu
        355                 360                 365

Gly Asn Pro Leu Thr Val Lys Cys Thr Tyr Ser Val Ser Gly Asn Pro
    370                 375                 380

Tyr Leu Phe Trp Tyr Val Gln Tyr Pro Asn Arg Gly Leu Gln Phe Leu
385                 390                 395                 400
```

-continued

```
Leu Lys Tyr Ile Thr Gly Asp Asn Leu Val Lys Gly Ser Tyr Gly Phe
                405                 410                 415

Glu Ala Glu Phe Asn Lys Ser Gln Thr Ser Phe His Leu Lys Lys Pro
            420                 425                 430

Ser Ala Leu Val Ser Asp Ser Ala Leu Tyr Phe Cys Ala Val Arg Asp
        435                 440                 445

Leu Phe Thr Gly Ala Gly Ser Tyr Gln Leu Thr Phe Gly Lys Gly Thr
    450                 455                 460

Lys Leu Ser Val Ile Pro Asn Ile Gln Asn Pro Asp Pro Ala Val Tyr
465                 470                 475                 480

Gln Leu Arg Asp Ser Lys Ser Ser Asp Lys Ser Val Cys Leu Phe Thr
                485                 490                 495

Asp Phe Asp Ser Gln Thr Asn Val Ser Gln Ser Lys Asp Ser Asp Val
            500                 505                 510

Tyr Ile Thr Asp Lys Thr Val Leu Asp Met Arg Ser Met Asp Phe Lys
        515                 520                 525

Ser Asn Ser Ala Val Ala Trp Ser Asn Lys Ser Asp Phe Ala Cys Ala
    530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
        595                 600                 605

Trp Ser Ser
    610

<210> SEQ ID NO 183
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
        115                 120                 125
```

-continued

```
Val Leu Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Ala
                325                 330                 335

Ser Ala Pro Ile Ser Met Leu Ala Met Leu Phe Thr Leu Ser Gly Leu
            340                 345                 350

Arg Ala Gln Ser Val Ala Gln Pro Glu Asp Gln Val Asn Val Ala Glu
        355                 360                 365

Gly Asn Pro Leu Thr Val Lys Cys Thr Tyr Ser Val Ser Gly Asn Pro
    370                 375                 380

Tyr Leu Phe Trp Tyr Val Gln Tyr Pro Asn Arg Gly Leu Gln Phe Leu
385                 390                 395                 400

Leu Lys Tyr Ile Thr Gly Asp Asn Leu Val Lys Gly Ser Tyr Gly Phe
                405                 410                 415

Glu Ala Glu Phe Asn Lys Ser Gln Thr Ser Phe His Leu Lys Lys Pro
            420                 425                 430

Ser Ala Leu Val Ser Asp Ser Ala Leu Tyr Phe Cys Ala Val Arg Asp
        435                 440                 445

Leu Phe Thr Gly Ala Gly Ser Tyr Gln Leu Thr Phe Gly Lys Gly Thr
    450                 455                 460

Lys Leu Ser Val Ile Pro Asn Ile Gln Asn Pro Asp Pro Ala Val Tyr
465                 470                 475                 480

Gln Leu Arg Asp Ser Lys Ser Ser Asp Lys Ser Val Cys Leu Phe Thr
                485                 490                 495

Asp Phe Asp Ser Gln Thr Asn Val Ser Gln Ser Lys Asp Ser Asp Val
            500                 505                 510

Tyr Ile Thr Asp Lys Thr Val Leu Asp Met Arg Ser Met Asp Phe Lys
        515                 520                 525

Ser Asn Ser Ala Val Ala Trp Ser Asn Lys Ser Asp Phe Ala Cys Ala
    530                 535                 540

Asn Ala Phe Asn Asn Ser Ile Ile Pro Glu Asp Thr Phe Phe Pro Ser
```

```
545                 550                 555                 560
Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
        595                 600                 605

Trp Ser Ser Gly Ser
        610

<210> SEQ ID NO 184
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 184

Met Leu Ser Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
        115                 120                 125

Val Leu Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285
```

Tyr Ala Val Leu Val Ser Ala Leu Val Leu Met Ala Met Val Lys Arg
            290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
            340                 345                 350

Ala Gln Pro Glu Asp Gln Val Asn Val Ala Glu Gly Asn Pro Leu Thr
        355                 360                 365

Val Lys Cys Thr Tyr Ser Val Ser Gly Asn Pro Tyr Leu Phe Trp Tyr
370                 375                 380

Val Gln Tyr Pro Asn Arg Gly Leu Gln Phe Leu Leu Lys Tyr Ile Thr
385                 390                 395                 400

Gly Asp Asn Leu Val Lys Gly Ser Tyr Gly Phe Glu Ala Glu Phe Asn
                405                 410                 415

Lys Ser Gln Thr Ser Phe His Leu Lys Lys Pro Ser Ala Leu Val Ser
            420                 425                 430

Asp Ser Ala Leu Tyr Phe Cys Ala Val Arg Asp Leu Phe Thr Gly Ala
        435                 440                 445

Gly Ser Tyr Gln Leu Thr Phe Gly Lys Gly Thr Lys Leu Ser Val Ile
450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser
        595                 600                 605

<210> SEQ ID NO 185
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

-continued

```
Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
 50                  55                  60

Asn Gln Gly Ser Glu Ala Thr Tyr Glu Ser Gly Phe Val Ile Asp Lys
 65                  70                  75                  80

Phe Pro Ile Ser Arg Pro Asn Leu Thr Phe Ser Thr Leu Thr Val Ser
                 85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
            115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
            340                 345                 350

Ala Gln Pro Glu Asp Gln Val Asn Val Ala Glu Gly Asn Pro Leu Thr
        355                 360                 365

Val Lys Cys Thr Tyr Ser Val Ser Gly Asn Pro Tyr Leu Phe Trp Tyr
370                 375                 380

Val Gln Tyr Pro Asn Arg Gly Leu Gln Phe Leu Leu Lys Tyr Ile Thr
385                 390                 395                 400

Gly Asp Asn Leu Val Lys Gly Ser Tyr Gly Phe Glu Ala Glu Phe Asn
                405                 410                 415

Lys Ser Gln Thr Ser Phe His Leu Lys Lys Pro Ser Ala Leu Val Ser
            420                 425                 430

Asp Ser Ala Leu Tyr Phe Cys Ala Val Arg Asp Leu Phe Thr Gly Ala
        435                 440                 445

Gly Ser Tyr Gln Leu Thr Phe Gly Lys Gly Thr Lys Leu Ser Val Ile
```

```
                450             455             460
Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
            515                 520                 525

Ala Trp Ser Asn Lys Ser Asp Phe Ala Cys Ala Asn Ala Phe Asn Asn
        530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser Gly Ser
            595                 600                 605
```

<210> SEQ ID NO 186

<400> SEQUENCE: 186

000

<210> SEQ ID NO 187

<400> SEQUENCE: 187

000

<210> SEQ ID NO 188
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 188

```
Met Lys Ser Val Leu Leu Thr Thr Leu Leu Val Pro Ala His Leu
1               5                   10                  15

Val Ala Ala Val Ile Ser Gln Lys Pro Ser Arg Asp Ile Cys Gln Arg
                20                  25                  30

Gly Thr Ser Leu Thr Ile Gln Cys Gln Val Asp Ser Gln Val Thr Met
            35                  40                  45

Met Phe Trp Tyr Arg Gln Gln Pro Gly Gln Ser Leu Thr Leu Ile Ala
        50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
            115                 120                 125
```

```
Leu Thr Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
            340                 345                 350

Gly Leu Arg Ala Gln Ser Val Ala Gln Pro Glu Asp Gln Val Asn Val
        355                 360                 365

Ala Glu Gly Asn Pro Leu Thr Val Lys Cys Thr Tyr Ser Val Ser Gly
370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
            420                 425                 430

Lys Pro Ser Ala Leu Val Ser Asp Ser Ala Leu Tyr Phe Cys Ala Val
        435                 440                 445

Arg Asp Leu Phe Thr Gly Ala Gly Ser Tyr Gln Leu Thr Phe Gly Lys
450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Asp Lys Ser Val Cys Leu
                485                 490                 495

Phe Thr Asp Phe Asp Ser Gln Thr Asn Val Ser Gln Ser Lys Asp Ser
            500                 505                 510

Asp Val Tyr Ile Thr Asp Lys Thr Val Leu Asp Met Arg Ser Met Asp
        515                 520                 525

Phe Lys Ser Asn Ser Ala Val Ala Trp Ser Asn Lys Ser Asp Phe Ala
530                 535                 540

Cys Ala Asn Ala Phe Asn Asn Ser Ile Ile Pro Glu Asp Thr Phe Phe
```

```
545                 550                 555                 560
Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
                580                 585                 590

Arg Ile Leu Leu Lys Val Ala Gly Phe Asn Leu Leu Met Thr Leu
        595                 600                 605

Arg Leu Trp Ser Ser
    610

<210> SEQ ID NO 189
<211> LENGTH: 615
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 189

Met Lys Ser Val Leu Leu Thr Thr Leu Leu Val Pro Ala His Leu
1               5                   10                  15

Val Ala Ala Val Ile Ser Gln Lys Pro Ser Arg Asp Ile Cys Gln Arg
                20                  25                  30

Gly Thr Ser Leu Thr Ile Gln Cys Gln Val Asp Ser Gln Val Thr Met
                35                  40                  45

Met Phe Trp Tyr Arg Gln Gln Pro Gly Gln Ser Leu Thr Leu Ile Ala
        50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
                100                 105                 110

Gly Gly Ala Gly Val Thr Asp Thr Gln Tyr Phe Gly Pro Gly Thr Arg
            115                 120                 125

Leu Thr Val Leu Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285
```

```
Thr Leu Tyr Ala Val Leu Val Ser Ala Leu Val Leu Met Ala Met Val
    290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
            340                 345                 350

Gly Leu Arg Ala Gln Ser Val Ala Gln Pro Glu Asp Gln Val Asn Val
        355                 360                 365

Ala Glu Gly Asn Pro Leu Thr Val Lys Cys Thr Tyr Ser Val Ser Gly
370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
            420                 425                 430

Lys Pro Ser Ala Leu Val Ser Asp Ser Ala Leu Tyr Phe Cys Ala Val
        435                 440                 445

Arg Asp Leu Phe Thr Gly Ala Gly Ser Tyr Gln Leu Thr Phe Gly Lys
450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
            500                 505                 510

Asp Val Tyr Ile Thr Asp Lys Thr Val Leu Asp Met Arg Ser Met Asp
        515                 520                 525

Phe Lys Ser Asn Ser Ala Val Ala Trp Ser Asn Lys Ser Asp Phe Ala
530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
            580                 585                 590

Arg Ile Leu Leu Leu Lys Val Ala Gly Phe Asn Leu Leu Met Thr Leu
        595                 600                 605

Arg Leu Trp Ser Ser Gly Ser
610                 615

<210> SEQ ID NO 190
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190

Met Lys Ser Val Leu Leu Leu Thr Thr Leu Leu Val Pro Ala His Leu
1               5                   10                  15
```

Val Ala Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
        35                  40                  45

Met Phe Trp Tyr Arg Gln Gln Pro Gly Gln Ser Leu Thr Leu Ile Ala
50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ala Ser Ala Pro
                325                 330                 335

Ile Ser Met Leu Ala Met Leu Phe Thr Leu Ser Gly Leu Arg Ala Gln
            340                 345                 350

Ser Val Ala Gln Pro Glu Asp Gln Val Asn Val Ala Glu Gly Asn Pro
        355                 360                 365

Leu Thr Val Lys Cys Thr Tyr Ser Val Ser Gly Asn Pro Tyr Leu Phe
370                 375                 380

Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
                405                 410                 415

Phe Asn Lys Ser Gln Thr Ser Phe His Leu Lys Lys Pro Ser Ala Leu
            420                 425                 430

Val Ser Asp Ser Ala Leu Tyr Phe Cys Ala Val Arg Asp Leu Phe Thr

```
              435                 440                 445
Gly Ala Gly Ser Tyr Gln Leu Thr Phe Gly Lys Gly Thr Lys Leu Ser
    450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
        515                 520                 525

Ala Val Ala Trp Ser Asn Lys Ser Asp Phe Ala Cys Ala Asn Ala Phe
    530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
        595                 600                 605
```

<210> SEQ ID NO 191
<211> LENGTH: 610
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 191

```
Met Lys Ser Val Leu Leu Leu Thr Thr Leu Leu Val Pro Ala His Leu
1               5                   10                  15

Val Ala Ala Val Ile Ser Gln Lys Pro Ser Arg Asp Ile Cys Gln Arg
                20                  25                  30

Gly Thr Ser Leu Thr Ile Gln Cys Gln Val Asp Ser Gln Val Thr Met
            35                  40                  45

Met Phe Trp Tyr Arg Gln Gln Pro Gly Gln Ser Leu Thr Leu Ile Ala
        50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190
```

-continued

```
Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ala Ser Ala Pro
                325                 330                 335

Ile Ser Met Leu Ala Met Leu Phe Thr Leu Ser Gly Leu Arg Ala Gln
            340                 345                 350

Ser Val Ala Gln Pro Glu Asp Gln Val Asn Val Ala Glu Gly Asn Pro
        355                 360                 365

Leu Thr Val Lys Cys Thr Tyr Ser Val Ser Gly Asn Pro Tyr Leu Phe
    370                 375                 380

Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
                405                 410                 415

Phe Asn Lys Ser Gln Thr Ser Phe His Leu Lys Lys Pro Ser Ala Leu
            420                 425                 430

Val Ser Asp Ser Ala Leu Tyr Phe Cys Ala Val Arg Asp Leu Phe Thr
        435                 440                 445

Gly Ala Gly Ser Tyr Gln Leu Thr Phe Gly Lys Gly Thr Lys Leu Ser
    450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
        515                 520                 525

Ala Val Ala Trp Ser Asn Lys Ser Asp Phe Ala Cys Ala Asn Ala Phe
    530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
        595                 600                 605
```

-continued

```
Gly Ser
    610

<210> SEQ ID NO 192

<400> SEQUENCE: 192

000

<210> SEQ ID NO 193

<400> SEQUENCE: 193

000

<210> SEQ ID NO 194
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Leu Ser Asp Gly Ala Gly Ser Tyr Gln Leu Thr Phe Gly Lys
        115                 120                 125

Gly Thr Lys Leu Ser Val Ile Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270
```

```
Arg Leu Trp Ser Ser Arg Ala Lys Arg Ser Gly Ser Gly Ala Thr Asn
            275                 280                 285

Phe Ser Leu Leu Lys Gln Ala Gly Asp Val Glu Glu Asn Pro Gly Pro
        290                 295                 300

Met Leu Ser Leu Leu Leu Leu Leu Gly Leu Gly Ser Val Phe Ser
305                 310                 315                 320

Ala Val Ile Ser Gln Lys Pro Ser Arg Asp Ile Cys Gln Arg Gly Thr
                325                 330                 335

Ser Leu Thr Ile Gln Cys Gln Val Asp Ser Gln Val Thr Met Met Phe
            340                 345                 350

Trp Tyr Arg Gln Gln Pro Gly Gln Ser Leu Thr Leu Ile Ala Thr Ala
        355                 360                 365

Asn Gln Gly Ser Glu Ala Thr Tyr Glu Ser Gly Phe Val Ile Asp Lys
    370                 375                 380

Phe Pro Ile Ser Arg Pro Asn Leu Thr Phe Ser Thr Leu Thr Val Ser
385                 390                 395                 400

Asn Met Ser Pro Glu Asp Ser Ser Ile Tyr Leu Cys Ser Val Gly Gly
                405                 410                 415

Ala Gly Val Thr Asp Thr Gln Tyr Phe Gly Pro Gly Thr Arg Leu Thr
            420                 425                 430

Val Leu Glu Asp Leu Asn Lys Val Phe Pro Pro Glu Val Ala Val Phe
        435                 440                 445

Glu Pro Ser Glu Ala Glu Ile Ser His Thr Gln Lys Ala Thr Leu Val
    450                 455                 460

Cys Leu Ala Thr Gly Phe Phe Pro Asp His Val Glu Leu Ser Trp Trp
465                 470                 475                 480

Val Asn Gly Lys Glu Val His Ser Gly Val Ser Thr Asp Pro Gln Pro
                485                 490                 495

Leu Lys Glu Gln Pro Ala Leu Asn Asp Ser Arg Tyr Cys Leu Ser Ser
            500                 505                 510

Arg Leu Arg Val Ser Ala Thr Phe Trp Gln Asn Pro Arg Asn His Phe
        515                 520                 525

Arg Cys Gln Val Gln Phe Tyr Gly Leu Ser Glu Asn Asp Glu Trp Thr
    530                 535                 540

Gln Asp Arg Ala Lys Pro Val Thr Gln Ile Val Ser Ala Glu Ala Trp
545                 550                 555                 560

Gly Arg Ala Asp Cys Gly Phe Thr Ser Val Ser Tyr Gln Gln Gly Val
                565                 570                 575

Leu Ser Ala Thr Ile Leu Tyr Glu Ile Leu Leu Gly Lys Ala Thr Leu
            580                 585                 590

Tyr Ala Val Leu Val Ser Ala Leu Val Leu Met Ala Met Val Lys Arg
        595                 600                 605

Lys Asp Phe
    610

<210> SEQ ID NO 195

<400> SEQUENCE: 195

000

<210> SEQ ID NO 196
<211> LENGTH: 606
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 196

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Leu Ser Asp Gly Ala Gly Ser Tyr Gln Leu Thr Phe Gly Lys
            115                 120                 125

Gly Thr Lys Leu Ser Val Ile Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Gly Ser Gly Ala Thr Asn Phe Ser Leu Leu Lys
        275                 280                 285

Gln Ala Gly Asp Val Glu Glu Asn Pro Gly Pro Met Leu Ser Leu Leu
    290                 295                 300

Leu Leu Leu Leu Gly Leu Gly Ser Val Phe Ser Ala Val Ile Ser Gln
305                 310                 315                 320

Lys Pro Ser Arg Asp Ile Cys Gln Arg Gly Thr Ser Leu Thr Ile Gln
                325                 330                 335

Cys Gln Val Asp Ser Gln Val Thr Met Met Phe Trp Tyr Arg Gln Gln
            340                 345                 350

Pro Gly Gln Ser Leu Thr Leu Ile Ala Thr Ala Asn Gln Gly Ser Glu
        355                 360                 365

Ala Thr Tyr Glu Ser Gly Phe Val Ile Asp Lys Phe Pro Ile Ser Arg
    370                 375                 380
```

```
Pro Asn Leu Thr Phe Ser Thr Leu Thr Val Ser Asn Met Ser Pro Glu
385                 390                 395                 400

Asp Ser Ser Ile Tyr Leu Cys Ser Val Gly Gly Ala Gly Val Thr Asp
            405                 410                 415

Thr Gln Tyr Phe Gly Pro Gly Thr Arg Leu Thr Val Leu Glu Asp Leu
        420                 425                 430

Asn Lys Val Phe Pro Pro Glu Val Ala Val Phe Glu Pro Ser Glu Ala
    435                 440                 445

Glu Ile Ser His Thr Gln Lys Ala Thr Leu Val Cys Leu Ala Thr Gly
450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
            485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
        515                 520                 525

Phe Tyr Gly Leu Ser Glu Asn Asp Glu Trp Thr Gln Asp Arg Ala Lys
    530                 535                 540

Pro Val Thr Gln Ile Val Ser Ala Glu Ala Trp Gly Arg Ala Asp Cys
545                 550                 555                 560

Gly Phe Thr Ser Val Ser Tyr Gln Gln Gly Val Leu Ser Ala Thr Ile
            565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Phe
        595                 600                 605

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
```

```
            20                  25                  30
Ser Leu Thr Ile Gln Cys Gln Val Asp Ser Gln Val Thr Met Met Phe
        35                  40                  45
Trp Tyr Arg Gln Gln Pro Gly Gln Ser Leu Thr Leu Ile Ala Thr Ala
        50                  55                  60
Asn Gln Gly Ser Glu Ala Thr Tyr Glu Ser Gly Phe Val Ile Asp Lys
65                  70                  75                  80
Phe Pro Ile Ser Arg Pro Asn Leu Thr Phe Ser Thr Leu Thr Val Ser
                85                  90                  95
Asn Met Ser Pro Glu Asp Ser Ser Ile Tyr Leu Cys Ser Val Gly Gly
                100                 105                 110
Ala Gly Val Thr Asp Thr Gln Tyr Phe Gly Pro Gly Thr Arg Leu Thr
                115                 120                 125
Val Leu Glu Asp Leu Asn Lys Val Phe Pro Pro Glu Val Ala Val Phe
                130                 135                 140
Glu Pro Ser Glu Ala Glu Ile Ser His Thr Gln Lys Ala Thr Leu Val
145                 150                 155                 160
Cys Leu Ala Thr Gly Phe Phe Pro Asp His Val Glu Leu Ser Trp Trp
                165                 170                 175
Val Asn Gly Lys Glu Val His Ser Gly Val Ser Thr Asp Pro Gln Pro
                180                 185                 190
Leu Lys Glu Gln Pro Ala Leu Asn Asp Ser Arg Tyr Cys Leu Ser Ser
                195                 200                 205
Arg Leu Arg Val Ser Ala Thr Phe Trp Gln Asn Pro Arg Asn His Phe
        210                 215                 220
Arg Cys Gln Val Gln Phe Tyr Gly Leu Ser Glu Asn Asp Glu Trp Thr
225                 230                 235                 240
Gln Asp Arg Ala Lys Pro Val Thr Gln Ile Val Ser Ala Glu Ala Trp
                245                 250                 255
Gly Arg Ala Asp Cys Gly Phe Thr Ser Val Ser Tyr Gln Gln Gly Val
                260                 265                 270
Leu Ser Ala Thr Ile Leu Tyr Glu Ile Leu Leu Gly Lys Ala Thr Leu
                275                 280                 285
Tyr Ala Val Leu Val Ser Ala Leu Val Leu Met Ala Met Val Lys Arg
        290                 295                 300
Lys Asp Phe Arg Ala Lys Arg Ser Gly Ser Gly Ala Thr Asn Phe Ser
305                 310                 315                 320
Leu Leu Lys Gln Ala Gly Asp Val Glu Glu Asn Pro Gly Pro Met Ala
                325                 330                 335
Ser Ala Pro Ile Ser Met Leu Ala Met Leu Phe Thr Leu Ser Gly Leu
                340                 345                 350
Arg Ala Gln Ser Val Ala Gln Pro Glu Asp Gln Val Asn Val Ala Glu
                355                 360                 365
Gly Asn Pro Leu Thr Val Lys Cys Thr Tyr Ser Val Ser Gly Asn Pro
        370                 375                 380
Tyr Leu Phe Trp Tyr Val Gln Tyr Pro Asn Arg Gly Leu Gln Phe Leu
385                 390                 395                 400
Leu Lys Tyr Ile Thr Gly Asp Asn Leu Val Lys Gly Ser Tyr Gly Phe
                405                 410                 415
Glu Ala Glu Phe Asn Lys Ser Gln Thr Ser Phe His Leu Lys Lys Pro
                420                 425                 430
Ser Ala Leu Val Ser Asp Ser Ala Leu Tyr Phe Cys Ala Val Arg Asp
                435                 440                 445
```

```
Leu Ser Asp Gly Ala Gly Ser Tyr Gln Leu Thr Phe Gly Lys Gly Thr
    450                 455                 460

Lys Leu Ser Val Ile Pro Asn Ile Gln Asn Pro Asp Pro Ala Val Tyr
465                 470                 475                 480

Gln Leu Arg Asp Ser Lys Ser Asp Lys Ser Val Cys Leu Phe Thr
            485                 490                 495

Asp Phe Asp Ser Gln Thr Asn Val Ser Gln Ser Lys Asp Ser Asp Val
            500                 505                 510

Tyr Ile Thr Asp Lys Thr Val Leu Asp Met Arg Ser Met Asp Phe Lys
            515                 520                 525

Ser Asn Ser Ala Val Ala Trp Ser Asn Lys Ser Asp Phe Ala Cys Ala
    530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
            565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
            595                 600                 605

Trp Ser Ser
    610

<210> SEQ ID NO 201

<400> SEQUENCE: 201

000

<210> SEQ ID NO 202
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
            85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
            115                 120                 125

Val Leu Glu Asp Leu Asn Lys Val Phe Pro Pro Glu Val Ala Val Phe
130                 135                 140
```

```
Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
            340                 345                 350

Ala Gln Pro Glu Asp Gln Val Asn Val Ala Glu Gly Asn Pro Leu Thr
        355                 360                 365

Val Lys Cys Thr Tyr Ser Val Ser Gly Asn Pro Tyr Leu Phe Trp Tyr
    370                 375                 380

Val Gln Tyr Pro Asn Arg Gly Leu Gln Phe Leu Leu Lys Tyr Ile Thr
385                 390                 395                 400

Gly Asp Asn Leu Val Lys Gly Ser Tyr Gly Phe Glu Ala Glu Phe Asn
                405                 410                 415

Lys Ser Gln Thr Ser Phe His Leu Lys Lys Pro Ser Ala Leu Val Ser
            420                 425                 430

Asp Ser Ala Leu Tyr Phe Cys Ala Val Arg Asp Leu Ser Asp Gly Ala
        435                 440                 445

Gly Ser Tyr Gln Leu Thr Phe Gly Lys Gly Thr Lys Leu Ser Val Ile
    450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
    530                 535                 540

Ser Ile Ile Pro Glu Asp Thr Phe Phe Pro Ser Pro Glu Ser Ser Cys
545                 550                 555                 560
```

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser
        595                 600                 605

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 206

Met Lys Ser Val Leu Leu Leu Thr Thr Leu Leu Val Pro Ala His Leu
1               5                   10                  15

Val Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
        35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu

```
                195                 200                 205
Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
            340                 345                 350

Gly Leu Arg Ala Gln Ser Val Ala Gln Pro Glu Asp Gln Val Asn Val
        355                 360                 365

Ala Glu Gly Asn Pro Leu Thr Val Lys Cys Thr Tyr Ser Val Ser Gly
    370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
            420                 425                 430

Lys Pro Ser Ala Leu Val Ser Asp Ser Ala Leu Tyr Phe Cys Ala Val
        435                 440                 445

Arg Asp Leu Ser Asp Gly Ala Gly Ser Tyr Gln Leu Thr Phe Gly Lys
    450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
            500                 505                 510

Asp Val Tyr Ile Thr Asp Lys Thr Val Leu Asp Met Arg Ser Met Asp
        515                 520                 525

Phe Lys Ser Asn Ser Ala Val Ala Trp Ser Asn Lys Ser Asp Phe Ala
    530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
            580                 585                 590

Arg Ile Leu Leu Leu Lys Val Ala Gly Phe Asn Leu Leu Met Thr Leu
        595                 600                 605

Arg Leu Trp Ser Ser
    610
```

<210> SEQ ID NO 207

<400> SEQUENCE: 207

000

<210> SEQ ID NO 208
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 208

```
Met Lys Ser Val Leu Leu Thr Thr Leu Leu Val Pro Ala His Leu
1               5                   10                  15

Val Ala Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
            35                  40                  45

Met Phe Trp Tyr Arg Gln Gln Pro Gly Gln Ser Leu Thr Leu Ile Ala
50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
            115                 120                 125

Leu Thr Val Leu Glu Asp Leu Asn Lys Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Gly Lys Ala
            275                 280                 285

Thr Leu Tyr Ala Val Leu Val Ser Ala Leu Val Leu Met Ala Met Val
            290                 295                 300

Lys Arg Lys Asp Phe Gly Ser Gly Ala Thr Asn Phe Ser Leu Leu Lys
305                 310                 315                 320
```

```
Gln Ala Gly Asp Val Glu Glu Asn Pro Gly Pro Met Ala Ser Ala Pro
                325                 330                 335

Ile Ser Met Leu Ala Met Leu Phe Thr Leu Ser Gly Leu Arg Ala Gln
                340                 345                 350

Ser Val Ala Gln Pro Glu Asp Gln Val Asn Val Ala Glu Gly Asn Pro
                355                 360                 365

Leu Thr Val Lys Cys Thr Tyr Ser Val Ser Gly Asn Pro Tyr Leu Phe
            370                 375                 380

Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
                405                 410                 415

Phe Asn Lys Ser Gln Thr Ser Phe His Leu Lys Lys Pro Ser Ala Leu
                420                 425                 430

Val Ser Asp Ser Ala Leu Tyr Phe Cys Ala Val Arg Asp Leu Ser Asp
            435                 440                 445

Gly Ala Gly Ser Tyr Gln Leu Thr Phe Gly Lys Gly Thr Lys Leu Ser
        450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
                500                 505                 510

Asp Lys Thr Val Leu Asp Met Arg Ser Met Asp Phe Lys Ser Asn Ser
            515                 520                 525

Ala Val Ala Trp Ser Asn Lys Ser Asp Phe Ala Cys Ala Asn Ala Phe
        530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
        595                 600                 605

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212
<211> LENGTH: 611
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212
```

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Asp Leu Val Gly Ala Gly Ser Tyr Gln Leu Thr Phe Gly Lys
        115                 120                 125

Gly Thr Lys Leu Ser Val Ile Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Arg Ala Lys Arg Ser Gly Ser Gly Ala Thr Asn
        275                 280                 285

Phe Ser Leu Leu Lys Gln Ala Gly Asp Val Glu Glu Asn Pro Gly Pro
    290                 295                 300

Met Leu Ser Leu Leu Leu Leu Leu Gly Leu Gly Ser Val Phe Ser
305                 310                 315                 320

Ala Val Ile Ser Gln Lys Pro Ser Arg Asp Ile Cys Gln Arg Gly Thr
                325                 330                 335

Ser Leu Thr Ile Gln Cys Gln Val Asp Ser Gln Val Thr Met Met Phe
            340                 345                 350

Trp Tyr Arg Gln Gln Pro Gly Gln Ser Leu Thr Leu Ile Ala Thr Ala
        355                 360                 365

Asn Gln Gly Ser Glu Ala Thr Tyr Glu Ser Gly Phe Val Ile Asp Lys

```
                370             375                 380
    Phe Pro Ile Ser Arg Pro Asn Leu Thr Phe Ser Thr Leu Thr Val Ser
    385                 390                 395                 400

Asn Met Ser Pro Glu Asp Ser Ser Ile Tyr Leu Cys Ser Val Gly Gly
                    405                 410                 415

Ala Gly Val Thr Asp Thr Gln Tyr Phe Gly Pro Gly Thr Arg Leu Thr
                420                 425                 430

Val Leu Glu Asp Leu Asn Lys Val Phe Pro Pro Glu Val Ala Val Phe
                435                 440                 445

Glu Pro Ser Glu Ala Glu Ile Ser His Thr Gln Lys Ala Thr Leu Val
                450                 455                 460

Cys Leu Ala Thr Gly Phe Phe Pro Asp His Val Glu Leu Ser Trp Trp
    465                 470                 475                 480

Val Asn Gly Lys Glu Val His Ser Gly Val Ser Thr Asp Pro Gln Pro
                    485                 490                 495

Leu Lys Glu Gln Pro Ala Leu Asn Asp Ser Arg Tyr Cys Leu Ser Ser
                    500                 505                 510

Arg Leu Arg Val Ser Ala Thr Phe Trp Gln Asn Pro Arg Asn His Phe
                515                 520                 525

Arg Cys Gln Val Gln Phe Tyr Gly Leu Ser Glu Asn Asp Glu Trp Thr
                530                 535                 540

Gln Asp Arg Ala Lys Pro Val Thr Gln Ile Val Ser Ala Glu Ala Trp
    545                 550                 555                 560

Gly Arg Ala Asp Cys Gly Phe Thr Ser Val Ser Tyr Gln Gln Gly Val
                    565                 570                 575

Leu Ser Ala Thr Ile Leu Tyr Glu Ile Leu Leu Gly Lys Ala Thr Leu
                580                 585                 590

Tyr Ala Val Leu Val Ser Ala Leu Val Leu Met Ala Met Val Lys Arg
                595                 600                 605

Lys Asp Phe
    610

<210> SEQ ID NO 213

<400> SEQUENCE: 213

000

<210> SEQ ID NO 214
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 214

Met Ala Ser Ala Pro Ile Ser Met Leu Ala Met Leu Phe Thr Leu Ser
    1               5                   10                  15

Gly Leu Arg Ala Gln Ser Val Ala Gln Pro Glu Asp Gln Val Asn Val
                20                  25                  30

Ala Glu Gly Asn Pro Leu Thr Val Lys Cys Thr Tyr Ser Val Ser Gly
                35                  40                  45

Asn Pro Tyr Leu Phe Trp Tyr Val Gln Tyr Pro Asn Arg Gly Leu Gln
                50                  55                  60

Phe Leu Leu Lys Tyr Ile Thr Gly Asp Asn Leu Val Lys Gly Ser Tyr
```

-continued

```
                65                  70                  75                  80
Gly Phe Glu Ala Glu Phe Asn Lys Ser Gln Thr Ser Phe His Leu Lys
                    85                  90                  95

Lys Pro Ser Ala Leu Val Ser Asp Ser Ala Leu Tyr Phe Cys Ala Val
                100                 105                 110

Arg Asp Asp Leu Val Gly Ala Gly Ser Tyr Gln Leu Thr Phe Gly Lys
                115                 120                 125

Gly Thr Lys Leu Ser Val Ile Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
                180                 185                 190

Phe Lys Ser Asn Ser Ala Val Ala Trp Ser Asn Lys Ser Asp Phe Ala
                195                 200                 205

Cys Ala Asn Ala Phe Asn Asn Ser Ile Ile Pro Glu Asp Thr Phe Phe
                210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
                260                 265                 270

Arg Leu Trp Ser Ser Gly Ser Gly Ala Thr Asn Phe Ser Leu Leu Lys
                275                 280                 285

Gln Ala Gly Asp Val Glu Glu Asn Pro Gly Pro Met Leu Ser Leu Leu
                290                 295                 300

Leu Leu Leu Leu Gly Leu Gly Ser Val Phe Ser Ala Val Ile Ser Gln
305                 310                 315                 320

Lys Pro Ser Arg Asp Ile Cys Gln Arg Gly Thr Ser Leu Thr Ile Gln
                325                 330                 335

Cys Gln Val Asp Ser Gln Val Thr Met Met Phe Trp Tyr Arg Gln Gln
                340                 345                 350

Pro Gly Gln Ser Leu Thr Leu Ile Ala Thr Ala Asn Gln Gly Ser Glu
                355                 360                 365

Ala Thr Tyr Glu Ser Gly Phe Val Ile Asp Lys Phe Pro Ile Ser Arg
                370                 375                 380

Pro Asn Leu Thr Phe Ser Thr Leu Thr Val Ser Asn Met Ser Pro Glu
385                 390                 395                 400

Asp Ser Ser Ile Tyr Leu Cys Ser Val Gly Gly Ala Gly Val Thr Asp
                405                 410                 415

Thr Gln Tyr Phe Gly Pro Gly Thr Arg Leu Thr Val Leu Glu Asp Leu
                420                 425                 430

Asn Lys Val Phe Pro Pro Glu Val Ala Val Phe Glu Pro Ser Glu Ala
                435                 440                 445

Glu Ile Ser His Thr Gln Lys Ala Thr Leu Val Cys Leu Ala Thr Gly
450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
                485                 490                 495
```

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
            515                 520                 525

Phe Tyr Gly Leu Ser Glu Asn Asp Glu Trp Thr Gln Asp Arg Ala Lys
530                 535                 540

Pro Val Thr Gln Ile Val Ser Ala Glu Ala Trp Gly Arg Ala Asp Cys
545                 550                 555                 560

Gly Phe Thr Ser Val Ser Tyr Gln Gln Gly Val Leu Ser Ala Thr Ile
                565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Phe
            595                 600                 605

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 218

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
        115                 120                 125

-continued

```
Val Leu Glu Asp Leu Asn Lys Val Phe Pro Pro Glu Val Ala Val Phe
    130                 135                 140
Glu Pro Ser Glu Ala Glu Ile Ser His Thr Gln Lys Ala Thr Leu Val
145                 150                 155                 160
Cys Leu Ala Thr Gly Phe Phe Pro Asp His Val Glu Leu Ser Trp Trp
                165                 170                 175
Val Asn Gly Lys Glu Val His Ser Gly Val Ser Thr Asp Pro Gln Pro
            180                 185                 190
Leu Lys Glu Gln Pro Ala Leu Asn Asp Ser Arg Tyr Cys Leu Ser Ser
        195                 200                 205
Arg Leu Arg Val Ser Ala Thr Phe Trp Gln Asn Pro Arg Asn His Phe
210                 215                 220
Arg Cys Gln Val Gln Phe Tyr Gly Leu Ser Glu Asn Asp Glu Trp Thr
225                 230                 235                 240
Gln Asp Arg Ala Lys Pro Val Thr Gln Ile Val Ser Ala Glu Ala Trp
                245                 250                 255
Gly Arg Ala Asp Cys Gly Phe Thr Ser Val Ser Tyr Gln Gln Gly Val
            260                 265                 270
Leu Ser Ala Thr Ile Leu Tyr Glu Ile Leu Leu Gly Lys Ala Thr Leu
        275                 280                 285
Tyr Ala Val Leu Val Ser Ala Leu Val Leu Met Ala Met Val Lys Arg
290                 295                 300
Lys Asp Phe Arg Ala Lys Arg Ser Gly Ser Gly Ala Thr Asn Phe Ser
305                 310                 315                 320
Leu Leu Lys Gln Ala Gly Asp Val Glu Glu Asn Pro Gly Pro Met Ala
                325                 330                 335
Ser Ala Pro Ile Ser Met Leu Ala Met Leu Phe Thr Leu Ser Gly Leu
            340                 345                 350
Arg Ala Gln Ser Val Ala Gln Pro Glu Asp Gln Val Asn Val Ala Glu
        355                 360                 365
Gly Asn Pro Leu Thr Val Lys Cys Thr Tyr Ser Val Ser Gly Asn Pro
370                 375                 380
Tyr Leu Phe Trp Tyr Val Gln Tyr Pro Asn Arg Gly Leu Gln Phe Leu
385                 390                 395                 400
Leu Lys Tyr Ile Thr Gly Asp Asn Leu Val Lys Gly Ser Tyr Gly Phe
                405                 410                 415
Glu Ala Glu Phe Asn Lys Ser Gln Thr Ser Phe His Leu Lys Lys Pro
            420                 425                 430
Ser Ala Leu Val Ser Asp Ser Ala Leu Tyr Phe Cys Ala Val Arg Asp
        435                 440                 445
Asp Leu Val Gly Ala Gly Ser Tyr Gln Leu Thr Phe Gly Lys Gly Thr
450                 455                 460
Lys Leu Ser Val Ile Pro Asn Ile Gln Asn Pro Asp Pro Ala Val Tyr
465                 470                 475                 480
Gln Leu Arg Asp Ser Lys Ser Ser Asp Lys Ser Val Cys Leu Phe Thr
                485                 490                 495
Asp Phe Asp Ser Gln Thr Asn Val Ser Gln Ser Lys Asp Ser Asp Val
            500                 505                 510
Tyr Ile Thr Asp Lys Thr Val Leu Asp Met Arg Ser Met Asp Phe Lys
        515                 520                 525
Ser Asn Ser Ala Val Ala Trp Ser Asn Lys Ser Asp Phe Ala Cys Ala
530                 535                 540
Asn Ala Phe Asn Asn Ser Ile Ile Pro Glu Asp Thr Phe Phe Pro Ser
```

```
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
        595                 600                 605

Trp Ser Ser
    610

<210> SEQ ID NO 219

<400> SEQUENCE: 219

000

<210> SEQ ID NO 220
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 220

Met Leu Ser Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
        50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
        115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
```

```
            245                 250                 255
Gly Arg Ala Asp Cys Gly Phe Thr Ser Val Ser Tyr Gln Gln Gly Val
            260                 265                 270
Leu Ser Ala Thr Ile Leu Tyr Glu Ile Leu Leu Gly Lys Ala Thr Leu
            275                 280                 285
Tyr Ala Val Leu Val Ser Ala Leu Val Leu Met Ala Met Val Lys Arg
            290                 295                 300
Lys Asp Phe Gly Ser Gly Ala Thr Asn Phe Ser Leu Leu Lys Gln Ala
305                 310                 315                 320
Gly Asp Val Glu Glu Asn Pro Gly Pro Met Ala Ser Ala Pro Ile Ser
                325                 330                 335
Met Leu Ala Met Leu Phe Thr Leu Ser Gly Leu Arg Ala Gln Ser Val
                340                 345                 350
Ala Gln Pro Glu Asp Gln Val Asn Val Ala Glu Gly Asn Pro Leu Thr
                355                 360                 365
Val Lys Cys Thr Tyr Ser Val Ser Gly Asn Pro Tyr Leu Phe Trp Tyr
            370                 375                 380
Val Gln Tyr Pro Asn Arg Gly Leu Gln Phe Leu Leu Lys Tyr Ile Thr
385                 390                 395                 400
Gly Asp Asn Leu Val Lys Gly Ser Tyr Gly Phe Glu Ala Glu Phe Asn
                405                 410                 415
Lys Ser Gln Thr Ser Phe His Leu Lys Lys Pro Ser Ala Leu Val Ser
                420                 425                 430
Asp Ser Ala Leu Tyr Phe Cys Ala Val Arg Asp Asp Leu Val Gly Ala
                435                 440                 445
Gly Ser Tyr Gln Leu Thr Phe Gly Lys Gly Thr Lys Leu Ser Val Ile
            450                 455                 460
Pro Asn Ile Gln Asn Pro Asp Pro Ala Val Tyr Gln Leu Arg Asp Ser
465                 470                 475                 480
Lys Ser Ser Asp Lys Ser Val Cys Leu Phe Thr Asp Phe Asp Ser Gln
                485                 490                 495
Thr Asn Val Ser Gln Ser Lys Asp Ser Asp Val Tyr Ile Thr Asp Lys
                500                 505                 510
Thr Val Leu Asp Met Arg Ser Met Asp Phe Lys Ser Asn Ser Ala Val
            515                 520                 525
Ala Trp Ser Asn Lys Ser Asp Phe Ala Cys Ala Asn Ala Phe Asn Asn
            530                 535                 540
Ser Ile Ile Pro Glu Asp Thr Phe Phe Pro Ser Pro Glu Ser Ser Cys
545                 550                 555                 560
Asp Val Lys Leu Val Glu Lys Ser Phe Glu Thr Asp Thr Asn Leu Asn
                565                 570                 575
Phe Gln Asn Leu Ser Val Ile Gly Phe Arg Ile Leu Leu Leu Lys Val
                580                 585                 590
Ala Gly Phe Asn Leu Leu Met Thr Leu Arg Leu Trp Ser Ser
            595                 600                 605

<210> SEQ ID NO 221

<400> SEQUENCE: 221

000

<210> SEQ ID NO 222

<400> SEQUENCE: 222
```

000

<210> SEQ ID NO 223

<400> SEQUENCE: 223

000

<210> SEQ ID NO 224
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 224

```
Met Lys Ser Val Leu Leu Thr Thr Leu Leu Val Pro Ala His Leu
1               5                   10                  15

Val Ala Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
                35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300
```

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
                340                 345                 350

Gly Leu Arg Ala Gln Ser Val Ala Gln Pro Glu Asp Gln Val Asn Val
                355                 360                 365

Ala Glu Gly Asn Pro Leu Thr Val Lys Cys Thr Tyr Ser Val Ser Gly
370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
                420                 425                 430

Lys Pro Ser Ala Leu Val Ser Asp Ser Ala Leu Tyr Phe Cys Ala Val
                435                 440                 445

Arg Asp Asp Leu Val Gly Ala Gly Ser Tyr Gln Leu Thr Phe Gly Lys
450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
                500                 505                 510

Asp Val Tyr Ile Thr Asp Lys Thr Val Leu Asp Met Arg Ser Met Asp
                515                 520                 525

Phe Lys Ser Asn Ser Ala Val Ala Trp Ser Asn Lys Ser Asp Phe Ala
530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
                580                 585                 590

Arg Ile Leu Leu Leu Lys Val Ala Gly Phe Asn Leu Leu Met Thr Leu
                595                 600                 605

Arg Leu Trp Ser Ser
    610

<210> SEQ ID NO 225

<400> SEQUENCE: 225

000

<210> SEQ ID NO 226
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 226

```
Met Lys Ser Val Leu Leu Thr Thr Leu Val Pro Ala His Leu
1               5                   10                  15

Val Ala Val Ile Ser Gln Lys Pro Ser Arg Asp Ile Cys Gln Arg
        20                  25                  30

Gly Thr Ser Leu Thr Ile Gln Cys Gln Val Asp Ser Gln Val Thr Met
            35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
            115                 120                 125

Leu Thr Val Leu Glu Asp Leu Asn Lys Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ala Ser Ala Pro
            325                 330                 335

Ile Ser Met Leu Ala Met Leu Phe Thr Leu Ser Gly Leu Arg Ala Gln
            340                 345                 350

Ser Val Ala Gln Pro Glu Asp Gln Val Asn Val Ala Glu Gly Asn Pro
            355                 360                 365

Leu Thr Val Lys Cys Thr Tyr Ser Val Ser Gly Asn Pro Tyr Leu Phe
            370                 375                 380

Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
                405                 410                 415

Phe Asn Lys Ser Gln Thr Ser Phe His Leu Lys Lys Pro Ser Ala Leu
```

```
            420                 425                 430
Val Ser Asp Ser Ala Leu Tyr Phe Cys Ala Val Arg Asp Asp Leu Val
            435                 440                 445

Gly Ala Gly Ser Tyr Gln Leu Thr Phe Gly Lys Gly Thr Lys Leu Ser
        450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
        515                 520                 525

Ala Val Ala Trp Ser Asn Lys Ser Asp Phe Ala Cys Ala Asn Ala Phe
    530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
        595                 600                 605
```

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 230

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60
```

-continued

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Met Ala Asn Gly Ala Gly Ser Tyr Gln Leu Thr Phe Gly Lys
            115                 120                 125

Gly Thr Lys Leu Ser Val Ile Pro Asn Ile Gln Asn Pro Asp Pro Ala
        130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Arg Ala Lys Arg Ser Gly Ser Gly Ala Thr Asn
        275                 280                 285

Phe Ser Leu Leu Lys Gln Ala Gly Asp Val Glu Glu Asn Pro Gly Pro
        290                 295                 300

Met Leu Ser Leu Leu Leu Leu Leu Gly Leu Gly Ser Val Phe Ser
305                 310                 315                 320

Ala Val Ile Ser Gln Lys Pro Ser Arg Asp Ile Cys Gln Arg Gly Thr
            325                 330                 335

Ser Leu Thr Ile Gln Cys Gln Val Asp Ser Gln Val Thr Met Met Phe
            340                 345                 350

Trp Tyr Arg Gln Gln Pro Gly Gln Ser Leu Thr Leu Ile Ala Thr Ala
        355                 360                 365

Asn Gln Gly Ser Glu Ala Thr Tyr Glu Ser Gly Phe Val Ile Asp Lys
        370                 375                 380

Phe Pro Ile Ser Arg Pro Asn Leu Thr Phe Ser Thr Leu Thr Val Ser
385                 390                 395                 400

Asn Met Ser Pro Glu Asp Ser Ser Ile Tyr Leu Cys Ser Val Gly Gly
                405                 410                 415

Ala Gly Val Thr Asp Thr Gln Tyr Phe Gly Pro Gly Thr Arg Leu Thr
            420                 425                 430

Val Leu Glu Asp Leu Asn Lys Val Phe Pro Pro Glu Val Ala Val Phe
            435                 440                 445

Glu Pro Ser Glu Ala Glu Ile Ser His Thr Gln Lys Ala Thr Leu Val
        450                 455                 460

Cys Leu Ala Thr Gly Phe Phe Pro Asp His Val Glu Leu Ser Trp Trp
465                 470                 475                 480

Val Asn Gly Lys Glu Val His Ser Gly Val Ser Thr Asp Pro Gln Pro
                485                 490                 495

Leu Lys Glu Gln Pro Ala Leu Asn Asp Ser Arg Tyr Cys Leu Ser Ser
            500                 505                 510

Arg Leu Arg Val Ser Ala Thr Phe Trp Gln Asn Pro Arg Asn His Phe
        515                 520                 525

Arg Cys Gln Val Gln Phe Tyr Gly Leu Ser Glu Asn Asp Glu Trp Thr
    530                 535                 540

Gln Asp Arg Ala Lys Pro Val Thr Gln Ile Val Ser Ala Glu Ala Trp
545                 550                 555                 560

Gly Arg Ala Asp Cys Gly Phe Thr Ser Val Ser Tyr Gln Gln Gly Val
                565                 570                 575

Leu Ser Ala Thr Ile Leu Tyr Glu Ile Leu Leu Gly Lys Ala Thr Leu
            580                 585                 590

Tyr Ala Val Leu Val Ser Ala Leu Val Leu Met Ala Met Val Lys Arg
        595                 600                 605

Lys Asp Phe
    610

<210> SEQ ID NO 231

<400> SEQUENCE: 231

000

<210> SEQ ID NO 232
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 232

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Met Ala Asn Gly Ala Gly Ser Tyr Gln Leu Thr Phe Gly Lys
        115                 120                 125

Gly Thr Lys Leu Ser Val Ile Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

```
Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
            210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
            245                 250                 255

Arg Ile Leu Leu Leu Lys Val Ala Gly Phe Asn Leu Leu Met Thr Leu
            260                 265                 270

Arg Leu Trp Ser Ser Gly Ser Gly Ala Thr Asn Phe Ser Leu Leu Lys
            275                 280                 285

Gln Ala Gly Asp Val Glu Glu Asn Pro Gly Pro Met Leu Ser Leu Leu
            290                 295                 300

Leu Leu Leu Leu Gly Leu Gly Ser Val Phe Ser Ala Val Ile Ser Gln
305                 310                 315                 320

Lys Pro Ser Arg Asp Ile Cys Gln Arg Gly Thr Ser Leu Thr Ile Gln
            325                 330                 335

Cys Gln Val Asp Ser Gln Val Thr Met Met Phe Trp Tyr Arg Gln Gln
            340                 345                 350

Pro Gly Gln Ser Leu Thr Leu Ile Ala Thr Ala Asn Gln Gly Ser Glu
            355                 360                 365

Ala Thr Tyr Glu Ser Gly Phe Val Ile Asp Lys Phe Pro Ile Ser Arg
            370                 375                 380

Pro Asn Leu Thr Phe Ser Thr Leu Thr Val Ser Asn Met Ser Pro Glu
385                 390                 395                 400

Asp Ser Ser Ile Tyr Leu Cys Ser Val Gly Ala Gly Val Thr Asp
            405                 410                 415

Thr Gln Tyr Phe Gly Pro Gly Thr Arg Leu Thr Val Leu Glu Asp Leu
            420                 425                 430

Asn Lys Val Phe Pro Pro Glu Val Ala Val Phe Glu Pro Ser Glu Ala
            435                 440                 445

Glu Ile Ser His Thr Gln Lys Ala Thr Leu Val Cys Leu Ala Thr Gly
450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
            485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
            515                 520                 525

Phe Tyr Gly Leu Ser Glu Asn Asp Glu Trp Thr Gln Asp Arg Ala Lys
            530                 535                 540

Pro Val Thr Gln Ile Val Ser Ala Glu Ala Trp Gly Arg Ala Asp Cys
545                 550                 555                 560

Gly Phe Thr Ser Val Ser Tyr Gln Gln Gly Val Leu Ser Ala Thr Ile
            565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Phe
```

595                 600                 605

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 236

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
        115                 120                 125

Val Leu Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
            245                 250                 255

Gly Arg Ala Asp Cys Gly Phe Thr Ser Val Ser Tyr Gln Gln Gly Val
        260                 265                 270

Leu Ser Ala Thr Ile Leu Tyr Glu Ile Leu Gly Lys Ala Thr Leu
    275                 280                 285

Tyr Ala Val Leu Val Ser Ala Leu Val Leu Met Ala Met Val Lys Arg
    290                 295                 300

Lys Asp Phe Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Ala
                325                 330                 335

Ser Ala Pro Ile Ser Met Leu Ala Met Leu Phe Thr Leu Ser Gly Leu
                340                 345                 350

Arg Ala Gln Ser Val Ala Gln Pro Glu Asp Gln Val Asn Val Ala Glu
                355                 360                 365

Gly Asn Pro Leu Thr Val Lys Cys Thr Tyr Ser Val Ser Gly Asn Pro
370                 375                 380

Tyr Leu Phe Trp Tyr Val Gln Tyr Pro Asn Arg Gly Leu Gln Phe Leu
385                 390                 395                 400

Leu Lys Tyr Ile Thr Gly Asp Asn Leu Val Lys Gly Ser Tyr Gly Phe
                405                 410                 415

Glu Ala Glu Phe Asn Lys Ser Gln Thr Ser Phe His Leu Lys Lys Pro
                420                 425                 430

Ser Ala Leu Val Ser Asp Ser Ala Leu Tyr Phe Cys Ala Val Arg Asp
                435                 440                 445

Met Ala Asn Gly Ala Gly Ser Tyr Gln Leu Thr Phe Gly Lys Gly Thr
                450                 455                 460

Lys Leu Ser Val Ile Pro Asn Ile Gln Asn Pro Asp Pro Ala Val Tyr
465                 470                 475                 480

Gln Leu Arg Asp Ser Lys Ser Ser Asp Lys Ser Val Cys Leu Phe Thr
                485                 490                 495

Asp Phe Asp Ser Gln Thr Asn Val Ser Gln Ser Lys Asp Ser Asp Val
                500                 505                 510

Tyr Ile Thr Asp Lys Thr Val Leu Asp Met Arg Ser Met Asp Phe Lys
                515                 520                 525

Ser Asn Ser Ala Val Ala Trp Ser Asn Lys Ser Asp Phe Ala Cys Ala
530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
                580                 585                 590

Leu Leu Leu Lys Val Ala Gly Phe Asn Leu Leu Met Thr Leu Arg Leu
                595                 600                 605

Trp Ser Ser
    610

<210> SEQ ID NO 237

<400> SEQUENCE: 237

000

<210> SEQ ID NO 238
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 238

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
        35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
            100                 105                 110

Ala Gly Val Thr Asp Thr Gln Tyr Phe Gly Pro Gly Thr Arg Leu Thr
        115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
            340                 345                 350

Ala Gln Pro Glu Asp Gln Val Asn Val Ala Glu Gly Asn Pro Leu Thr
               355                 360                 365

Val Lys Cys Thr Tyr Ser Val Ser Gly Asn Pro Tyr Leu Phe Trp Tyr
370                 375                 380

Val Gln Tyr Pro Asn Arg Gly Leu Gln Phe Leu Lys Tyr Ile Thr
385                 390                 395                 400

Gly Asp Asn Leu Val Lys Gly Ser Tyr Gly Phe Glu Ala Glu Phe Asn
                405                 410                 415

Lys Ser Gln Thr Ser Phe His Leu Lys Lys Pro Ser Ala Leu Val Ser
                420                 425                 430

Asp Ser Ala Leu Tyr Phe Cys Ala Val Arg Asp Met Ala Asn Gly Ala
                435                 440                 445

Gly Ser Tyr Gln Leu Thr Phe Gly Lys Gly Thr Lys Leu Ser Val Ile
                450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
                500                 505                 510

Thr Val Leu Asp Met Arg Ser Met Asp Phe Lys Ser Asn Ser Ala Val
                515                 520                 525

Ala Trp Ser Asn Lys Ser Asp Phe Ala Cys Ala Asn Ala Phe Asn Asn
                530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
                580                 585                 590

Ala Gly Phe Asn Leu Leu Met Thr Leu Arg Leu Trp Ser Ser
                595                 600                 605

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 242

Met Lys Ser Val Leu Leu Thr Thr Leu Leu Val Pro Ala His Leu
1               5                   10                  15

Val Ala Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
                35                  40                  45

Met Phe Trp Tyr Arg Gln Gln Pro Gly Gln Ser Leu Thr Leu Ile Ala
        50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
                115                 120                 125

Leu Thr Val Leu Glu Asp Leu Asn Lys Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
        290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
            340                 345                 350

Gly Leu Arg Ala Gln Ser Val Ala Gln Pro Glu Asp Gln Val Asn Val
                355                 360                 365

Ala Glu Gly Asn Pro Leu Thr Val Lys Cys Thr Tyr Ser Val Ser Gly
370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415
```

-continued

Gly Phe Glu Ala Glu Phe Asn Lys Ser Gln Thr Ser Phe His Leu Lys
            420                 425                 430

Lys Pro Ser Ala Leu Val Ser Asp Ser Ala Leu Tyr Phe Cys Ala Val
            435                 440                 445

Arg Asp Met Ala Asn Gly Ala Gly Ser Tyr Gln Leu Thr Phe Gly Lys
            450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                    485                 490                 495

Phe Thr Asp Phe Asp Ser Gln Thr Asn Val Ser Gln Ser Lys Asp Ser
            500                 505                 510

Asp Val Tyr Ile Thr Asp Lys Thr Val Leu Asp Met Arg Ser Met Asp
            515                 520                 525

Phe Lys Ser Asn Ser Ala Val Ala Trp Ser Asn Lys Ser Asp Phe Ala
            530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                    565                 570                 575

Glu Thr Asp Thr Asn Leu Asn Phe Gln Asn Leu Ser Val Ile Gly Phe
            580                 585                 590

Arg Ile Leu Leu Leu Lys Val Ala Gly Phe Asn Leu Leu Met Thr Leu
            595                 600                 605

Arg Leu Trp Ser Ser
        610

<210> SEQ ID NO 243

<400> SEQUENCE: 243

000

<210> SEQ ID NO 244
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 244

Met Lys Ser Val Leu Leu Leu Thr Thr Leu Leu Val Pro Ala His Leu
1               5                   10                  15

Val Ala Ala Val Ile Ser Gln Lys Pro Ser Arg Asp Ile Cys Gln Arg
                20                  25                  30

Gly Thr Ser Leu Thr Ile Gln Cys Gln Val Asp Ser Gln Val Thr Met
            35                  40                  45

Met Phe Trp Tyr Arg Gln Gln Pro Gly Gln Ser Leu Thr Leu Ile Ala
        50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

-continued

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
                195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
        290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ala Ser Ala Pro
                325                 330                 335

Ile Ser Met Leu Ala Met Leu Phe Thr Leu Ser Gly Leu Arg Ala Gln
                340                 345                 350

Ser Val Ala Gln Pro Glu Asp Gln Val Asn Val Ala Glu Gly Asn Pro
        355                 360                 365

Leu Thr Val Lys Cys Thr Tyr Ser Val Ser Gly Asn Pro Tyr Leu Phe
        370                 375                 380

Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
                405                 410                 415

Phe Asn Lys Ser Gln Thr Ser Phe His Leu Lys Lys Pro Ser Ala Leu
                420                 425                 430

Val Ser Asp Ser Ala Leu Tyr Phe Cys Ala Val Arg Asp Met Ala Asn
        435                 440                 445

Gly Ala Gly Ser Tyr Gln Leu Thr Phe Gly Lys Gly Thr Lys Leu Ser
        450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
                500                 505                 510

Asp Lys Thr Val Leu Asp Met Arg Ser Met Asp Phe Lys Ser Asn Ser
        515                 520                 525

```
Ala Val Ala Trp Ser Asn Lys Ser Asp Phe Ala Cys Ala Asn Ala Phe
        530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
                580                 585                 590

Lys Val Ala Gly Phe Asn Leu Leu Met Thr Leu Arg Leu Trp Ser Ser
                595                 600                 605
```

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 248

```
Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
                20                  25                  30

Ala Glu Gly Asn Pro Leu Thr Val Lys Cys Thr Tyr Ser Val Ser Gly
                35                  40                  45

Asn Pro Tyr Leu Phe Trp Tyr Val Gln Tyr Pro Asn Arg Gly Leu Gln
50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
                100                 105                 110

Arg Asp Val Ala Ser Gly Ala Gly Ser Tyr Gln Leu Thr Phe Gly Lys
                115                 120                 125

Gly Thr Lys Leu Ser Val Ile Pro Asn Ile Gln Asn Pro Asp Pro Ala
                130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
```

-continued

```
                165                 170                 175
Asp Val Tyr Ile Thr Asp Lys Thr Val Leu Asp Met Arg Ser Met Asp
                    180                 185                 190
Phe Lys Ser Asn Ser Ala Val Ala Trp Ser Asn Lys Ser Asp Phe Ala
                    195                 200                 205
Cys Ala Asn Ala Phe Asn Asn Ser Ile Ile Pro Glu Asp Thr Phe Phe
    210                 215                 220
Pro Ser Pro Glu Ser Ser Cys Asp Val Lys Leu Val Glu Lys Ser Phe
225                 230                 235                 240
Glu Thr Asp Thr Asn Leu Asn Phe Gln Asn Leu Ser Val Ile Gly Phe
                    245                 250                 255
Arg Ile Leu Leu Leu Lys Val Ala Gly Phe Asn Leu Leu Met Thr Leu
                    260                 265                 270
Arg Leu Trp Ser Ser Arg Ala Lys Arg Ser Gly Ser Gly Ala Thr Asn
                    275                 280                 285
Phe Ser Leu Leu Lys Gln Ala Gly Asp Val Glu Glu Asn Pro Gly Pro
                    290                 295                 300
Met Leu Ser Leu Leu Leu Leu Leu Gly Leu Gly Ser Val Phe Ser
305                 310                 315                 320
Ala Val Ile Ser Gln Lys Pro Ser Arg Asp Ile Cys Gln Arg Gly Thr
                    325                 330                 335
Ser Leu Thr Ile Gln Cys Gln Val Asp Ser Gln Val Thr Met Met Phe
                    340                 345                 350
Trp Tyr Arg Gln Gln Pro Gly Gln Ser Leu Thr Leu Ile Ala Thr Ala
                    355                 360                 365
Asn Gln Gly Ser Glu Ala Thr Tyr Glu Ser Gly Phe Val Ile Asp Lys
                    370                 375                 380
Phe Pro Ile Ser Arg Pro Asn Leu Thr Phe Ser Thr Leu Thr Val Ser
385                 390                 395                 400
Asn Met Ser Pro Glu Asp Ser Ser Ile Tyr Leu Cys Ser Val Gly Gly
                    405                 410                 415
Ala Gly Val Thr Asp Thr Gln Tyr Phe Gly Pro Gly Thr Arg Leu Thr
                    420                 425                 430
Val Leu Glu Asp Leu Asn Lys Val Phe Pro Pro Glu Val Ala Val Phe
                    435                 440                 445
Glu Pro Ser Glu Ala Glu Ile Ser His Thr Gln Lys Ala Thr Leu Val
                    450                 455                 460
Cys Leu Ala Thr Gly Phe Phe Pro Asp His Val Glu Leu Ser Trp Trp
                    465                 470                 475                 480
Val Asn Gly Lys Glu Val His Ser Gly Val Ser Thr Asp Pro Gln Pro
                    485                 490                 495
Leu Lys Glu Gln Pro Ala Leu Asn Asp Ser Arg Tyr Cys Leu Ser Ser
                    500                 505                 510
Arg Leu Arg Val Ser Ala Thr Phe Trp Gln Asn Pro Arg Asn His Phe
                    515                 520                 525
Arg Cys Gln Val Gln Phe Tyr Gly Leu Ser Glu Asn Asp Glu Trp Thr
                    530                 535                 540
Gln Asp Arg Ala Lys Pro Val Thr Gln Ile Val Ser Ala Glu Ala Trp
545                 550                 555                 560
Gly Arg Ala Asp Cys Gly Phe Thr Ser Val Ser Tyr Gln Gln Gly Val
                    565                 570                 575
Leu Ser Ala Thr Ile Leu Tyr Glu Ile Leu Leu Gly Lys Ala Thr Leu
                    580                 585                 590
```

```
Tyr Ala Val Leu Val Ser Ala Leu Val Leu Met Ala Met Val Lys Arg
            595                 600                 605

Lys Asp Phe
    610

<210> SEQ ID NO 249

<400> SEQUENCE: 249

000

<210> SEQ ID NO 250
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 250

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Val Ala Ser Gly Ala Gly Ser Tyr Gln Leu Thr Phe Gly Lys
        115                 120                 125

Gly Thr Lys Leu Ser Val Ile Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Gly Ser Gly Ala Thr Asn Phe Ser Leu Leu Lys
        275                 280                 285
```

```
Gln Ala Gly Asp Val Glu Asn Pro Gly Pro Met Leu Ser Leu Leu
    290                 295                 300

Leu Leu Leu Leu Gly Leu Gly Ser Val Phe Ser Ala Val Ile Ser Gln
305                 310                 315                 320

Lys Pro Ser Arg Asp Ile Cys Gln Arg Gly Thr Ser Leu Thr Ile Gln
                325                 330                 335

Cys Gln Val Asp Ser Gln Val Thr Met Met Phe Trp Tyr Arg Gln Gln
                340                 345                 350

Pro Gly Gln Ser Leu Thr Leu Ile Ala Thr Ala Asn Gln Gly Ser Glu
            355                 360                 365

Ala Thr Tyr Glu Ser Gly Phe Val Ile Asp Lys Phe Pro Ile Ser Arg
        370                 375                 380

Pro Asn Leu Thr Phe Ser Thr Leu Thr Val Ser Asn Met Ser Pro Glu
385                 390                 395                 400

Asp Ser Ser Ile Tyr Leu Cys Ser Val Gly Ala Gly Val Thr Asp
                405                 410                 415

Thr Gln Tyr Phe Gly Pro Gly Thr Arg Leu Thr Val Leu Glu Asp Leu
                420                 425                 430

Asn Lys Val Phe Pro Pro Glu Val Ala Val Phe Glu Pro Ser Glu Ala
            435                 440                 445

Glu Ile Ser His Thr Gln Lys Ala Thr Leu Val Cys Leu Ala Thr Gly
        450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
                485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
        515                 520                 525

Phe Tyr Gly Leu Ser Glu Asn Asp Glu Trp Thr Gln Asp Arg Ala Lys
530                 535                 540

Pro Val Thr Gln Ile Val Ser Ala Glu Ala Trp Gly Arg Ala Asp Cys
545                 550                 555                 560

Gly Phe Thr Ser Val Ser Tyr Gln Gln Gly Val Leu Ser Ala Thr Ile
                565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Phe
        595                 600                 605

<210> SEQ ID NO 251

<400> SEQUENCE: 251

000

<210> SEQ ID NO 252

<400> SEQUENCE: 252

000

<210> SEQ ID NO 253

<400> SEQUENCE: 253
```

-continued

```
000
```

<210> SEQ ID NO 254
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 254

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
    50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
                100                 105                 110

Ala Gly Val Thr Asp Thr Gln Tyr Phe Gly Pro Gly Thr Arg Leu Thr
            115                 120                 125

Val Leu Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
    210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
    290                 295                 300

Lys Asp Phe Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Ala
                325                 330                 335

Ser Ala Pro Ile Ser Met Leu Ala Met Leu Phe Thr Leu Ser Gly Leu

```
                  340                 345                 350
Arg Ala Gln Ser Val Ala Gln Pro Glu Asp Gln Val Asn Val Ala Glu
            355                 360                 365

Gly Asn Pro Leu Thr Val Lys Cys Thr Tyr Ser Val Ser Gly Asn Pro
        370                 375                 380

Tyr Leu Phe Trp Tyr Val Gln Tyr Pro Asn Arg Gly Leu Gln Phe Leu
385                 390                 395                 400

Leu Lys Tyr Ile Thr Gly Asp Asn Leu Val Lys Gly Ser Tyr Gly Phe
            405                 410                 415

Glu Ala Glu Phe Asn Lys Ser Gln Thr Ser Phe His Leu Lys Lys Pro
        420                 425                 430

Ser Ala Leu Val Ser Asp Ser Ala Leu Tyr Phe Cys Ala Val Arg Asp
            435                 440                 445

Val Ala Ser Gly Ala Gly Ser Tyr Gln Leu Thr Phe Gly Lys Gly Thr
        450                 455                 460

Lys Leu Ser Val Ile Pro Asn Ile Gln Asn Pro Asp Pro Ala Val Tyr
465                 470                 475                 480

Gln Leu Arg Asp Ser Lys Ser Ser Asp Lys Ser Val Cys Leu Phe Thr
            485                 490                 495

Asp Phe Asp Ser Gln Thr Asn Val Ser Gln Ser Lys Asp Ser Asp Val
        500                 505                 510

Tyr Ile Thr Asp Lys Thr Val Leu Asp Met Arg Ser Met Asp Phe Lys
            515                 520                 525

Ser Asn Ser Ala Val Ala Trp Ser Asn Lys Ser Asp Phe Ala Cys Ala
        530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
            565                 570                 575

Asp Thr Asn Leu Asn Phe Gln Asn Leu Ser Val Ile Gly Phe Arg Ile
        580                 585                 590

Leu Leu Leu Lys Val Ala Gly Phe Asn Leu Leu Met Thr Leu Arg Leu
            595                 600                 605

Trp Ser Ser
        610

<210> SEQ ID NO 255

<400> SEQUENCE: 255

000

<210> SEQ ID NO 256
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 256

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe
```

```
                35                  40                  45
Trp Tyr Arg Gln Gln Pro Gly Gln Ser Leu Thr Leu Ile Ala Thr Ala
 50                  55                  60

Asn Gln Gly Ser Glu Ala Thr Tyr Glu Ser Gly Phe Val Ile Asp Lys
 65                  70                  75                  80

Phe Pro Ile Ser Arg Pro Asn Leu Thr Phe Ser Thr Leu Thr Val Ser
                 85                  90                  95

Asn Met Ser Pro Glu Asp Ser Ser Ile Tyr Leu Cys Ser Val Gly Gly
                100                 105                 110

Ala Gly Val Thr Asp Thr Gln Tyr Phe Gly Pro Gly Thr Arg Leu Thr
                115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
                195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
                260                 265                 270

Leu Ser Ala Thr Ile Leu Tyr Glu Ile Leu Leu Gly Lys Ala Thr Leu
                275                 280                 285

Tyr Ala Val Leu Val Ser Ala Leu Val Leu Met Ala Met Val Lys Arg
290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
                340                 345                 350

Ala Gln Pro Glu Asp Gln Val Asn Val Ala Glu Gly Asn Pro Leu Thr
                355                 360                 365

Val Lys Cys Thr Tyr Ser Val Ser Gly Asn Pro Tyr Leu Phe Trp Tyr
                370                 375                 380

Val Gln Tyr Pro Asn Arg Gly Leu Gln Phe Leu Leu Lys Tyr Ile Thr
385                 390                 395                 400

Gly Asp Asn Leu Val Lys Gly Ser Tyr Gly Phe Glu Ala Glu Phe Asn
                405                 410                 415

Lys Ser Gln Thr Ser Phe His Leu Lys Lys Pro Ser Ala Leu Val Ser
                420                 425                 430

Asp Ser Ala Leu Tyr Phe Cys Ala Val Arg Asp Val Ala Ser Gly Ala
                435                 440                 445

Gly Ser Tyr Gln Leu Thr Phe Gly Lys Gly Thr Lys Leu Ser Val Ile
                450                 455                 460
```

```
Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
            515                 520                 525

Ala Trp Ser Asn Lys Ser Asp Phe Ala Cys Ala Asn Ala Phe Asn Asn
            530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
                580                 585                 590

Ala Gly Phe Asn Leu Leu Met Thr Leu Arg Leu Trp Ser Ser
                595                 600                 605

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 260

Met Lys Ser Val Leu Leu Leu Thr Thr Leu Leu Val Pro Ala His Leu
1               5                   10                  15

Val Ala Ala Val Ile Ser Gln Lys Pro Ser Arg Asp Ile Cys Gln Arg
                20                  25                  30

Gly Thr Ser Leu Thr Ile Gln Cys Gln Val Asp Ser Gln Val Thr Met
            35                  40                  45

Met Phe Trp Tyr Arg Gln Gln Pro Gly Gln Ser Leu Thr Leu Ile Ala
        50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95
```

```
Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
        290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
            340                 345                 350

Gly Leu Arg Ala Gln Ser Val Ala Gln Pro Glu Asp Gln Val Asn Val
        355                 360                 365

Ala Glu Gly Asn Pro Leu Thr Val Lys Cys Thr Tyr Ser Val Ser Gly
370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
            420                 425                 430

Lys Pro Ser Ala Leu Val Ser Asp Ser Ala Leu Tyr Phe Cys Ala Val
        435                 440                 445

Arg Asp Val Ala Ser Gly Ala Gly Ser Tyr Gln Leu Thr Phe Gly Lys
        450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
            500                 505                 510

Asp Val Tyr Ile Thr Asp Lys Thr Val Leu Asp Met Arg Ser Met Asp
```

```
                515                 520                 525
Phe Lys Ser Asn Ser Ala Val Ala Trp Ser Asn Lys Ser Asp Phe Ala
    530                 535                 540
Cys Ala Asn Ala Phe Asn Asn Ser Ile Ile Pro Glu Asp Thr Phe Phe
545                 550                 555                 560
Pro Ser Pro Glu Ser Ser Cys Asp Val Lys Leu Val Glu Lys Ser Phe
                565                 570                 575
Glu Thr Asp Thr Asn Leu Asn Phe Gln Asn Leu Ser Val Ile Gly Phe
            580                 585                 590
Arg Ile Leu Leu Leu Lys Val Ala Gly Phe Asn Leu Leu Met Thr Leu
        595                 600                 605
Arg Leu Trp Ser Ser
    610

<210> SEQ ID NO 261

<400> SEQUENCE: 261

000

<210> SEQ ID NO 262
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 262

Met Lys Ser Val Leu Leu Leu Thr Thr Leu Leu Val Pro Ala His Leu
1               5                   10                  15
Val Ala Ala Val Ile Ser Gln Lys Pro Ser Arg Asp Ile Cys Gln Arg
                20                  25                  30
Gly Thr Ser Leu Thr Ile Gln Cys Gln Val Asp Ser Gln Val Thr Met
            35                  40                  45
Met Phe Trp Tyr Arg Gln Gln Pro Gly Gln Ser Leu Thr Leu Ile Ala
    50                  55                  60
Thr Ala Asn Gln Gly Ser Glu Ala Thr Tyr Glu Ser Gly Phe Val Ile
65                  70                  75                  80
Asp Lys Phe Pro Ile Ser Arg Pro Asn Leu Thr Phe Ser Thr Leu Thr
                85                  90                  95
Val Ser Asn Met Ser Pro Glu Asp Ser Ser Ile Tyr Leu Cys Ser Val
                100                 105                 110
Gly Gly Ala Gly Val Thr Asp Thr Gln Tyr Phe Gly Pro Gly Thr Arg
            115                 120                 125
Leu Thr Val Leu Glu Asp Leu Asn Lys Val Phe Pro Pro Glu Val Ala
    130                 135                 140
Val Phe Glu Pro Ser Glu Ala Glu Ile Ser His Thr Gln Lys Ala Thr
145                 150                 155                 160
Leu Val Cys Leu Ala Thr Gly Phe Phe Pro Asp His Val Glu Leu Ser
                165                 170                 175
Trp Trp Val Asn Gly Lys Glu Val His Ser Gly Val Ser Thr Asp Pro
                180                 185                 190
Gln Pro Leu Lys Glu Gln Pro Ala Leu Asn Asp Ser Arg Tyr Cys Leu
            195                 200                 205
Ser Ser Arg Leu Arg Val Ser Ala Thr Phe Trp Gln Asn Pro Arg Asn
```

-continued

```
            210                 215                 220
His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ala Ser Ala Pro
                325                 330                 335

Ile Ser Met Leu Ala Met Leu Phe Thr Leu Ser Gly Leu Arg Ala Gln
                340                 345                 350

Ser Val Ala Gln Pro Glu Asp Gln Val Asn Val Ala Glu Gly Asn Pro
                355                 360                 365

Leu Thr Val Lys Cys Thr Tyr Ser Val Ser Gly Asn Pro Tyr Leu Phe
370                 375                 380

Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
                405                 410                 415

Phe Asn Lys Ser Gln Thr Ser Phe His Leu Lys Lys Pro Ser Ala Leu
                420                 425                 430

Val Ser Asp Ser Ala Leu Tyr Phe Cys Ala Val Arg Asp Val Ala Ser
                435                 440                 445

Gly Ala Gly Ser Tyr Gln Leu Thr Phe Gly Lys Gly Thr Lys Leu Ser
                450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
                485                 490                 495

Ser Gln Thr Asn Val Ser Gln Ser Lys Asp Ser Asp Val Tyr Ile Thr
                500                 505                 510

Asp Lys Thr Val Leu Asp Met Arg Ser Met Asp Phe Lys Ser Asn Ser
                515                 520                 525

Ala Val Ala Trp Ser Asn Lys Ser Asp Phe Ala Cys Ala Asn Ala Phe
                530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
                580                 585                 590

Lys Val Ala Gly Phe Asn Leu Leu Met Thr Leu Arg Leu Trp Ser Ser
                595                 600                 605
```

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 266

Arg Glu Leu Tyr Ser
1               5

<210> SEQ ID NO 267
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 267

Gly Ala Gly Ser Tyr
1               5

<210> SEQ ID NO 268
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 268

Gly Ala Gly Val Thr
1               5

<210> SEQ ID NO 269
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 269

Ala Gly Val Thr Asp
1               5

<210> SEQ ID NO 270
<211> LENGTH: 105

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (36)..(37)
<223> OTHER INFORMATION: a, c, t or g
<220> FEATURE:
<221> NAME/KEY: modified_base
<222> LOCATION: (39)..(40)
<223> OTHER INFORMATION: a, c, t or g
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (45)..(46)
<223> OTHER INFORMATION: a, c, t or g
<220> FEATURE:
<221> NAME/KEY: modified_base
<222> LOCATION: (48)..(49)
<223> OTHER INFORMATION: a, c, t or g

<400> SEQUENCE: 270
tcgtcggcag cgtcagatgc tcttcgtgtg ctgtgnnknn knnknnknnk ggggctggga    60
gttaccaact cactttcgga tgaagagcct ccgagcccac gagac                  105

<210> SEQ ID NO 271
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (51)..(52)
<223> OTHER INFORMATION: a, c, t or g
<220> FEATURE:
<221> NAME/KEY: modified_base
<222> LOCATION: (54)..(55)
<223> OTHER INFORMATION: a, c, t or g
<220> FEATURE:
<221> NAME/KEY: modified_base
<222> LOCATION: (57)..(58)
<223> OTHER INFORMATION: a, c, t or g
<220> FEATURE:
<221> NAME/KEY: modified_base
<222> LOCATION: (60)..(61)
<223> OTHER INFORMATION: a, c, t or g
<220> FEATURE:
<221> NAME/KEY: modified_base
<222> LOCATION: (63)..(64)
<223> OTHER INFORMATION: a, c, t or g

<400> SEQUENCE: 271
tcgtcggcag cgtcagatgc tcttcgtgtg ctgtgagaga attatactct nnknnknnkn    60
nknnkcaact cactttcgga tgaagagcct ccgagcccac gagac                  105

<210> SEQ ID NO 272
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:

-continued

```
<221> NAME/KEY: modified_base
<222> LOCATION: (39)..(40)
<223> OTHER INFORMATION: a, c, t or g
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (45)..(46)
<223> OTHER INFORMATION: a, c, t or g
<220> FEATURE:
<221> NAME/KEY: modified_base
<222> LOCATION: (48)..(49)
<223> OTHER INFORMATION: a, c, t or g
<220> FEATURE:
<221> NAME/KEY: modified_base
<222> LOCATION: (51)..(52)
<223> OTHER INFORMATION: a, c, t or g

<400> SEQUENCE: 272
tcgtcggcag cgtcagatgc tcttcgtgta gcgttgggnn knnknnknnk nnkgatacgc    60
agtattttgg gtgaagagcc tccgagccca cgagac                             96

<210> SEQ ID NO 273
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (42)..(43)
<223> OTHER INFORMATION: a, c, t or g
<220> FEATURE:
<221> NAME/KEY: modified_base
<222> LOCATION: (45)..(46)
<223> OTHER INFORMATION: a, c, t or g
<220> FEATURE:
<221> NAME/KEY: modified_base
<222> LOCATION: (48)..(49)
<223> OTHER INFORMATION: a, c, t or g
<220> FEATURE:
<221> NAME/KEY: modified_base
<222> LOCATION: (51)..(52)
<223> OTHER INFORMATION: a, c, t or g
<220> FEATURE:
<221> NAME/KEY: modified_base
<222> LOCATION: (54)..(55)
<223> OTHER INFORMATION: a, c, t or g

<400> SEQUENCE: 273
tcgtcggcag cgtcagatgc tcttcgtgta gcgttggggg cnnknnknnk nnknnkacgc    60
agtattttgg gtgaagagcc tccgagccca cgagac                             96

<210> SEQ ID NO 274
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 274

Lys Ala Ser Glu Lys Ile Phe Tyr Val
1               5

<210> SEQ ID NO 275
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 275

Ala Leu Leu Met Trp Ile Thr Gln Val
1               5

<210> SEQ ID NO 276
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 276

Cys Leu Leu Met Trp Ile Thr Gln Val
1               5

<210> SEQ ID NO 277
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 277

Asp Leu Leu Met Trp Ile Thr Gln Val
1               5

<210> SEQ ID NO 278
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 278

Glu Leu Leu Met Trp Ile Thr Gln Val
1               5

<210> SEQ ID NO 279
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 279

Phe Leu Leu Met Trp Ile Thr Gln Val
1               5

<210> SEQ ID NO 280
<211> LENGTH: 9
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 280

Gly Leu Leu Met Trp Ile Thr Gln Val
1               5

<210> SEQ ID NO 281
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 281

His Leu Leu Met Trp Ile Thr Gln Val
1               5

<210> SEQ ID NO 282
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 282

Ile Leu Leu Met Trp Ile Thr Gln Val
1               5

<210> SEQ ID NO 283
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 283

Lys Leu Leu Met Trp Ile Thr Gln Val
1               5

<210> SEQ ID NO 284
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 284

Leu Leu Leu Met Trp Ile Thr Gln Val
1               5

<210> SEQ ID NO 285
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 285

Met Leu Leu Met Trp Ile Thr Gln Val
1               5

<210> SEQ ID NO 286
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 286

Asn Leu Leu Met Trp Ile Thr Gln Val
1               5

<210> SEQ ID NO 287
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 287

Pro Leu Leu Met Trp Ile Thr Gln Val
1               5

<210> SEQ ID NO 288
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 288

Gln Leu Leu Met Trp Ile Thr Gln Val
1               5

<210> SEQ ID NO 289
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 289

Arg Leu Leu Met Trp Ile Thr Gln Val
1               5

<210> SEQ ID NO 290
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 290

Thr Leu Leu Met Trp Ile Thr Gln Val
1               5
```

```
<210> SEQ ID NO 291
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 291

Val Leu Leu Met Trp Ile Thr Gln Val
1               5

<210> SEQ ID NO 292
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 292

Trp Leu Leu Met Trp Ile Thr Gln Val
1               5

<210> SEQ ID NO 293
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 293

Tyr Leu Leu Met Trp Ile Thr Gln Val
1               5

<210> SEQ ID NO 294
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 294

Ser Leu Ala Met Trp Ile Thr Gln Val
1               5

<210> SEQ ID NO 295
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 295

Ser Leu Cys Met Trp Ile Thr Gln Val
1               5

<210> SEQ ID NO 296
<211> LENGTH: 9
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 296

Ser Leu Asp Met Trp Ile Thr Gln Val
1               5

<210> SEQ ID NO 297
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 297

Ser Leu Glu Met Trp Ile Thr Gln Val
1               5

<210> SEQ ID NO 298
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 298

Ser Leu Phe Met Trp Ile Thr Gln Val
1               5

<210> SEQ ID NO 299
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 299

Ser Leu Gly Met Trp Ile Thr Gln Val
1               5

<210> SEQ ID NO 300
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 300

Ser Leu His Met Trp Ile Thr Gln Val
1               5

<210> SEQ ID NO 301
<211> LENGTH: 9
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic peptide"

<400> SEQUENCE: 301

Ser Leu Ile Met Trp Ile Thr Gln Val
1               5

<210> SEQ ID NO 302
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 302

Ser Leu Lys Met Trp Ile Thr Gln Val
1               5

<210> SEQ ID NO 303
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 303

Ser Leu Met Met Trp Ile Thr Gln Val
1               5

<210> SEQ ID NO 304
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 304

Ser Leu Asn Met Trp Ile Thr Gln Val
1               5

<210> SEQ ID NO 305
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 305

Ser Leu Pro Met Trp Ile Thr Gln Val
1               5

<210> SEQ ID NO 306
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 306
```

```
Ser Leu Gln Met Trp Ile Thr Gln Val
1               5

<210> SEQ ID NO 307
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 307

Ser Leu Arg Met Trp Ile Thr Gln Val
1               5

<210> SEQ ID NO 308
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 308

Ser Leu Ser Met Trp Ile Thr Gln Val
1               5

<210> SEQ ID NO 309
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 309

Ser Leu Thr Met Trp Ile Thr Gln Val
1               5

<210> SEQ ID NO 310
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 310

Ser Leu Val Met Trp Ile Thr Gln Val
1               5

<210> SEQ ID NO 311
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 311

Ser Leu Trp Met Trp Ile Thr Gln Val
1               5
```

```
<210> SEQ ID NO 312
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 312

Ser Leu Tyr Met Trp Ile Thr Gln Val
1               5

<210> SEQ ID NO 313
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 313

Ser Leu Leu Ala Trp Ile Thr Gln Val
1               5

<210> SEQ ID NO 314
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 314

Ser Leu Leu Cys Trp Ile Thr Gln Val
1               5

<210> SEQ ID NO 315
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 315

Ser Leu Leu Asp Trp Ile Thr Gln Val
1               5

<210> SEQ ID NO 316
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 316

Ser Leu Leu Glu Trp Ile Thr Gln Val
1               5

<210> SEQ ID NO 317
<211> LENGTH: 9
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 317

Ser Leu Leu Phe Trp Ile Thr Gln Val
1               5

<210> SEQ ID NO 318
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 318

Ser Leu Leu Gly Trp Ile Thr Gln Val
1               5

<210> SEQ ID NO 319
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 319

Ser Leu Leu His Trp Ile Thr Gln Val
1               5

<210> SEQ ID NO 320
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 320

Ser Leu Leu Ile Trp Ile Thr Gln Val
1               5

<210> SEQ ID NO 321
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 321

Ser Leu Leu Lys Trp Ile Thr Gln Val
1               5

<210> SEQ ID NO 322
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
```

```
        Synthetic peptide"

<400> SEQUENCE: 322

Ser Leu Leu Leu Trp Ile Thr Gln Val
1               5

<210> SEQ ID NO 323
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 323

Ser Leu Leu Asn Trp Ile Thr Gln Val
1               5

<210> SEQ ID NO 324
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 324

Ser Leu Leu Pro Trp Ile Thr Gln Val
1               5

<210> SEQ ID NO 325
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 325

Ser Leu Leu Gln Trp Ile Thr Gln Val
1               5

<210> SEQ ID NO 326
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 326

Ser Leu Leu Arg Trp Ile Thr Gln Val
1               5

<210> SEQ ID NO 327
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 327
```

```
Ser Leu Leu Ser Trp Ile Thr Gln Val
1               5

<210> SEQ ID NO 328
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 328

Ser Leu Leu Thr Trp Ile Thr Gln Val
1               5

<210> SEQ ID NO 329
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 329

Ser Leu Leu Val Trp Ile Thr Gln Val
1               5

<210> SEQ ID NO 330
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 330

Ser Leu Leu Trp Trp Ile Thr Gln Val
1               5

<210> SEQ ID NO 331
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 331

Ser Leu Leu Tyr Trp Ile Thr Gln Val
1               5

<210> SEQ ID NO 332
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 332

Ser Leu Leu Met Ala Ile Thr Gln Val
1               5
```

```
<210> SEQ ID NO 333
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 333

Ser Leu Leu Met Cys Ile Thr Gln Val
1               5

<210> SEQ ID NO 334
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 334

Ser Leu Leu Met Asp Ile Thr Gln Val
1               5

<210> SEQ ID NO 335
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 335

Ser Leu Leu Met Glu Ile Thr Gln Val
1               5

<210> SEQ ID NO 336
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 336

Ser Leu Leu Met Phe Ile Thr Gln Val
1               5

<210> SEQ ID NO 337
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 337

Ser Leu Leu Met Gly Ile Thr Gln Val
1               5

<210> SEQ ID NO 338
<211> LENGTH: 9
<212> TYPE: PRT
<213> ORGANISM: Artificial Sequence
```

-continued

<220> FEATURE:
<221> NAME/KEY: source
<223> OTHER INFORMATION: /note="Description of Artificial Sequence:
      Synthetic peptide"

<400> SEQUENCE: 338

Ser Leu Leu Met His Ile Thr Gln Val
1               5

<210> SEQ ID NO 339
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 339

Ser Leu Leu Met Ile Ile Thr Gln Val
1               5

<210> SEQ ID NO 340
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 340

Ser Leu Leu Met Lys Ile Thr Gln Val
1               5

<210> SEQ ID NO 341
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 341

Ser Leu Leu Met Leu Ile Thr Gln Val
1               5

<210> SEQ ID NO 342
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 342

Ser Leu Leu Met Met Ile Thr Gln Val
1               5

<210> SEQ ID NO 343
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 343

Ser Leu Leu Met Asn Ile Thr Gln Val
1               5

<210> SEQ ID NO 344
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 344

Ser Leu Leu Met Pro Ile Thr Gln Val
1               5

<210> SEQ ID NO 345
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 345

Ser Leu Leu Met Gln Ile Thr Gln Val
1               5

<210> SEQ ID NO 346
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 346

Ser Leu Leu Met Arg Ile Thr Gln Val
1               5

<210> SEQ ID NO 347
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 347

Ser Leu Leu Met Ser Ile Thr Gln Val
1               5

<210> SEQ ID NO 348
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 348

Ser Leu Leu Met Thr Ile Thr Gln Val
```

```
1               5

<210> SEQ ID NO 349
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 349

Ser Leu Leu Met Val Ile Thr Gln Val
1               5

<210> SEQ ID NO 350
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 350

Ser Leu Leu Met Tyr Ile Thr Gln Val
1               5

<210> SEQ ID NO 351
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 351

Ser Leu Leu Met Trp Ala Thr Gln Val
1               5

<210> SEQ ID NO 352
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 352

Ser Leu Leu Met Trp Cys Thr Gln Val
1               5

<210> SEQ ID NO 353
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 353

Ser Leu Leu Met Trp Asp Thr Gln Val
1               5

<210> SEQ ID NO 354
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 354

Ser Leu Leu Met Trp Glu Thr Gln Val
1               5

<210> SEQ ID NO 355
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 355

Ser Leu Leu Met Trp Phe Thr Gln Val
1               5

<210> SEQ ID NO 356
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 356

Ser Leu Leu Met Trp Gly Thr Gln Val
1               5

<210> SEQ ID NO 357
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 357

Ser Leu Leu Met Trp His Thr Gln Val
1               5

<210> SEQ ID NO 358
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 358

Ser Leu Leu Met Trp Lys Thr Gln Val
1               5

<210> SEQ ID NO 359
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 359

Ser Leu Leu Met Trp Leu Thr Gln Val
1               5

<210> SEQ ID NO 360
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 360

Ser Leu Leu Met Trp Met Thr Gln Val
1               5

<210> SEQ ID NO 361
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 361

Ser Leu Leu Met Trp Asn Thr Gln Val
1               5

<210> SEQ ID NO 362
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 362

Ser Leu Leu Met Trp Pro Thr Gln Val
1               5

<210> SEQ ID NO 363
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 363

Ser Leu Leu Met Trp Gln Thr Gln Val
1               5

<210> SEQ ID NO 364
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 364

Ser Leu Leu Met Trp Arg Thr Gln Val
1               5

<210> SEQ ID NO 365
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 365

Ser Leu Leu Met Trp Ser Thr Gln Val
1               5

<210> SEQ ID NO 366
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 366

Ser Leu Leu Met Trp Thr Thr Gln Val
1               5

<210> SEQ ID NO 367
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 367

Ser Leu Leu Met Trp Val Thr Gln Val
1               5

<210> SEQ ID NO 368
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 368

Ser Leu Leu Met Trp Trp Thr Gln Val
1               5

<210> SEQ ID NO 369
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 369

Ser Leu Leu Met Trp Tyr Thr Gln Val
1               5
```

-continued

```
<210> SEQ ID NO 370
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 370

Ser Leu Leu Met Trp Ile Ala Gln Val
1               5

<210> SEQ ID NO 371
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 371

Ser Leu Leu Met Trp Ile Cys Gln Val
1               5

<210> SEQ ID NO 372
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 372

Ser Leu Leu Met Trp Ile Asp Gln Val
1               5

<210> SEQ ID NO 373
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 373

Ser Leu Leu Met Trp Ile Glu Gln Val
1               5

<210> SEQ ID NO 374
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 374

Ser Leu Leu Met Trp Ile Phe Gln Val
1               5

<210> SEQ ID NO 375
<211> LENGTH: 9
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 375

Ser Leu Leu Met Trp Ile Gly Gln Val
1               5

<210> SEQ ID NO 376
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 376

Ser Leu Leu Met Trp Ile His Gln Val
1               5

<210> SEQ ID NO 377
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 377

Ser Leu Leu Met Trp Ile Ile Gln Val
1               5

<210> SEQ ID NO 378
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 378

Ser Leu Leu Met Trp Ile Lys Gln Val
1               5

<210> SEQ ID NO 379
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 379

Ser Leu Leu Met Trp Ile Leu Gln Val
1               5

<210> SEQ ID NO 380
<211> LENGTH: 9
<212> TYPE: PRT
<213> ORGANISM: Artificial Sequence
<220> FEATURE:
<221> NAME/KEY: source
```

-continued

```
<223> OTHER INFORMATION: /note="Description of Artificial Sequence:
      Synthetic peptide"

<400> SEQUENCE: 380

Ser Leu Leu Met Trp Ile Met Gln Val
1               5

<210> SEQ ID NO 381
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 381

Ser Leu Leu Met Trp Ile Asn Gln Val
1               5

<210> SEQ ID NO 382
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 382

Ser Leu Leu Met Trp Ile Pro Gln Val
1               5

<210> SEQ ID NO 383
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 383

Ser Leu Leu Met Trp Ile Gln Gln Val
1               5

<210> SEQ ID NO 384
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 384

Ser Leu Leu Met Trp Ile Arg Gln Val
1               5

<210> SEQ ID NO 385
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 385
```

```
Ser Leu Leu Met Trp Ile Ser Gln Val
1               5

<210> SEQ ID NO 386
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 386

Ser Leu Leu Met Trp Ile Val Gln Val
1               5

<210> SEQ ID NO 387
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 387

Ser Leu Leu Met Trp Ile Trp Gln Val
1               5

<210> SEQ ID NO 388
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 388

Ser Leu Leu Met Trp Ile Tyr Gln Val
1               5

<210> SEQ ID NO 389
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 389

Ser Leu Leu Met Trp Ile Thr Ala Val
1               5

<210> SEQ ID NO 390
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 390

Ser Leu Leu Met Trp Ile Thr Cys Val
1               5
```

```
<210> SEQ ID NO 391
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 391

Ser Leu Leu Met Trp Ile Thr Asp Val
1               5

<210> SEQ ID NO 392
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 392

Ser Leu Leu Met Trp Ile Thr Glu Val
1               5

<210> SEQ ID NO 393
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 393

Ser Leu Leu Met Trp Ile Thr Phe Val
1               5

<210> SEQ ID NO 394
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 394

Ser Leu Leu Met Trp Ile Thr Gly Val
1               5

<210> SEQ ID NO 395
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 395

Ser Leu Leu Met Trp Ile Thr His Val
1               5

<210> SEQ ID NO 396
<211> LENGTH: 9
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 396

Ser Leu Leu Met Trp Ile Thr Ile Val
1               5

<210> SEQ ID NO 397
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 397

Ser Leu Leu Met Trp Ile Thr Lys Val
1               5

<210> SEQ ID NO 398
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 398

Ser Leu Leu Met Trp Ile Thr Leu Val
1               5

<210> SEQ ID NO 399
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 399

Ser Leu Leu Met Trp Ile Thr Met Val
1               5

<210> SEQ ID NO 400
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 400

Ser Leu Leu Met Trp Ile Thr Asn Val
1               5

<210> SEQ ID NO 401
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 401

Ser Leu Leu Met Trp Ile Thr Pro Val
1               5

<210> SEQ ID NO 402
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 402

Ser Leu Leu Met Trp Ile Thr Arg Val
1               5

<210> SEQ ID NO 403
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 403

Ser Leu Leu Met Trp Ile Thr Ser Val
1               5

<210> SEQ ID NO 404
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 404

Ser Leu Leu Met Trp Ile Thr Thr Val
1               5

<210> SEQ ID NO 405
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 405

Ser Leu Leu Met Trp Ile Thr Val Val
1               5

<210> SEQ ID NO 406
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 406

Ser Leu Leu Met Trp Ile Thr Trp Val
1               5

<210> SEQ ID NO 407
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 407

Ser Leu Leu Met Trp Ile Thr Tyr Val
1               5

<210> SEQ ID NO 408
<211> LENGTH: 257
<212> TYPE: PRT
<213> ORGANISM: Homo sapiens

<400> SEQUENCE: 408

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
        50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Val Ala
                85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
                145                 150                 155                 160

Thr Asp Lys Thr Val Leu Asp Met Arg Ser Met Asp Phe Lys Ser Asn
            165                 170                 175

Ser Ala Val Ala Trp Ser Asn Lys Ser Asp Phe Ala Cys Ala Asn Ala
        180                 185                 190

Phe Asn Asn Ser Ile Ile Pro Glu Asp Thr Phe Phe Pro Ser Pro Glu
    195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser

<210> SEQ ID NO 409
<211> LENGTH: 261

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 409

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Val Ala
                85                  90                  95

Ser Gly Ala Gly Ser Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala Lys Arg
            260

<210> SEQ ID NO 410
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 410

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
```

```
            35                  40                  45
Tyr Ile Thr Gly Asp Asn Leu Val Lys Gly Ser Tyr Gly Phe Glu Ala
 50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Val Ala
                 85                  90                  95

Ser Gly Ala Gly Ser Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu
                115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
                180                 185                 190

Phe Asn Asn Ser Ile Ile Pro Glu Asp Thr Phe Phe Pro Ser Pro Glu
                195                 200                 205

Ser Ser Cys Asp Val Lys Leu Val Glu Lys Ser Phe Glu Thr Asp Thr
                210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala

<210> SEQ ID NO 411
<211> LENGTH: 278
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 411

Gln Ser Val Ala Gln Pro Glu Asp Gln Val Asn Val Ala Glu Gly Asn
  1               5                  10                  15

Pro Leu Thr Val Lys Cys Thr Tyr Ser Val Ser Gly Asn Pro Tyr Leu
                 20                  25                  30

Phe Trp Tyr Val Gln Tyr Pro Asn Arg Gly Leu Gln Phe Leu Leu Lys
                 35                  40                  45

Tyr Ile Thr Gly Asp Asn Leu Val Lys Gly Ser Tyr Gly Phe Glu Ala
 50                  55                  60

Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Asp Val Ala
                 85                  90                  95

Ser Gly Ala Gly Ser Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu
                115                 120                 125
```

```
Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
                180                 185                 190

Phe Asn Asn Ser Ile Ile Pro Glu Asp Thr Phe Phe Pro Ser Pro Glu
                195                 200                 205

Ser Ser Cys Asp Val Lys Leu Val Glu Lys Ser Phe Glu Thr Asp Thr
            210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Gly Ser Gly Ala Thr Asn Phe Ser Leu Leu Lys Ala Gly Asp
                260                 265                 270

Val Glu Glu Asn Pro Gly
        275

<210> SEQ ID NO 412
<211> LENGTH: 257
<212> TYPE: PRT
<213> ORGANISM: Homo sapiens

<400> SEQUENCE: 412

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
                20                  25                  30

Phe Trp Tyr Val Gln Tyr Pro Asn Arg Gly Leu Gln Phe Leu Leu Lys
            35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Ala Thr Val Asp Tyr Gln Leu Thr Phe Gly Lys Gly Thr Lys Leu
                100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
                180                 185                 190

Phe Asn Asn Ser Ile Ile Pro Glu Asp Thr Phe Phe Pro Ser Pro Glu
                195                 200                 205

Ser Ser Cys Asp Val Lys Leu Val Glu Lys Ser Phe Glu Thr Asp Thr
            210                 215                 220
```

-continued

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser

<210> SEQ ID NO 413
<211> LENGTH: 261
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 413

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Ala Thr Val Asp Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala Lys Arg
            260

<210> SEQ ID NO 414
<211> LENGTH: 259
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 414

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Glu Leu Tyr
                85                  90                  95

Ser Ala Thr Val Asp Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
    130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Arg Ala

<210> SEQ ID NO 415
<211> LENGTH: 278
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 415

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

```
Glu Phe Asn Lys Ser Gln Thr Ser Phe His Leu Lys Lys Pro Ser Ala
 65                  70                  75                  80

Leu Val Ser Asp Ser Ala Leu Tyr Phe Cys Ala Val Arg Glu Leu Tyr
                 85                  90                  95

Ser Ala Thr Val Asp Tyr Gln Leu Thr Phe Gly Lys Gly Thr Lys Leu
            100                 105                 110

Ser Val Ile Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
        130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
            195                 200                 205

Ser Ser Cys Asp Val Lys Leu Val Glu Lys Ser Phe Glu Thr Asp Thr
        210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser Gly Ser Gly Ala Thr Asn Phe Ser Leu Leu Lys Gln Ala Gly Asp
            260                 265                 270

Val Glu Glu Asn Pro Gly
            275

<210> SEQ ID NO 416
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 416

Met Ala Ser Ala Pro Ile Ser Met Leu Ala Met Leu Phe Thr Leu Ser
 1               5                  10                  15

Gly Leu Arg Ala Gln Ser Val Ala Gln Pro Glu Asp Gln Val Asn Val
             20                  25                  30

Ala Glu Gly Asn Pro Leu Thr Val Lys Cys Thr Tyr Ser Val Ser Gly
         35                  40                  45

Asn Pro Tyr Leu Phe Trp Tyr Val Gln Tyr Pro Asn Arg Gly Leu Gln
 50                  55                  60

Phe Leu Leu Lys Tyr Ile Thr Gly Asp Asn Leu Val Lys Gly Ser Tyr
 65                  70                  75                  80

Gly Phe Glu Ala Glu Phe Asn Lys Ser Gln Thr Ser Phe His Leu Lys
                 85                  90                  95

Lys Pro Ser Ala Leu Val Ser Asp Ser Ala Leu Tyr Phe Cys Ala Val
            100                 105                 110

Arg Glu Leu Tyr Ser Ala Thr Val Asp Tyr Gln Leu Thr Phe Gly Lys
        115                 120                 125

Gly Thr Lys Leu Ser Val Ile Pro Asn Ile Gln Asn Pro Asp Pro Ala
```

```
            130                 135                 140
Val Tyr Gln Leu Arg Asp Ser Lys Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
                180                 185                 190

Phe Lys Ser Asn Ser Ala Val Ala Trp Ser Asn Lys Ser Asp Phe Ala
                195                 200                 205

Cys Ala Asn Ala Phe Asn Asn Ser Ile Ile Pro Glu Asp Thr Phe Phe
                210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
                260                 265                 270

Arg Leu Trp Ser Ser Arg Ala Lys Arg Ser Gly Ser Gly Ala Thr Asn
                275                 280                 285

Phe Ser Leu Leu Lys Gln Ala Gly Asp Val Glu Glu Asn Pro Gly Pro
                290                 295                 300

Met Leu Ser Leu Leu Leu Leu Leu Gly Leu Gly Ser Val Phe Ser
305                 310                 315                 320

Ala Val Ile Ser Gln Lys Pro Ser Arg Asp Ile Cys Gln Arg Gly Thr
                325                 330                 335

Ser Leu Thr Ile Gln Cys Gln Val Asp Ser Gln Val Thr Met Met Phe
                340                 345                 350

Trp Tyr Arg Gln Gln Pro Gly Gln Ser Leu Thr Leu Ile Ala Thr Ala
                355                 360                 365

Asn Gln Gly Ser Glu Ala Thr Tyr Glu Ser Gly Phe Val Ile Asp Lys
                370                 375                 380

Phe Pro Ile Ser Arg Pro Asn Leu Thr Phe Ser Thr Leu Thr Val Ser
385                 390                 395                 400

Asn Met Ser Pro Glu Asp Ser Ser Ile Tyr Leu Cys Ser Val Gly Gly
                405                 410                 415

Ala Gly Val Thr Asp Thr Gln Tyr Phe Gly Pro Gly Thr Arg Leu Thr
                420                 425                 430

Val Leu Glu Asp Leu Asn Lys Val Phe Pro Pro Glu Val Ala Val Phe
                435                 440                 445

Glu Pro Ser Glu Ala Glu Ile Ser His Thr Gln Lys Ala Thr Leu Val
450                 455                 460

Cys Leu Ala Thr Gly Phe Phe Pro Asp His Val Glu Leu Ser Trp Trp
465                 470                 475                 480

Val Asn Gly Lys Glu Val His Ser Gly Val Ser Thr Asp Pro Gln Pro
                485                 490                 495

Leu Lys Glu Gln Pro Ala Leu Asn Asp Ser Arg Tyr Cys Leu Ser Ser
                500                 505                 510

Arg Leu Arg Val Ser Ala Thr Phe Trp Gln Asn Pro Arg Asn His Phe
                515                 520                 525

Arg Cys Gln Val Gln Phe Tyr Gly Leu Ser Glu Asn Asp Glu Trp Thr
                530                 535                 540

Gln Asp Arg Ala Lys Pro Val Thr Gln Ile Val Ser Ala Glu Ala Trp
545                 550                 555                 560
```

```
Gly Arg Ala Asp Cys Gly Phe Thr Ser Val Ser Tyr Gln Gln Gly Val
            565                 570                 575

Leu Ser Ala Thr Ile Leu Tyr Glu Ile Leu Leu Gly Lys Ala Thr Leu
            580                 585                 590

Tyr Ala Val Leu Val Ser Ala Leu Val Leu Met Ala Met Val Lys Arg
        595                 600                 605

Lys Asp Phe
    610

<210> SEQ ID NO 417
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 417

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Glu Leu Tyr Ser Ala Thr Val Asp Tyr Gln Leu Thr Phe Gly Lys
        115                 120                 125

Gly Thr Lys Leu Ser Val Ile Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Gly Ser Gly Ala Thr Asn Phe Ser Leu Leu Lys
        275                 280                 285
```

Gln Ala Gly Asp Val Glu Glu Asn Pro Gly Pro Met Leu Ser Leu Leu
    290                 295                 300

Leu Leu Leu Leu Gly Leu Gly Ser Val Phe Ser Ala Val Ile Ser Gln
305                 310                 315                 320

Lys Pro Ser Arg Asp Ile Cys Gln Arg Gly Thr Ser Leu Thr Ile Gln
                325                 330                 335

Cys Gln Val Asp Ser Gln Val Thr Met Met Phe Trp Tyr Arg Gln Gln
            340                 345                 350

Pro Gly Gln Ser Leu Thr Leu Ile Ala Thr Ala Asn Gln Gly Ser Glu
        355                 360                 365

Ala Thr Tyr Glu Ser Gly Phe Val Ile Asp Lys Phe Pro Ile Ser Arg
    370                 375                 380

Pro Asn Leu Thr Phe Ser Thr Leu Thr Val Ser Asn Met Ser Pro Glu
385                 390                 395                 400

Asp Ser Ser Ile Tyr Leu Cys Ser Val Gly Ala Gly Val Thr Asp
                405                 410                 415

Thr Gln Tyr Phe Gly Pro Gly Thr Arg Leu Thr Val Leu Glu Asp Leu
            420                 425                 430

Asn Lys Val Phe Pro Pro Glu Val Ala Val Phe Glu Pro Ser Glu Ala
        435                 440                 445

Glu Ile Ser His Thr Gln Lys Ala Thr Leu Val Cys Leu Ala Thr Gly
    450                 455                 460

Phe Phe Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
                485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
        515                 520                 525

Phe Tyr Gly Leu Ser Glu Asn Asp Glu Trp Thr Gln Asp Arg Ala Lys
    530                 535                 540

Pro Val Thr Gln Ile Val Ser Ala Glu Ala Trp Gly Arg Ala Asp Cys
545                 550                 555                 560

Gly Phe Thr Ser Val Ser Tyr Gln Gln Gly Val Leu Ser Ala Thr Ile
                565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Phe
        595                 600                 605

<210> SEQ ID NO 418
<211> LENGTH: 611
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 418

Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
            20                  25                  30

Ser Leu Thr Ile Gln Cys Gln Val Asp Ser Gln Val Thr Met Met Phe

```
                35                  40                  45
Trp Tyr Arg Gln Gln Pro Gly Gln Ser Leu Thr Leu Ile Ala Thr Ala
 50                  55                  60

Asn Gln Gly Ser Glu Ala Thr Tyr Glu Ser Gly Phe Val Ile Asp Lys
 65                  70                  75                  80

Phe Pro Ile Ser Arg Pro Asn Leu Thr Phe Ser Thr Leu Thr Val Ser
                 85                  90                  95

Asn Met Ser Pro Glu Asp Ser Ser Ile Tyr Leu Cys Ser Val Gly Gly
                100                 105                 110

Ala Gly Val Thr Asp Thr Gln Tyr Phe Gly Pro Gly Thr Arg Leu Thr
                115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
                180                 185                 190

Leu Lys Glu Gln Pro Ala Leu Asn Asp Ser Arg Tyr Cys Leu Ser Ser
                195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
                260                 265                 270

Leu Ser Ala Thr Ile Leu Tyr Glu Ile Leu Leu Gly Lys Ala Thr Leu
                275                 280                 285

Tyr Ala Val Leu Val Ser Ala Leu Val Leu Met Ala Met Val Lys Arg
290                 295                 300

Lys Asp Phe Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Ala
                325                 330                 335

Ser Ala Pro Ile Ser Met Leu Ala Met Leu Phe Thr Leu Ser Gly Leu
                340                 345                 350

Arg Ala Gln Ser Val Ala Gln Pro Glu Asp Gln Val Asn Val Ala Glu
                355                 360                 365

Gly Asn Pro Leu Thr Val Lys Cys Thr Tyr Ser Val Ser Gly Asn Pro
                370                 375                 380

Tyr Leu Phe Trp Tyr Val Gln Tyr Pro Asn Arg Gly Leu Gln Phe Leu
385                 390                 395                 400

Leu Lys Tyr Ile Thr Gly Asp Asn Leu Val Lys Gly Ser Tyr Gly Phe
                405                 410                 415

Glu Ala Glu Phe Asn Lys Ser Gln Thr Ser Phe His Leu Lys Lys Pro
                420                 425                 430

Ser Ala Leu Val Ser Asp Ser Ala Leu Tyr Phe Cys Ala Val Arg Glu
                435                 440                 445

Leu Tyr Ser Ala Thr Val Asp Tyr Gln Leu Thr Phe Gly Lys Gly Thr
                450                 455                 460
```

```
Lys Leu Ser Val Ile Pro Asn Ile Gln Asn Pro Asp Pro Ala Val Tyr
465                 470                 475                 480

Gln Leu Arg Asp Ser Lys Ser Asp Lys Ser Val Cys Leu Phe Thr
            485                 490                 495

Asp Phe Asp Ser Gln Thr Asn Val Ser Gln Ser Lys Ser Asp Val
        500                 505                 510

Tyr Ile Thr Asp Lys Thr Val Leu Asp Met Arg Ser Met Asp Phe Lys
            515                 520                 525

Ser Asn Ser Ala Val Ala Trp Ser Asn Lys Ser Asp Phe Ala Cys Ala
530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
                565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
            595                 600                 605

Trp Ser Ser
    610
```

<210> SEQ ID NO 419
<211> LENGTH: 606
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 419

```
Met Leu Ser Leu Leu Leu Leu Leu Gly Leu Gly Ser Val Phe Ser
1               5                   10                  15

Ala Val Ile Ser Gln Lys Pro Ser Arg Asp Ile Cys Gln Arg Gly Thr
                20                  25                  30

Ser Leu Thr Ile Gln Cys Gln Val Asp Ser Gln Val Thr Met Met Phe
            35                  40                  45

Trp Tyr Arg Gln Gln Pro Gly Gln Ser Leu Thr Leu Ile Ala Thr Ala
50                  55                  60

Asn Gln Gly Ser Glu Ala Thr Tyr Glu Ser Gly Phe Val Ile Asp Lys
65                  70                  75                  80

Phe Pro Ile Ser Arg Pro Asn Leu Thr Phe Ser Thr Leu Thr Val Ser
                85                  90                  95

Asn Met Ser Pro Glu Asp Ser Ser Ile Tyr Leu Cys Ser Val Gly Gly
                100                 105                 110

Ala Gly Val Thr Asp Thr Gln Tyr Phe Gly Pro Gly Thr Arg Leu Thr
            115                 120                 125

Val Leu Glu Asp Leu Asn Lys Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
                180                 185                 190
```

```
Leu Lys Glu Gln Pro Ala Leu Asn Asp Ser Arg Tyr Cys Leu Ser Ser
            195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Val Ser Tyr Gln Gln Gly Val
                260                 265                 270

Leu Ser Ala Thr Ile Leu Tyr Glu Ile Leu Leu Gly Lys Ala Thr Leu
                275                 280                 285

Tyr Ala Val Leu Val Ser Ala Leu Val Leu Met Ala Met Val Lys Arg
            290                 295                 300

Lys Asp Phe Gly Ser Gly Ala Thr Asn Phe Ser Leu Leu Lys Gln Ala
305                 310                 315                 320

Gly Asp Val Glu Glu Asn Pro Gly Pro Met Ala Ser Ala Pro Ile Ser
                325                 330                 335

Met Leu Ala Met Leu Phe Thr Leu Ser Gly Leu Arg Ala Gln Ser Val
                340                 345                 350

Ala Gln Pro Glu Asp Gln Val Asn Val Ala Glu Gly Asn Pro Leu Thr
            355                 360                 365

Val Lys Cys Thr Tyr Ser Val Ser Gly Asn Pro Tyr Leu Phe Trp Tyr
            370                 375                 380

Val Gln Tyr Pro Asn Arg Gly Leu Gln Phe Leu Leu Lys Tyr Ile Thr
385                 390                 395                 400

Gly Asp Asn Leu Val Lys Gly Ser Tyr Gly Phe Glu Ala Glu Phe Asn
                405                 410                 415

Lys Ser Gln Thr Ser Phe His Leu Lys Lys Pro Ser Ala Leu Val Ser
                420                 425                 430

Asp Ser Ala Leu Tyr Phe Cys Ala Val Arg Glu Leu Tyr Ser Ala Thr
            435                 440                 445

Val Asp Tyr Gln Leu Thr Phe Gly Lys Gly Thr Lys Leu Ser Val Ile
450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
                500                 505                 510

Thr Val Leu Asp Met Arg Ser Met Asp Phe Lys Ser Asn Ser Ala Val
            515                 520                 525

Ala Trp Ser Asn Lys Ser Asp Phe Ala Cys Ala Asn Ala Phe Asn Asn
            530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
                580                 585                 590

Ala Gly Phe Asn Leu Leu Met Thr Leu Arg Leu Trp Ser Ser
            595                 600                 605
```

-continued

```
<210> SEQ ID NO 420
<211> LENGTH: 613
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 420

Met Lys Ser Val Leu Leu Leu Thr Thr Leu Leu Val Pro Ala His Leu
1               5                   10                  15

Val Ala Val Ile Ser Gln Lys Pro Ser Arg Asp Ile Cys Gln Arg
            20                  25                  30

Gly Thr Ser Leu Thr Ile Gln Cys Gln Val Asp Ser Gln Val Thr Met
        35                  40                  45

Met Phe Trp Tyr Arg Gln Gln Pro Gly Gln Ser Leu Thr Leu Ile Ala
    50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95

Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
        115                 120                 125

Leu Thr Val Leu Glu Asp Leu Asn Lys Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Ala Ser Ala Pro Ile Ser Met Leu Ala Met Leu Phe Thr Leu Ser
            340                 345                 350

Gly Leu Arg Ala Gln Ser Val Ala Gln Pro Glu Asp Gln Val Asn Val
        355                 360                 365
```

```
Ala Glu Gly Asn Pro Leu Thr Val Lys Cys Thr Tyr Ser Val Ser Gly
        370                 375                 380

Asn Pro Tyr Leu Phe Trp Tyr Val Gln Tyr Pro Asn Arg Gly Leu Gln
385                 390                 395                 400

Phe Leu Leu Lys Tyr Ile Thr Gly Asp Asn Leu Val Lys Gly Ser Tyr
                405                 410                 415

Gly Phe Glu Ala Glu Phe Asn Lys Ser Gln Thr Ser Phe His Leu Lys
                420                 425                 430

Lys Pro Ser Ala Leu Val Ser Asp Ser Ala Leu Tyr Phe Cys Ala Val
                435                 440                 445

Arg Glu Leu Tyr Ser Ala Thr Val Asp Tyr Gln Leu Thr Phe Gly Lys
        450                 455                 460

Gly Thr Lys Leu Ser Val Ile Pro Asn Ile Gln Asn Pro Asp Pro Ala
465                 470                 475                 480

Val Tyr Gln Leu Arg Asp Ser Lys Ser Ser Asp Lys Ser Val Cys Leu
                485                 490                 495

Phe Thr Asp Phe Asp Ser Gln Thr Asn Val Ser Gln Ser Lys Asp Ser
                500                 505                 510

Asp Val Tyr Ile Thr Asp Lys Thr Val Leu Asp Met Arg Ser Met Asp
        515                 520                 525

Phe Lys Ser Asn Ser Ala Val Ala Trp Ser Asn Lys Ser Asp Phe Ala
        530                 535                 540

Cys Ala Asn Ala Phe Asn Asn Ser Ile Ile Pro Glu Asp Thr Phe Phe
545                 550                 555                 560

Pro Ser Pro Glu Ser Ser Cys Asp Val Lys Leu Val Glu Lys Ser Phe
                565                 570                 575

Glu Thr Asp Thr Asn Leu Asn Phe Gln Asn Leu Ser Val Ile Gly Phe
                580                 585                 590

Arg Ile Leu Leu Leu Lys Val Ala Gly Phe Asn Leu Leu Met Thr Leu
                595                 600                 605

Arg Leu Trp Ser Ser
        610

<210> SEQ ID NO 421
<211> LENGTH: 608
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 421

Met Lys Ser Val Leu Leu Leu Thr Thr Leu Leu Val Pro Ala His Leu
1               5                   10                  15

Val Ala Ala Val Ile Ser Gln Lys Pro Ser Arg Asp Ile Cys Gln Arg
                20                  25                  30

Gly Thr Ser Leu Thr Ile Gln Cys Gln Val Asp Ser Gln Val Thr Met
                35                  40                  45

Met Phe Trp Tyr Arg Gln Gln Pro Gly Gln Ser Leu Thr Leu Ile Ala
        50                  55                  60

Thr Ala Asn Gln Gly Ser Glu Ala Thr Tyr Glu Ser Gly Phe Val Ile
65                  70                  75                  80

Asp Lys Phe Pro Ile Ser Arg Pro Asn Leu Thr Phe Ser Thr Leu Thr
                85                  90                  95
```

```
Val Ser Asn Met Ser Pro Glu Asp Ser Ser Ile Tyr Leu Cys Ser Val
            100                 105                 110

Gly Gly Ala Gly Val Thr Asp Thr Gln Tyr Phe Gly Pro Gly Thr Arg
            115                 120                 125

Leu Thr Val Leu Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Ala Ser Ala Pro
            325                 330                 335

Ile Ser Met Leu Ala Met Leu Phe Thr Leu Ser Gly Leu Arg Ala Gln
            340                 345                 350

Ser Val Ala Gln Pro Glu Asp Gln Val Asn Val Ala Glu Gly Asn Pro
        355                 360                 365

Leu Thr Val Lys Cys Thr Tyr Ser Val Ser Gly Asn Pro Tyr Leu Phe
    370                 375                 380

Trp Tyr Val Gln Tyr Pro Asn Arg Gly Leu Gln Phe Leu Leu Lys Tyr
385                 390                 395                 400

Ile Thr Gly Asp Asn Leu Val Lys Gly Ser Tyr Gly Phe Glu Ala Glu
            405                 410                 415

Phe Asn Lys Ser Gln Thr Ser Phe His Leu Lys Lys Pro Ser Ala Leu
            420                 425                 430

Val Ser Asp Ser Ala Leu Tyr Phe Cys Ala Val Arg Glu Leu Tyr Ser
        435                 440                 445

Ala Thr Val Asp Tyr Gln Leu Thr Phe Gly Lys Gly Thr Lys Leu Ser
    450                 455                 460

Val Ile Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
            485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
```

```
            515                 520                 525
Ala Val Ala Trp Ser Asn Lys Ser Asp Phe Ala Cys Ala Asn Ala Phe
        530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
                565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
        595                 600                 605
```